United States Patent
Krzemiński et al.

(10) Patent No.: US 12,325,701 B2
(45) Date of Patent: Jun. 10, 2025

(54) YKL-40 INHIBITORS AND THEIR THERAPEUTIC

(71) Applicant: Molecure S.A., Warsaw (PL)

(72) Inventors: Łukasz Krzemiński, Warsaw (PL); Wojciech Czestkowski, Pabianice (PL); Marzena Mazur, Łódź (PL); Gleb Andryianau, Irvine, CA (US); Sylwia Olejniczak, Łódź (PL); Michał Czesław Piotrowicz, Łódź (PL); Robert Koralewski, Łódź (PL); Elżbieta Pluta, Dębe Wielkie (PL); Krzysztof Matyszewski, Łódź (PL); Michał Kowaiski, Godziszka (PL); Barbara Dymek, Warsaw (PL); Rafał Kozieł, Lesznowola (PL); Jacek Olozak, Łódź (PL); Adam Gołębiowski, Madison, CT (US); Agnieszka Bartoszewicz, Warsaw (PL); Katarzyna Krysztofiak, Warsaw (PL)

(73) Assignee: Molecure S.A., Warsaw (PL)

( * ) Notice: Subject to any disclaimer, the term of this patent is extended or adjusted under 35 U.S.C. 154(b) by 0 days.

(21) Appl. No.: 18/117,193

(22) Filed: Mar. 3, 2023

(65) Prior Publication Data

US 2023/0278996 A1 Sep. 7, 2023

Related U.S. Application Data

(60) Provisional application No. 63/316,477, filed on Mar. 4, 2022.

(30) Foreign Application Priority Data

Mar. 4, 2022 (PL) .......................... 440558

(51) Int. Cl.
| | | |
|---|---|---|
| C07D 413/14 | (2006.01) | |
| C07D 487/04 | (2006.01) | |
| C07D 495/04 | (2006.01) | |
| G01N 33/543 | (2006.01) | |
| G01N 33/68 | (2006.01) | |

(52) U.S. Cl.
CPC ......... *C07D 413/14* (2013.01); *C07D 487/04* (2013.01); *C07D 495/04* (2013.01); *G01N 33/5438* (2013.01); *G01N 33/6893* (2013.01); *G01N 2500/02* (2013.01)

(58) Field of Classification Search
CPC ... C07D 413/14; C07D 487/04; C07D 495/04
See application file for complete search history.

(56) References Cited

U.S. PATENT DOCUMENTS 9,944,624 B2 * 4/2018 Mazur ..................... A61P 27/02

OTHER PUBLICATIONS

Lto, N. et al. A medium-term rat liver bioassay for rapid in vivo detection of carcinogenic potential of chemicals. Cancer Science, 2003. vol. 93, No. 1: 3-8 (Year: 2003).*
Goel, M. et al. MoleGuLAR: Molecule Generation using Reinforcement Learning with Alternating Rewards. ChemRxiv, 2021. (Year: 2021).*
Patani, G. A. et al. "Bioisosterism: A Rational Approach in Drug Design." Chemical reviews 1996, vol. 96, 8: 3147-3176. (Year: 1996 ).*
Mazur, M. et al., Chitinases and Chitinase-Like Proteins as Therapeutic Targets in Inflammatory Diseases, with a Special Focus on Inflammatory Bowel Diseases *Int. J. Mol. Sci.* 2021, 22, 6966.
Bartoszewicz et al., "Structure based discovery of small molecule modulators of binding between YKL-40 and carbohydrates resulting in anti-inflammatory activity in in vitro and in vivo models," SCI / RSC 22nd Medicinal Chemistry Symposium—Cambridge, United Kingdom, Sep. 10-13, 2023.
Czestkowski et al., "Discovery of small molecule compounds that modulate binding of YKL-40 with carbohydrates as potential therapeutics for cancer," XXVII EFMC International Symposium on Medicinal Chemistry—Nice, France, Sep. 4-8, 2022.
Czestkowski et al., "Structure-Based Discovery of High-Affinity Small Molecule Ligands and Development of Tool Probes to Study the Role of Chitinase-3-Like Protein 1," J. Med. Chem. 2024, https://doi.org/10.1021/acs.jmedchem.3c02255.
Drzewicka et al., "Targeting Chi3l1 by a small molecule activates macrophages," Immunochemistry and Immunobiology Gordon Research Conference (GRC) Immune system in Health, Disease and Therapy—Castelldefels, B, Spain, Jun. 5-10, 2022.
Grajda et al., "Discovery of small molecule compounds that modulate binding of YKL-40 with carbohydrates or galectin-3 as potential therapeutics for cancer," ACS—New York, Jun. 26-29, 2022.
Krzeminski et al., "Discovery of small molecule compounds interfering with YKL-40 carbohydrate binding as potential therapeutics for cancer," ACS—San Diego, CA, Aug. 25-29, 2019.
Przysucha et al., "The role of Chitinases in Chronic Airway Inflammation Associated with Tobacco Smoke Exposure", Cells 11, 3765 (2022).

* cited by examiner

*Primary Examiner* — Jean P Cornet
*Assistant Examiner* — Chihyi Lee
(74) *Attorney, Agent, or Firm* — Foley Hoag LLP; Dana M. Gordon; Laura A. Wzorek

(57) ABSTRACT

Disclosed are assays for screening active compounds interfering with interaction between chitinase-like protein YKL-40 and chitin oligomers, as well as interfering with interaction between chitinase-like protein YKL-40 and heparan sulfate. Moreover, disclosed are active compounds identified by these assays as inhibitors of chitinase-like protein YKL-40, their therapeutic applications, and their use in biosensors measuring the level of chitinase-like protein YKL-40 in biological samples.

6 Claims, 1 Drawing Sheet

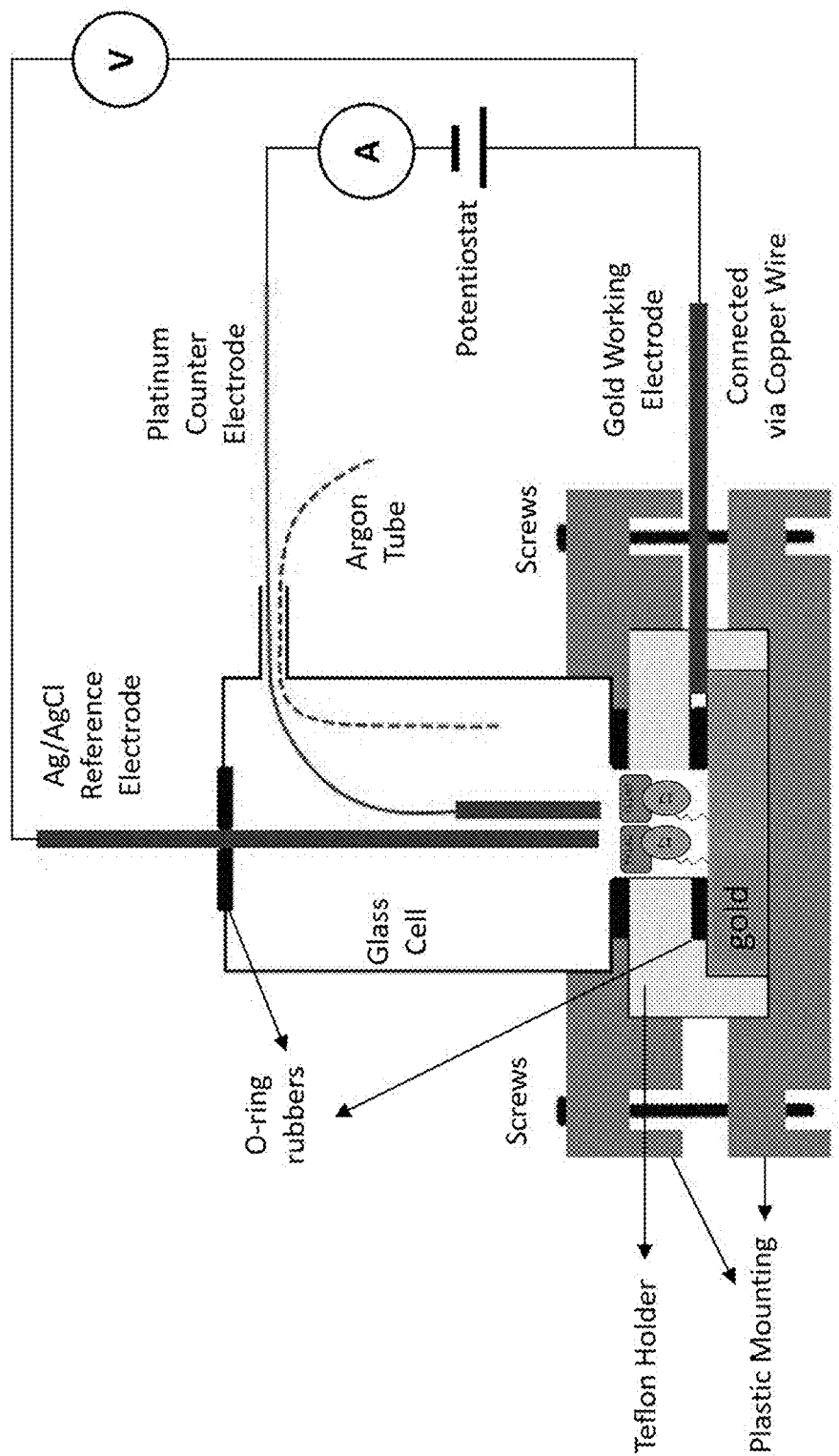

YKL-40 INHIBITORS AND THEIR THERAPEUTIC

CROSS-REFERENCE TO RELATED APPLICATIONS

This application claims the benefit of priority to Polish Patent Application number P.440558, filed Mar. 4, 2022; and U.S. Provisional Patent Application Ser. No. 63/316,477, filed Mar. 4, 2022; the contents of which are hereby incorporated by reference.

FIELD OF THE INVENTION

This invention is related to assays for screening active compounds interfering with interaction between chitinase-like protein YKL-40 and chitin oligomers, as well as interfering with interaction between chitinase-like protein YKL-40 and heparan sulfate. Moreover, this invention is related to active compounds identified by these assays as inhibitors of chitinase-like protein YKL-40, their therapeutic applications, and their use in biosensors measuring the level of chitinase-like protein YKL-40 in biological samples.

BACKGROUND OF THE INVENTION

The glycosyl hydrolase family 18 (GH 18) is an ancient gene family that is widely expressed in species as diverse as plants, insects and mammals. GH 18 protein family in humans, consists of two enzymatically active chitinases, CHIT1 and AMCase, and the non-active chitinase-like proteins (CLPs): YKL-40, YKL-39, oviductin and stabilin-interacting protein that lack enzymatic activity due to amino acid substitutions in the active site. Although chitinases and CLPs are evolutionary highly conserved, their physiological role in mammals has not been fully elucidated. In most mammals, e.g., rodents, chitinases protect against chitin-containing organisms which are either inhaled or ingested. Mammals are not known to synthesize chitin or metabolize it as a nutrient, yet the human genome encodes eight GH18 family members (Funkhouser et al., Chitinase family GH18: evolutionary insights from the genomic history of a diverse protein family. BMC *Evol Biol*. June 26:7-96, 2007). In humans, chitinases and CLPs are thought to have evolved to perform different functions, often associated with inflammatory and fibrotic pathologies as well as tissue remodeling and cancer progression (Lee et al., Role of chitin and chitinase/chitinase-like proteins in inflammation, tissue remodeling, and injury. *Annu Rev Physiol.* 73:479-501, 2011). Chitinase-3-like protein 1 (CHI3L1), also known as YKL-40 is a secreted glycoprotein that was first identified in culture media of a human osteosarcoma cell line MG63 (Johansen et al., Identification of proteins secreted by human osteoblastic cells in culture. Journal of Bone & Mineral Research 7:501-512, 1992). YKL-40 protein is approximately 40 kDa in size that in humans is encoded by the CHI3L1 gene, located on chromosome 1931-1932 and consists of 10 exons and spans about 8 kilobases of genomic DNA (Rehli et al., Molecular characterization of the gene for human cartilage gp-39 (CHI3L1), a member of the chitinase protein family and marker for late stages of macrophage differentiation. *Genomics* 43(2):221-5, 1997). The name YKL-40 derives from the three N-terminal amino acids present on the secreted form and its molecular mass in kilodaltons. YKL-40 lacks chitinase activity due to mutations of one of the three amino acids (Asp, Glu and Asp) essential for the chitinase-like catalytic activity, namely Glu→Leu, which completely deprives chitinase activity (Renkema et al., Chitotriosidase, a chitinase, and the 39-kDa human cartilage glycoprotein, a chitin-binding lectin, are homologues of family 18 glycosyl hydrolases secreted by human macrophages. *Eur. J Biochem.* 251: 504-509, 1998). YKL-40 has been shown to bind chitin oligomers, chitin-like oligosaccharides, hyalurorian, heparin (Ngernyuang, N. et al. A Heparin Binding Motif Rich in Arginine and Lysine is the Functional Domain of YKL-40 *Neoplasia.* 2018 February; 20(2):182-192), and heparan sulfate (Fusetti, F. et al. Crystal structure and carbohydrate binding properties of the human cartilage glycoprotein-39. *J. Biol. Chem.* 2003; 278:37753-60). However, the biological role of YKL-40 still remains unclear. YKL-40 is not even known to have a specific receptor, although it has been proposed to act through IL13Ra2 (Chuanet at al., Chitinase 3-like 1 Regulates Cellular and Tissue Responses via IL-13 Receptor α2. *Cell Rep.* 4(4): 830-841, 2013) and Syndecan-1 (Shao et al., YKL-40, a secreted glycoprotein, promotes tumor angiogenesis, *Oncogene.* 28:4456-4468, 2009) receptors via respectively chitin-binding and heparin-binding domains but its detailed biological functions are still poorly understood.

Despite the fact that the exact function of YKL-40 is still unknown, the pattern of YKL-40 expression is associated with pathogenic processes related to inflammation, extracellular tissue remodeling, fibrosis and solid carcinomas. YKL-40 is expressed and secreted by various cell-types including macrophages, chondrocytes, fibroblast-like synovial cells, vascular smooth muscle cells, hepatic stellate cells as well as cancer cells. In accordance to these observations, elevated levels of YKL-40 protein have been detected in a wide range of diseases, comprising infections, arthritis, inflammatory bowel disease, chronic obstructive lung disease, idiopathic pulmonary fibrosis, asthma, hepatitis, diabetes, atherosclerosis, giant cell arteritis (Lee et al., Chitin, chitinases and chitinase-like proteins in allergic inflammation and tissue remodeling. *Yonsei Med J* 50:22-30, 2009; Lee et al., Role of chitin and chitinase/chitinase-like proteins in inflammation, tissue remodeling and injury. *Annu Rev Physiol* 73:479-501, 2011; Lee et al., Role of breast regression protein-39/YKL-40 in asthma and allergic responses. *Allergy Asthma Immunol Res* 2:20-7, 2010; 7. Lee et al. Role of breast regression protein 39 (BRP-39)/chitinase 3-like-1 in Th2 and IL-13-induced tissue responses and apoptosis. *J Exp Med* 206:1149-66, 2009; Dela Cruz et al., Chitinase 3-like-1 (Chi3l1) Regulation of *Streptococcus pneumoniae* Lung Infection. Cell Host Microbe 12:34-4, 2012; Johansen et al., A new biochemical marker for joint injury. Analysis of YKL-40 in serum and synovial fluid. *Br J Rheumatol* 32:949-55, 1993), neurodegenerative diseases like Alzheimer disease (Muszyński et al., YKL-40 as a Potential Biomarker and a Possible Target in Therapeutic Strategies of Alzheimer's Disease. *Curr Neuropharmacol.* 15(6):906-917, 2017), cancer and many others.

Cancer is a group of diseases caused by abnormal and uncontrolled cell proliferation with the potential to invade or spread to other organs of the body. YKL-40 is produced and secreted by several types of human cancer cells and tumor-associated macrophages. It has been postulated that it may play a role in cell proliferation, differentiation, cell survival, invasiveness, metastasis, in angiogenesis, inflammatory response to cancer and tissue remodeling. YKL-40 serum protein level is considered as prognostic biomarker in a variety of different cancer types (breast, liver, colon, lung, kidney, ovarian, prostate, uterine, osteosarcoma, oligodendroglioma, glioblastoma and germ cell tumors), elevated serum YKL-40 level has been correlated with poor prognosis and shorter survival of patients with cancer (Johansen et al., Is YKL-40 a new therapeutic target in cancer?*Expert Opin Ther Targets*. 11(2):219-34, 2017). Studies in animal models have demonstrated that YKL-40 overexpression enhances breast (MDA-MB-231 cells) and colon (HCT116 cells) tumor growth and angiogenesis in vivo, on the other hand, U87 glioblastoma cancer cells expressing YKL-40 siRNA had abrogated tumor angiogenesis and tumor growth in vivo (Shao et al., YKL-40, a secreted glycoprotein, promotes tumor angiogenesis. *Oncogene* 28(50): 4456-4468, 2009). Moreover, overexpression of YKL-40 in GL261 glioblastoma cancer cells increased the tumor growth in the syngeneic mouse model. This was accompanied by higher number of M2-like tumor associated macrophages and reduced number of lymphocytes T, showing the immunosupressive role of YKL-40 (Chen et al., Chitinase-3-like 1 protein complexes modulate macrophage-mediated immune suppression in glioblastoma. *The Journal of clinical investigation*, 131(16), 2021). It has been also reported that YKL-40 neutralizing antibodies are effective in blocking tumor angiogenesis and tumor progression (Faibish et al., A YKL-40-neutralizing antibody blocks tumor angiogenesis and progression: a potential therapeutic agent in cancers. *Mol. Cancer Ther.* 10(5):742-51, 2011; Shao R et al., Anti-YKL-40 antibody and ionizing irradiation synergistically inhibit tumor vascularization and malignancy in glioblastoma. *Carcinogenesis* 2014; 35:373-382; Kang K et al., Selection and Characterization of YKL-40-Targeting Monoclonal Antibodies from Human Synthetic Fab Phage Display Libraries. *Int. J Mol. Sci.* 2020 Sep. 1; 21(17):6354).

Chitinase and chitinase-like proteins are over expressed in many cancers including brain tumors such as glioblastoma (Francescone et al. *J. Biol. Chem.* 2011; 286:15332-43; Ku et al. *Int. J. Cancer* 2011; 128:1316-26) or astrocytoma (Zhang et al. *Cancer.* 2010; 116:2688), breast cancer (Johansen et al. *Breast Cancer Res Treat* 2003; 80:15-21), colon cancer (Nutt et al., 2005, Pelloski et al., 2005; Fijneman et al. *Clin Cancer Res.* 2012; 18:2613; Chen et al. *Am J Pathol.* 2011; 179:1494), primary and metastatic lung cancer (Wang et al. *Tumour Biol* 2015; 36:901-7; Johansen et al. *Lung Cancer* 2004; 46:333-40), mesothelioma (Corradi et al. *Anticancer Res.* 2013 December; 33(12):5517), osteosarcoma, malignant melanoma (Ma et al. *Cancer Res.* 2015; 75:487-96), ovarian cancer (Hogdall et al. *BMC Cancer* 2009; 9:8; Dupont et al. *J Clin Oncol.* 2004; 22:3330), cervical cancer (Ngernyuang et al. *Int J Biochem CellBiol* 2014; 51:45-52), prostate cancer (Jeet et al. *Endocr Relat Cancer.* 2014; 21:723), liver cancer (Pan et al. *J Cancer Res Clin Oncol* 2013; 139:1043-54), gastric cancer (Li et al. *Chin Med J* 2012; 125:1777), metastatic renal cancer (Zhangg et al. *Tumour Biol* 2014; 35:12131-7), hematologic malignancies such as leukemia or lymphoma (Mactier et al. *JProteome Res.* 2011; 10:1030; Marchesi et al. *Vet Pathol.* 2006; 43:773-6; Marchesi et al. *J Vet Med A Physiol Pathol Clin Med.* 2003; 50:103) and other types of cancers with inflammatory background (Quershi et al. *Genes Cancer.* 2011; 2:74; Eurich et al. *World J Gastroenterol.* 2009; 15:5249; Roslind and Johansen, *Methods of Mol Biol.* 2009; 511:159). In fact, higher plasma levels indicate poor prognosis and increased metastatic potential for several cancers (Johansen et al., *Cancer Epidemiol. Biomarkers Prev.,* 15(2):194-202, 2006). Inhibition of chitinase and chitinase-like protein biological function with one or more compounds described in this invention is anticipated to have therapeutic utility in subjects with cancer.

Interstitial lung diseases (ILDs) is a group of over 300 lung disorders which affect lung interstitium: the most common are sarcoidosis and idiopathic pulmonary fibrosis (IPF). These diseases, many with unknown etiology, are characterized by the alveolar damage which often leads to a chronic inflammation and fibrosis resulting in diminished lung functions.

Sarcoidosis is a multiorgan systemic disease characterized by a formation of granulomas that can develop in various organs, with most patients developing pulmonary presentation. Spontaneous remission occurs in a majority of cases, but up to one-third of patients develop a chronic, progressive or relapsing disease with a concomitant interstitial fibrosis and decline in lung functions (Valeyre et al., *Sarcoidosis. Lancet* 383(9923):1155-67, 2014). The clinical studies demonstrated highly elevated YKL-40 serum levels in sarcoidosis patients compared to controls (Long et al., Serum YKL-40 as predictor of outcome in hypersensitivity pneumonitis. *Eur Respir J.* 23:49-51, 2017) and YKL-40 serum protein level has been postulated as new sarcoidosis marker (Johansen et al., Increased serum YKL-40 in patients with pulmonary sarcoidosis-a potential marker of disease activity?*Respir Med.* 99(4):396-402, 2005).

IPF is a progressive fibroproliferative disorder with no curative therapies with a median survival of only 3-5 years following diagnosis. IPF is a devastating disease characterized by excessive matrix deposition that disrupts the normal architecture of the lung parenchyma and impairs lung functions. The key pathological features of IPF include fibroblastic foci, areas of epithelial cysts associated with the honeycombing appearance of the lung, and mild lymphoplasmacytic interstitial inflammation that is associated with areas of type II cell hyperplasia (Richeldi et al., Idiopathic pulmonary fibrosis. *Lancet* 389(10082):1941-1952, 2017). A series of clinical studies have demonstrated an increased YKL-40 protein levels in serum and bronchoalveolar lavage fluid (BALF) of patients with idiopathic pulmonary fibrosis (Furuhashi et al., Increased expression of YKL-40, a chitinase-like protein, in serum and lung of patients with idiopathic pulmonary fibrosis. *Respir Med.* 104(8):1204-10, 2010; Vij et al., Peripheral blood biomarkers in idiopathic pulmonary fibrosis. *Transl Res.* 159(4):218-27, 2012) suggesting that YKL-40 protein might be involved in remodeling and tissue damage seen in lungs from IPF patients. Furthermore, elevated YKL-40 serum and BALF level are considered as predictors of survival in idiopathic pulmonary fibrosis (Korthagen et al., Serum and BALF YKL-40 levels are predictors of survival in idiopathic pulmonary fibrosis. *Respir Med.* 2011 January; 105(1):106-13).

Obstructive lung diseases (among them asthma and chronic obstructive lung disease COPD) are chronic inflammatory disorders that involve the small airways and cause airflow limitation. Asthma is characterized by recurrent episodes of reversible airway obstruction and airway hyper responsiveness. Typical clinical manifestations include shortness of breath, wheezing, coughing and chest tightness that can become life threatening or fatal. While existing therapies focus on reducing the symptomatic bronchospasm and pulmonary inflammation, there is a growing recognition of the role of long-term airway remodeling in the accelerated lung deterioration in asthmatics. (Papi et al., Asthma. *Lancet* 391(10122):783-800, 2018). COPD is a disease characterized by a progressive, irreversible limitation of airflow due to emphysema and remodeling of small airways. Currently, no drugs reducing COPD progression are available with smoking cessation the only intervention demonstrated to slow the rate of decline in lung function. (Rabe et al., Chronic obstructive pulmonary disease. *Lancet* 389(10082): 1931-1940, 2017). Multiple studies have demonstrated that YKL-40 may be implicated in bronchial inflammation and remodeling in COPD and its elevated level may be considered as a useful biomarker for COPD diagnosis and monitoring (Xiang et al., The YKL-40 protein is a potential biomarker for COPD: a meta-analysis and systematic review. *Int J Chron Obstruct Pulmon Dis.* 13: 409-418, 2018). Another meta-analysis suggested that YKL-40 protein may play an important role in the pathogenesis of asthma and its serum levels may correlate with exacerbation attacks and severity as well (Xiang et al., The serum YKL-40 is a useful biomarker for asthma. *European Respiratory Journal* 50: PA3566, 2017).

There is a need for an assay for screening active compounds interfering with interactions of YKL-40 and other biomolecules such as chitin oligomers and heparins. Such active compounds could act as YKL-40 inhibitors, and be of use as therapeutic agents for the treatment a variety of diseases and disorders, including cancers, inflammation, and pulmonary diseases.

SUMMARY OF THE INVENTION

In one aspect, this invention concerns a compound represented by formula (I)

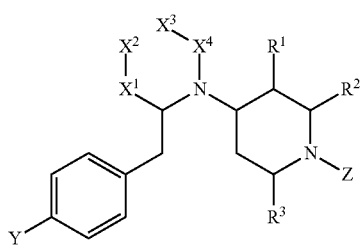

(I)

wherein:
$X^1$ is a single bond, —C(O)—, or —C($R^4R^5$)—;
$X^2$ is —C($R^6R^7$)—, —N($R^8$)—, or —O—;
$X^3$ is —C($R^9R^{10}$)— or benzo;
$X^4$ is a single bond, —$CH_2$—, or —C(O)—;
or $X^3$ and $X^4$, taken together, represent benzo;
Y is halo, ($C_1$-$C_3$)alkyl, ($C_1$-$C_3$)alkoxy, or ($C_1$-$C_3$)alkylthio;
Z is aryl, heteroaryl, or ($C_1$-$C_6$)alkoxycarbonyl;
$R^1$ is hydrogen or ($C_1$-$C_6$)alkoxy;
$R^2$ is hydrogen, ($C_1$-$C_6$)alkyl, or (($C_1$-$C_6$)alkyl)$_2$ aminocarboxy($C_1$-$C_6$)alkyl;
or $R^2$, taken together with the carbon atom bearing it, represents —C(O)—;
$R^3$ is hydrogen;
or $R^2$ and $R^3$, taken together, represent —$CH_2CH_2$— or —$CH_2CH_2CH_2$—;
$R^4$ is hydrogen or ($C_1$-$C_6$)alkyl;
$R^5$ is hydrogen or ($C_1$-$C_6$)alkyl;
$R^6$ is hydrogen or ($C_1$-$C_6$)alkyl;
$R^7$ is hydroxy or ($C_1$-$C_6$)alkoxy;
$R^8$ is hydrogen, ($C_1$-$C_6$)alkyl, hydroxy-($C_1$-$C_6$)alkyl, ($C_1$-$C_6$)alkoxy-($C_1$-$C_6$)alkyl, ($C_1$-$C_6$)-alkoxycarbonyl, ($C_1$-$C_6$)alkoxycarbonylmethyl, ($C_1$-$C_6$)alkylaminocarbonyl, ($C_1$-$C_6$)alkylaminocarbonylmethyl, ($C_1$-$C_6$) alkylaminocarboxymethyl, (($C_1$-$C_6$)alkyl)$_2$aminocarbonyl, (($C_1$-$C_6$)alkyl)$_2$aminocarbonylmethyl, (($C_1$-$C_6$)alkyl)$_2$aminocarboxymethyl, or HO—C(O)—($C_1$-$C_6$)alkyl;

$R^9$ is hydrogen, ($C_1$-$C_6$)alkyl, hydroxy, hydroxy-($C_1$-$C_6$)alkyl, ($C_1$-$C_6$)alkoxy-($C_1$-$C_6$)alkyl, amino-($C_1$-$C_6$)alkyl, aryl-($C_1$-$C_6$)alkyl, aryloxy-($C_1$-$C_6$)alkyl, aryl-($C_1$-$C_6$)alkoxy-($C_1$-$C_6$)alkyl, heterocyclyl-($C_1$-$C_6$)alkyl, ($C_1$-$C_6$)alkylaminocarbonyl, ($C_1$-$C_6$)alkylaminocarbonyl-methyl, ($C_1$-$C_6$)alkylaminocarboxymethyl, (($C_1$-$C_6$)alkyl)$_2$aminocarboxymethyl, or arylaminocarboxymethyl;
$R^{10}$ is hydrogen;
or $R^9$ and $R^{10}$, taken together, represent —$CH_2CH_2$—, —$CH_2CH_2CH_2$—, or —$CH_2CH_2CH_2CH_2$—;
wherein any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of hydroxy, halo, —$NH_2$, —NH(($C_1$-$C_6$)alkyl), —N(($C_1$-$C_6$)alkyl)$_2$, —CN, —$NO_2$, ($C_1$-$C_6$)alkyl, ($C_1$-$C_6$)haloalkyl, ($C_1$-$C_6$)alkoxy, aryl, heteroaryl, aryl($C_1$-$C_6$)alkyl, heteroaryl($C_1$-$C_6$)alkyl, ($C_3$-$C_7$)cycloalkyl, heterocyclyl, —C(O)OH, —C(O)O($C_1$-$C_6$)alkyl, —C(O)$NH_2$, —C(O)NH($C_1$-$C_6$)alkyl, and —C(O)N (($C_1$-$C_6$)alkyl)$_2$; and
wherein any occurrence of —$CH_2$— is optionally replaced by —C(O)—;
provided that Z is not 2-amino-1,3,4-triazol-5-yl nor any tautomer of 2-amino-1,3,4-triazol-5-yl; or a tautomer, stereoisomer, pharmaceutically acceptable salt, solvate, or polymorph thereof.

Another aspect of the invention provides a pharmaceutical composition comprising a therapeutically effective amount of a compound of formula (I) according to the invention, and a pharmaceutically acceptable carrier.

Another aspect of the invention provides a method for inhibiting the chitinase-like protein YKL-40 in a cell or a tissue, comprising contacting a cell or a tissue with an effective amount of at least one compound of formula (I) according to the invention.

Another aspect of the invention provides a method for the treatment or prevention of a disease, disorder, or condition associated with aberrant expression or activity of the chitinase-like protein YKL-40, comprising administering to a subject in need thereof a therapeutically effective amount of at least one compound of formula (I) according to the invention, or a pharmaceutical composition according to the invention.

In another aspect, this invention concerns a compound represented by formula (II)

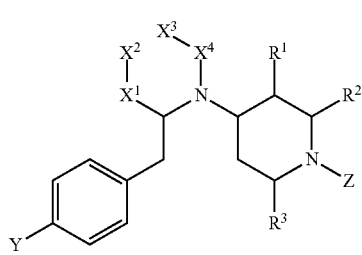

(II)

wherein:
$X^1$, $X^2$, $X^3$, $X^4$, Y, Z, $R^1$, $R^2$, $R^3$, $R^4$, $R^5$, $R^6$, $R^7$, $R^8$, $R^9$, and $R^{10}$ are as defined in formula (I) according to the invention, provided that at least one amino, carboxy, or hydroxy group of the compound of formula (II) is replaced by amide or ester linkage to form a derivative with PEGn-biotin, PEGn-glutathione, PEGn-fluorescein, PEGn-FLAG octapeptide or PEGn-digoxigenin, where n is an integer of from 9 to 15, optionally for use in a method of high-throughput screening assay for compounds capable of binding YKL-40.

In another aspect, this invention provides a method of identifying compounds that interfere with the chitinase-like protein YKL-40 and biotin tagged chitin oligomer interaction by subjecting compound of formula (I) to a binding competition assay and assessing the resulting AlphaScreen luminescence signal, wherein an emission signal declines from the high level at lowest inhibitor concentration to the low level at highest inhibitor concentrationindicates that the compound interferes with the chitinase-like protein YKL-40 and chitin oligomer interaction.

In another aspect, this invention concerns a method of identifying compounds that interfere with the chitinase-like protein YKL-40 and heparan sulfate interaction by:
(1) in a binding competition assay, subjecting (i) a compound of formula I and (ii) biotinylated heparin sulfate to YKL-40 or derivative of YKL-40 comprising a purification tag; and
(2) assessing the resulting AlphaScreen luminescence signal;
wherein an emission signal decline from the high level at lowest inhibitor concentration to the lower level (diminished by the value of at least 3× standard deviation of the noise displayed at plateau values at highest concentrations of inhibitor in the response plots for IC50 determinations) level at highest inhibitor concentration indicates that the compound interferes with the chitinase-like protein YKL-40 and heparin sulfate oligomer interaction.

In another aspect, this invention concerns an electrochemical impedimetric biosensor for monitoring chitinase-like protein YKL-40, wherein the biosensor comprises an electrochemical cell, a gold working electrode, the platinum counter-electrode, a reference electrode, and a potentiostat, characterized in that the gold working electrode is modified by reaction with a thiolated derivative of a compound of formula (I) or formula (II) according to the invention.

BRIEF DESCRIPTION OF THE DRAWING

FIG. 1 presents a general diagram of an impedimetric biosensor device for detecting chitinase-like protein YKL-40 level in biological samples using the active compounds of the invention.

DETAILED DESCRIPTION OF THE INVENTION

Definitions

The articles "a" and "an" are used herein to refer to one or to more than one (i.e., to at least one) of the grammatical object of the article. By way of example, "an element" means one element or more than one element.

The terms "group" and "radical" are used interchangeably herein and denote a portion of a molecule in question which is bound to the rest of the molecule by a covalent bond (or bonds, as results from the previous paragraph).

The terms used herein may be preceded and/or followed by a single dash "-", or a double dash "=", to indicate the bond order of the bond between the named substituent and its parent moiety; a single dash indicates a single bond and a double dash indicates a double bond. In the absence of a single or double dash, it is understood that a single bond is formed between the substituent and its parent moiety; further, substituents are intended to be read "from left to right," unless a dash indicates otherwise. For example, $(C_1-C_6)$ alkylcarboxy and —OC(O)($C_1$-$C_6$)alkyl indicate the same functionality; similarly, arylalkyl and -alkylaryl indicate the same functionality.

The term "single bond" as used herein, denotes a single covalent bond between two atoms, such as C—C, C—H, or C—O.

The term "alkyl" as used herein is a term of art and refers to saturated aliphatic groups, including straight-chain alkyl groups and branched-chain alkyl groups. The subscripts following C indicate the number (or range of numbers) of carbon atoms in the straight-chain or branched-chain alkyl. From the practical reasons, the number of carbon atoms in a straight-chain alkyl is limited to the range of 1-8, inclusive, and the number of carbon atoms in a branched-chain alkyl is in the range of 3-8, inclusive. If there is no subscript specified defining the number of carbon atoms in an alkyl group, then this number is not greater than 8. Representative examples of $(C_1-C_6)$alkyl include, but are not limited to, methyl, ethyl, n-propyl, isopropyl, n-butyl, sec-butyl, isobutyl, tert-butyl, n-pentyl, isopentyl, neopentyl, and n-hexyl. Examples of $(C_1-C_3)$alkyl include methyl, ethyl, n-propyl, and isopropyl. Alkyl may represent a group, as already defined, or a portion of a larger moiety, such as $(C_1-C_3)$alkoxy$(C_1-C_3)$alkyl. A $(C_1-C_3)$alkoxy$(C_1-C_3)$alkyl is bound to the rest of the molecule through the $(C_1-C_3)$alkyl moiety. If a name of particular alkyl group appears in the name of a chemical compound, the prefixes such as iso-, sec-, tert-, or neo-, indicate an appropriately branched alkyl, as understood by the person skilled in the art; the prefix n- or lack of any prefix means that the alkyl group in question is a straight-chain alkyl.

The term "cycloalkyl" means mono- or bicyclic or bridged saturated or partially saturated carbocyclic rings, each having from 3 to 12 carbon atoms. Certain cycloalkyls have from 3-8, or from 3-6 carbon atoms in their ring structure. Certain cycloalkyls have from 5-12 carbon atoms in their ring structure, and may have 6-10 carbons in the ring structure. Preferably, cycloalkyl is $(C_3-C_7)$cycloalkyl, which represents a monocyclic saturated carbocyclic ring, having from 3 to 7 carbon atoms. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "cycloalkylalkyl" as used herein refers to an alkyl group substituted with one or more cycloalkyl groups. An example of cycloalkylalkyl is cyclohexylmethyl group.

The terms "heterocyclyl" and "heterocycloalkyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 14, or 3 to 12 atoms other than hydrogen, including at least one heteroatom, such as nitrogen, oxygen, or sulfur. More preferred heterocycloalkyl groups have from 5-10 ring members where from 1-4 of the ring members are hetero atoms selected from the group consisting of O, N, and S, the remaining ring atoms being C. For purposes of exemplification, which should not be construed as limiting the scope of this invention, the following are examples of heterocycloalkyl: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocycloalkyl group is optionally substituted by one or more substituents as described below.

As used herein, the terms "heterocyclylene" and "heterocycloalkylene" refers to a bivalent heterocyclyl (heterocycloalkyl) group, i.e., a cyclic alkylene group, having from 3-10 members and from 1-4 hetero atoms selected from S, O, and N. An example is piperidine-2,3-dicarboxylic acid, i.e., in that compound, the piperidine ring is a heterocyclylene group.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "heterocycloalkylalkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Preferably, alkenyl contains from 2 to 6 carbons. Representative examples of alkenyl include, but are not limited to, ethenyl, 2-propenyl, 2-methyl-2-propenyl, 3-butenyl, 4-pentenyl, and 5-hexenyl. The unsaturated bond(s) of the alkenyl group can be located anywhere in the moiety and can have either the (Z) or the (E) configuration about the double bond(s).

The molecules differing only in their configuration about the double bond are called geometrical isomers.

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

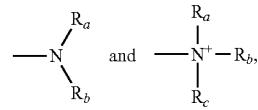

wherein $R_a$, $R_b$, and $R_c$ each independently represent a hydrogen, an alkyl, an alkenyl, $-(CH_2)_x-R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or $-(CH_2)_x-R_d$. In certain embodiments, the term "amino" refers to $-NH_2$.

The term "amido", as used herein, means $-NHC(=O)-$, wherein the amido group is bound to the parent molecular moiety through the nitrogen. Examples of amido include alkylamido such as $CH_3C(=O)N(H)-$ and $CH_3CH_2C(=O)N(H)-$.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "azide" or "azido", as used herein, means an $-N_3$ group.

The term "carbonyl" as used herein refers to $-C(=O)-$.

The term "thiocarbonyl" as used herein refers to —C(=S)—.

The term "alkylthio" as used herein refers to alkyl-S-. Representative examples of $(C_1-C_6)$alkylthio include methylthio, ethylthio, n-propylthio, and tert-butylthio. Representative examples of $(C_1-C_3)$alkylthio include methylthio, ethylthio, and n-propylthio.

The term "mercaptoalkyl" as used herein refers to an alkyl group substituted by an —SH moiety. Representative examples of $(C_1-C_6)$mercaptoalkyl include mercaptomethyl, mercaptoethyl, and mercapto-n-propyl.

The term "carboxy" as used herein refers to a —C(=O)—O— moiety, forming a portion of another substituents, such as alkylaminocarboxymethyl, or a portion of carboxylic acid esters.

There is an exception to this convention in the case of functionalized cellulose derivatives, such as carboxymethylcellulose, wherein "carboxymethyl" denotes $HO_2C$—$CH_2$—.

The terms "carboxyl", and "hydroxycarbonyl", as used herein, refer to a —$CO_2H$ group. This group can form a portion of another substituent, such as hydroxycarbonylmethyl, i.e., $HO_2C$—$CH_2$—.

The term "aryl" is a term of art and as used herein refers to include monocyclic, bicyclic, and polycyclic aromatic hydrocarbon groups, for example, benzene, naphthalene, 1,2,3,4-tetrahydronaphthalene, indene, 2,3-dihydroindene, and pyrene. The aromatic ring may be substituted at one or more ring positions with one or more substituents, such as halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocycloalkyls. Representative examples of the polycyclic aryl ring systems include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-6-yl, 2,3-dihydrobenzo[b][1,4]dioxan-5-yl, 2,3-dihydrobenzo[b][1,4]dioxan-6-yl, 2H-benzo[b][1,4]-oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl, or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted. In certain embodiments, the term "aryl" refers to $C_6$-$C_{10}$aryl. In certain embodiments, the term "aryl" refers to a phenyl group or a naphthyl group.

The term "heteroaryl" is a term of art and as used herein refers to a monocyclic or bicyclic aromatic group having 3 to 14, 5 to 14, 3 to 12, 3 to 10, or 6 to 10 total atoms (other than hydrogen) including one or more heteroatoms such as nitrogen, oxygen, or sulfur in the ring structure. More preferred heteroaryl groups have from 5-10 ring members where from 1-4 of the ring members are heteroatoms selected from the group consisting of O, N, and S. Exemplary heteroaryl groups include, for example, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazo-pyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. Any heteroaryl can be optionally substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as triflurom-ethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroiso-quinolin-1-yl, thienopyridinyl, 4,5,6,7-tetrahydrobenzo[c][1,2,5]oxadiazolyl, and 6,7-dihydro-benzo[c][1,2,5]oxadiazol-4(5H)-onyl. Any heteroaryl or bicyclic heteroaryl can be optionally substituted as detailed below.

The term "aralkyl", "arylalkyl", or "aryl($C_1$-$C_6$)alkyl" is a term of art and as used herein refers to an alkyl group, for example a $C_1$-$C_6$ alkyl group, substituted with an aryl group, wherein the moiety is appended to the parent molecule through the alkyl group. An example of aralkyl is the benzyl group, i.e., the phenyl-methyl-group.

The term "arylene" is art-recognized, and as used herein pertains to a diradical obtained by removing two hydrogen atoms of an aryl group, as defined above. An exemplary arylene group is 1,4-phenylene. Another exemplary arylene group is benzo, or 1,2-phenylene, of the following structural formula:

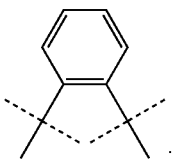

The term "heteroaralkyl", "heteroarylalkyl", or "heteroaryl($C_1$-$C_6$)alkyl" is a term of art and as used herein refers to an alkyl group, for example a $C_1$-$C_6$ alkyl group, substituted with a heteroaryl group, appended to the parent molecular moiety through the alkyl group.

The term "alkoxy" or "alkoxyl" as used herein means an alkyl group, as defined herein, appended to the parent molecular moiety through an oxygen atom. Preferably, the alkoxy group is ($C_1$-$C_6$)alkoxy. Representative examples include, but are not limited to, methoxy, ethoxy, propoxy, 2-propoxy, butoxy, tert-butoxy, pentyloxy, and hexyloxy. Representative examples of ($C_1$-$C_3$)alkoxy include methoxy, ethoxy, and propoxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl. Alkoxycarbonyl can form a portion of another moiety, e.g., methoxycarbonylmethyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2$=CH—$CH_2$—O—) and vinyloxy (i.e., $CH_2$=CH—O—).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The terms "cyano" and "nitrile" are terms of art and as used herein refers to —CN.

The term "nitro", as used herein, means —$NO_2$.

The term "halo" or "halogen" is a term of art and as used herein refers to —F, —Cl, —Br, or —I.

The term "haloalkyl" as used herein refers to an alkyl group, as defined herein, wherein one or more or all of the hydrogens are replaced with halogen atoms. The term "haloalkoxyl" refers to an alkoxy group, as defined herein, wherein one or more or all of the hydrogens are replaced with halogen atoms. An exemplary ($C_1$-$C_6$)haloalkyl group is trifluoromethyl.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein.

Representative examples of ($C_1$-$C_6$)hydroxyalkyl include, but are not limited to, hydroxymethyl, 2-hydroxyethyl, 3-hydroxypropyl, and 2,3-dihydroxypentyl.

The term "sulfonyl", as used herein, refers to the group —S(O)$_2$— that may form a portion of larger moieties, such as methanesulfonyl or p-toluenesulfonyl.

The term "silyl", as used herein, includes hydrocarbyl derivatives of the silyl ($H_3$Si—) group (i.e., (hydrocarbyl)$_3$Si—), wherein a hydrocarbon radicals are univalent groups formed by removing a hydrogen atom from a hydrocarbon, e.g., ethyl, phenyl. The hydrocarbon radicals can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

The term "PEG", is a term of art and, as used herein, refers to a poly(ethylene glycol) group. The number appearing after PEG denotes the number of repeating ethylene glycol units. PEG may appear as a part of a substituent attached to the molecule in question. For example, a full structural formula of the biotin-attaching substituent, such as:

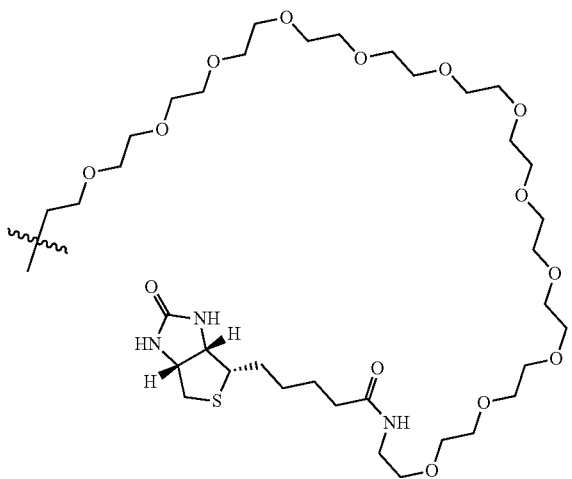 [SMILES: *CCOCCOCCOCCOCCOCCOCCOCCOCCOCCOCCOCCOCCNC(=O)CCCC[C@@H]1SC[C@@H]2NC(=O)N[C@@H]21]

may be drawn as:

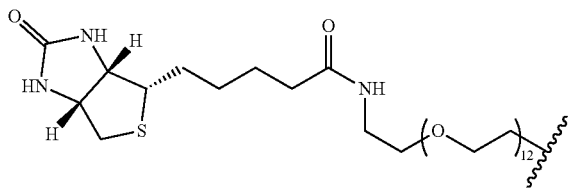

or even written as -PEG12-biotin for brevity.
Similarly, -PEG12OMe means:

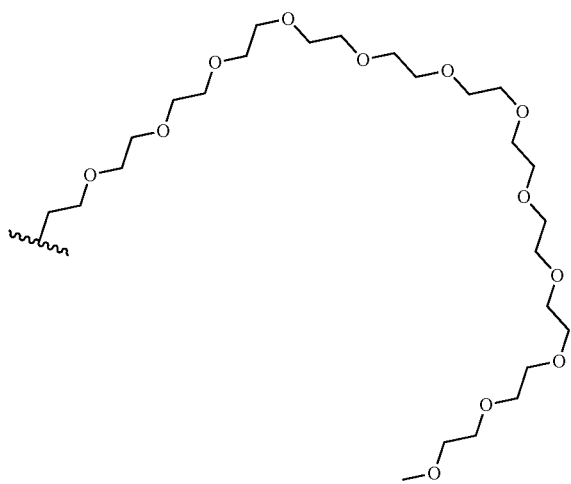 [SMILES: *CCOCCOCCOCCOCCOCCOCCOCCOCCOCCOCCOCCOC]

Analogously, -PEGn-fluorescein represents:

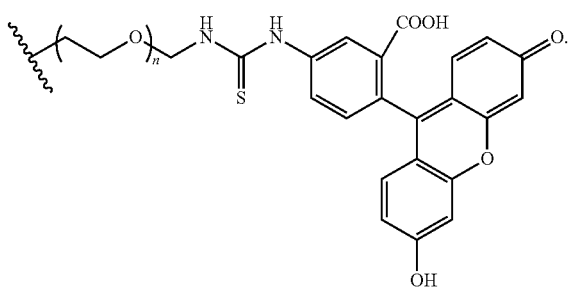

Likewise, -PEGn-glutathione denotes:

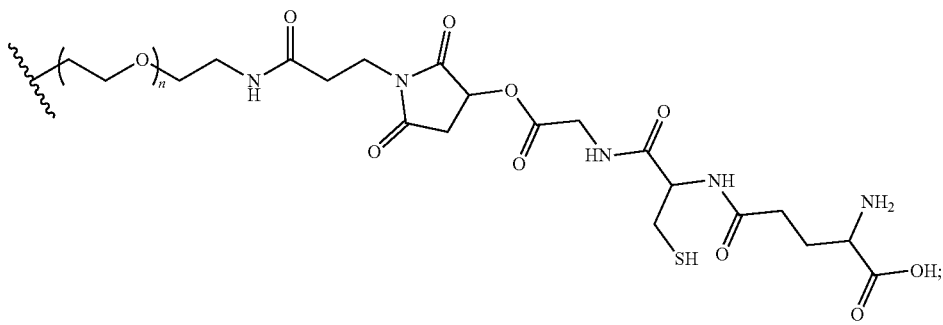

and -PEGn-digoxigenin represents:

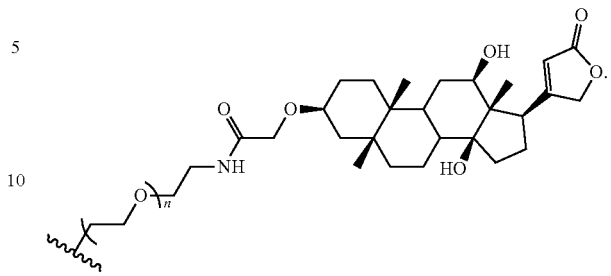

In the above-presented formulas and abbreviations, n represents an integer of from 5 to 1000, preferably from 9 to 15, more preferably from 10 to 13.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

The term "racemic mixture" refers to a mixture containing equal proportions of the first enantiomer of the molecule and of the second enantiomer of this molecule, wherein the second enantiomer is the mirror image of the first one.

The term "scalemic mixture" refers to any non-racemic mixture of stereoisomers of the molecule.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Organic compounds frequently occur in more than one crystalline form, that can differ in their physical and biological properties, such as melting point, stability, solubility, bioavailability. Such crystalline forms are termed polymorphs. All polymorphs of the inventive compounds of formula (I) and (II) and of their salts are intended to be within the scope of this invention.

Since many chemical elements can occur as isotopes, their abundance in the molecule of the inventive compound of formula (I) or (II) may be identical as in the nature or altered. Some isotopes exhibit different spectral or biological properties, and this phenomenon may be used for analysis of distribution and metabolism of drugs in the body of the recipient. All forms of the compounds of formula (I) and (II), both having a natural or unnatural abundance of isotopes of any of their constituent elements are intended to be within the scope of this invention.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocycloalkyl, heterocycloalkyl-alkyl, (heterocycloalkyl)alkoxyl, aromatic or heteroaromatic moieties, aminoalkyl, haloalkyl, fluoroalkyl (such as trifluoromethyl), haloalkoxyl, cyano, or other substitutents described above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$* ed.; Wiley: New York, 1991). Protected forms of the inventive compounds are included within the scope of this invention.

A "saturated" or "fully saturated" compound means that the referenced chemical structure does not contain any multiple carbon-carbon bonds. For example, a saturated cycloalkyl group as defined herein includes cyclohexyl, cyclopropyl, and the like.

A "unsaturated" or "partially saturated" compound means that the referenced chemical structure may contain one or more multiple carbon-carbon bonds, but is not aromatic. For example, a unsaturated cycloalkyl group as defined herein includes cyclohexenyl, cyclopentenyl, cyclohexadienyl, and the like.

For purposes of the invention, the chemical elements are identified in accordance with the Periodic Chart of the Elements, IUPAC version, The Merck Index, Twelfth Edition, 1996, inside cover.

Other chemistry terms herein are used according to conventional usage in the art, as exemplified by The McGraw-Hill Dictionary of Chemical Terms (ed. Parker, S., 1985), McGraw-Hill, San Francisco). Unless otherwise defined, all technical and scientific terms used herein have the same meaning as commonly understood by one of ordinary skill in the art to which this invention pertains.

Unless otherwise stated, structures depicted herein include all stereochemical configurations consistent with the depicted structure. For example, (i) a structure with a single stereocenter encompasses both the R and S configurations at the stereocenter and mixtures thereof, including racemic mixtures, and (ii) in a structure with two or more stereocenters, any wedged and dashed bonds show relative stereochemistry unless otherwise noted, such that the structure encompasses the individual enantiomers of the depicted compound and mixtures thereof, including racemic mixtures. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure. Similarly, indications of stereochemistry in chemical structures with two or more chiral centers convey relative stereochemistry unless otherwise defined.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of formula (I). As another example, the salt may comprise less than one inorganic or organic acid molecule per molecule of base, such as two molecules of compound of formula (I) per molecule of tartaric acid.

As used herein, a protic solvent is a solvent that has a hydrogen atom bound to an oxygen (as in a hydroxyl group) or a nitrogen (as in an amine group). In general terms, any solvent that contains labile H$^+$ is called a protic solvent. The molecules of such solvents readily donate protons (H$^+$) to reagents. In contrast, an aprotic solvent is a solvent that does not have a hydrogen atom bound to an oxygen (as in a hydroxyl group) or a nitrogen (as in an amine group), and it cannot donate hydrogen.

As used herein, a polar protic solvent is a protic solvent that will dissolve many salts. In general, these solvents have high dielectric constants and high polarity. Non-limiting examples of polar protic solvents include acetic acid, ammonia, ethanol, formic acid, isopropanol, methanol, n-butanol, nitromethane, n-propanol, t-butanol, and water.

As used herein, a polar aprotic solvent is a solvent that will dissolve many salts, but lacks an acidic hydrogen; these solvents generally have intermediate to high dielectric constants and polarity. Non-limiting examples of polar aprotic solvents include acetone, acetonitrile, dichloromethane (DCM), dimethyl sulfoxide (DMSO), ethyl acetate, hexamethylphosphoric triamide (HMPT), N,N-dimethylformamide (DMF), and tetrahydrofuran (THF).

As used herein, a nonpolar aprotic solvent is a solvent that will dissolve many salts, but lacks an acidic hydrogen; these solvents generally have low dielectric constants and polarity. Non-limiting examples of nonpolar aprotic solvents include benzene, chloroform, cyclohexane, diethyl ether, hexane, pentane, and toluene.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, the mode of administration, the bioavailability of the particular compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

"Modulating" or "modulate" refers to the treating, prevention, suppression, enhancement or induction of a function, condition or disorder.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof). In certain embodiments, the methods of the invention are for therapeutically treating.

As used herein, "subject" refers to a warm blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

High-Throughput Screening Assays for Compounds Capable of Binding YKL-40 Chitin Binding Site and Interfering with YKL-40: Heparan Sulfate Interactions 1. Introduction and Key Aspects of the Invention The present invention relates to set of two high-throughput screening assays for compounds capable of binding YKL-40 at the chitin binding site and second assay determining the interfering activity of these compounds towards YKL-40: heparan sulfate interaction. The postulated biological role of YKL-40 protein is manifested through the protein sites involved in above-mentioned interactions (He at al., 2013; Libreros et al., 2013; Shao 2013; Lee et al., 2010; Ngernyuang et al., 2017; Pouyafar et al., 2018). There is great interest in the over-expressed YKL-role in pathological conditions across many diseases, including pulmonary diseases and cancer. Since YKL-40 is suggested to actively contribute to these pathological conditions, the ability to block the protein's interactions is of great interest for companies developing drug discovery programs for this molecular target. As of today, none of the assays exists in literature or patents. Moreover, the combination of the two assays represents an unprecedented approach to tackle YKL-40 binding activity towards two natural ligands in the same time. This is because both assays can run in parallel, enabling determination with what strength and to what degree they interfere with YKL-40 interaction with chitin and heparan sulfate.

YKL-40 is a non-enzymatic protein and hence regular enzymatic assay approach cannot be used in screening or to determine $IC_{50}$ values of inhibitors competing for the same protein binding site as chitin oligomers. On the other hand, direct binding biophysical assays, including Surface Plasmon Resonance (SPR), Isothermal Titration Calorimetry (ITC), MicroScale Thermophoresis (MST) or Bio-Layer Interferometry (BLI) can monitor any compound binding to YKL-40 protein but without the information about the site of the compounds' binding. Therefore, we set out to devise biotinylated tool compound that can be successfully used in competitive binding assay against chitin binding site (CBS) of YKL-40 based on a sensitive and high-throughput AlphaScreen assay (AS) technology. First, we identified YKL-40 binders through direct binding studies using MicroScale Thermophoresis technology. Next, we confirmed the compounds are specifically binding to chitin binding site CBS of YKL-40 using X-Ray and MST displacement assays with chitin hexamer. Following this, the most active compound 17 (see, Table 1, and Example 17) was biotinylated, yielding the compound 4 (see, Table 1, and Example 4), which binding activity against CBS of YKL-40 was re-examined and confirmed with MST.

The biotinylated compound 4 enabled competitive chitin binding site YKL-40 AlphaScreen assay. This assay also aided characterization of YKL-40 interaction with different forms of heparin and heparan sulfate ligands and helped setting up a key complementary AlphaScreen assay probing inhibitory activity of YKL-40 CBS-bound compounds on the protein: heparan sulfate interaction. Moreover, 4 and its analogs also present potential value as sensing elements in YKL-40 biosensors.

2. Human YKL-40 Direct Binding Assay Based on MicroScale Thermophoresis (MST)

a. Utilizing Existing Technologies and Knowledge to Identify First YKL-40 Compound Binders MicroScale Thermophoresis is an innovative technology utilizing thermophoretic principle to study molecular interactions in solution (Duhr et al., 2004; Baaske et al., 2010; Jerabek-Willemsen et al., 2011). In the assay, the fluorescently active molecules move through IR-induced temperature gradient in a buffer and their thermophoretic path is followed by fluorescence optics of a specialized instrument. Temperature dependent molecular diffusion or movement of these molecules is sensitive to changes in their size, charge, and hydration shell; parameters that often change upon molecular binding. Therefore the travel of molecules through the temperature gradient may change after they bind to increasing concentrations of another molecules under study. The difference in thermophoretic mobility can be detected by analyzing the spatial distribution of concentration of fluorescently active molecules that are bound or unbound to interacting molecules within the reaction chamber (capillary). Therefore, changes in thermophoresis of fluorescent molecules due to binding to second-type non-fluorescent molecules can serve to calculate equilibrium binding constant (affinity, $K_D$) using the law of mass action.

In the present invention, the patented MicroScale Thermophoresis technology (NanoTemper Technologies GmbH, Munich, Germany) had been used at very early stages of hit discovery for YKL-40 protein. At that time, the only well-documented molecules binding chitin cleft of YKL-40 protein were soluble chitin oligomers with low uM affinity as demonstrated by the protein's intrinsic tryptophan fluorescence binding studies (Houston et al., 2003) and X-Ray co-crystallization studies (Houston et al., 2003; Fusetti et al., 2003). Selected potent hCHIT1 and hAMCase chitinase inhibitors that had been developed, patented and recently published by Oncoarendi Therapeutics SA (e.g., international patent application WO 2016/099311, Mazur et al., 2018; Mazur et al., 2019) did not bind to YKL-40 protein as tested with Microscale Thermophoresis. The biotinylated variants of these chitinase compounds were also found inactive against YKL-40 using patented AlphaScreen technology, while the activity of the biotinylated compounds was validated through their interaction with chitinases.

Yet, Oncoarendi Therapeutics SA (abbreviated to OAT in the following; currently Molecure SA) confirmed binding of chitin oligomers to YKL-40 protein using MST method. However, biotinylation of these ligands that is necessary for high-throughput competitive AlphaScreen (section 3) was troublesome. Likewise the affinity of chitin oligomers towards the protein (tens to hundreds of uM depending on the length of chitin oligomer) was inadequate to set up an effective competitive binding assay for chitin binding site of YKL-40. Therefore, OAT's library of over 200 chitinase inhibitors of diversified structures and activities was screened towards YKL-40 protein using MST technology until compound 17 was found. Compound 17 lacked high potency towards chitinases, presented relatively high affinity towards YKL-40 protein (100 nM) and structurally resembled potent chitinase inhibitors that were previously biotinylated and adopted for the chitinases' competitive AlphaScreen assay. These apparent similarities enabled for rational and successful biotinylation of 17 yielding 4 to be used in high throughput competitive AlphaScreen (section 3).

b. Experimental Procedures

Monolith NT.115 instrument (NanoTemper Technologies GmbH, Munich, Germany) was used to track thermophoretic movements of molecules. The instrument requires fluorescent labeling of molecules to be tracked with fluorescence optics. In the Monolith NT.115, visible light is used for fluorescence excitation for which three types of LED-filter combinations are available: blue (excitation 460-480 nm, emission 515-530 nm), green (excitation 515-525 nm, emission 560-585 nm) and red (excitation 605-645 nm, emission 680-685 nm). His-tagged YKL-40 (SinoBiological, Inc) or home-made YKL-40 without a tag was randomly labelled on deprotonated primary amines of N-terminus and/or lysine residues using N-Hydroxysuccinimide (NHS) modified NT647 fluorescent dye (Monolith Protein Labeling Kit RED-NHS kit, NanoTemper Technologies GmbH, Munich, Germany). The labeling reaction was carried out in 50 mM sodium bicarbonate buffer of pH 8.3, at 5 uM YKL-40 protein concentration and 6× molar excess of NHS-NT647, for 1 hour at RT. Next, the labelled protein was purified from unconjugated fluorescent dye excess using disposable PD MiniTrap desalting columns with Sephadex G-25 resin of 5 kDa cut-off (GE Healthcare Life Sciences). Following purification, the labeled protein was aliquoted, snap frozen in liquid nitrogen and stored in −80° C. to be used within next few weeks. The labeling efficiency was quantified using UV-Vis and excitation coefficients for YKL-40 protein ($\varepsilon_{280\,nm}$=68000$M^{-1}$ $cm^{-1}$) and NT647 fluorescent dye ($\varepsilon_{650\,nm}$=250000$M^{-1}$ $cm^{-1}$) and stayed in the range of 50-100% of YKL-40 molecules labeled with one NT647 fluorophore molecule.

The standard experimental protocol for MST assay of YKL-40-NT647 was as follows. The labeled protein aliquot from −80° C. used for the MST measurement was first spun down at 20000 g for 10 minutes at 4° C. to remove potential aggregates. Fixed working concentration of NT647 labeled YKL-40 stayed in the range of 10-20 nM inside the capillary. The binding activity of the YKL-40-NT647 protein was always confirmed using natural ligand of the protein, chitin hexamer (chitohexose, Elicityl SA, Crolles, France). The bound MST signal of YKL-40-NT647, i.e., the protein at saturating concentration of chitin hexamer, and the unbound signal of YKL-40-NT647, i.e., free protein in the buffer served respectively as the protein activity check and 'no interaction' gold standard (negative control). During MST single-point screening, duplicates of fixed 250 uM concentration of small molecule compounds were used with duplicates of positive (chitin hexamer) and negative (buffer) controls included at the start and at the end of each run. The stocks of compounds stayed in DMSO at 25 mM concentration. MST screening data were analyzed using the MO. Affinity Analysis software (NanoTemper Technologies GmbH, Munich, Germany) and a statistical cut-off of nine standard deviations either side of the mean negative control was applied. Potential YKL-40 binders identified in the MST screening were further verified in the $K_D$ titration experiments where compounds were serially diluted from high uM down to low nM concentration using max of 16 data points/capillaries fitting the Monolith NT.115 instrument. MST compound titration data were analyzed using the same software as above and a $K_D$ model for binding with 1:1 stoichiometry.

MST measurements were carried out at 37° C. after 10 min protein-compound pre-incubation in the same temperature in MST buffer (50 mM TrisHCl pH 7.4, 150 mM NaCl, 10 mM $MgCl_2$, 0.05% Tween 20, 1 mg/ml BSA 1% DMSO) and premium capillaries. The real time measurements were performed at 60% LED fluorophore excitation (red channel), 60% and 80% MST IR laser power. First, the average fluorescence of homogeneously distributed YKL-40-NT647 inside the capillary was monitored for 5 seconds. Then IR laser was switched on for another seconds during which thermophoretic curves were recorded. After that, the IR laser was switched off and the signal was monitored for another 5 seconds during which fluorescently labeled molecules were returning to initial homogenous distribution.

3. YKL-40 Competitive Chitin Binding Site Assay Based on AlphaScreen a. Utilizing Existing Technologies and Knowledge to Set-Up HTS Assay for YKL-40 Chitin Site The Amplified Luminescent Proximity Homogenous Assay Screen (AlphaScreen, PerkinElmer, Waltham, Massachusetts, USA) is a robust proximity-based assays enabling identification of small molecule modulators for a variety of biological targets (Bosse et al., 2001; Eglen et al., 2008; Taouji et al., 2009). AlphaScreen assay is designed for high throughput screening (96, 384, or 1536 well plate) using readily accessible laboratory microplate reader instrument. In this luminescence assay, a far-red 680 nm wavelength light excites photosensitizers in the first type donor beads to generate singlet oxygen species of certain lifetime that can only diffuse at certain distance (ca. 200 nm) from the beads. The generated strong oxidizer species (singlet oxygen) can chemically excite light emission (520-620 nm) from dyes present in the second type acceptor beads, but only if the two types of beads are close enough (≤200 nm). Since the beads are generally introduced at low concentrations (ca. 10 ug/mL), the non-specific interactions among bead pairs are rare and hence AS background is very low. However, the AS signal can intensely rise once molecular affinity is introduced between donor and acceptor beads. For example, when using AlphaScreen Streptavidin Donor and Nickel Chelate Acceptor beads loaded respectively with strongly interacting biotinylated compound and his-tagged protein, one dramatically intensifies contacts between beads and hereafter AS signal.

In the present invention, the patented AlphaScreen technology (AlphaScreen, PerkinElmer, Waltham, Massachusetts, USA) has been used to establish high-throughput competitive binding assays for small molecule compounds binding chitin site of YKL-40 protein (this section) and to verify the compounds interference with YKL-40: heparan sulfate interaction (section 4). Neither in literature nor in the patents there is an assay enabling identification of potential YKL-40 binding compounds that can interfere with the protein's binding activity to its natural ligands, i.e. chitin oligomers and heparan sulfate. Hence, the most active compound 17 identified from previously described MST direct binding assay for YKL-40 had been first confirmed to bind chitin cleft of the protein (X-ray of YKL-40 with 8—a close analog of 17) and subsequently biotinylated yielding compound 4. The activity of 4 was re-confirmed in MST assay and utilized as a tool compound for the competitive YKL-40 chitin binding site AlphaScreen assay. The assay would not be possible if not for the OAT discoveries in the field of chitinase and chitinase-like proteins inhibitors and successful biotinylation of potent YKL-40 binder, i.e. newly identified compound 17.

b. Setting Up the New Assay

In the first AS assay set-up experiment, biotinylated compound 4 was cross-titrated with histagged YKL-40 to determine interaction between the two partners, and to choose appropriate (fixed) concentrations of both molecules for indirect competitive assay. The 8×8 protein-compound cross-titration matrix was created using 2× serial dilutions resulting in cross-reacting YKL-40-histag and compound 4 at concentrations from 80 nM down to 0.625 nM. Based on that, the histagged protein was fixed at 2.5 nM and the biotinylated compound was fixed at 20 nM final concentrations. Such concentrations resulted in 50-75% bead occupancy while using 10 ug/mL of both Streptavidin Donor and Nickel Chelate Acceptor beads and ensured reactivity only between engaged beads prohibiting potential reactivity of free YKL-40-histag with 4 in the solution. The AlphaScreen readout from interacting molecules and beads set at these concentrations gave highly reproducible AS positive control signal over two orders of magnitude higher than AS negative control signal when YKL-40-histag was not included in the reaction. The Z' factor, an index for assay quality control, was determined to be ≥0.75.

In the second displacement (validation) experiment, non-biotinylated variant of compound 4, i.e. 17 was used to compete with compound 4 for YKL-40 protein. Titration of compound 17 predictively diminished established AlphaScreen signal in dose-dependent manner yielding $IC_{50}$ value (100-200 nM) for 17 competition with YKL-40:4 interaction. Another compound used to validate the assay was chitin hexamer which also fully hampered YKL-40:4 interaction at sufficiently high carbohydrate concentration yielding $IC_{50}$ value 3-6 uM. These experiments validated the AlphaScreen assay for use in screening and $IC_{50}$ determination of potential small molecule compounds binding the chitin site of YKL-40 protein and furthermore established $IC_{50}$ value for compound 17 as a reference activity for the quality control of proper assay performance.

In addition a third, false positive experiment was conducted to eliminate potential interference of small molecule compounds with biotinylated 4 or histagged YKL-40 attachment on respective beads, which could non-specifically diminish the AS signal. Herein, a non-specific short biotinylated histag peptide (AlphaScreen, PerkinElmer, Waltham, Massachusetts, USA) was used to generate AS signal and to verify if potential YKL-40 binders can interfere with AS signal and thereby with tests components (beads). The false positive test was routinely used throughout screening and $IC_{50}$ determination campaign for YKL-40 binders to exclude the possibility of false hits. Chitohexose and reference compound 17 were found non-interfering.

c. Experimental Procedures

The YKL-40 competitive binding AlphaScreen test was established to serve as a high-throughput primary screening assay for potential compounds binding chitin site of YKL-40 protein. The two-point screening was performed using duplicates of 100 uM and 1 uM compound concentrations and their inhibitory activity towards YKL-40:4 interaction was compared to averaged 8-data point positive control (YKL-40-histag, 4, beads) and averaged 8-data point negative control (4, beads) AS signal. Up to 20 different compounds, positive and negative controls were run on one 96-well plate in the same buffer as used in MST assay (50 mM Tris HCl pH 7.4, 150 mM NaCl, 10 mM $MgCl_2$, 0.05% Tween 20, 1 mg/mL BSA 1% DMSO). Data were normalized to positive control meaning 0% inhibition and negative control meaning 100% inhibition. Compounds of at least 75% inhibition at 100 uM concentration (or better, i.e. compounds with any inhibition at 1 uM concentration) were considered promising and their $IC_{50}$ was determined in duplicates and two repeats in subsequent experiments.

The standard experimental protocol for YKL-40 indirect binding AlphaScreen assay comprised of 5 step additions to wells of 96 well plate: (i) in the $1^{st}$ step, 8 uL of biotinylated compound 4 was added at 5×20 nM concentration in MST buffer containing 1% DMSO; (ii) in the $2^{nd}$ step, 8 uL of a small molecule compound inhibitor was added at 5×1 uM or 5×100 uM concentration in MST buffer containing 2% DMSO; (iii) in the $3^{rd}$ step, 8 uL of YKL-40-histag was added at concentration 5×2.5 nM in MST buffer containing 0% DMSO, after which the plate was spun down for 2 minutes at 1500 g and incubated 1 h at 37° C.; (iv) in the $4^{th}$ step, 8 uL of Nickel Chelate Acceptor beads were added at concentration 5×10 ug/mL in MST buffer containing 1% DMSO, after which the plate was spun down for 1 minute at 250 g and incubated in dark for 1 hour at RT; (v) in the $5^{th}$ step, 8 uL of Streptavidin Donor beads were added at concentration 5×10 ug/mL in MST buffer containing 1% DMSO, after which the plate was spun down for 1 minute at 250 g and incubated in dark for 1 hour at RT. Positive and negative control wells received just 8 uL of MST buffer containing 2% DMSO without inhibitor in the $2^{nd}$ step (ii). In addition negative control received just 8 uL of MST buffer containing 0% DMSO without YKL-40-histag in the $3^{nd}$ step (iii). Finally, the plate luminescence was excited at 680 nm and the emission read at 520-620 nm using the AlphaScreen module in the The Spark™ 10M multimode microplate reader (Tecan Trading AG, Mannedorf, Switzerland). Inhibition percentage and $IC_{50}$ values were determined using GraphPad Prism 7.0 software (GraphPad Software, San Diego, CA, USA).

4. Various Other Modifications of Compound 17 (and Other) Enabling Additional Assays Biotinylation of compound 17 that enabled competitive AlphaScreen for chitin binding site of YKL-40 is not the only compound's modification that can be used to set up high-throughput screening assay. 17 can be modified with Fluorescein isothiocyanate (FITC) fluorescent dye and subsequently linked to Anti-FITC AlphaScreen Acceptor Beads which, when coupled with Nickel Chelate AlphaScreen Donor Beads modified with histag YKL-40, can build up functionally similar AlphaScreen for CBS of YKL-40 but based on different components.

Moreover, FITC-modified 17 can be used to set up fluorescence polarization (FP) and micro scale thermophoresis (MST) high-throughput competitive assays for small molecule screening against chitin binding site of YKL-40. However, in both FP and MST screening methods more specialized fluorescent dye modification should be considered. In case of FP, more advisable are the long-wavelength BODIPY TMR and BODIPY TR fluorescent dyes that possess longer excited-state lifetimes than fluorescein, making their fluorescence polarization sensitive to binding interactions over a larger molecular weight range. While, in case of MST, more advisable are the long-wavelength fluorescent environment-sensitive dyes of high molar excitation coefficients, such as Alexa Fluor 647 and ATTO647N fluorescent dyes.

5. YKL-40: Heparan Sulfate Interference Binding Assay Based on AlphaScreen a. Utilizing Existing Technologies and Knowledge to Set-Up HTS for YKL-40: HS Interference YKL-40 has been speculated to belong to proteins binding heparin and heparan sulfate. These speculations come mainly from routinely used purification protocol of the untagged variant of the protein using heparin-sepharose affinity chromatography (Hu et al., 1996; Shao et al., 2009; Ngernyuang et al., 2018). However, there are no actual and/or publicly available binding data demonstrating interactions of YKL-40 protein with both ligands and therefore, OAT set out to explore these binding properties of the protein. By using MicroScale Thermophoresis and competitive AlphaScreen assay for YKL-40 chitin binding site, OAT found that YKL-40 does bind heparin and heparan sulfate ligands with high nM affinity dependent on the length of both ligands, their sulphation properties and that divalent magnesium ions are important in these interactions. Following this the company ordered a custom synthesis of a biotinylated 9 kDa heparan sulfate fraction III (Iduron Ltd, Macclesfield, UK) that later served as a biotinylated tool compound to set up high-throughput screening assay for compounds interfering with YKL-40. heparan sulfate interaction (just as OAT-produced biotinylated compound 4 was previously used to set-up competitive chitin binding site AlphaScreen assay in section 3). The assay would not be possible if not for the OAT discoveries of YKL-40 molecular interaction properties and achievement-driven custom synthesis order of a particular biotinylated heparan sulfate for the AlphaScreen assay.

b. Setting-Up the New Assay

In the similar way to establishing YKL-40 chitin binding site competitive AlphaScreen assay (section 3), the YKL-40 AlphaScreen assay using biotinylated 9 kDa heparan sulfate fraction III was established, including the same buffer conditions (50 mM Tris HCl pH 7.4, 150 mM NaCl, 10 mM $MgCl_2$, 0.05% Tween 20, 1 mg/mL BSA 1% DMSO). The binding of 17-19 kDa non-biotinylated heparin sodium salt (Sigma-Aldrich Company Ltd, Poole, Dorset, UK) and 9 kDa heparan sulfate fraction III (Iduron Ltd, Macclesfield, UK) to YKL-40 protein was first confirmed using MST direct assay and YKL-40 indirect chitin binding site AS assay. Next, biotinylated heparan sulfate fraction III custom-ordered from Iduron was cross-titrated with histagged YKL-using AlphaScreen assay described above. Both carbohydrates interacted with YKL-40 and their respective AlphaScreen assays were set up using the same 50-75% bead capacity rule and the same general AlphaScreen experimental protocol as described in the previous section 3. This resulted in heparan sulfate AlphaScreen interference assay with YKL-40 protein fixed at 10 nM concentration and with biotinylated heparan sulfate fixed at 60 nM concentration in the AS tests. This carbohydrate AS assays were validated by displacement experiments with non-biotinylated variants of heparin and heparan sulfate mentioned above, the ligands that also came out not-interfering in false positive AS test. The assay was next used in screening and $IC_{50}$ determination of potential small molecule compounds (17 and its analogs) capable of interfering with YKL-40 heparan sulfate interaction.

6. Compound 4 and its Analogues as Biosensing Elements in Impedimetric Biosensors of YKL-40 Biomarker a. Utilizing Existing Technologies and Knowledge in Conceptual YKL-40 Biosensor Design YKL-40 protein has been long considered as prognostic biomarker of multiple diseases, including inflammatory, neurodegenerative, cardiovascular and cancer (Rathcke et al., 2006; Johansen et al., 2006, Rathcke et al., 2009, Baldacci et al.; 2019). So far, there is one literature report on YKL-40 electrochemical immunosensor based on gold surface electrode modified with polyclonal anti-YKL-40 IgG (Chaocharoen et al., 2015). However, relatively high costs of biologicals (antibodies), limited robustness and stability issues of active proteins at metal electrode surface work in favor of using cheap and durable biosensing elements instead. Compound 4 (or its analogs), the YKL-40 selective binders can meet these requirements in biosensor-like devices. Moreover, a dynamic range of impedimetric biosensor based on small molecules compared to antibodies is vastly improved due to orders of magnitude difference in size of these sensing elements.

The physicochemical technique that can probe features of chemically-modified electrodes with great sensitivity is Electrochemical Impedance Spectroscopy (EIS). EIS is well-suited for development of binding-type electrochemical (impedimetric) biosensors (Bertok et al., 2018). EIS describes how the electric circuit resists the current flow when an alternating current (AC) voltage is applied to the electrode. Here, the impedance (Z) is a ratio of the excitation AC sinusoidal voltage E(t) over resulting AC sinusoidal current I(t) time functions. In a linear system (at small excitation voltage applied), the two functions, E(t) and I(t), have the same frequency (o) but the current is shifted in phase ($\phi$) with respect to the potential. The phase shift between the sinusoidal AC voltage and AC current is $\phi=+900$ for inductors, $0°$ for resistors, and $\phi=-90°$ for capacitors. When a working electrode surface is modified with a molecular layer, the current flow depends on resistivity of an electrolyte and the layer. The cell response can be then simulated as a combination of a resistor (RBulk) in series with a parallel resistor/capacitor couple (RLayer/CLayer). In such equivalent electric circuit, RB tells about the bulk resistance between a reference and a working electrode, while RL and CL about the resistance and the capacitance of the molecular layer, respectively. Thus, the circuit allows for convenient characterization of modified electrodes by following the CL and RL values that are characteristic to molecular layers.

b. A Prototype Proposal for Impedimetric Biosensor Device for YKL-40 Protein

The biotinylated compound 4 can be directly used as a YKL-40 sensing element on electrodes modified with streptavidin. Alternatively, a selective YKL-40 binding compound can be thiolated (at the site of biotinylation) and reacted with gold electrode to form self-assembled monolayer of a sensing element without a need of using another molecular layer of streptavidin protein. This will further increase the dynamic range of the sensor and its stability by excluding any biologicals from the sensor. Either way, the OAT-discovered compounds selective for YKL-are key to a YKL-40 biosensor, where antibodies are replaced by small molecule compounds capturing the protein.

FIG. 1 presents a general diagram of an impedimetric biosensor device for detecting chitinase-like protein YKL-40 level in biological samples using the active compounds of the invention.

In order to set-up a working prototype of such impedimetric biosensor device for YKL-40, one can use an electrochemical cell of all-glass construction, with the main compartment housing a gold working electrode, a platinum wire counter electrode and a saturated silver/silver chloride reference electrode (Ag/AgCl, sat. KCl). Double layer capacitance changes on gold electrode after its modification with thiolated YKL-40 selective compounds and later by YKL-40 protein can be monitored with use of electrochemical impedance spectroscopy (EIS). The experiments should be conducted using a frequency domain of hundreds kHz to hundreds MHz with multiple recording points taken on a logarithmic scale with a bias potential of 0.0 V vs. Ag/AgCl reference electrode at an small amplitude of around 10 mV. Spectra can be recorded using a potentiostat equipped with frequency analyzer. EIS data after electrode surface modification with each layer ($1^{st}$ layer YKL-40 selective OAT compounds, $2^{nd}$ layer YKL-40 protein) can be than fitted to RBulk(RLayerQLayer) equivalent circuit using freeware, where Q stands for the unideal double layer capacitance accounting for surface roughness of gold electrodes. Such double-layer capacitance or resistance changes after YKL-40 binding to OAT-modified electrode can be correlated with the protein concentration to establish a respective calibration curve and the dynamic range of the biosensor.

In one aspect, this invention concerns a method of performing high-throughput screening assay for identifying compounds interfering with the chitinase-like protein YKL-40. chitin oligomer interaction by diminishing the AlphaScreen luminescence signal under conditions of binding competition with a compound of formula (I) or formula (II) according to the invention.

In some embodiments, the invention provides a method of identifying compounds that interfere with the chitinase-like protein YKL-40 and biotin tagged chitin oligomer interaction by subjecting compound of formula (I) to a binding competition assay and assessing the resulting AlphaScreen luminescence signal, wherein an emission signal declines from the high level at lowest inhibitor concentration to the low level at highest inhibitor concentrationindicates that the compound interferes with the chitinase-like protein YKL-40 and chitin oligomer interaction.

In some embodiments, the invention provides a method of identifying compounds that interfere with the chitinase-like protein YKL-40 and compound of formula 4 or compounds of formula II interaction by subjecting a compound of formula I to a binding competition assay and assessing the resulting AlphaScreen luminescence signal, wherein an emission signal declines from the high level at lowest inhibitor concentration to the low level at highest inhibitor concentration indicates that the compound interferes with the complex between chitinase-like protein YKL-40 and compound 4 or compounds of formula II.

In another aspect, this invention concerns a method of performing high-throughput screening assay for identifying compounds interfering with the chitinase-like protein YKL-40: heparan sulfate interaction by diminishing the AlphaScreen luminescence signal under conditions of binding competition with a compound of formula (I) or formula (II) according to the invention.

In some embodiments, the invention provides a method of identifying compounds that interfere with the chitinase-like protein YKL-40 and heparan sulfate interaction by:

(1) in a binding competition assay, subjecting (i) a compound of formula I and (ii) biotinylated heparin sulfate to YKL-40 or derivative of YKL-40 comprising a purification tag; and (2) assessing the resulting AlphaScreen luminescence signal;

wherein an emission signal decline from the high level at lowest inhibitor concentration to the lower level (diminished by the value of at least 3× standard deviation of the noise displayed at plateau values at highest concentrations of inhibitor in the response plots for IC50 determinations) level at highest inhibitor concentration indicates that the compound interferes with the chitinase-like protein YKL-40 and heparin sulfate oligomer interaction.

In some embodiments, the derivative of YKL-40 comprising a purification tag is YKL-40-histag.

In another aspect, this invention concerns an electrochemical impedimetric biosensor for monitoring chitinase-like protein YKL-40, wherein the biosensor comprises an electrochemical cell, a gold working electrode, a platinum counter-electrode, a reference electrode, and a potentiostat, characterized in that the gold working electrode is modified by reaction with a thiolated derivative of a compound of formula (I) or formula (II) according to the invention.

Compounds of the Invention

In one aspect, this invention concerns a compound represented by formula (I)

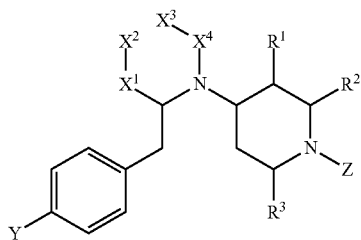

(I)

wherein:
$X^1$ is a single bond, —C(O)—, or —C($R^4R^5$)—;
$X^2$ is —C($R^6R^7$)—, —N($R^8$)—, or —O—;
$X^3$ is —C($R^9R^{10}$)— or benzo;
$X^4$ is a single bond, —$CH_2$—, or —C(O)—;
or $X^3$ and $X^4$, taken together, represent benzo;
Y is halo, ($C_1$-$C_3$)alkyl, ($C_1$-$C_3$)alkoxy, or ($C_1$-$C_3$)alkylthio;
Z is aryl, heteroaryl, or ($C_1$-$C_6$)alkoxycarbonyl;
$R^1$ is hydrogen or ($C_1$-$C_6$)alkoxy;
$R^2$ is hydrogen, ($C_1$-$C_6$)alkyl, or (($C_1$-$C_6$)alkyl)$_2$aminocarboxy($C_1$-$C_6$)alkyl;
or $R^2$, taken together with the carbon atom bearing it, represents —C(O)—;
$R^3$ is hydrogen;
or $R^2$ and $R^3$, taken together, represent —$CH_2CH_2$— or —$CH_2CH_2CH_2$—;
$R^4$ is hydrogen or ($C_1$-$C_6$)alkyl;
$R^5$ is hydrogen or ($C_1$-$C_6$)alkyl;
$R^6$ is hydrogen or ($C_1$-$C_6$)alkyl;
$R^7$ is hydroxy or ($C_1$-$C_6$)alkoxy;
$R^8$ is hydrogen, ($C_1$-$C_6$)alkyl, hydroxy-($C_1$-$C_6$)alkyl, ($C_1$-$C_6$)alkoxy-($C_1$-$C_6$)alkyl, ($C_1$-$C_6$)-alkoxycarbonyl, ($C_1$-$C_6$)alkoxycarbonylmethyl, ($C_1$-$C_6$)alkylaminocarbonyl, ($C_1$-$C_6$)alkylaminocarbonylmethyl, ($C_1$-$C_6$)alkylaminocarboxymethyl, (($C_1$-$C_6$)alkyl)$_2$aminocarbonyl, (($C_1$-$C_6$)alkyl)$_2$aminocarbonylmethyl, (($C_1$-$C_6$)alkyl)$_2$aminocarboxymethyl, or HO—C(O)—($C_1$-$C_6$)alkyl;
$R^9$ is hydrogen, ($C_1$-$C_6$)alkyl, hydroxy, hydroxy-($C_1$-$C_6$)alkyl, ($C_1$-$C_6$)alkoxy-($C_1$-$C_6$)alkyl, amino-($C_1$-$C_6$)alkyl, aryl-($C_1$-$C_6$)alkyl, aryloxy-($C_1$-$C_6$)alkyl, aryl-($C_1$-$C_6$)alkoxy-($C_1$-$C_6$)alkyl, heterocyclyl-($C_1$-$C_6$)alkyl, ($C_1$-$C_6$)alkylaminocarbonyl, ($C_1$-$C_6$)alkylaminocarbonyl-methyl, ($C_1$-$C_6$)alkylaminocarboxymethyl, (($C_1$-$C_6$)alkyl)$_2$aminocarboxymethyl, or arylaminocarboxymethyl;
$R^{10}$ is hydrogen;
or $R^9$ and $R^{10}$, taken together, represent —$CH_2CH_2$—, —$CH_2CH_2CH_2$—, or —$CH_2CH_2CH_2CH_2$—;
wherein any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of hydroxy, halo, —$NH_2$, —NH(($C_1$-$C_6$)alkyl), —N(($C_1$-$C_6$)alkyl)$_2$, —CN, —$NO_2$, ($C_1$-$C_6$)alkyl, ($C_1$-$C_6$)haloalkyl, ($C_1$-$C_6$)alkoxy, aryl, heteroaryl, aryl($C_1$-$C_6$)alkyl, heteroaryl($C_1$-$C_6$)alkyl, ($C_3$-$C_7$)cycloalkyl, heterocyclyl, —C(O)OH, —C(O)O($C_1$-$C_6$)alkyl, —C(O)$NH_2$, —C(O)NH($C_1$-$C_6$)alkyl, and —C(O)N(($C_1$-$C_6$)alkyl)$_2$; and
wherein any occurrence of —$CH_2$— is optionally replaced by —C(O)—;

provided that Z is not 2-amino-1,3,4-triazol-5-yl nor any tautomer of 2-amino-1,3,4-triazol-5-yl; or a tautomer, stereoisomer, pharmaceutically acceptable salt, solvate, or polymorph thereof.

In a preferred embodiment of the invention, the compound of the formula (I) has the parameter Z selected from aryl, ($C_1$-$C_6$)alkoxycarbonyl, and 6- to 10-membered heteroaryl having at least one nitrogen atom in the ring.

In a preferred embodiment of the invention, the compound of the formula (I) has the parameter Z selected from 6- to 10-membered heteroaryl having at least one nitrogen atom in the ring.

In a preferred embodiment of the invention, the compound of the formula (I) has the parameter Z selected from phenyl, pyridinyl, pyridazinyl, isoquinolinyl, quinolinyl, imidazopyridinyl, oxadiazolyl, tetrazolyl, oxazolyl, triazinyl, thiadiazolyl, thiazolyl, imidazolyl, pyrrolyl, and pyrazolyl.

In a preferred embodiment of the invention, the compound of the formula (I) has the parameter Z selected from pyrimidinyl and pyridinyl.

In a preferred embodiment of the invention, the compound of the formula (I) has the following values of parameters:
$X^1$ is a single bond, —C(O)—, or —C($R^4R^5$)—;
$X^2$ is —C($R^6R^7$)—, —N($R^8$)—, or —O—;
$X^3$ is —C($R^9R^{10}$)— or benzo;
$X^4$ is a single bond, —$CH_2$—, or —C(O)—;
or $X^3$ and $X^4$, taken together, represent benzo;
Y is halo;
Z is phenyl, pyridin-2-yl, pyridin-3-yl, pyridin-4-yl, pyridazin-3-yl, pyrimidin-2-yl, pyrimidin-4-yl, pyrimidin-5-yl, pyrazin-2-yl, isoquinolin-1-yl, imidazo[1,2-a]pyridin-5-yl, 1,2,4-oxadiazol-3-yl, 1,2,4-oxadiazol-5-yl, 1H-tetrazol-5-yl, 1,3-oxazol-2-yl, 1,3,5-triazin-2-yl, 1,2,4-thiadiazol-5-yl, 1,3-thiazol-2-yl, or tert-butoxycarbonyl;
$R^1$ is hydrogen or methoxy;
$R^2$ is hydrogen, methyl, or dimethylaminocarboxymethyl;
or $R^2$, taken together with the carbon atom bearing it, represents —C(O)—;
$R^3$ is hydrogen;
or $R^2$ and $R^3$, taken together, represent —$CH_2CH_2$—;
$R^4$ is hydrogen or methyl;
$R^5$ is hydrogen or methyl;
$R^6$ is hydrogen or methyl;
$R^7$ is hydroxy or methoxy;
$R^8$ is hydrogen, ($C_1$-$C_6$)alkyl, hydroxy-($C_1$-$C_6$)alkyl, ($C_1$-$C_6$)alkoxy-($C_1$-$C_6$)alkyl, ($C_1$-$C_6$)alkoxycarbonyl, ($C_1$-$C_6$)alkoxycarbonylmethyl, ($C_1$-$C_6$)alkylaminocarbonyl, ($C_1$-$C_6$)alkylaminocarbonylmethyl, ($C_1$-$C_6$)alkylaminocarboxymethyl, (($C_1$-$C_6$)alkyl)$_2$aminocarbonyl, (($C_1$-$C_6$)alkyl)$_2$aminocarbonylmethyl, (($C_1$-$C_6$)alkyl)$_2$aminocarboxymethyl, or HO—C(O)—($C_1$-$C_6$)alkyl;
$R^9$ is hydrogen, ($C_1$-$C_6$)alkyl, hydroxy, hydroxy-($C_1$-$C_6$)alkyl, ($C_1$-$C_6$)alkoxy-($C_1$-$C_6$)alkyl, amino-($C_1$-$C_6$)alkyl, aryl-($C_1$-$C_6$)alkyl, aryloxy-($C_1$-$C_6$)alkyl, aryl-($C_1$-$C_6$)alkoxy-($C_1$-$C_6$)alkyl, heterocyclyl-($C_1$-$C_6$)alkyl, ($C_1$-$C_6$)alkylaminocarbonyl, ($C_1$-$C_6$)alkylaminocarbonyl-methyl, ($C_1$-$C_6$)alkylaminocarboxymethyl, (($C_1$-$C_6$)alkyl)$_2$aminocarboxymethyl, or aryl-aminocarboxymethyl;
or $R^1$ and $R^9$, taken together, represent —$CH_2CH_2CH_2$— or —$CH_2CH_2OCH_2$—, optionally substituted with one or more substituents selected from hydroxy, methoxy, and fluoro;

$R^{10}$ is hydrogen;

or $R^9$ and $R^{10}$, taken together, represent —CH$_2$CH$_2$CH$_2$—;

wherein any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of hydroxy, halo, methyl, cyano, methoxy, amino, —NH(C$_1$-C$_6$)alkyl, —N((C$_1$-C$_6$)alkyl)$_2$, trifluoromethyl, aminocarbonyl, methoxycarbonyl, —C(O)OH, hydroxy-(C$_1$-C$_6$)alkyl, formyl, acetyl, propionyl, (C$_1$-C$_6$)alkylsulfonyl, methoxy-(C$_1$-C$_6$)alkyl, acetoxy-(C$_1$-C$_6$)-alkyl and phenoxy-(C$_1$-C$_6$)alkyl; and wherein any occurrence of —CH$_2$— is optionally replaced by —C(O)—.

In a further preferred embodiment of the invention, the compound of the formula (I) has the following values of parameters:

$X^1$ is a single bond, —C(O)—, or —C(R$^4$R$^5$)—;

$X^2$ is —C(R$^6$R$^7$)—, —N(R$^8$)—, or —O—;

$X^3$ is —C(R$^9$R$^{10}$)— or benzo;

$X^4$ is a single bond, —CH$_2$—, or —C(O)—;

or $X^3$ and $X^4$, taken together, represent benzo;

Y is bromo or chloro;

Z is pyridin-2-yl, 5-fluoro-pyridin-2-yl, 6-fluoro-pyridin-2-yl, 3-chloro-pyridin-6-yl, pyrazin-2-yl, 3-fluoro-pyridin-2-yl, 5-chloro-pyridin-2-yl, 6-chloro-pyridin-2-yl, 2-fluoro-pyridin-4-yl, 2-chloro-pyridin-6-yl, 4-chloro-pyridin-2-yl, 3-methyl-pyridin-2-yl, 6-cyano-pyridin-2-yl, 5-cyano-pyridin-2-yl, 4-trifluoromethyl-pyridin-2-yl, 4-cyano-pyridin-2-yl, 3-cyano-pyridin-2-yl, 3-chloro-pyridin-2-yl, 6-fluoro-pyrimidin-4-yl, 3,5-difluoro-pyridin-2-yl, pyrimidin-4-yl, pyridin-3-yl, pyridin-4-yl, 4-methoxy-pyridin-2-yl, 4-methyl-pyridazin-6-yl, phenyl, 4-methyl-pyrimidin-2-yl, pyrimidin-2-yl, 5-fluoro-pyrimidin-2-yl, 3-cyano-4-methyl-pyridin-2-yl, 3-trifluoromethyl-pyridin-2-yl, 2-chloro-pyrimidin-4-yl, 2-amino-pyrimidin-4-yl, tert-butoxycarbonyl, 4-fluoro-pyridin-2-yl, 3-fluoro-4-methyl-pyridin-2-yl, 4-bromo-pyridin-2-yl, 3-aminocarbonyl-pyridin-2-yl, 2-cyano-5-chloro-phenyl, isoquinolin-1-yl, 3-methoxycarbonyl-pyridin-2-yl, 2-cyano-6-fluoro-phenyl, 2-cyano-phenyl, 3-hydroxymethyl-pyridin-2-yl, 2-fluoro-4-methoxycarbonyl-pyridin-3-yl, 3-fluoro-4-methoxycarbonyl-pyridin-2-yl, 3-fluoro-4-hydroxycarbonyl-pyridin-3-yl, 2-fluoro-4-hydroxycarbonyl-pyridin-3-yl, 2,6-difluoro-phenyl, 4-methoxycarbonyl-pyridin-2-yl, 4-hydroxycarbonyl-pyridin-2-yl, 2-fluorophenyl, 3-fluorophenyl, 4-aminocarbonyl-pyridin-2-yl, 4-(hydroxymethyl)-pyridin-2-yl, 4-(2-hydroxyprop-2-yl)-pyridin-2-yl, pyrimidin-5-yl, 6-methyl-pyridin-2-yl, 5-methyl-pyridin-2-yl, 4-methyl-pyridin-2-yl, 4-trifluoromethyl-pyrimidin-6-yl, 4-trifluoromethyl-pyrimidin-2-yl, 2-trifluoromethyl-pyrazin-6-yl, 2-bromo-pyridin-4-yl, imidazo[1,2-a]pyridin-5-yl, 2-trifluoromethyl-pyrazin-5-yl, 3-methoxy-pyridin-2-yl, 4-hydroxy-pyridin-2-yl, 3-hydroxy-pyridin-2-yl, 5-isopropyl-1,2,4-oxadiazol-3-yl, 5-trifluoromethyl-1,2,4-oxadiazol-3-yl, 5-oxo-1,2,4-oxadiazol-3-yl, 1H-tetrazol-5-yl, 6-oxo-pyrimidin-4-yl, 3-methyl-1,2,4-oxadiazol-5-yl, 5-trifluoromethyl-oxazol-2-yl, 2-amino-1,3,5-triazin-6-yl, 2-dimethylamino-1,3,5-triazin-6-yl, 2-methyl-1,3,5-triazin-6-yl, 2-methoxy-1,3,5-triazin-6-yl, 2-hydroxy-1,3,5-triazin-6-yl, 2-chloro-1,3,5-triazin-6-yl, 2-methyl-1,3,4-thiadiazol-5-yl, 1,3,4-thiadiazol-5-yl, 3-methyl-1,2,4-thiadiazol-5-yl, 2-cyano-1,3,5-triazin-6-yl, 1,2,4-thiadiazol-5-yl, 4,5-dimethyl-thiazol-2-yl, 4-methyl-thiazol-2-yl, or 5-methyl-thiazol-2-yl;

$R^1$ is hydrogen or methoxy;

$R^2$ is hydrogen, methyl, or dimethylaminocarboxymethyl;

or $R^2$, taken together with the carbon atom bearing it, represents —C(O)—;

$R^3$ is hydrogen;

or $R^2$ and $R^3$, taken together, represent —CH$_2$CH$_2$—;

$R^4$ is hydrogen or methyl;

$R^5$ is hydrogen or methyl;

$R^6$ is hydrogen or methyl;

$R^7$ is hydroxy or methoxy;

$R^8$ is hydrogen, methyl, isobutyl, tert-butoxycarbonyl, tert-butoxycarbonylmethyl, 2-methoxyethyl, Me-NH—C(O)—CH$_2$—, 2-hydroxy-2,2-dimethyl-ethyl, 2-methoxy-2,2-dimethyl-ethyl, dimethylaminocarbonylmethyl, 2-hydroxypropyl, cyclopropylamino-carbonylmethyl, methylaminocarbonylmethyl, 2-methoxypropyl, or HO—C(O)—CH$_2$—;

$R^9$ is hydrogen, methyl, ethyl, isopropyl, hydroxy, hydroxymethyl, p-chlorobenzyl, cyclopentyl, cyclopropyl, 4-morpholino-methyl, imidazolylmethyl, 4-methylpiperazinyl, benzyloxy-methyl, 2-naphthyl-methoxymethyl, dimethylaminocarboxymethyl, dimethylamino-ethyl(methyl)aminomethyl, acetylaminomethyl, phthalimidomethyl, succinimidomethyl, (2,5-dioxo-imidazolidin-1-yl)methyl, pyrrolidinylmethyl, methylsulfonylmethyl, methoxymethyl, 1-hydroxyethyl, acetoxymethyl, phenoxymethyl, isopropoxymethyl, cyclopropylaminocarboxymethyl, 1-hydroxyisopropyl, 1-methoxyisopropyl, methylaminocarbonyl, cyclohexylaminocarboxymethyl, or phenylaminocarboxymethyl;

or $R^1$ and $R^9$, taken together, represent —CH$_2$CH$_2$CH$_2$— or —CH$_2$CH$_2$OCH$_2$—, optionally substituted with one or more substituents selected from hydroxy, methoxy, and fluoro;

$R^{10}$ is hydrogen;

or $R^9$ and $R^{10}$, taken together, represent —CH$_2$CH$_2$CH$_2$—;

wherein any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of hydroxy, halo, methyl, cyano, methoxy, or amino; and wherein any occurrence of —CH$_2$— is optionally replaced by —C(O)—.

In a further preferred embodiment of the invention, the compound of the formula (I) has the following values of parameters:

$X^1$ is —C(R$^4$R$^5$)—;

$X^2$ is —C(R$^6$R$^7$)—, —N(R')—, or —O—;

$X^3$ is —C(R$^9$R$^{10}$)—;

$X^4$ is —CH$_2$—;

Y is chloro;

Z is pyridin-2-yl, 5-fluoro-pyridin-2-yl, 6-fluoro-pyridin-2-yl, 4-chloro-pyridin-2-yl, pyrazin-2-yl, 3-fluoro-pyridin-2-yl, 6-chloro-pyridin-2-yl, 2-fluoro-pyridin-4-yl, 3-methyl-pyridin-2-yl, 6-cyano-pyridin-2-yl, 5-cyano-pyridin-2-yl, 4-trifluoromethyl-pyridin-2-yl, 4-cyano-pyridin-2-yl, 3-cyano-pyridin-2-yl, 3-chloro-pyridin-2-yl, 6-fluoro-pyrimidin-4-yl, 3,5-difluoro-pyridin-2-yl, pyrimidin-4-yl, pyridin-3-yl, pyridin-4-yl, 4-methoxy-pyridin-2-yl, 4-methyl-pyridazin-6-yl, phenyl, 4-methyl-pyrimidin-2-yl, pyrimidin-2-yl, 5-fluoro-pyrimidin-2-yl, 3-cyano-4-methyl-pyridin-2-yl, 3-trifluoromethyl-pyridin-2-yl, 2-chloro-pyrimidin-4-yl, 2-amino-pyrimidin-4-yl, 4-fluoro-pyridin-2-yl, 4-bromo-pyridin-2-yl, 3-methoxycarbonyl-pyridin-2-yl, 2-cyano-6-fluoro-phenyl, 2-cyano-phenyl, 3-hydroxymethyl-pyridin-2-yl, 2-fluoro-4-methoxycarbonyl-pyridin-3-yl, 3-fluoro-4-methoxycarbonyl-pyridin-2-yl, 2-fluoro-4-hydroxycarbonyl-pyridin-3-yl, 2,6-difluoro-phenyl, 4-methoxycarbonyl-pyridin-2-yl, 4-hydroxycarbonyl-pyridin-2-yl, 2-fluoro-phenyl, 3-fluorophenyl, 4-aminocarbonyl-pyridin-2-yl, 4-(hydroxymethyl)-pyridin-2-yl, 4-(2-hydroxyprop-2-yl)-pyridin-2-yl, pyrimidin-5-yl, 6-methyl-pyridin-2-yl, 5-methyl-pyridin-2-yl, 4-methyl-pyridin-2-yl, 4-trifluoromethyl-pyrimidin-6-yl, 2-trifluoromethyl-pyrazin-6-yl, 2-trifluoromethyl-pyrazin-5-yl, 3-methoxy-pyridin-2-yl, 4-hydroxy-pyridin-2-yl, 3-hydroxy-pyridin-2-yl, 2-amino-1,3,5-triazin-6-yl, 2-dimethylamino-1,3,5-triazin-6-yl, 2-methyl-1,3,5-triazin-6-yl, 2-methoxy-1,3,5-triazin-6-yl, 2-hydroxy-1,3,5-triazin-6-yl, 2-chloro-1,3,5-triazin-6-yl, or 2-cyano-1,3,5-triazin-6-yl;
- $R^1$ is hydrogen;
- $R^2$ is hydrogen or methyl;
- $R^3$ is hydrogen;
- $R^4$ is hydrogen;
- $R^5$ is hydrogen;
- $R^6$ is hydrogen or methyl;
- $R^7$ is hydroxy or methoxy;
- $R^8$ is methyl, isobutyl, or 2-hydroxypropyl;
- $R^9$ is hydrogen, methyl, hydroxymethyl, 4-morpholinomethyl, 4-methyl-piperazinyl, dimethylaminocarboxymethyl, dimethylaminoethyl(methyl)aminomethyl, acetylamino-methyl, phthalimidomethyl, succinimidomethyl, (2,5-dioxo-imidazolidin-1-yl) methyl, pyrrolidinylmethyl, isobutyl, methylsulfonylmethyl, isopropyl, or 1-hydroxyethyl, or $R^1$ and $R^9$, taken together, represent —CH$_2$CH$_2$CH$_2$—, optionally substituted with one or more substituents selected from hydroxy, methoxy, and fluoro;
- $R^{10}$ is hydrogen; and
- wherein any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of hydroxy or halo.

More preferably, $X^2$ is —N(R$^8$)—.

In another preferred embodiment, $X^2$ is —O—.

In a further preferred embodiment of the invention, the compound of the formula (I) has the following values of parameters:

Z is pyridin-2-yl, 5-fluoro-pyridin-2-yl, 6-fluoro-pyridin-2-yl, 4-chloro-pyridin-2-yl, 3-fluoro-pyridin-2-yl, 6-chloro-pyridin-2-yl, 2-fluoro-pyridin-4-yl, 3-methyl-pyridin-2-yl, 6-cyano-pyridin-2-yl, 5-cyano-pyridin-2-yl, 4-trifluoromethyl-pyridin-2-yl, 4-cyano-pyridin-2-yl, 3-cyano-pyridin-2-yl, 3-chloro-pyridin-2-yl, 3,5-difluoro-pyridin-2-yl, pyridin-3-yl, pyridin-4-yl, 4-methoxy-pyridin-2-yl, 3-cyano-4-methyl-pyridin-2-yl, 3-trifluoromethyl-pyridin-2-yl, 4-fluoro-pyridin-2-yl, 4-bromo-pyridin-2-yl, 3-methoxycarbonyl-pyridin-2-yl, 3-hydroxymethyl-pyridin-2-yl, 2-fluoro-4-methoxycarbonyl-pyridin-3-yl, 3-fluoro-4-methoxycarbonyl-pyridin-2-yl, 2-fluoro-4-hydroxycarbonyl-pyridin-3-yl, 4-methoxy-carbonyl-pyridin-2-yl, 4-hydroxycarbonyl-pyridin-2-yl, 4-aminocarbonyl-pyridin-2-yl, 4-(hydroxymethyl)-pyridin-2-yl, 4-(2-hydroxyprop-2-yl)-pyridin-2-yl, 6-methyl-pyridin-2-yl, 5-methyl-pyridin-2-yl, 4-methyl-pyridin-2-yl, 3-methoxy-pyridin-2-yl, 4-hydroxy-pyridin-2-yl, or 3-hydroxy-pyridin-2-yl.

Preferably, the compound of the invention is represented by any one of the following structural formulae:

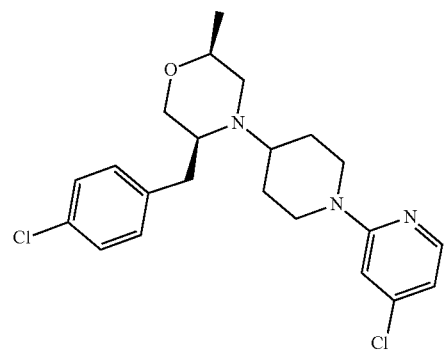

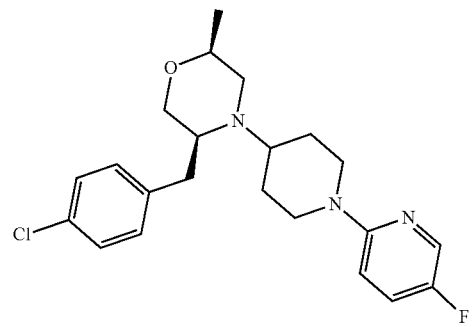

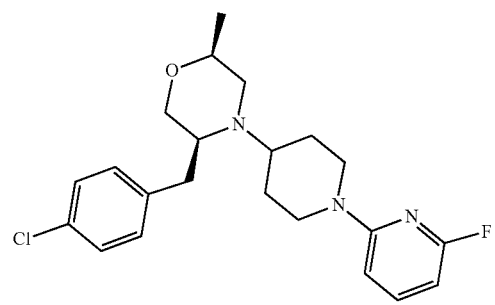

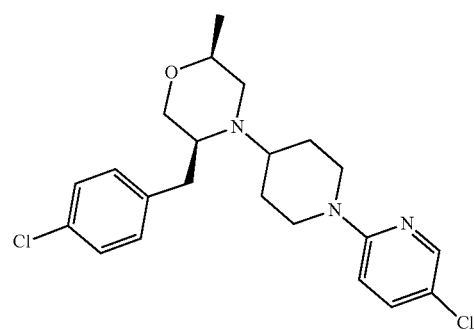

35
-continued
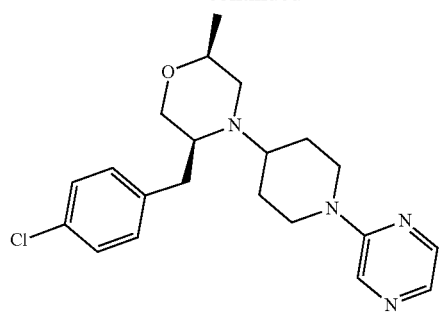
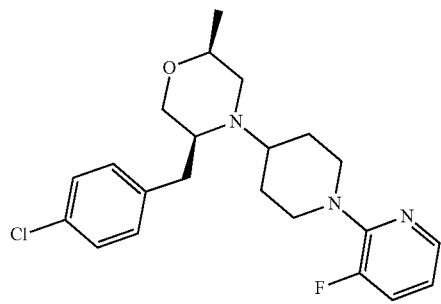
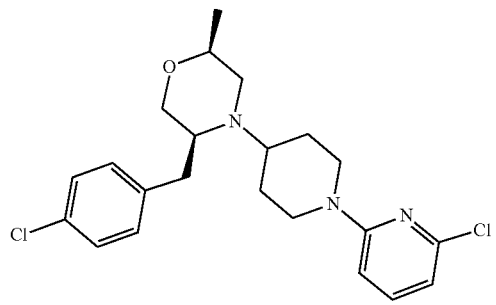
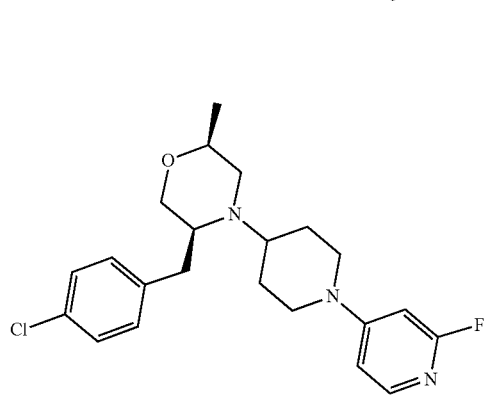
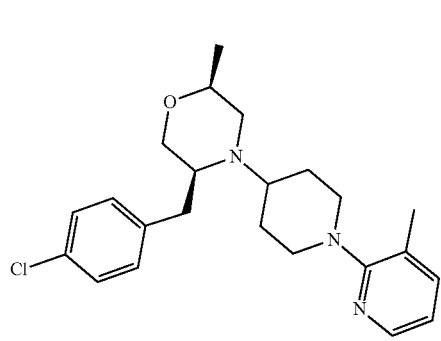
36
-continued
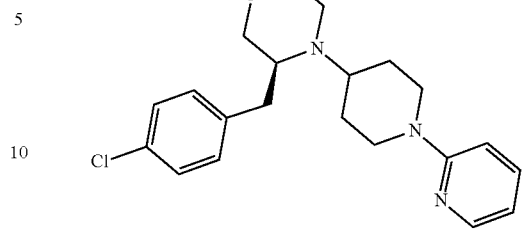
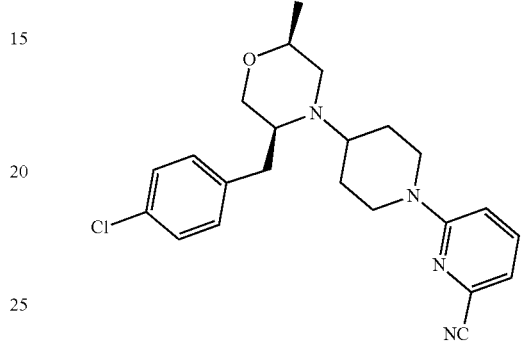
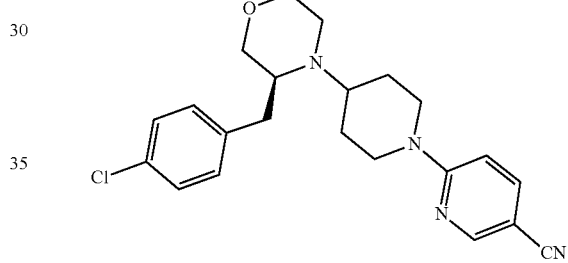
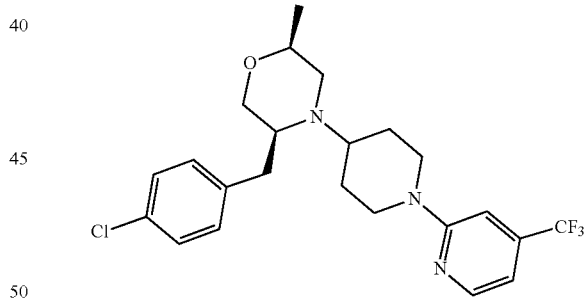
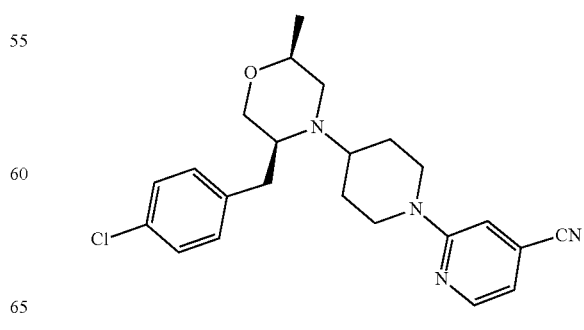

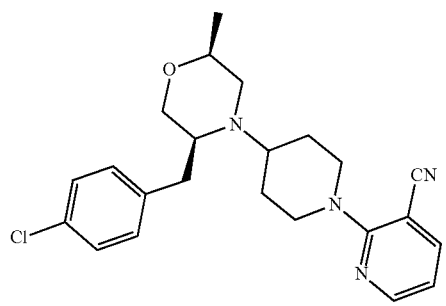
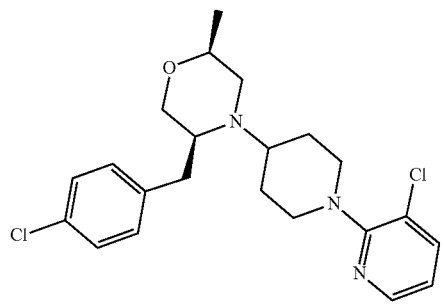
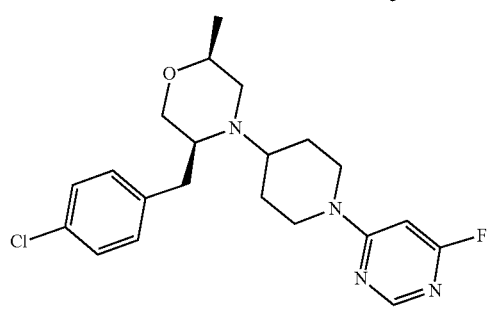
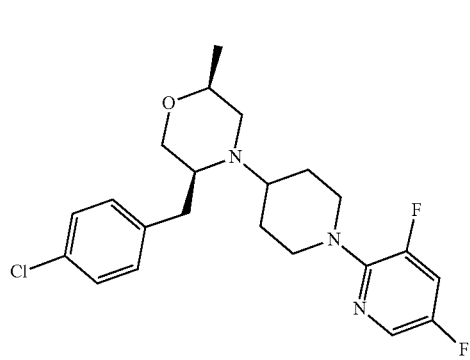
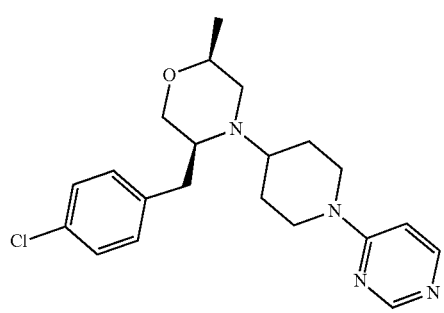
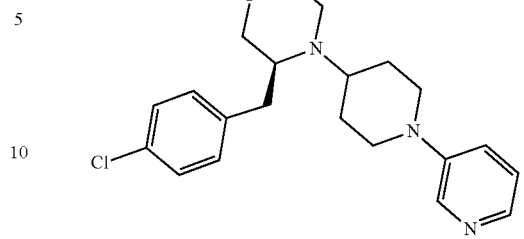
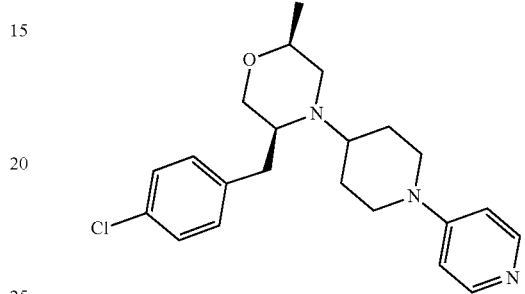
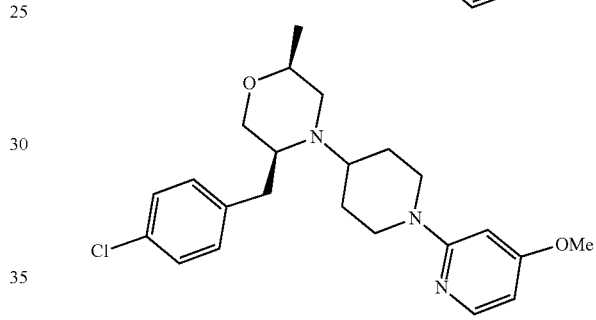
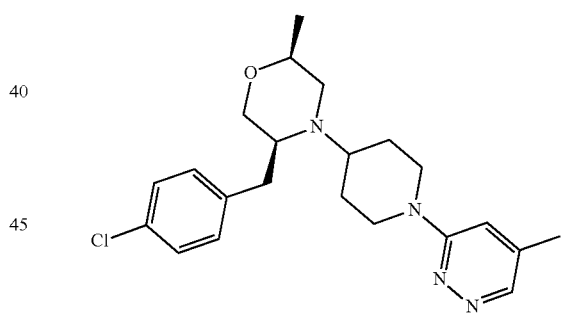
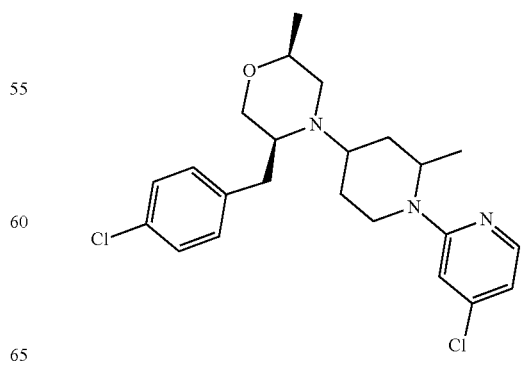

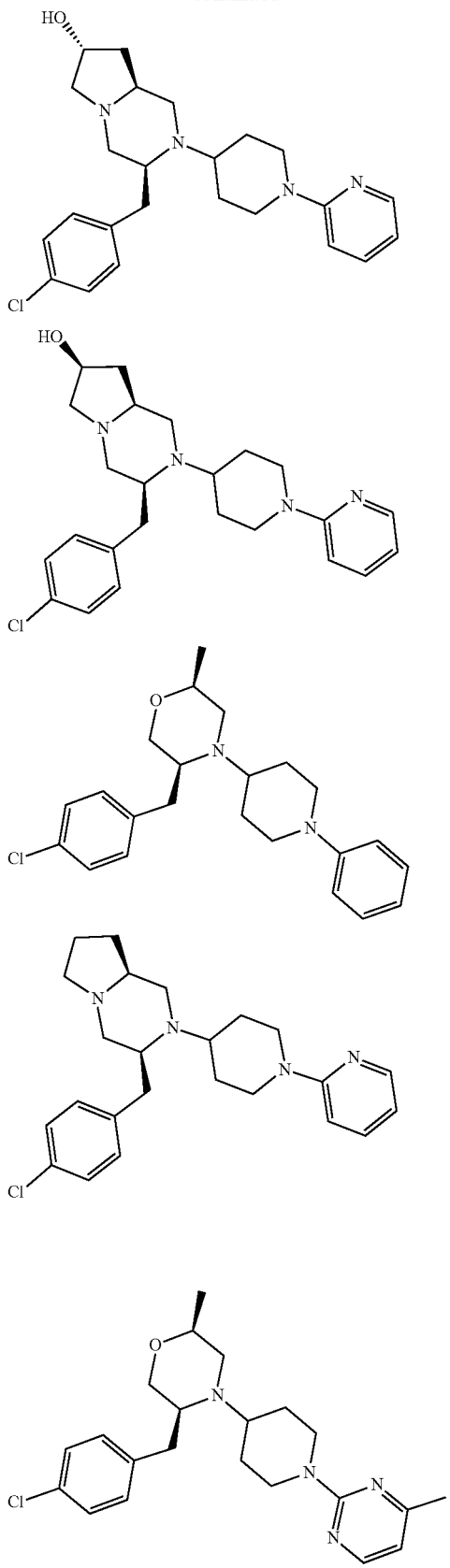
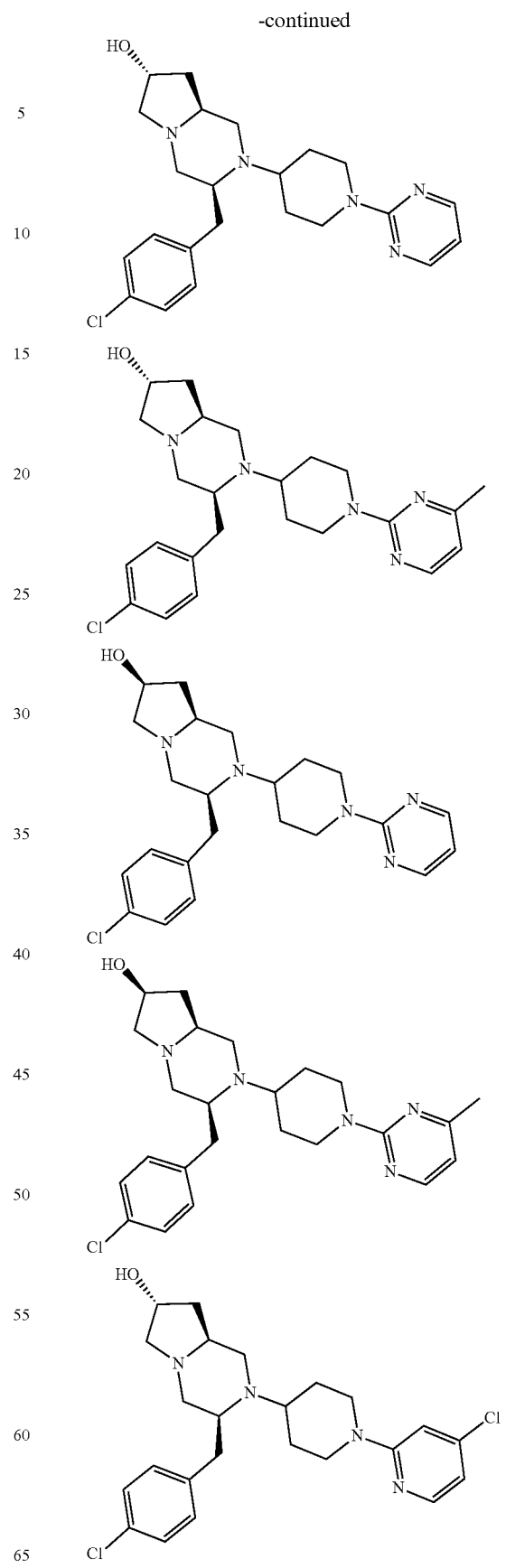

41
-continued
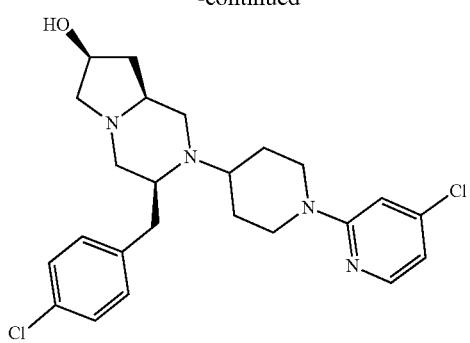
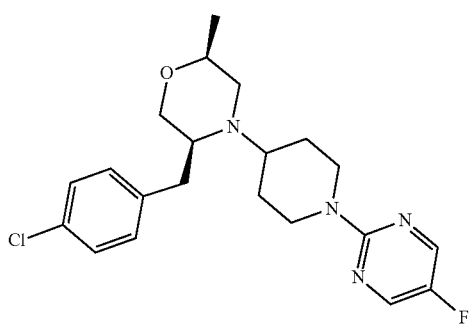
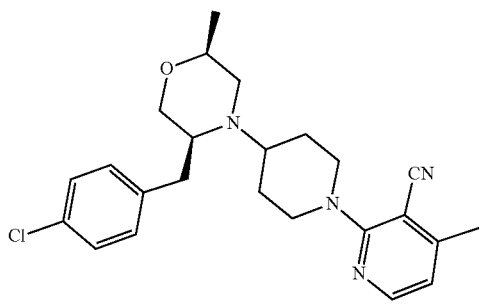
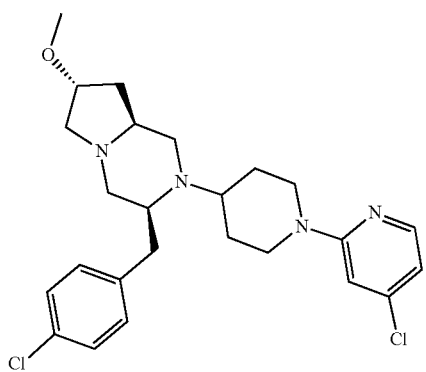
42
-continued
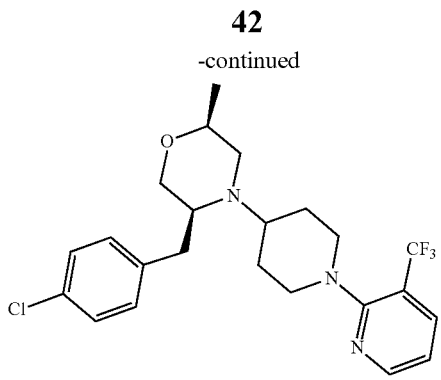
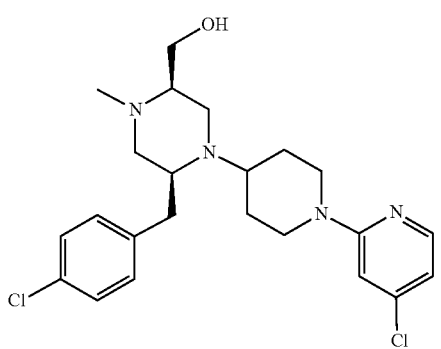
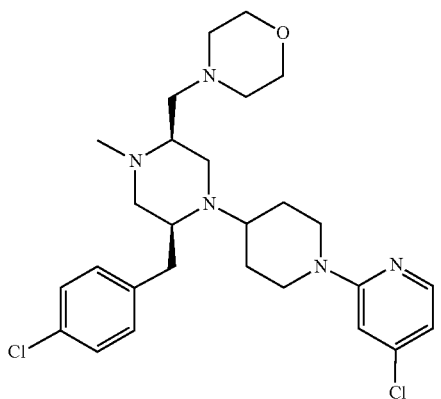
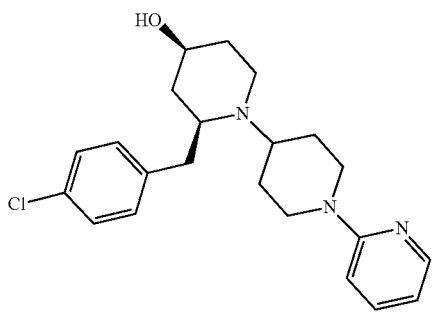

-continued

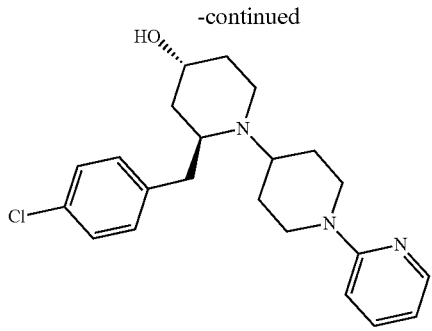

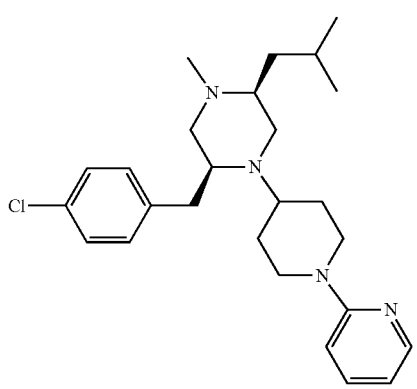

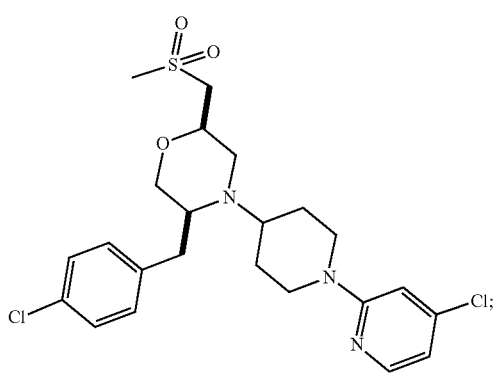

or it is a tautomer, stereoisomer, pharmaceutically acceptable salt, solvate, or polymorph thereof.

The compounds described herein are useful in treating inflammatory diseases, such as esophageal eosinophilic inflammation, keratoconjunctivitis, seasonal allergic conjunctivitis, dry eye syndrome, or chronic rhinosinusitis with or without nasal polyps. The compounds can be used in treating diseases caused by infectious agents, such as fungi, worms and parasites. The compounds can be used in treating chronic obstructive pulmonary disease (COPD) or autoimmune diseases including but not restricted to inflammatory bowel disease or rheumatoid arthritis.

Another aspect of the invention concerns the derivatives of the compounds of formula (I) of the invention, containing additional moieties required for screening assays.

According to such an aspect, the invention concerns a compound represented by formula (II)

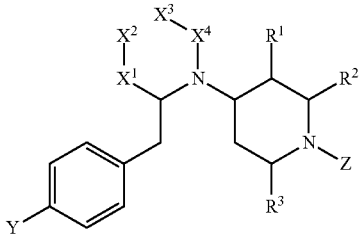

wherein:
$X^1$, $X^2$, $X^3$, $X^4$, Y, Z, $R^1$, $R^2$, $R^3$, $R^4$, $R^5$, $R^6$, $R^7$, $R^8$, $R^9$, and $R^{10}$ are as defined in formula (I) according to the invention, wherein the compound comprises at least one amino, carboxy, or hydroxy group, and the at least one amino, carboxy, or hydroxy group is bound by amide or ester linkage to a residue of PEGn-biotin, PEGn-glutathione, PEGn-fluorescein, PEGn-FLAG octapeptide or PEGn-digoxigenin, wherein n is an integer of from 9 to 15.

In some embodiments, the compound of formula (II) is for use in the method of high-throughput screening assay for compounds capable of binding YKL-40, optionally in a high-throughput screening assay.

In a preferred embodiment, the invention concerns the compound of formula (II) according to the invention, wherein the at least one amino, carboxy, or hydroxy group is bound by amide or ester linkage to with a residue of PEGn-biotin, wherein n is an integer of from 10 to 13.

In some embodiments, the compound of formula (II) is for use in the method of performing screening assay for compounds capable of binding YKL-40, optionally in a high-throughput screening assay.

In particular, the invention concerns the compound of formula (II) according to the invention represented by any one of the following structural formulas:

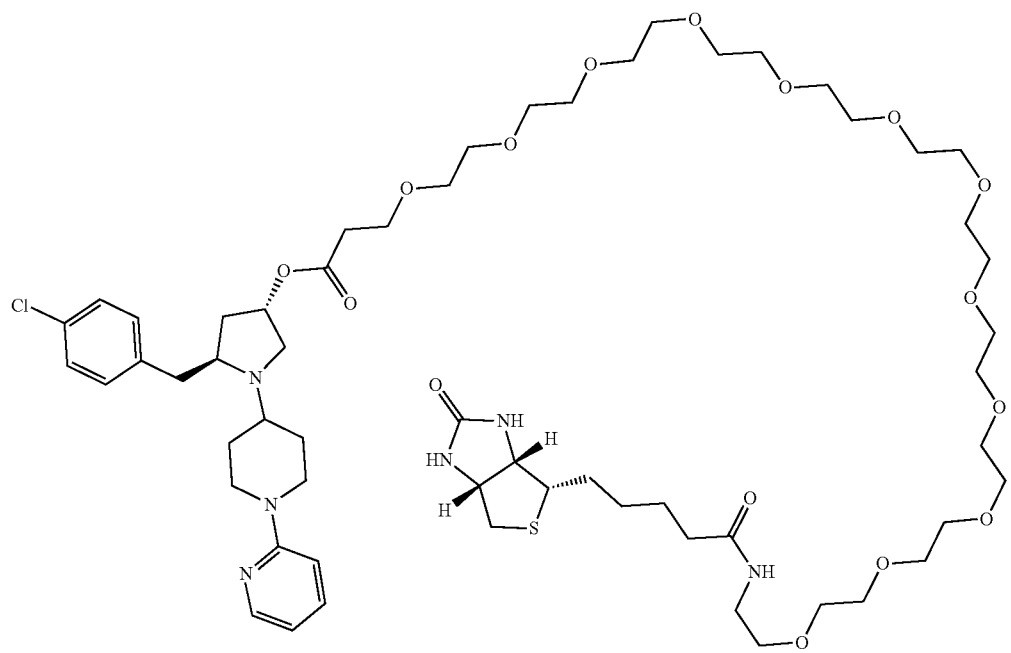
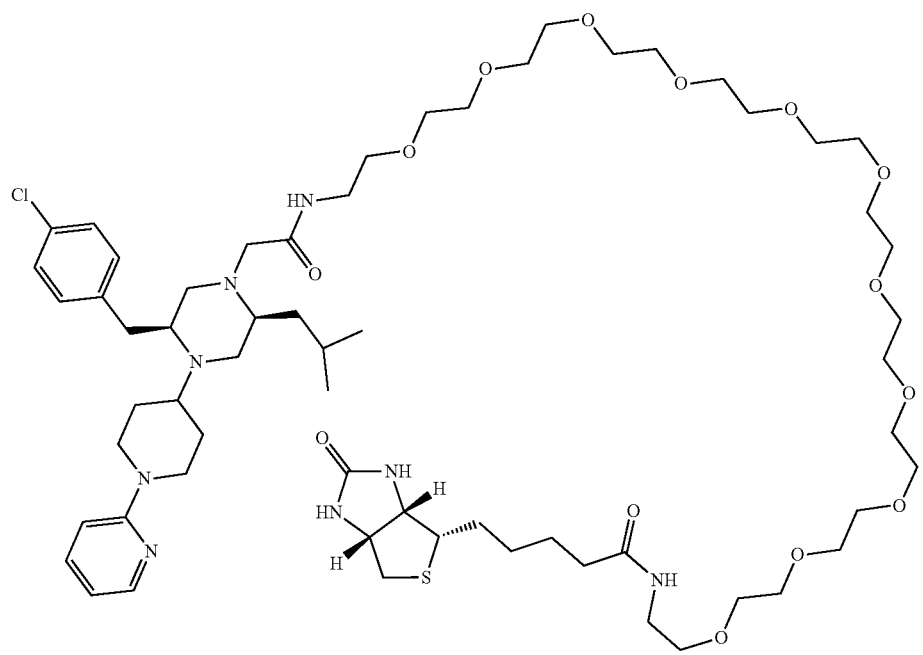

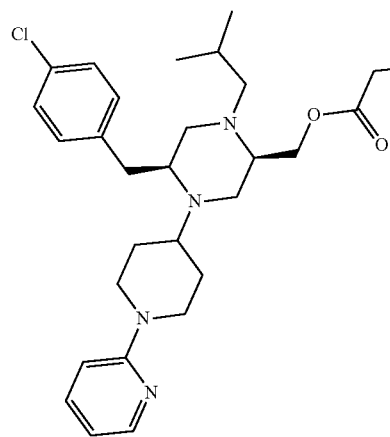
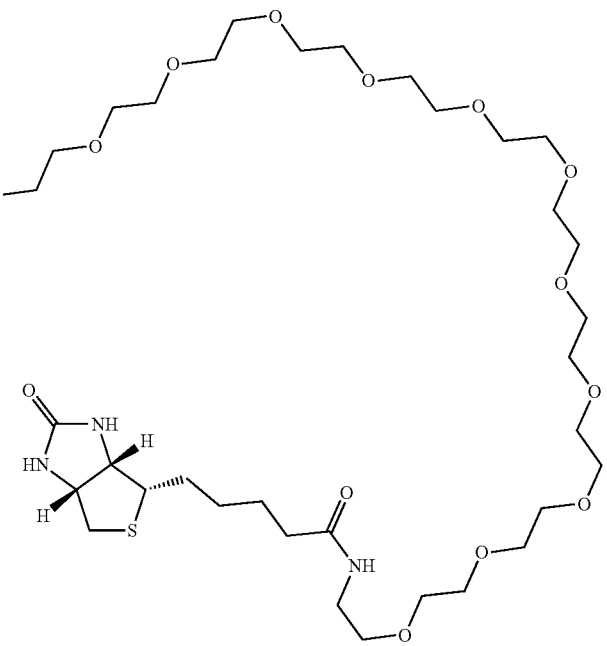
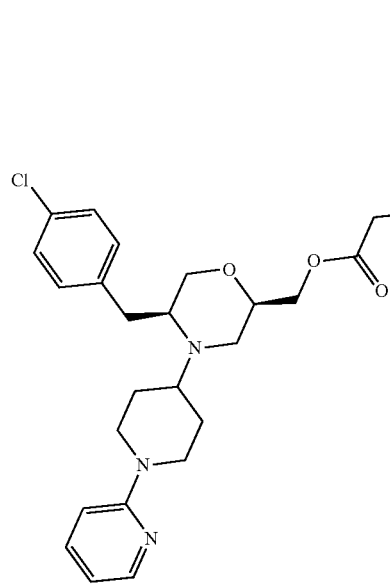
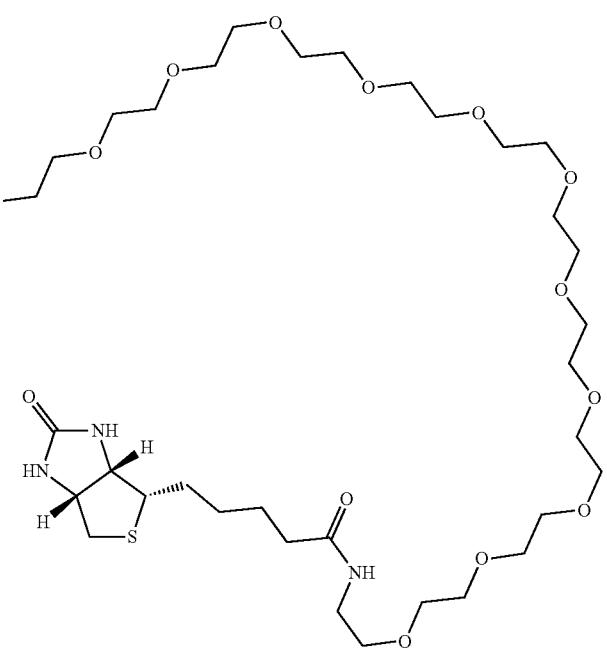

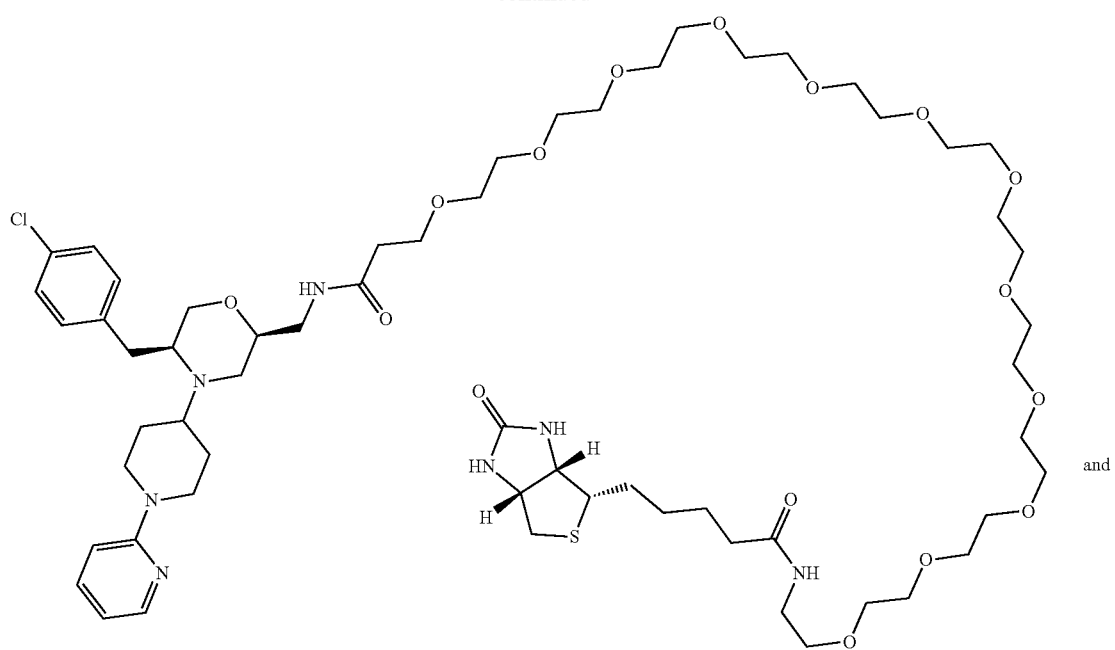
and
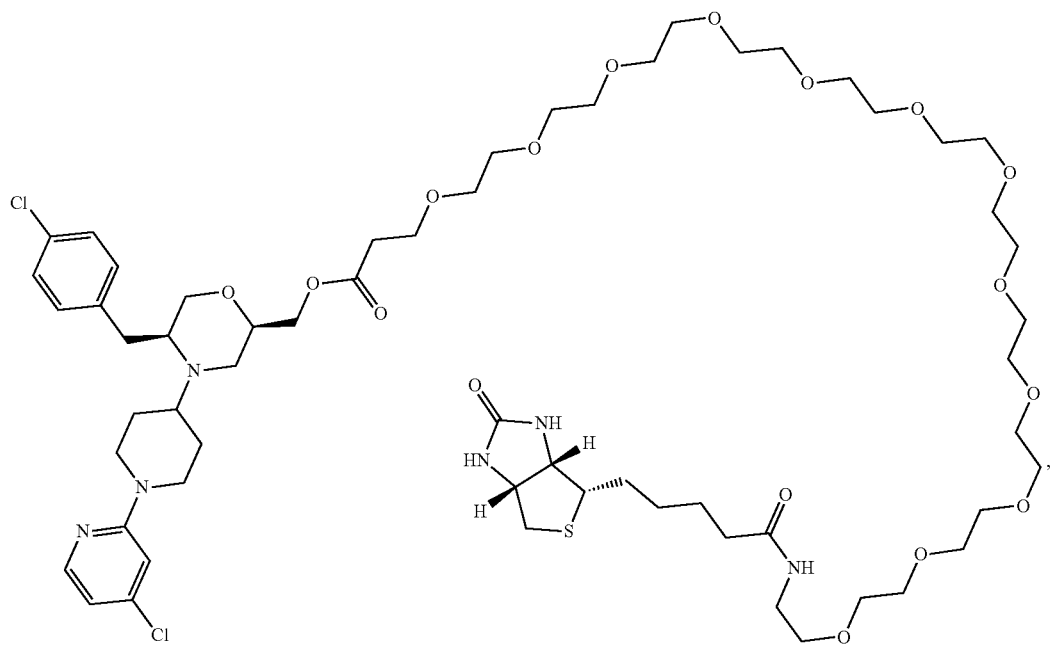

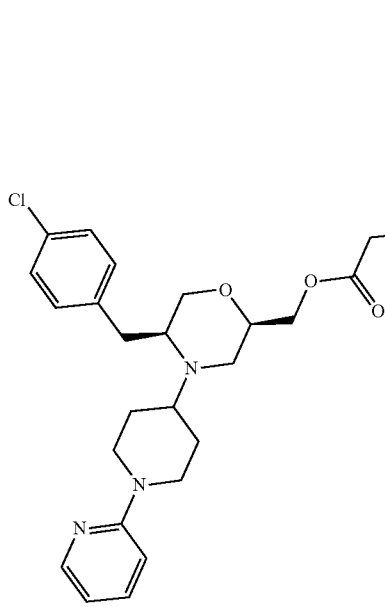

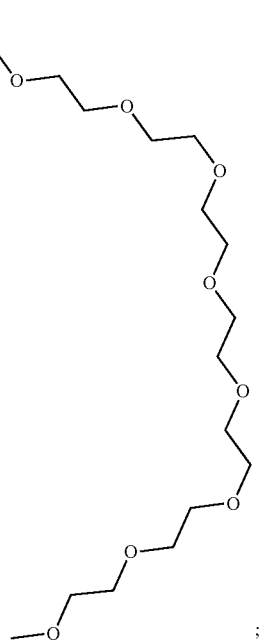

In some embodiments, the compounds depicted above are for use in the method of performing screening assay for compounds capable of binding YKL-40, optionally in a high-throughput screening assay.

In some embodiments, the preferred compound of formula (II) of the invention has the following structural formula:

Pharmaceutical Compositions of the Invention

Another aspect of the invention provides a pharmaceutical composition comprising a therapeutically effective amount of a compound of formula (I) according to the invention, and a pharmaceutically acceptable carrier.

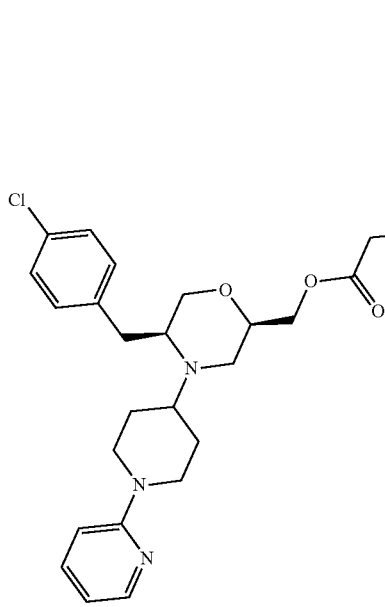

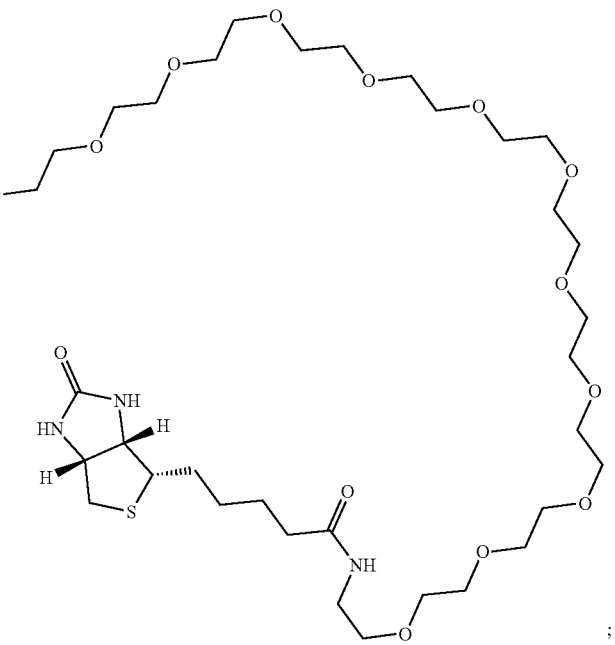

In some embodiments, this compound is for use in the method of performing screening assay for compounds capable of binding YKL-40, optionally in a high-throughput screening assay.

The exact nature of the carrier, or, for example excipient or diluent, will depend upon the desired use for the composition, and may be suitable or acceptable for veterinary use and/or suitable or acceptable for human use. The composition may optionally include one or more additional compounds, including one or more additional therapeutic agents.

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents that may be administered with the compounds of the invention include steroids, membrane stabilizers, 5LO inhibitors, leukotriene synthesis and receptor inhibitors, inhibitors of IgE isotype switching or IgE synthesis, inhibitors of IgG isotype switching or IgG synthesis, β-agonists, tryptase inhibitors, aspirin, COX inhibitors, methotrexate, anti-TNF drugs, rituxin, PD4 inhibitors, p38 inhibitors, PDE4 inhibitors, and antihistamines.

Thus, another aspect of the invention provides a pharmaceutical composition comprising a therapeutically effective amount of a compound of the invention and a second therapeutic agent selected from the group consisting of steroids, membrane stabilizers, 5LO inhibitors, leukotriene synthesis and receptor inhibitors, inhibitors of IgE isotype switching or IgE synthesis, inhibitors of IgG isotype switching or IgG synthesis, β-agonists, tryptase inhibitors, acetylosalicylic acid, COX inhibitors, methotrexate, anti-TNF drugs, rituxin and other B-cell targeting agents, TNF-targeting agents, PD4 inhibitors, p38 inhibitors, PDE4 inhibitors, and antihistamines.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.0001 milligrams/kg per day, 0.001 milligrams/kg per day, or 0.01 milligrams/kg per day to about 100 milligrams/kg per day or 1000 milligrams/kg per day. It is expected that oral doses in the range of 0.5 to 50 milligrams/kg, in one or several administrations per day, will yield the desired results. Dosage may be adjusted appropriately to achieve desired drug levels sufficient to achieve or maintain a desired therapeutic effect, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds. The compounds may be administered once per week, several times per week (e.g., every other day), once per day or multiple times per day, depending upon, among other things, the mode of administration, the specific indication being treated and the judgment of the prescribing physician.

In one embodiment, intravenous administration of a compound of the invention may typically be from 0.1 mg/kg/day to 20 mg/kg/day.

Determination of an effective dosage of a compound for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

Pharmaceutical compositions comprising the compound of the invention may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, buccal, nasal, rectal, vaginal, ocular, topical, intravenous, intramuscular, intraperitoneal, subcutaneous, transdermal, intrathecal, direct injection (for example, into an abscess), mucosal, inhalation, and insufflation.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, lozenges, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, binding agents, fillers, lubricants, disintegrants, and wetting agents. Suitable fillers include sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethylcellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes.

Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichloro-fluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (al-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; the Spinhaler powder inhaler, manufactured by Fisons Corp., Bedford, Mass.; and the Respimat Soft Mist Inhaler, manufactured by Boehringer Ingelheim, Germany. Other hand-driven or human-powered inhaler devices are also applicable.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet, ultrasonic, or soft mist type, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoro-ethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (µm), most preferably 0.5 to 5 µm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as sterile suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, buffer, dextrose solution, before use. To this end, the active compound may be dried by any art-known technique, such as lyophilization, and reconstituted prior to use.

The compounds may also be formulated in rectal or vaginal compositions such as suppositories or retention enemas, e.g., containing conventional suppository bases such as cocoa butter or other glycerides.

For transmucosal administration, penetrants appropriate to the barrier to be permeated are used in the formulation. Such penetrants are known in the art.

For ocular administration, the compound(s) may be formulated as a solution, emulsion, suspension, etc. suitable for administration to the eye. A variety of vehicles suitable for administering compounds to the eye are known in the art.

In addition to the formulations described above, for prolonged delivery, the compounds may also be formulated as a depot preparation for administration by, for example, implantation or intramuscular injection. Such long acting formulations may be formulated with suitable polymeric or hydrophobic materials (for example as an emulsion in an acceptable oil) or ion exchange resins, or as sparingly soluble derivatives, for example, as a sparingly soluble salt. Alternatively, transdermal delivery systems manufactured as an adhesive disc or patch which slowly releases the compound for percutaneous absorption may be used. To this end, permeation enhancers may be used to facilitate transdermal penetration of the compound.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group. Typically, such salts are more soluble in aqueous solutions than the corresponding free acids and bases, but salts having lower solubility than the corresponding free acids and bases may also be formed.

The compounds may alternatively be formulated in the pharmaceutical composition per se, or in the form of a hydrate, solvate, or N-oxide.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

Methods and Uses

As shown herein, the compounds of the invention are useful for inhibiting binding activity of the chitinase-like protein YKL-40.

Accordingly, the invention provides methods for inhibiting the chitinase-like protein YKL-40 in a cell or a tissue, comprising contacting a cell or a tissue with at least one compound according to the invention, or with a pharmaceutical composition according to the invention.

In other aspects, the invention provides methods for the treatment or prevention of a disease, disorder, or condition associated with aberrant expression of the chitinase-like protein YKL-40, comprising administering to a subject in need thereof a therapeutically effective amount of at least one compound according to the invention, or a pharmaceutical composition according to the invention.

Preferably, the disease, disorder, or condition is selected from the group consisting of cancer, allergic diseases, acute and chronic inflammatory diseases, autoimmune diseases, dental diseases, neurologic diseases, metabolic diseases, liver diseases, kidney diseases, polycystic ovary syndrome, endometriosis, asthma, and fibrotic disorders.

In one particular aspect, the disease is cancer selected from the group consisting of glioblastoma, breast cancer, colon cancer, kidney cancer, uterine cancer, primary and metastatic lung cancer, mesothelioma, osteosarcoma, malignant melanoma, ovarian cancer, cervical cancer, prostate cancer, liver cancer, gastric cancer, metastatic renal cancer, leukemia, lymphoma, oligodendroglioma, glioblastoma, and germ cell tumors.

In another particular aspect, the disease, disorder, or condition is an allergic disease selected from the group consisting of asthma, allergic rhinitis, seasonal allergic rhinitis, chronic rhinosinusitis with or without nasal polyps, conjunctivitis, keratoconjunctivitis, seasonal allergic conjunctivitis, dry eye syndrome, eosinophilic esophagitis, celiac disease, food allergy, irritable bowel syndrome, irritable bowel disease, atopic eczema, atopic dermatitis, allergic contact dermatitis, eosinophilic otitis media, eosinophilic pneumonia, and IgG4 mediated diseases.

In a further particular aspect, disease, disorder, or condition is an acute or chronic inflammatory disease selected from the group consisting of fungal diseases, parasitic infections, celiac disease, microscopic colitis, chronic obstructive pulmonary disease (COPD), idiopathic pulmonary fibrosis, interstitial lung diseases, cystic fibrosis, Hermansky-Pudlak syndrome, and Alzheimer's disease.

In another aspect, the disease, disorder, or condition is an autoimmune disorder selected from the group consisting of inflammatory bowel disease, ulcerative colitis, Crohn's disease, rheumatoid arthritis, osteoarthritis, psoriasis, scleroderma, multiple sclerosis, Sjögren's syndrome, atherosclerosis, and sarcoidosis.

In one particular aspect, the disease, disorder, or condition is periodontitis.

In another aspect, the disease, disorder, or condition is a metabolic disease selected from the group consisting of insulin-dependent diabetes mellitus and non-insulin-dependent diabetes mellitus.

In a further aspect, the disease, disorder, or condition is a liver disease selected from the group consisting of non-alcoholic fatty liver disease, non-alcoholic steatohepatitis, hepatitis-C virus-induced fibrosis and cirrhosis, and alcoholic fibrosis.

In another aspect, the disease is a kidney disease selected from the group consisting of nephropathy (e.g., diabetic nephropathy), focal segmental glomerulosclerosis, tubulointerstitial fibrosis, posttransplant fibrosis, and retroperitoneal fibrosis (Ormond's disease).

In one particular aspect, the disease, disorder, or condition is a fibrotic disorder.

Preferably, the fibrotic disorder is idiopathic pulmonary fibrosis (IPF).

In another aspect, the disease is a storage disease selected from the group consisting of Gaucher disease, Fabry disease, lysosomal storage disorders, Niemann-Pick disease, nephropatic cysteinosis, and X-linked globotriaosylceramidosis.

Moreover, the invention provides methods of treating diseases caused by infectious agents, such as fungi, worms, and parasites, the method comprising administering to a subject in need of such treatment an effective amount of one or more compounds of the invention.

In one embodiment, the invention provides methods of treating allergies, comprising administering to a subject in need of such treatment an effective amount of one or more compounds of the invention. In certain embodiments, such allergies are caused by any of a variety of antigens including biological sources such as dust mites, mold, cockroaches and other insects, dander from pets or other mammals, pollens, spores, mold, other fungal sources, and other plant antigens, or non-biological sources such as chemicals (e.g., isocyanates).

In other embodiments, the invention provides a method of screening for therapeutic agents useful for treating asthma in a mammal, comprising: (a) contacting the chitinase-like protein YKL-40 with a compound (e.g., a compound of the invention) and a substrate of said chitinase-like protein; and (b) determining if the compound inhibits the binding activity of the chitinase-like protein; wherein if the compound inhibits the binding activity of the chitinase-like protein, then the compound is a therapeutic agent useful for treating asthma.

In other aspects, the invention provides methods for monitoring the efficacy of a treatment for asthma, comprising (a) administering a compound of the invention to a mammal, and (b) monitoring the expression of the chitinase-like protein YKL-40 in the mammal after administration of the compound, wherein a decrease in the expression of the chitinase-like protein YKL-40 indicates that the compound is useful in treating asthma, allergic diseases such as hay fever, allergic rhinitis, atopic dermatitis or other Th-2 mediated or associated diseases.

In other aspects, the invention provides methods for monitoring the efficacy of a treatment for asthma and other allergic diseases, comprising (a) administering a compound of the invention to a mammal, and (b) monitoring the expression of inflammatory mediators such as IL-13, IL-5, IL-4, eotaxin, or IgE or inflammatory cells such as eosinophils, neutrophils, or lymphocytes in broncho-alveolar washings, sputum, or tissues obtained from the mammal after administration of the compound; wherein a decrease in expression indicates that the compound is useful in treating asthma or allergic diseases such as hay fever, allergic rhinitis, atopic dermatitis or other Th-2 mediated or associated diseases.

In another aspect, the invention provides methods for assessing the efficacy of an agent for treating asthma in a subject, comprising the steps of:
 a) detecting in a subject sample collected at a first point in time the expression level of the chitinase-like protein YKL-40;
 b) repeating step a) at one or more subsequent points in time after administration of the agent; and
 c) comparing expression level of the chitinase-like protein YKL-40 detected in step a) with the expression level(s) detected in step b),
 wherein a higher expression level of the chitinase-like protein YKL-40 at the first point in time relative to at least one subsequent point in time indicates that the agent is efficacious in treating asthma.

In certain embodiments, an agent identified by such a method is efficacious in treating asthma, hay fever, allergic rhinitis, atopic dermatitis, allergic reactions, or a disorder associated with Th-2.

Alternatively, the efficacy of an agent for treating asthma or an allergic reaction can be assessed via measuring the expression level of an inflammatory mediator such as IL-13, IL-5, IL-4, eotaxin, IgE, or measuring the amount of inflammatory cells such as eosinophils, neutrophils, or lymphocytes in broncho-alveolar washings, sputum, or tissues obtained from a mammal. In certain such embodiments, the expression level can be measured prior to and after administration of an agent. When the expression level of the inflammatory mediator or the level of inflammatory cells decreases after administration of an agent, such an agent is efficacious in treating asthma, hay fever, allergic rhinitis, atopic dermatitis, allergic reactions, or a disorder associated with Th-2.

Another aspect of the invention provides methods of identifying an agent for treating asthma, comprising:

a) contacting a sample comprising the chitinase-like protein YKL-40 with the agent; and
b) determining the ability of the agent to inhibit binding activity of the chitinase-like protein YKL-40, wherein decreased activity of the chitinase-like protein YKL-40 identifies an agent for treating asthma.

In certain embodiments, the binding activity of the chitinase-like protein YKL-40 is assessed by MicroScale Thermophoresis direct binding assay and AlphaScreen indirect binding assays using fluorescently labelled YKL-40 protein and biotinylated small molecule compound binding YKL-40, respectively.

In certain embodiments, the invention provides a method for inhibiting the chitinase-like protein YKL-40 in a cell or a tissue, comprising contacting a cell or a tissue with at least one compound of the invention.

Therapeutic Applications

The inventive compounds are useful for inhibiting the biological activity of the chitinase-like protein YKL-40. The expression of chitinase-like protein YKL-40 has been linked to interstitial lung diseases (ILDs) including idiopathic pulmonary fibrosis (IPF) and chronic obstructive pulmonary disease (COPD).

More specifically, the invention provides methods for inhibiting YKL-40 in a cell, comprising contacting a cell with at least one compound according to the present invention, or a composition thereof as described herein.

In some embodiments, the invention provides methods for treatment or prevention of a disease or condition associated with expression or biological activity of YKL-40 in a subject in need thereof. For instance, the disease, disorder, or condition is selected from the group consisting of allergic diseases, acute and chronic inflammatory diseases, autoimmune diseases, dental diseases, neurologic diseases, metabolic diseases, liver diseases, polycystic ovary syndrome, endometriosis, and cancer.

According to certain embodiments, the compounds of the invention are useful for treating allergic diseases, such as asthma, allergic rhinitis, seasonal allergic rhinitis, chronic rhinosinusitis with or without nasal polyps, conjunctivitis, keratoconjunctivitis, seasonal allergic conjunctivitis, dry eye syndrome, eosinophilic esophagitis, celiac disease, food allergies, irritable bowel syndrome, irritable bowel disease, atopic eczema, atopic dermatitis, allergic contact dermatitis, eosinophilic otitis media, eosinophilic pneumonia, and IgG4 mediated disease.

In certain embodiments, the reaction caused by an allergen is allergic rhinitis or atopic dermatitis.

In certain embodiments, the reaction caused by an allergen is characterized by the occurrence of one or more symptoms, which can include red eyes, itchiness, runny nose, eczema, impaired hearing, hives, an asthma attack, increased mucus production in the lungs, coughing, wheezing, and shortness of breath.

Exemplary acute and chronic inflammatory disorders that can be treated using the compounds of the invention include fungal diseases, parasitic infection, celiac disease, microscopic colitis, chronic obstructive pulmonary disease (COPD), idiopathic pulmonary fibrosis, interstitial lung diseases, Cystic Fibrosis (CF), Hermansky-Pudlak and Alzheimer's disease (AD).

In certain embodiments, the disease or condition treated by the methods of the invention is an autoimmune disorder selected from the group consisting of inflammatory bowel disease, ulcerative colitis (UC), Crohn's disease (CD), rheumatoid arthritis (RA), osteoarthritis, psoriasis, scleroderma, multiple sclerosis (MS), Sjögren's syndrome, atherosclerosis, and sarcoidosis.

Compounds in accordance with the present invention are also useful for treating dental diseases such as periodontitis.

The compounds of the invention are also useful for treating metabolic diseases such as insulin-dependent diabetes mellitus (IDDM) and non-insulin-dependent diabetes mellitus (NIDDM).

In certain embodiments, the invention provides methods of treating a liver disease selected from group consisting of non-alcoholic fatty liver disease, non-alcoholic steatohepatitis, hepatitis-C virus-induced fibrosis and cirrhosis, and alcoholic fibrosis.

In some embodiments, the methods of the invention are used in the treatment of cancer, wherein the cancer is selected from the group consisting of glioblastoma, breast cancer, colon cancer, kidney cancer, uterine cancer, primary and metastatic lung cancer, mesothelioma, osteosarcoma, malignant melanoma, ovarian cancer, cervical cancer, prostate cancer, liver cancer, gastric cancer, metastatic renal cancer, leukemia, lymphoma, oligodendroglioma, glioblastoma and germ cell tumors.

In certain embodiments, the disease or condition treated by the methods of the invention is a kidney disease selected from the group consisting of nephropathy (e.g., diabetic nephropathy), focal segmental glomerulosclerosis, tubulointerstitial fibrosis, postransplant fibrosis, and retroperitoneal fibrosis (Ormond's disease).

In certain embodiments, the disease or condition treated by the methods of the invention is a storage disease selected from the group consisting of Gaucher disease, Fabry disease, lysosomal storage disorders, Niemann-Pick disease, nephropathic cysteinosis, and X-linked globotriaosylceramidosis.

In some embodiments, the subject receiving treatment is a mammal. For instance, the methods and uses described herein are suitable for medical use in humans. Alternatively, the methods and uses are also suitable in a veterinary context, wherein the invention may be administered to warm-blooded animals, birds and reptiles. Warm-blooded animals include, for example, all non-human primates (e.g., chimpanzee and ape), ruminants (e.g., cow, sheep and goat), porcines (e.g., pig), equines (e.g., horse, mule and donkey), camelines (e.g camel and dromedary), canines (e.g., dog), felines (e.g., cat), leporine (e.g., rabbit), murines (e.g., mouse and rat) cavines (e.g., guinea pig), gerbiline (e.g gerbil), cricetine (e.g hamster), mustelines (e.g ferret and weasel) and chinchilines (e.g., chinchilla). Birds include animals of the avian class, for example, all phasianines (e.g., chicken and quail), anserines (e.g., goose), anatines (e.g., ducks), meleagridines (e.g turkey), daruduelines (e.g., canary), psittacines (e.g., parrot, macaw, parakeet and lovebird), cacatuines (e.g., cockatoo) and columbines (e.g., pigeon and turtle dove).

In certain embodiments, the invention is preferably administered to domesticated companion animals and to productive and breeding animals.

In certain embodiments, the method of the invention further comprises administering a second therapeutic agent. Exemplary second therapeutic agents include steroids, membrane stabilizers, 5LO inhibitors, leukotriene synthesis and receptor inhibitors, inhibitors of IgE isotype switching or IgE synthesis, inhibitors of IgG isotype switching or IgG synthesis, β-agonists, tryptase inhibitors, acetylosalicylic acid, COX inhibitors, methotrexate, anti-TNF drugs, rituxin and other B-cell targeting agents, THF-targeting agents, PD4 inhibitors, p38 inhibitors, PDE4 inhibitors, and antihistamines.

EXAMPLES

The present invention is further illustrated by the following examples, which in no way should be construed as limiting the scope of the claimed invention.

Materials and Methods of Preparation and Characterization

The compounds of the present disclosure may be prepared by use of known chemical reactions and procedures. Representative methods for synthesizing compounds of the disclosure are presented below. It is understood that the nature of the substituents required for the desired target compound often determines the preferred method of synthesis. All variable groups of these methods are as described in the generic description if they are not specifically defined below. Substituents carry the same meaning as defined above, unless otherwise noted.

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978).

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "*Protective Groups in Organic Chemistry*," Plenum Press, London and New York 1973, in T. W. Greene and P. G. M. Wuts, "*Protective Groups in Organic Synthesis*," Third edition, Wiley, New York 1999, in "*The Peptides*;" Volume 3 (editors: E. Gross and J. Meienhofer), Academic Press, London and New York 1981, in "*Methoden der organischen Chemie*," Houben-Weyl, 4th edition, Vol. 15/1, Georg Thieme Verlag, Stuttgart 1974, in H.-D. Jakubke and H. Jescheit, "*Aminosauren, Peptide, Proteine,*" Verlag Chemie, Weinheim, Deerfield Beach, and Basel 1982, and/or in Jochen Lehmann, "*Chemie der Kohlenhydrate: Monosaccharide und Derivate*," Georg Thieme Verlag, Stuttgart 1974. The protecting groups may be removed at a convenient subsequent stage using methods known from the art.

The disclosures of all articles and references mentioned in this application, including patents, are incorporated herein by reference in their entirety.

Starting materials can be obtained from commercial sources or prepared by well-established literature methods known to those skilled in the art.

All solvents, substrates and reagents that were commercially available were used without further purification. TLC analysis was performed using pre-coated glass plates (0.2±0.03 mm thickness, GF-254, particle size 0.01-0.04 mm) from Fluorochem Ltd, UK or using pre-coated glass plates (TLC silica gel 60 $F_{254}$) or using pre-coated aluminium plates (TLC silica gel 60 $F_{254}$) from Merck. TLC analysis was performed for compounds before their transferring in the appropriate salts (hydrochloride or TFA salt). The column chromatography was performed using high-purity grade silica gel (pore size 60 Å, 220-440 mesh particle size, 35-75 μm particle size) from Fluka or using high-purity grade silica gel (pore size 60 Å, 230-400 mesh particle size, 40-63 μm particle size) from Merck.

Column chromatography (LCC) was performed using high-purity grade silica gel (pore size 60 Å, 220-440 mesh particle size, 35-75 μm particle size) purchased from Fluka.

Flash column chromatography (FLCC) was performed using Buchi Reverelis® X2-UV equipped in evaporative light scattering detector (ELSD), with UV detection in range UV 200-500 nm, purchased from BUCHI Labortechnik AG, using puriFlash® pre-packed cartridges with amorphous or spherical virgin silica gel, 50 m, from InterChim®.

Preparative HPLC were performed on LC-20AP Shimadzu with ELSD-LTII detector equipped with Luna 21.2/250 mm, 5 μm C-18(2) 100 Å LC column or equipped with:

Hypersil GOLD 21.2/250 mm, 5 μm C-18 column;
Luna® 5 mm Phenyl-Hexyl 10, LC Column 250×30 mm;
Lux® 5 mm Cellulose-4 LC Column 250×21.2 mm.

The target compounds, when subjected to reversed-phase chromatographic purification in the presence of TFA, were usually obtained in the form of TFA salts.

$^1$H NMR spectra were recorded on an Agilent 400-MR DD2 400 MHz spectrometer and on Bruker AVANCE DRX500, AVANCE DRX600 and on Bruker AVANCE II PLUS (respectively at 500, 600, or 700 MHz) NMR spectrometers.

All spectra were recorded in appropriate deuterated solvents ($CDCl_3$, DMSO-$d_6$, $D_2O$, Methanol-$d_4$, etc.) that were commercially available.

Resonances are given in parts per million (ppm) relative to tetramethylsilane internal standard. Data are reported as follows: chemical shift (6), multiplicity (s=singlet, d=doublet, t=triplet, m=multiplet, bs=broad singlet), coupling constants (J in Hz) and integration.

ESI-MS spectra were obtained on a Waters Alliance 2695 separation module with a PDA 1996 UV detector and Waters Micromass ZQ 2000 mass detector equipped with Kinetex 2.1/50 mm, 2.6 μm C-18 column eluted with 0.3 mL/min flow of 3-100% gradient (over 6 min) of acetonitrile in water, and a Shimadzu Prominence LC-20AD separation module with a SPD-M20 Å PDA detector and Shimadzu LCMS-2020 mass detector equipped with Luna, C18, 2 μm, 100 Å, 150×3 mm column eluted with 0.5 mL/min flow of 15-90% gradient (over 13 min) of acetonitrile in water or equipped with Kinetex 2.1/30 mm, 1.7 μm XB-C18 100 Å LC column eluted with 1 mL/min flow of 10-90% gradient (over 3 min) of acetonitrile in water.

LC-MS spectra were recorded on a Shimadzu LC-20AD LPG separation module with a SPD-M20 Å UV detector and LCMS-2020 mass detector equipped with:

Kinetex 2.1/50 mm, 2.6 μm C-18 column eluted with 0.5 mL/min flow of 10-90% gradient (over 6 or 8 min) of acetonitrile in water;

Kinetex 2.1/50 mm, 2.6 μm C-18 column eluted with 0.5 mL/min flow of 10-90% gradient (over 6 or 8 min) of acetonitrile in water;

Kinetex® 2.6 mm XBC18 100 Å LC Column 50×2.1 mm eluted with 0.5 mL/min flow of 10-90% gradient (over 10 or 16 min) of acetonitrile in water;

Luna® 3 mm Phenyl-Hexyl 100 Å LC Column 100×3 mm eluted with 0.5 mL/min flow of 10-90% gradient (over 10 or 16 or 25 min) of acetonitrile in water.

Microwave-assisted reactions were performed using CEM MARS 6™ Synthesis system (240/50, Model no. 911105).

Abbreviations used are those conventional in the art or the following: Ac=acetyl, AcCl=acetyl chloride, AcOH=acetic acid, Alloc=allyloxycarbonyl, aq=aqueous, BINAP=2,2'-bis(diphenylphosphino)-1,1'-binaphthyl, Bn=benzyl, Boc=tert-butoxycarbonyl, tBu=tert-butyl, ° C.=degree Celsius, CDI=carbonyldiimidazole, DAST=diethylaminosulfur trifluoride, dba=dibenzylideneacetone, DCE=1,2-dichloroethane, DCM=dichloromethane, DIAD=diisopropyl azodicarboxylate, DIPEA=N,N-diisopropylethylamine, DMAP=4-dimethylaminopyridine, DMF=N,N-dimethylformamide, DMS=dimethyl sulfide, DMSO=dimethyl sulfoxide, EDCI=1-ethyl-3-(3-dimethylaminopropyl)carbodiimide, ELSD=evaporative light scattering detector, EtOAc or AcOEt=ethyl acetate, EtOH=ethanol, ESI-MS=electrospray ionization mass spectrometry, g=gram, h=hour(s), HATU=1-[bis(dimethylamino)methylene]-1H-1,2,3-triazolo[4,5-b]pyridinium 3-oxide hexafluorophosphate, HPLC=high pressure liquid chromatography, K=kelvin, L=liter, LC-MS=liquid chromatography and mass spectrometry, MeCN=acetonitrile, MeOH=methanol, min=minutes, mL=milliliter(s), M=molar, mmol=millimoles, Ms=mesyl, MTBE=methyl tert-butyl ether, m/z=mass to charge ratio, nM=nanomolar, NMM=N-methylmorpholine, NMP=N-methyl-2-pyrrolidone, NMR=nuclear magnetic resonance, N=normal, PEG12=polyoxyethylene glycol, RT or rt=room temperature, TBDMSCl=tert-butyldimethylsilyl chloride, TBTU=2-(1H-benzotriazole-1-yl)-1,1,3,3-tetramethylaminium tetrafluoroborate, TFA=trifluoroacetic acid, THF=tetrahydrofuran, TLC=thin layer chromatography, TMSCl=chlorotrimethylsilane.

If not otherwise defined, purity of a solid substance is expressed as a ratio of the weight of the component in question to the total weight, multiplied by 100 (weight %); purity of a liquid is expressed as a ratio of the volume of the component in question to the total volume, multiplied by 100 (volume %); concentration of a solution is expressed as a ratio of the weight of the solute (in grams) to the total volume (in mL) of the solution, multiplied by 100 (w/v %). Yield of a reaction is expressed as a ratio of the weight of the product in question to the theoretical yield of this product, multiplied by 100(%). Composition of a mixed solvent is expressed as a proportion of volume parts of the component solvents (e.g., 3:1).

YKL-40: 4 Assay

The standard experimental protocol for YKL-40 indirect binding AlphaScreen assay comprised of 5 step additions to wells of a 96 well plate: (i) in the $1^{st}$ step, 8 uL of biotinylated compound 4 was added at 5×20 nM concentration in MST buffer containing 1% DMSO; (ii) in the $2^{nd}$ step, 8 uL of a small molecule compound inhibitor was added at 5×1 uM or 5×100 uM concentration in MST buffer containing 2% DMSO; (iii) in the $3^{rd}$ step, 8 uL of YKL-40-histag was added at concentration 5×2.5 nM in MST buffer containing 0% DMSO, after which the plate was spun down for 2 minutes at 1500 g and incubated 1 h at 37° C.; (iv) in the $4^{th}$ step, 8 uL of Nickel Chelate Acceptor beads were added at concentration 5×10 ug/mL in MST buffer containing 1% DMSO, after which the plate was spun down for 1 minute at 250 g and incubated in dark for 1 hour at RT; (v) in the $5^{th}$ step, 8 uL of Streptavidin Donor beads were added at concentration 5×10 ug/mL in MST buffer containing 1% DMSO, after which the plate was spun down for 1 minute at 250 g and incubated in dark for 1 hour at RT. Positive and negative control wells received just 8 uL of MST buffer containing 2% DMSO without inhibitor in the $2^{nd}$ step (ii). In addition, negative control received just 8 uL of MST buffer containing 0% DMSO without YKL-40-histag in the $3^{nd}$ step (iii). Finally, the plate luminescence was excited at 680 nm and the emission read at 520-620 nm using the AlphaScreen module in the The Spark™ 10M multimode microplate reader (Tecan Trading AG, Mannedorf, Switzerland). Inhibition percentage and $IC_{50}$ values were determined using GraphPad Prism 7.0 software (GraphPad Software, San Diego, CA, USA).

BLITz system (Sartorius) that used Bio-layer interferometry technology was applied to assess Kd of biotinylated compounds. 10 min before Kd measurement, streptavidin biosensors were dehydrated in the MST buffer. During dehydration process the 10 mM stock of biotinylated compound in DMSO was diluted in MST buffer to final concentration of 0.5 μM. In addition, protein stock of recombinant YKL40 (un-tagged, purified in-house) was also prepared in MST buffer at two concentrations: 200 μM and 400 μM. The dehydrated biosensor was applied on the BLITz system that was followed by 5-step procedure: 1) initial baseline for 30 s with MST buffer in tube, 2) loading of 4 μl of biotinylated compound on drop, 3) baseline for 30 s with MST buffer in tube, 4) association of 4 μl of protein stock at one concentration or MST buffer (negative control), 5) dissociation with MST buffer in tube. The same multi-step measurement was done twice for each protein stock concentration and once for negative control. Kd was measured by the BLITz software based on global fitting using the negative control as a reference.

Third column of Table 1 summarizes results of the YKL-40: Example 4 assay. The compounds disclosed in Table 1 have the $IC_{50}$ values towards YKL-40 generally ranging from about 0.001 μM to about 100 μM. Their ranges of activity have been assigned as follows:

A: <0. μM;
B: 0.1-1 μM;
C: 1-10 μM;
D: 10-10 μM; and
E: >10 μM.

In Table 1, whenever the symbol of range of activity is preceded by asterisk (*), this symbol represents the Kd range rather than the $IC_{50}$ value range. The ranges of activity have been assigned as follows:

*A: <0.1 μM;
*B: 0.1-1 μM;
*C: 1-1 μM;
*D: 10-10 μM; and
*E: >10 μM.

YKL-40: HS Assay

The standard experimental protocol for YKL-40 indirect binding AlphaScreen assay comprised of 5 step additions to wells of a 96 well plate: (i) in the $1^{st}$ step, 8 uL of biotinylated heparan sulphate was added at 5×60 nM concentration in MST buffer containing 1% DMSO; (ii) in the 2nd step, 8 uL of a small molecule compound inhibitor was added at 5×1 uM or 5×100 uM concentration in MST buffer containing 2% DMSO; (iii) in the 3rd step, 8 uL of YKL-40-histag was added at concentration 5×7.5 nM in MST buffer containing 0% DMSO, after which the plate was spun down for 2 minutes at 1500 g and incubated 1 h at 37° C.; (iv) in the 4th step, 8 uL of Nickel Chelate Acceptor beads were added at concentration 5×10 ug/mL in MST buffer containing 1% DMSO, after which the plate was spun down for 1 minute at 250 g and incubated in dark for 1 hour at RT; (v) in the 5th step, 8 uL of Streptavidin Donor beads were added at concentration 5×10 ug/mL in MST buffer containing 1% DMSO, after which the plate was spun down for 1 minute at 250 g and incubated in dark for 1 hour at RT. Positive and negative control wells received just 8 uL of MST buffer containing 2% DMSO without inhibitor in the 2nd step (ii). In addition, negative control received just 8 uL of MST buffer containing 0% DMSO without YKL-40-histag in the 3rd step (iii). Finally, the plate luminescence was excited at 680 nm and the emission read at 520-620 nm using the AlphaScreen module in the The Spark™ 1 µM multimode microplate reader (Tecan Trading AG, Mannedorf, Switzerland). Inhibition percentage and $IC_{50}$ values were determined using GraphPad Prism 7.0 software (GraphPad Software, San Diego, CA, USA).

Fourth column of Table 1 summarizes results of YKL-40:HS assay. The compounds disclosed in Table 1 have the $IC_{50}$ values towards YKL-40 generally ranging from about 0.001 µM to about 100 µM. Their ranges of activity have been assigned as follows:

A: <0. µM;
B: 0.1-1 µM;
C: 1-10 PM;
D: 10-10 µM; and
E: >10 µM.

TABLE 1

| Ex. # | Structure | YKL-40:4, $IC_{50}$/Kd | YKL-40:HS, $IC_{50}$/max % inh |
|---|---|---|---|
| 1. | 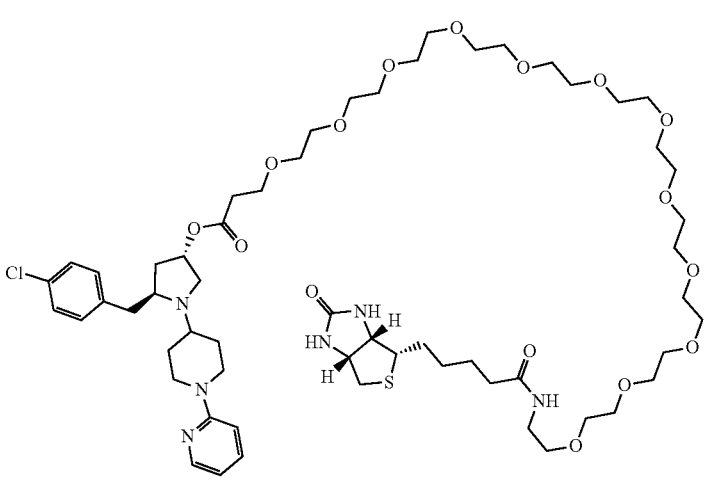 [SMILES: O=C(CCCC[C@@H]1SC[C@@H]2NC(=O)N[C@@H]21)NCCOCCOCCOCCOCCOCCOCCOCCOCCOCCOCCOCCOCCC(=O)O[C@H]1C[C@H](Cc2ccc(Cl)cc2)N(C2CCN(c3ccccn3)CC2)C1] | | |
| 2 | 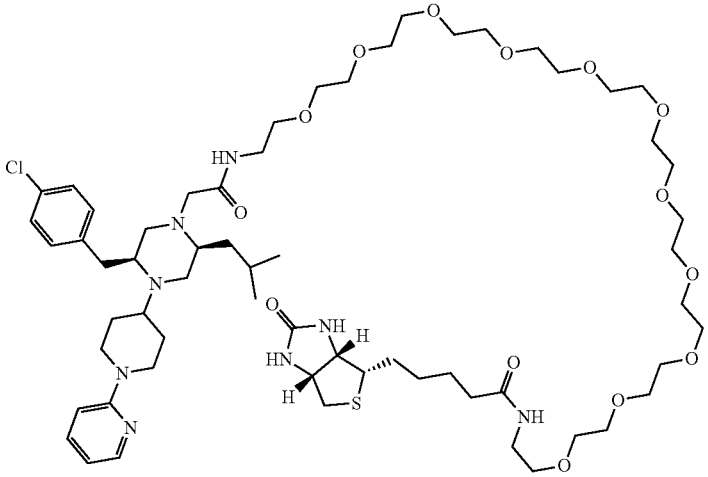 [SMILES: CC(C)C[C@H]1CN(C2CCN(c3ccccn3)CC2)[C@@H](Cc2ccc(Cl)cc2)CN1CC(=O)NCCOCCOCCOCCOCCOCCOCCOCCOCCOCCOCCOCCNC(=O)CCCC[C@@H]1SC[C@@H]2NC(=O)N[C@@H]21] | | |

TABLE 1-continued

| Ex. # | Structure | YKL-40:4, IC$_{50}$/Kd | YKL-40:HS, IC$_{50}$/max % inh |
|---|---|---|---|
| 2e. | 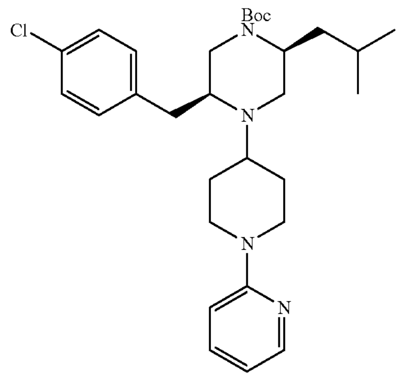 [SMILES: CC(C)C[C@H]1CN(C2CCN(c3ccccn3)CC2)[C@@H](Cc2ccc(Cl)cc2)CN1C(=O)OC(C)(C)C] | E | |
| 2f. | 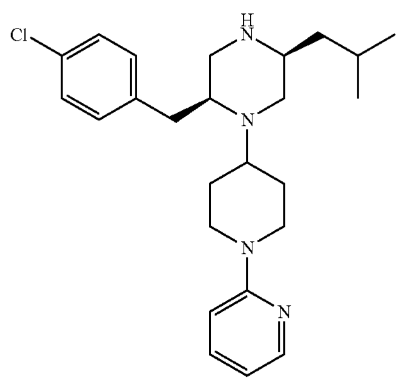 | B | |
| 2g. | 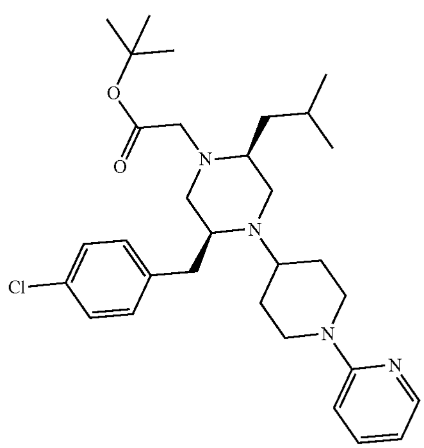 [SMILES: CC(C)C[C@H]1CN(C2CCN(c3ccccn3)CC2)[C@@H](Cc2ccc(Cl)cc2)CN1CC(=O)OC(C)(C)C] | E | |

TABLE 1-continued
| Ex. # | Structure | YKL-40:4, IC$_{50}$/Kd | YKL-40:HS, IC$_{50}$/max % inh |
|---|---|---|---|
| 3. | 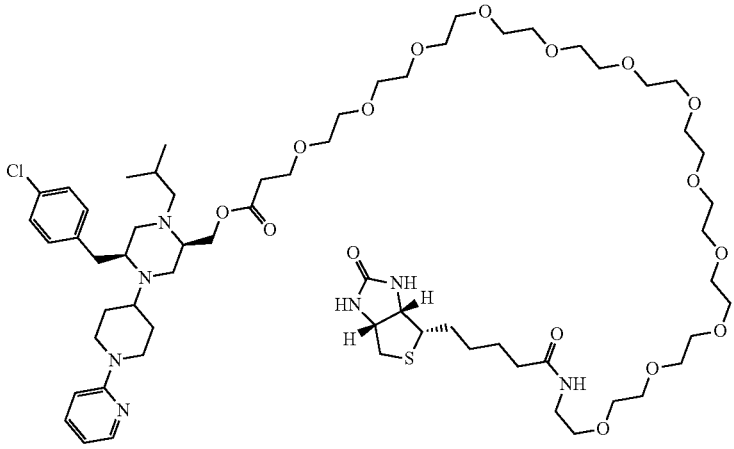 [SMILES: CC(C)CN1C[C@H](Cc2ccc(Cl)cc2)N(C2CCN(c3ccccn3)CC2)C[C@@H]1COC(=O)CCOCCOCCOCCOCCOCCOCCOCCOCCOCCOCCOCCOCCNC(=O)CCCC[C@@H]1SC[C@@H]2NC(=O)N[C@@H]21] | | |
| 3g. | 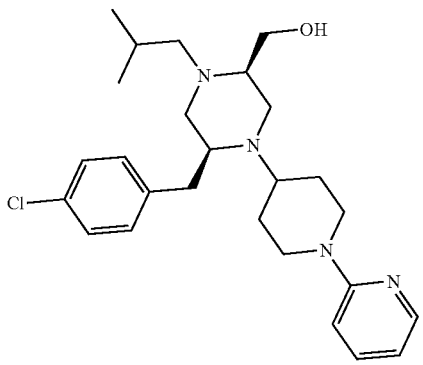 [SMILES: CC(C)CN1C[C@H](Cc2ccc(Cl)cc2)N(C2CCN(c3ccccn3)CC2)C[C@@H]1CO] | A | |
| 4. | 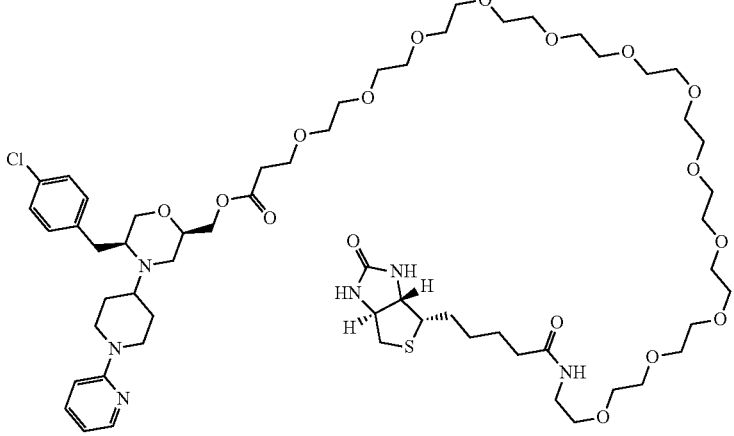 | | |

TABLE 1-continued

| Ex. # | Structure | YKL-40:4, IC$_{50}$/Kd | YKL-40:HS, IC$_{50}$/max % inh |
|---|---|---|---|
| 4e. | 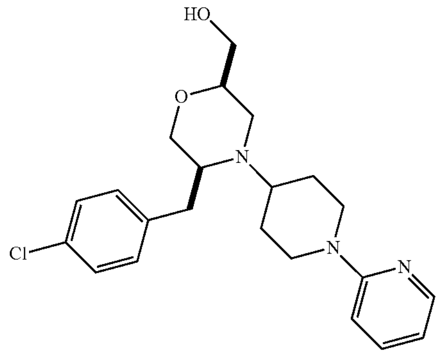 | B | A/28% |
| 5. | 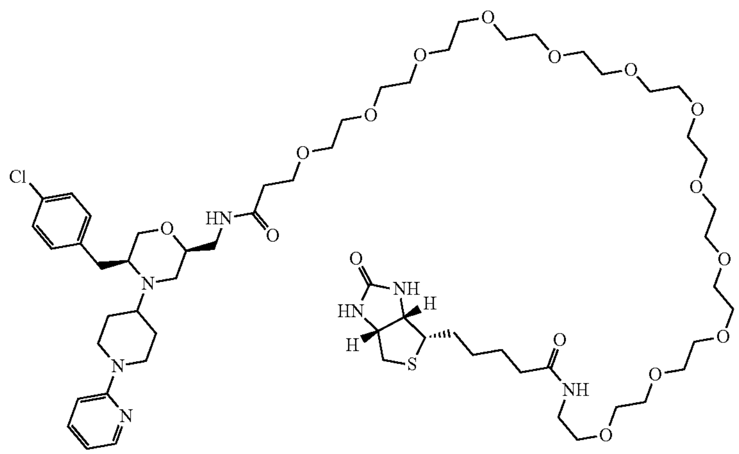 [SMILES: O=C(CCCC[C@@H]1SC[C@@H]2NC(=O)N[C@@H]21)NCCOCCOCCOCCOCCOCCOCCOCCOCCOCCOCCOCCOCCC(=O)NC[C@H]1CN(C2CCN(c3ccccn3)CC2)[C@@H](Cc2ccc(Cl)cc2)CO1] | *A | |
| 6. | 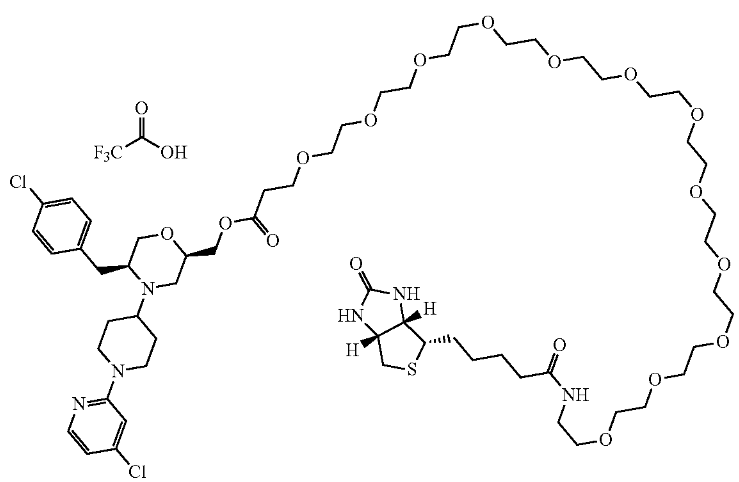 [SMILES: O=C(CCCC[C@@H]1SC[C@@H]2NC(=O)N[C@@H]21)NCCOCCOCCOCCOCCOCCOCCOCCOCCOCCOCCOCCOCCC(=O)OC[C@H]1CN(C2CCN(c3cc(Cl)ccn3)CC2)[C@@H](Cc2ccc(Cl)cc2)CO1 ; O=C(O)C(F)(F)F] | | |

TABLE 1-continued

| Ex. # | Structure | YKL-40:4, IC$_{50}$/Kd | YKL-40:HS, IC$_{50}$/max % inh |
|---|---|---|---|
| 6b. | (structure with HCl) | A | |
| 7. | (structure with F$_3$C-COOH and PEG chain) | B | |
| 8. | (structure with F$_3$C-COOH) | A | A/27% |
| 8d. | (structure with NBoc) | E | |

TABLE 1-continued
| Ex. # | Structure | YKL-40:4, IC$_{50}$/Kd | YKL-40:HS, IC$_{50}$/max % inh |
|---|---|---|---|
| 9. | 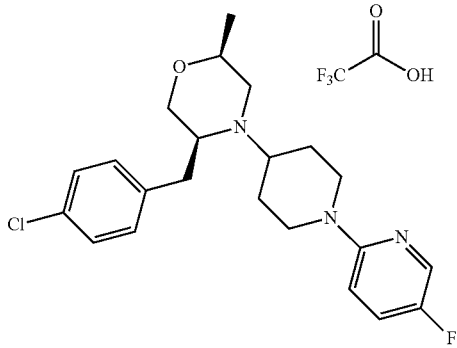 [SMILES: C[C@H]1CN(C2CCN(c3ccc(F)cn3)CC2)[C@@H](Cc2ccc(Cl)cc2)CO1 ; O=C(O)C(F)(F)F] | C | |
| 10. | 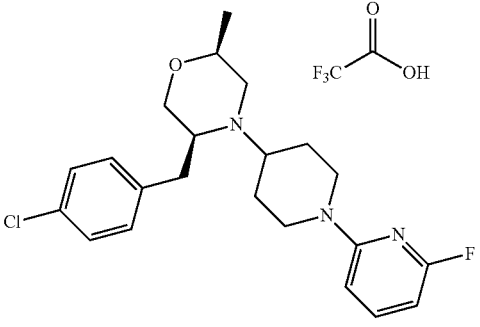 [SMILES: C[C@H]1CN(C2CCN(c3cccc(F)n3)CC2)[C@@H](Cc2ccc(Cl)cc2)CO1 ; O=C(O)C(F)(F)F] | C | |
| 11. | 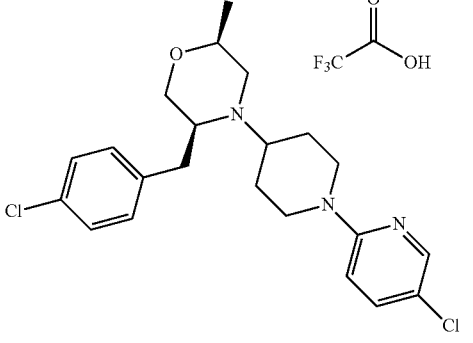 | B | |
| 12. | 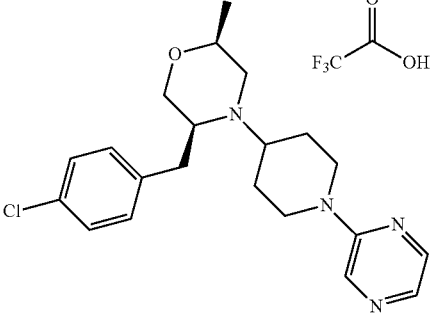 | C | |

TABLE 1-continued
| Ex. # | Structure | YKL-40:4, IC$_{50}$/Kd | YKL-40:HS, IC$_{50}$/max % inh |
|---|---|---|---|
| 13. | 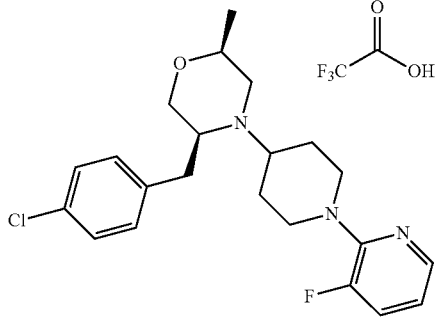 [SMILES: C[C@H]1CN(C2CCN(c3ncccc3F)CC2)[C@@H](Cc2ccc(Cl)cc2)CO1 ; O=C(O)C(F)(F)F] | | B |
| 14. | 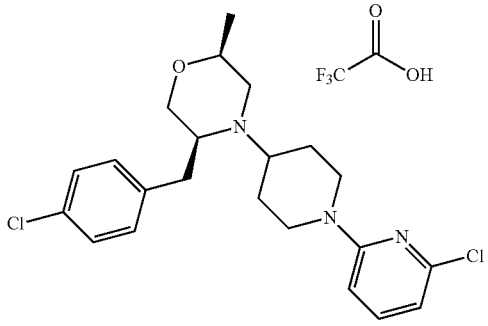 [SMILES: C[C@H]1CN(C2CCN(c3cccc(Cl)n3)CC2)[C@@H](Cc2ccc(Cl)cc2)CO1 ; O=C(O)C(F)(F)F] | | C |
| 15. | 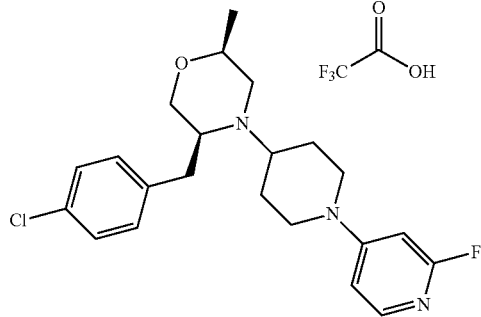 [SMILES: C[C@H]1CN(C2CCN(c3ccnc(F)c3)CC2)[C@@H](Cc2ccc(Cl)cc2)CO1 ; O=C(O)C(F)(F)F] | | C |
| 16. | 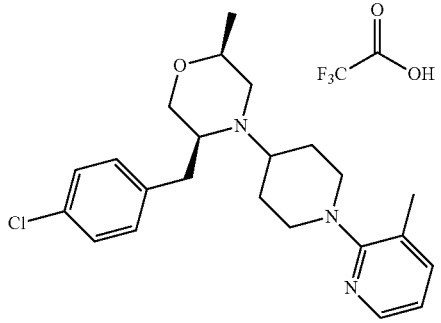 [SMILES: Cc1cccnc1N1CCC(N2C[C@H](C)OC[C@@H]2Cc2ccc(Cl)cc2)CC1 ; O=C(O)C(F)(F)F] | | E |

TABLE 1-continued

| Ex. # | Structure | YKL-40:4, IC$_{50}$/Kd | YKL-40:HS, IC$_{50}$/max % inh |
|---|---|---|---|
| 17. | 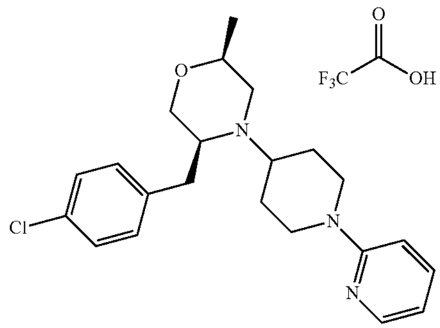 [SMILES: C[C@H]1CN(C2CCN(c3ccccn3)CC2)[C@@H](Cc2ccc(Cl)cc2)CO1 ; O=C(O)C(F)(F)F] | B | A/27% |
| 18. | 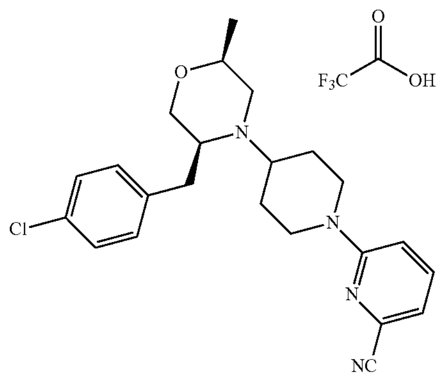 [SMILES: C[C@H]1CN(C2CCN(c3cccc(C#N)n3)CC2)[C@@H](Cc2ccc(Cl)cc2)CO1 ; O=C(O)C(F)(F)F] | E | |
| 19. | 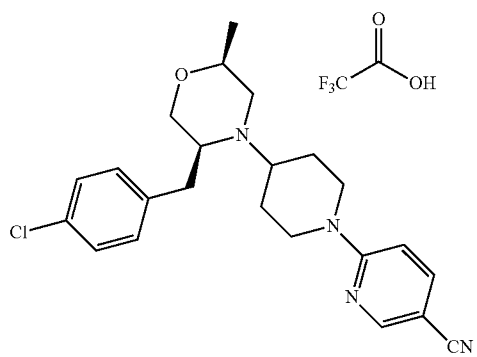 [SMILES: C[C@H]1CN(C2CCN(c3ccc(C#N)cn3)CC2)[C@@H](Cc2ccc(Cl)cc2)CO1 ; O=C(O)C(F)(F)F] | E | |
| 20. | 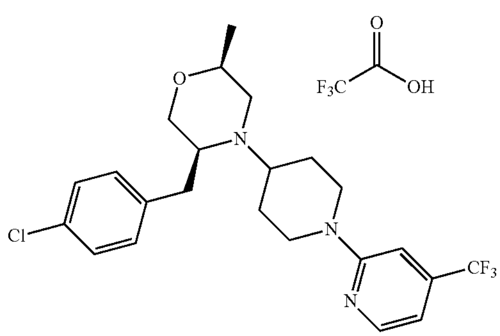 [SMILES: C[C@H]1CN(C2CCN(c3cc(C(F)(F)F)ccn3)CC2)[C@@H](Cc2ccc(Cl)cc2)CO1 ; O=C(O)C(F)(F)F] | C | |

TABLE 1-continued
| Ex. # | Structure | YKL-40:4, IC$_{50}$/Kd | YKL-40:HS, IC$_{50}$/max % inh |
|---|---|---|---|
| 21. | 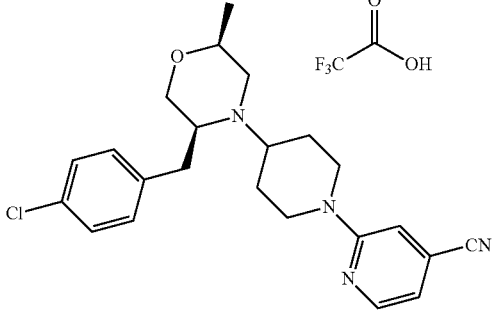 | | E |
| 22. | 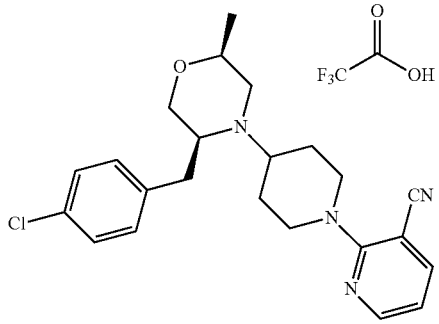 [SMILES: C[C@H]1CN(C2CCN(c3ncccc3C#N)CC2)[C@@H](Cc2ccc(Cl)cc2)CO1 ; O=C(O)C(F)(F)F] | | B |
| 23. | 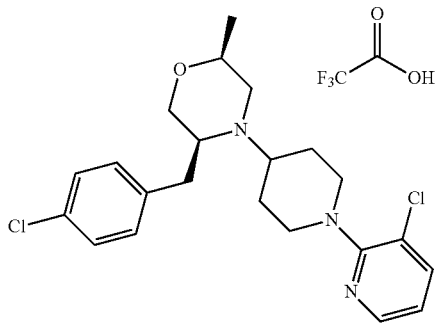 [SMILES: C[C@H]1CN(C2CCN(c3ncccc3Cl)CC2)[C@@H](Cc2ccc(Cl)cc2)CO1 ; O=C(O)C(F)(F)F] | | C |
| 24. | 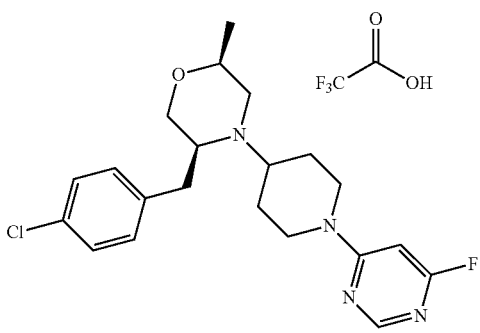 [SMILES: C[C@H]1CN(C2CCN(c3cc(F)ncn3)CC2)[C@@H](Cc2ccc(Cl)cc2)CO1 ; O=C(O)C(F)(F)F] | | E |

TABLE 1-continued
| Ex. # | Structure | YKL-40:4, IC$_{50}$/Kd | YKL-40:HS, IC$_{50}$/max % inh |
|---|---|---|---|
| 25. | 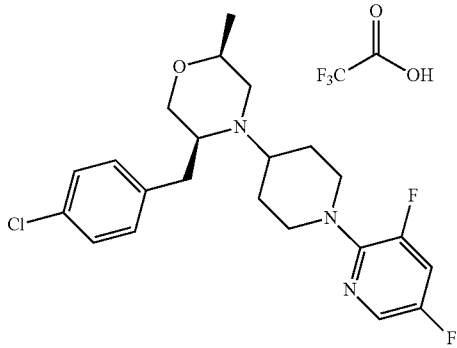 [SMILES: C[C@H]1CN(C2CCN(c3ncc(F)cc3F)CC2)[C@@H](Cc2ccc(Cl)cc2)CO1 ; O=C(O)C(F)(F)F] | E | |
| 26. | 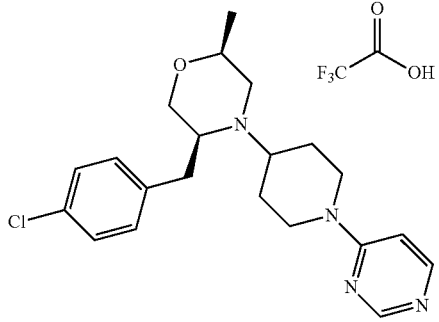 [SMILES: C[C@H]1CN(C2CCN(c3ccncn3)CC2)[C@@H](Cc2ccc(Cl)cc2)CO1 ; O=C(O)C(F)(F)F] | E | |
| 27. | 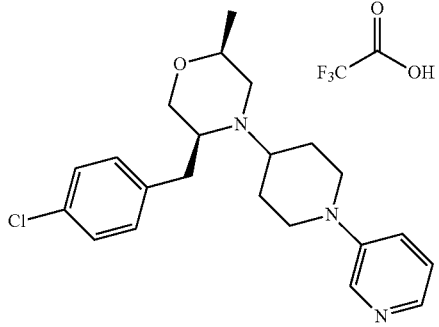 [SMILES: C[C@H]1CN(C2CCN(c3cccnc3)CC2)[C@@H](Cc2ccc(Cl)cc2)CO1 ; O=C(O)C(F)(F)F] | E | |
| 28. | 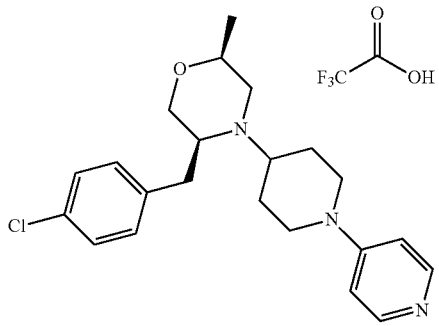 [SMILES: C[C@H]1CN(C2CCN(c3ccncc3)CC2)[C@@H](Cc2ccc(Cl)cc2)CO1 ; O=C(O)C(F)(F)F] | E | |

TABLE 1-continued
| Ex. # | Structure | YKL-40:4, IC$_{50}$/Kd | YKL-40:HS, IC$_{50}$/max % inh |
|---|---|---|---|
| 29. | 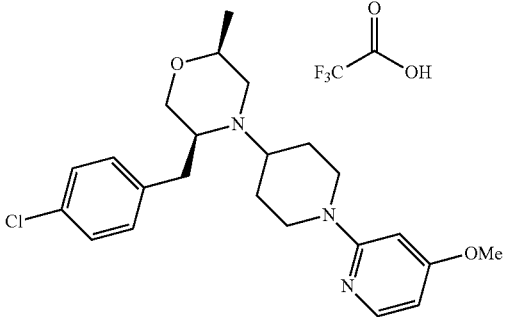 [SMILES: COc1ccnc(N2CCC(N3C[C@H](C)OC[C@@H]3Cc3ccc(Cl)cc3)CC2)c1 ; O=C(O)C(F)(F)F] | | B |
| 30. | 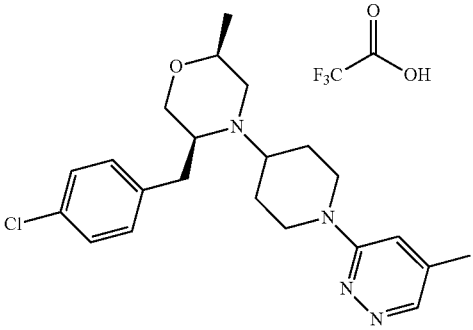 [SMILES: Cc1cnnc(N2CCC(N3C[C@H](C)OC[C@@H]3Cc3ccc(Cl)cc3)CC2)c1 ; O=C(O)C(F)(F)F] | | C |
| 31. | 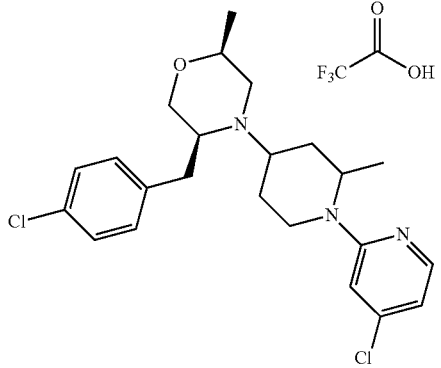<br>single diastereoisomer | | C |
| 32. | 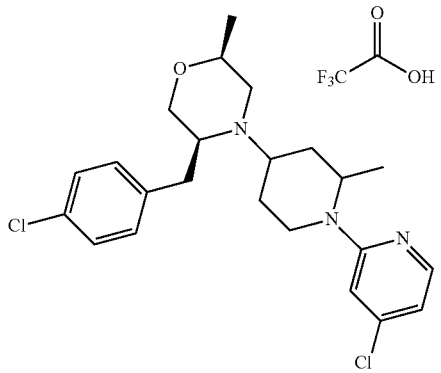<br>single diastereoisomer | | A** |

TABLE 1-continued

| Ex. # | Structure | YKL-40:4, IC$_{50}$/Kd | YKL-40:HS, IC$_{50}$/max % inh |
|---|---|---|---|
| 33. | a mixture of two diastereoisomers (31:33 in a ratio of 1:3.5) | C | |
| 34. | a mixture of two diastereoisomers (33:34 in a ratio of 1:2.5) | B | |
| 35. | 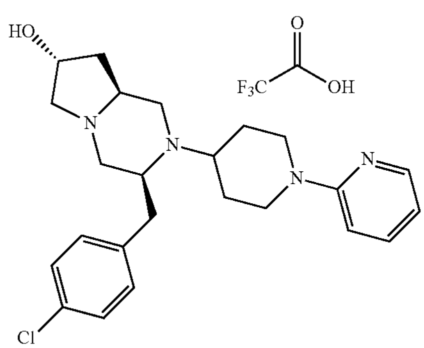 | A | |
| 36. | 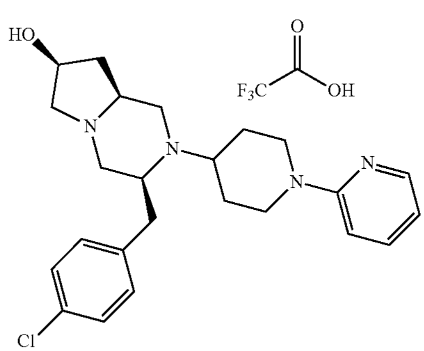 | A | |

TABLE 1-continued
| Ex. # | Structure | YKL-40:4, IC$_{50}$/Kd | YKL-40:HS, IC$_{50}$/max % inh |
|---|---|---|---|
| 37. | 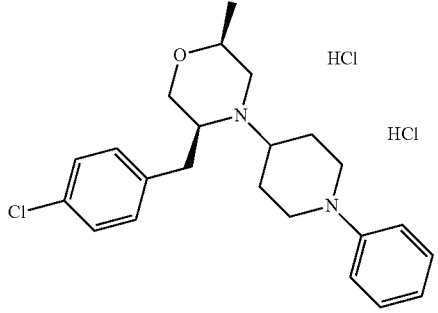 [SMILES: C[C@H]1CN(C2CCN(c3ccccc3)CC2)[C@@H](Cc2ccc(Cl)cc2)CO1 ; Cl ; Cl] | E | |
| 38. | 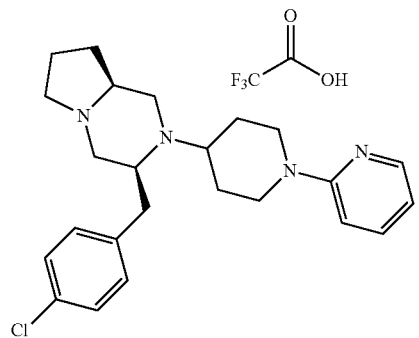 | A | |
| 39. | 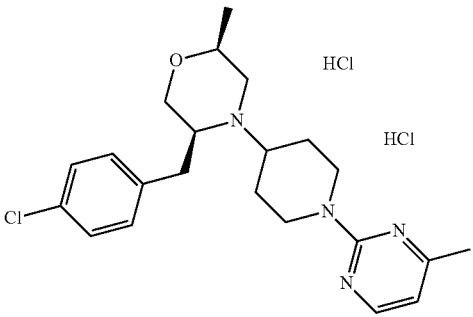 [SMILES: Cc1ccnc(N2CCC(N3C[C@H](C)OC[C@@H]3Cc3ccc(Cl)cc3)CC2)n1 ; Cl ; Cl] | B | |
| 40. | 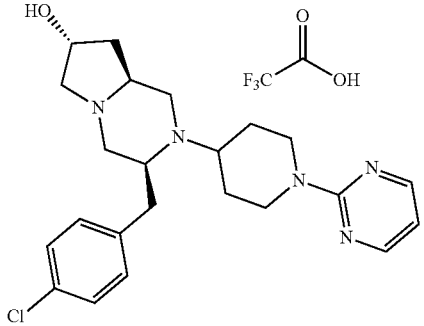 | B | |

TABLE 1-continued

| Ex. # | Structure | YKL-40:4, IC$_{50}$/Kd | YKL-40:HS, IC$_{50}$/max % inh |
|---|---|---|---|
| 41. | 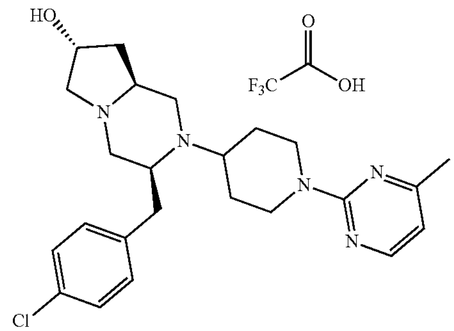 | | B |
| 42. | 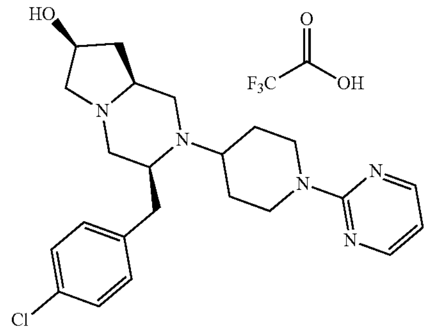 | | B |
| 43. | 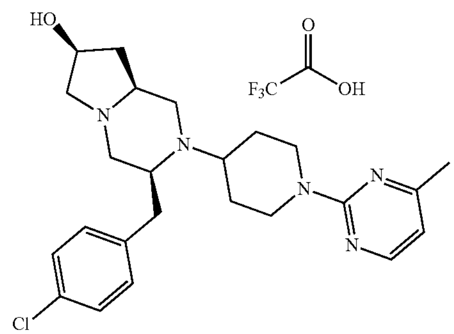 | | B |
| 44. | 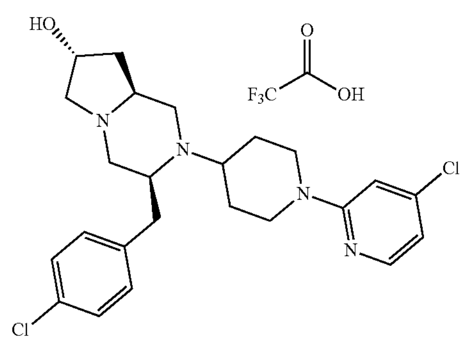 | | A |

TABLE 1-continued
| Ex. # | Structure | YKL-40:4, IC$_{50}$/Kd | YKL-40:HS, IC$_{50}$/max % inh |
|---|---|---|---|
| 45. | 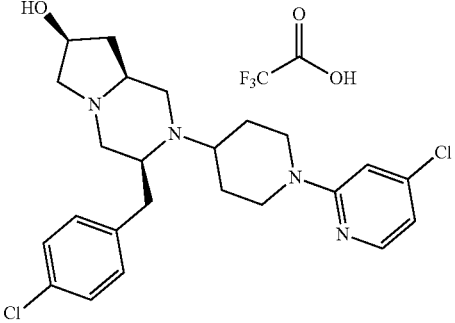 | A | A/22% |
| 46. | 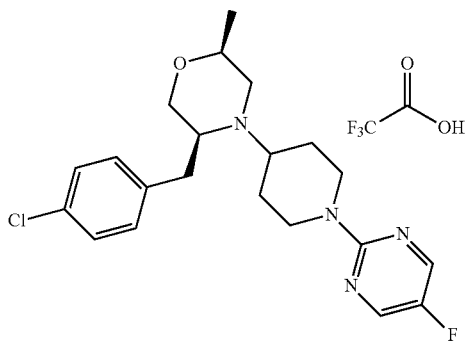 | C | |
| 47. | 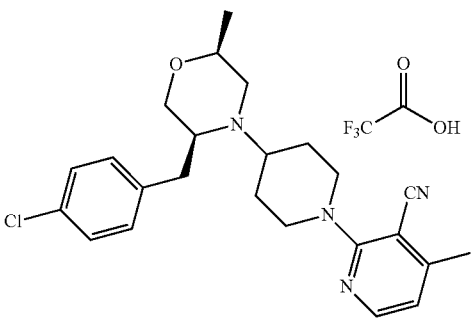 | B | |
| 48. | 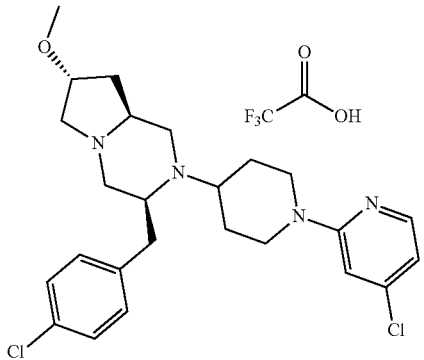 | A | |

TABLE 1-continued
| Ex. # | Structure | YKL-40:4, IC$_{50}$/Kd | YKL-40:HS, IC$_{50}$/max % inh |
|---|---|---|---|
| 49. | 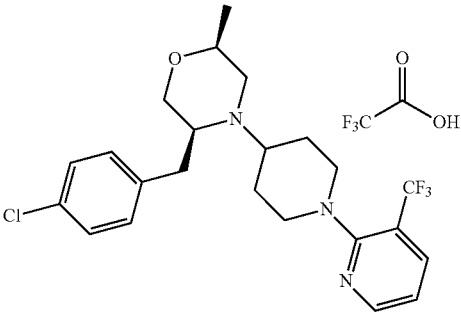 | D | |
| 50. | 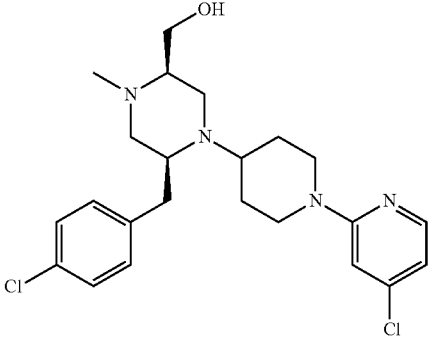 [SMILES: CN1C[C@H](Cc2ccc(Cl)cc2)N(C2CCN(c3cc(Cl)ccn3)CC2)C[C@@H]1CO] | A | |
| 50f. | 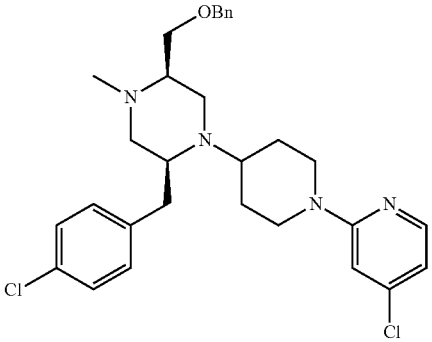 [SMILES: CN1C[C@H](Cc2ccc(Cl)cc2)N(C2CCN(c3cc(Cl)ccn3)CC2)C[C@@H]1COCc1ccccc1] | B | A/83% |
| 51. | 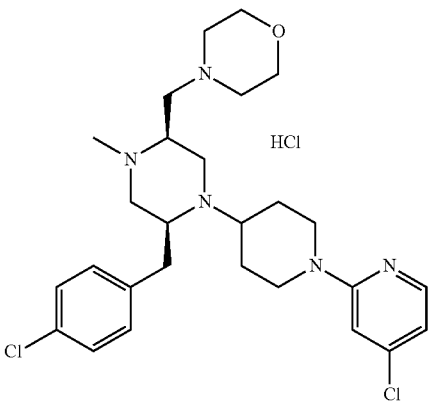 [SMILES: CN1C[C@H](Cc2ccc(Cl)cc2)N(C2CCN(c3cc(Cl)ccn3)CC2)C[C@@H]1CN1CCOCC1 ; Cl] | A | A/52% |

TABLE 1-continued
| Ex. # | Structure | YKL-40:4, IC$_{50}$/Kd | YKL-40:HS, IC$_{50}$/max % inh |
|---|---|---|---|
| 52. | 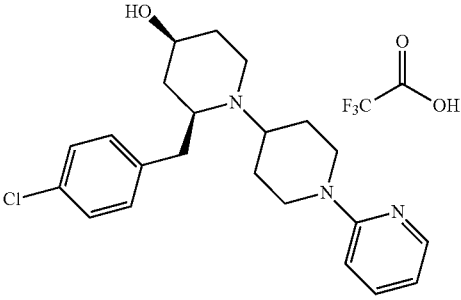 | B | |
| 53. | 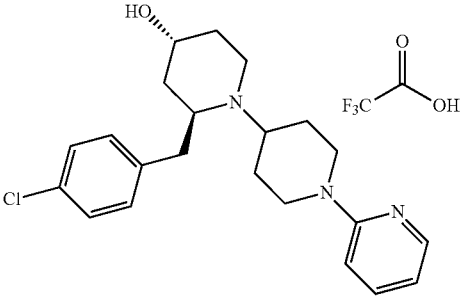 | A | |
| 54. | 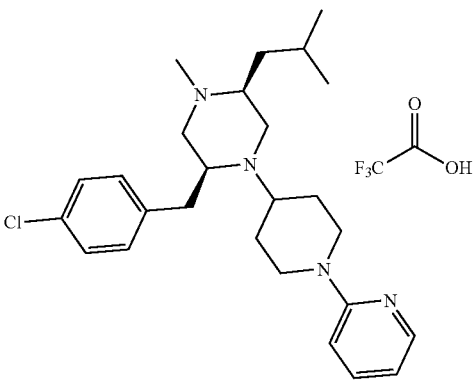 [SMILES: CC(C)C[C@H]1CN(C2CCN(c3ccccn3)CC2)[C@@H](Cc2ccc(Cl)cc2)CN1C ; O=C(O)C(F)(F)F] | B | A/83% |
| 55. | 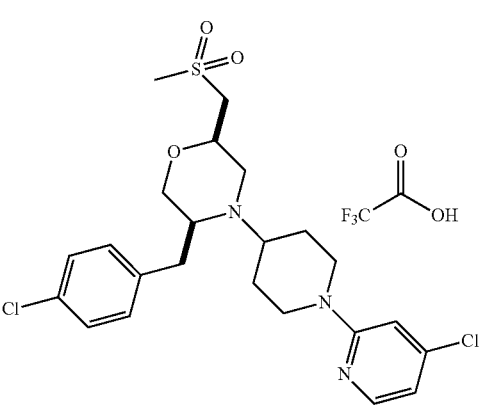 | A** | |

TABLE 1-continued
| Ex. # | Structure | YKL-40:4, IC$_{50}$/Kd | YKL-40:HS, IC$_{50}$/max % inh |
|---|---|---|---|
| 56. | 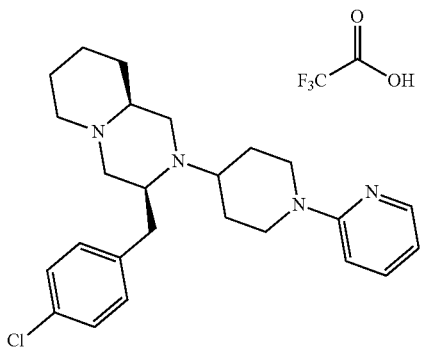 [SMILES: Clc1ccc(C[C@H]2CN3CCCC[C@H]3CN2C2CCN(c3ccccn3)CC2)cc1 ; O=C(O)C(F)(F)F] | B | |
| 57. | 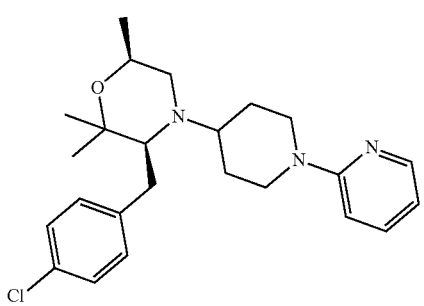 [SMILES: C[C@H]1CN(C2CCN(c3ccccn3)CC2)[C@@H](Cc2ccc(Cl)cc2)C(C)(C)O1] | E | |
| 58. | 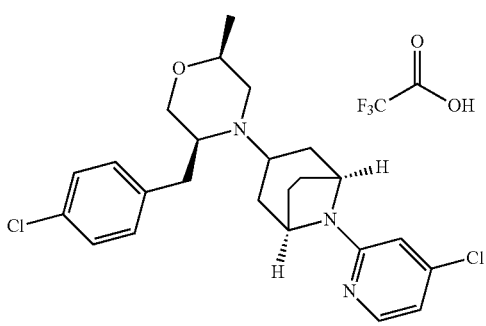 [SMILES: C[C@H]1CN(C2C[C@H]3CC[C@@H](C2)N3c2cc(Cl)ccn2)[C@@H](Cc2ccc(Cl)cc2)CO1 ; O=C(O)C(F)(F)F] | E | |
| 59. | 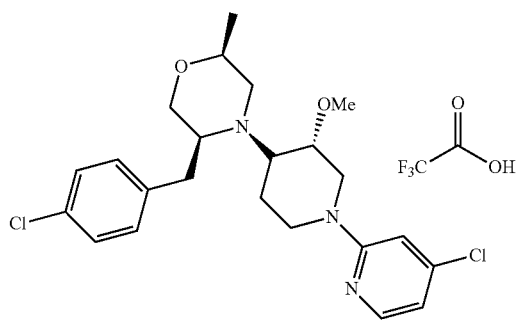 | C | |

TABLE 1-continued

| Ex. # | Structure | YKL-40:4, IC$_{50}$/Kd | YKL-40:HS, IC$_{50}$/max % inh |
|---|---|---|---|
| 60. | 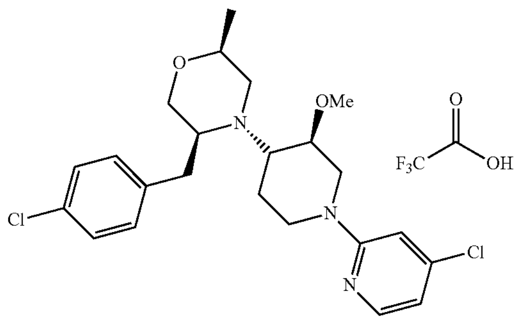 | D | |
| 61. | 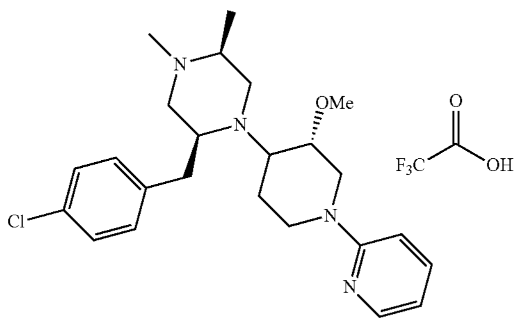 [SMILES: CO[C@@H]1CN(c2ccccn2)CCC1N1C[C@H](C)N(C)C[C@@H]1Cc1ccc(Cl)cc1 ; O=C(O)C(F)(F)F] | B | B/17% |
| 62. | 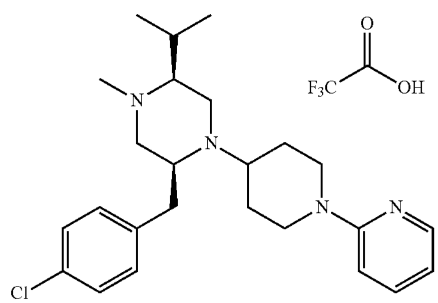 [SMILES: CC(C)[C@H]1CN(C2CCN(c3ccccn3)CC2)[C@@H](Cc2ccc(Cl)cc2)CN1C ; O=C(O)C(F)(F)F] | A** | |
| 63. | 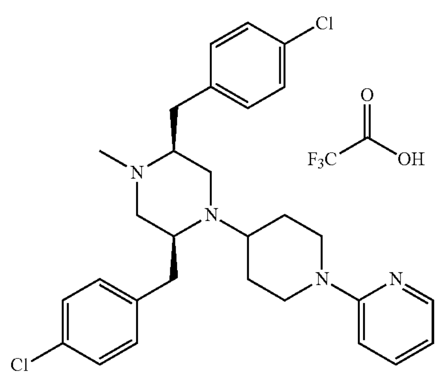 [SMILES: CN1C[C@H](Cc2ccc(Cl)cc2)N(C2CCN(c3ccccn3)CC2)C[C@@H]1Cc1ccc(Cl)cc1 ; O=C(O)C(F)(F)F] | C | B/85% |

TABLE 1-continued

| Ex. # | Structure | YKL-40:4, IC$_{50}$/Kd | YKL-40:HS, IC$_{50}$/max % inh |
|---|---|---|---|
| 64. | 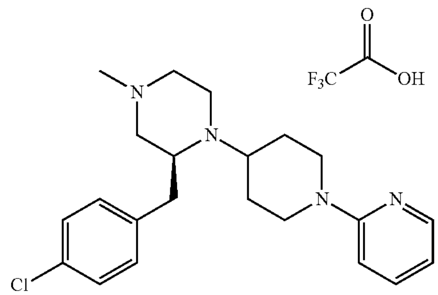 [SMILES: CN1CCN(C2CCN(c3ccccn3)CC2)[C@@H](Cc2ccc(Cl)cc2)C1 ; O=C(O)C(F)(F)F] | B | |
| 65. | 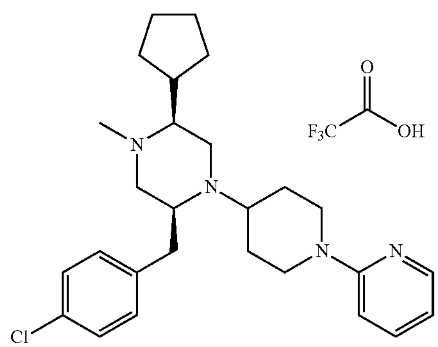 [SMILES: CN1C[C@H](Cc2ccc(Cl)cc2)N(C2CCN(c3ccccn3)CC2)C[C@@H]1C1CCCC1 ; O=C(O)C(F)(F)F] | B | A/81% |
| 66. | 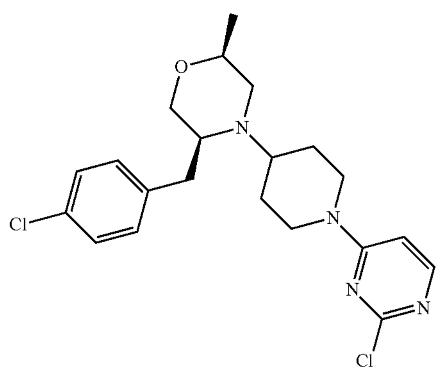 [SMILES: C[C@H]1CN(C2CCN(c3ccnc(Cl)n3)CC2)[C@@H](Cc2ccc(Cl)cc2)CO1] | E | |
| 67. | 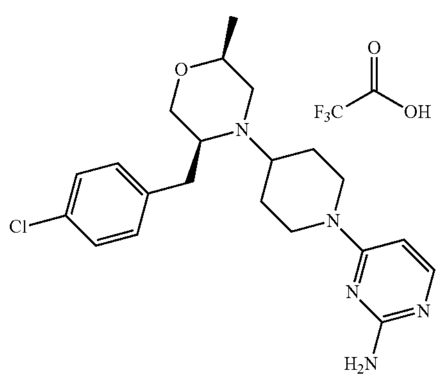 | E | |

TABLE 1-continued

| Ex. # | Structure | YKL-40:4, IC$_{50}$/Kd | YKL-40:HS, IC$_{50}$/max % inh |
|---|---|---|---|
| 68. | 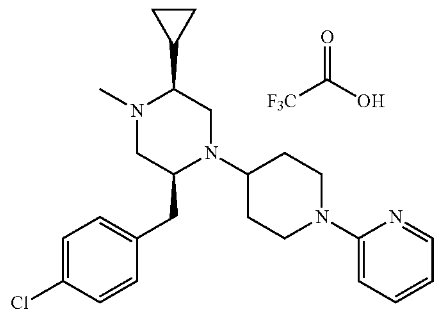 | B | A/46% |
| 69. | 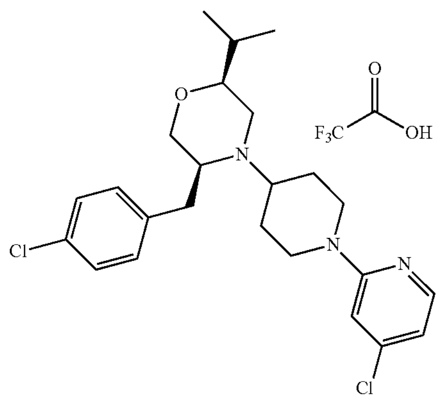 | B | |
| 70. | 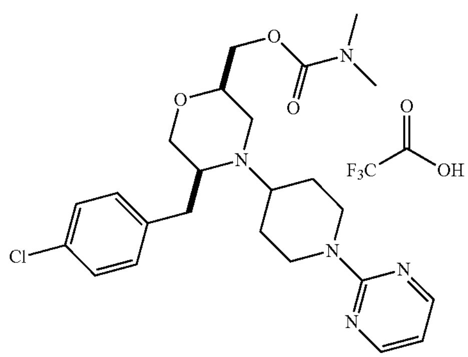 | C | |
| 71. | 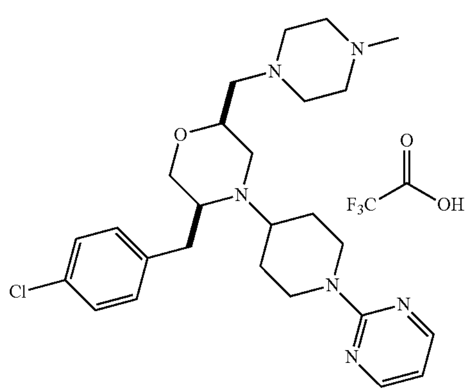 | C | |

TABLE 1-continued

| Ex. # | Structure | YKL-40:4, IC$_{50}$/Kd | YKL-40:HS, IC$_{50}$/max % inh |
|---|---|---|---|
| 72. | 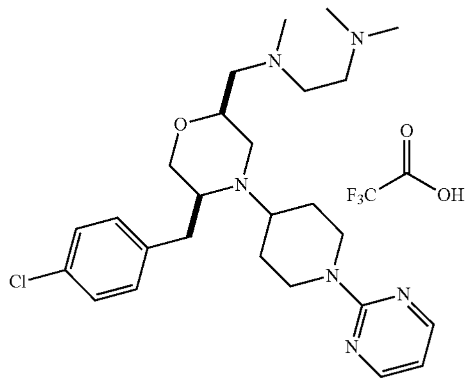 | C | |
| 73. | 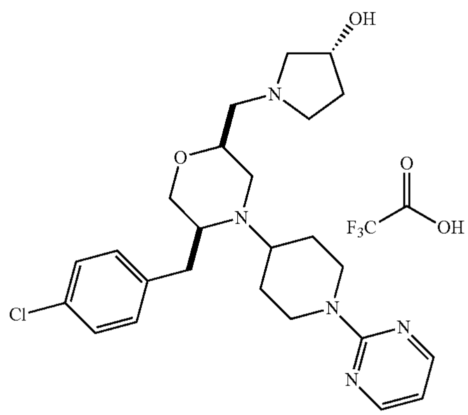 | C | |
| 74. | 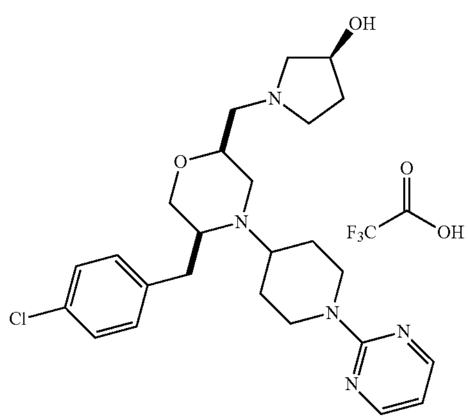 | C | |
| 75. | 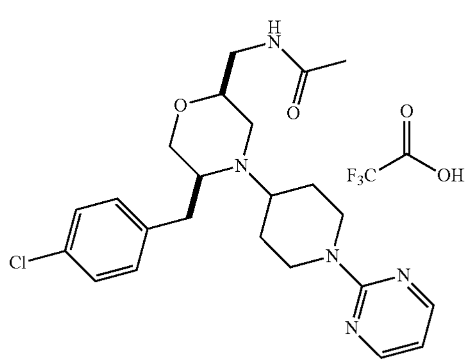 | B | |

TABLE 1-continued
| Ex. # | Structure | YKL-40:4, IC$_{50}$/Kd | YKL-40:HS, IC$_{50}$/max % inh |
|---|---|---|---|
| 76. | 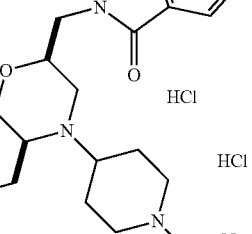 | | E |
| 77. | 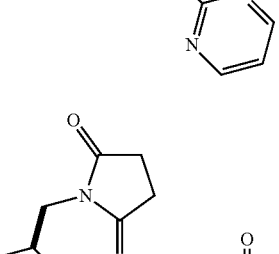 | | C |
| 78. | 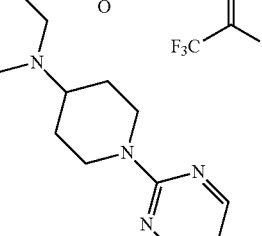 | | C |
| 79. | 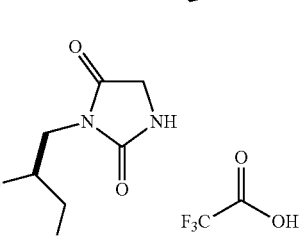 | | B** |

TABLE 1-continued

| Ex. # | Structure | YKL-40:4, IC$_{50}$/Kd | YKL-40:HS, IC$_{50}$/max % inh |
|---|---|---|---|
| 80. | 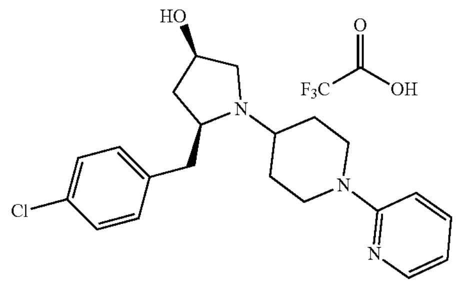 | E | |
| 81. | 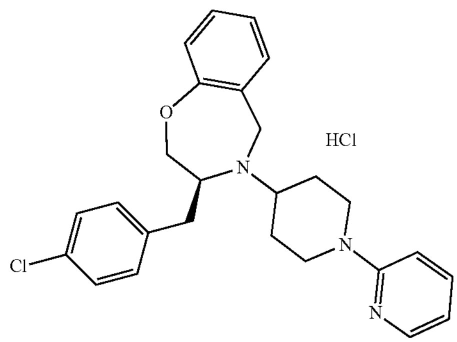 [SMILES: Clc1ccc(C[C@H]2COc3ccccc3CN2C2CCN(c3ccccn3)CC2)cc1 ; Cl] | E | |
| 82. | 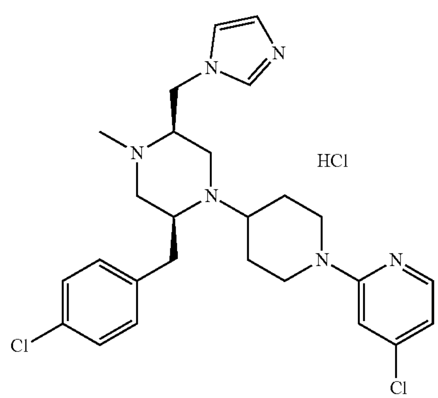 [SMILES: CN1C[C@H](Cc2ccc(Cl)cc2)N(C2CCN(c3cc(Cl)ccn3)CC2)C[C@@H]1Cn1ccnc1 ; Cl] | A | A/75% |
| 83. | 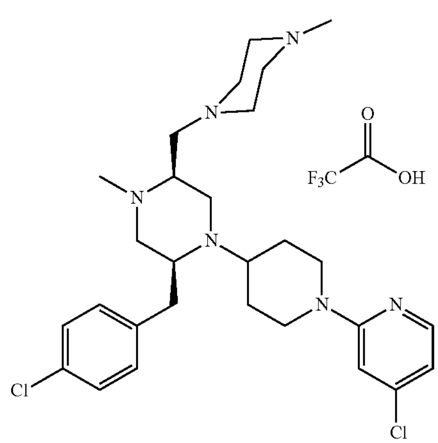 [SMILES: CN1CCN(C[C@H]2CN(C3CCN(c4cc(Cl)ccn4)CC3)[C@@H](Cc3ccc(Cl)cc3)CN2C)CC1 ; O=C(O)C(F)(F)F] | A | |

TABLE 1-continued
| Ex. # | Structure | YKL-40:4, IC$_{50}$/Kd | YKL-40:HS, IC$_{50}$/max % inh |
|---|---|---|---|
| 84. | 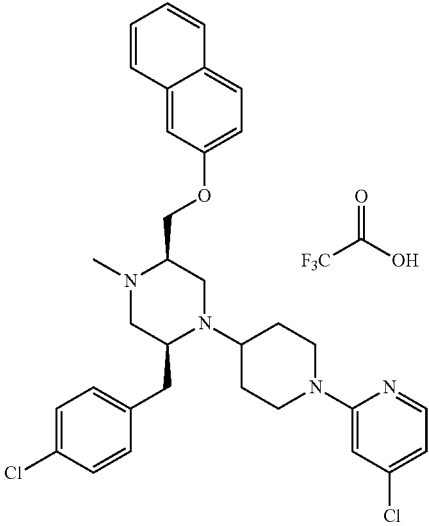 [SMILES: CN1C[C@H](Cc2ccc(Cl)cc2)N(C2CCN(c3cc(Cl)ccn3)CC2)C[C@@H]1COc1ccc2ccccc2c1 ; O=C(O)C(F)(F)F] | | E |
| 85. | 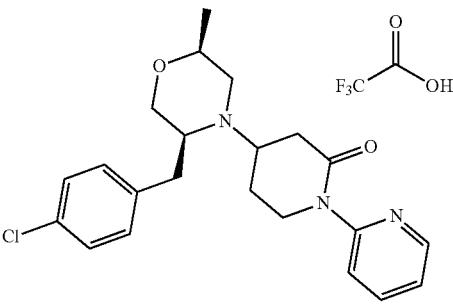 [SMILES: C[C@H]1CN(C2CCN(c3ccccn3)C(=O)C2)[C@@H](Cc2ccc(Cl)cc2)CO1 ; O=C(O)C(F)(F)F] | | D |
| 86. | 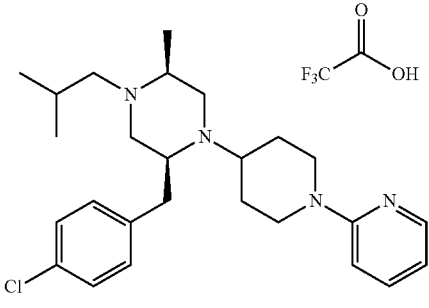 [SMILES: CC(C)CN1C[C@H](Cc2ccc(Cl)cc2)N(C2CCN(c3ccccn3)CC2)C[C@@H]1C ; O=C(O)C(F)(F)F] | | B |
| 87. | 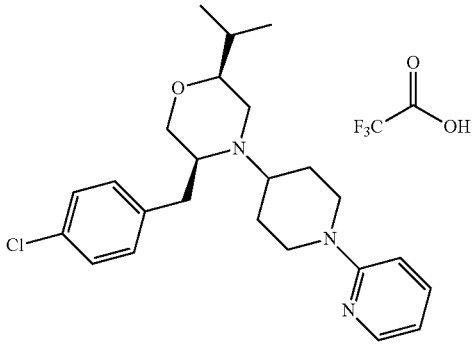 [SMILES: CC(C)[C@H]1CN(C2CCN(c3ccccn3)CC2)[C@@H](Cc2ccc(Cl)cc2)CO1 ; O=C(O)C(F)(F)F] | | B |

TABLE 1-continued
| Ex. # | Structure | YKL-40:4, IC$_{50}$/Kd | YKL-40:HS, IC$_{50}$/max % inh |
|---|---|---|---|
| 88. | 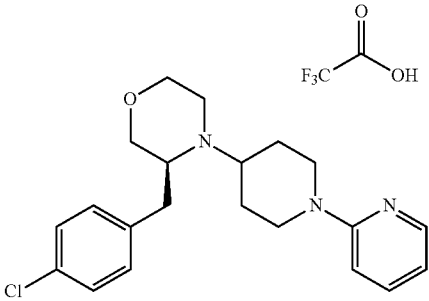 [SMILES: O=C(O)C(F)(F)F ; Clc1ccc(C[C@H]2COCCN2C2CCN(c3ccccn3)CC2)cc1] | | B |
| 89. | 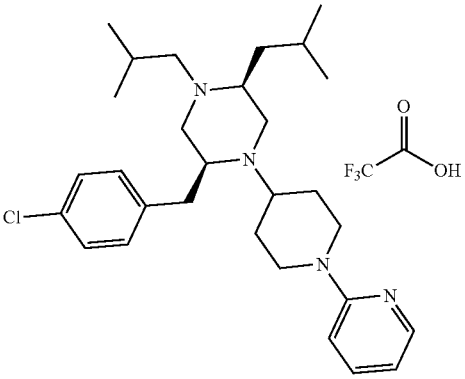 | | C |
| 90. | 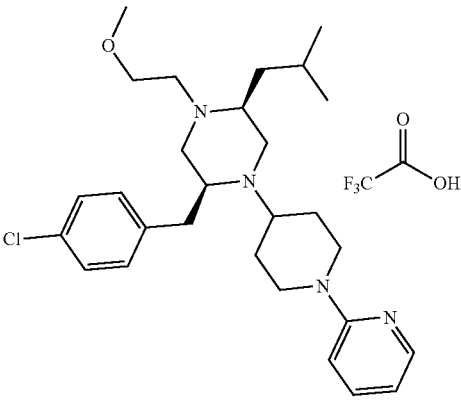 | | C |
| 91. | 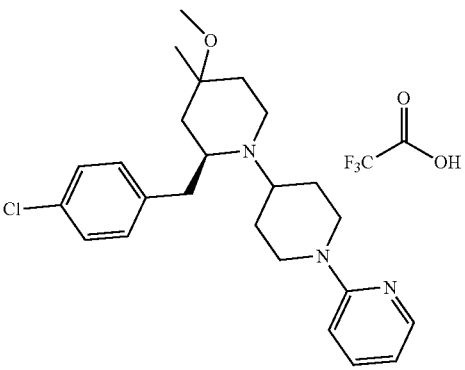 | | A |

TABLE 1-continued

| Ex. # | Structure | YKL-40:4, IC$_{50}$/Kd | YKL-40:HS, IC$_{50}$/max % inh |
|---|---|---|---|
| 92. | 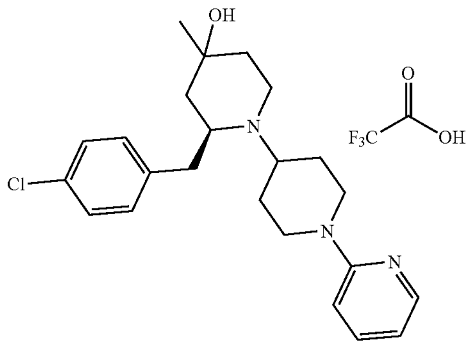 | A | |
| 93. | 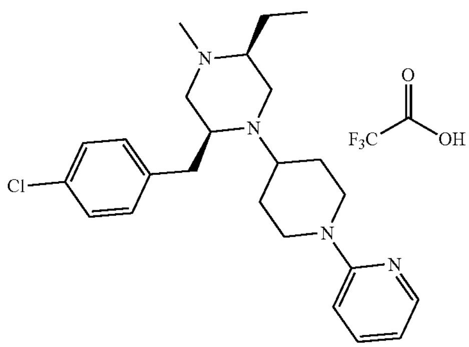 | D | |
| 94. | 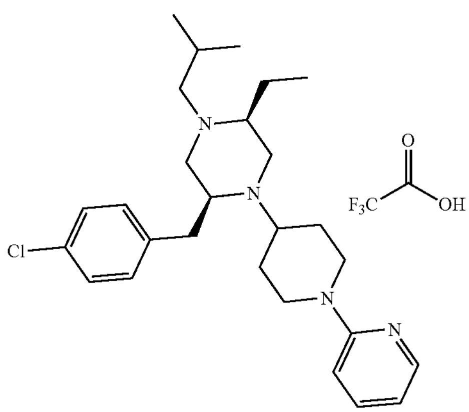 | C | |
| 95. | 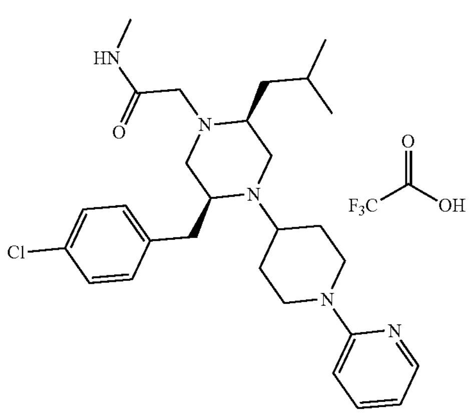 | A | A/85% |

TABLE 1-continued

| Ex. # | Structure | YKL-40:4, IC$_{50}$/Kd | YKL-40:HS, IC$_{50}$/max % inh |
|---|---|---|---|
| 96. | 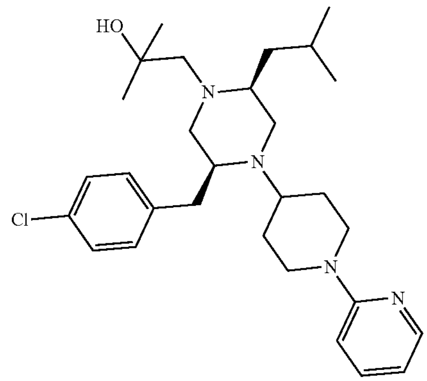 [SMILES: CC(C)C[C@H]1CN(C2CCN(c3ccccn3)CC2)[C@@H](Cc2ccc(Cl)cc2)CN1CC(C)(C)O] | C | |
| 97. | 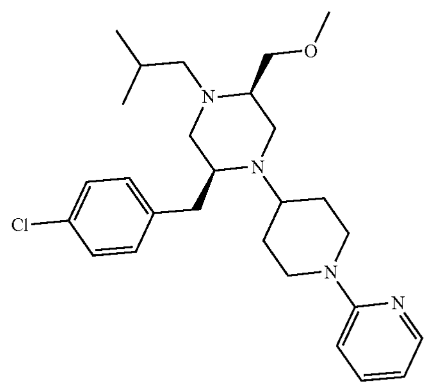 [SMILES: COC[C@H]1CN(C2CCN(c3ccccn3)CC2)[C@@H](Cc2ccc(Cl)cc2)CN1CC(C)C] | B | |
| 98. | 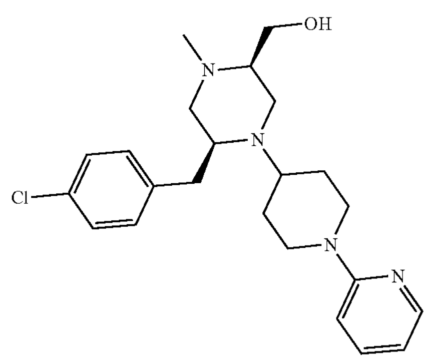 [SMILES: CN1C[C@H](Cc2ccc(Cl)cc2)N(C2CCN(c3ccccn3)CC2)C[C@@H]1CO] | B | A/20% |
| 99. | 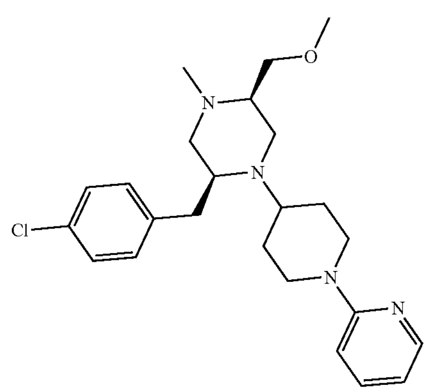 [SMILES: COC[C@H]1CN(C2CCN(c3ccccn3)CC2)[C@@H](Cc2ccc(Cl)cc2)CN1C] | A | |

TABLE 1-continued

| Ex. # | Structure | YKL-40:4, IC$_{50}$/Kd | YKL-40:HS, IC$_{50}$/max % inh |
|---|---|---|---|
| 100. | 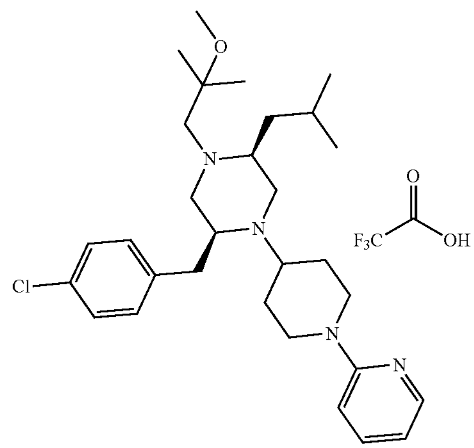 | C | |
| 101 | 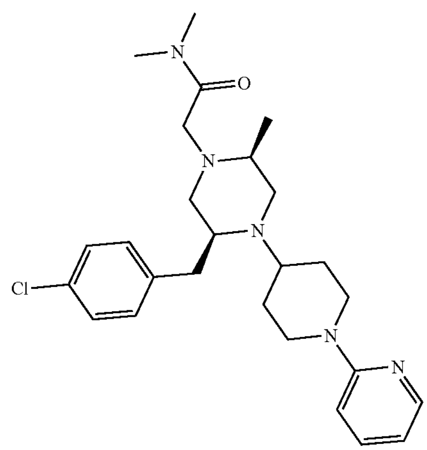 [SMILES: C[C@H]1CN(C2CCN(c3ccccn3)CC2)[C@@H](Cc2ccc(Cl)cc2)CN1CC(=O)N(C)C] | B | |
| 102. | 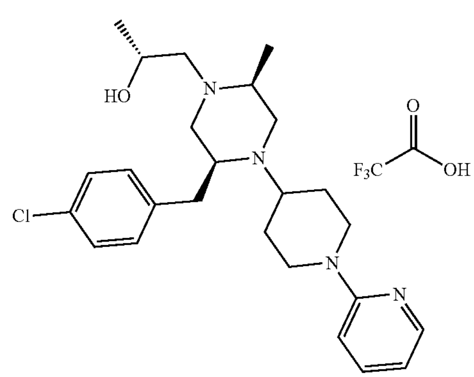 | B | |

TABLE 1-continued
| Ex. # | Structure | YKL-40:4, IC$_{50}$/Kd | YKL-40:HS, IC$_{50}$/max % inh |
|---|---|---|---|
| 103. | 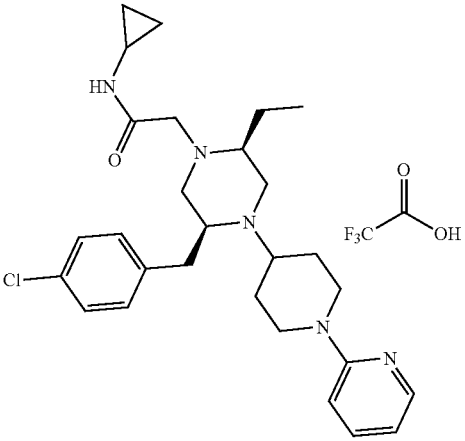 | B | |
| 104. | 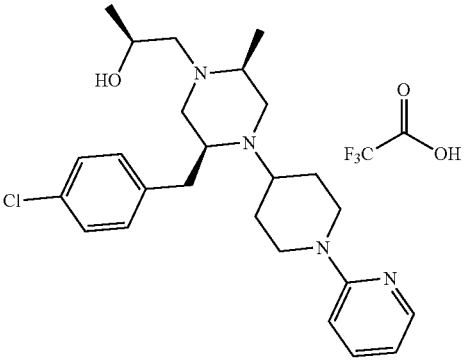 | A | |
| 105. | 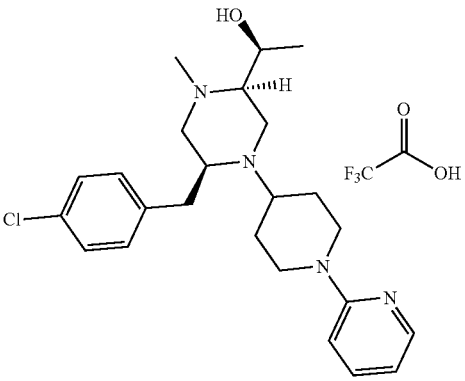 | A | |
| 106. | 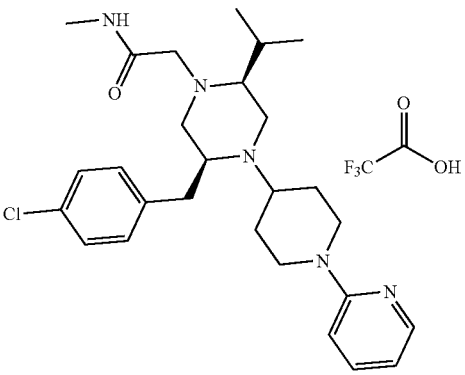 | A | A/27% |

TABLE 1-continued
| Ex. # | Structure | YKL-40:4, IC$_{50}$/Kd | YKL-40:HS, IC$_{50}$/max % inh |
|---|---|---|---|
| 107. | 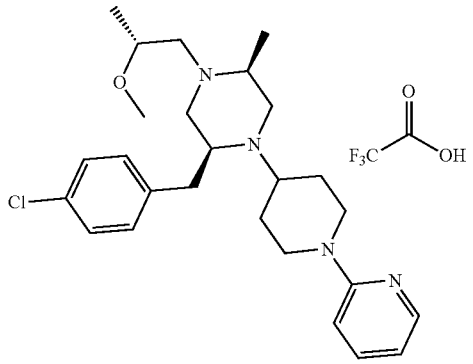 | | B |
| 108. | 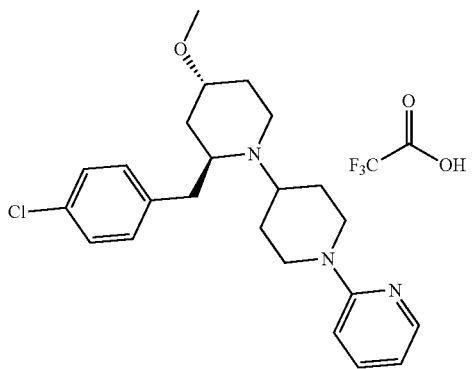 | | A |
| 109. | 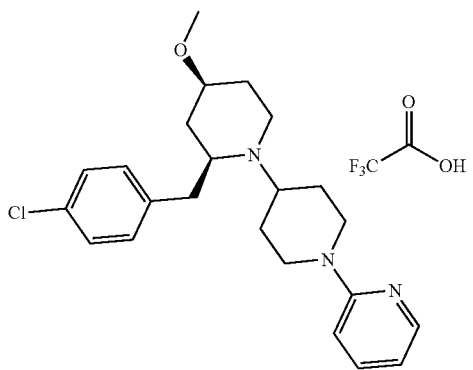 | | B |
| 110. | 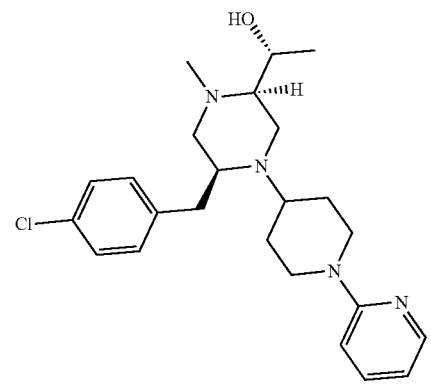 [SMILES: C[C@@H](O)[C@H]1CN(C2CCN(c3ccccn3)CC2)[C@@H](Cc2ccc(Cl)cc2)CN1C] | | A |

TABLE 1-continued
| Ex. # | Structure | YKL-40:4, IC$_{50}$/Kd | YKL-40:HS, IC$_{50}$/max % inh |
|---|---|---|---|
| 111. | 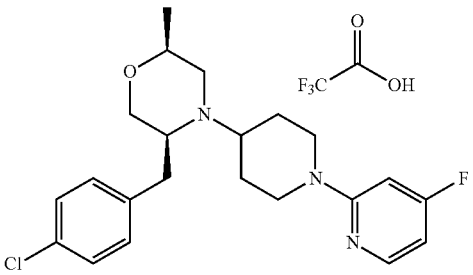 | A | |
| 112. | 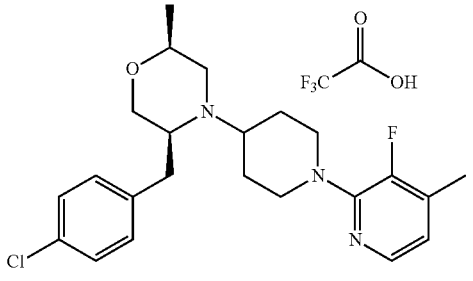 | B | A/30% |
| 113. | 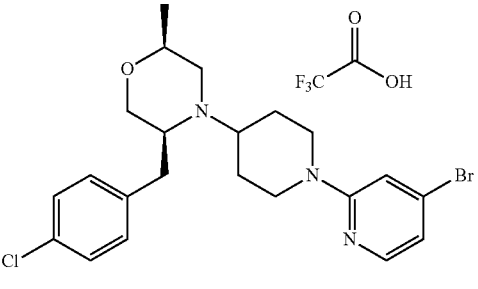 | B | |
| 114. | 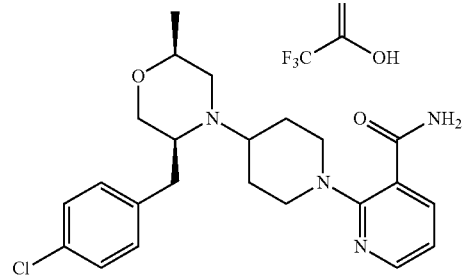 | E | |
| 115. | 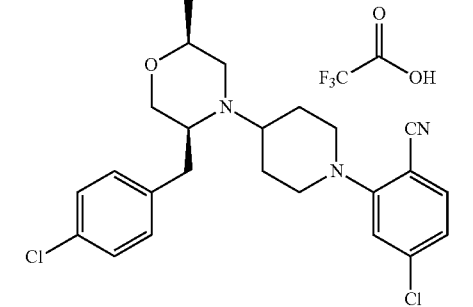 | E | |

TABLE 1-continued
| Ex. # | Structure | YKL-40:4, IC$_{50}$/Kd | YKL-40:HS, IC$_{50}$/max % inh |
|---|---|---|---|
| 116. | 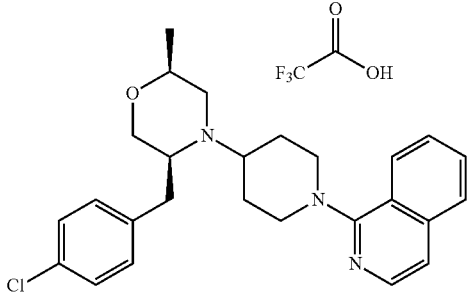 [SMILES: C[C@H]1CN(C2CCN(c3nccc4ccccc34)CC2)[C@@H](Cc2ccc(Cl)cc2)CO1 ; O=C(O)C(F)(F)F] | | E |
| 117. | 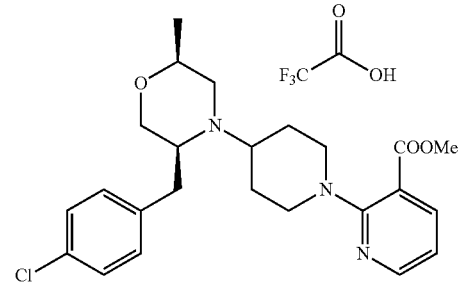 | | E |
| 118. | 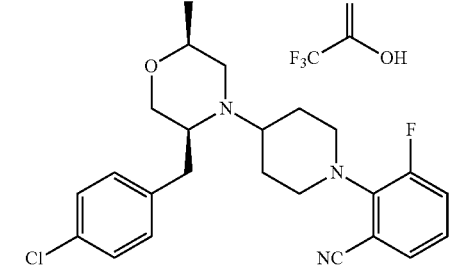 | | E |
| 119. | 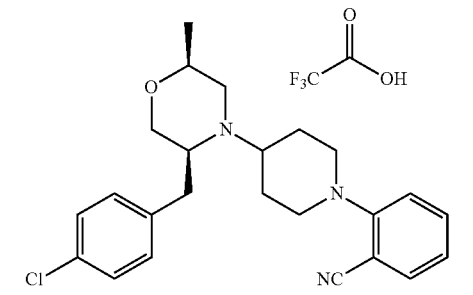 | | E |
| 120. | 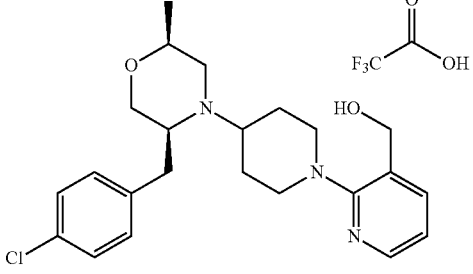 | | E |

TABLE 1-continued

| Ex. # | Structure | YKL-40:4, IC$_{50}$/Kd | YKL-40:HS, IC$_{50}$/max % inh |
|---|---|---|---|
| 121. | 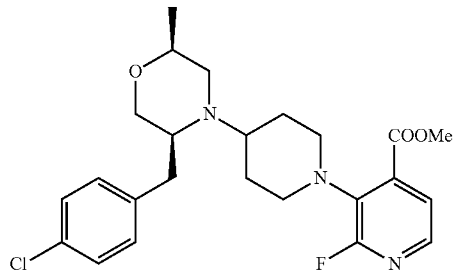 [SMILES: COC(=O)c1ccnc(F)c1N1CCC(N2C[C@H](C)OC[C@@H]2Cc2ccc(Cl)cc2)CC1] | | E |
| 122. | 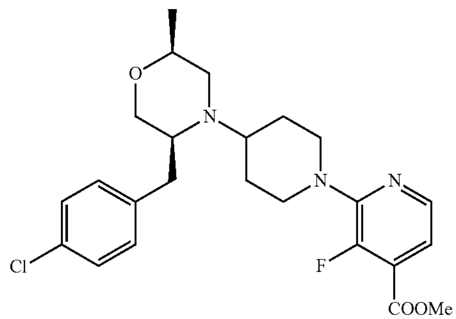 [SMILES: COC(=O)c1ccnc(N2CCC(N3C[C@H](C)OC[C@@H]3Cc3ccc(Cl)cc3)CC2)c1F] | | E |
| 123. | 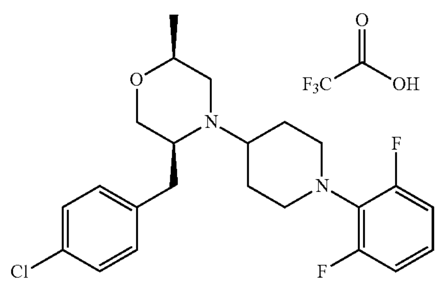 | | E |
| 124 | 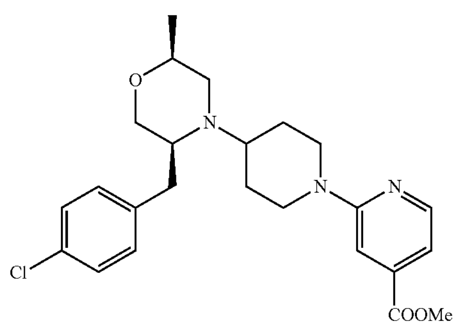 [SMILES: COC(=O)c1ccnc(N2CCC(N3C[C@H](C)OC[C@@H]3Cc3ccc(Cl)cc3)CC2)c1] | | E |
| 125. | 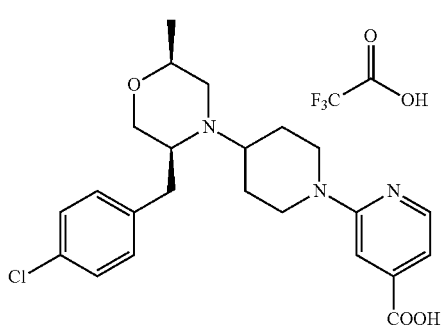 | | E |

TABLE 1-continued
| Ex. # | Structure | YKL-40:4, IC$_{50}$/Kd | YKL-40:HS, IC$_{50}$/max % inh |
|---|---|---|---|
| 126. | 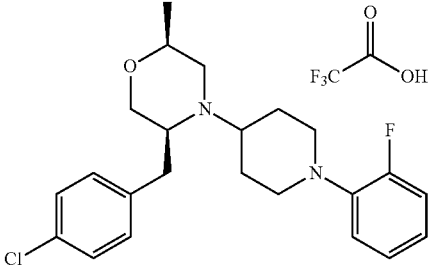 | | E |
| 127. | 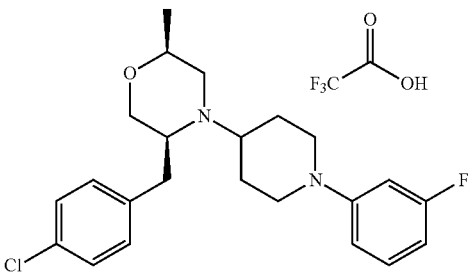 | | E |
| 128. | 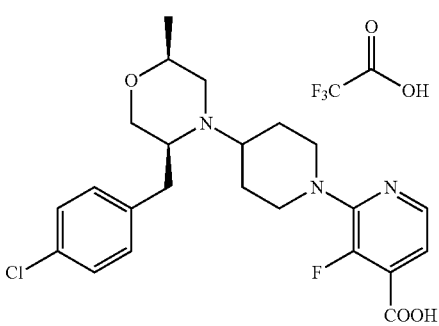 | | E |
| 129. | 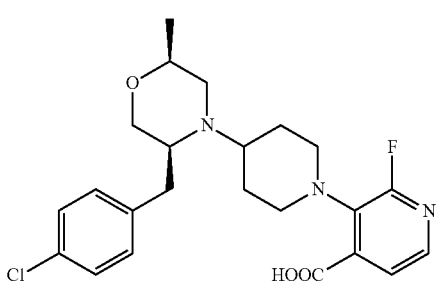 [SMILES: C[C@H]1CN(C2CCN(c3c(C(=O)O)ccnc3F)CC2)[C@@H](Cc2ccc(Cl)cc2)CO1] | | E |
| 130. | 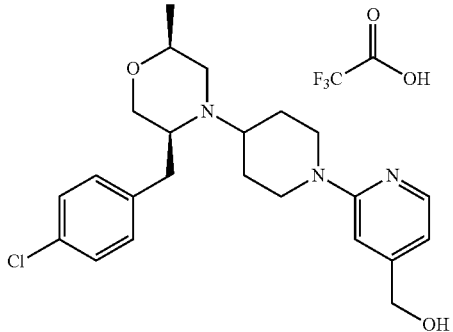 | | E |

TABLE 1-continued

| Ex. # | Structure | YKL-40:4, IC$_{50}$/Kd | YKL-40:HS, IC$_{50}$/max % inh |
|---|---|---|---|
| 131. | 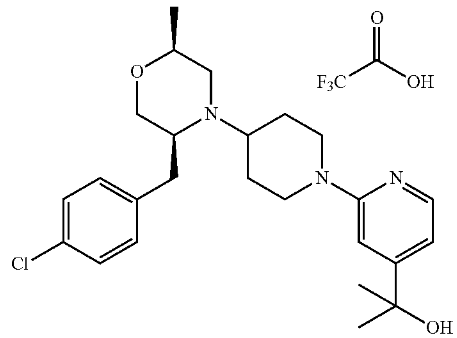 | E | |
| 132. | 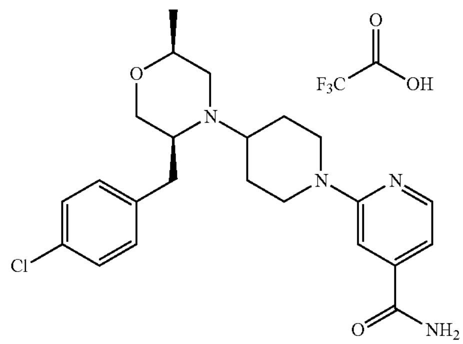 | E | |
| 133. | 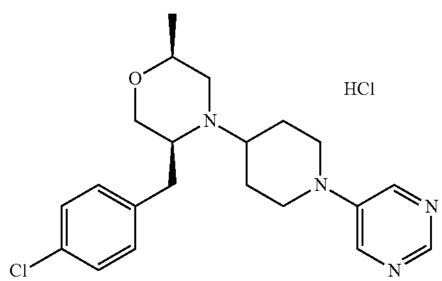 [SMILES: C[C@H]1CN(C2CCN(c3cncnc3)CC2)[C@@H](Cc2ccc(Cl)cc2)CO1 ; Cl] | B | |
| 134. | 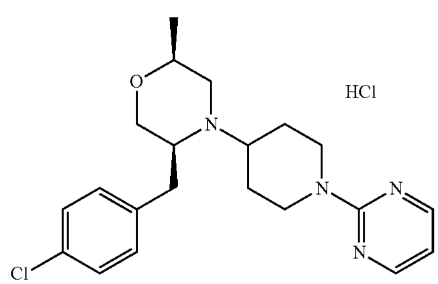 [SMILES: C[C@H]1CN(C2CCN(c3ncccn3)CC2)[C@@H](Cc2ccc(Cl)cc2)CO1 ; Cl] | B | |
| 135. | 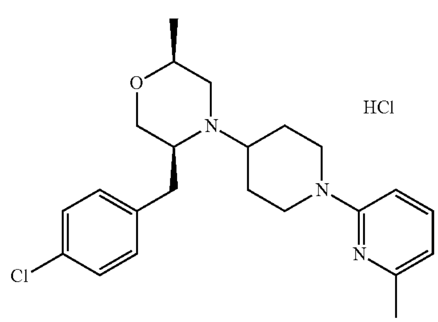 [SMILES: Cc1cccc(N2CCC(N3C[C@H](C)OC[C@@H]3Cc3ccc(Cl)cc3)CC2)n1 ; Cl] | E | |

TABLE 1-continued
| Ex. # | Structure | YKL-40:4, IC$_{50}$/Kd | YKL-40:HS, IC$_{50}$/max % inh |
|---|---|---|---|
| 136. | 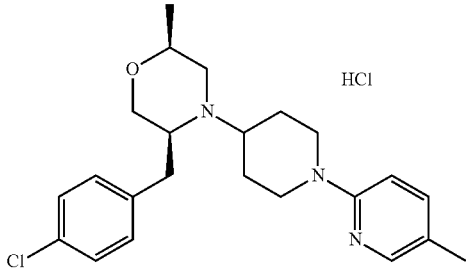 [SMILES: Cc1ccc(N2CCC(N3C[C@H](C)OC[C@@H]3Cc3ccc(Cl)cc3)CC2)nc1 ; Cl] HCl | E | |
| 137. | 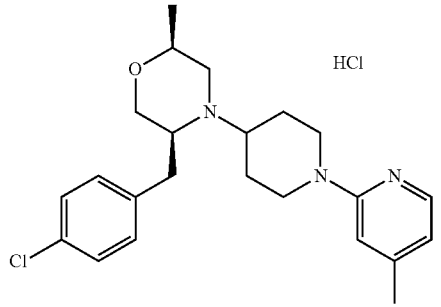 [SMILES: Cc1ccnc(N2CCC(N3C[C@H](C)OC[C@@H]3Cc3ccc(Cl)cc3)CC2)c1 ; Cl] HCl | A | |
| 138. | 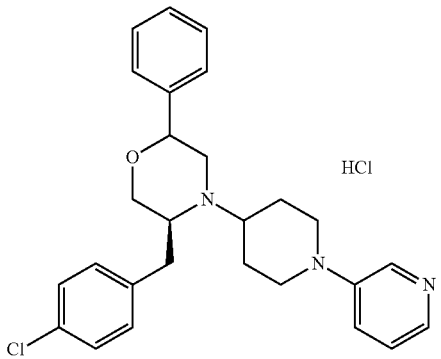 [SMILES: Clc1ccc(C[C@H]2COC(c3ccccc3)CN2C2CCN(c3cccnc3)CC2)cc1 ; Cl] HCl | C | B/81% |
| 139. | 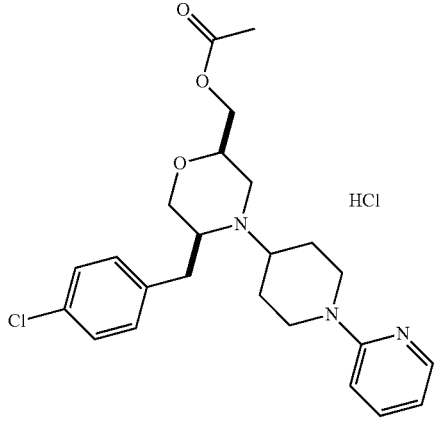 HCl | B | B/40% |

TABLE 1-continued

| Ex. # | Structure | YKL-40:4, IC$_{50}$/Kd | YKL-40:HS, IC$_{50}$/max % inh |
|---|---|---|---|
| 140. | 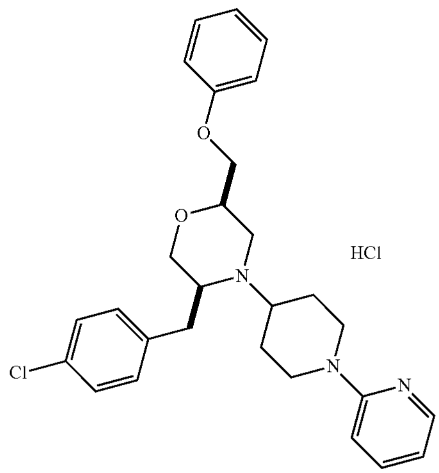 | E | |
| 141. | 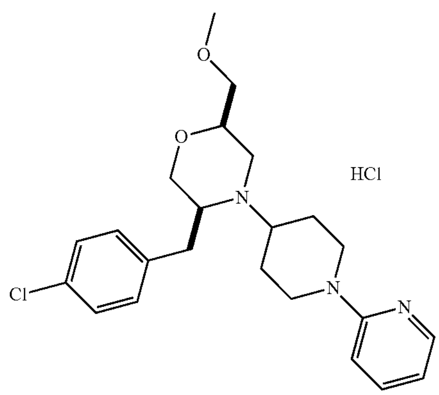 | B | |
| 142. | 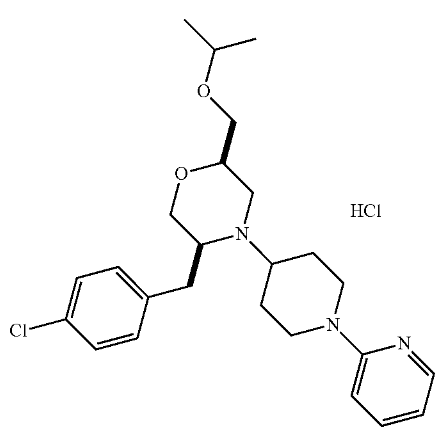 | B | A/73% |

TABLE 1-continued
| Ex. # | Structure | YKL-40:4, IC$_{50}$/Kd | YKL-40:HS, IC$_{50}$/max % inh |
|---|---|---|---|
| 143. | 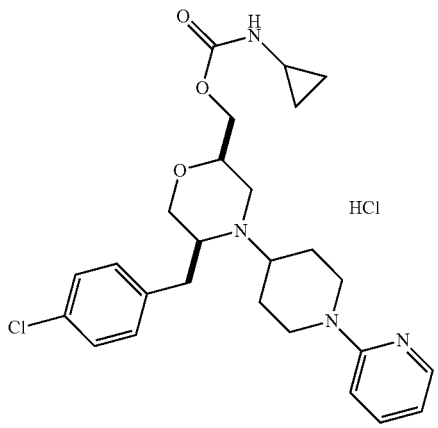 | B | B/56% |
| 144. | 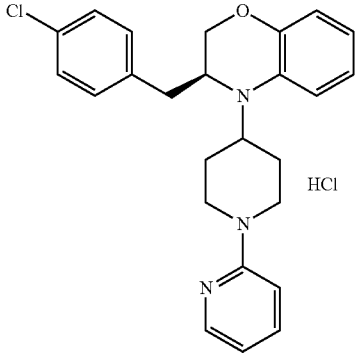 [SMILES: Clc1ccc(C[C@H]2COc3ccccc3N2C2CCN(c3ccccn3)CC2)cc1 ; Cl] | | E |
| 145 | 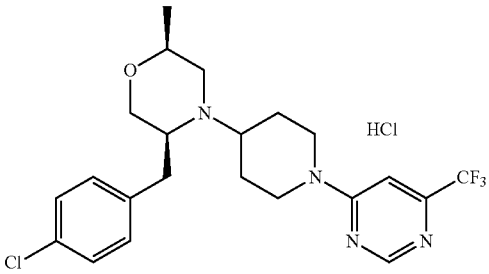 [SMILES: C[C@H]1CN(C2CCN(c3cc(C(F)(F)F)ncn3)CC2)[C@@H](Cc2ccc(Cl)cc2)CO1 ; Cl] | | E |
| 146. | 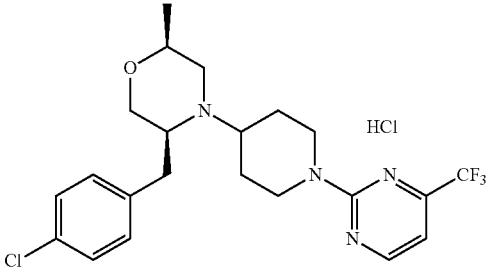 [SMILES: C[C@H]1CN(C2CCN(c3nccc(C(F)(F)F)n3)CC2)[C@@H](Cc2ccc(Cl)cc2)CO1 ; Cl] | | C |
| 147. | 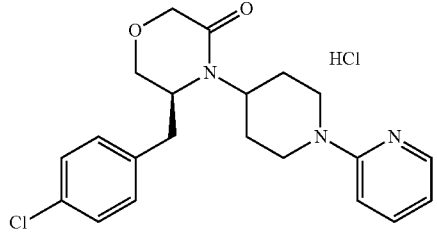 [SMILES: O=C1COC[C@H](Cc2ccc(Cl)cc2)N1C1CCN(c2ccccn2)CC1 ; Cl] | | E |

TABLE 1-continued
| Ex. # | Structure | YKL-40:4, IC$_{50}$/Kd | YKL-40:HS, IC$_{50}$/max % inh |
|---|---|---|---|
| 148. | 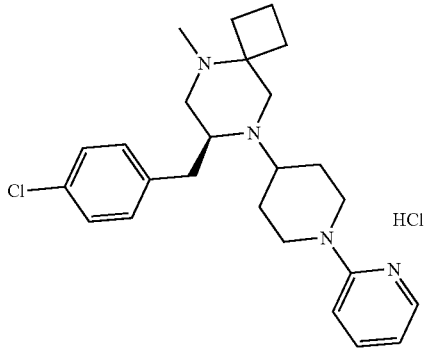 [SMILES: CN1C[C@H](Cc2ccc(Cl)cc2)N(C2CCN(c3ccccn3)CC2)CC12CCC2 ; Cl] | B | |
| 149. | 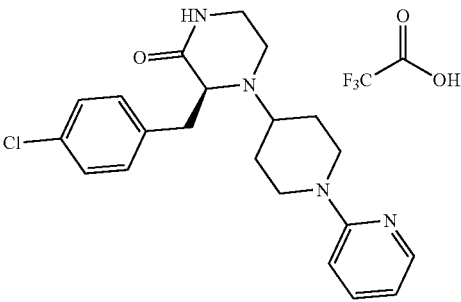 [SMILES: O=C1NCCN(C2CCN(c3ccccn3)CC2)[C@H]1Cc1ccc(Cl)cc1 ; O=C(O)C(F)(F)F] | E | |
| 150. | 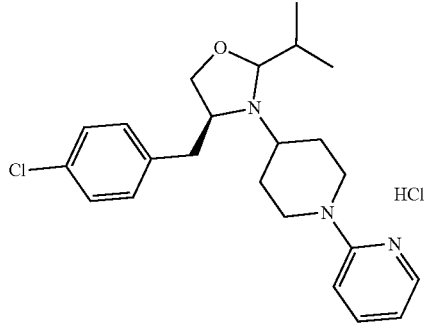<br>2 isomers due to undefined isopropyl stereocentre | E | |
| 151. | 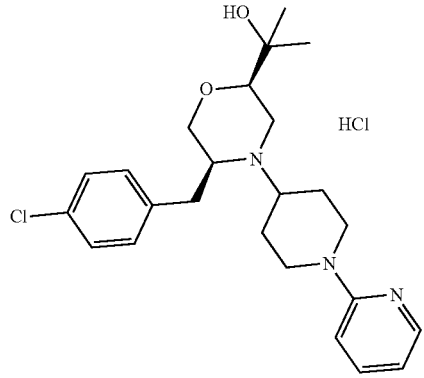 [SMILES: CC(C)(O)[C@H]1CN(C2CCN(c3ccccn3)CC2)[C@@H](Cc2ccc(Cl)cc2)CO1 ; Cl] | A | A/25% |

TABLE 1-continued
| Ex. # | Structure | YKL-40:4, IC$_{50}$/Kd | YKL-40:HS, IC$_{50}$/max % inh |
|---|---|---|---|
| 152. | 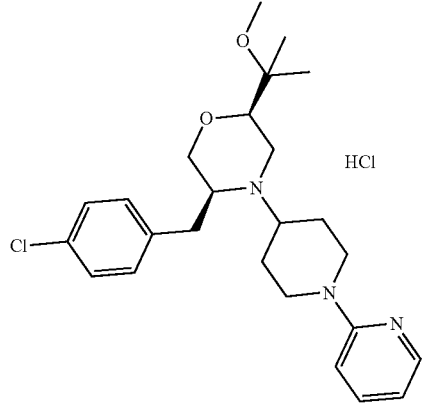 [SMILES: COC(C)(C)[C@H]1CN(C2CCN(c3ccccn3)CC2)[C@@H](Cc2ccc(Cl)cc2)CO1 ; Cl] HCl | B | |
| 153. | 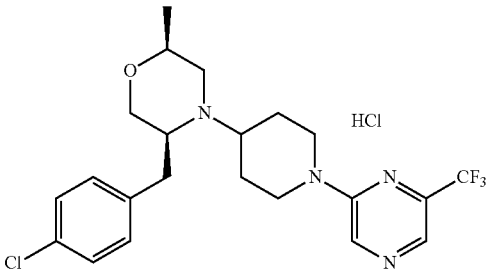 [SMILES: C[C@H]1CN(C2CCN(c3cncc(C(F)(F)F)n3)CC2)[C@@H](Cc2ccc(Cl)cc2)CO1 ; Cl] HCl | E | |
| 154. | 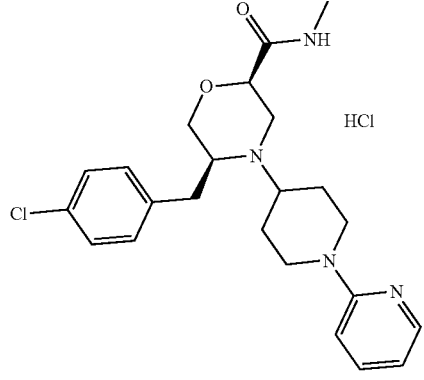 [SMILES: CNC(=O)[C@H]1CN(C2CCN(c3ccccn3)CC2)[C@@H](Cc2ccc(Cl)cc2)CO1 ; Cl] HCl | B | |
| 155. | 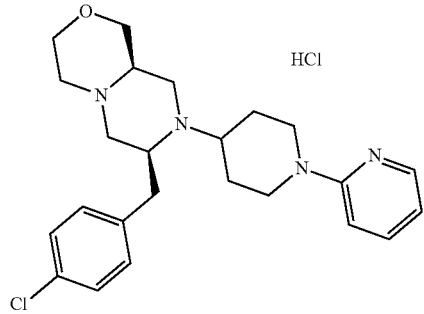 [SMILES: Clc1ccc(C[C@H]2CN3CCOC[C@H]3CN2C2CCN(c3ccccn3)CC2)cc1 ; Cl] HCl | A | |

TABLE 1-continued
| Ex. # | Structure | YKL-40:4, IC$_{50}$/Kd | YKL-40:HS, IC$_{50}$/max % inh |
|---|---|---|---|
| 156. | 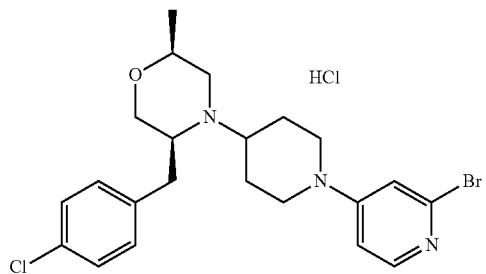 [SMILES: C[C@H]1CN(C2CCN(c3ccnc(Br)c3)CC2)[C@@H](Cc2ccc(Cl)cc2)CO1 ; Cl] | D | |
| 157. | 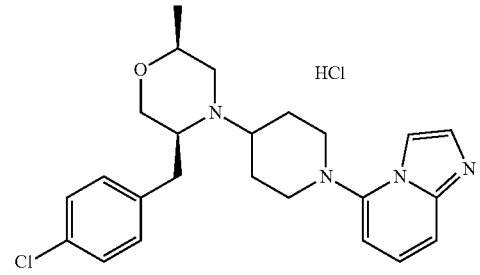 [SMILES: C[C@H]1CN(C2CCN(c3cccc4nccn34)CC2)[C@@H](Cc2ccc(Cl)cc2)CO1 ; Cl] | D | |
| 158. | 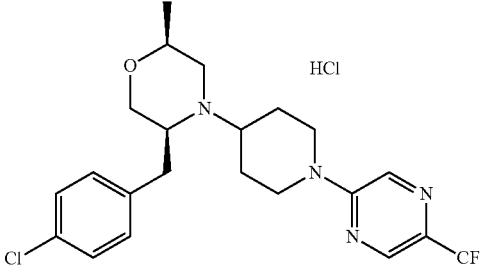 | E | |
| 159. | 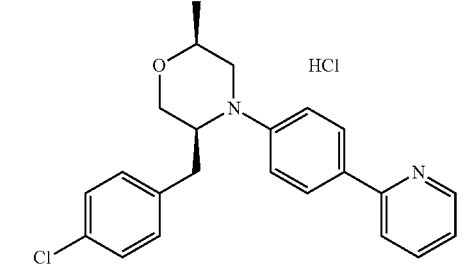 [SMILES: C[C@H]1CN(c2ccc(-c3ccccn3)cc2)[C@@H](Cc2ccc(Cl)cc2)CO1 ; Cl] | B | |
| 160. | 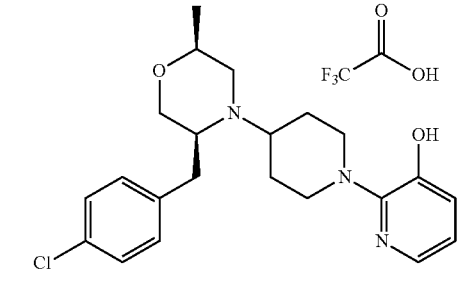 | E | |

TABLE 1-continued
| Ex. # | Structure | YKL-40:4, IC$_{50}$/Kd | YKL-40:HS, IC$_{50}$/max % inh |
|---|---|---|---|
| 161. | 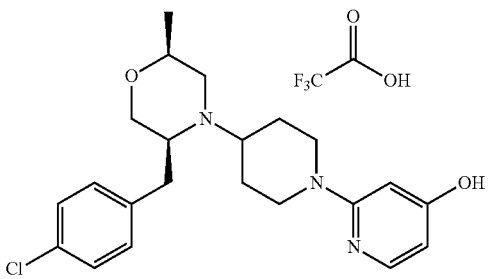 | D | |
| 162. | 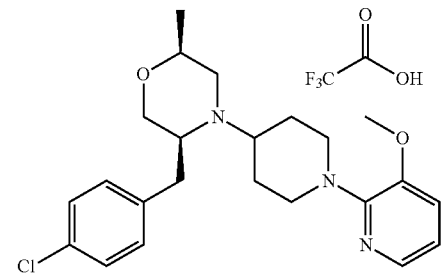 | E | |
| 163. | 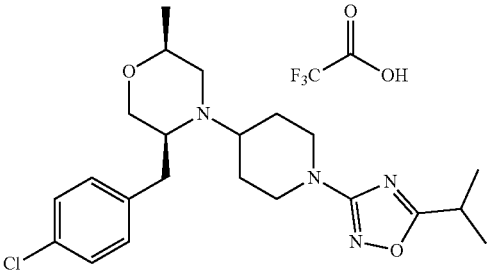 | E | |
| 164. | 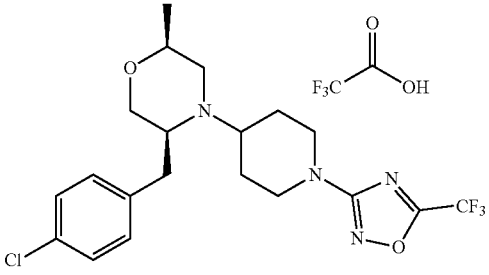 | E | |
| 165. | 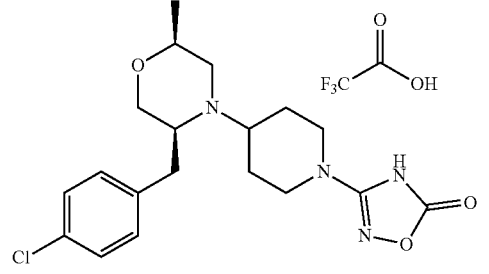 | E | |

TABLE 1-continued
| Ex. # | Structure | YKL-40:4, IC$_{50}$/Kd | YKL-40:HS, IC$_{50}$/max % inh |
|---|---|---|---|
| 166. | 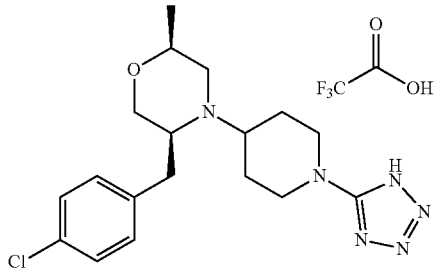 | | E |
| 167. | 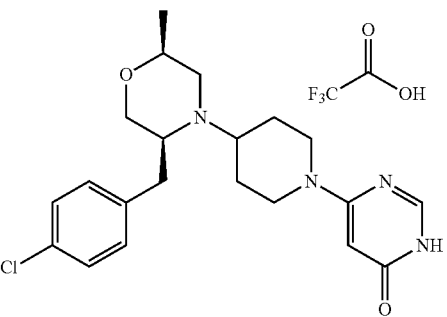 | | E |
| 168. | 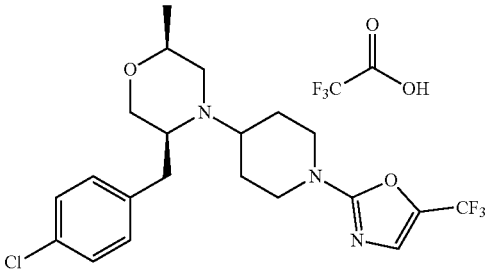 | | E |
| 169. | 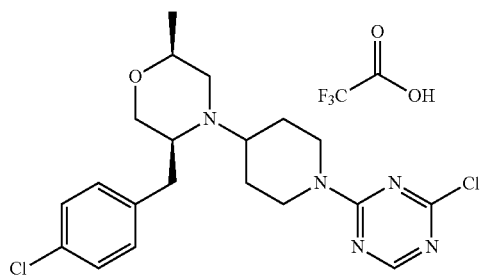 | | E |
| 170. | 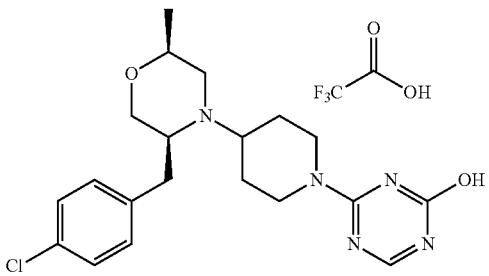 | | E |

TABLE 1-continued
| Ex. # | Structure | YKL-40:4, IC$_{50}$/Kd | YKL-40:HS, IC$_{50}$/max % inh |
|---|---|---|---|
| 171. | 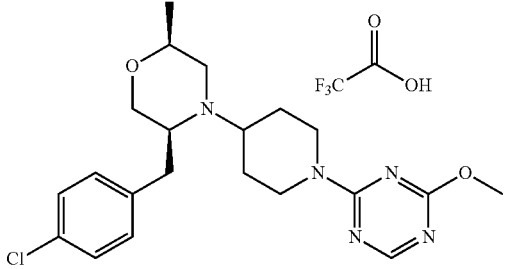 | | E |
| 172. | 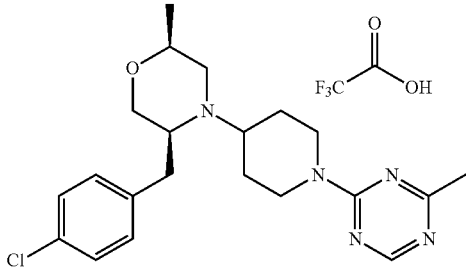 | | E |
| 173. | 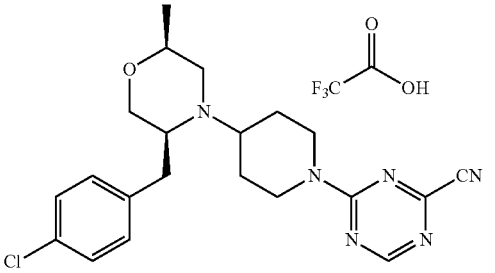 | | E |
| 174. | 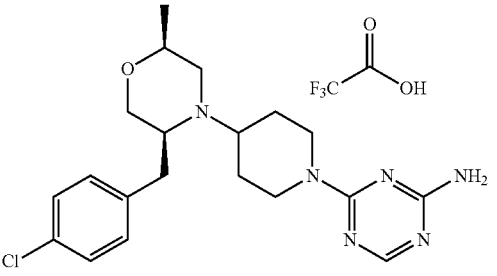 | | E |
| 175. | 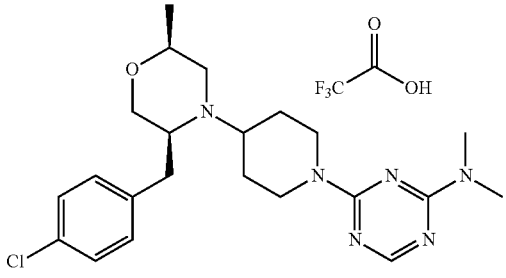 | | E |

TABLE 1-continued

| Ex. # | Structure | YKL-40:4, IC$_{50}$/Kd | YKL-40:HS, IC$_{50}$/max % inh |
|---|---|---|---|
| 176. | 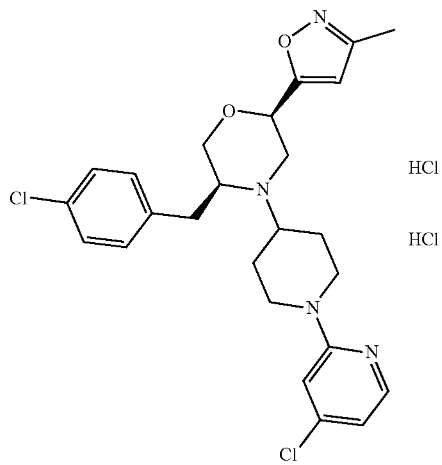 [SMILES: Cc1cc([C@H]2CN(C3CCN(c4cc(Cl)ccn4)CC3)[C@@H](Cc3ccc(Cl)cc3)CO2)on1 ; Cl ; Cl] | C | |
| 177. | 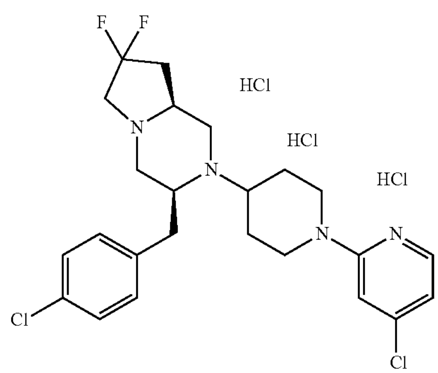 [SMILES: FC1(F)C[C@H]2CN(C3CCN(c4cc(Cl)ccn4)CC3)[C@@H](Cc3ccc(Cl)cc3)CN2C1 ; Cl ; Cl ; Cl] | B | |
| 178. | 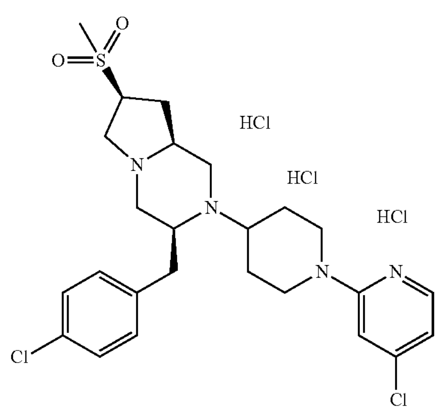 [SMILES: CS(=O)(=O)[C@H]1C[C@H]2CN(C3CCN(c4cc(Cl)ccn4)CC3)[C@@H](Cc3ccc(Cl)cc3)CN2C1 ; Cl ; Cl ; Cl] | A | |
| 179. | 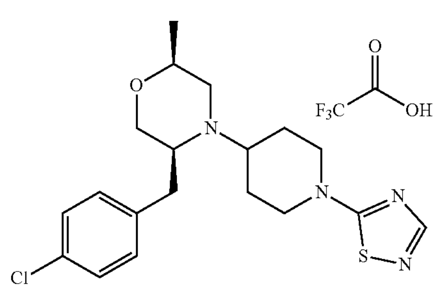 | E | |

TABLE 1-continued
| Ex. # | Structure | YKL-40:4, IC$_{50}$/Kd | YKL-40:HS, IC$_{50}$/max % inh |
|---|---|---|---|
| 180. | 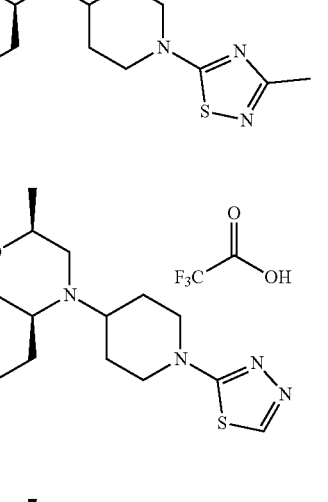 | E | |
| 181. | 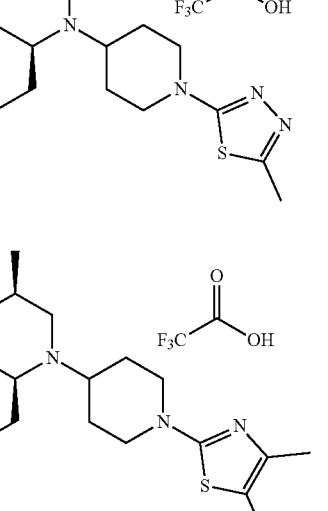 | E | |
| 182. | 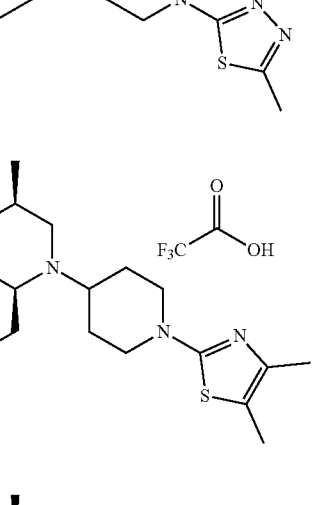 | E | |
| 183. | 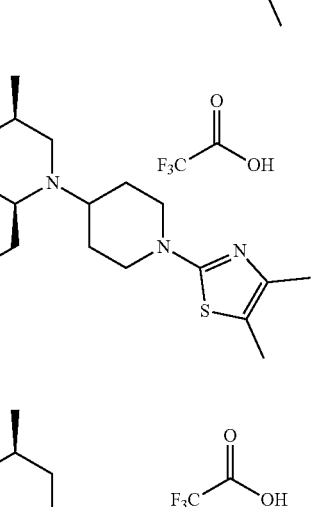 | A | A/53% |
| 184. | 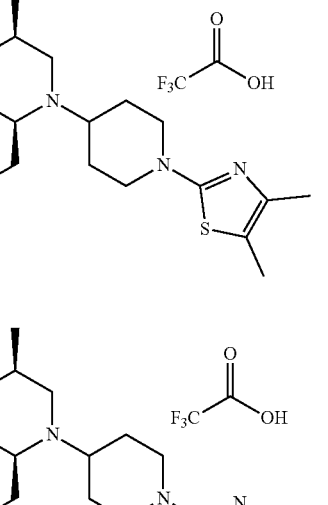 | C | |

TABLE 1-continued
| Ex. # | Structure | YKL-40:4, IC$_{50}$/Kd | YKL-40:HS, IC$_{50}$/max % inh |
|---|---|---|---|
| 185. | 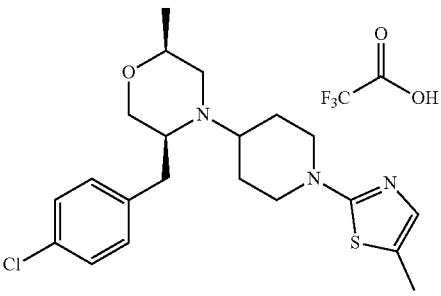 | A | B/36% |
| 186. | 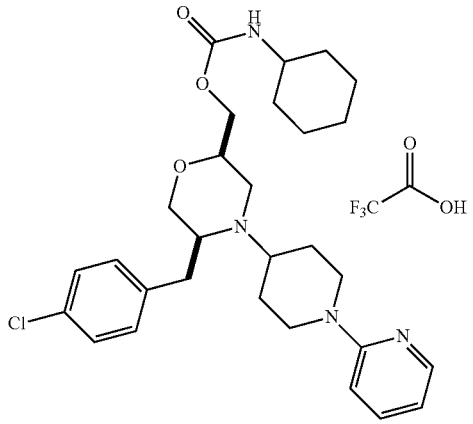 | C | |
| 187. | 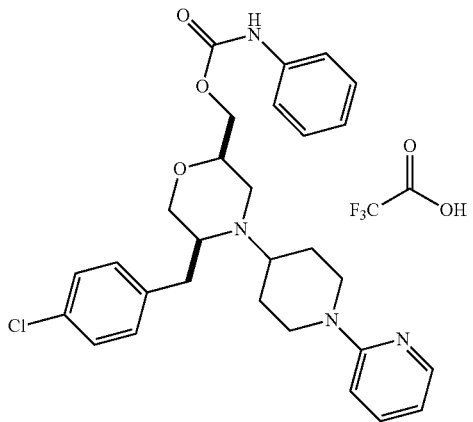 | E | |
| 188. | 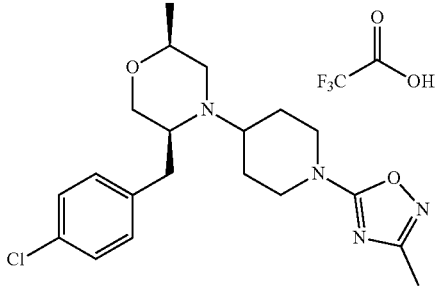 | E | |
**indicates that the range of activity was reassigned following repeated assays.

General Synthetic Procedures
General Procedure Ia
Reduction of an α-Amino Acid to the Corresponding Amino Alcohol

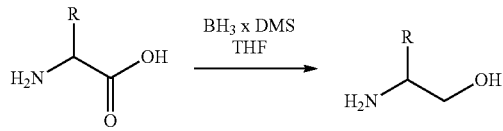

To a suspension of an amino acid in anhydrous tetrahydrofuran (THF) (3 mL/mmol) borane-dimethylsulfide complex (BH$_3$×DMS; 3 equivalents) was added dropwise at 0° C. (Caution: foaming!) The cooling bath was removed and the reaction mixture was refluxed overnight, after which time TLC control indicated completion of the reaction. The mixture was cooled to room temperature and 6M HCl (8 equivalents with respect to the starting material) was carefully added (Caution: foaming!) and the mixture was again refluxed for 1.5 hours. The mixture was cooled to room temperature and pH was brought up to 10 with suitable addition of 4M NaOH. Product was extracted several times with ethyl acetate (AcOEt), extracts were combined, dried over anhydrous MgSO$_4$, filtered and concentrated in vacuo. The crude product was triturated with ethyl ether (Et$_2$O) and filtered off.

General Procedure Ib
Reduction of a Morpholin-3-One to a Morpholine or an Amide to an Amine

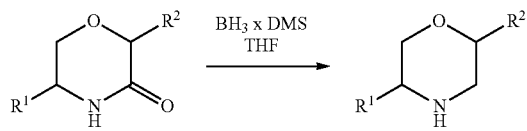

To the solution of either morpholin-3-one or 2-piperazinone or amide in THF (6 mL/mmol) borane-dimethylsulfide complex (BH$_3$×DMS; 5 equivalents) was added and the reaction mixture was refluxed overnight, after which time the TLC or LC-MS control indicated completed consumption of the starting material. Reaction mixture was cooled to room temperature and 2M or 6M HCl was cautiously added (6 equivalents with respect to the starting material). The resulting reaction mixture was refluxed for 2 hours and cooled back to room temperature. The pH of the solution was then adjusted to strongly alkaline (~10) by a dropwise addition of 6M NaOH. The organic layer was separated and the aqueous layer was additionally extracted with diethyl ether or AcOEt. The combined organic extracts were then dried over anhydrous MgSO$_4$, filtered and the solvents were evaporated in vacuo. The crude product obtained was, in most cases, sufficiently pure to be used to the next step without any additional purification.

General Procedure II
Cyclization of an α-Haloamide to a Morpholin-3-One

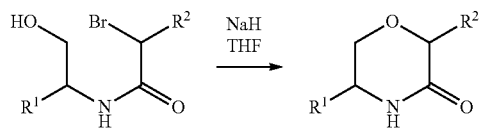

To the solution of the α-haloamide (i.e., α-chloro- or α-bromoamide) in THF (10 mL/mmol) 3 equivalents of sodium hydride (NaH) was added in one portion (cooling the solution prior to the addition of NaH may was advisable when working on larger scale) and the reaction mixture was allowed to stir at room temperature for 2 hours. The excess of NaH was then carefully quenched by dropwise addition of brine and then additional volume of brine (equal to the initial volume of THF) was added causing phases separation. The organic layer was separated and the aqueous layer was additionally extracted with diethyl ether. The combined organic extracts were then dried over anhydrous MgSO$_4$, filtered and the solvents were evaporated. The crude product was in most cases sufficiently pure to be used to the next step without any additional purification.

General Procedure III
Amino-Selective Acylation of an Amino Alcohol with an α-Bromoacid with the Use of an Amide-Forming Reagent

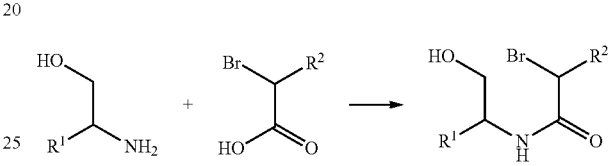

To the solution of α-bromoacid or another acid (1-1.1 equivalent) in dichloromethane (5-7 mL/mmol) diisopropylethylamine (DIPEA, 1 equivalent with respect to the starting α-bromoacid) or Et$_3$N (4 equivalents), coupling reagent (1-1.05 equivalent; typically TBTU or HATU, but other commonly used coupling reagents may be used as well) and amino alcohol (1 equivalent) were added sequentially and the reaction mixture was stirred for 1.5-3.5 hours at room temperature. After this time TLC and LC-MS control showed complete consumption of the starting materials and the reaction mixture was transferred to the separatory funnel and washed sequentially with 1M HCl, 1M NaOH, and brine. The organic phase was dried over anhydrous MgSO$_4$, filtered and evaporated to give the crude product which was further purified by crystallization or by silica-gel chromatography.

General Procedure IVa
Removal of the Tert-Butoxycarbonyl (Boc-) Group from an Amine with HCl.

The N-Boc protected amine was treated with a 4M solution of HCl (5 mL/mmol of starting material) in an appropriate organic solvent (e.g., AcOEt, 1,4-dioxane, MeOH, DCM) for the time necessary for complete consumption of the starting material (typically 30 minutes-2 hours). The volatiles were then removed in vacuo providing de-protected amine in the form of its hydrochloride salt. The crude product was usually sufficiently pure to be used in the following step, but additional trituration with diethyl ether may help to remove any colored impurities or the crude product was purified by preparative reversed-phase column chromatography to give the corresponding product.

General Procedure IVb
Removal of the Tert-Butoxycarbonyl (Boc-) Group from an Amine with TFA.

The N-Boc protected amine was treated with solution of TFA (6 equivalents) in DCM for the time necessary for complete consumption of the starting material (typically 30 minutes-2 hours). The volatiles were then removed in vacuo providing de-protected amine in the form of its TFA salt. The crude product was usually purified by preparative reversed-phase column chromatography to give the corresponding product.

General Procedure V
Addition of the Grignard Reagent to a Carbonyl Group.

An appropriate Grignard reagent (3 equivalents) was added dropwise to a solution of carbonyl compound in Et$_2$O or THE (6 mL/mmol) at −40° C. After this reaction was allowed to warm up to room temperature. The reaction progress was monitored by TLC and LC-MS analysis of small aliquots of the crude reaction mixture. When analyses were indicated completion of the reaction, the mixture was poured into saturated solution of NH$_4$Cl. The organic phase was separated, and the aqueous phase was extracted with AcOEt. The combined organic phases were dried over anhydrous MgSO$_4$, concentrated in vacuo. The crude product was purified by silica-gel chromatography or by flash column chromatography on silica or by reversed-phase column chromatography.

General Procedure VI
Reductive Amination of the Cyclic Ketone with an Appropriate Amine

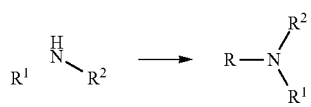

An appropriate amine or an amine hydrochloride (1 equivalent) was dissolved in DCE and acetic acid (AcOH, 2 equivalents) and appropriate ketone (2 equivalents) were added and the mixture was heated at 50° C. for 2 days. The reaction mixture was cooled to room temperature and sodium triacetoxyborohydride (NaBH(OAc)$_3$) (4 equivalents) was then added in one portion and the mixture was stirred overnight at room temperature. After this time a 5% aqueous solution of sodium bicarbonate (NaHCO$_3$) and dichloromethane (DCM) were added and the mixture was stirred for 30 minutes. The layers were separated and the aqueous layer was additionally extracted with dichloromethane. The organic extracts were combined, washed with brine, dried over anhydrous MgSO$_4$, filtered and evaporated to dryness. The crude product was purified by flash column chromatography on silica or by preparative reversed-phase column chromatography.

General Procedure VIIa
Reaction of BiotinPEG$_{12}$COOH or MeOPEG$_{12}$ Acid with Compounds with an Appropriate Hydroxyl Group or with an Amine

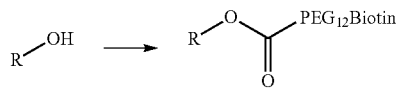

To the solution of PEG12-biotin acid (1-1.5 equivalent) or MeOPEG$_{12}$ acid (1 equivalent) and diisopropylethylamine (DIPEA; 3-5 equivalents) or triethylamine (Et$_3$N; 6 equivalents) in dichloromethane/acetonitrile mixture (6 mL/mmol; 1:1 v/v) or in DMF (5 mL/mmol) appropriate alcohol (1-1.2 equivalent) or amine (1 equivalent) was added. Then EDCI hydrochloride (1.1-1.5 equivalent) or HATU (1.1-1.5 equivalent) and DMAP (0.05-0.1 equivalent) were added sequentially and the reaction mixture was stirred for 3 days at room temperature. After this time LC-MS control showed complete consumption of the starting materials and the reaction mixture was evaporated to dryness and dissolved in DCM and the crude product was further purified by silica-gel column chromatography or by preparative reversed-phase column chromatography. After evaporation of solvent, product was dissolved in tert-butanol and lyophilized.

General Procedure VIIb
Biotynylation (with BiotinPEG$_{11}$NH$_2$) of an Appropriate Carboxylic Acid

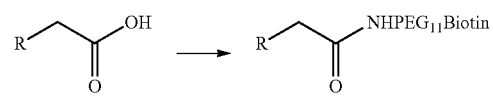

To the solution of appropriate carboxylic acid (1.2 equivalent) in DMF, Et$_3$N (6 equivalents) and BiotinPEG$_{11}$NH$_2$ (1 equivalent) in DMF were added followed by addition of HATU (1.1. equivalent) and the reaction mixture was stirred overnight at room temperature. After this time LC-MS control showed complete consumption of the starting materials and the reaction mixture was evaporated to dryness and the crude product was further purified by preparative reversed-phase column chromatography.

General Procedure VIII
Removal of the Tert-Butoxycarbonyl (Boc-) from an Amine Followed by Cyclization to the Six-Membered Ring (i.e., Morpholin-3-One, Piperazin-2-One, Etc.) and Seven-Membered Ring (1,4-Oxazepine, 1,4-Benzoxazepine, 1,4-Benzodiazepines, Etc.)

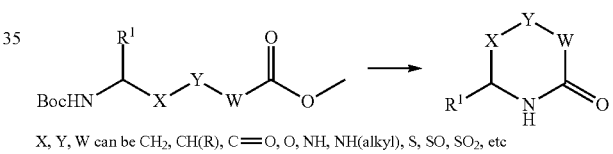

X, Y, W can be CH$_2$, CH(R), C═O, O, NH, NH(alkyl), S, SO, SO$_2$, etc

The crude amine hydrochloride salt of the typical Boc-group removal procedure (see the General Procedure IVa) was suspended in methanol (3 mL/mmol), triethylamine (5 equivalents) was added and the mixture was refluxed for the appropriate time (TLC control). Methanol and excess of triethylamine were removed in vacuo, the residue was taken into ethyl acetate and aqueous acid/base wash, dried over anhydrous MgSO$_4$, filtered off and filtrate was concentrated in vacuo. The crude product was purified by crystallization or by silica-gel column chromatography.

General Procedure IX
Reaction of a Secondary Amine with an Appropriate Halopyridine or Halopyrimidine

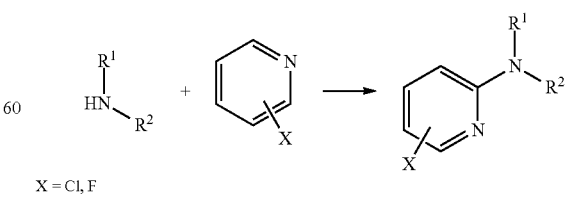

X = Cl, F

The mixture of an amine (1 equivalent), an appropriate halopyridine or halopyrimidine (1.4-5 equivalents) or 2-methylthio-4-pyrimidone (3 equivalents) and K₂CO₃ (2-3 equivalents) was stirred at 120° C. in a sealed vial overnight. The reaction progress was monitored by LC-MS. After analytical control was indicated completion of the reaction, the mixture was concentrated in vacuo. The crude product obtained was, in most cases, sufficiently pure to be used to the next step without any additional purification or was purified by reversed-phase column chromatography.

General Procedure X

Reaction of a Secondary Amine with an Appropriate Halopyridine

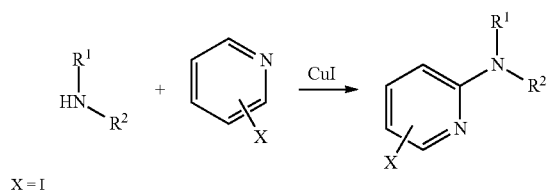

X = I

To the solution of amine (1 equivalent) and an appropriate halopyridine (1 equivalent) in DMSO (3 mL/mmol), CuI (0.2 equivalent), K₂CO₃ (2-3 equivalents) and L-proline (0.33 equivalent) were added and the reaction mixture was heated at 100° C. for 10 hours. The reaction progress was monitored by LC-MS. After analytical control was indicated completion of the reaction, the crude product was extracted with water and MTBE. The organic fractions were dried over anhydrous Na₂SO₄, filtered off and a filtrate was concentrated in vacuo. The crude product was purified by reversed-phase column chromatography.

General Procedure XI

Installation of the Methyl or Ethyl or 2-Propyl Group on the Appropriate Amine or Alcohol

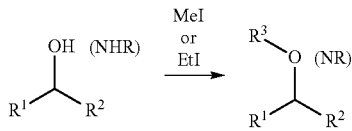

To a solution of alcohol (1 equivalent) or amine (1 equivalent) in dry DMF or THF (3 mL/mmol), sodium hydride (2.2 equivalents; 60% dispersion in mineral oil) was added at 0° C. After 5 minutes MeI (2.2 equivalents) was added dropwise at 0° C. and the reaction mixture was warm up to room temperature and then stirred until full consumption of starting material (TLC or LC-MS control). To the reaction mixture H₂O was then added and extracted with DCM or AcOEt (when the THF was used), dried over anhydrous Na₂SO₄, filtered and concentrated in vacuo. The crude product was then purified by silica-gel column chromatography or by preparative reversed-phase column chromatography.

General Procedure XII

Reaction an Appropriate Amine or Amide or Alcohol with a Mesylated Compound or Appropriate Carbamoyl Chloride or Methyl Iodide

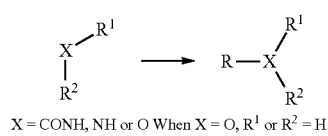

X = CONH, NH or O When X = O, R¹ or R² = H

To a solution of amine (1 equivalent) or amide (2 equivalents) or alcohol (3 equivalents) in THF (1.5 mL/mmol) NaH (60% in oil; 3 equivalents) was added slowly and the mixture was stirred for 15 minutes and then solution of mesylate (1 equivalent) in THF (1.5 mL/mmol) or carbamoyl chloride (3 equivalents) or methyl iodide (2 equivalents) was added dropwise and then refluxed overnight or for carbamoyl chloride and for methyl iodide stirred at room temperature overnight. The reaction progress was monitored by LC-MS analysis of small aliquots of the crude reaction mixture. When analysis were indicated completion of the reaction, the mixture was poured into water and extracted with AcOEt or with Et₂O or with DCM. The combined organic phases were dried over anhydrous MgSO₄, concentrated in vacuo. The crude product was in most cases sufficiently pure to be used to the next step without any additional purification or crude product was purified by preparative reversed-phase column chromatography.

General Procedure XIII

Substitution of the Mesylate Compound with an Appropriate Amine

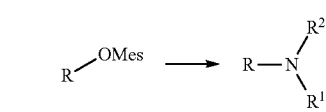

The solution of mesylate (1 equivalent), amine (2 equivalents) and K₂CO₃ (3 equivalents) in acetonitrile was heated at 100° C. in a sealed vial overnight. Then solid was removed by filtration and the filtrate was concentrated in vacuo. The crude product was purified by silica-gel chromatography or flash chromatography or by preparative reversed-phase column chromatography.

General Procedure XIV

Mesylation of an Appropriate Hydroxyl Group

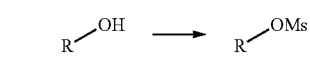

To a cooled to 0° C. solution of alcohol, triethylamine (Et₃N, 1.6 equivalent) in DCM (20 mL/mmol) a solution of methanesulfonic anhydride (1.5 equivalent) or methanesulfonic chloride (1.2 equivalent) in DCM (6 mL/mmol) was added dropwise and the mixture was stirred at room temperature for 30 minutes. After this time the reaction was washed with 1M K₂CO₃, brine, dried over anhydrous MgSO₄, filtered and the solvents were evaporated in vacuo. The crude product was in most cases sufficiently pure to be used to the next step without any additional purification.

General Procedure XV

Formation of Weinreb Amide from Carboxylic Acid and N,O-dimethylhydroxylamine Hydrochloride with the Use of the Amide Forming Reagent

To a solution of carboxylic acid in dichloromethane (2 mL/mmol), DIPEA (2.1 equivalents) was added, followed by N,O-dimethylhydroxylamine hydrochloride (1.1 equivalent). TBTU (1.1 equivalent) was added to the reaction mixture and reaction was stirred at room temperature for the time necessary for the complete consumption of the starting material (usually 16-24 hours) as judged by TLC or LC-MS. The reaction mixture was diluted with dichloromethane, then washed with 2M HCl and brine. An organic layer was dried over anhydrous MgSO$_4$, filtered and concentrated in vacuo. Product was purified by silica-gel column chromatography.

General Procedure XVI

Activation of a Carboxylic Group by Mixed Anhydride Followed by Formation of an Amide

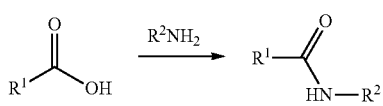

The carboxylic acid was dissolved in dichloromethane (DCM) (3-8 mL/mmol depending on the solubility) and N-methylmorpholine (1.2 equivalent) was added. The solution was cooled to −15° C. and alkyl (typically methyl, ethyl or isobutyl) chloroformate (1.2 equivalent) was added and the mixture was stirred for additional 10 minutes at which time the appropriate amine (neat, 1.2 equivalent) was added. The reaction mixture was allowed to warm to room temperature and was typically stirred overnight, though in the cases of reactive amines the coupling was usually completed within minutes. The crude product was isolated by washing of organic phase (DCM) subsequentially with 1M HCl, 1M NaOH, and brine. The organic phase was dried over anhydrous MgSO$_4$, filtered and evaporated to give the crude product which was further purified by crystallization or by silica-gel column chromatography.

General Procedure XVII

Installation of the Appropriate R-Group on the Primary or Secondary Amine or Alcohol

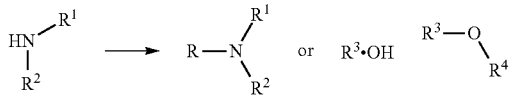

To a solution of the primary or secondary amine or alcohol in DCM (10 mL/mmol) or THF (4 mL/mmol), Et$_3$N (2-4 equivalents) or DIPEA (2 equivalents) followed by DMAP (0.1 equivalent) were added and then N-succinimidyl-N-methyl carbamate (2.5 equivalents) or appropriate carbamoyl chloride (2.5 equivalents) or appropriate isocyanate (1.1-2.5 equivalents) or acid chloride (1-2 equivalents) or appropriate anhydride (2 equivalents) was added at room temperature. The reaction progress was monitored by TLC and LC-MS. When analysis indicated completion of the reaction, the mixture was quenched by addition of 4M NaOH. Product was extracted with DCM (2 times). Combined organic solutions were dried over Na$_2$SO$_4$, filtered and concentrated in vacuo and the crude product was purified by preparative reversed-phase column chromatography.

General Procedure XVIII

Coupling of a Boc-Protected Amino Alcohol with a Phenol Via Mitsunobu Reaction

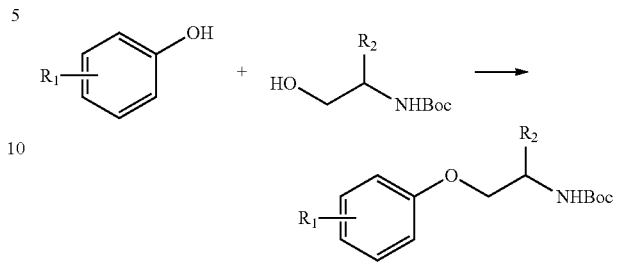

To a solution of phenol (1-1.5 equivalents) and a Boc-protected amino alcohol (1-1.25 equivalent) in dry THF (3 mL/mmol) or DCM (4 mL/mmol) under atmosphere of inert gas (usually argon), triphenylphosphine (1.5 equivalent) was added and the mixture was cooled down to −15° C. DIAD (1.5 equivalent) was added dropwise at this temperature, then cooling bath was removed and the reaction was stirred at room temperature for 24 hours. The reaction mixture was concentrated and the oily residue was purified by silica-gel column chromatography.

General Procedure XIX

Reduction of the Weinreb Amide to the Corresponding Aldehyde or Methyl Esters to Alcohols

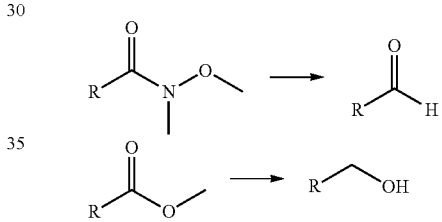

To a solution of the Weinreb amide (1 equivalent) or methyl ester (1 equivalent) in dry THF (5 mL/mmol) under atmosphere of inert gas, lithium aluminum hydride (1 equivalent) was added at 0° C. and the mixture was stirred at this temperature until starting material was consumed (usually 30 minutes-2 hours) as judged by TLC. Reaction was quenched with saturated aqueous solution of potassium hydrogen sulfate and product extracted with diethyl ether (4×10 mL). Combined organic layers were washed with brine, dried over anhydrous MgSO$_4$, filtered and concentrated. The crude aldehyde was sufficiently pure to be directly used to the next step or the residue was purified by preparative reversed-phase column chromatography.

General Procedure XX

Removal of a tert-butoxycarbonyl (Boc-) from an Amine Followed by Cyclisation of Seven-Membered Ring (i.e. Benzoxazepine) and Subsequent Reduction of Imine to Amine

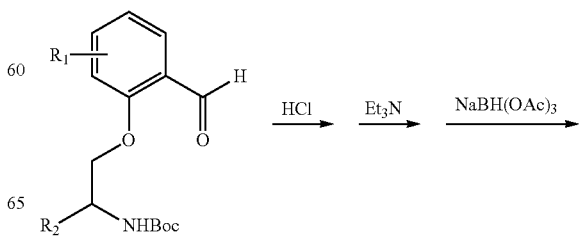

-continued

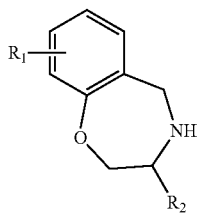

The crude amine hydrochloride salt of the typical Boc-group removal procedure (see the General Procedure IVa and IVb) was suspended in 1,2-dichloroethane (2 mL/mmol) triethylamine (1.1 equivalent) was added and the mixture was heated to 70° C. for 1-2 hours. After cooling down to room temperature sodium triacetoxyborohydride (2.5 equivalents) was added and the mixture was stirred overnight. The excess of reducing agent was decomposed with 5% aqueous solution of sodium hydrogen carbonate (twice the volume of DCE used) and the product was extracted with dichloromethane. The layers were separated and the aqueous one was additionally extracted with dichloromethane. The combined organic extracts were dried over anhydrous MgSO$_4$, filtered and concentrated in vacuo. The crude amine was sufficiently pure to be used to the next step without any additional purification.

General Procedure XXI
Reduction of a Boc-Protected Amino Acid to the Corresponding Boc-Protected Amino Alcohol Via Mixed Anhydride

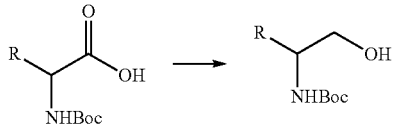

The starting Boc-protected amino acid was dissolved in THF (4 mL/mmol) and the carboxylic group was activated by formation of the mixed anhydride as it was described in the General Procedure XVI. The precipitated N-methylmorpholine hydrochloride was filtered off quickly and filtrate was transferred into a larger round bottomed flask. The suspension of NaBH$_4$ (2-3 equivalents) in water (1 mL/mmol) was then cautiously added (Caution: intense foaming!) and the reaction mixture was allowed to stirred at room temperature overnight. 1M NaOH was added in volume equal to that of THF used and the mixture was stirred for additional 30 minutes after which time it was extracted 3 times with ethyl acetate. Drying the solution and removal of the solvent yielded product that was usually sufficiently pure to be directly used to the next step, though crystallization or trituration with appropriate solvent may further improve its purity.

General Procedure XXII
Opening of an Epoxide to the Corresponding Amino Alcohol

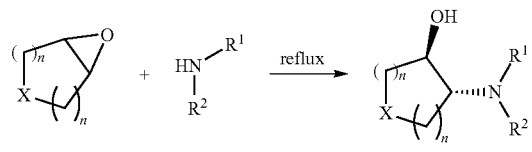

n = 1, 2, 3 X = CH$_2$, O, NR

To an equimolar solution of secondary amine and epoxide in acetonitrile, LiCl (1 equivalent) was added and the resulting mixture was refluxed overnight. The reaction progress was monitored by TLC and LC-MS analysis of small aliquots of the crude reaction mixture. When analysis indicated completion of the reaction, the mixture was concentrated in vacuo, and the residue was dissolved in DCM, washed with water and brine, dried over anhydrous MgSO$_4$ and the crude product was purified by preparative reversed-phase column chromatography.

General Procedure XXIII
Reaction of a Secondary Amine with an Appropriate Halopyridine

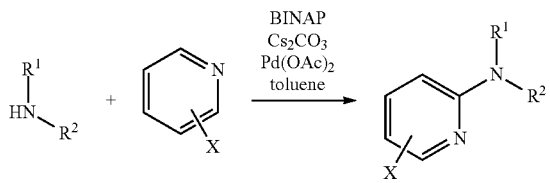

The mixture of BINAP (0.1 equivalent), Pd(OAc)$_2$ (0.05 equivalent), Cs$_2$CO$_3$ (5 equivalents) and an appropriate halopyridine (1 equivalent) were placed in Schlenk tube and degassed (3×), flushed with argon. Then toluene (1 mL/mmol) was added, degassed and flushed with argon. The mixture was stirred for 30 minutes at room temperature. Then an amine (1.2 equivalent) was added and resulting mixture was refluxed for 5 hours. The reaction progress was monitored by LC-MS. After analytical control was indicated completion of the reaction, the mixture was taken into water/AcOEt. An organic layer was washed with brine, dried over anhydrousMgSO$_4$, filtered off and filtrate was concentrated in vacuo. The crude product was purified by preparative reversed-phase column chromatography.

General Procedure XXIV
Reaction of a Secondary Amine with an Appropriate Halopyridine

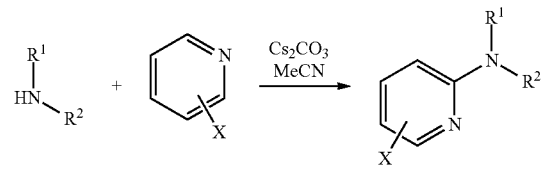

The mixture of an amine (1 equivalent), Cs$_2$CO$_3$ (2 equivalents) and an appropriate halopyridine (1.5 equivalent) in MeCN (2.5 mL/mmol) was refluxed overnight. The reaction progress was monitored by LC-MS. After analytical control was indicated completion of the reaction, Cs$_2$CO$_3$

General Procedure XXV
Reaction of a Secondary Amine with an Appropriate Halopyridine

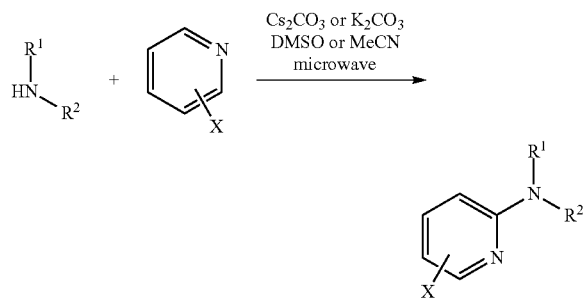

The mixture of an amine (1 equivalent), $Cs_2CO_3$ (2 equivalents) or $K_2CO_3$ (2 equivalents) and an appropriate halopyridine (1.5-2 equivalents) in DMSO (4.5 mL/mmol) or MeCN (3 mL/mmol) was stirred for 30 minutes at 100-180° C. in microwave oven. The reaction progress was monitored by LC-MS. After analytical control was indicated completion of the reaction, the mixture was diluted with DCM/MeOH (9:1, v/v), filtered off and the filtrate was evaporated to dryness. The crude product was purified by preparative reversed-phase column chromatography.

General Procedure XXVI
Reaction of a Secondary Amine with an Appropriate Bromothiadiazole or Bromothiazole

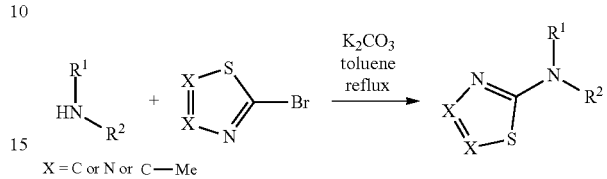

X = C or N or C—Me

The mixture of an amine (1 equivalent), an appropriate bromothiadiazole or bromothiazole (1.3 equivalent) and $K_2CO_3$ (2 equivalents) in toluene (5 mL/mmol) was stirred at 110-130° C. in a sealed vial overnight. The reaction progress was monitored by LC-MS. After analytical control was indicated completion of the reaction, the mixture was concentrated in vacuo. The crude product was purified by preparative reversed-phase column chromatography Scheme 1.

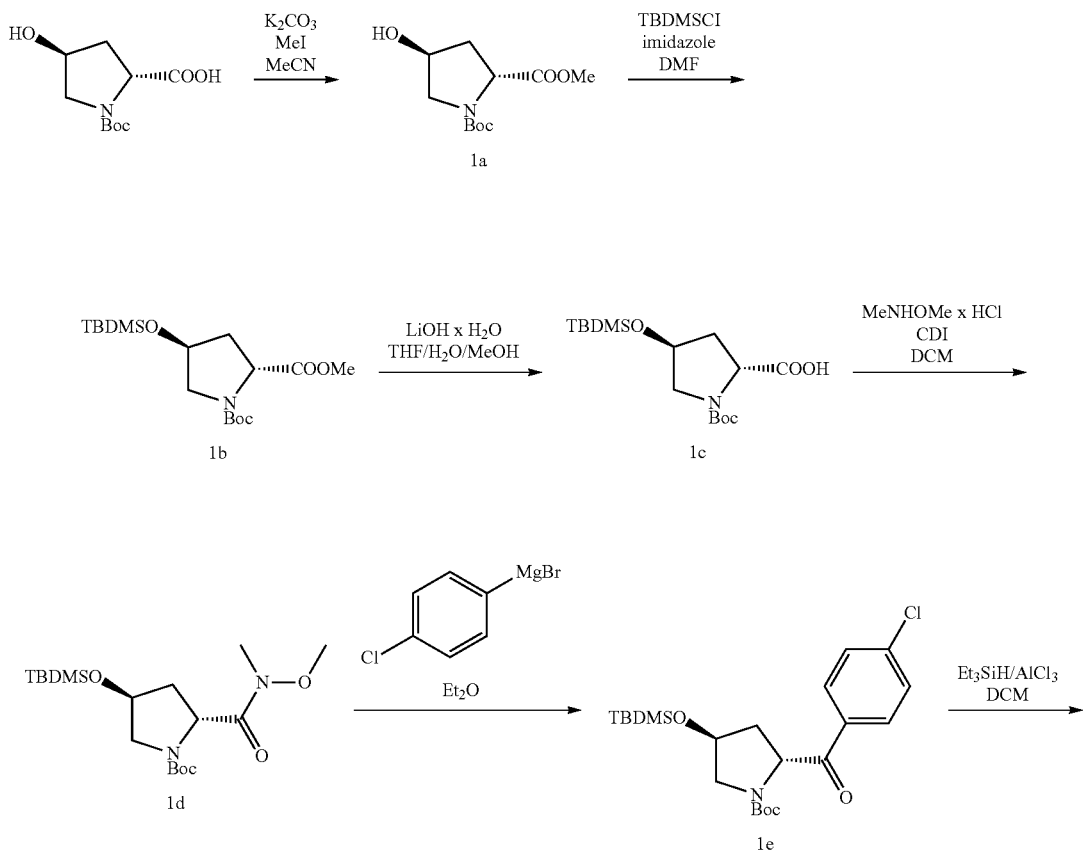

-continued
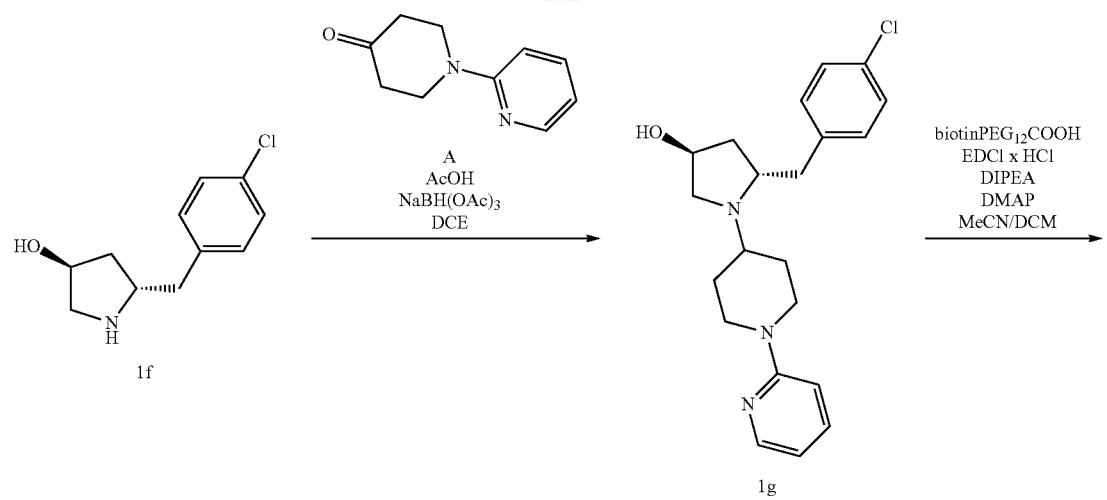
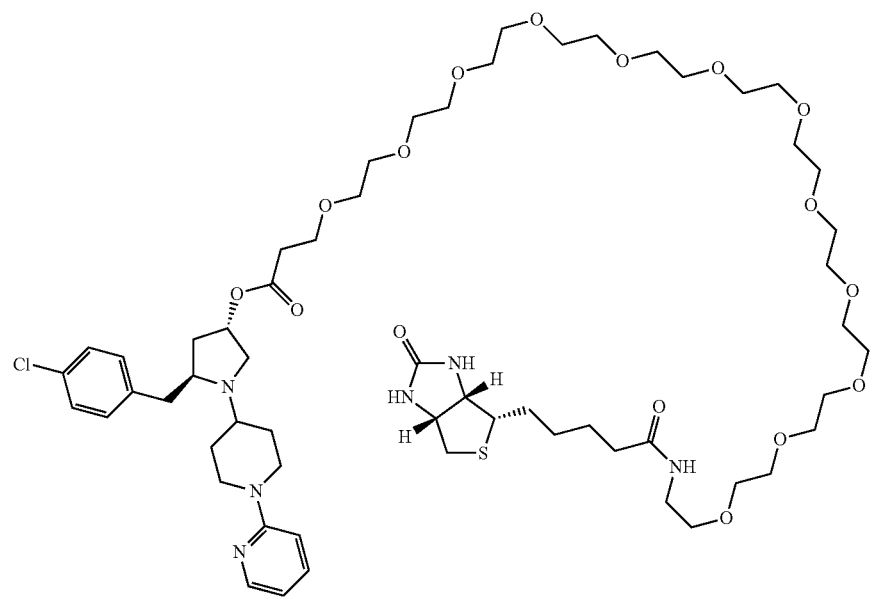

Example 1

Synthesis of (3S,5S)-5-(4-chlorobenzyl)-1-(1-(pyridin-2-yl)piperidin-4-yl)pyrrolidin-3-yl 41-oxo-45-((3aS,4S,6aR)-2-oxohexahydro-1H-thieno[3,4-d]imidazol-4-yl)-4,7,10,13,16,19,22,25,28,31,34,37-dodecaoxa-40-azapentatetracontanoate (1)

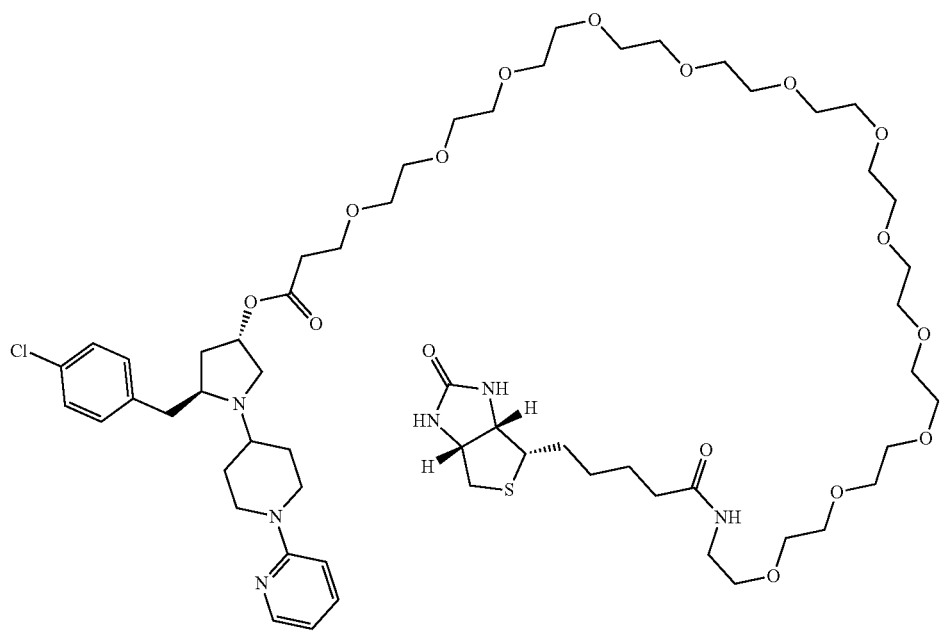

Step 1

Synthesis of (2R,4S)-1-tert-butyl 2-methyl 4-hydroxypyrrolidine-1,2-dicarboxylate (1a)

Step 2

Synthesis of (2R,4S)-1-tert-butyl 2-methyl 4-((tert-butyldimethylsilyl)oxy)pyrrolidine-1,2-dicarboxylate (1b)

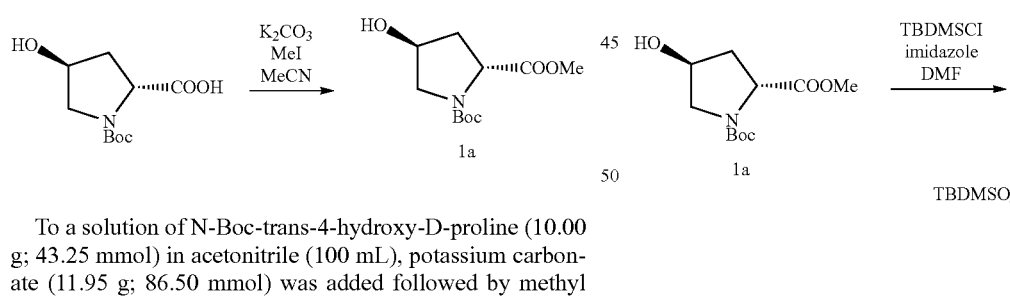

To a solution of N-Boc-trans-4-hydroxy-D-proline (10.00 g; 43.25 mmol) in acetonitrile (100 mL), potassium carbonate (11.95 g; 86.50 mmol) was added followed by methyl iodide (5.40 mL, 86.50 mmol) and resulting mixture was stirred overnight. LC-MS indicated presence of substrate. Another portion of potassium carbonate (5.98 g; 43.25 mmol) and methyl iodide was added (2.7 mL; 43.25 mmol) and the reaction was stirred for 2 days after which time LC-MS indicated completion of the reaction. The reaction mixture was filtered and the solid residue was washed with EtOAc. After evaporation of an organic phase the product 1a was obtained as a yellowish oil in 88% yield (9.37 g; 38.22 mmol).

ESI-MS m/z for $C_{11}H_{19}NO_5$ found 145.9 [M+H-Boc]$^+$, 268.0 [M+Na]$^+$

To a solution of 1a (5 g; 20.38 mmol) in DMF (60 mL), imidazole (6.94 g; 101.90 mmol) was added followed by TBDMSCl (4.61 g; 30.57 mmol) and the reaction was stirred overnight. After LC-MS indicated completion of the reaction, the reaction mixture was taken between water and EtOAc. An organic layer was washed with water, brine, dried over anhydrous MgSO$_4$, and concentrated in vacuo. The crude product was purified by silica-gel column chromatography (hexane/AcOEt, 8:1, v/v) to give 1b as a colorless oil in 92% yield (6.7 g; 18.63 mmol). ESI-MS m/z for $C_{17}H_{33}NO_5Si$ found 260.2 [M+H-Boc]$^+$, 382.1 [M+Na]$^+$; $^1$H NMR (700 MHz, CDCl$_3$) δ [4.43-4.40 (m); 4.33 (d, J=7.7 Hz); 2H], [3.74 (s); 3.72 (s); 3H], [3.61 (dd, J=11.2, 4.6 Hz); 3.57 (dd, J=11.0, 4.8 Hz); 1H], [3.40 (dd, J=11.4, 1.3 Hz); 3.37 (dd, J=11.2, 2.4 Hz); 1H], 2.20-2.14 (m, 1H), 2.04-1.98 (m, 1H), [1.46(s); 1.41(s); 9H], 087 (s, 9H), 0.06 (s, 6H).

Step 3

Synthesis of (2R,4S)-1-(tert-butoxycarbonyl)-4-((tert-butyldimethylsilyl)oxy)pyrrolidine-2-carboxylic acid (1c)

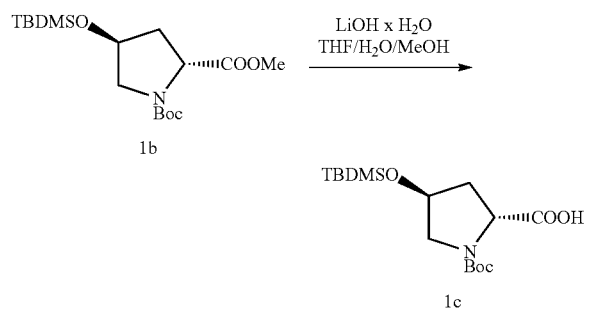

Compound 1b (6.70 g; 18.63 mmol) was dissolved in a mixture of 200 mL THF and 100 mL MeOH. A solution of lithium hydroxide hydrate in 100 mL of water was added to the reaction mixture and the resulting mixture was stirred overnight. After LC-MS control indicated completion of the reaction, the reaction mixture was concentrated in vacuo. The water residue was acidified to pH 4 with 2N HCl at 0° C. and the product was extracted with EtOAc. An organic layer was washed with brine, dried over anhydrous MgSO$_4$, and evaporated to give product 1c as a yellowish oil in 80% yield (5.13 g; 14.85 mmol).

ESI-MS m/z for $C_{16}H_{31}NO_5Si$ found 246.1 [M+H-Boc]$^+$, 368.1 [M+Na]$^+$, 344.1 [M−H]$^-$

Step 4

Synthesis of (2R,4S)-tert-butyl 4-((tert-butyldimethylsilyl)oxy)-2-(methoxy(methyl)carbamoyl)pyrrolidine-1-carboxylate (1d)

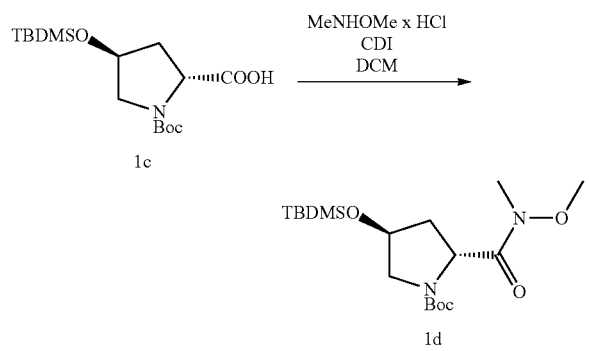

To a solution of compound 1c (10 g; 14.85 mmol) in DCM (40 mL), triethylamine (5.2 mL; 37.12 mmol) was added, followed by carbonyldiimidazole (CDI; 3.61 g; 22.28 mmol), and the reaction was stirred for 1 hour. N,O-dimethylhydroxylamine hydrochloride (2.17 g; 22.28 mmol) was added and the reaction was stirred overnight, after which time LC-MS control indicated completion of the reaction. The reaction mixture was washed with water and brine. An organic layer was dried over anhydrous MgSO$_4$ and concentrated in vacuo. The crude product was purified by silica-gel column chromatography (hexane/AcOEt, 5:1, v/v) to give 1d as a colorless oil in 72% yield (4.15 g; 10.68 mmol).

ESI-MS m/z for $C_{18}H_{36}N_2O_5Si$ found 289.7/290.3 [M+H-Boc]$^+$, 411.1/412.3 [M+Na]$^+$; $^1$H NMR (700 MHz, CDCl$_3$) δ [4.82 (brs); 4.73 (t, J=7.0 Hz); 1H], 4.45 (dq, 1H, J=18.0, 4.8 Hz), [3.79 (s); 3.72 (s); 3H], [3.68 (dd, J=11.0, 5.3 Hz); 3.64 (dd, J=11.0, 5.3 Hz); 1H], [3.40 (dd, J=11.0, 3.1 Hz); 3.32 (dd, J=10.8, 3.7 Hz); 1H], 3.20 (s, 3H), 2.18-2.12 (m, 1H), 2.00-1.95 (m, 1H), [1.45 (s); 1.41 (s); 9H], 0.88 (s, 9H), 0.06 (s, 6H).

Step 5

Synthesis of (2R,4S)-tert-butyl 4-((tert-butyldimethylsilyl)oxy)-2-(4-chlorobenzoyl)pyrrolidine-1-carboxylate (1e)

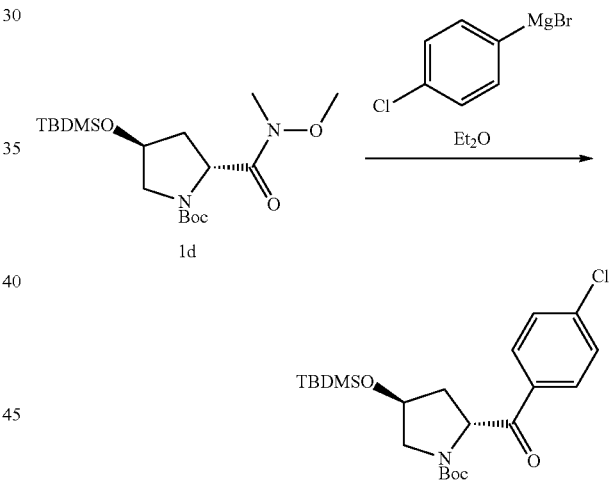

The title compound (1e) was obtained from 1d (1.00 g; 2.57 mmol) according to the General Procedure V in 86% yield (970 mg; 2.20 mmol).

ESI-MS m/z for $C_{22}H_{34}ClNO_4Si$ found 340.0/341.9 [M+H-Boc]$^+$, 462.1 [M+Na]$^+$; $^1$H NMR (700 MHz, DMSO-d$_6$+D$_2$O) δ 7.97-7.95 (m, 2H), 7.61-7.59 (m, 2H), 5.27-5.22 (m, 1H), 4.44-4.39 (m, 1H), [3.52 (dd, J=11.4, 4.4 Hz); 3.48 (dd, J=11.4, 4.4 Hz); 1H], [3.34 (m); 3.30 (m); 1H], 2.24-2.19 (m, 1H), [1.92 (ddd, J=12.9, 7.8, 4.8 Hz); 1.85 (ddd, J=13.0, 7.7, 4.8 Hz); 1H], [1.34 (s); 1.11 (s); 9H], 0.83 (s, 9H), [0.04 (s); 0.03 (s); 6H].

Step 6

Synthesis of (3S,5S)-5-(4-chlorobenzyl)pyrrolidin-3-ol (1f)

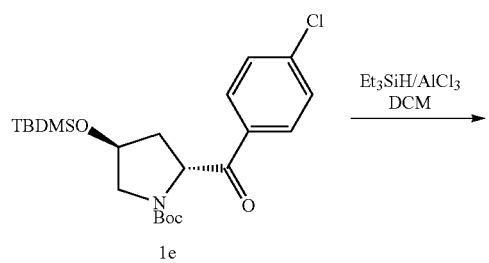

1e

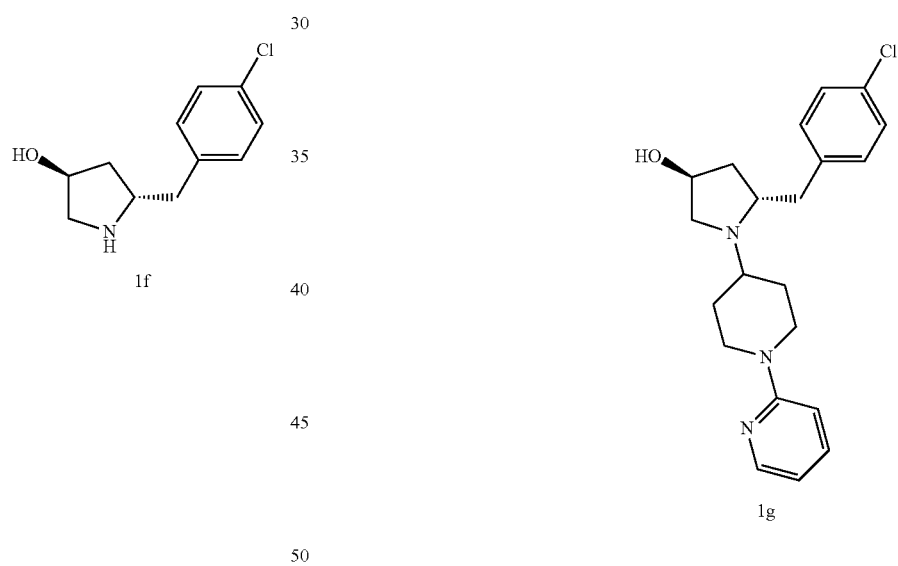

1f

To a solution of compound 1e (970 mg; 2.20 mmol) in DCM (11 mL) AlCl3 (880 mg; 6.60 mmol) was added under argon, followed by triethylsilane (1.05 mL; 6.60 mmol). The reaction was stirred for 45 minutes after which LC-MS control indicated completion of the reaction. The reaction was quenched with 4M NaOH, saturated with sodium chloride, and filtrated through the Celite pad. The product was extracted from water phase with DCM (3×20 mL). The combined organic layers were dried over anhydrous MgSO$_4$ and evaporated to give 1f as a yellowish oil in 99% yield (460 mg; 2.18 mmol).

ESI-MS m/z for $C_{11}H_{15}ClNO$ found 211.9 [M+H]$^+$.

Step 7

Synthesis of (3S,5S)-5-(4-chlorobenzyl)-1-(1-(pyridin-2-yl)piperidin-4-yl)pyrrolidin-3-ol (1g)

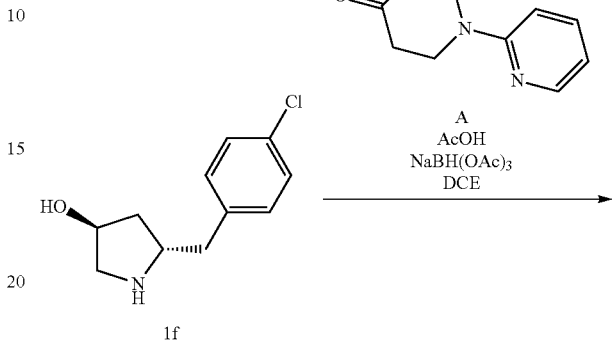

1g

The title compound (1g) was obtained from 1f (156 mg; 0.74 mmol) according to the General Procedure VI in 66% yield (180 mg; 0.49 mmol).

ESI-MS m/z for $C_{21}H_{27}ClN_3O$ found 372.2/374.2 [M+H]$^+$; $^1$H NMR (700 MHz, D$_2$O) δ 8.36-8.29 (m, 1H), 8.23-8.17 (m, 1H), 7.76-7.70 (m, 2H), 7.65-7.56 (m, 3H), 7.35-7.25 (m, 1H), 4.93-4.82 (m, 1H), 4.59-4.46 (m, 3H), 4.03 (dd, J=13.1, 4.9 Hz, 1H), 3.99-3.90 (m, 1H), 3.69-3.49 (m, 4H), 3.39-3.28 (m, 1H), 2.63-2.52 (m, 2H), 2.48-2.33 (m, 2H), 2.22-2.12 (m, 2H).

Step 8
Synthesis of (3S,5S)-5-(4-chlorobenzyl)-1-(1-(pyridin-2-yl)piperidin-4-yl)pyrrolidin-3-yl 41-oxo-45-((3aS,4S,6aR)-2-oxohexahydro-1H-thieno[3,4-d]imidazol-4-yl)-4,7,10,13,16,19,22,25,28,31,34,37-dodecaoxa-40-azapentatetracontanoate (1)
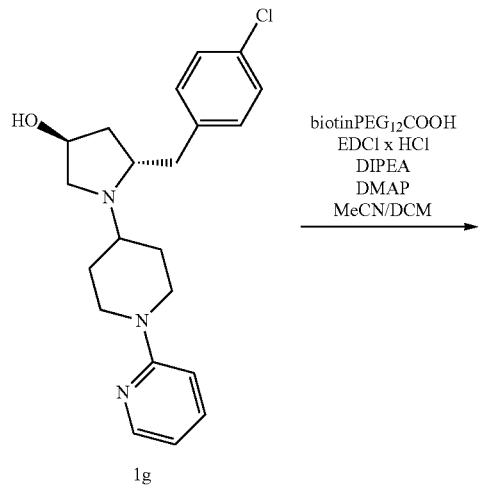
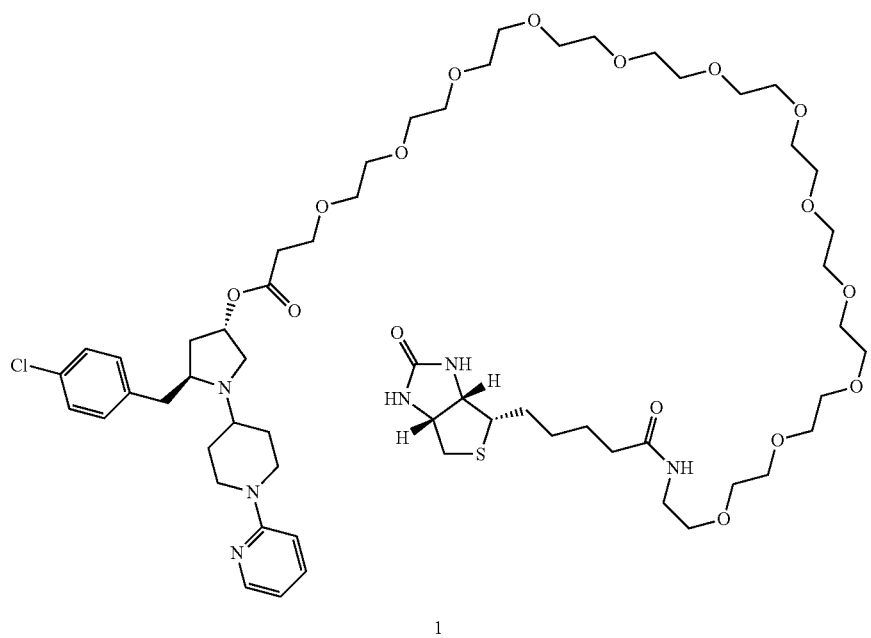 [SMILES: O=C(CCCC[C@@H]1SC[C@@H]2NC(=O)N[C@@H]21)NCCOCCOCCOCCOCCOCCOCCOCCOCCOCCOCCOCCOCCC(=O)O[C@H]1C[C@H](Cc2ccc(Cl)cc2)N(C2CCN(c3ccccn3)CC2)C1]
The title compound (1) was obtained from 1g (20 mg; 0.05 mmol) according to the General Procedure VIIa in 40% yield (24 mg; 0.02 mmol).
ESI-MS m/z for $C_{58}H_{94}ClN_6O_{16}S$ found 1197.6/1199.6 $[M+H]^+$

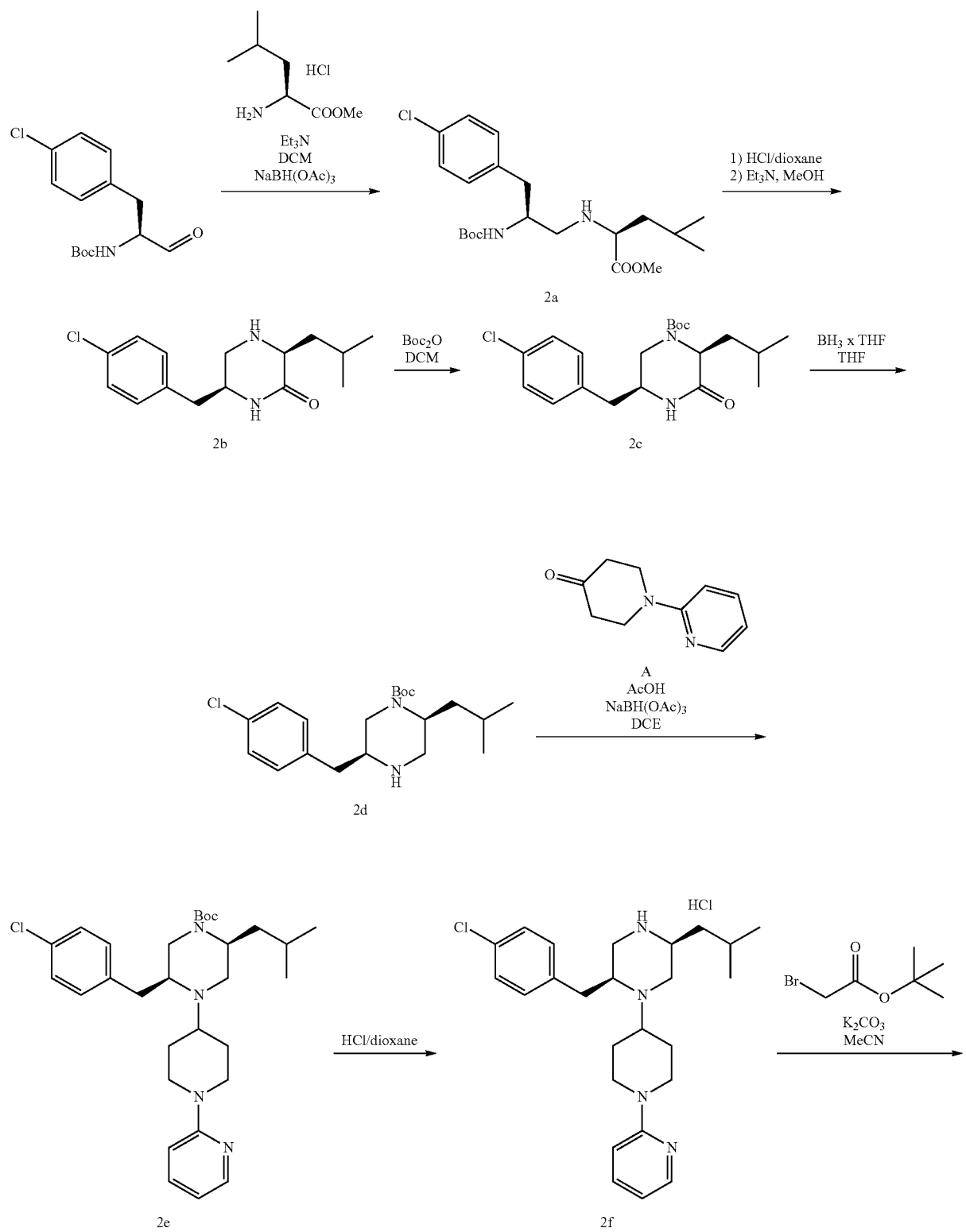
Scheme 2.

191 192
-continued
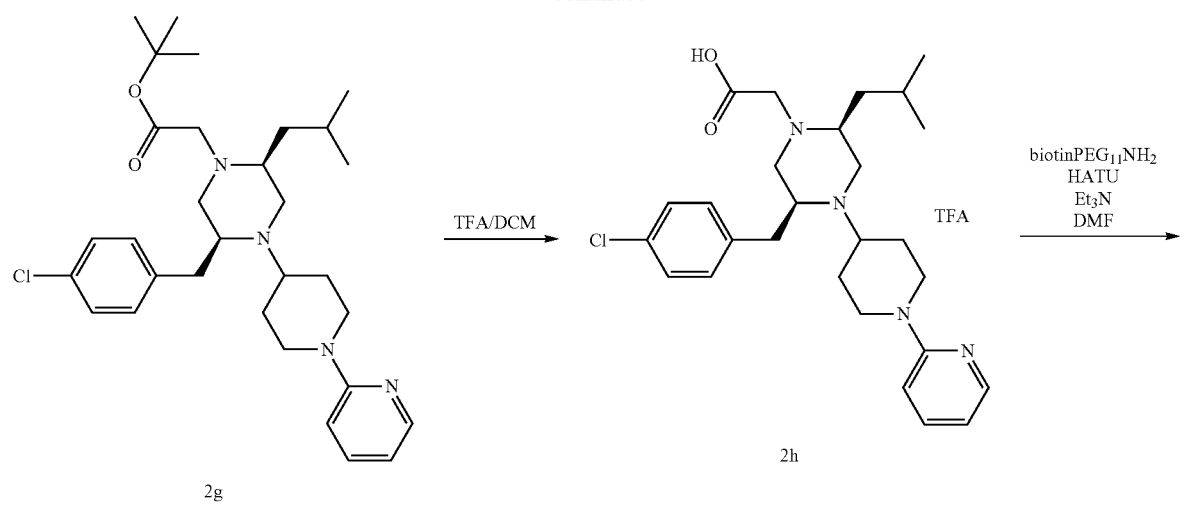
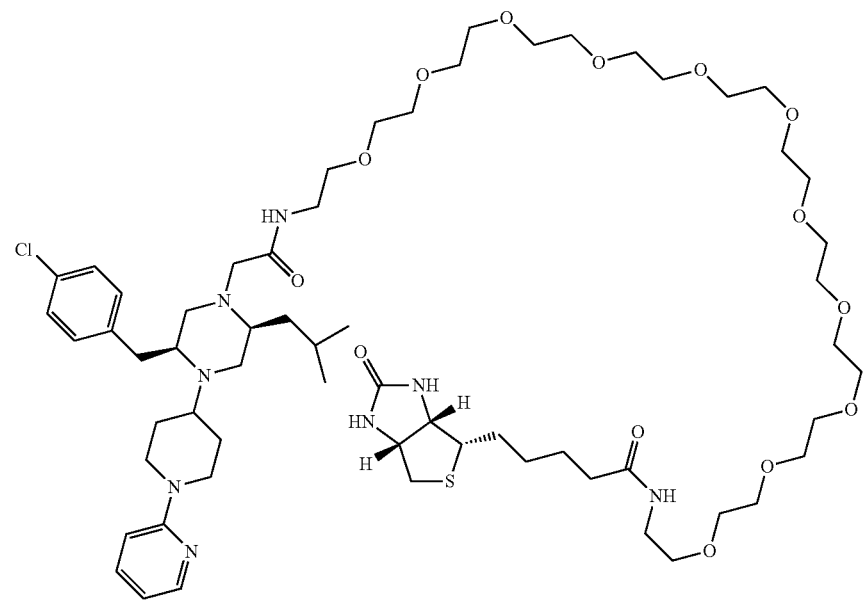

Example 2

Synthesis of N-(1-(((2S,5S)-5-(4-chlorobenzyl)-2-isobutyl-4-(1-(pyridin-2-yl)piperidin-4-yl)piperazin-1-yl)-2-oxo-6,9,12,15,18,21,24,27,30,33,36-undecaoxa-3-azaoctatriacontan-38-yl)-5-((3aS,4S,6aR)-2-oxohexahydro-1H-thieno[3,4-d]imidazol-4-yl)pentanamide (2)

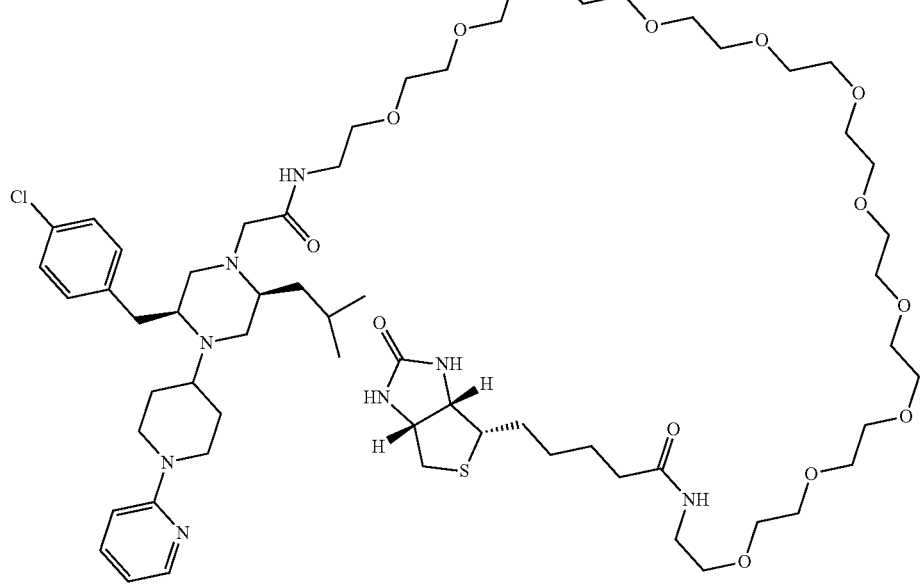

Step 1

Synthesis of methyl ((S)-2-((tert-butoxycarbonyl)amino)-3-(4-chlorophenyl)propyl)-L-leucinate (2a)

The reductive amination of a known aldehyde (3.6 g; 12.68 mmol) with a L-leucine methyl ester hydrochloride (2.3 g; 12.68 mmol) was accomplished according to the General Procedure VI. The crude product 2a was obtained in 31% yield (1.6 g, 3.88 mmol).

ESI-MS m/z for $C_{21}H_{34}ClN_2O_4$ found 413.1/415.1 [M+H]$^+$; $^1$H NMR (700 MHz, DMSO-d$_6$+D$_2$O, 348 K) δ 7.26-7.21 (m, 2H), 7.17-7.13 (m, 2H), 3.60-3.54 (m, 4H), 3.20-3.10 (m, 1H), 2.79-2.70 (m, 1H), 2.58-2.50 (m, 2H), 2.37-2.32 (m, 1H), 1.67-1.59 (m, 1H), 1.38-1.31 (m, 2H), 1.26 (s, 9H), 0.88-0.74 (m, 6H).

Step 2

Synthesis of (3S,6S)-6-(4-chlorobenzyl)-3-isobutylpiperazin-2-one (2b)

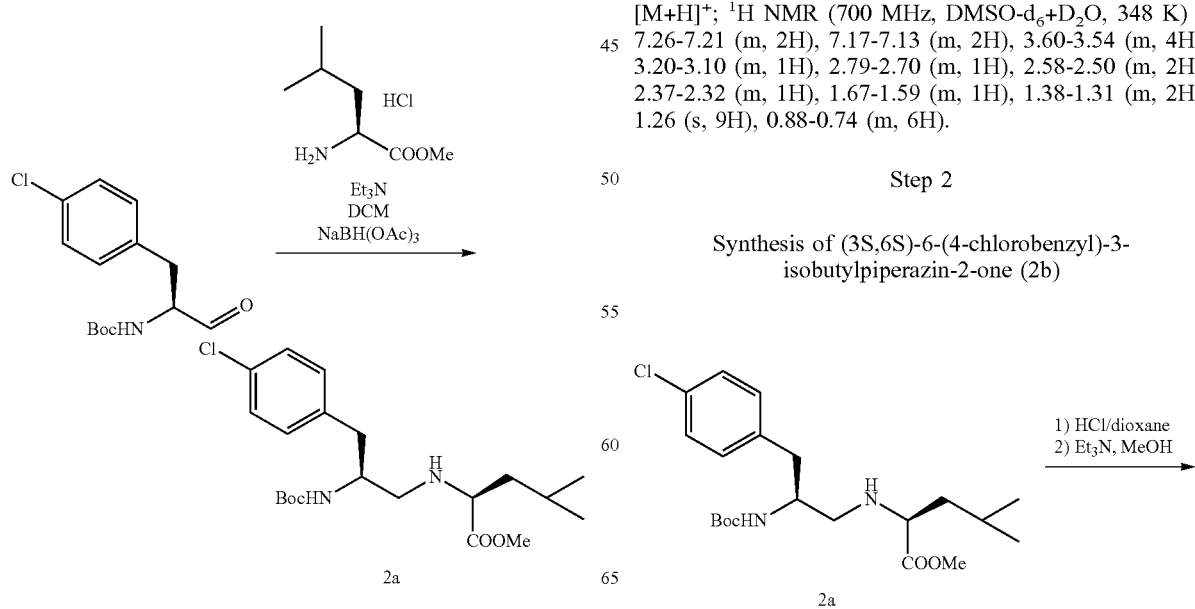

-continued

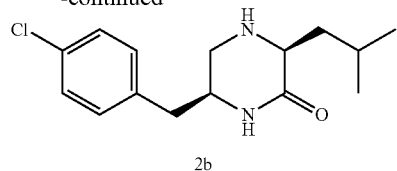

2b

The title compound (2b) was obtained from 2a (1.6 g, 3.88 mmol) according to the General Procedure VIII in 99% yield (1.08 g; 3.84 mmol).

ESI-MS m/z for $C_{15}H_{22}ClN_2O$ found 281.1/283.1 [M+H]$^+$; $^1$H NMR (700 MHz, DMSO-d$_6$+D$_2$O, 348 K) δ 7.31-7.25 (m, 2H), 7.21-7.16 (m, 2H), 3.52-3.47 (m, 1H), 3.17-3.12 (m, 1H), 2.81-2.71 (m, 3H), 2.63 (dd, J=13.2, 5.3 Hz, 1H), 1.76-1.68 (m, 1H), 1.51-1.44 (m, 1H), 1.36-1.27 (m, 1H), 0.84 (d, J=6.7 Hz, 3H), 0.80 (d, J=6.7 Hz, 3H).

Step 3

Synthesis of tert-butyl (2S,5S)-5-(4-chlorobenzyl)-2-isobutyl-3-oxopiperazine-1-carboxylate (2c)

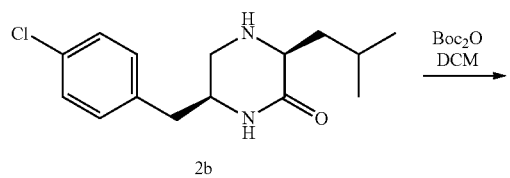

To a solution of 2b (1 g, 3.56 mmol) in dichloromethane (15 mL), di-tert-butyl dicarbonate (Boc$_2$O) (0.85 g, 3.91 mmol) was added and the reaction mixture was stirred at room temperature overnight, after which time TLC showed almost complete consumption of the starting material. The volatiles were removed in vacuo and the residue was purified by silica-gel column chromatography (hexane/AcOEt, 1.1, v/v) giving 2c as white foam in 87% yield (1.18 g; 3.1 mmol).

ESI-MS m/z for $C_{20}H_{30}ClN_2O_3$ found 381.2/383.2 [M+H]$^+$; $^1$H NMR (700 MHz, DMSO-d$_6$+D$_2$O, 348 K) δ 7.35-7.27 (m, 2H), 7.27-7.18 (m, 2H), 4.30-4.21 (m, 1H), 3.77-3.69 (m, 1H), 3.60-3.54 (m, 1H), 2.92-2.79 (m, 1H), 2.72-2.65 (m, 1H), 2.64-2.55 (m, 1H), 1.56-1.50 (m, 1H), 1.46-1.38 (m, 2H), 1.30 (s, 9H), 0.88-0.78 (m, 6H).

Step 4

Synthesis of tert-butyl (2S,5S)-5-(4-chlorobenzyl)-2-isobutylpiperazine-1-carboxylate (2d)

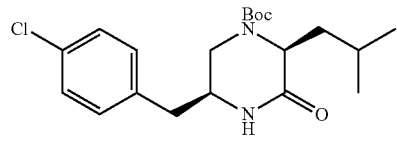

The title compound (2d) was obtained from 2c (1.18 g; 3.1 mmol) according to the General Procedure Ib in 99% yield (1.12 g; 3.07 mmol).

ESI-MS m/z for $C_{20}H_{32}ClN_2O_2$ found 367.2/369.2 [M+H]$^+$

Step 5

Synthesis of tert-butyl (2S,5S)-5-(4-chlorobenzyl)-2-isobutyl-4-(1-(pyridin-2-yl)piperidin-4-yl)piperazine-1-carboxylate (2e)

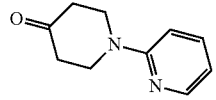

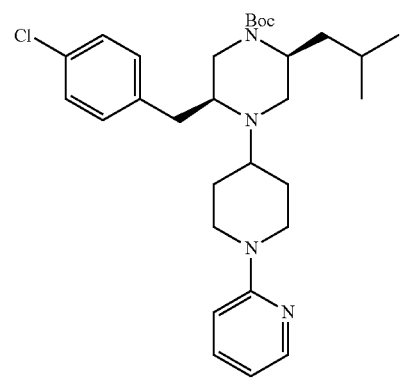

2e

The title compound (2e) was obtained from 2d (0.7 g; 1.9 mmol) according to the General Procedure VI in 62% yield (621 mg; 1.18 mmol).

ESI-MS m/z for $C_{30}H_{44}ClN_4O_2$ found 527.3/529.3 [M+H]$^+$; $^1$H NMR (700 MHz, DMSO-d$_6$+D$_2$O, 348 K) δ 8.07-7.97 (m, 1H), 7.49-7.40 (m, 1H), 7.33-7.28 (m, 2H), 7.28-7.22 (m, 2H), 6.75-6.68 (m, 1H), 6.59-6.51 (m, 1H), 4.33-4.18 (m, 2H), 3.93-3.81 (m, 1H), 3.50-3.40 (m, 1H), 3.10-3.04 (m, 1H), 3.04-2.97 (m, 1H), 2.79-2.74 (m, 1H), 2.70-2.65 (m, 1H), 2.65-2.60 (m, 2H), 2.53-2.50 (m, 1H), 2.47-2.43 (m, 1H), 2.35-2.30 (m, 1H), 1.68-1.64 (m, 1H), 1.57-1.50 (m, 2H), 1.42-1.37 (m, 3H), 1.28-1.21 (m, 10H), 0.85 (d, J=6.0 Hz, 3H), 0.83-0.81 (m, 3H).

Step 6

Synthesis of (2S,5S)-2-(4-chlorobenzyl)-5-isobutyl-1-(1-(pyridin-2-yl)piperidin-4-yl)piperazine tetrahydrochloride (2f)

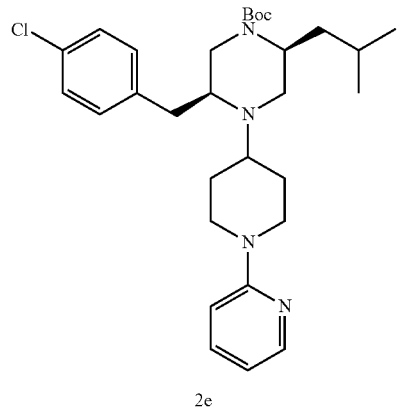

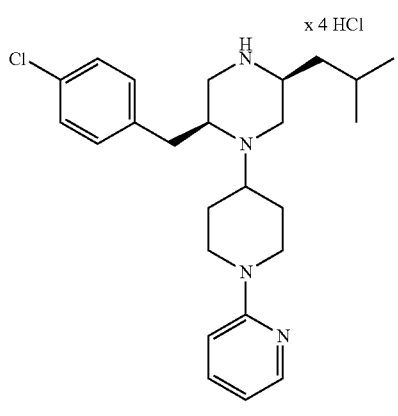

The title compound (2f) was obtained as a tetrahydrochloride salt from 2e (0.6 g; 1.14 mmol) according to the General Procedure IVa in 99% yield (646 mg; 1.13 mmol).

ESI-MS m/z for $C_{25}H_{36}ClN_4$ found 427.0/429.0 [M+H]$^+$; $^1$H NMR (700 MHz, DMSO-d$_6$+D$_2$O, 348 K) δ 7.93-7.82 (m, 2H), 7.37-7.27 (m, 4H), 7.25-7.15 (m, 1H), 6.89-6.72 (m, 1H), 4.09-3.89 (m, 2H), 3.36-3.28 (m, 1H), 3.18-3.05 (m, 4H), 3.01-2.84 (m, 5H), 2.76-2.66 (m, 1H), 1.92-1.81 (m, 2H), 1.70-1.61 (m, 1H), 1.53-1.40 (m, 4H), 0.93-0.83 (m, 6H).

Step 7

Synthesis of tert-butyl 2-((2S,5S)-5-(4-chlorobenzyl)-2-isobutyl-4-(1-(pyridin-2-yl)piperidin-4-yl)piperazin-1-yl)acetate (2g)

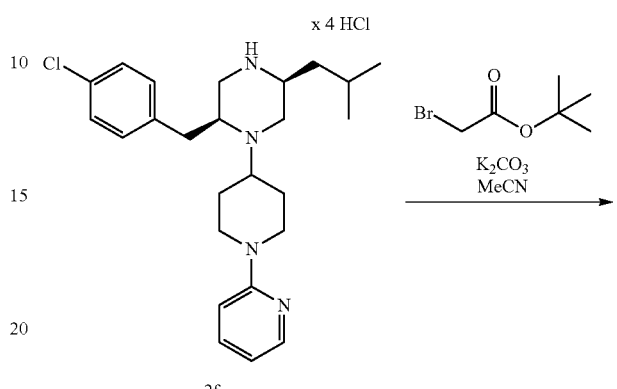

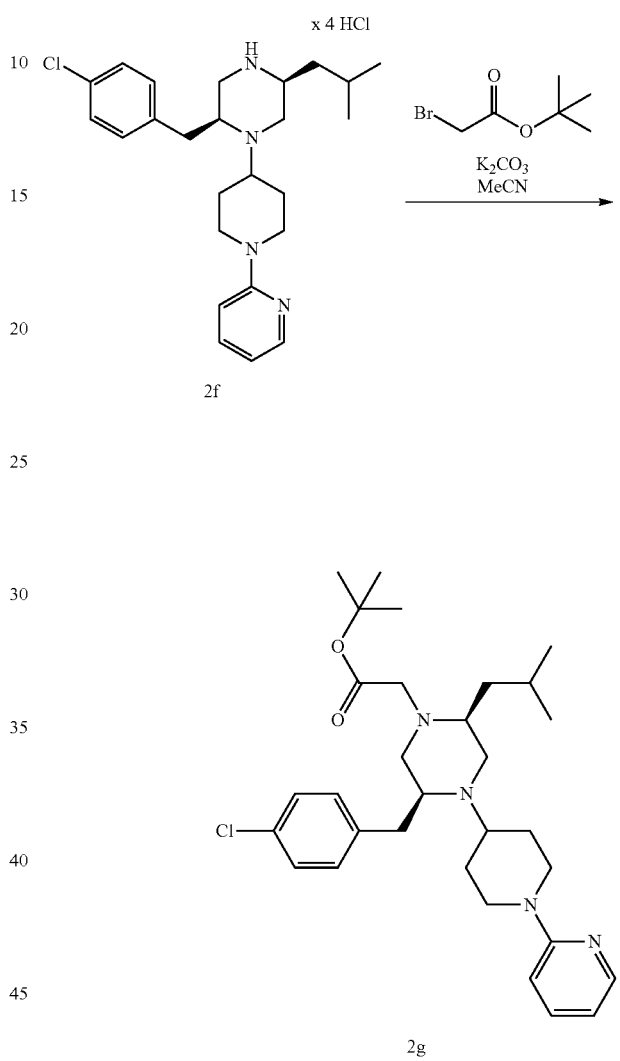

To a solution of 2f (0.1 g; 0.17 mmol) in acetonitrile (1 mL), potassium carbonate (117 mg; 0.85 mmol) was added followed by tert-butyl bromoacetate (38 μL, 0.26 mmol) and the resulting mixture was heated to 100° C. overnight. LC-MS indicated completion of the reaction. The reaction mixture was filtered and the solid residue was washed with AcOEt. After evaporation of an organic phase the crude product was purified by silica-gel column chromatography (hexane/AcOEt, 4:1, v/v) giving 2g in 76% yield (72 mg; 0.13 mmol).

ESI-MS m/z for $C_{31}H_{46}ClN_4O_2$ found 541.2/543.2 [M+H]$^+$; $^1$H NMR (700 MHz, DMSO-d$_6$+D$_2$O, 348 K) δ 8.07-7.97 (m, 1H), 7.50-7.39 (m, 1H), 7.28-7.21 (m, 2H), 7.21-7.14 (m, 2H), 6.78-6.66 (m, 1H), 6.62-6.50 (m, 1H), 4.12 (d, J=12.8 Hz, 2H), 3.11-3.01 (m, 2H), 2.97-2.92 (m, 1H), 2.90-2.67 (m, 6H), 2.55-2.51 (m, 1H), 2.47-2.43 (m, 1H), 2.39-2.31 (m, 2H), 1.88-1.77 (m, 2H), 1.56-1.48 (m, 1H), 1.38-1.29 (m, 12H), 1.24-1.19 (m, 1H), 0.85 (d, J=6.5 Hz, 3H), 0.80 (d, J=6.5 Hz, 3H).

Step 8

Synthesis of 2-((2S,5S)-5-(4-chlorobenzyl)-2-isobutyl-4-(1-(pyridin-2-yl)piperidin-4-yl)piperazin-1-yl)acetic acid 2,2,2-trifluoroacetate (2h)

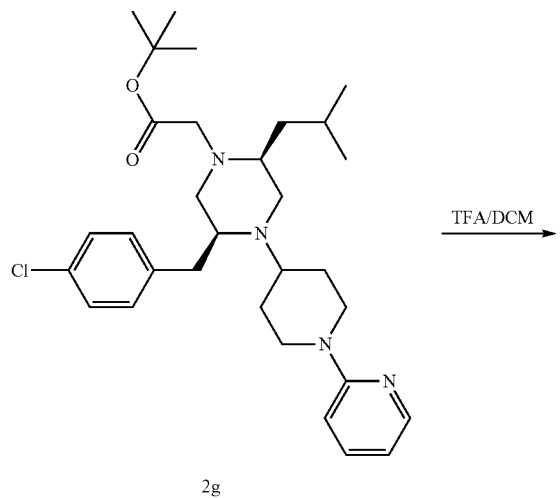

2g

TFA/DCM →

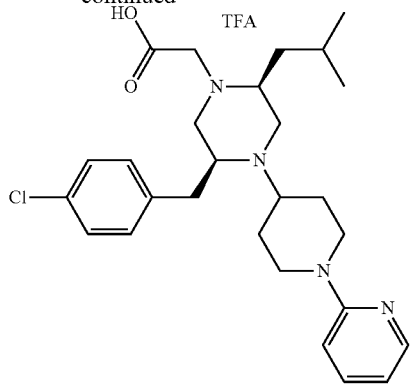

2h

The title compound (2h) was obtained as a TFA salt from 2g (54 mg; 0.09 mmol) according to the General Procedure IVb in 99% yield (53 mg; 0.089 mmol).

ESI-MS m/z for $C_{27}H_{38}ClN_4O_2$ found 485.0/487.0 $[M+H]^+$

Step 9

Synthesis of N-(1-((2S,5S)-5-(4-chlorobenzyl)-2-isobutyl-4-(1-(pyridin-2-yl)piperidin-4-yl)piperazin-1-yl)-2-oxo-6,9,12,15,18,21,24,27,30,33,36-undecaoxa-3-azaoctatriacontan-38-yl)-5-((3aS,4S,6aR)-2-oxohexahydro-1H-thieno[3,4-d]imidazol-4-yl)pentanamide (2)

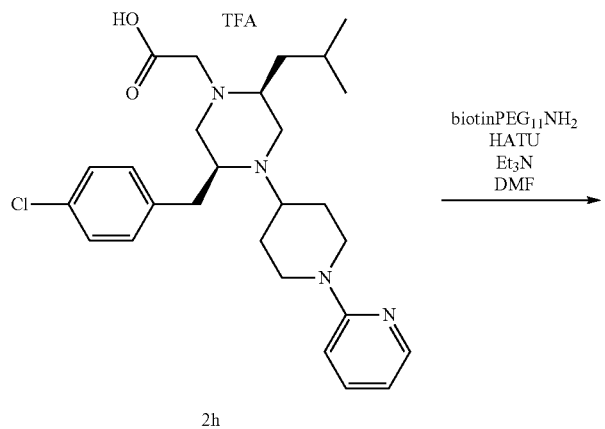

2h biotinPEG₁₁NH₂
HATU
Et₃N
DMF
→

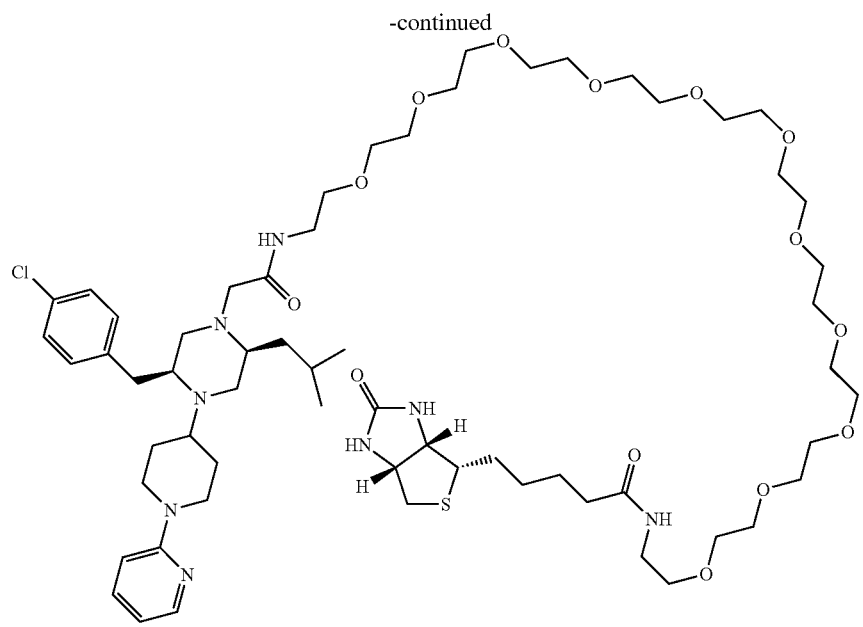
2
The title compound (2) was obtained from 2h (27 mg; 0.046 mmol) according to the General Procedure VIIb in 22% yield (12 mg; 0.01 mmol).
ESI-MS m/z for $C_{61}H_{102}ClN_8O_{14}S$ found 1237.8/1239.8 $[M+H]^+$
Scheme 3.
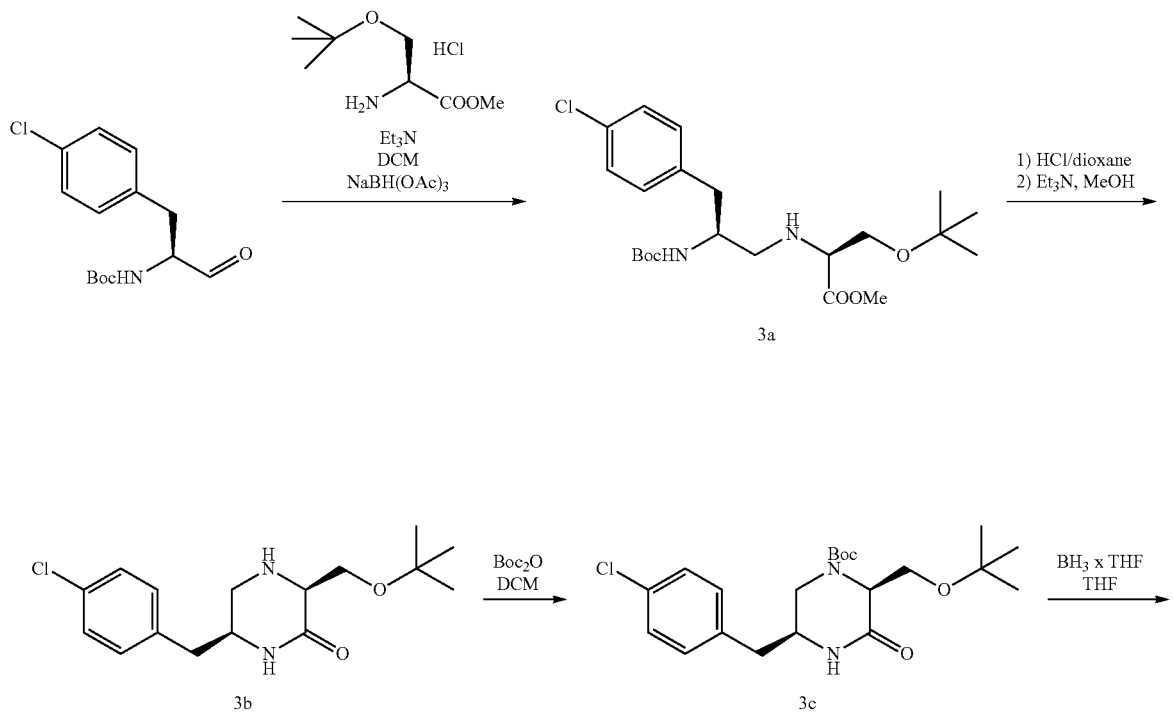

-continued
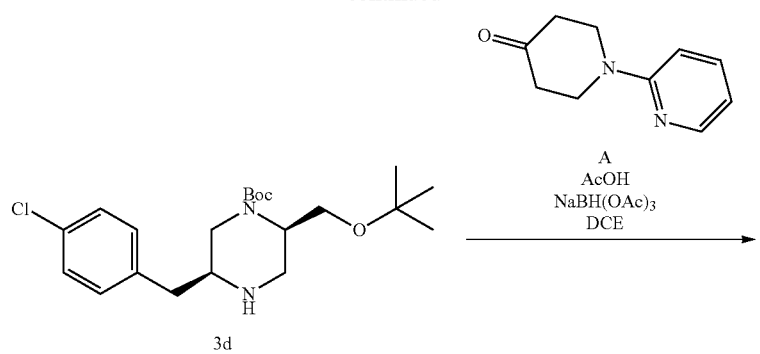
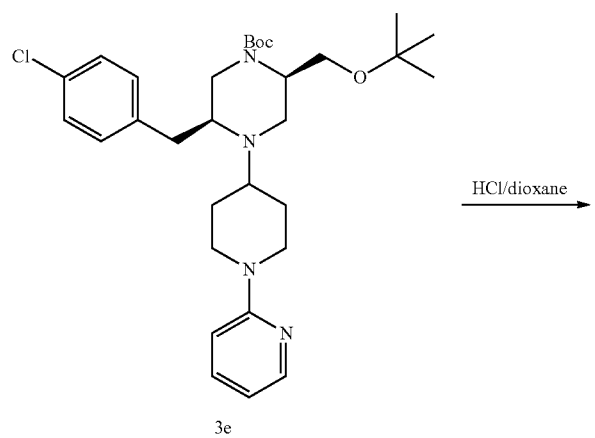
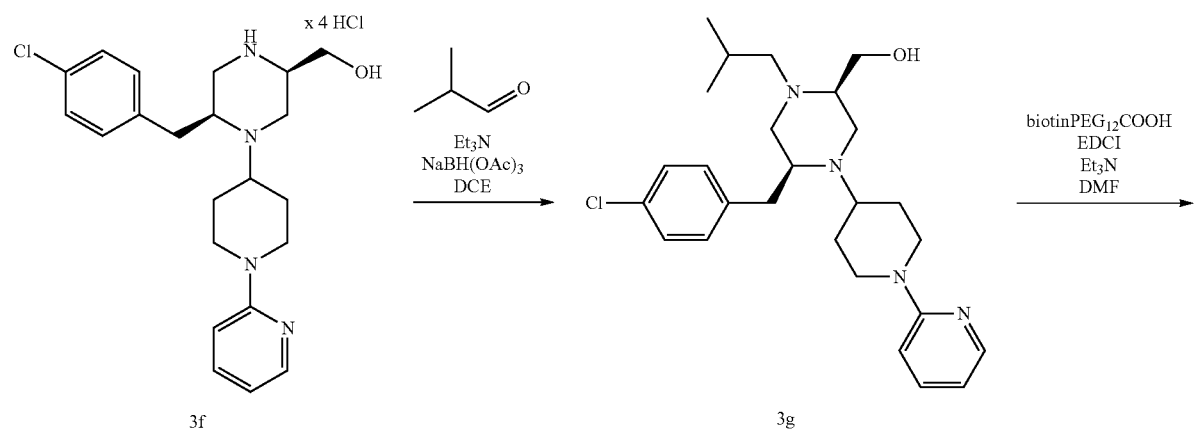

-continued
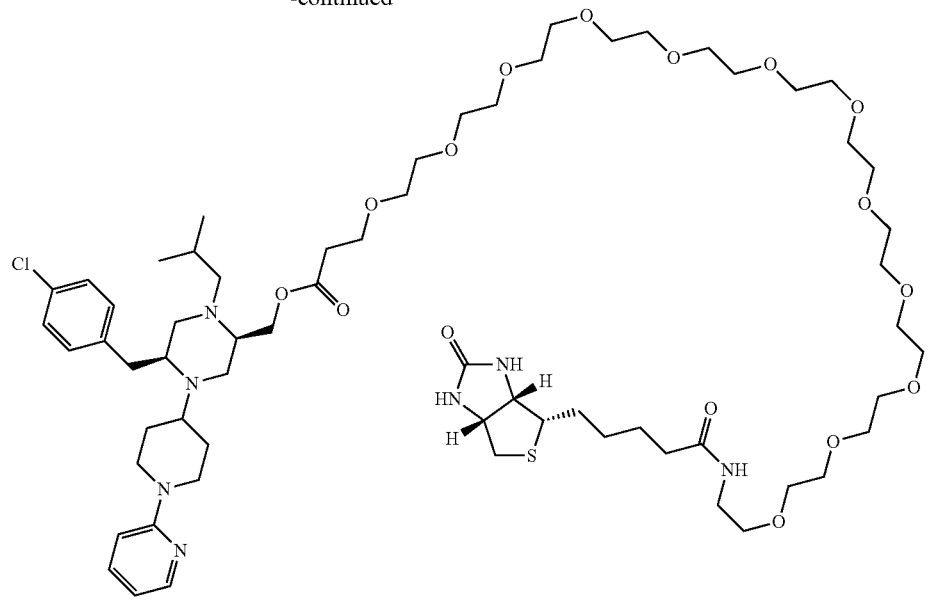
3
Example 3
Synthesis of ((2R,5S)-5-(4-chlorobenzyl)-1-isobutyl-4-(1-(pyridin-2-yl)piperidin-4-yl)piperazin-2-yl)methyl 41-oxo-45-((3aS,4S,6aR)-2-oxohexahydro-1H-thieno[3,4-d]imidazol-4-yl)-4,7,10,13,16,19,22,25,28,31,34,37-dodecaoxa-40-azapentatetracontanoate (3)
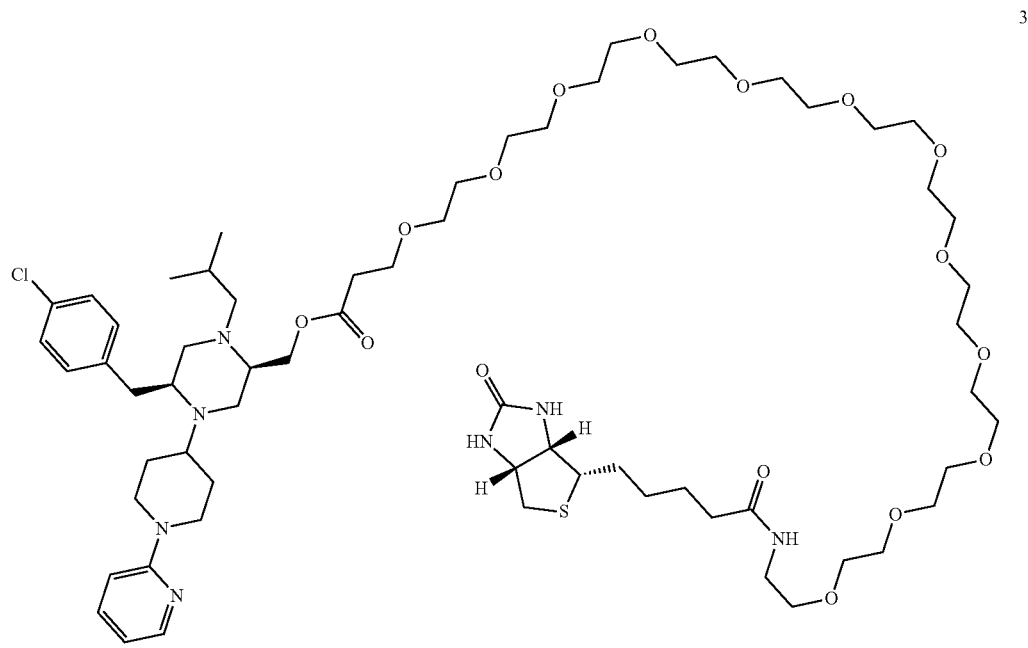 [SMILES: CC(C)CN1C[C@H](Cc2ccc(Cl)cc2)N(C2CCN(c3ccccn3)CC2)C[C@@H]1COC(=O)CCOCCOCCOCCOCCOCCOCCOCCOCCOCCOCCOCCOCCNC(=O)CCCC[C@@H]1SC[C@@H]2NC(=O)N[C@@H]21]
3

Step 1

Synthesis of methyl N-((S)-2-((tert-butoxycarbonyl)amino)-3-(4-chlorophenyl)propyl)-O-(tert-butyl)-L-serinate (3a)

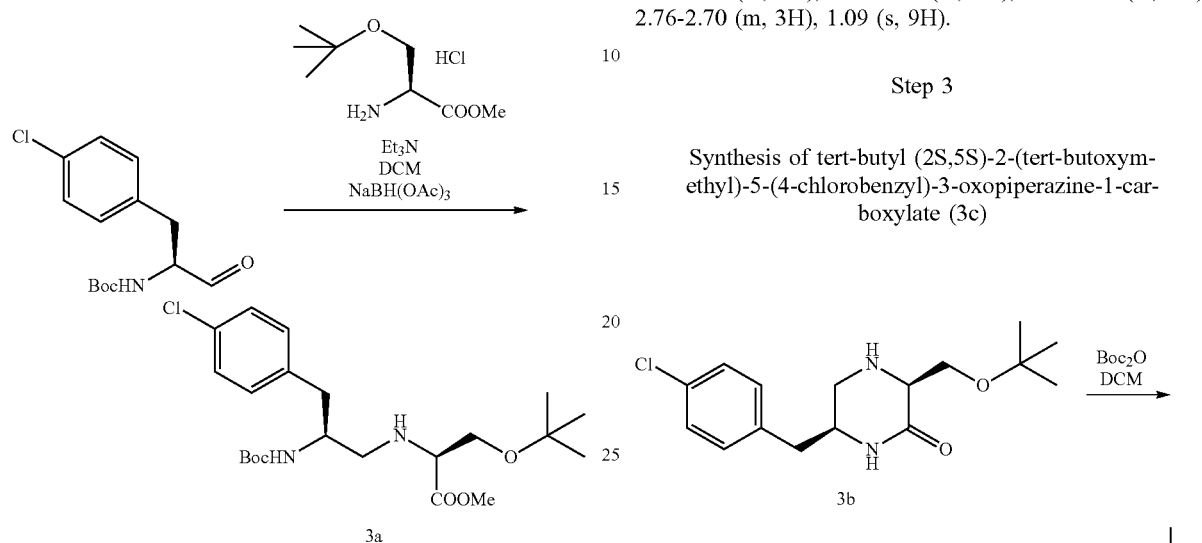

The reductive amination of a known aldehyde (4 g; 14.09 mmol) with a L-serine methyl ester hydrochloride (3 g; 14.09 mmol) was accomplished according to the General Procedure VI. The crude product 3a was obtained in 44% yield (2.62 g, 6.2 mmol).

ESI-MS m/z for $C_{22}H_{36}ClN_2O_5$ found 443.1/445.1 [M+H]$^+$; $^1$H NMR (700 MHz, DMSO-d$_6$+D$_2$O, 348 K) δ 7.25-7.21 (m, 2H), 7.18-7.12 (m, 2H), 3.60-3.56 (m, 4H), 3.42 (d, J=5.4 Hz, 2H), 3.27-3.22 (m, 1H), 2.74-2.69 (m, 1H), 2.57 (dd, J=12.1, 5.3 Hz, 2H), 2.43 (dd, J=12.1, 6.9 Hz, 1H), 1.25 (s, 9H), 1.05 (s, 9H).

Step 2

Synthesis of (3S,6S)-3-(tert-butoxymethyl)-6-(4-chlorobenzyl)piperazin-2-one (3b)

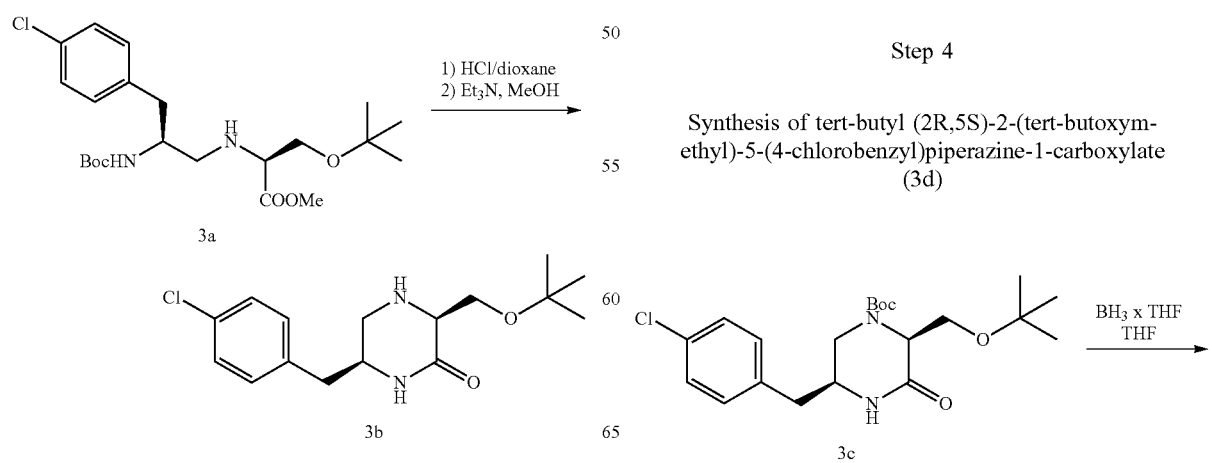

The title compound (3b) was obtained from 3a (2.77 g, 6.25 mmol) according to the General Procedure VIII in 82% yield (1.59 g; 5.13 mmol).

ESI-MS m/z for $C_{16}H_{24}ClN_2O_2$ found 311.1/313.1 [M+H]$^+$; $^1$H NMR (700 MHz, DMSO-d$_6$+D$_2$O, 348 K) δ 7.30-7.26 (m, 2H), 7.19-7.14 (m, 2H), 3.53-3.51 (m, 1H), 3.48-3.45 (m, 2H), 3.23-3.19 (m, 1H), 2.83-2.78 (m, 1H), 2.76-2.70 (m, 3H), 1.09 (s, 9H).

Step 3

Synthesis of tert-butyl (2S,5S)-2-(tert-butoxymethyl)-5-(4-chlorobenzyl)-3-oxopiperazine-1-carboxylate (3c)

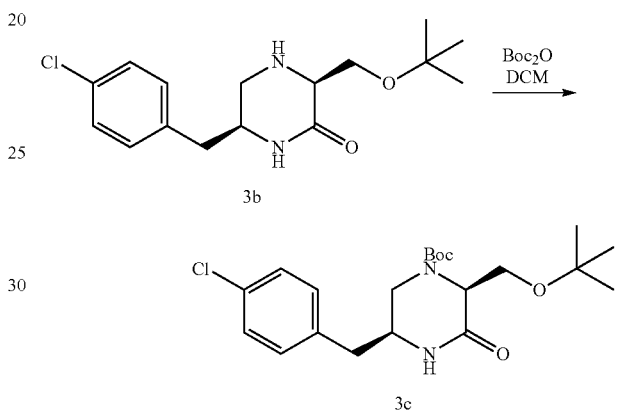

To a solution of 3b (1.59 g; 5.13 mmol) in dichloromethane (25 mL), di-tert-butyl dicarbonate (Boc$_2$O) (1.67 g, 7.67 mmol) was added and the reaction mixture was stirred at room temperature overnight, after which time TLC showed almost complete consumption of the starting material. The volatiles were removed in vacuo and the residue was purified by silica-gel column chromatography (hexane/AcOEt, 1:1, v/v) giving 2c as a white foam in 90% yield (1.9 g; 4.63 mmol).

ESI-MS m/z for $C_{21}H_{32}ClN_2O_4$ found 411.2/413.2 [M+H]$^+$

Step 4

Synthesis of tert-butyl (2R,5S)-2-(tert-butoxymethyl)-5-(4-chlorobenzyl)piperazine-1-carboxylate (3d)

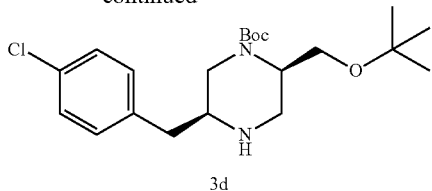

3d

The title compound (3d) was obtained from 3c (1.9 g; 4.63 mmol) according to the General Procedure Ib in 99% yield (1.81 g; 4.58 mmol).

ESI-MS m/z for $C_{21}H_{34}ClN_2O_3$ found 397.0/399.0 $[M+H]^+$

Step 5

Synthesis of tert-butyl (2R,5S)-2-(tert-butoxymethyl)-5-(4-chlorobenzyl)-4-(1-(pyridin-2-yl)piperidin-4-yl)piperazine-1-carboxylate (3e)

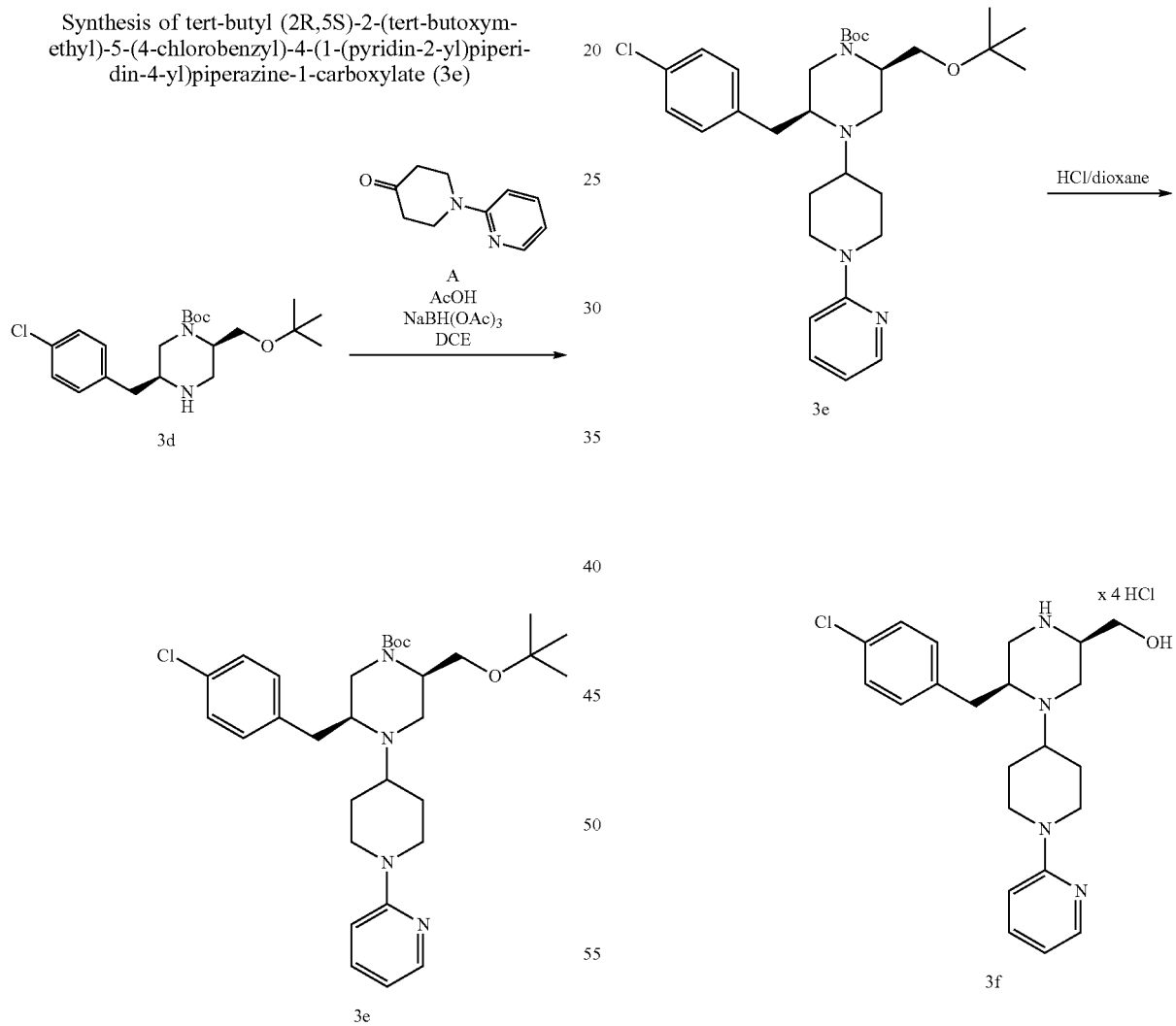

The title compound (3e) was obtained from 3d (1.2 g; 3.02 mmol) according to the General Procedure VI in 42% yield (0.71 g; 1.28 mmol).

ESI-MS m/z for $C_{31}H_{46}ClN_4O_3$ found 557.0/559.0 $[M+H]^+$; $^1$H NMR (700 MHz, DMSO-d$_6$+D$_2$O, 348 K) δ 8.05-7.98 (m, 1H), 7.48-7.42 (m, 1H), 7.29-7.27 (m, 2H), 7.22-7.13 (m, 2H), 6.75-6.70 (m, 1H), 6.56-6.48 (m, 1H), 4.27-4.18 (m, 1H), 3.82-3.75 (m, 1H), 3.59-3.52 (m, 1H), 3.46-3.40 (m, 1H), 3.24-3.17 (m, 1H), 3.05-2.99 (m, 1H), 2.96-2.86 (m, 1H), 2.85-2.78 (m, 1H), 2.78-2.69 (m, 1H), 2.63-2.56 (m, 1H), 2.55-2.50 (m, 1H), 2.47-2.43 (m, 1H), 2.43-2.36 (m, 1H), 2.35-2.29 (m, 1H), 1.69-1.61 (m, 1H), 1.56-1.50 (m, 1H), 1.40-1.34 (m, 1H), 1.33-1.29 (m, 1H), 1.30-1.23 (m, 9H), 1.08-1.04 (m, 9H), 0.93 (t, J=7.1 Hz, 1H).

Step 6

Synthesis of ((2R,5S)-5-(4-chlorobenzyl)-4-(1-(pyridin-2-yl)piperidin-4-yl)piperazin-2-yl)methanol tetrahydrochloride (3f)

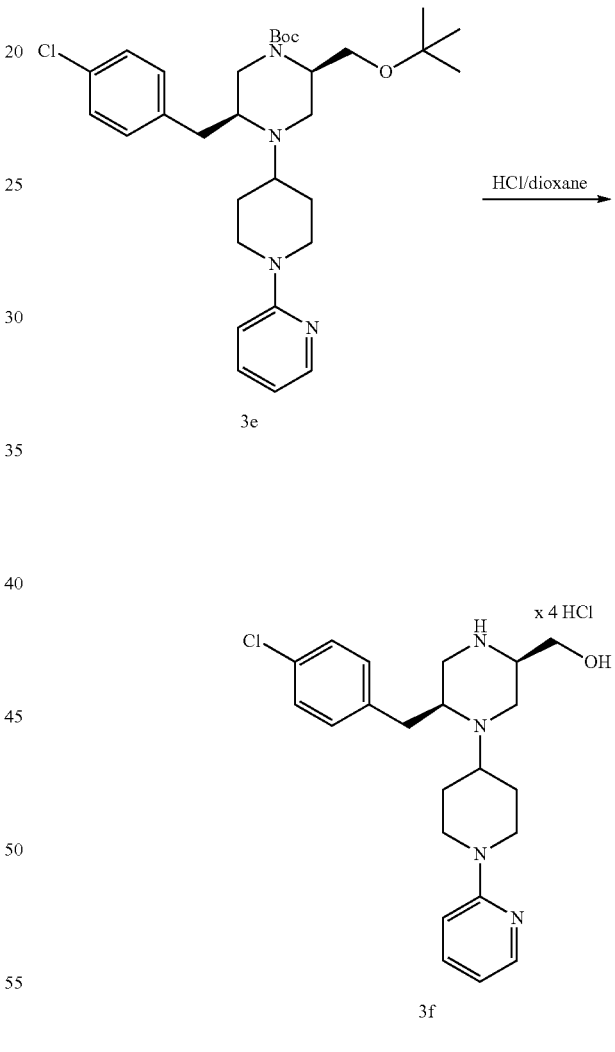

The title compound (3f) was obtained as a tetrahydrochloride salt from 3e (0.71 g; 1.28 mmol) according to the General Procedure IVa in 99% yield (693 mg; 1.27 mmol).

ESI-MS m/z for $C_{22}H_{30}ClN_4O$ found 401.0/403.0 $[M+H]^+$

211

Step 7

Synthesis of ((2R,5S)-5-(4-chlorobenzyl)-1-isobutyl-4-(1-(pyridin-2-yl)piperidin-4-yl)piperazin-2-yl)methanol (3g)

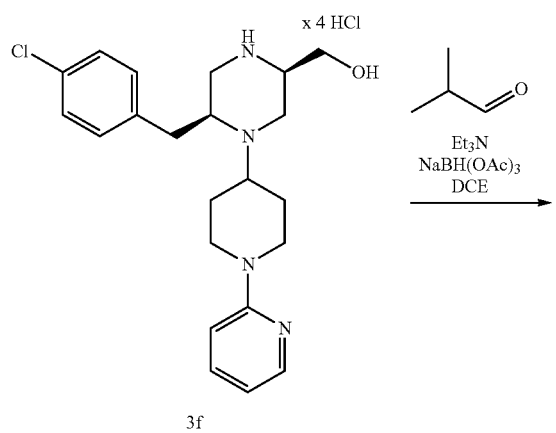

3f

212

-continued

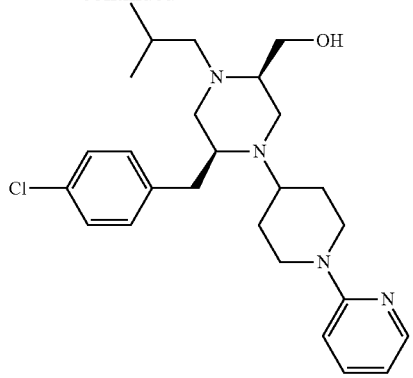

3g

The title compound (3g) was obtained from 3f (0.33 g; 0.61 mmol) according to the General Procedure VI in 90% yield (0.25 g; 0.55 mmol).

ESI-MS m/z for $C_{26}H_{38}ClN_4O$ found 457.1/459.1 [M+H]$^+$; $^1$H NMR (700 MHz, CDCl$_3$) δ 8.29-8.18 (m, 1H), 7.98-7.82 (m, 1H), 7.40-7.36 (m, 2H), 7.28-7.23 (m, 2H), 7.02-6.96 (m, 1H), 6.93-6.88 (m, 1H), 4.50-4.37 (m, 3H), 4.15-4.02 (m, 2H), 3.76-3.63 (m, 1H), 3.48-2.88 (m, 11H), 2.75-2.63 (m, 1H), 2.15-1.91 (m, 4H), 1.91-1.76 (m, 1H), 1.09-0.95 (m, 6H).

Step 8

Synthesis of ((2R,5S)-5-(4-chlorobenzyl)-1-isobutyl-4-(1-(pyridin-2-yl)piperidin-4-yl)piperazin-2-yl)methyl 41-oxo-45-((3aS,4S,6aR)-2-oxohexahydro-1H-thieno[3,4-d]imidazol-4-yl)-4,7,10,13,16,19,22,25,28,31,34,37-dodecaoxa-40-azapentatetracontanoate (3)

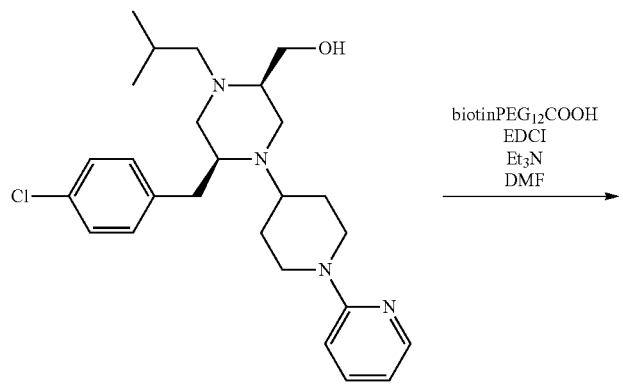

3g

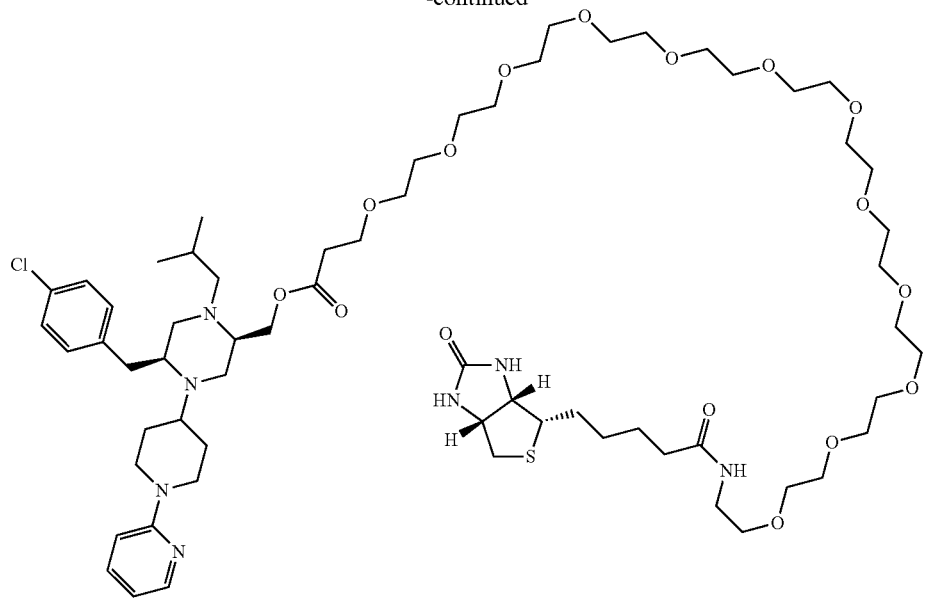
3
The title compound (3) was obtained from 3g (19 mg; 0.04 mmol) according to the General Procedure VIIa in 23% yield (11 mg; 0.009 mmol).
ESI-MS m/z for $C_{63}H_{105}ClN_7O_{16}S$ found 642.5/644.5 $[M+H]^+/2$
Scheme 4.
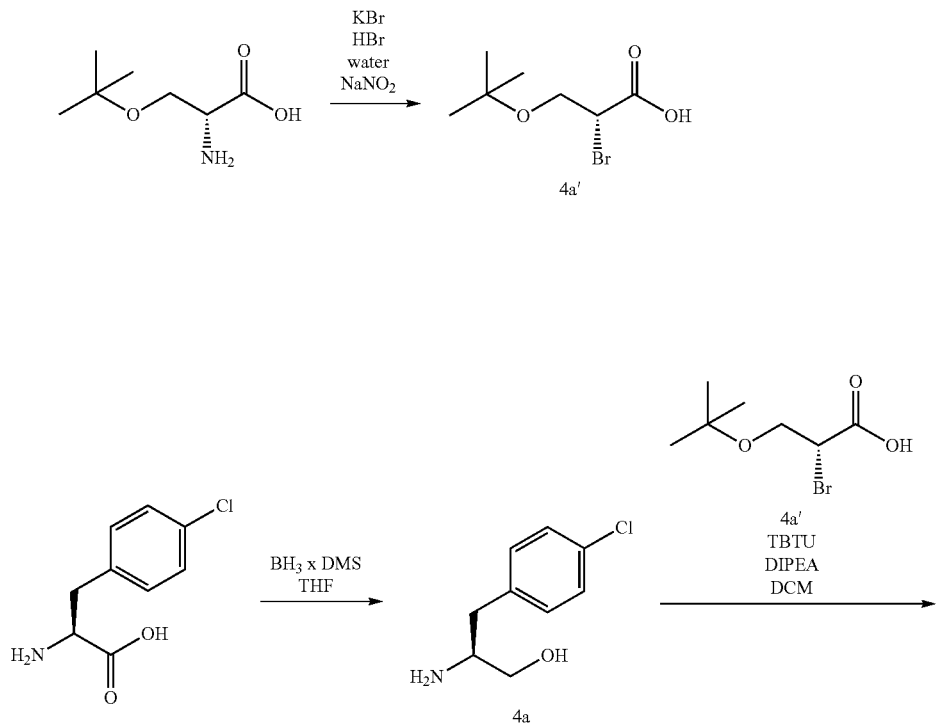

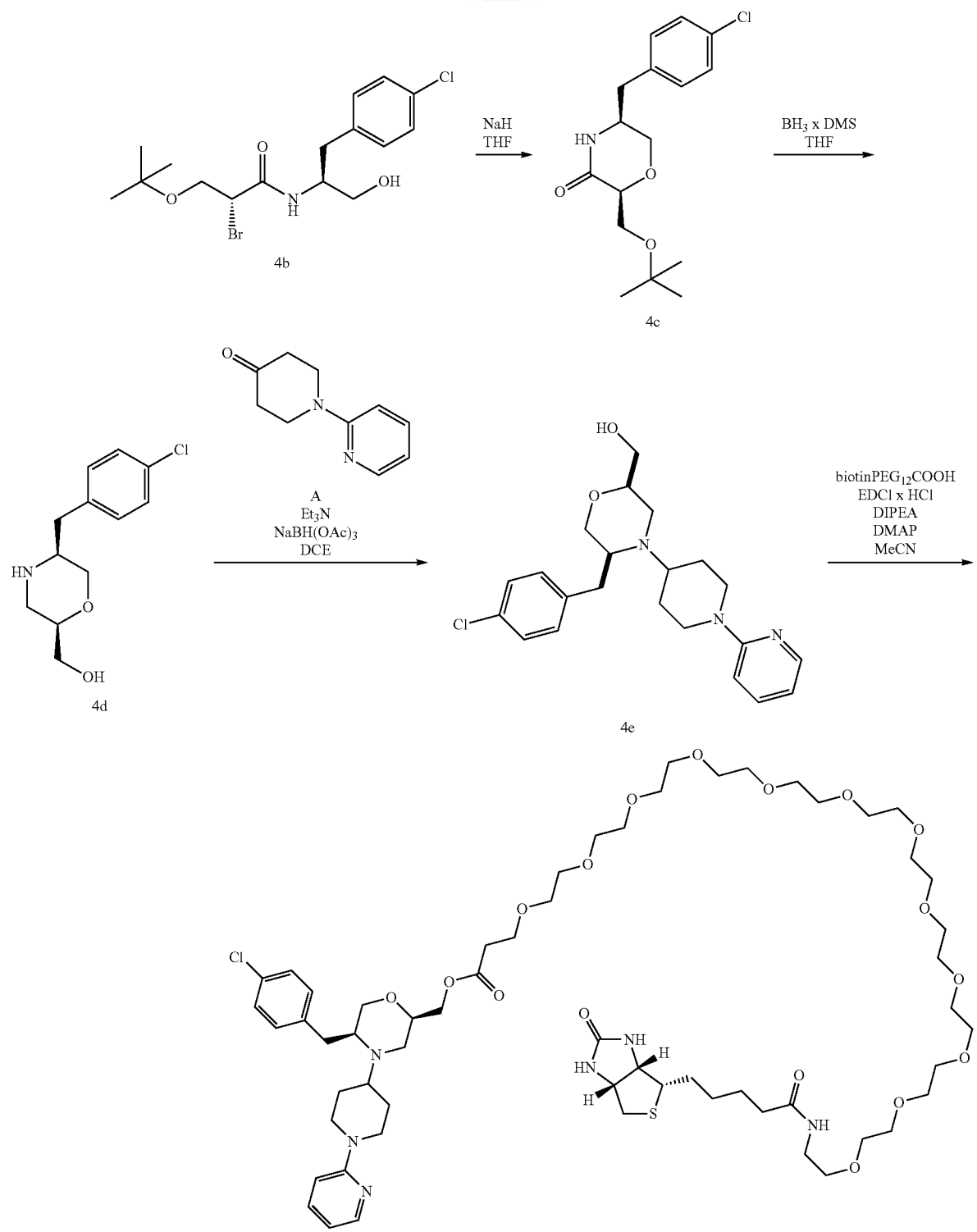

Example 4

Synthesis of ((2R,5S)-5-(4-chlorobenzyl)-4-(1-(pyridin-2-yl)piperidin-4-yl)morpholin-2-yl)methyl 41-oxo-45-((3aS,4S,6aR)-2-oxohexahydro-1H-thieno[3,4-d]imidazol-4-yl)-4,7,10,13,16,19,22,25,28,31,34,37-dodecaoxa-40-azapentatetracontanoate (4)

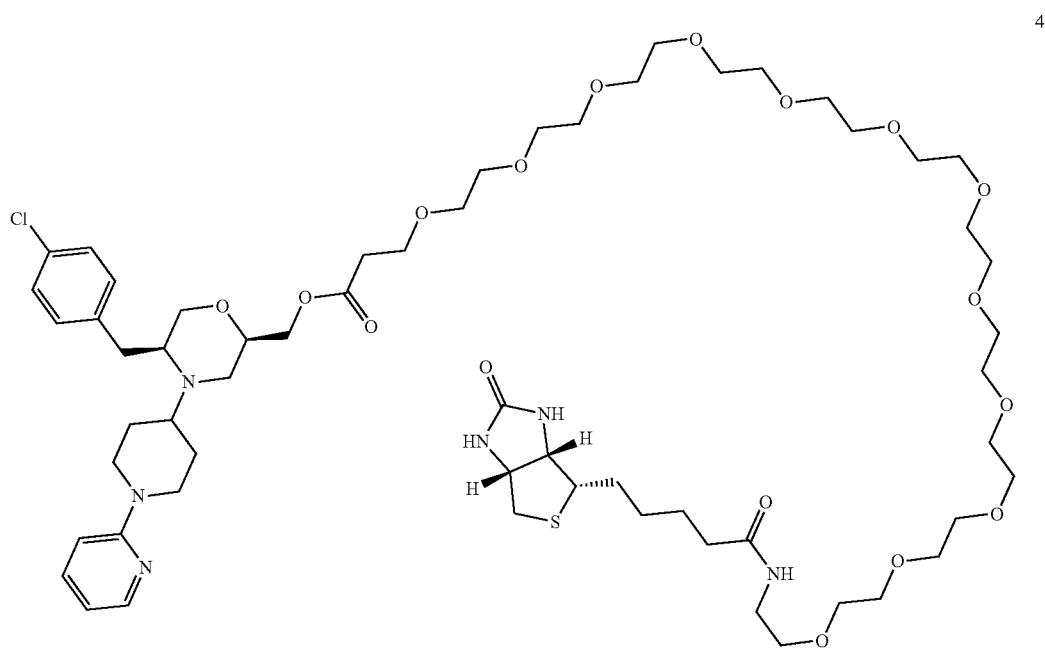 [SMILES: O=C(CCCC[C@@H]1SC[C@@H]2NC(=O)N[C@@H]21)NCCOCCOCCOCCOCCOCCOCCOCCOCCOCCOCCOCCOCCC(=O)OC[C@H]1CN(C2CCN(c3ccccn3)CC2)[C@@H](Cc2ccc(Cl)cc2)CO1]

Step 1

Synthesis of (S)-2-amino-3-(4-chlorophenyl)propan-1-ol (4a)

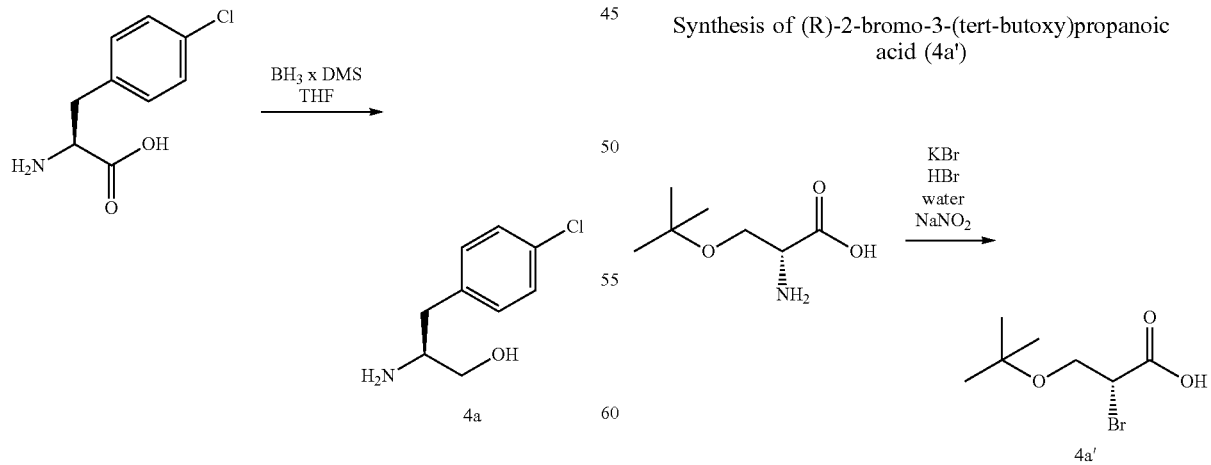

The title compound (4a) was obtained from an optically pure L-p-chlorophenylalanine ((2S)-2-amino-3-(4-chlorophenyl)propanoic acid) (10.67 g; 53.45 mmol) according to the General Procedure 1a in 87% yield (8.61 g; 46.50 mmol).

ESI-MS m/z for $C_9H_{12}ClNO$ found 185.7/187.7 [M+H]$^+$; $^1$H NMR (500 MHz, CDCl$_3$) δ 7.28 (d, J=8.3 Hz, 2H), 7.11 (d, J=8.3 Hz, 2H), 3.62 (dd, J=10.6, 3.8 Hz, 1H), 3.37 (dd, J=10.5, 6.9 Hz, 1H), 3.11-3.07 (brs, 1H), 2.76 (dd, J=13.6, 5.4 Hz, 1H), 2.50 (dd, J=13.6, 8.6 Hz, 1H).

Step 2

Synthesis of (R)-2-bromo-3-(tert-butoxy)propanoic acid (4a')

To a solution of O-(tert-butyl)-D-serine (26.8 g; 166 mmol) and KBr (69.2 g; 582 mmol) in water (134 mL) HBr (48%; 45 mL) was added at room temperature. Then the mixture was cooled to −10° C. and a solution of NaNO$_2$ (13.8 g; 200 mmol) in water (20 mL) was added by syringe pump over the period of 2 hours keeping the temperature below −5° C. Then the mixture was stirred for 2 hours at 0° C. The yellow foam appeared. To this mixture, a 10% solution of $Na_2SO_3$ in water (50 mL) was added (to remove an excess of bromine). The phases were separated and an aqueous one was extracted with MTBE (4×250 mL). The combined organic phases were dried over anhydrous $Na_2SO_4$, filtered, and concentrated in vacuo and the crude bromoacid was then dissolved in a solution of 1M NaOH (340 mL) and extracted with MTBE (100 mL). To the aqueous phase, a solution of 1M HCl (340 mL) was added (the white precipitate appeared) and the whole was transferred to the separatory funnel and extracted with MTBE (4×500 mL). The combined organic phases were dried over anhydrous $Na_2SO_4$, filtered, and concentrated in vacuo and the obtained product was used to the next step without additional purification. Compound 4a' was obtained in 95% yield (35.6 g; 158 mmol).

Step 3

Synthesis of (R)-2-bromo-3-(tert-butoxy)-N-((S)-1-(4-chlorophenyl)-3-hydroxypropan-2-yl)propanamide (4b)

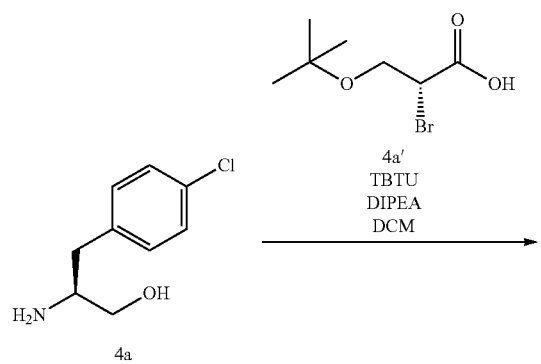

(S)-2-amino-3-(4-chlorophenyl)propan-1-ol (4a) (1.89 g; 10.2 mmol) was coupled with (R)-2-bromo-3-(tert-butoxy) propanoic acid (4a') (2.28 g; 10.2 mmol) according to the General Procedure III using TBTU as an amide bond forming reagent. The title compound 4b was obtained in 70% yield (2.96 g; 7.14 mmol).

ESI-MS m/z for $C_{16}H_{23}BrClNO_3Na$ found 414.3/416.3 $[M+Na]^+$

Step 4

Synthesis of (2S,5S)-2-(tert-butoxymethyl)-5-(4-chlorobenzyl)morpholin-3-one (4c)

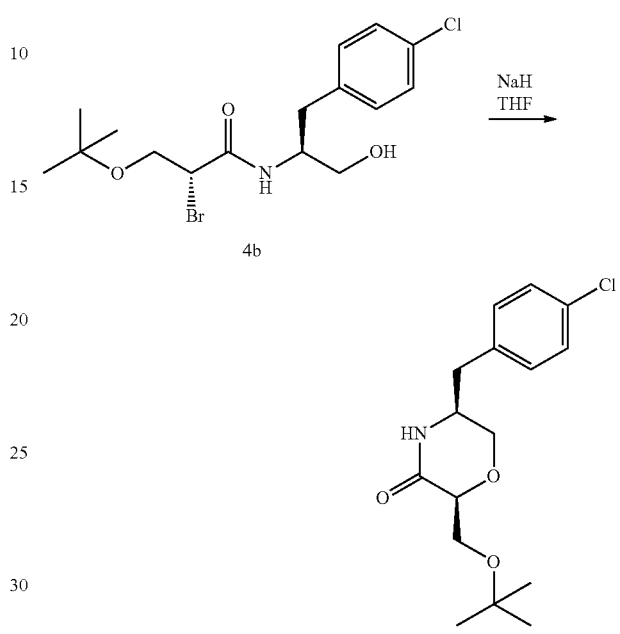

The title compound (4c) was obtained from 4b (1.2 g, 3.05 mmol) according to the General Procedure II in 89% yield (0.85 g; 2.71 mmol).

ESI-MS m/z for $C_{16}H_{22}ClNO_3Na$ found 334.1/336.1 $[M+Na]^+$

Step 5

Synthesis of ((2R,5S)-5-(4-chlorobenzyl)morpholin-2-yl)methanol (4d)

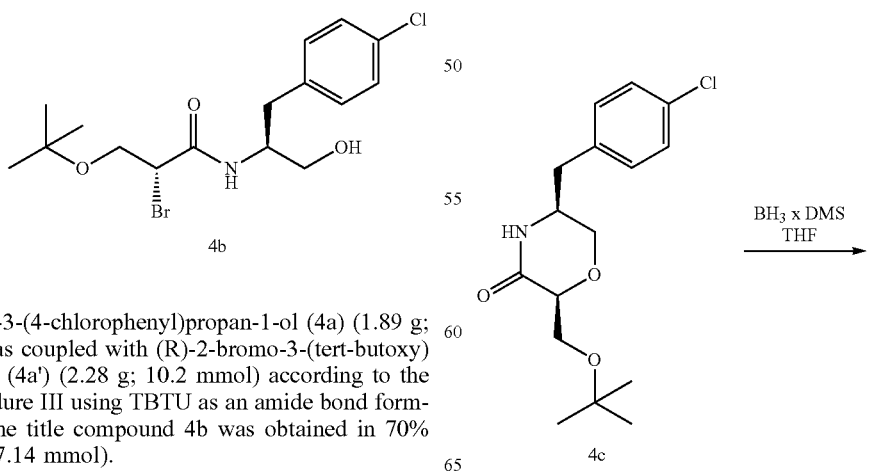

-continued

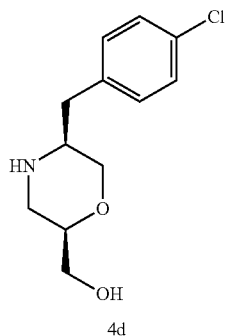

4d

The title compound (4d) was obtained from 4c (0.85 g; 2.71 mmol) according to the General Procedure Ib in 74% yield (0.48 g; 2.01 mmol).

ESI-MS m/z for $C_{12}H_{17}ClNO_2$ found 242.2/244.2 [M+H]$^+$

Step 6

Synthesis of ((2R,5S)-5-(4-chlorobenzyl)-4-(1-(pyridin-2-yl)piperidin-4-yl)morpholin-2-yl)methanol (4e)

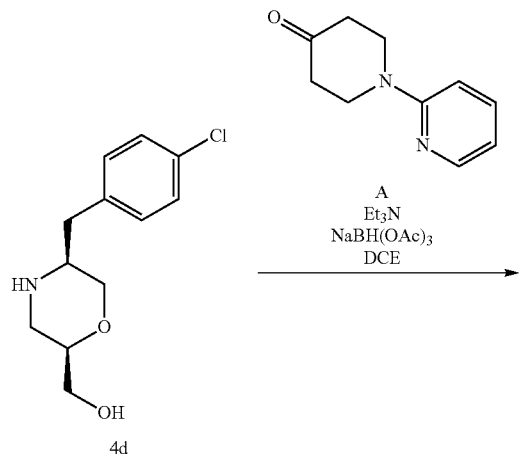

-continued

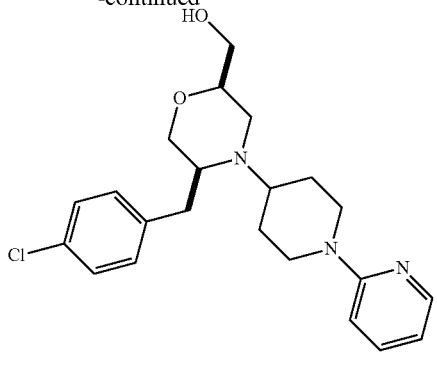

4e

The title compound (4e) was obtained from 4d (1.7 g; 7.04 mmol) according to the General Procedure VI in 88% yield (2.5 g; 6.23 mmol).

ESI-MS m/z for $C_{22}H_{29}ClN_3O_2$ found 402.2/404.2 [M+H]$^+$; $^1$H NMR (700 MHz, DMSO-d$_6$+D$_2$O, 348 K) δ 8.03-8.00 (m, 1H), 7.85-7.80 (m, 1H), 7.40-7.36 (m, 2H), 7.34-7.30 (m, 2H), 7.18-7.15 (m, 1H), 6.88-6.83 (m, 1H), 4.39-4.28 (m, 2H), 3.87-3.74 (m, 3H), 3.74-3.68 (m, 1H), 3.60-3.58 (m, 1H), 3.58-3.52 (m, 2H), 3.46-3.44 (m, 1H), 3.22-3.06 (m, 5H), 2.33-2.22 (m, 2H), 1.81-1.72 (m, 2H).

Step 7

Synthesis of ((2R,5S)-5-(4-chlorobenzyl)-4-(1-(pyridin-2-yl)piperidin-4-yl)morpholin-2-yl)methyl 41-oxo-45-((3aS,4S,6aR)-2-oxohexahydro-1H-thieno[3,4-d]imidazol-4-yl)-4,7,10,13,16,19,22,25,28,31,34,37-dodecaoxa-40-azapentatetracontanoate (4)

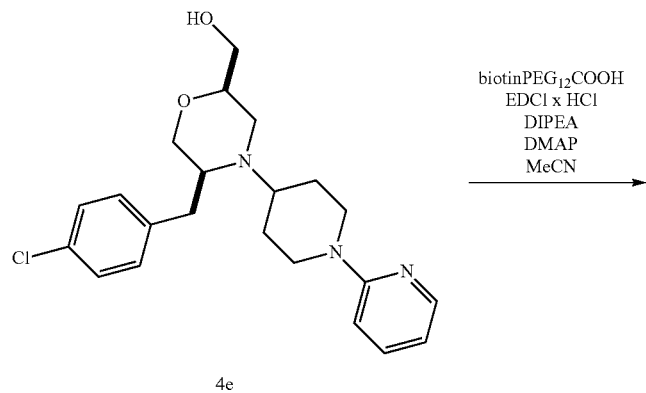

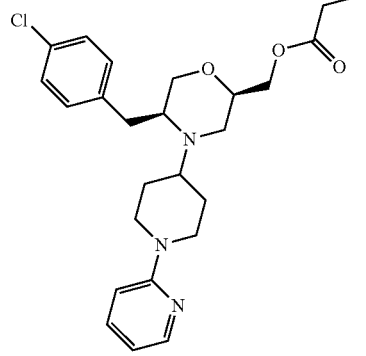
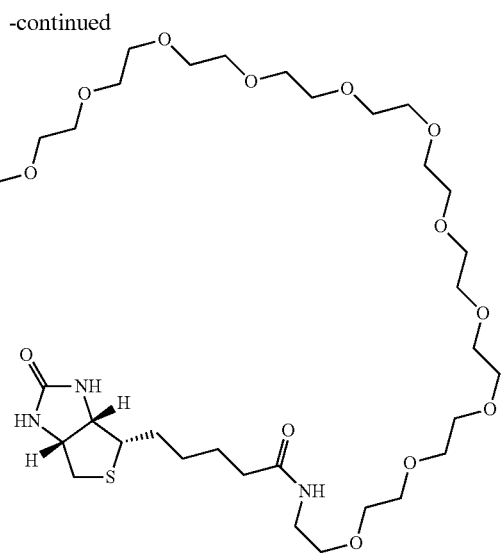
4
The title compound (4) was obtained from 4e (20 mg; 0.047 mmol) according to the General Procedure VIIa in 26% yield (15 mg; 0.012 mmol).
ESI-MS m/z for $C_{59}H_{96}ClN_6O_{17}S$ found 614.9/616.9 $[M+H]^+/2$
Example 5
Synthesis of N-(((2S,5S)-5-(4-chlorobenzyl)-4-(1-(pyridin-2-yl)piperidin-4-yl)morpholin-2-yl)methyl)-1-(5-((3aS,4S,6aR)-2-oxohexahydro-1H-thieno[3,4-d]imidazol-4-yl)pentanamido)-3,6,9,12,15,18,21,24,27,30,33,36-dodecaoxanonatriacontan-39-amide (5)
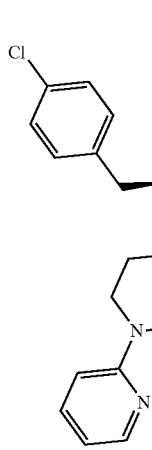
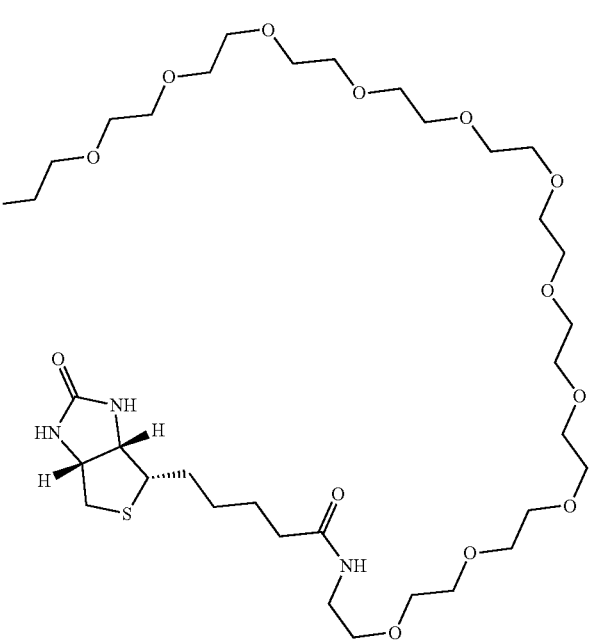
5

Step 1

Synthesis of ((2S,5S)-5-(4-chlorobenzyl)-4-(1-(pyridin-2-yl)piperidin-4-yl)morpholin-2-yl)methanamine (5a)

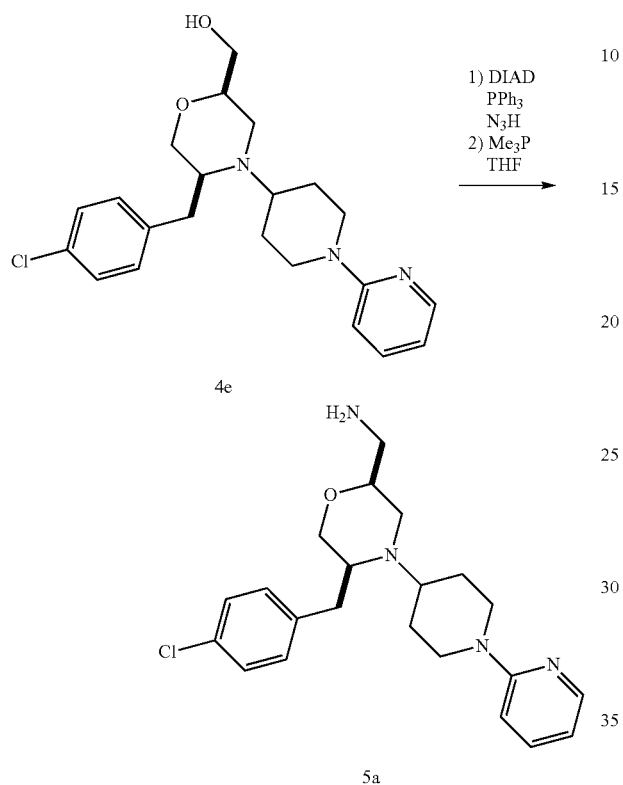

To a solution of PPh$_3$ (1.06 g; 4.03 mmol) in DCM (5 mL) cooled to −10° C. DIAD (0.81 mL; 4.03 mmol) was added dropwise and the mixture was stirred at −5° C. for 20 minutes. Then a solution of N$_3$H in toluene (3M; excess) was added and stirred at −5° C. for 20 minutes. Then 4e (600 mg; 1.49 mmol) was added and stirred overnight at room temperature. The reaction progress was monitored by TLC. When analysis indicated completion of the reaction, the reaction mixture was evaporated in vacuo and the crude product was diluted with THF/H$_2$O (10 mL/11 mL) and then 1M solution of Me$_3$P (4.47 mL; 4.47 mmol) in THF was added and stirred at room temperature overnight. When analysis indicated completion of the reaction, the reaction mixture was diluted with DCM and layers were separated. An organic layer was concentrated in vacuo and purified by flash column chromatography on silica (DCM/MeOH, 200:1 to 0:1, v/v). Compound 5a was obtained in 13% yield (80 mg; 0.2 mmol).

ESI-MS C$_{22}$H$_{30}$ClN$_4$O found 401.2/403.2 [M+H]$^+$

Step 2

Synthesis of N-(((2S,5S)-5-(4-chlorobenzyl)-4-(1-(pyridin-2-yl)piperidin-4-yl)morpholin-2-yl)methyl)-1-(5-((3aS,4S,6aR)-2-oxohexahydro-1H-thieno[3,4-d]imidazol-4-yl)pentanamido)-3,6,9,12,15,18,21,24,27,30,33,36-dodecaoxanonatriacontan-39-amide (5)

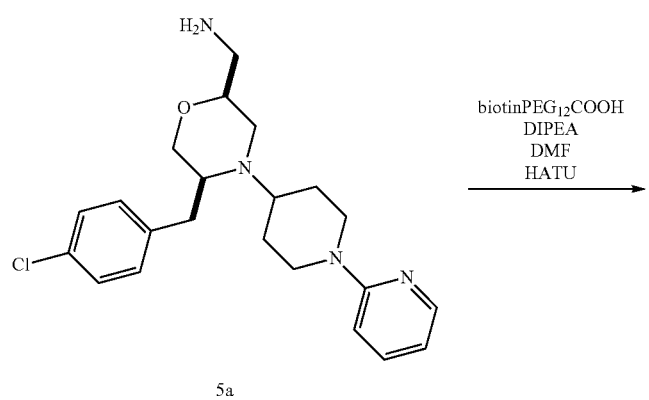

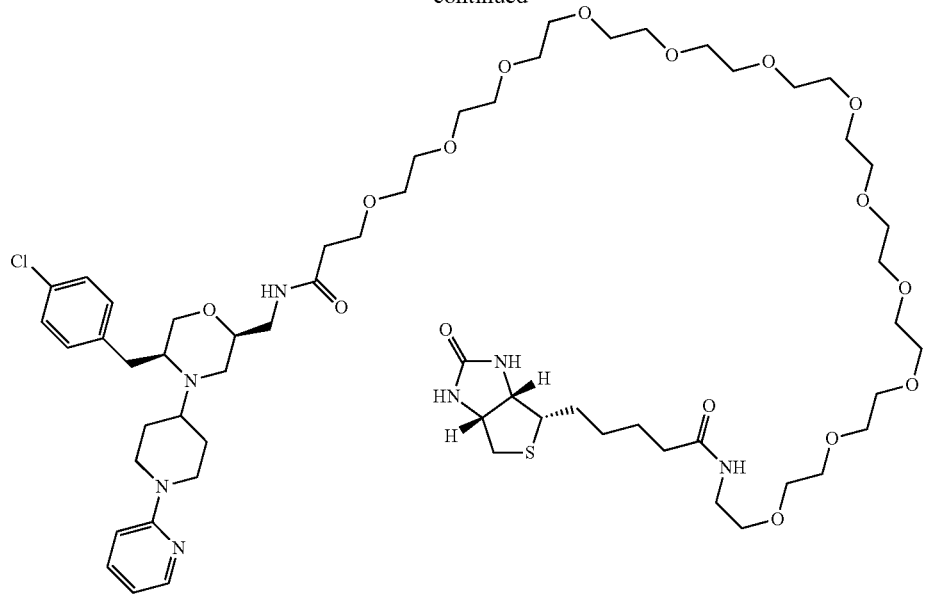
5
The title compound (5) was obtained from 5a (80 mg; 0.2 mmol) according to the General Procedure VIIa in 10% yield (25 mg; 0.02 mmol).
ESI-MS m/z for $C_{59}H_{97}ClN_7O_{16}S$ found 1226.9/1228.9 $[M+H]^+$
Example 6
Synthesis of ((2R,5S)-5-(4-chlorobenzyl)-4-(1-(4-chloropyridin-2-yl)piperidin-4-yl)morpholin-2-yl) methyl 41-oxo-45-((3aS,4S,6aR)-2-oxohexahydro-1H-thieno[3,4-d]imidazol-4-yl)-4,7,10,13,16,19,22, 25,28,31,34,37-dodecaoxa-40-azapentatetracontanoate 2,2,2-trifluoroacetate (6)
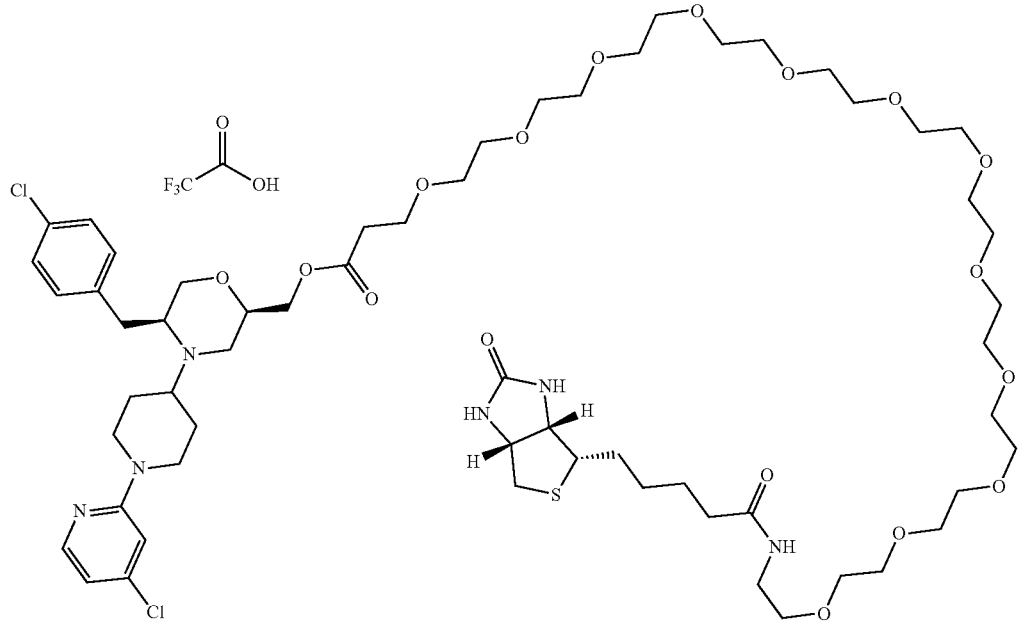
6

Step 1

Synthesis of 8-(4-chloropyridin-2-yl)-1,4-dioxa-8-azaspiro[4.5]decane (6a)

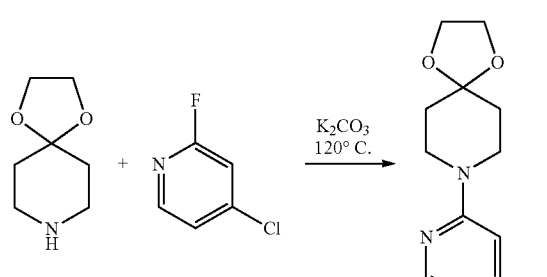

The title compound (6a) was obtained from 1,4-dioxa-8-azaspiro[4,5]decane (3 g; 20.95 mmol) and 2-fluoro-4-choropyridine (3.58 g; 27.24 mmol) according to the General Procedure IX in 99% yield (5.27 g; 20.74 mmol).

ESI-MS m/z for $C_{12}H_{16}ClN_2O_2$ found 255.1/257.1 $[M+H]^+$

Step 2

Synthesis of 1-(4-chloropyridin-2-yl)piperidin-4-one (B)

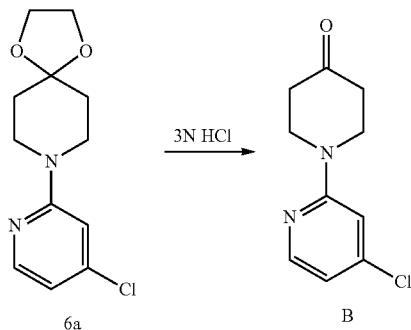

The mixture of 6a (5.27 g; 20.74 mmol) in 3N HCl (80 mL) was heated to 70° C. and stirred overnight. The reaction progress was monitored by LC-MS. After analytical control indicated completion of the reaction, the mixture was carefully alkalized, triturated with brine, extracted with AcOEt (3×). The combined organic solutions were dried over anhydrous $Na_2SO_4$, filtered and concentrated in vacuo. The product was purified by flash column chromatography on silica (cyclohexane/AcOEt, 8:1 to 2.5:1, v/v). Ketone B was obtained in 64% yield (2.79 g; 13.27 mmol). ESI-MS m/z for $C_{10}H_{12}ClN_2O$ found 211.1/213.1 $[M+H]^+$; $^1H$ NMR (700 MHz, $CDCl_3$) δ 8.17-8.11 (m, 1H), 6.80-6.76 (m, 1H), 6.76-6.68 (m, 1H), 3.99-3.94 (m, 4H), 2.61-2.53 (m, 4H).

Step 3

Synthesis of ((2R,5S)-5-(4-chlorobenzyl)-4-(1-(4-chloropyridin-2-yl)piperidin-4-yl)morpholin-2-yl)methanol hydrochloride (6b)

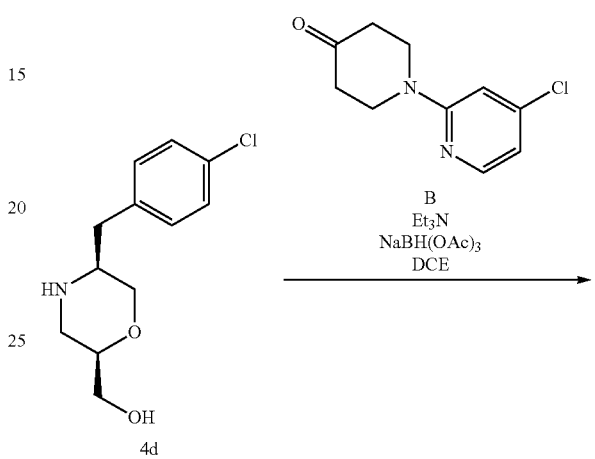

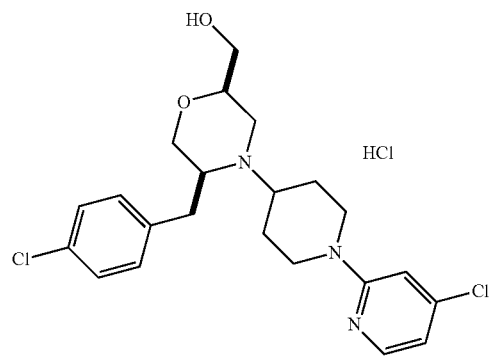

The title compound (6b) was obtained as a hydrochloride salt from 4d (200 mg; 0.83 mmol) according to the General Procedure VI in 25% yield (100 mg; 0.21 mmol).

ESI-MS m/z for $C_{22}H_{28}C_{12}N_3O_2$ found 436.2/438.2 $[M+H]^+$; $^1H$ NMR (700 MHz, DMSO-$d_6$+$D_2O$, 348 K) δ 8.08-8.04 (m, 1H), 7.42-7.39 (m, 2H), 7.37-7.33 (m, 2H), 7.05-7.02 (m, 1H), 6.79-6.76 (m, 1H), 4.44-4.36 (m, 2H), 3.87-3.70 (m, 4H), 3.64-3.55 (m, 3H), 3.44-3.40 (m, 1H), 3.23-3.12 (m, 3H), 3.05-2.95 (m, 2H), 2.31-2.18 (m, 2H), 1.76-1.66 (m, 2H).

Step 4
Synthesis of ((2R,5S)-5-(4-chlorobenzyl)-4-(1-(4-chloropyridin-2-yl)piperidin-4-yl)morpholin-2-yl) methyl 41-oxo-45-((3aS,4S,6aR)-2-oxohexahydro-1H-thieno[3,4-d]imidazol-4-yl)-4,7,10,13,16,19,22,25,28,31,34,37-dodecaoxa-40-azapentatetracontanoate (6)
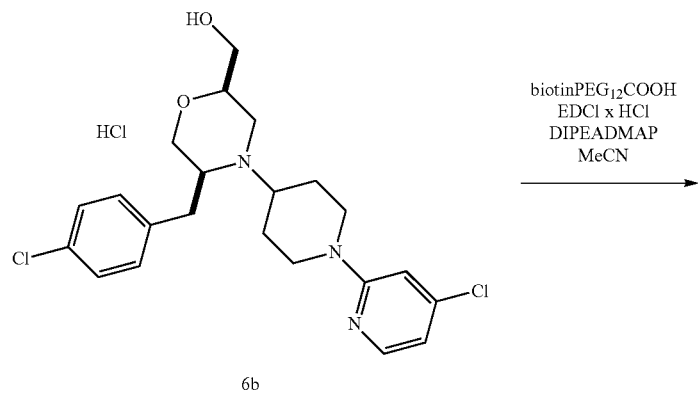
6b
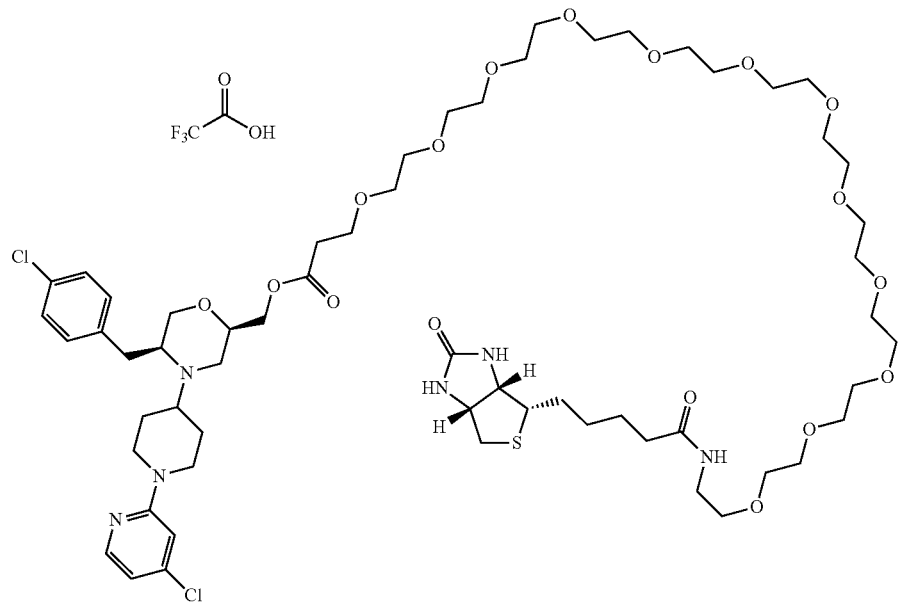
6
The title compound (6) was obtained as a TFA salt from 6b (18.5 mg; 0.042 mmol) according to the General Procedure VIIa in 74% yield (43 mg; 0.031 mmol).
ESI-MS m/z for $C_{59}H_{95}Cl_2N_6O_{17}S$ found 632.1/634.1 $[M+H]^+/2$ Example 7

Synthesis of ((2R,5S)-5-(4-chlorobenzyl)-4-(1-(pyridin-2-yl)piperidin-4-yl)morpholin-2-yl)methyl 2,5,8,11,14,17,20,23,26,29,32,35-dodecaoxaoctatriacontan-38-oate 2,2,2-trifluoroacetate (7)

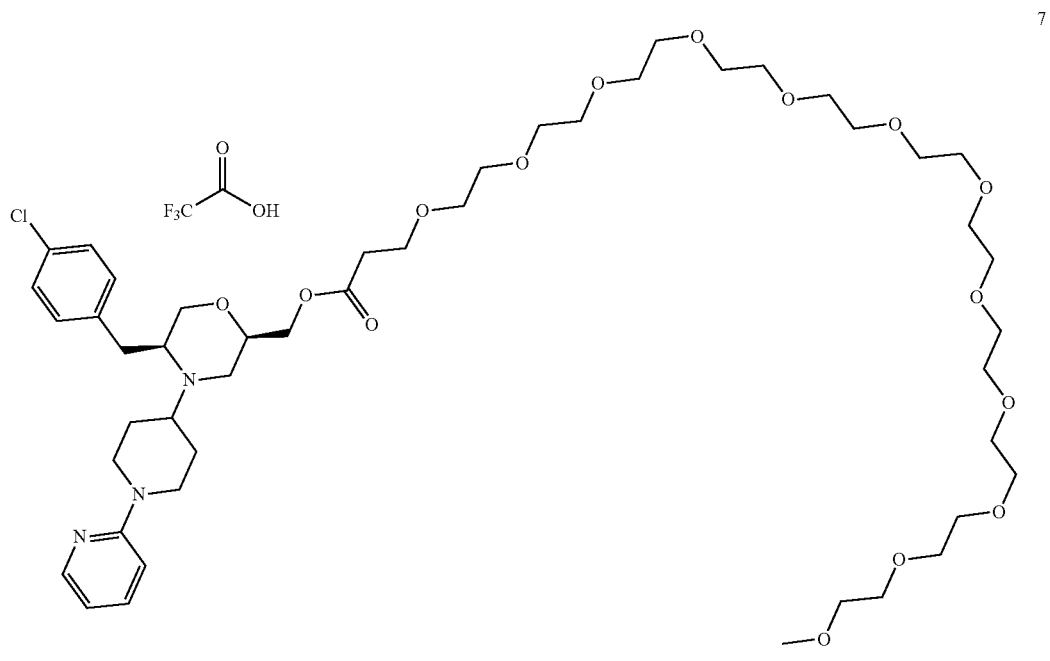 [SMILES: COCCOCCOCCOCCOCCOCCOCCOCCOCCOCCOCCOCCC(=O)OC[C@H]1CN(C2CCN(c3ccccn3)CC2)[C@@H](Cc2ccc(Cl)cc2)CO1 ; O=C(O)C(F)(F)F]

The title compound (7) was obtained as a TFA salt as a colorless oil from 4e (20.5 mg; 0.051 mmol) according to the General Procedure VIIa in 47% yield (26 mg; 0.024 mmol).

ESI-MS m/z for $C_{48}H_{79}ClN_3O_{15}$ found 972.5/974.5 $[M+H]^+$

Example 8

Synthesis of (2S,5S)-5-(4-chlorobenzyl)-4-(1-(4-chloropyridin-2-yl)piperidin-4-yl)-2-methyl-morpholine 2,2,2-trifluoroacetate (8)

Step 1

Synthesis of (R)-2-bromo-N-((S)-1-(4-chlorophenyl)-3-hydroxypropan-2-yl)propanamide (8a)

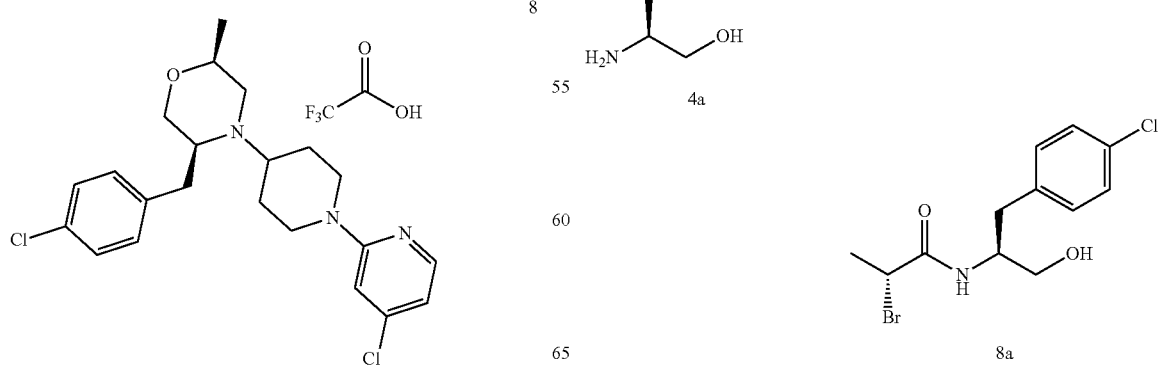

The title compound (8a) was obtained from 4a (1 g; 5.4 mmol) according to the General Procedure III in 64% yield (1.1 g; 3.46 mmol).

ESI-MS m/z for $C_{12}H_{16}BrClNO_2$ found 320.7/322.7 [M+H]$^+$; $^1$H NMR (500 MHz, CDCl$_3$) δ 7.25 (d, J=8.2 Hz, 2H), 7.14 (d, J=8.2 Hz, 2H), 6.58 (d, J=6.7 Hz, 1H), 4.33 (dd, J=14.1, 7.1 Hz, 1H), 4.13-4.06 (m, 1H), 3.69-3.64 (m, 1H), 3.61-3.57 (m, 1H), 2.90-2.81 (m, 2H), 2.17 (brs, 1H), 1.82 (d, J=6.9 Hz, 3H).

Step 2

Synthesis of (2S,5S)-5-(4-chlorobenzyl)-2-methyl-morpholin-3-one (8b)

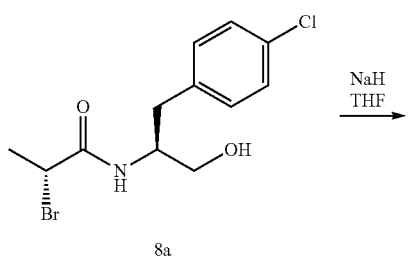

The title compound (8b) was obtained from compound 8a (1.1 g; 3.46 mmol) according to the General Procedure II in 79% yield (650 mg; 2.71 mmol).

ESI-MS m/z for $C_{12}H_{15}ClNO_2$ found 240.1/242.1 [M+H]$^+$; $^1$H NMR (500 MHz, CDCl$_3$) δ 7.27 (d, J=8.2 Hz, 2H), 7.10 (d, J=8.2 Hz, 2H), 6.13 (brs, 1H), 4.18 (m, 1H), 3.76 (d, J=3.0 Hz, 2H), 3.55-3.50 (m, 1H), 2.91-2.83 (m, 2H), 1.46 (d, J=6.9 Hz, 3H).

Step 3

Synthesis of (2S,5S)-5-(4-chlorobenzyl)-2-methyl-morpholine (8c)

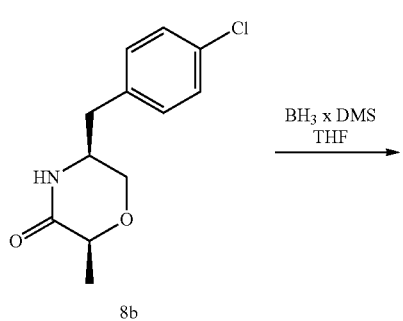

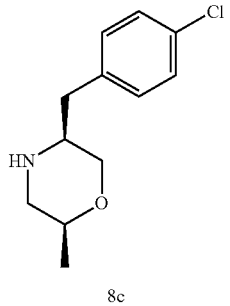

The title compound (8c) was obtained from 8b (1.1 g; 4.6 mmol) according to the General Procedure Ib in 90% yield (932 mg; 4.14 mmol).

ESI-MS m/z for $C_{12}H_{17}ClNO$ found 226.4/228.4 [M+H]$^+$; $^1$H NMR (500 MHz, DMSO-d$_6$+D$_2$O) δ 7.33 (d, J=8.3 Hz, 2H), 7.23 (d, J=8.3 Hz, 2H), 3.50-3.48 (m, 1H), 3.49-3.47 (m, 2H), 2.87-2.81 (m, 1H), 2.80-2.76 (m, 2H), 2.65 (dd, J=12.4 Hz, 8.3 Hz, 1H), 2.58 (dd, J=12.4 Hz, 3.0 Hz, 1H), 1.09 (d, J=6.2 Hz, 3H).

Step 4

Synthesis of tert-butyl 4-((2S,5S)-5-(4-chlorobenzyl)-2-methylmorpholino)piperidine-1-carboxylate (8d)

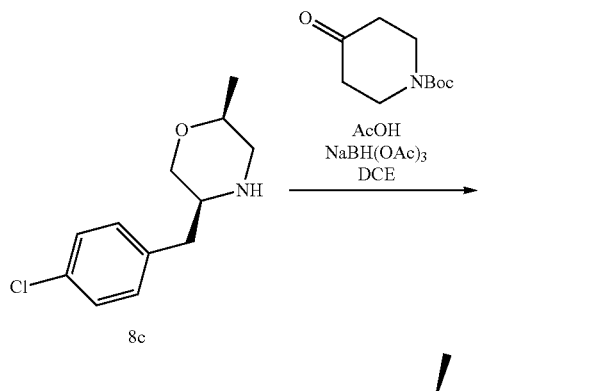

The title compound (8d) was obtained from 8c (1.36 g; 6.02 mmol) according to the General Procedure VI in 45% yield (1.1 g; 2.71 mmol).

ESI-MS m/z for $C_{22}H_{34}ClN_2O_3$ found 409.2/411.2 [M+H]$^+$; $^1$H NMR (500 MHz, DMSO-d$_6$+D$_2$O) δ 7.33 (d, J=8.3 Hz, 2H), 7.21 (d, J=8.3 Hz, 2H), 3.84 (brs, 2H), 3.51-3.46 (m, 1H), 3.44-3.40 (m, 1H), 3.35-3.33 (m, 1H), 2.90-2.85 (m, 3H), 2.82 (brs, 1H), 2.73-2.69 (m, 2H), 2.64-2.60 (m, 1H), 2.28-2.25 (m, 1H), 1.90-1.85 (m, 2H), 1.40 (s, 9H), 1.26-1.21 (m, 1H), 1.20-1.14 (m, 1H), 1.1 (d, J=6.2 Hz, 3H).

Step 5

Synthesis of (2S,5S)-5-(4-chlorobenzyl)-2-methyl-4-(piperidin-4-yl)morpholine hydrochloride (8e)

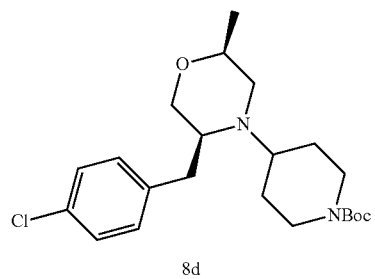

The title compound (8e) was obtained from the compound 8d (1.1 g; 2.71 mmol) according to the General Procedure IVa in 79% yield (737 mg; 2.14 mmol).

ESI-MS m/z for $C_{17}H_{26}ClN_2O$ found 309.9/311.9 [M+H]$^+$; $^1$H NMR (500 MHz, DMSO-d$_6$) δ 7.35 (d, J=8.4 Hz, 2H), 7.33 (d, J=8.4 Hz, 2H), 4.04 (brs, 2H), 3.59 (brs, 2H), 3.45 (brs, 1H), 3.40 (m, 1H), 3.39-3.36 (m, 2H), 3.10 (brs, 2H), 2.98 (brs, 1H), 2.87 (brs, 2H), 2.31 (brs, 2H), 2.17 (brs, 2H), 1.21 (d, J=6.2 Hz, 3H).

Step 6

Synthesis of (2S,5S)-5-(4-chlorobenzyl)-4-(1-(4-chloropyridin-2-yl)piperidin-4-yl)-2-methylmorpholine 2,2,2-trifluoroacetate (8)

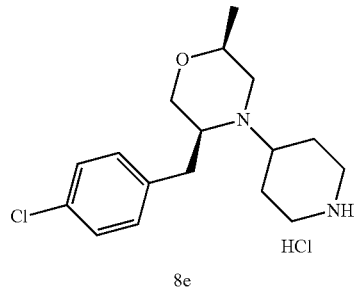

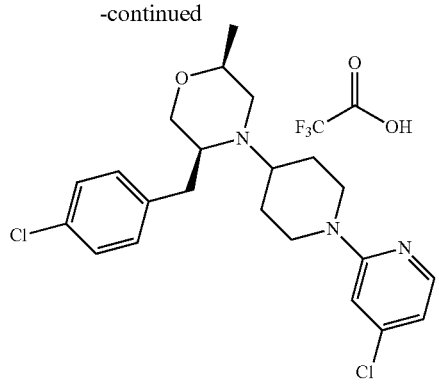

The title compound (8) was obtained as a TFA salt from 8e (34 mg; 0.1 mmol) according to the General Procedure IX in 94% yield (50 mg; 0.094 mmol).

ESI-MS m/z for $C_{22}H_{28}Cl_2N_3O$ found 420.1/422.1 [M+H]$^+$; $^1$H NMR (400 MHz, Methanol-d$_4$) δ 8.08-8.01 (m, 1H), 7.42-7.37 (m, 2H), 7.36-7.29 (m, 2H), 7.14-7.06 (m, 1H), 6.80-6.74 (m, 1H), 4.59-4.45 (m, 2H), 3.90-3.71 (m, 4H), 3.68-3.55 (m, 2H), 3.21-2.96 (m, 5H), 2.42-2.32 (m, 2H), 1.78-1.61 (m, 2H), 1.33 (d, J=6.3 Hz, 3H).

Example 9

Synthesis of (2S,5S)-5-(4-chlorobenzyl)-4-(1-(5-fluoropyridin-2-yl)piperidin-4-yl)-2-methylmorpholine 2,2,2-trifluoroacetate (9)

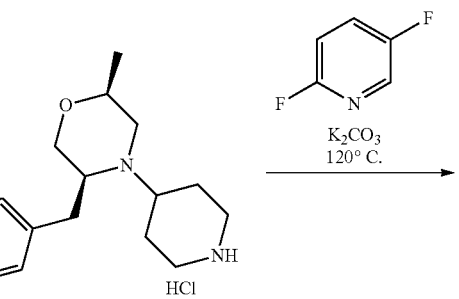

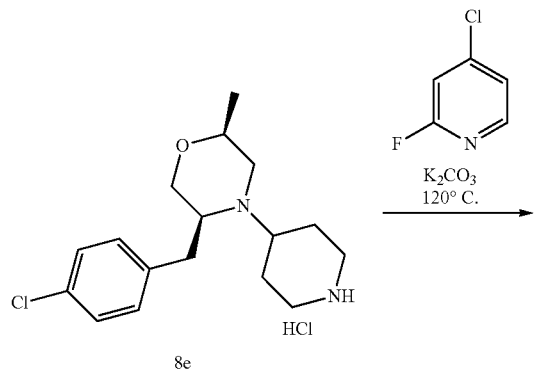

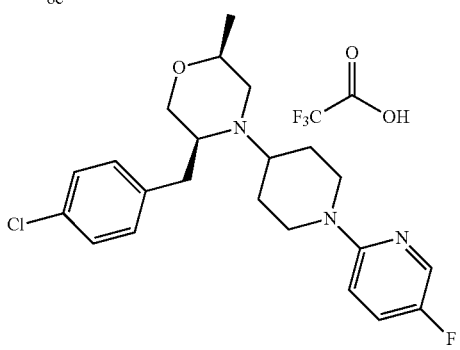

The title compound (9) was obtained as a TFA salt from 8e (34 mg; 0.1 mmol) according to the General Procedure IX in 19% yield (10 mg; 0.019 mmol).

ESI-MS m/z for $C_{22}H_{28}ClFN_3O$ found 404.2/406.2 [M+H]$^+$; $^1$H NMR (400 MHz, Methanol-d$_4$) δ 8.09-7.97 (m, 1H), 7.48-7.42 (m, 1H), 7.41-7.37 (m, 2H), 7.36-7.30 (m, 2H), 6.99-6.92 (m, 1H), 4.50-4.37 (m, 2H), 3.87-3.69 (m, 4H), 3.66-3.57 (m, 2H), 3.26-2.90 (m, 5H), 2.39-2.25 (m, 2H), 1.79-1.57 (m, 2H), 1.38-1.30 (m, 3H).

Example 10

Synthesis of (2S,5S)-5-(4-chlorobenzyl)-4-(1-(6-fluoropyridin-2-yl)piperidin-4-yl)-2-methylmorpholine 2,2,2-trifluoroacetate (10)

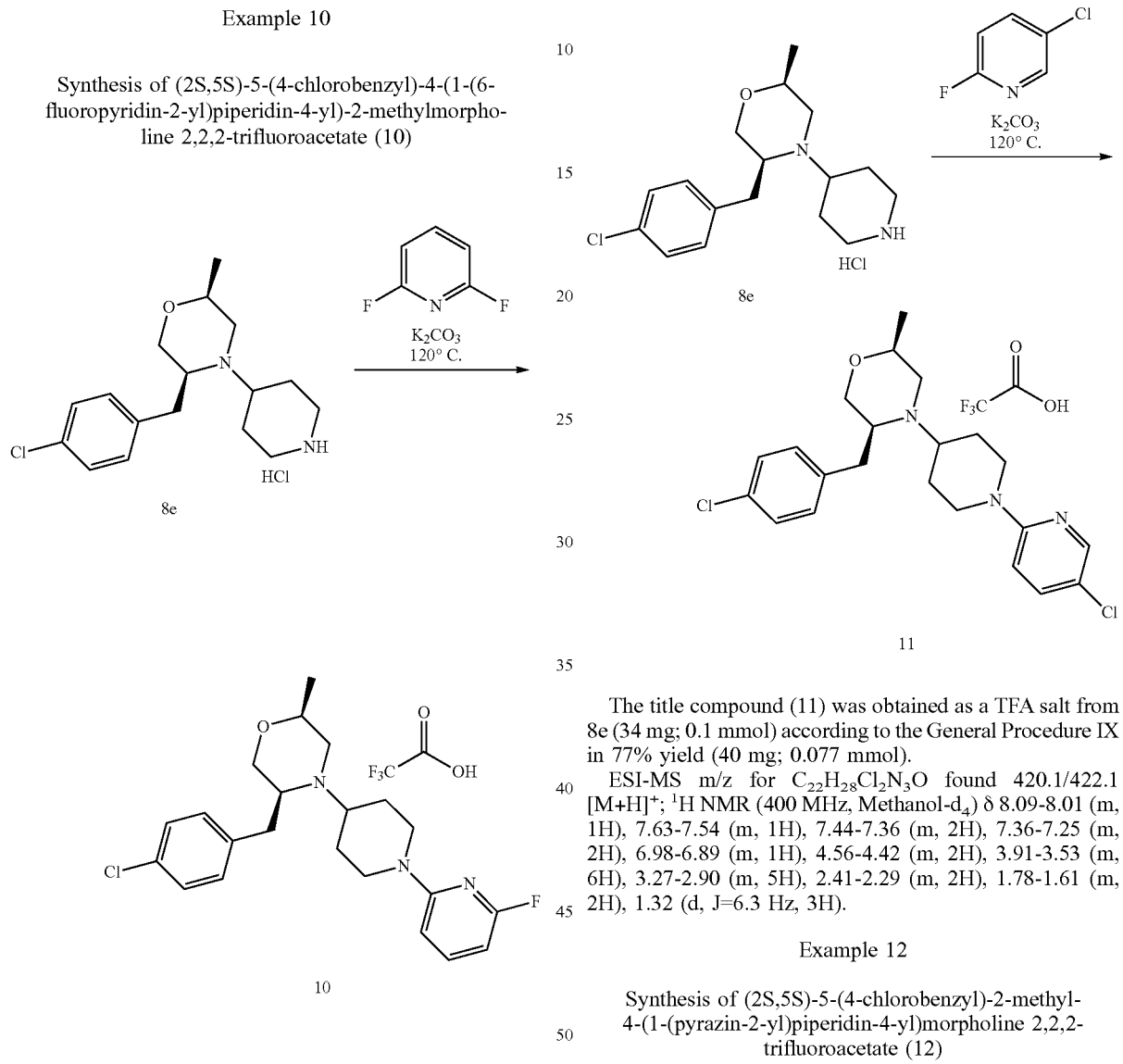

The title compound (10) was obtained as a TFA salt from 8e (34 mg; 0.1 mmol) according to the General Procedure IX in 77% yield (40 mg; 0.077 mmol).

ESI-MS m/z for $C_{22}H_{28}ClFN_3O$ found 404.1/406.1 [M+H]$^+$; $^1$H NMR (400 MHz, Methanol-d$_4$) δ 7.69-7.57 (m, 1H), 7.42-7.25 (m, 4H), 6.75-6.64 (m, 1H), 6.28-6.15 (m, 1H), 4.57-4.44 (m, 2H), 3.95-3.48 (m, 6H), 3.25-2.87 (m, 5H), 2.42-2.27 (m, 2H), 1.77-1.58 (m, 2H), 1.32 (d, J=6.3 Hz, 3H).

Example 11

Synthesis of (2S,5S)-5-(4-chlorobenzyl)-4-(1-(5-chloropyridin-2-yl)piperidin-4-yl)-2-methylmorpholine 2,2,2-trifluoroacetate (11)

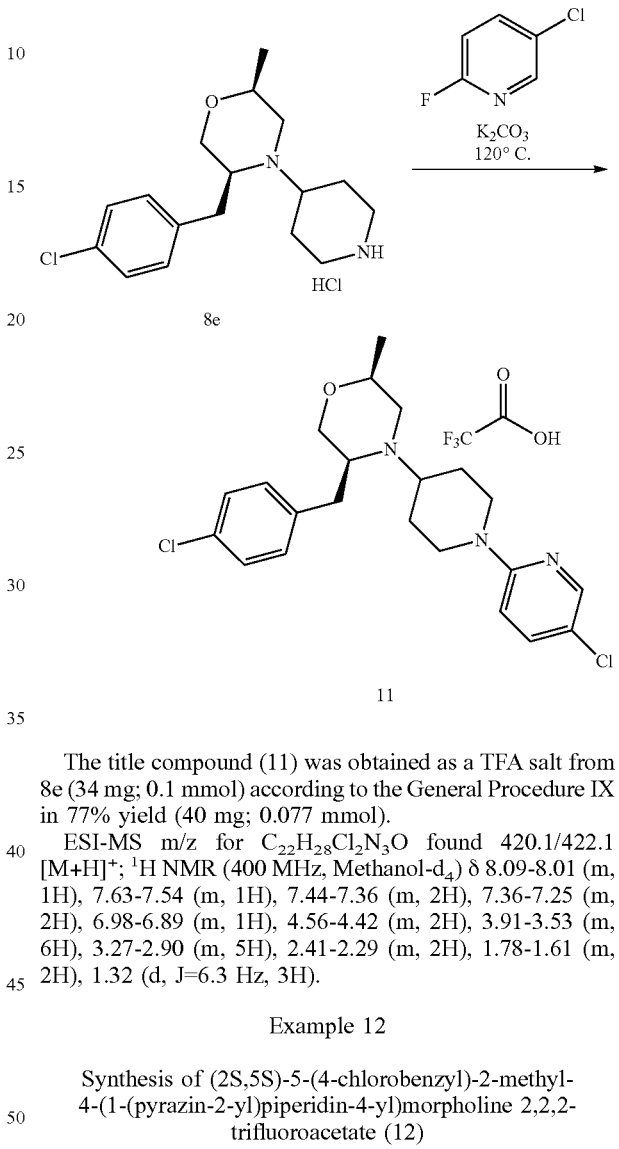

The title compound (11) was obtained as a TFA salt from 8e (34 mg; 0.1 mmol) according to the General Procedure IX in 77% yield (40 mg; 0.077 mmol).

ESI-MS m/z for $C_{22}H_{28}Cl_2N_3O$ found 420.1/422.1 [M+H]$^+$; $^1$H NMR (400 MHz, Methanol-d$_4$) δ 8.09-8.01 (m, 1H), 7.63-7.54 (m, 1H), 7.44-7.36 (m, 2H), 7.36-7.25 (m, 2H), 6.98-6.89 (m, 1H), 4.56-4.42 (m, 2H), 3.91-3.53 (m, 6H), 3.27-2.90 (m, 5H), 2.41-2.29 (m, 2H), 1.78-1.61 (m, 2H), 1.32 (d, J=6.3 Hz, 3H).

Example 12

Synthesis of (2S,5S)-5-(4-chlorobenzyl)-2-methyl-4-(1-(pyrazin-2-yl)piperidin-4-yl)morpholine 2,2,2-trifluoroacetate (12)

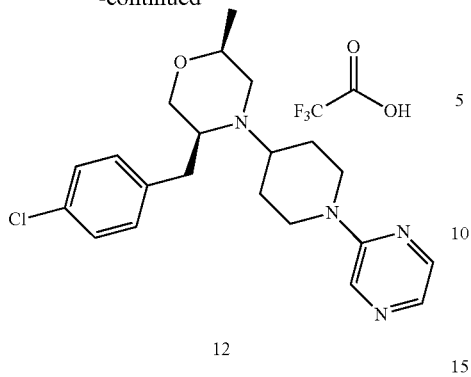

12

The title compound (12) was obtained as a TFA salt from 8e (34 mg; 0.1 mmol) according to the General Procedure IX in 68% yield (34 mg; 0.068 mmol).

ESI-MS m/z for $C_{21}H_{28}ClN_4O$ found 387.2/389.2 [M+H]+; $^1$H NMR (400 MHz, Methanol-$d_4$) δ 8.36-8.28 (m, 1H), 8.22-8.14 (m, 1H), 7.88-7.79 (m, 1H), 7.42-7.35 (m, 2H), 7.35-7.27 (m, 2H), 4.70-4.49 (m, 2H), 3.95-3.54 (m, 6H), 3.26-2.93 (m, 5H), 2.47-2.21 (m, 2H), 1.87-1.62 (m, 2H), 1.33 (d, J=6.3 Hz, 3H).

Example 13

Synthesis of (2S,5S)-5-(4-chlorobenzyl)-4-(1-(3-fluoropyridin-2-yl)piperidin-4-yl)-2-methylmorpholine 2,2,2-trifluoroacetate (13)

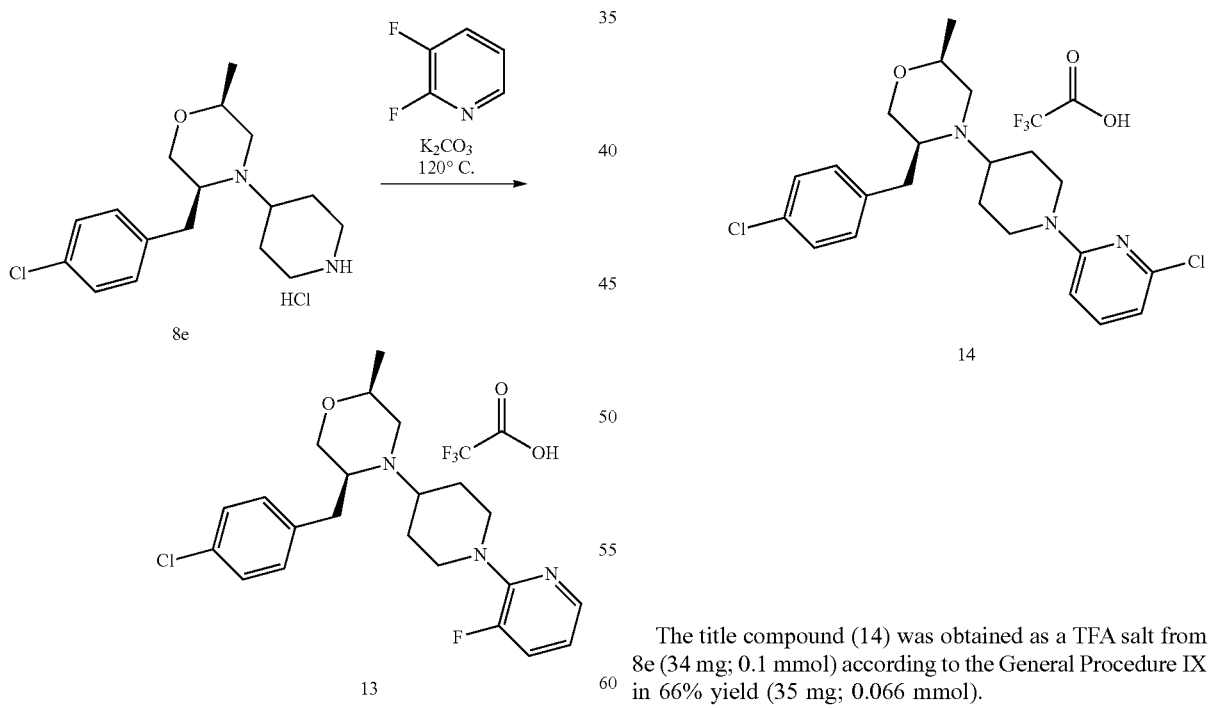

The title compound (13) was obtained as a TFA salt from 8e (34 mg; 0.1 mmol) according to the General Procedure IX in 19% yield (10 mg; 0.019 mmol).

ESI-MS m/z for $C_{22}H_{28}ClFN_3O$ found 404.1/406.1 [M+H]+; $^1$H NMR (400 MHz, Methanol-$d_4$) δ 8.00-7.92 (m, 1H), 7.51-7.45 (m, 1H), 7.44-7.36 (m, 2H), 7.36-7.28 (m, 2H), 7.00-6.84 (m, 1H), 4.37-4.21 (m, 2H), 3.91-3.52 (m, 6H), 3.25-2.99 (m, 5H), 2.45-2.28 (m, 2H), 1.95-1.76 (m, 2H), 1.41-1.28 (m, 3H).

Example 14

Synthesis of (2S,5S)-5-(4-chlorobenzyl)-4-(1-(6-chloropyridin-2-yl)piperidin-4-yl)-2-methylmorpholine 2,2,2-trifluoroacetate (14)

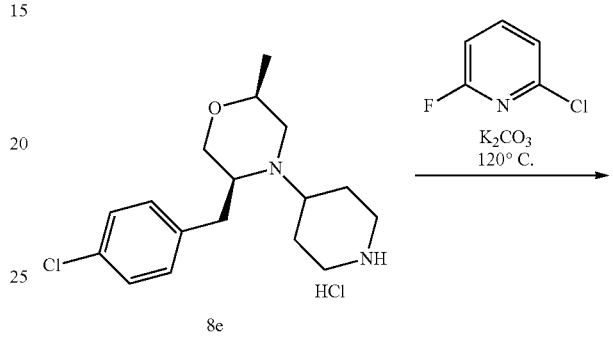

14

The title compound (14) was obtained as a TFA salt from 8e (34 mg; 0.1 mmol) according to the General Procedure IX in 66% yield (35 mg; 0.066 mmol).

ESI-MS m/z for $C_{22}H_{28}Cl_2N_3O$ found 420.1/422.1 [M+H]+; $^1$H NMR (400 MHz, Methanol-$d_4$) δ 7.58-7.47 (m, 1H), 7.45-7.37 (m, 2H), 7.35-7.26 (m, 2H), 6.87-6.75 (m, 1H), 6.69-6.56 (m, 1H), 4.60-4.48 (m, 2H), 3.85-3.71 (m, 4H), 3.66-3.55 (m, 2H), 3.24-2.92 (m, 5H), 2.42-2.28 (m, 2H), 1.74-1.54 (m, 2H), 1.33 (d, J=6.2 Hz, 3H).

Example 15

Synthesis of (2S,5S)-5-(4-chlorobenzyl)-4-(1-(2-fluoropyridin-4-yl)piperidin-4-yl)-2-methylmorpholine 2,2,2-trifluoroacetate (15)

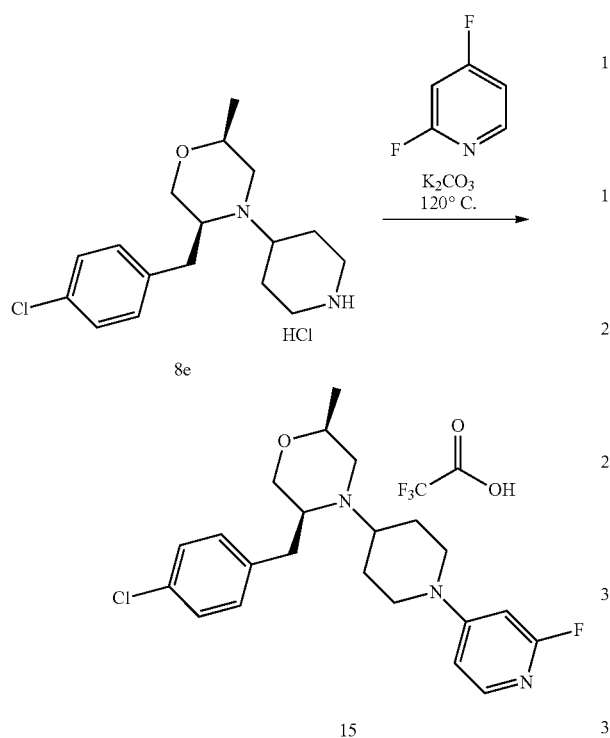

The title compound (15) was obtained as a TFA salt from 8e (34 mg; 0.1 mmol) according to the General Procedure IX in 58% yield (30 mg; 0.058 mmol).

ESI-MS m/z for $C_{22}H_{28}ClFN_3O$ found 404.2/406.2 [M+H]$^+$; $^1$H NMR (400 MHz, Methanol-$d_4$) δ 7.86-7.80 (m, 1H), 7.42-7.38 (m, 2H), 7.35-7.25 (m, 2H), 6.90-6.78 (m, 1H), 6.63-6.53 (m, 1H), 4.32-4.18 (m, 2H), 3.90-3.73 (m, 4H), 3.66-3.54 (m, 2H), 3.23-3.01 (m, 5H), 2.49-2.32 (m, 2H), 1.77-1.62 (m, 2H), 1.33 (d, J=6.2 Hz, 3H).

Example 16

Synthesis of (2S,5S)-5-(4-chlorobenzyl)-2-methyl-4-(1-(3-methylpyridin-2-yl)piperidin-4-yl)morpholine 2,2,2-trifluoroacetate (16)

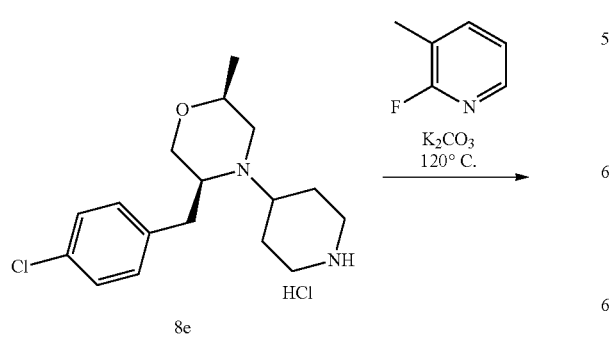

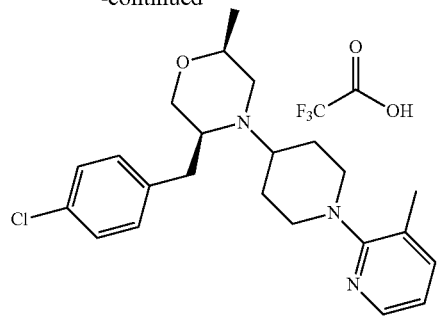

The title compound (16) was obtained as a TFA salt from 8e (34 mg; 0.1 mmol) according to the General Procedure IX in 10% yield (5 mg; 0.001 mmol).

ESI-MS m/z for $C_{23}H_{31}ClN_3O$ found 400.2/402.2 [M+H]$^+$; $^1$H NMR (400 MHz, Methanol-$d_4$) δ 8.18-8.05 (m, 1H), 8.04-7.97 (m, 1H), 7.48-7.30 (m, 4H), 7.28-7.17 (m, 1H), 4.02-3.73 (m, 7H), 3.67-3.56 (m, 1H), 3.28-3.05 (m, 5H), 2.55-2.38 (m, 5H), 2.04-1.84 (m, 2H), 1.34 (d, J=6.3 Hz, 3H).

Example 17

Synthesis of (2S,5S)-5-(4-chlorobenzyl)-2-methyl-4-(1-(pyridin-2-yl)piperidin-4-yl)morpholine 2,2,2-trifluoroacetate (17)

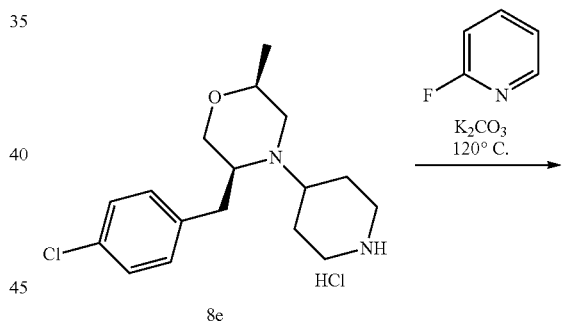

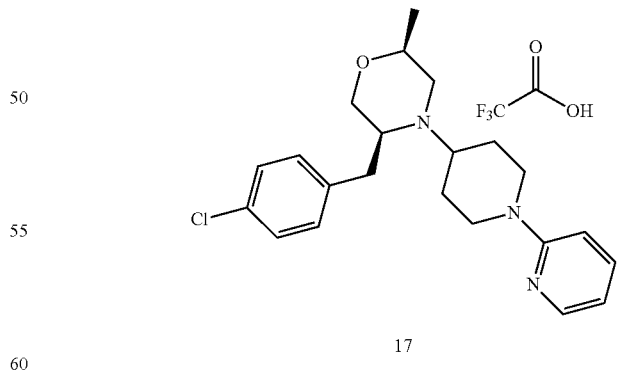

The title compound (17) was obtained as a TFA salt from 8e (296 mg; 0.86 mmol) according to the General Procedure IX in 16% yield (70 mg; 0.14 mmol) with the exception that DMF (2 mL) was additionally used in this step.

ESI-MS m/z for $C_{22}H_{29}ClN_3O$ found 386.4/388.4 [M+H]$^+$; $^1$H NMR (400 MHz, Methanol-$d_4$) δ 8.11-8.02 (m, 1H), 8.00-7.90 (m, 1H), 7.43-7.36 (m, 2H), 7.36-7.24 (m, 3H), 6.99-6.92 (m, 1H), 4.48-4.33 (m, 2H), 3.94-3.65 (m, 5H), 3.61-3.50 (m, 1H), 3.28-3.02 (m, 5H), 2.55-2.36 (m, 2H), 1.95-1.71 (m, 2H), 1.33 (d, J=6.2 Hz, 3H).

Example 18

Synthesis of 6-(4-((2S,5S)-5-(4-chlorobenzyl)-2-methylmorpholino)piperidin-1-yl)picolinonitrile 2,2,2-trifluoroacetate (18)

Example 19

Synthesis of 6-(4-((2S,5S)-5-(4-chlorobenzyl)-2-methylmorpholino)piperidin-1-yl)nicotinonitrile 2,2,2-trifluoroacetate (19)

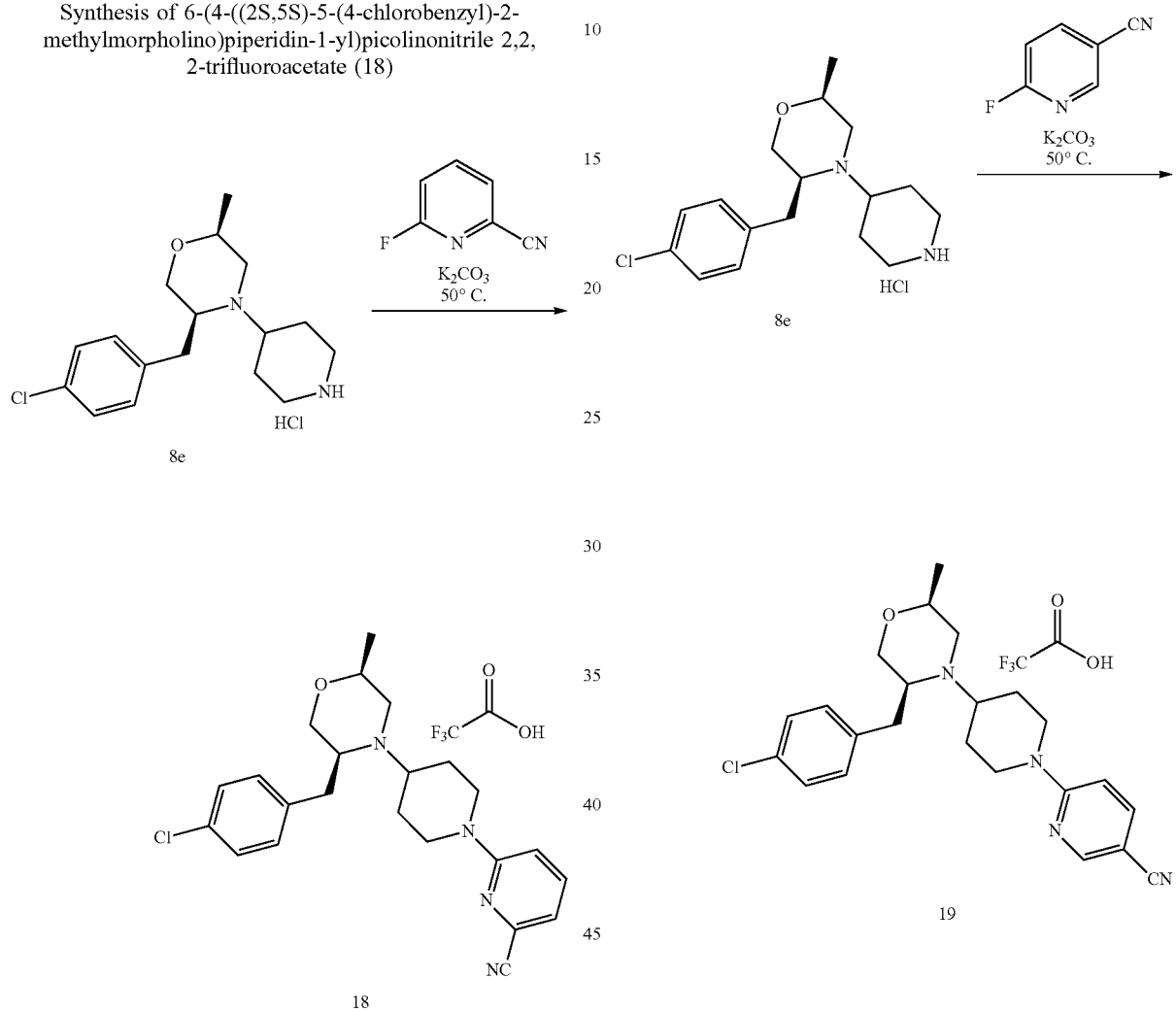

The title compound (18) was obtained as a TFA salt from 8e (52 mg; 0.15 mmol) according to the General Procedure IX in 76% yield (60 mg; 0.114 mmol) with the exception that the temperature of this reaction was reduced to 50° C. instead of 120° C.

ESI-MS m/z for $C_{23}H_{28}ClN_4O$ found 411.3/413.3 [M+H]$^+$; $^1$H NMR (400 MHz, Methanol-$d_4$) δ 7.71-7.66 (m, 1H), 7.43-7.37 (m, 2H), 7.37-7.30 (m, 2H), 7.21-7.14 (m, 1H), 7.15-7.08 (m, 1H), 4.70-4.56 (m, 2H), 3.87-3.71 (m, 4H), 3.67-3.55 (m, 2H), 3.22-2.92 (m, 5H), 2.42-2.32 (m, 2H), 1.71-1.56 (m, 2H), 1.33 (d, J=6.2 Hz, 3H).

The title compound (19) was obtained as a TFA salt from 8e (52 mg; 0.15 mmol) according to the General Procedure IX in 57% yield (45 mg; 0.086 mmol) with the exception that the temperature of this reaction was reduced to 50° C. instead of 120° C.

ESI-MS m/z for $C_{23}H_{28}ClN_4O$ found 411.3/413.3 [M+H]$^+$; $^1$H NMR (400 MHz, Methanol-$d_4$) δ 8.46-8.39 (m, 1H), 7.80-7.73 (m, 1H), 7.43-7.37 (m, 2H), 7.37-7.28 (m, 2H), 6.99-6.91 (m, 1H), 4.78-4.65 (m, 2H), 3.89-3.53 (m, 6H), 3.25-2.97 (m, 5H), 2.45-2.31 (m, 2H), 1.74-1.56 (m, 2H), 1.33 (d, J=6.3 Hz, 3H).

Example 20

Synthesis of (2S,5S)-5-(4-chlorobenzyl)-2-methyl-4-(1-(4-(trifluoromethyl)pyridin-2-yl)piperidin-4-yl)morpholine 2,2,2-trifluoroacetate (20)

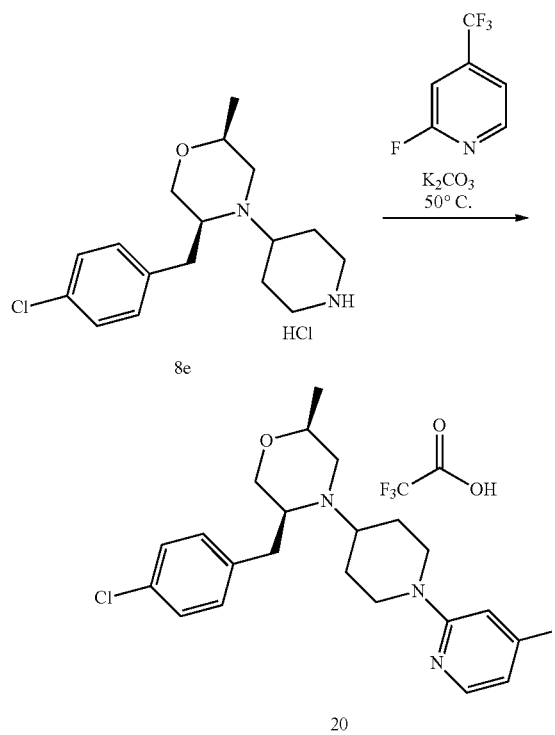

The title compound (20) was obtained as a TFA salt from 8e (52 mg; 0.15 mmol) according to the General Procedure IX in 59% yield (50 mg; 0.088 mmol) with the exception that the temperature of this reaction was reduced to 50° C. instead of 120° C.

ESI-MS m/z for $C_{23}H_{28}ClF_3N_3O$ found 454.3/456.3 [M+H]$^+$; $^1$H NMR (400 MHz, Methanol-d$_4$) δ 8.35-8.23 (m, 1H), 7.43-7.37 (m, 2H), 7.35-7.30 (m, 2H), 7.22-7.09 (m, 1H), 6.93-6.85 (m, 1H), 4.70-4.54 (m, 2H), 3.90-3.54 (m, 6H), 3.27-2.96 (m, 5H), 2.46-2.28 (m, 2H), 1.79-1.59 (m, 2H), 1.32 (d, J=6.3 Hz, 3H).

Example 21

Synthesis of 2-(4-((2S,5S)-5-(4-chlorobenzyl)-2-methylmorpholino)piperidin-1-yl)isonicotino-nitrile 2,2,2-trifluoroacetate (21)

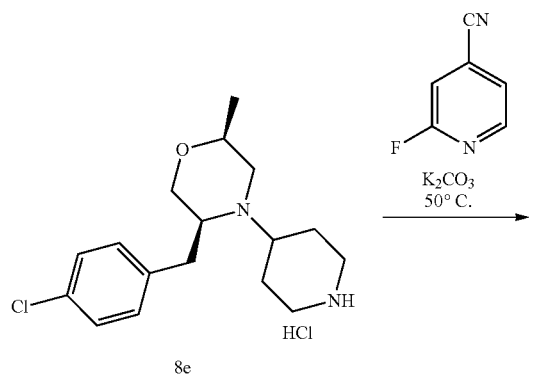

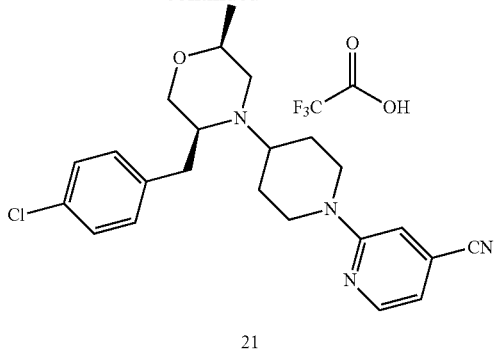

The title compound (21) was obtained as a TFA salt from 8e (52 mg; 0.15 mmol) according to the General Procedure IX in 57% yield (45 mg; 0.086 mmol) with the exception that the temperature of this reaction was reduced to 50° C. instead of 120° C.

ESI-MS m/z for $C_{23}H_{28}ClN_4O$ found 411.3/413.3 [M+H]$^+$; $^1$H NMR (400 MHz, Methanol-d$_4$) δ 8.32-8.24 (m, 1H), 7.42-7.35 (m, 2H), 7.35-7.29 (m, 2H), 7.26-7.19 (m, 1H), 6.95-6.86 (m, 1H), 4.74-4.54 (m, 2H), 3.88-3.70 (m, 4H), 3.68-3.52 (m, 2H), 3.21-2.89 (m, 5H), 2.44-2.23 (m, 2H), 1.74-1.56 (m, 2H), 1.37-1.29 (m, 3H).

Example 22

Synthesis of 2-(4-((2S,5S)-5-(4-chlorobenzyl)-2-methylmorpholino)piperidin-1-yl)nicotinonitrile 2,2,2-trifluoroacetate (22)

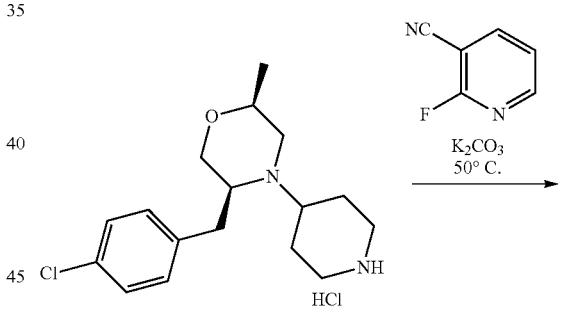

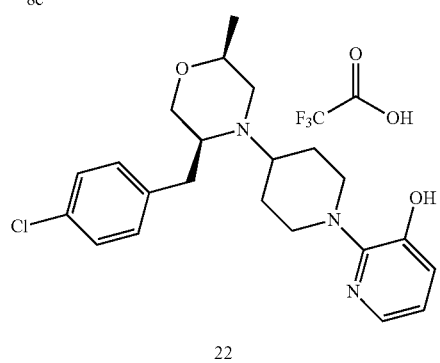

The title compound (22) was obtained as a TFA salt from 8e (52 mg; 0.15 mmol) according to the General Procedure IX in 70% yield (55 mg; 0.105 mmol) with the exception that the temperature of this reaction was reduced to 50° C. instead of 120° C.

ESI-MS m/z for $C_{23}H_{28}ClN_4O$ found 411.3/413.3 [M+H]$^+$; $^1$H NMR (400 MHz, Methanol-$d_4$) δ 8.42-8.38 (m, 1H), 8.01-7.95 (m, 1H), 7.43-7.36 (m, 2H), 7.36-7.30 (m, 2H), 6.98-6.91 (m, 1H), 4.55-4.44 (m, 2H), 3.89-3.56 (m, 6H), 3.27-3.02 (m, 5H), 2.49-2.33 (m, 2H), 1.94-1.76 (m, 2H), 1.33 (d, J=6.3 Hz, 3H).

Example 23

Synthesis of (2S,5S)-5-(4-chlorobenzyl)-4-(1-(3-chloropyridin-2-yl)piperidin-4-yl)-2-methylmorpholine 2,2,2-trifluoroacetate (23)

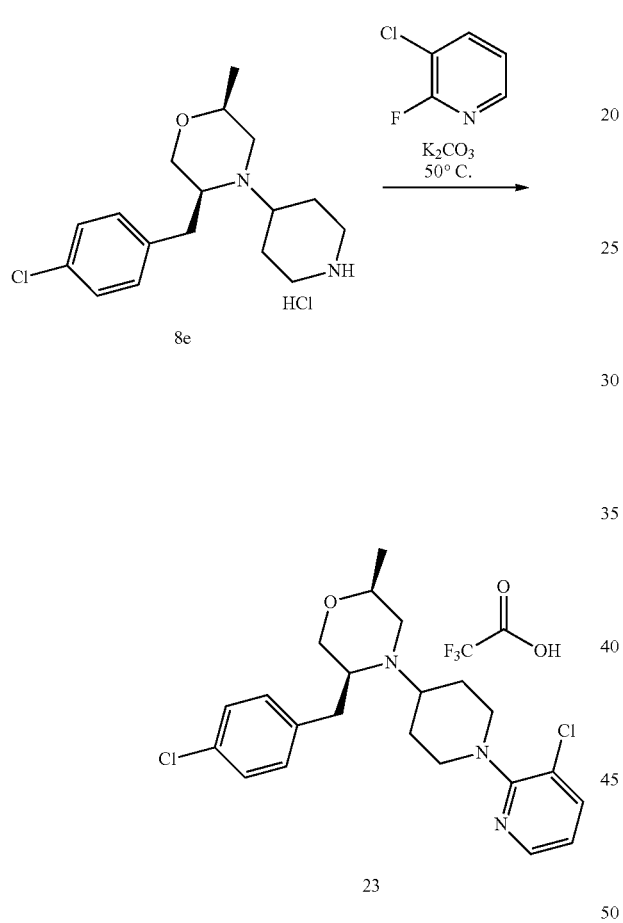

Example 24

Synthesis of (2S,5S)-5-(4-chlorobenzyl)-4-(1-(6-fluoropyrimidin-4-yl)piperidin-4-yl)-2-methylmorpholine 2,2,2-trifluoroacetate (24)

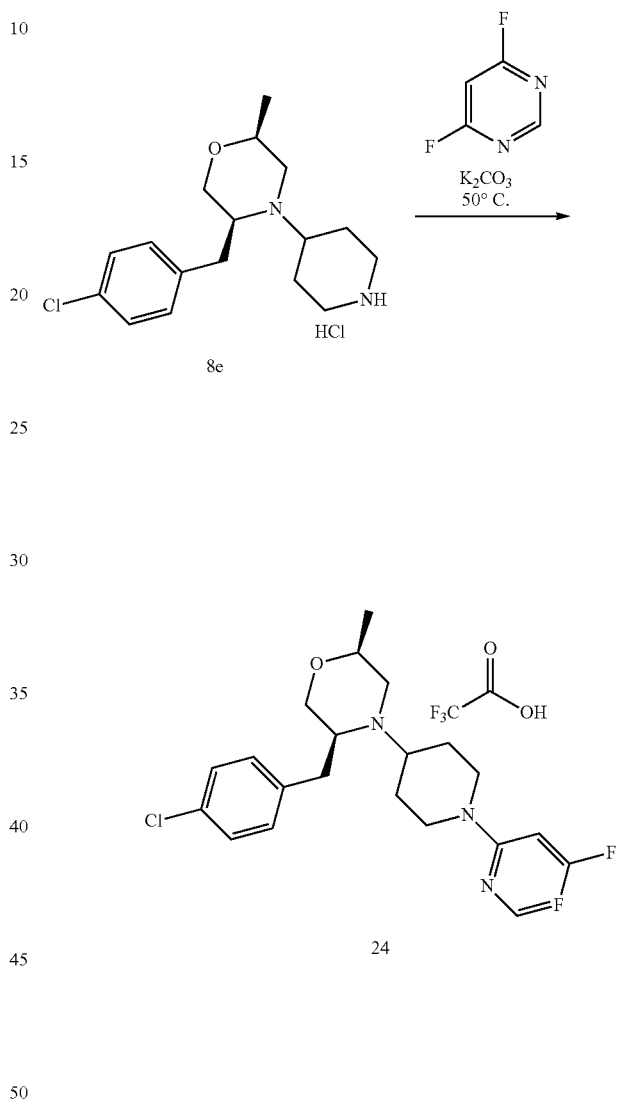

The title compound (23) was obtained as a TFA salt from 8e (52 mg; 0.15 mmol) according to the General Procedure IX in 50% yield (40 mg; 0.075 mmol) with the exception that the temperature of this reaction was reduced to 50° C. instead of 120° C.

ESI-MS m/z for $C_{22}H_{28}Cl_2N_3O$ found 420.2/422.2 [M+H]$^+$; $^1$H NMR (400 MHz, Methanol-$d_4$) δ 8.22-8.14 (m, 1H), 7.81-7.72 (m, 1H), 7.42-7.34 (m, 2H), 7.34-7.26 (m, 2H), 7.03-6.95 (m, 1H), 4.11-3.96 (m, 2H), 3.96-3.54 (m, 6H), 3.26-2.84 (m, 5H), 2.48-2.31 (m, 2H), 2.00-1.81 (m, 2H), 1.33 (d, J=6.3 Hz, 3H).

The title compound (24) was obtained as a TFA salt from 8e (52 mg; 0.15 mmol) according to the General Procedure IX in 39% yield (30 mg; 0.058 mmol) with the exception that the temperature of this reaction was reduced to 50° C. instead of 120° C.

ESI-MS m/z for $C_{21}H_{27}ClFN_4O$ found 405.3/407.3 [M+H]$^+$; $^1$H NMR (400 MHz, Methanol-$d_4$) δ 8.32-8.23 (m, 1H), 7.40-7.25 (m, 4H), 6.50-6.40 (m, 1H), 4.77-4.59 (m, 2H), 4.03-3.55 (m, 6H), 3.25-2.97 (m, 5H), 2.47-2.31 (m, 2H), 1.72-1.51 (m, 2H), 1.33 (d, J=6.3 Hz, 3H).

Example 25

Synthesis of (2S,5S)-5-(4-chlorobenzyl)-4-(1-(3,5-difluoropyridin-2-yl)piperidin-4-yl)-2-methylmorpholine 2,2,2-trifluoroacetate (25)

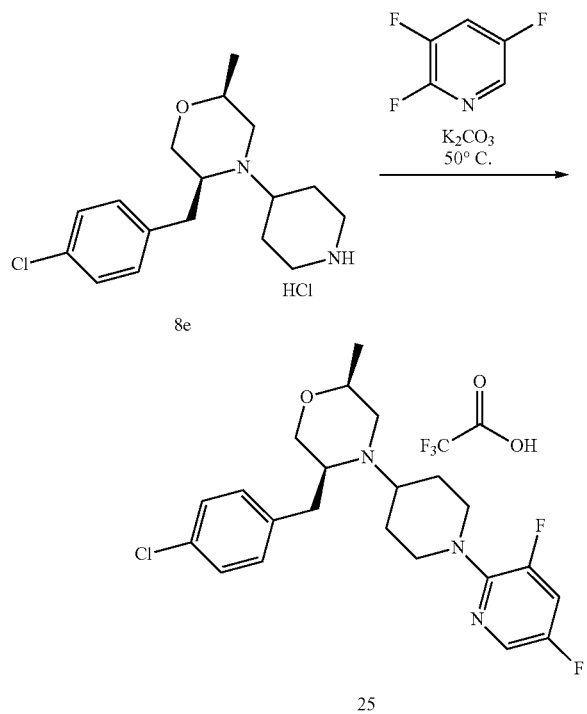

The title compound (25) was obtained as a TFA salt from 8e (52 mg; 0.15 mmol) according to the General Procedure IX in 20% yield (16 mg; 0.03 mmol) with the exception that the temperature of this reaction was reduced to 50° C. instead of 120° C.

ESI-MS m/z for $C_{22}H_{27}ClF_2N_3O$ found 422.2/424.2 [M+H]+; 1H NMR (400 MHz, Methanol-$d_4$) δ 7.99-7.97 (m, 1H), 7.49-7.42 (m, 1H), 7.41-7.36 (m, 2H), 7.35-7.29 (m, 2H), 4.19-4.09 (m, 2H), 3.90-3.57 (m, 6H), 3.27-2.93 (m, 5H), 2.41-2.29 (m, 2H), 1.91-1.73 (m, 2H), 1.33 (d, J=6.3 Hz, 3H).

Example 26

Synthesis of (2S,5S)-5-(4-chlorobenzyl)-2-methyl-4-(1-(pyrimidin-4-yl)piperidin-4-yl)morpholi-ne 2,2,2-trifluoroacetate (26)

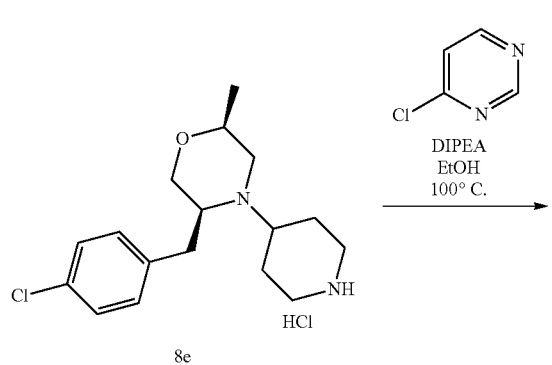

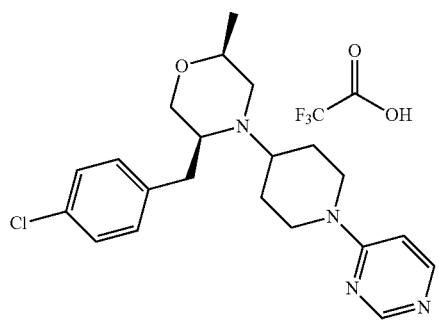

The mixture of 8e (34 mg; 0.1 mmol), 4-chloropyrimidine (11 mg; 0.1 mmol) in absolute EtOH (2 mL) and DIPEA (52 μL; 0.3 mmol) was heated to 100° C. and stirred overnight. The reaction progress was monitored by LC-MS. After analytical control indicated completion of the reaction, the mixture was concentrated in vacuo and water was added. The aqueous mixture was extracted with AcOEt (2×), washed with water, brine and dried over anhydrous $Na_2SO_4$, filtered and concentrated in vacuo. The crude product was purified by preparative reversed-phase column chromatography (Luna® 5 μm Phenyl-Hexyl, LC Column 250×21.2 mm, water/MeCN+1% TFA, 70:30 to 40:60, 30 min). Compound 26 was obtained as a TFA salt in 4% yield (2 mg; 0.004 mmol).

ESI-MS m/z for $C_{21}H_{28}ClN_4O$ found 387.3/389.3 [M+H]+; 1H NMR (400 MHz, Methanol-$d_4$) δ 8.78-8.69 (m, 1H), 8.29-8.17 (m, 1H), 7.41-7.30 (m, 4H), 7.23-7.16 (m, 1H), 3.98-3.82 (m, 2H), 3.82-3.64 (m, 4H), 3.63-3.50 (m, 2H), 3.29-2.97 (m, 5H), 2.57-2.43 (m, 2H), 1.89-1.69 (m, 2H), 1.33 (d, J=6.3 Hz, 3H).

Example 27

Synthesis of (2S,5S)-5-(4-chlorobenzyl)-2-methyl-4-(1-(pyridin-3-yl)piperidin-4-yl)morpholine 2,2,2-trifluoroacetate (27)

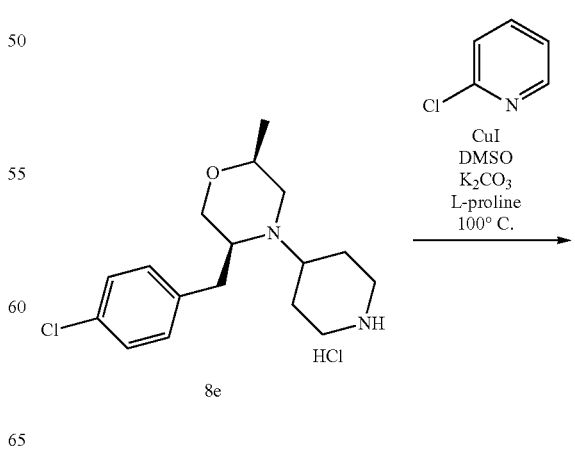

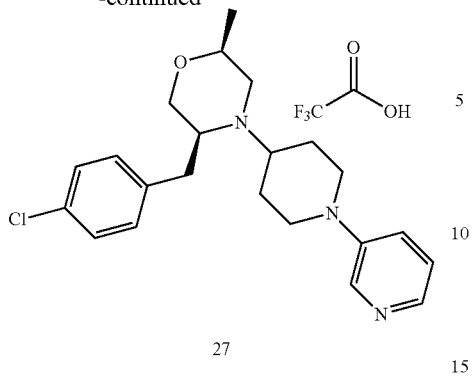

27

The title compound (27) was obtained as a TFA salt from 8e (104 mg; 0.3 mmol) according to the General Procedure X in 13% yield (20 mg; 0.04 mmol).

ESI-MS m/z for $C_{22}H_{29}ClN_3O$ found 386.3/388.3 [M+H]$^+$; $^1$H NMR (400 MHz, Methanol-d$_4$) δ 8.49-8.37 (m, 1H), 8.19-8.10 (m, 2H), 7.90-7.80 (m, 1H), 7.42-7.25 (m, 4H), 4.24-4.12 (m, 2H), 3.96-3.85 (m, 1H), 3.85-3.69 (m, 4H), 3.63-3.57 (m, 1H), 3.27-3.00 (m, 5H), 2.54-2.34 (m, 2H), 1.94-1.74 (m, 2H), 1.33 (d, J=6.3 Hz, 3H).

Example 28

Synthesis of (2S,5S)-5-(4-chlorobenzyl)-2-methyl-4-(1-(pyridin-4-yl)piperidin-4-yl)morpholine 2,2,2-trifluoroacetate (28)

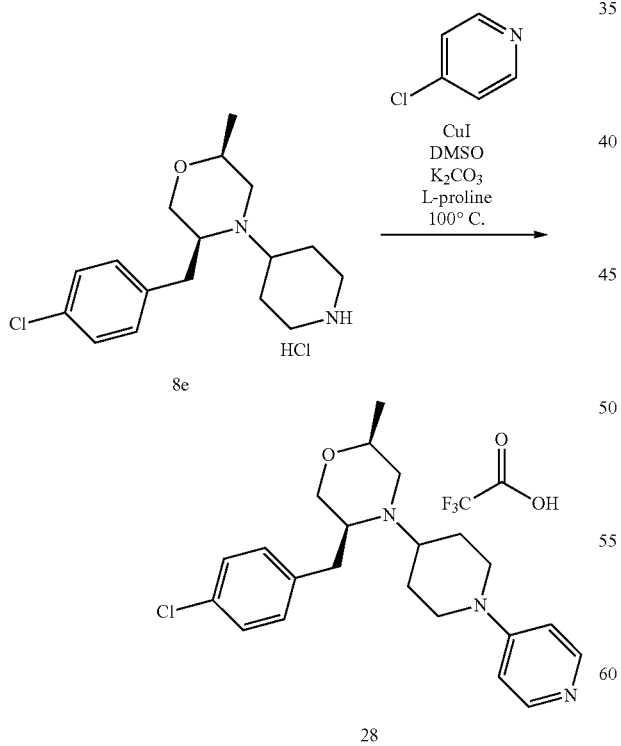

The title compound (28) was obtained as a TFA salt from 8e (104 mg; 0.3 mmol) according to the General Procedure X in 9% yield (13 mg; 0.026 mmol).

ESI-MS m/z for $C_{22}H_{29}ClN_3O$ found 386.3/388.3 [M+H]+; $^1$H NMR (400 MHz, Methanol-d$_4$) δ 8.21-8.15 (m, 2H), 7.42-7.37 (m, 2H), 7.37-7.30 (m, 2H), 7.27-7.20 (m, 2H), 4.54-4.40 (m, 2H), 3.98-3.84 (m, 2H), 3.84-3.68 (m, 3H), 3.64-3.52 (m, 1H), 3.38-3.32 (m, 1H), 3.28-3.03 (m, 4H), 2.51-2.43 (m, 2H), 1.89-1.69 (m, 2H), 1.33 (d, J=6.3 Hz, 3H).

Example 29

Synthesis of (2S,5S)-5-(4-chlorobenzyl)-4-(1-(4-methoxypyridin-2-yl)piperidin-4-yl)-2-methylmorpholine 2,2,2-trifluoroacetate (29)

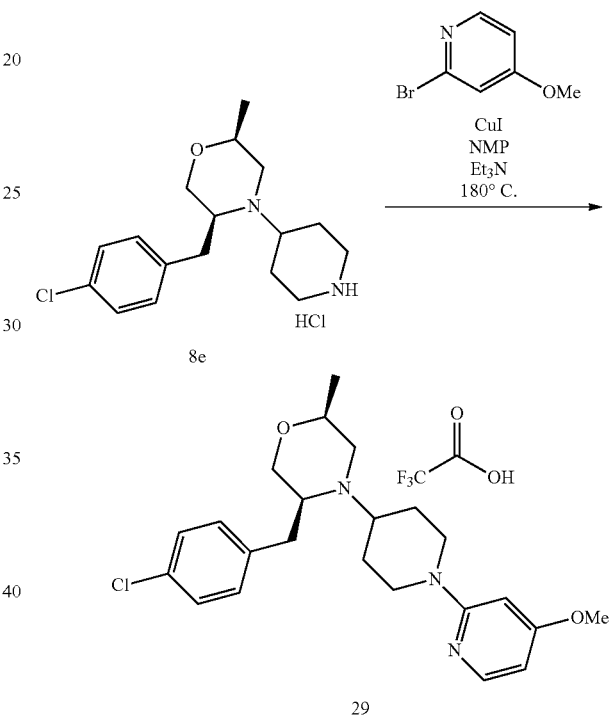

The mixture of 8e (69 mg; 0.2 mmol), 2-bromo-4-methoxypyridine (56 mg; 0.3 mmol), CuI (38 mg; 0.2 mmol), N-methyl-2-pyrrolidone (NMP; 1 mL), Et$_3$N (58 μL; 0.8 mmol) was heated to 180° C. and stirred for 12 hours. The reaction progress was monitored by LC-MS. After analytical control indicated completion of the reaction, the crude product was extracted with AcOEt and water. An organic fraction was dried over anhydrous Na$_2$SO$_4$, filtered and concentrated in vacuo. The crude product was purified by preparative reversed-phase column chromatography (Luna® 5 μm Phenyl-Hexyl, LC Column 250×21.2 mm, water/MeCN+10% TFA, 70:30 to 40:60, 30 min). Compound 29 was obtained as a TFA salt in 19% yield (20 mg; 0.038 mmol).

ESI-MS m/z for $C_{23}H_{31}ClN_3O_2$ found 416.2/418.2 [M+H]$^+$; $^1$H NMR (400 MHz, Methanol-d$_4$) δ 7.90-7.82 (m, 1H), 7.42-7.27 (m, 4H), 6.73-6.64 (m, 2H), 4.37-4.25 (m, 2H), 4.03 (s, 3H), 3.97-3.67 (m, 5H), 3.64-3.54 (m, 1H), 3.41-3.31 (m, 2H), 3.29-3.02 (m, 3H), 2.53-2.40 (m, 2H), 2.03-1.80 (m, 2H), 1.32 (d, J=6.3 Hz, 3H).

Example 30

Synthesis of (2S,5S)-5-(4-chlorobenzyl)-2-methyl-4-(1-(5-methylpyridazin-3-yl)piperidin-4-yl)morpholine 2,2,2-trifluoroacetate (30)

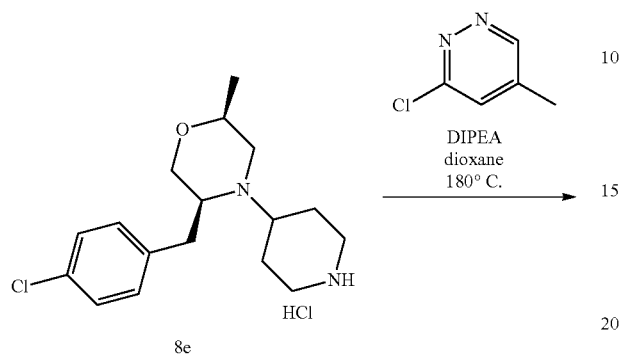

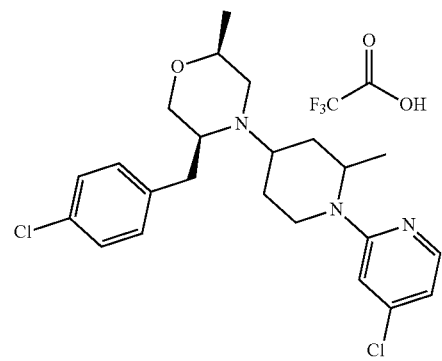

The mixture of 8e (69 mg; 0.2 mmol), 3-chloro-5-methylpyridazine (38 mg; 0.3 mmol), DIPEA (139 µL; 0.8 mmol) in dioxane (1 mL) was heated to 180° C. and stirred for 12 hours. The reaction progress was monitored by LC-MS. After analytical control indicated completion of the reaction, the crude product was extracted with AcOEt and water. An organic fraction was dried over anhydrous Na$_2$SO$_4$, filtered and concentrated in vacuo. The crude product was purified by preparative reversed-phase column chromatography (Luna® 5 µm Phenyl-Hexyl, LC Column 250×21.2 mm, water/MeCN+1% TFA, 70:30 to 40:60, 30 min). Compound 30 was obtained as a TFA salt in 5% yield (5 mg; 0.01 mmol).

ESI-MS m/z for C$_{22}$H$_{30}$ClN$_4$O found 401.2/403.2 [M+H]+; $^1$H NMR (400 MHz, Methanol-d$_4$) δ 8.63-8.58 (m, 1H), 7.87-7.83 (m, 1H), 7.43-7.37 (m, 2H), 7.37-7.31 (m, 2H), 4.65-4.52 (m, 2H), 3.98-3.67 (m, 6H), 3.63-3.55 (m, 1H), 3.24-3.02 (m, 4H), 2.55-2.40 (m, 5H), 1.90-1.75 (m, 2H), 1.33 (d, J=6.3 Hz, 3H).

Example 31

Synthesis of (2S,5S)-5-(4-chlorobenzyl)-4-(1-(4-chloropyridin-2-yl)-2-methylpiperidin-4-yl)-2-methylmorpholine 2,2,2-trifluoroacetate (31)

Step 1

Synthesis of tert-butyl 4-((2S,5S)-5-(4-chlorobenzyl)-2-methylmorpholino)-2-methylpiperidine-1-carboxylate (31a)

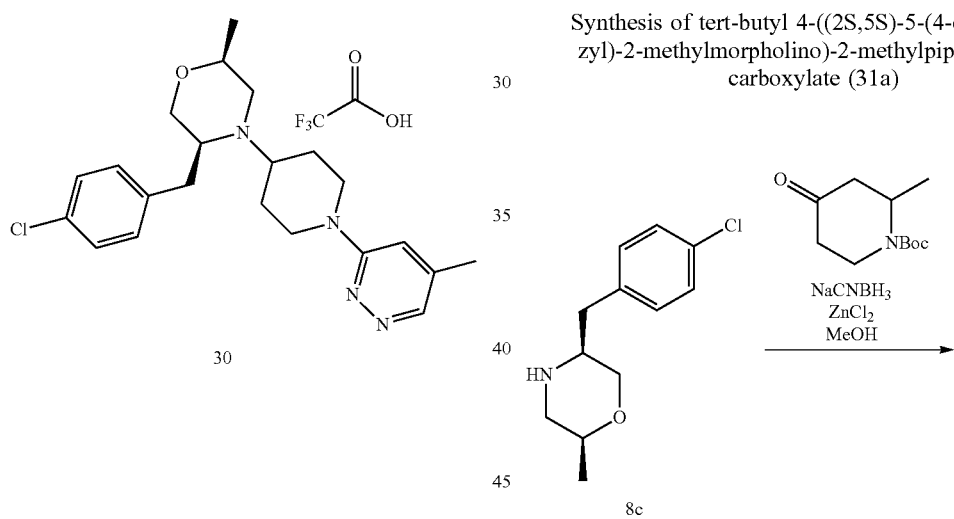

To the solution of 8c (80 mg; 0.3 mmol), 1-Boc-2-methyl-4-piperidinone (96 mg; 0.45 mmol) and zinc chloride (ZnCl$_2$; 61 mg; 0.45 mmol) in methanol (1 mL), sodium cyanoborohydride (NaCNBH$_3$; 19 mg; 0.3 mmol) was added portionwise and the reaction was stirred at room temperature overnight. The reaction progress was monitored by LC-MS. After analytical control indicated completion of the reaction, the mixture was partitioned between AcOEt and 1M NaOH. The aqueous layer was extracted with AcOEt. The combined organic extracts were washed with brine, dried over anhydrous Na₂SO₄, filtered and concentrated in vacuo. The crude product was used to the next step without additional purification. Compound 31a was obtained in 67% yield (84 mg; 0.2 mmol).

ESI-MS m/z for $C_{23}H_{36}ClN_2O_3$ found 423.2/425.2 [M+H]⁺

Step 2

Synthesis of (2S,5S)-5-(4-chlorobenzyl)-2-methyl-4-(2-methylpiperidin-4-yl)morpholine 2,2,2-trifluoroacetate (31b)

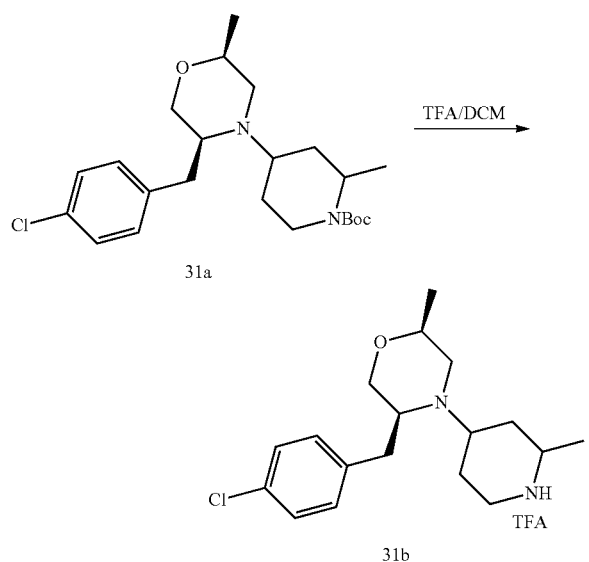

The title compound (31b) was obtained as a TFA salt from 31a (84 mg; 0.2 mmol) according to the General Procedure IVb in 99% yield (87 mg; 0.2 mmol).

ESI-MS m/z for $C_{18}H_{28}ClN_2O$ found 323.2/325.2 [M+H]⁺

Step 3

Synthesis of (2S,5S)-5-(4-chlorobenzyl)-4-(1-(4-chloropyridin-2-yl)-2-methylpiperidin-4-yl)-2-methylmorpholine 2,2,2-trifluoroacetate (31)

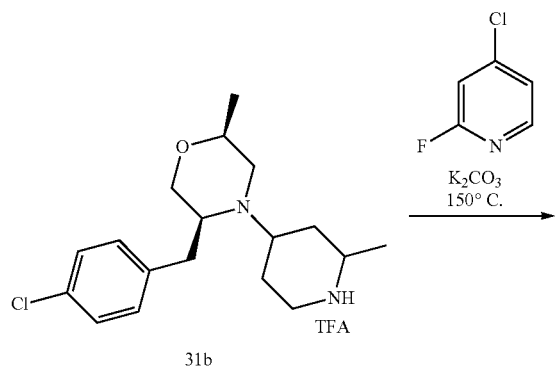

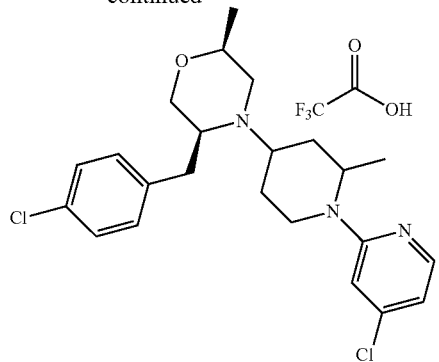

31

The title compound (31) was obtained as a single diastereoisomer as a TFA salt from 31b (87 mg; 0.2 mmol) according to the General Procedure IX in 4% yield (4 mg; 0.007 mmol) with the exception that the temperature of this reaction was 150° C. instead of 120° C.

ESI-MS m/z for $C_{23}H_{30}Cl_2N_3O$ found 434.2/436.2 [M+H]⁺; ¹H NMR (400 MHz, Methanol-d₄) δ 8.07-7.99 (m, 1H), 7.43-7.30 (m, 4H), 7.08-7.02 (m, 1H), 6.80-6.75 (m, 1H), 4.40-4.29 (m, 1H), 3.97-3.54 (m, 7H), 3.51-3.38 (m, 1H), 3.27-3.20 (m, 2H), 3.17-3.07 (m, 1H), 2.48-2.30 (m, 2H), 1.89-1.79 (m, 1H), 1.76-1.64 (m, 1H), 1.34 (d, J=6.2 Hz, 3H), 1.29 (d, J=7.0 Hz, 3H).

Example 32

Synthesis of (2S,5S)-5-(4-chlorobenzyl)-4-(1-(4-chloropyridin-2-yl)-2-methylpiperidin-4-yl)-2-methylmorpholine 2,2,2-trifluoroacetate (32)

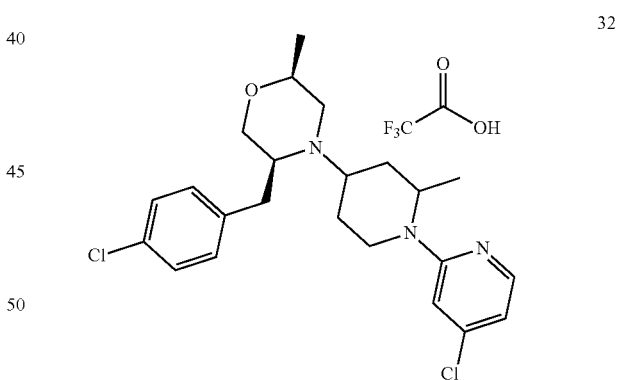

The title compound (32) was obtained during the synthesis of compound 31 as a second single diastereoisomer (different to 31) as a TFA salt from 31b (87 mg; 0.2 mmol) according to the General Procedure IX in 5% yield (5 mg; 0.009 mmol) with the exception that the temperature of this reaction was 150° C. instead of 120° C.

ESI-MS m/z for $C_{23}H_{30}Cl_2N_3O$ found 434.2/436.2 [M+H]⁺; ¹H NMR (400 MHz, Methanol-d₄) δ 8.04-7.95 (m, 1H), 7.38-7.30 (m, 2H), 7.30-7.23 (m, 2H), 7.07-7.04 (m, 1H), 6.89-6.82 (m, 1H), 4.16-4.00 (m, 2H), 3.94-3.82 (m, 1H), 3.80-3.43 (m, 6H), 3.25-3.14 (m, 1H), 3.14-3.01 (m, 2H), 2.63-2.49 (m, 2H), 1.99-1.75 (m, 2H), 1.39-1.26 (m, 6H).

Example 33

Synthesis of (2S,5S)-5-(4-chlorobenzyl)-4-(1-(4-chloropyridin-2-yl)-2-methylpiperidin-4-yl)-2-methylmorpholine 2,2,2-trifluoroacetate (33)

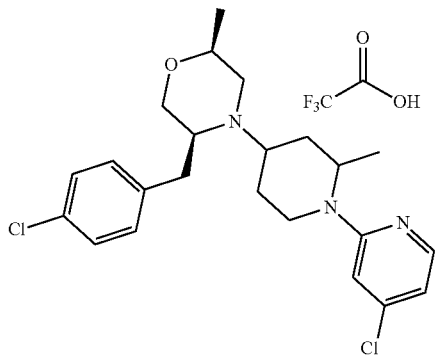

33

The title compound (33) was obtained during the synthesis of compound 31 as a mixture of two diastereoisomers (31:33 in ratio 1:3.5) as a TFA salt from 31b (87 mg; 0.2 mmol) according to the General Procedure IX in 5% yield (5 mg; 0.009 mmol) with the exception that the temperature of this reaction was 150° C. instead of 120° C.

ESI-MS m/z for $C_{23}H_{30}Cl_2N_3O$ found 434.2/436.2 [M+H]$^+$; $^1$H NMR (400 MHz, Methanol-$d_4$) δ 8.05-7.94 (m, 1H), 7.42-7.23 (m, 4H), 7.21-7.06 (m, 1H), 6.93-6.76 (m, 1H), 4.23-4.00 (m, 2H), 3.95-3.69 (m, 4H), 3.66-3.47 (m, 3H), 3.25-3.01 (m, 3H), 2.61-2.38 (m, 2H), 1.98-1.84 (m, 2H), 1.41-1.19 (m, 6H).

Example 34

Synthesis of (2S,5S)-5-(4-chlorobenzyl)-4-(1-(4-chloropyridin-2-yl)-2-methylpiperidin-4-yl)-2-methylmorpholine 2,2,2-trifluoroacetate (34)

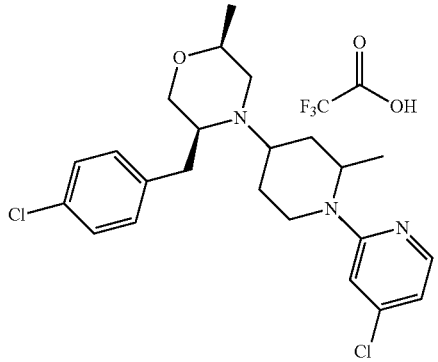

34

The title compound (34) was obtained during the synthesis of compound 31 as a mixture of two diastereoisomers (33:34 in ratio 1:2.5) as a TFA salt from 31b (87 mg; 0.2 mmol) according to the General Procedure IX in 5% yield (5 mg; 0.009 mmol) with the exception that the temperature of this reaction was 150° C. instead of 120° C.

ESI-MS m/z for $C_{23}H_{30}C12N_3O$ found 434.2/436.2 [M+H]$^+$; $^1$H NMR (400 MHz, Methanol-$d_4$) δ 8.10-7.95 (m, 1H), 7.48-7.29 (m, 4H), 7.27-7.14 (m, 1H), 6.96-6.77 (m, 1H), 4.22-4.03 (m, 2H), 3.99-3.46 (m, 7H), 3.27-2.99 (m, 3H), 2.67-2.43 (m, 2H), 2.08-1.82 (m, 2H), 1.49-1.18 (m, 6H).

Example 35

Synthesis of (3S,7R,8aS)-3-(4-chlorobenzyl)-2-(1-(pyridin-2-yl)piperidin-4-yl)octahydropyrrolo-[1,2-a]pyrazin-7-ol 2,2,2-trifluoroacetate (35)

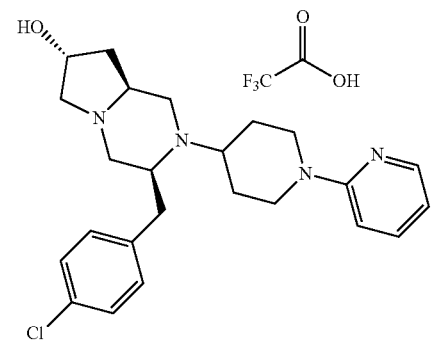

35

Step 1

Synthesis of methyl (2S,4R)-1-((R)-2-((tert-butoxycarbonyl)amino)-3-(4-chlorophenyl)-propanoyl)-4-hydroxypyrrolidine-2-carboxylate (35a)

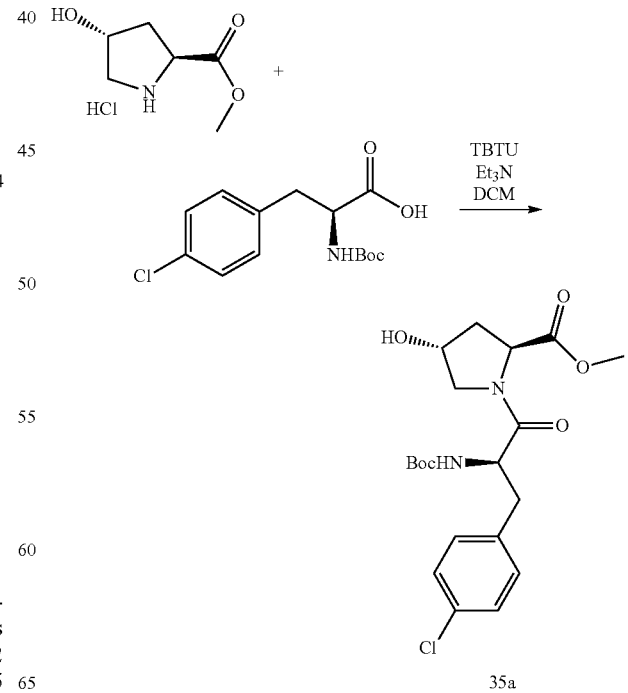

35a

The title compound (35a) was obtained as an yellow oil from a trans-4-hydroxy-L-proline methyl ester hydrochloride (5.45 g; 30 mmol) and Boc-4-chloro-L-phenylalanine (9.89 g; 33 mmol) according to the General Procedure III in 99% yield (12.66 g; 29.7 mmol).

ESI-MS m/z for $C_{20}H_{28}ClN_2O_6$ found 427.2/429.2 $[M+H]^+$

Step 2

Synthesis of methyl (2S,4R)-1-((R)-2-amino-3-(4-chlorophenyl)propanoyl)-4-hydroxy-pyrrolidine-2-carboxylate 2,2,2-trifluoroacetate (35b)

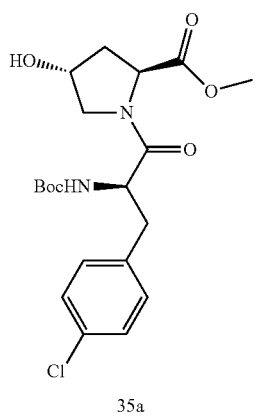

TFA/DCM →

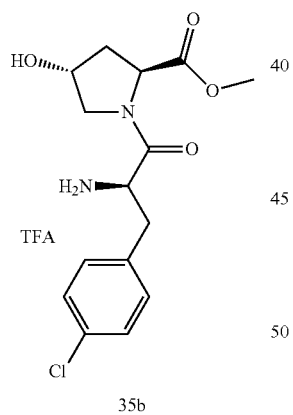

35b

The title compound (35b) was obtained as a TFA salt from 35a (12.66 g; 29.7 mmol) according to the General Procedure IVb in 99% yield (12.94 g; 29.4 mmol).

ESI-MS m/z for $C_{15}H_{20}ClN_2O_4$ found 327.1/329.1 $[M+H]^+$

Step 3

Synthesis of (3S,7R,8aS)-3-(4-chlorobenzyl)-7-hydroxyhexahydropyrrolo[1,2-a]pyrazine-1,4-dione (35c)

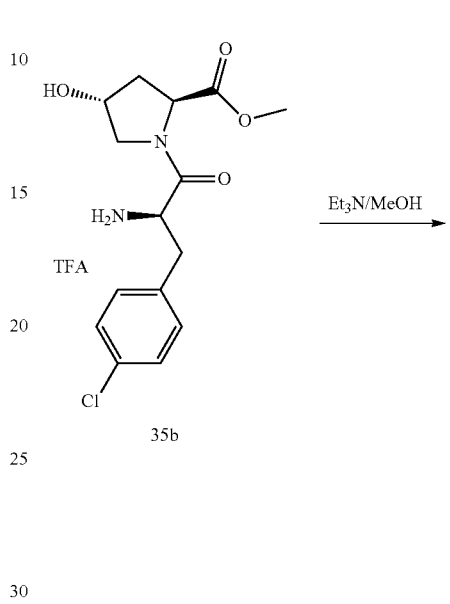

Et₃N/MeOH →

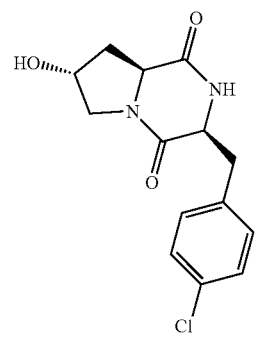

35c

To a solution of crude 35b (12.94 g; 29.4 mmol) in MeOH (90 mL) Et₃N (33.8 mL; 240 mmol) was added and the mixture was heated to reflux for 80 minutes and then at room temperature overnight. LC-MS showed completion of the reaction. The mixture was concentrated in vacuo and the yellow oily residue was partitioned between AcOEt (3×120 mL) and water (100 mL). The combined organic solutions were dried over anhydrous Na₂SO₄, filtered and concentrated in vacuo. The crude product was used in the next step without additional purification. Compound 35c was obtained as an yellow oil in 99% yield (8.56 g; 29.11 mmol).

ESI-MS m/z for $C_{14}H_{16}ClN_2O_3$ found 295.1/297.1 $[M+H]^+$

Step 4

Synthesis of (3S,7R,8aS)-3-(4-chlorobenzyl)octahydropyrrolo[1,2-a]pyrazin-7-ol (35d)

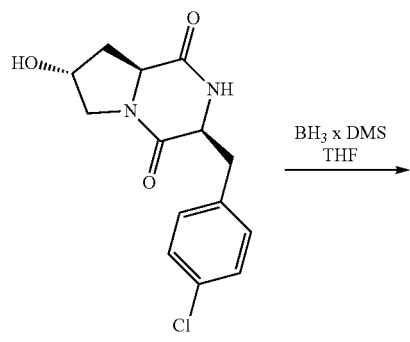

35c

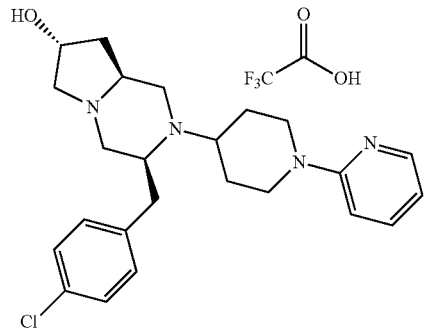

35

The title compound (35d) was obtained as an yellow oil from 35c (8.56 g; 29.11 mmol) according to the General Procedure Ib in 99% yield (7.67 g; 28.82 mmol).

ESI-MS m/z for $C_{14}H_{2}MClN_{2}O$ found 267.1/269.1 [M+H]$^+$

Step 5

Synthesis of (3S,7R,8aS)-3-(4-chlorobenzyl)-2-(1-(pyridin-2-yl)piperidin-4-yl)octahydro-pyrrolo[1,2-a]pyrazin-7-ol 2,2,2-trifluoroacetate (35)

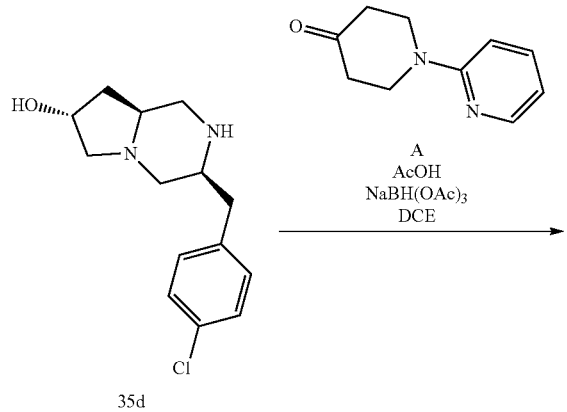

The title compound (35) was obtained as a TFA salt from 35d (0.25 g; 0.94 mmol) according to the General Procedure VI in 16% yield (83 mg; 0.15 mmol).

ESI-MS m/z for $C_{24}H_{32}ClN_{4}O$ found 427.2/429.2 [M+H]$^+$; $^1$H NMR (400 MHz, Methanol-d$_4$) δ 8.07-7.99 (m, 1H), 7.98-7.88 (m, 1H), 7.44-7.38 (m, 1H), 7.38-7.21 (m, 4H), 7.06-6.91 (m, 1H), 4.57-4.41 (m, 1H), 4.38-4.14 (m, 2H), 4.03-3.73 (m, 1H), 3.53-3.37 (m, 2H), 3.37-3.32 (m, 1H), 3.28-3.13 (m, 5H), 3.10-2.95 (m, 3H), 2.84-2.69 (m, 1H), 2.14-2.05 (m, 2H), 2.05-1.92 (m, 2H), 1.82-1.60 (m, 2H).

Example 36

Synthesis of (3S,7S,8aS)-3-(4-chlorobenzyl)-2-(1-(pyridin-2-yl)piperidin-4-yl)octahydro-pyrrolo[1,2-a]pyrazin-7-ol 2,2,2-trifluoroacetate (36)

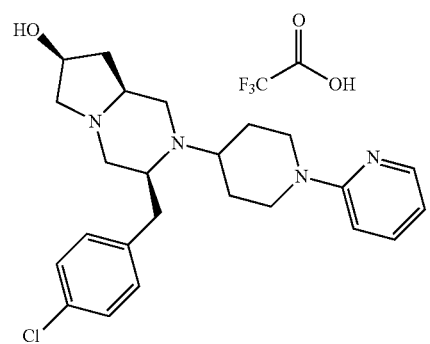

36

The title compound 36 was obtained as a TFA salt in 7% overall yield in a similar way to Example 35 with the exception that, in step 1 of the synthesis, cis-4-hydroxy-L-proline methyl ester hydrochloride was used instead of trans-4-hydroxy-L-proline methyl ester hydrochloride.

ESI-MS m/z for $C_{24}H_{32}ClN_{4}O$ found 427.2/429.2 [M+H]$^+$; $^1$H NMR for free base (400 MHz, Methanol-d$_4$) δ 8.08-8.04 (m, 1H), 7.58-7.51 (m, 1H), 7.31-7.18 (m, 4H), 6.86-6.80 (m, 1H), 6.66-6.60 (m, 1H), 4.32-4.21 (m, 3H), 3.27-3.15 (m, 2H), 3.07 (dd, J=11.4, 3.0 Hz, 1H), 2.98-2.79 (m, 5H), 2.72 (d, J=9.5 Hz, 1H), 2.57-2.48 (m, 1H), 2.31-2.23 (m, 1H), 2.20-1.95 (m, 5H), 1.56-1.37 (m, 3H).

Example 37

Synthesis of (2S,5S)-5-(4-chlorobenzyl)-2-methyl-4-(1-phenylpiperidin-4-yl)morpholine dihydrochloride (37)

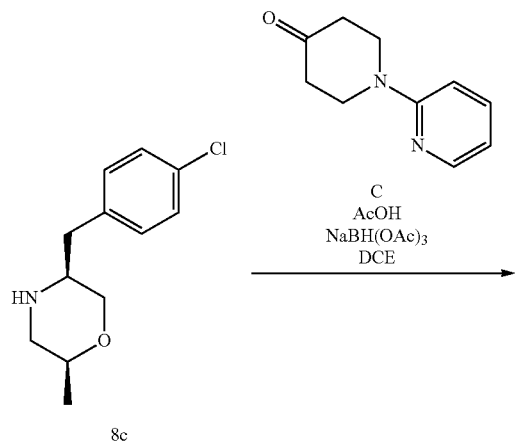

The title compound (37) was obtained as a dihydrochloride salt from 8c (0.2 g; 0.89 mmol) according to the General Procedure VI in 8% yield (32 mg; 0.07 mmol).

ESI-LCMS m/z for $C_{23}H_{30}ClN_2O$ found 385.3/387.3 [M+H]$^+$; $^1$H NMR (400 MHz, Methanol-d$_4$) δ 7.81-7.73 (m, 2H), 7.67-7.58 (m, 2H), 7.57-7.49 (m, 1H), 7.41-7.32 (m, 4H), 4.10-3.99 (m, 2H), 3.99-3.78 (m, 6H), 3.78-3.60 (m, 2H), 3.38-3.31 (m, 1H), 3.29-3.15 (m, 2H), 2.78-2.63 (m, 2H), 2.63-2.45 (m, 2H), 1.34 (d, J=6.3 Hz, 3H).

Example 38

Synthesis of (3S,8aS)-3-(4-chlorobenzyl)-2-(1-(pyridin-2-yl)piperidin-4-yl)octahydropyrrolo[1,2-a]pyrazine 2,2,2-trifluoroacetate (38)

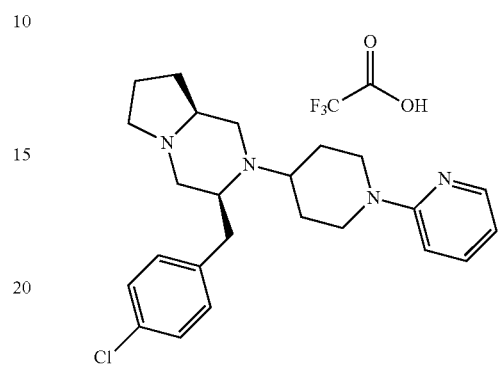

The title compound 38 was obtained as a TFA salt in 17% overall yield in a similar way to Example 35 with the exception that, in step 1 of the synthesis, L-proline methyl ester hydrochloride was used instead of trans-4-hydroxy-L-proline methyl ester hydrochloride.

ESI-MS m/z for $C_{24}H_{32}ClN_4$ found 411.3/413.3 [M+H]$^+$; $^1$H NMR (400 MHz, Methanol-d$_4$) δ 8.06-7.95 (m, 1H), 7.94-7.83 (m, 1H), 7.42-7.23 (m, 5H), 7.00-6.90 (m, 1H), 4.28-4.00 (m, 2H), 3.73-3.34 (m, 3H), 3.27-2.64 (m, 9H), 2.20-1.52 (m, 9H).

Example 39

Synthesis of (2S,5S)-5-(4-chlorobenzyl)-2-methyl-4-(1-(4-methylpyrimidin-2-yl)piperidin-4-yl)morpholine dihydrochloride (39)

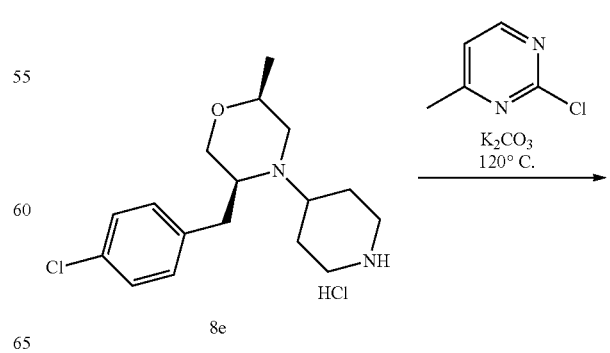

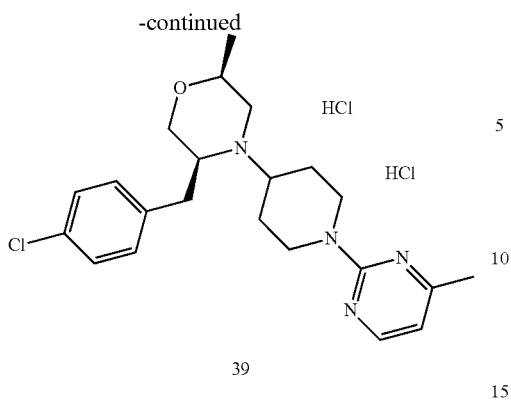

39

The title compound (39) was obtained as a dihydrochloride salt from 8e (200 mg; 0.65 mmol) according to the General Procedure IX in 55% yield (170 mg; 0.36 mmol).

ESI-MS m/z for $C_{22}H_{28}Cl_2N_3O$ found 401.2/403.2 [M+H]+; $^1$H NMR (400 MHz, $D_2O$) δ 8.13-8.02 (m, 1H), 7.34-7.24 (m, 2H), 7.22-7.11 (m, 2H), 6.81-6.70 (m, 1H), 4.63-4.52 (m, 2H), 3.90-3.44 (m, 6H), 3.21-2.98 (m, 5H), 2.42 (s, 3H), 2.40-2.28 (m, 2H), 1.77-1.55 (m, 2H), 1.19 (d, J=6.3 Hz, 3H).

Example 40

Synthesis of (3S,7R,8aS)-3-(4-chlorobenzyl)-2-(1-(pyrimidin-2-yl)piperidin-4-yl)octahydro-pyrrolo[1,2-a]pyrazin-7-ol 2,2,2-trifluoroacetate (40)

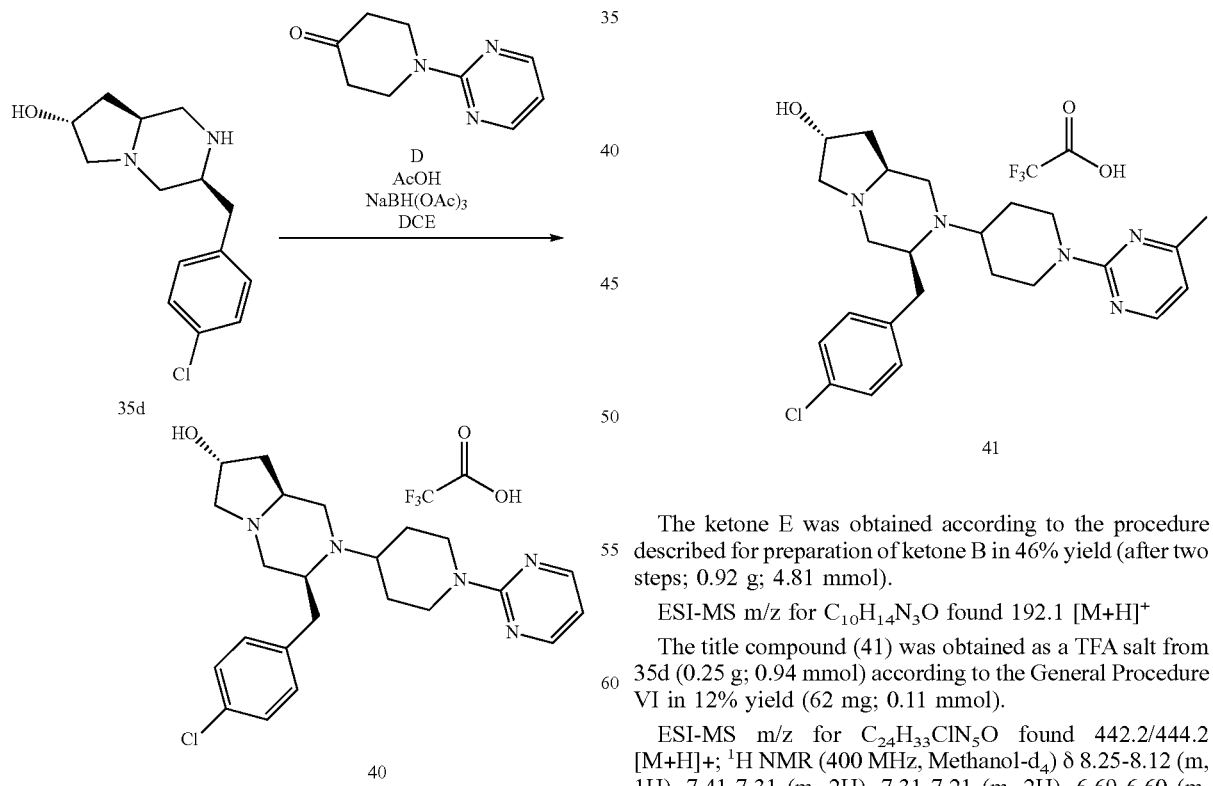

The title compound (40) was obtained as a TFA salt from 35d (0.25 g; 0.94 mmol) according to the General Procedure VI in 14% yield (70 mg; 0.13 mmol). ESI-MS m/z for $C_{23}H_{31}ClN_5O$ found 428.2/430.2 [M+H]+; $^1$H NMR (400 MHz, Methanol-$d_4$) δ 8.42-8.31 (m, 2H), 7.38-7.20 (m, 4H), 6.71-6.60 (m, 1H), 4.88-4.74 (m, 3H), 4.52-4.41 (m, 1H), 3.73-3.53 (m, 2H), 3.52-3.35 (m, 2H), 3.18-2.85 (m, 8H), 2.23-1.90 (m, 4H), 1.72-1.49 (m, 2H).

Example 41

Synthesis of (3S,7R,8aS)-3-(4-chlorobenzyl)-2-(1-(4-methylpyrimidin-2-yl)piperidin-4-yl)octa-hydro-pyrrolo[1,2-a]pyrazin-7-ol 2,2,2-trifluoroacetate (41)

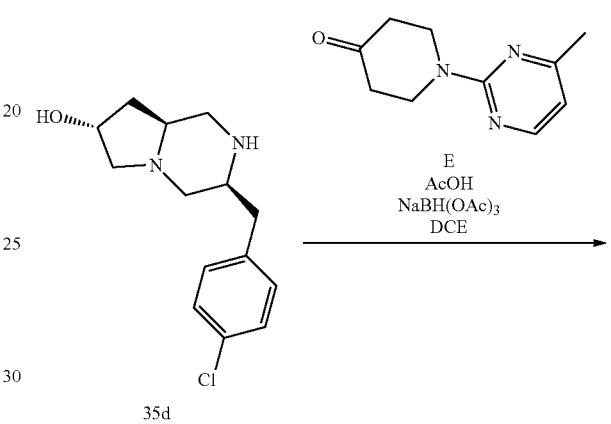

The ketone E was obtained according to the procedure described for preparation of ketone B in 46% yield (after two steps; 0.92 g; 4.81 mmol).

ESI-MS m/z for $C_{10}H_{14}N_3O$ found 192.1 [M+H]+

The title compound (41) was obtained as a TFA salt from 35d (0.25 g; 0.94 mmol) according to the General Procedure VI in 12% yield (62 mg; 0.11 mmol).

ESI-MS m/z for $C_{24}H_{33}ClN_5O$ found 442.2/444.2 [M+H]+; $^1$H NMR (400 MHz, Methanol-$d_4$) δ 8.25-8.12 (m, 1H), 7.41-7.31 (m, 2H), 7.31-7.21 (m, 2H), 6.69-6.60 (m, 1H), 4.84-4.68 (m, 2H), 4.52-4.40 (m, 1H), 3.61-3.32 (m, 3H), 3.25-2.68 (m, 9H), 2.45-2.31 (m, 3H), 2.18-1.83 (m, 5H), 1.70-1.47 (m, 2H).

Example 42

Synthesis of (3S,7S,8aS)-3-(4-chlorobenzyl)-2-(1-(pyrimidin-2-yl)piperidin-4-yl)octahydro-pyrrolo[1,2-a]pyrazin-7-ol 2,2,2-trifluoroacetate (42)

Example 43

Synthesis of (3S,7S,8aS)-3-(4-chlorobenzyl)-2-(1-(4-methylpyrimidin-2-yl)piperidin-4-yl)octa-hydro-pyrrolo[1,2-a]pyrazin-7-ol2,2,2-trifluoroacetate (43)

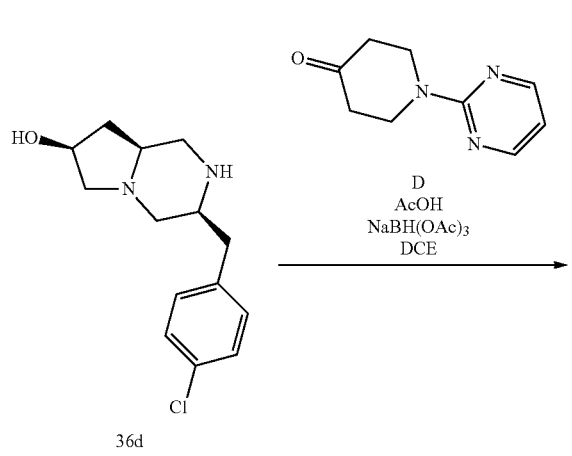

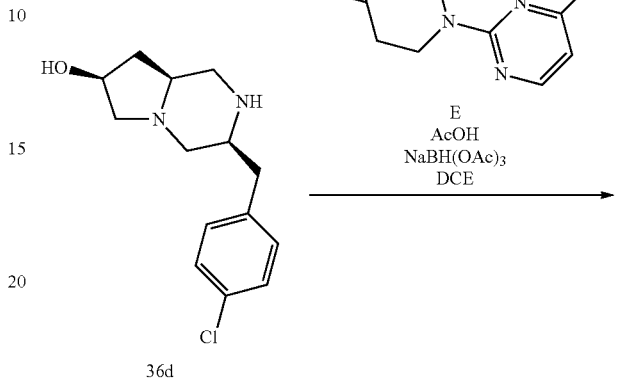

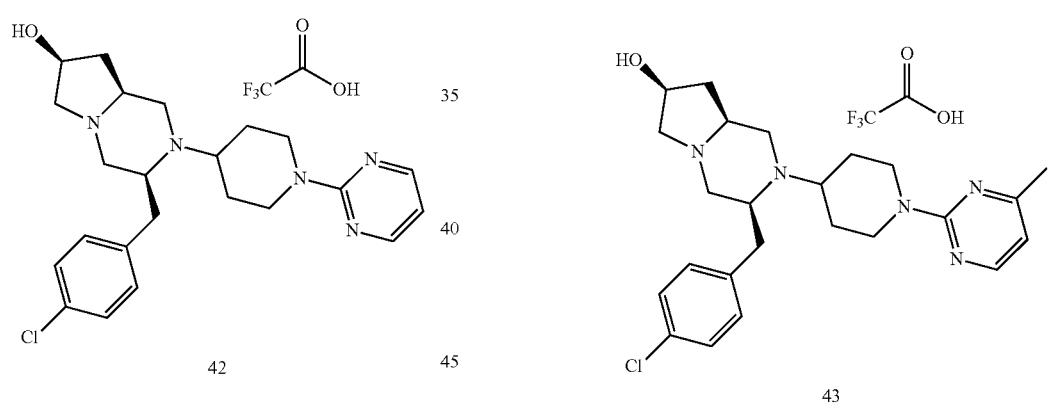

The title compound (42) was obtained as a TFA salt from 36d (0.25 g; 0.94 mmol) according to the General Procedure VI in 5% yield (26 mg; 0.05 mmol).

ESI-MS m/z for $C_{23}H_{31}ClN_5O$ found 428.3/430.3 [M+H]+; $^1$H NMR (400 MHz, Methanol-$d_4$) δ 8.53-8.35 (m, 2H), 7.43-7.25 (m, 4H), 6.83-6.71 (m, 1H), 4.81-4.69 (m, 2H), 4.56-4.47 (m, 1H), 3.75-3.46 (m, 3H), 3.41-3.32 (m, 3H), 3.29-3.21 (m, 2H), 3.17-2.93 (m, 5H), 2.56-2.41 (m, 1H), 2.16-1.93 (m, 3H), 1.82-1.59 (m, 2H).

The title compound (43) was obtained as a TFA salt from 36d (0.25 g; 0.94 mmol) according to the General Procedure VI in 6% yield (33 mg; 0.06 mmol).

ESI-MS m/z for $C_{24}H_{33}ClN_5O$ found 442.2/444.2 [M+H]+; $^1$H NMR (400 MHz, Methanol-$d_4$) δ 8.27-8.17 (m, 1H), 7.38-7.26 (m, 4H), 6.85-6.70 (m, 1H), 4.78-4.61 (m, 2H), 4.60-4.48 (m, 1H), 3.69-3.44 (m, 3H), 3.41-3.31 (m, 2H), 3.29-3.02 (m, 7H), 2.95-2.81 (m, 1H), 2.54-2.42 (m, 4H), 2.09-1.93 (m, 3H), 1.86-1.73 (m, 1H), 1.73-1.56 (m, 1H).

Example 44

Synthesis of (3S,7R,8aS)-3-(4-chlorobenzyl)-2-(1-(4-chloropyridin-2-yl)piperidin-4-yl)octa-hydropyrrolo[1,2-a]pyrazin-7-ol 2,2,2-trifluoroacetate (44)

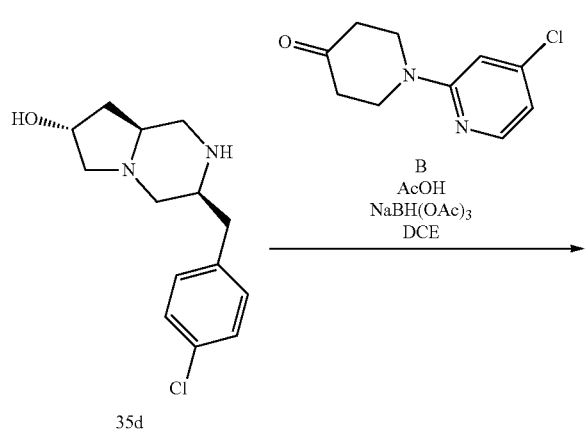

Example 45

Synthesis of (3S,7S,8aS)-3-(4-chlorobenzyl)-2-(1-(4-chloropyridin-2-yl)piperidin-4-yl)octahydro-pyrrolo[1,2-a]pyrazin-7-ol 2,2,2-trifluoroacetate (45)

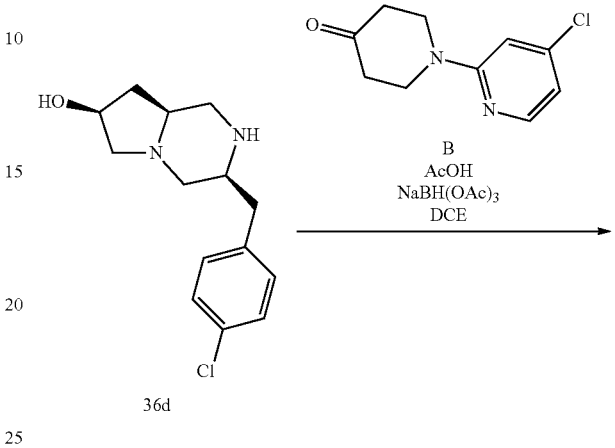

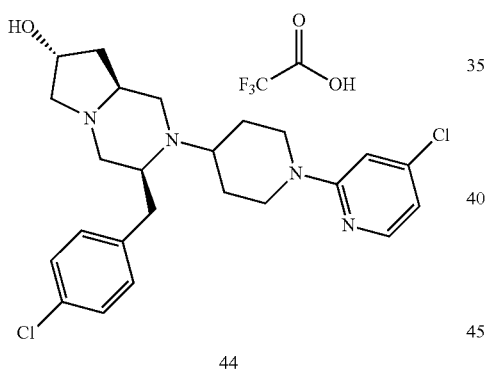

The title compound (44) was obtained as a TFA salt from 35d (0.25 g; 0.94 mmol) according to the General Procedure VI in 10% yield (53 mg; 0.09 mmol).

ESI-MS m/z for $C_{24}H_{31}C_{12}N_4O$ found 461.2/463.2 [M+H]$^+$; $^1$H NMR (400 MHz, Methanol-d$_4$) δ 7.97-7.89 (m, 1H), 7.51-7.43 (m, 1H), 7.37-7.31 (m, 2H), 7.31-7.23 (m, 2H), 6.99-6.92 (m, 1H), 4.55-4.44 (m, 1H), 4.30-4.15 (m, 2H), 3.96-3.71 (m, 1H), 3.55-3.40 (m, 1H), 3.38-3.31 (m, 2H), 3.29-3.12 (m, 5H), 3.11-2.97 (m, 3H), 2.84-2.73 (m, 1H), 2.16-1.91 (m, 4H), 1.85-1.57 (m, 2H).

The title compound (45) was obtained as a TFA salt from 36d (0.25 g; 0.94 mmol) according to the General Procedure VI in 9% yield (46 mg; 0.08 mmol).

ESI-MS m/z for $C_{24}H_{31}C_{12}N_4O$ found 461.2/463.2 [M+H]$^+$; $^1$H NMR (400 MHz, Methanol-d$_4$) δ 7.97-7.87 (m, 1H), 7.45-7.25 (m, 5H), 6.96-6.85 (m, 1H), 4.64-4.48 (m, 1H), 4.34-4.18 (m, 2H), 3.57-3.35 (m, 3H), 3.28-2.66 (m, 10H), 2.57-2.41 (m, 1H), 2.22-1.86 (m, 3H), 1.86-1.68 (m, 1H), 1.68-1.54 (m, 1H).

Example 46

Synthesis of (2S,5S)-5-(4-chlorobenzyl)-4-(1-(5-fluoropyrimidin-2-yl)piperidin-4-yl)-2-methyl-morpholine 2,2,2-trifluoroacetate (46)

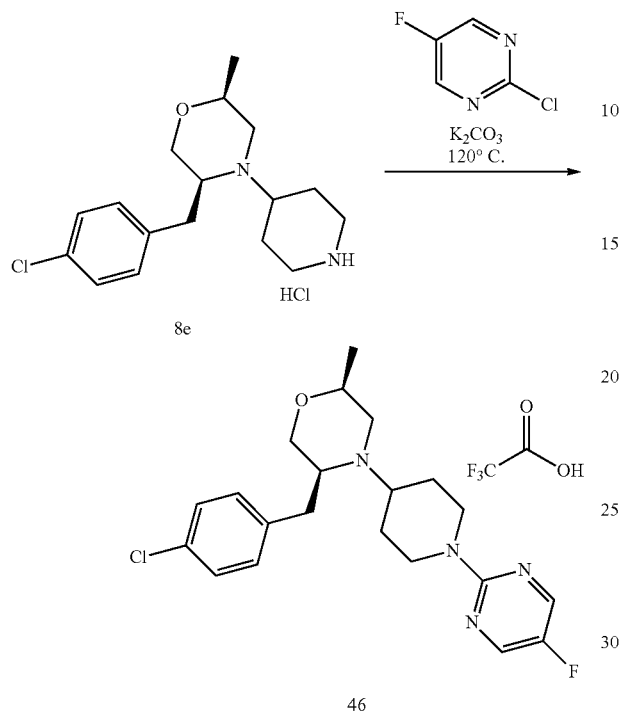

The title compound (46) was obtained as a TFA salt from 8e (150 mg; 0.49 mmol) according to the General Procedure IX in 55% yield (112 mg; 0.36 mmol).

ESI-MS m/z for $C_{21}H_{27}ClFN_4O$ found 405.2/407.2 [M+H]$^+$; $^1$H NMR (400 MHz, Methanol-$d_4$) δ 8.40-8.27 (m, 2H), 7.42-7.37 (m, 2H), 7.37-7.28 (m, 2H), 4.97-4.88 (m, 2H), 3.84-3.70 (m, 4H), 3.68-3.53 (m, 2H), 3.27-2.93 (m, 5H), 2.41-2.30 (m, 2H), 1.70-1.52 (m, 2H), 1.33 (d, J=6.2 Hz, 3H).

Example 47

Synthesis of 2-(4-((2S,5S)-5-(4-chlorobenzyl)-2-methylmorpholino)piperidin-1-yl)-4-methyl-nicotinonitrile 2,2,2-trifluoroacetate (47)

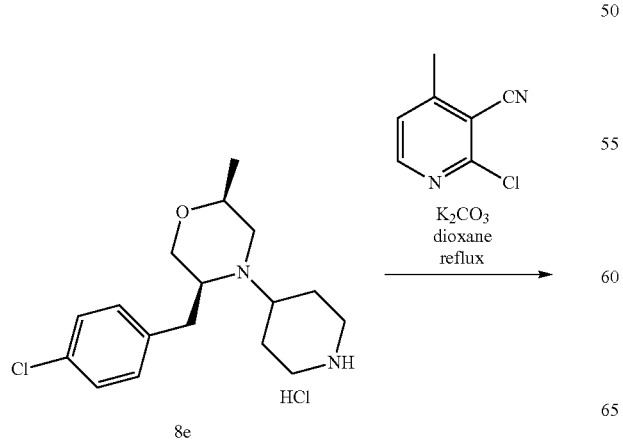

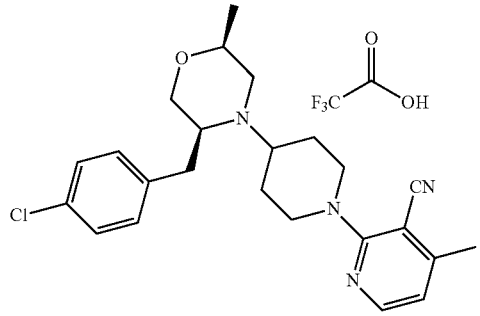

The title compound (47) was obtained as a TFA salt from 8e (125 mg; 0.41 mmol) according to the General Procedure IX in 54% yield (120 mg; 0.22 mmol) with the exception that, dioxane (1.5 mL) was used in this step and the reaction was refluxed overnight.

ESI-MS m/z for $C_{24}H_3MClN_4O$ found 425.3/427.3 [M+H]$^+$; $^1$H NMR (400 MHz, Methanol-$d_4$) δ 8.27-8.19 (m, 1H), 7.44-7.37 (m, 2H), 7.37-7.28 (m, 2H), 6.94-6.86 (m, 1H), 4.46-4.31 (m, 2H), 3.90-3.57 (m, 6H), 3.28-3.02 (m, 5H), 2.49 (s, 3H), 2.47-2.34 (m, 2H), 1.94-1.73 (m, 2H), 1.34 (d, J=6.2 Hz, 3H).

Example 48

Synthesis of (3S,7R,8aS)-3-(4-chlorobenzyl)-2-(1-(4-chloropyridin-2-yl)piperidin-4-yl)-7-methoxyoctahydropyrrolo[1,2-a]pyrazine 2,2,2-trifluoroacetate (48)

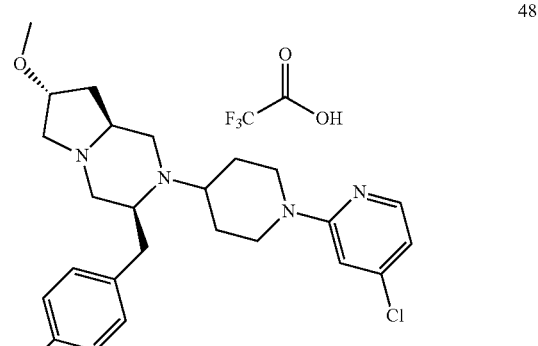

Step 1

Synthesis of (2S,4R)-1-((benzyloxy)carbonyl)-4-hydroxypyrrolidine-2-carboxylic acid (48a)

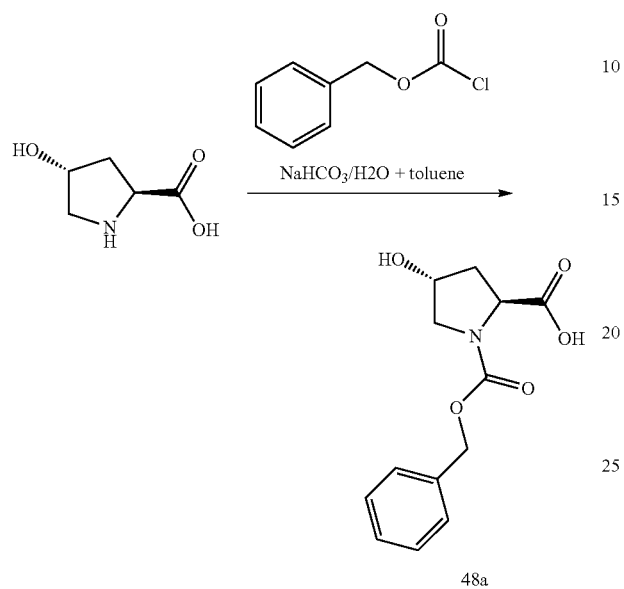

48a

To a solution of trans-hydroxy-L-proline (15 g; 114.39 mmol), NaHCO$_3$ (24.02 g; 286 mmol) in H$_2$O (220 mL) benzyl carbonochloridate (21.47 g; 125.83 mmol) in toluene (80 mL) was added at room temperature. The reaction was vigorously stirred at room temperature for 18 hours. The phases were allowed to separate, water solution was washed with Et$_2$O (4×50 mL), cooled to 0° C. and acidified to pH 2 with 6M HCl. The mixture was extracted with AcOEt (5×75 mL). The combined organic solutions were dried over anhydrous Na$_2$SO$_4$, filtered and concentrated in vacuo and the crude product was used to the next step without additional purification. Compound 48a was obtained in 99% yield (30 g; 113.25 mmol).

Step 2

Synthesis of (2S,4R)-1-benzyl 2-methyl 4-methoxypyrrolidine-1,2-dicarboxylate (48b)

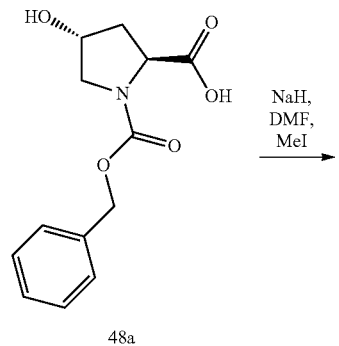

48a

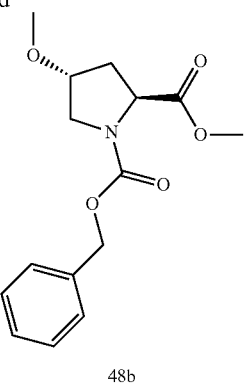

48b

The title compound (48b) was obtained from 48a (6 g; 22.62 mmol) according to the General Procedure XI in 96% yield (6.4 g; 21.72 mmol).

ESI-MS m/z for C$_{15}$H$_{20}$NO$_5$ found 294.1 [M+1]$^+$

Step 3

Synthesis of (2S,4R)-methyl 4-methoxypyrrolidine-2-carboxylate (48c)

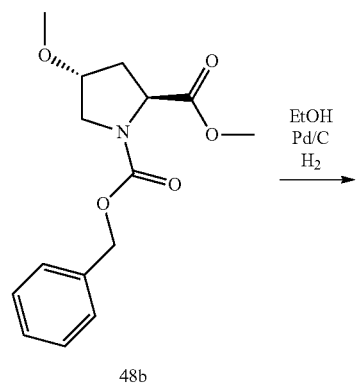

48b

48c

A solution of 48b (6.4 g; 21.72 mmol) in EtOH (150 mL) was purged with N$_2$. Then Pd/C (10%) (1.16 g; 1.09 mmol) was added and the suspension was purged with H$_2$ (balloon). The reaction was stirred under H$_2$ overnight. The reaction progress was monitored by TLC and LC-MS. When analyses indicated completion of the reaction, the catalyst was filtered off. The crude product was used to the next step without additional purification. Compound 48c was obtained in 94% yield (3.255 g; 20.46 mmol).

ESI-MS m/z for C$_7$H$_{14}$NO$_3$ found 160.1 [M+1]$^+$

Step 4

Synthesis of methyl (2S,4R)-1-((R)-2-((tert-butoxycarbonyl)amino)-3-(4-chlorophenyl)-propanoyl)-4-methoxypyrrolidine-2-carboxylate (48d)

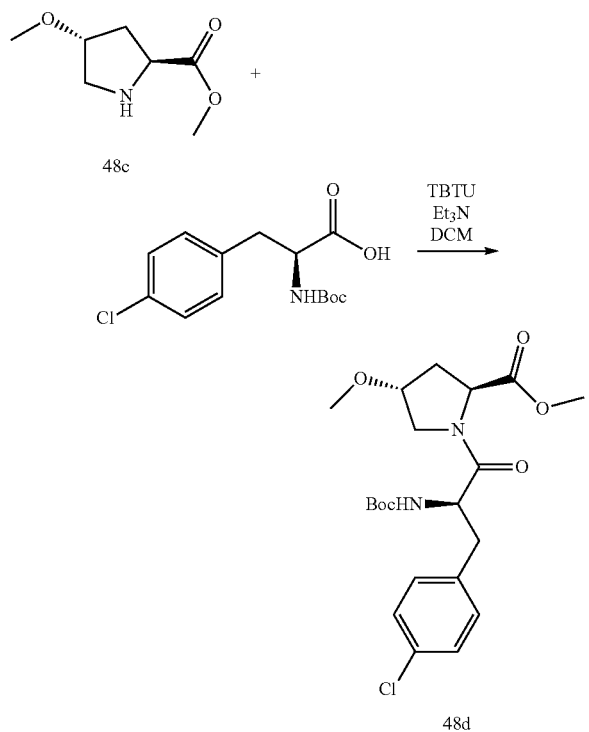

The title compound (48d) was obtained as an oil from 48c (2.3 g; 14.45 mmol) and Boc-4-chloro-L-phenylalanine (5.2 g; 17.34 mmol) according to the General Procedure III in 99% yield (6.31 g; 14.31 mmol).

ESI-MS m/z for $C_{21}H_{30}ClN_2O_6$ found 441.2/443.2 $[M+H]^+$

Step 5

Synthesis of methyl (2S,4R)-1-((R)-2-amino-3-(4-chlorophenyl)propanoyl)-4-methoxy-pyrrolidine-2-carboxylate 2,2,2-trifluoroacetate (48e)

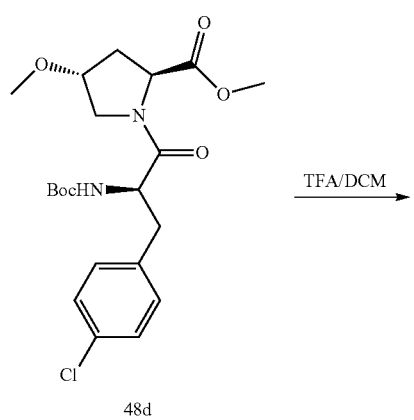

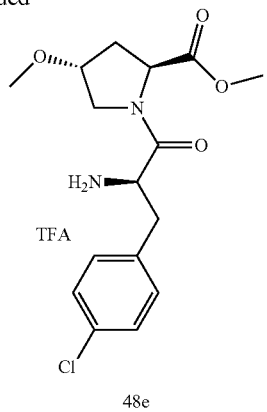

The title compound (48e) was obtained as a TFA salt from 48d (6.31 g; 14.31 mmol) according to the General Procedure IVb in 99% yield (6.43 g; 14.17 mmol).

ESI-MS m/z for $C_{16}H_{22}ClN_2O_4$ found 341.1/343.1 $[M+H]^+$

Step 6

Synthesis of (3S,7R,8aS)-3-(4-chlorobenzyl)-7-methoxyhexahydropyrrolo[1,2-a]pyrazine-1,4-dione (48f)

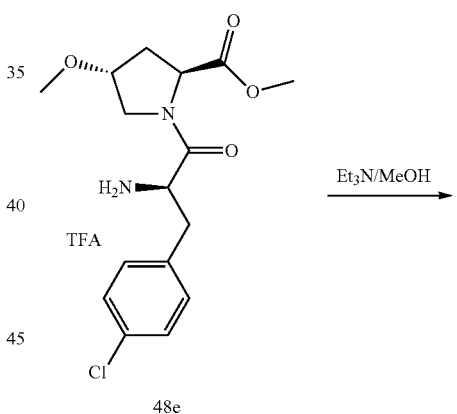

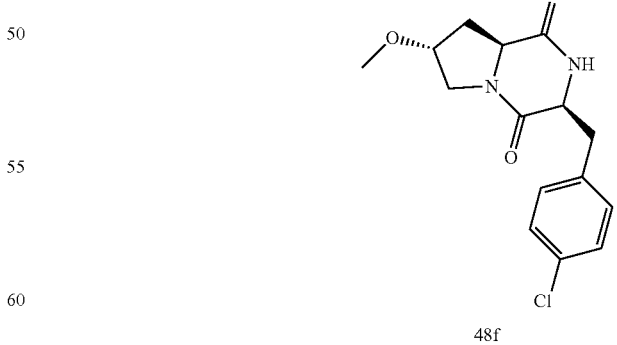

To a solution of crude 48e (0.43 g; 14.17 mmol) in MeOH (100 mL) Et$_3$N (14.1 mL; 101.15 mmol) was added and the mixture was heated to reflux for 40 minutes. LC-MS showed completion of the reaction. The mixture was concentrated in vacuo and the residue was partitioned between AcOEt (150 mL) and water (100 mL). An aqueous phase was additionally extracted with AcOEt (100 mL). The combined organic solutions were dried over anhydrous $Na_2SO_4$, filtered and concentrated in vacuo. The crude product was used to the next step without additional purification. Compound 48f was obtained as a red oil in 99% yield (4.32 g; 14.03 mmol).

ESI-MS m/z for $C_{15}H_{18}ClN_2O_3$ found 309.1/311.1 [M+H]$^+$

Step 7

Synthesis of (3S,7R,8aS)-3-(4-chlorobenzyl)-7-methoxyoctahydropyrrolo[1,2-a]pyrazine (48g)

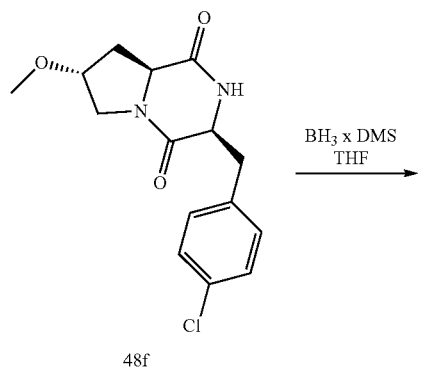

The title compound (48g) was obtained as an yellow oil from 48f (4.32 g; 14.03 mmol) according to the General Procedure Ib in 99% yield (3.89 g; 13.89 mmol).

ESI-MS m/z for $C_{15}H_{22}ClN_2O$ found 281.1/283.1 [M+H]$^+$

Step 8

Synthesis of (3S,7R,8aS)-3-(4-chlorobenzyl)-2-(1-(4-chloropyridin-2-yl)piperidin-4-yl)-7-methoxyoctahydropyrrolo[1,2-a]pyrazine 2,2,2-trifluoroacetate (48)

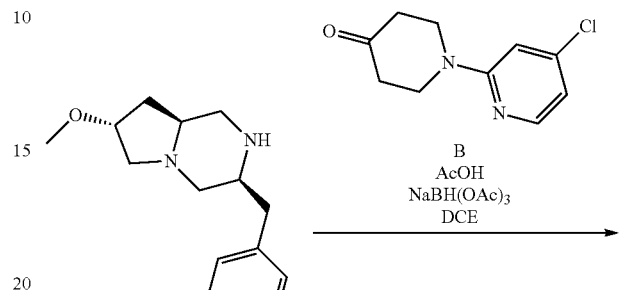

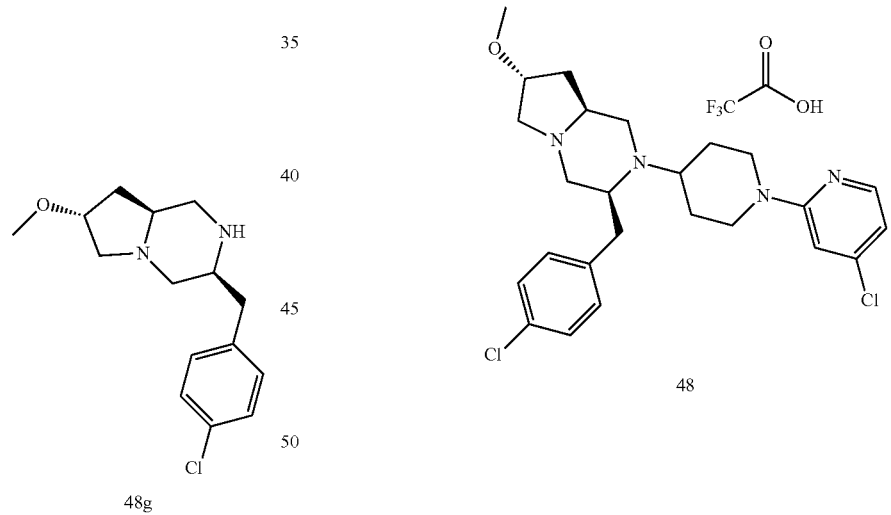

The title compound (48) was obtained as a TFA salt from 48g (0.25 g; 0.89 mmol) according to the General Procedure VI in 12% yield (66 mg; 0.11 mmol).

ESI-MS m/z for $C_{25}H_{33}Cl_2N_4O$ found 475.2/477.2 [M+H]$^+$; $^1$H NMR (400 MHz, Methanol-d$_4$) δ 8.00-7.90 (m, 1H), 7.38-7.16 (m, 5H), 6.89-6.79 (m, 1H), 4.42-4.20 (m, 2H), 4.12-4.03 (m, 1H), 3.73-3.46 (m, 2H), 3.46-3.32 (m, 3H), 3.21-2.90 (m, 7H), 2.85-2.57 (m, 2H), 2.30-1.81 (m, 5H), 1.78-1.52 (m, 3H).

Example 49

Synthesis of (2S,5S)-5-(4-chlorobenzyl)-2-methyl-4-(1-(3-(trifluoromethyl)pyridin-2-yl)-piperidin-4-yl) morpholine 2,2,2-trifluoroacetate (49)

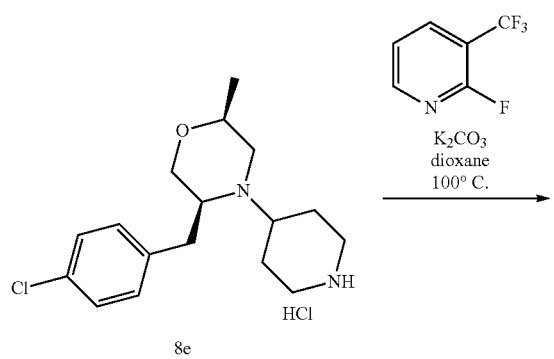

The title compound (49) was obtained as a TFA salt from 8e (100 mg; 0.32 mmol) according to the General Procedure IX in 45% yield (82 mg; 0.145 mmol) with the exception that, dioxane (1 mL) was used in this step and the reaction was maintained at 100° C.

ESI-MS m/z for $C_{23}H_{28}ClF_3N_3O$ found 454.2/456.2 [M+H]$^+$; $^1$H NMR (400 MHz, Methanol-d$_4$) δ 8.53-8.45 (m, 1H), 8.09-7.99 (m, 1H), 7.41-7.35 (m, 2H), 7.35-7.28 (m, 2H), 7.24-7.17 (m, 1H), 3.92-3.57 (m, 8H), 3.26-2.98 (m, 5H), 2.46-2.29 (m, 2H), 2.00-1.79 (m, 2H), 1.33 (d, J=6.3 Hz, 3H).

Example 50

Synthesis of ((2R,5S)-5-(4-chlorobenzyl)-4-(1-(4-chloropyridin-2-yl)piperidin-4-yl)-1-methyl-piperazin-2-yl)methanol (50)

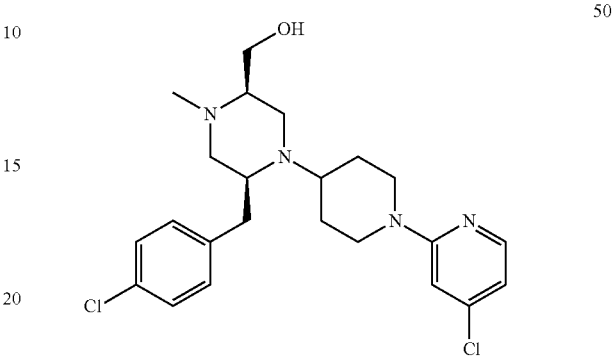

Step 1

Synthesis of O-benzyl-N-(tert-butoxycarbonyl)-N-methyl-L-serine (50a)

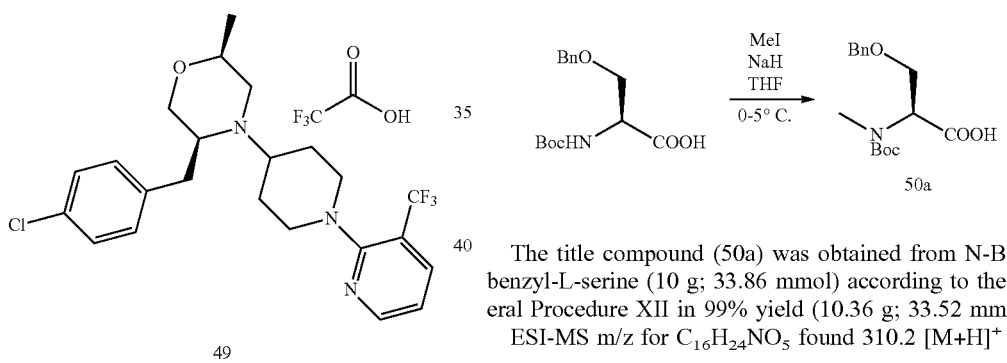

The title compound (50a) was obtained from N-Boc-O-benzyl-L-serine (10 g; 33.86 mmol) according to the General Procedure XII in 99% yield (10.36 g; 33.52 mmol). ESI-MS m/z for $C_{16}H_{24}NO_5$ found 310.2 [M+H]$^+$

Step 2

Synthesis of methyl O-benzyl-N-methyl-L-serinate hydrochloride (50b)

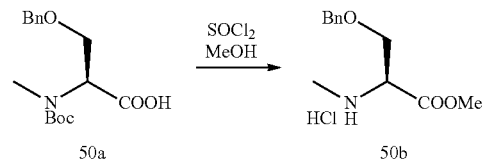 [SMILES: CN(C(=O)OC(C)(C)C)[C@@H](COCc1ccccc1)C(=O)O ; CN[C@@H](COCc1ccccc1)C(=O)OC ; Cl ; "SOCl2MeOH"]

Thionyl chloride (62 mL; 0.85 mol) was added dropwise to a cooled to −20° C. methanol (100 mL) and stirred at this temperature for 30 minutes. Then the solution of 50a (10.36 g; 33.52 mmol) in methanol (100 mL) was added and the cooling bath was removed. The reaction mixture was stirred at room temperature overnight. The reaction progress was monitored by TLC and LC-MS. Analyses showed mixture of product with substrate. The reaction mixture was then cooled to −20° C. and an another part of a thionyl chloride (30 mL; 0.41 mol) was added dropwise and the reaction mixture was stirred at room temperature overnight. When analyses indicated completion of the reaction, the solvent was evaporated to obtained a crude 50b as a hydrochloride salt in 99% yield (8.61 g; 33.18 mmol).

ESI-MS m/z for $C_{12}H_{18}NO_3$ found 224.1 $[M+H]^+$

Step 3

Synthesis of methyl O-benzyl-N-((S)-2-((tert-butoxycarbonyl)amino)-3-(4-chlorophenyl)-propanoyl)-N-methyl-L-serinate (50c)

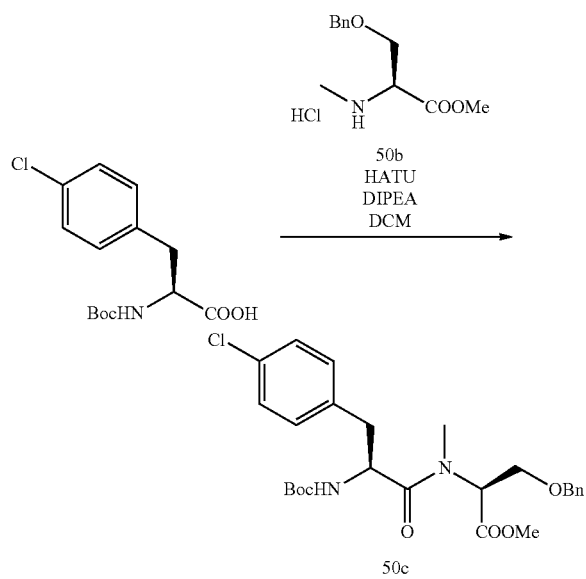

The title compound (50c) was obtained from 50b (8.61 g; 33.18 mmol) according to the General Procedure III in 45% yield (7.53 g; 14.94 mmol).

ESI-MS m/z for $C_{26}H_{34}ClN_2O_6$ found 505.2/507.2 $[M+H]^+$

Step 4

Synthesis of (3S,6S)-6-((benzyloxy)methyl)-3-(4-chlorobenzyl)-1-methylpiperazine-2,5-dione (50d)

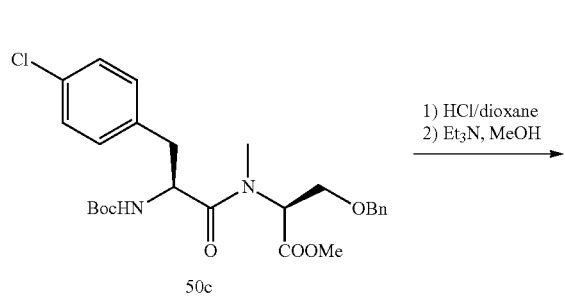

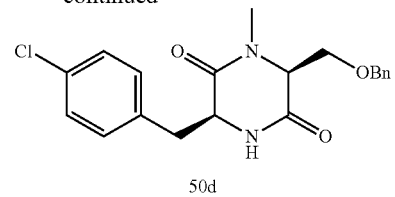

The title compound (50d) was obtained from 50c (7.53 g; 14.94 mmol) according to the General Procedure VIII in 99% yield (5.49 g; 14.75 mmol).

ESI-MS m/z for $C_{20}H_{22}ClN_2O_3$ found 373.1/375.1 $[M+H]^+$

Step 5

Synthesis of (2R,5S)-2-((benzyloxy)methyl)-5-(4-chlorobenzyl)-1-methylpiperazine (50e)

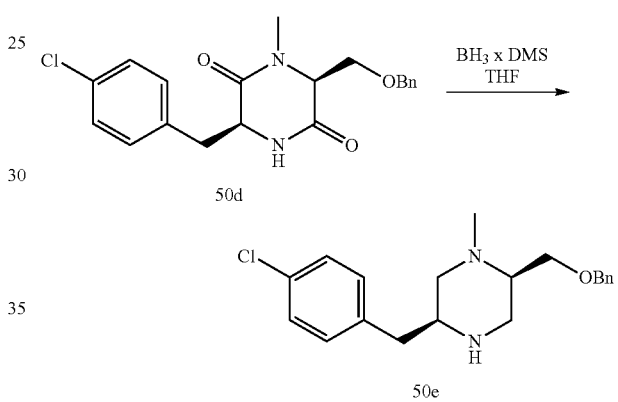

The title compound (50e) was obtained from 50d (5.49 g; 14.75 mmol) according to the General Procedure Ib in 50% yield (2.54 g; 7.38 mmol).

ESI-MS m/z for $C_{20}H_{26}ClN_2O$ found 345.2/347.2 $[M+H]^+$

Step 6

Synthesis of (2R,5S)-2-((benzyloxy)methyl)-5-(4-chlorobenzyl)-4-(1-(4-chloropyridin-2-yl)-piperidin-4-yl)-1-methylpiperazine (50f)

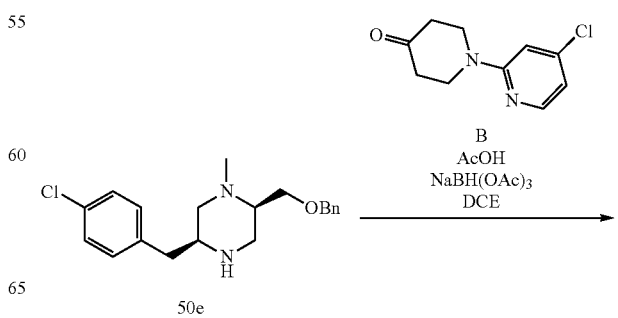

-continued

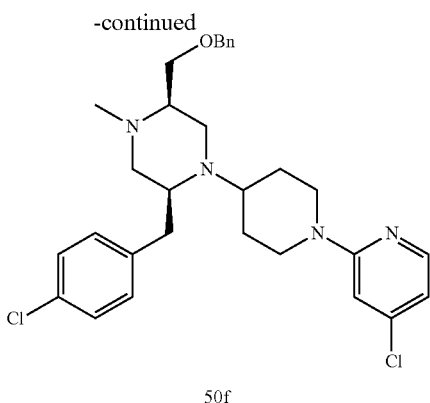

50f

The title compound (50f) was obtained from 50e (0.86 g; 2.49 mmol) according to the General Procedure VI in 64% yield (858 mg; 1.59 mmol).

ESI-MS m/z for $C_3NH_{37}C_{12}N_4O$ found 539.2/541.2 [M+H]$^+$; $^1$H NMR (700 MHz, CDCl$_3$) δ 8.11-8.08 (m, 1H), 7.44-7.37 (m, 4H), 7.36-7.33 (m, 1H), 7.31-7.27 (m, 2H), 7.18-7.14 (m, 2H), 6.70-6.67 (m, 1H), 6.64-6.61 (m, 1H), 4.62-4.55 (m, 2H), 4.30-4.22 (m, 2H), 3.73-3.67 (m, 1H), 3.52-3.45 (m, 1H), 3.12-3.05 (m, 2H), 3.05-2.94 (m, 3H), 2.87-2.73 (m, 2H), 2.58 (dd, J=11.8, 9.7 Hz, 1H), 2.52 (dd, J=11.5, 2.6 Hz, 1H), 2.43-2.35 (m, 1H), 2.24 (s, 3H), 2.22-2.15 (m, 1H), 2.04-1.96 (m, 2H), 1.62-1.53 (m, 2H).

Step 7

Synthesis of ((2R,5S)-5-(4-chlorobenzyl)-4-(1-(4-chloropyridin-2-yl)piperidin-4-yl)-1-methyl-piperazin-2-yl)methanol (50)

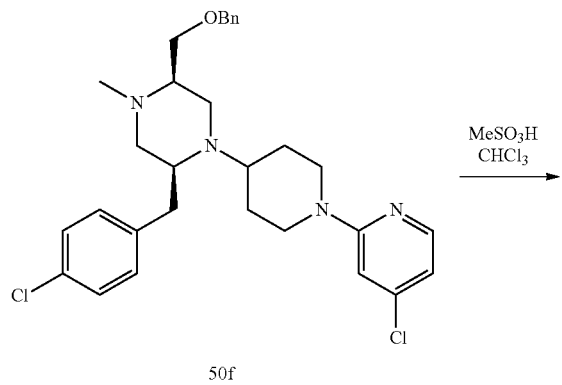

To a solution of 50f (705 mg; 1.31 mmol) in CHCl$_3$ (10 mL) methanesulfonic acid (1.69 mL; 26 mmol) was added and the reaction mixture was stirred at room temperature for 1 hour. The reaction progress was monitored by TLC and LC-MS. Another part of methanesulfonic acid (3.12 mL; 48 mmol) was added and the reaction mixture was stirred at room temperature overnight. When analyses indicated completion of the reaction, the reaction mixture was quenched with 4M NaOH and extracted with AcOEt (3×). The combined organic solutions were dried over anhydrous MgSO$_4$, filtered and concentrated in vacuo. The product was purified by silica-gel column chromatography (AcOEt/MeOH, 100:0 to 5:1, v/v). Compound 50 was obtained in 63% yield (370 mg; 0.83 mmol).

ESI-MS m/z for $C_{23}H_{31}C_{12}N_4O$ found 449.1/451.1 [M+H]$^+$; $^1$H NMR (700 MHz, Methanol-d$_4$) δ 8.03-8.01 (m, 1H), 7.32-7.29 (m, 2H), 7.28-7.24 (m, 2H), 6.89-6.86 (m, 1H), 6.67-6.65 (m, 1H), 4.34-4.26 (m, 2H), 3.78-3.74 (m, 1H), 3.67-3.62 (m, 1H), 3.19-3.13 (m, 1H), 3.09-3.05 (m, 1H), 3.05-3.01 (m, 1H), 3.01-2.94 (m, 2H), 2.93-2.83 (m, 2H), 2.63 (dd, J=12.0, 10.0 Hz, 1H), 2.57 (dd, J=11.7, 3.1 Hz, 1H), 2.27 (s, 3H), 2.24-2.15 (m, 2H), 2.15-2.03 (m, 2H), 1.56-1.44 (m, 2H).

Example 51

Synthesis of 4-(((2S,5S)-5-(4-chlorobenzyl)-4-(1-(4-chloropyridin-2-yl)piperidin-4-yl)-1-methyl-piperazin-2-yl)methyl)morpholine hydrochloride (51)

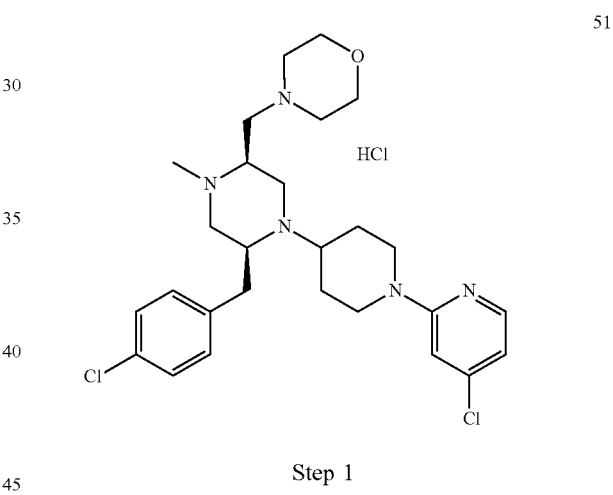

Step 1

Synthesis of ((2R,5S)-5-(4-chlorobenzyl)-4-(1-(4-chloropyridin-2-yl)piperidin-4-yl)-1-methyl-piperazin-2-yl)methyl methanesulfonate (51a)

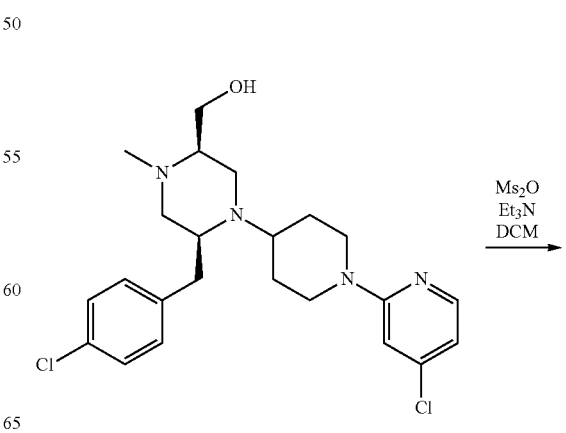

287

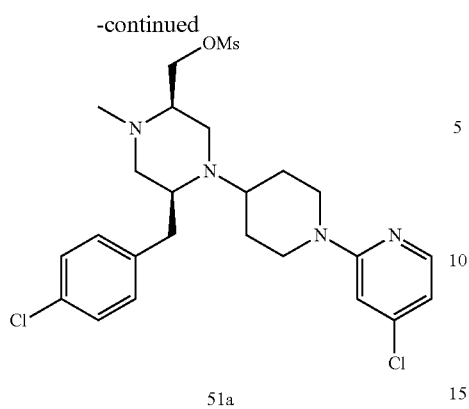

51a

The title compound (51a) was obtained from 50 (38 mg; 0.085 mmol) according to the General Procedure XIV in 99% yield (44 mg; 0.084 mmol).

ESI-MS m/z for $C_{24}H_{33}Cl_2N_4O_3S$ found 527.2/529.2 $[M+H]^+$

Step 2

Synthesis of 4-(((2S,5S)-5-(4-chlorobenzyl)-4-(1-(4-chloropyridin-2-yl)piperidin-4-yl)-1-methylpiperazin-2-yl)methyl)morpholine hydrochloride (51)

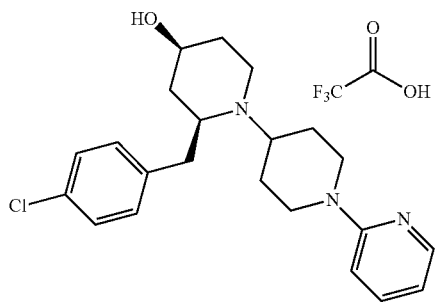

51

The title compound (51) was obtained as a hydrochloride salt from 51a (44 mg; 0.084 mmol) according to the General Procedure XIII in 50% yield (23 mg; 0.042 mmol).

ESI-MS m/z for $C_{27}H_{38}Cl_2N_5O$ found 518.2/520.2 $[M+H]^+$; $^1H$ NMR (700 MHz, $D_2O$) δ 7.84-7.76 (m, 1H), 7.44-7.34 (m, 3H), 7.30-7.24 (m, 2H), 7.01-6.94 (m, 1H), 4.14-4.06 (m, 2H), 4.01-3.88 (m, 4H), 3.78-3.69 (m, 2H), 3.68-3.62 (m, 1H), 3.56-3.38 (m, 7H), 3.37-3.27 (m, 1H), 3.27-3.19 (m, 2H), 3.19-3.10 (m, 1H), 3.06-2.98 (m, 1H), 2.96-2.89 (m, 1H), 2.89-2.82 (m, 1H), 2.63 (s, 3H), 2.16-2.07 (m, 2H), 1.87-1.79 (m, 1H), 1.79-1.69 (m, 1H).

Example 52

Synthesis of (2S,4S)-2-(4-chlorobenzyl)-1'-(pyridin-2-yl)-[1,4'-bipiperidin]-4-ol 2,2,2-trifluoro-acetate (52)

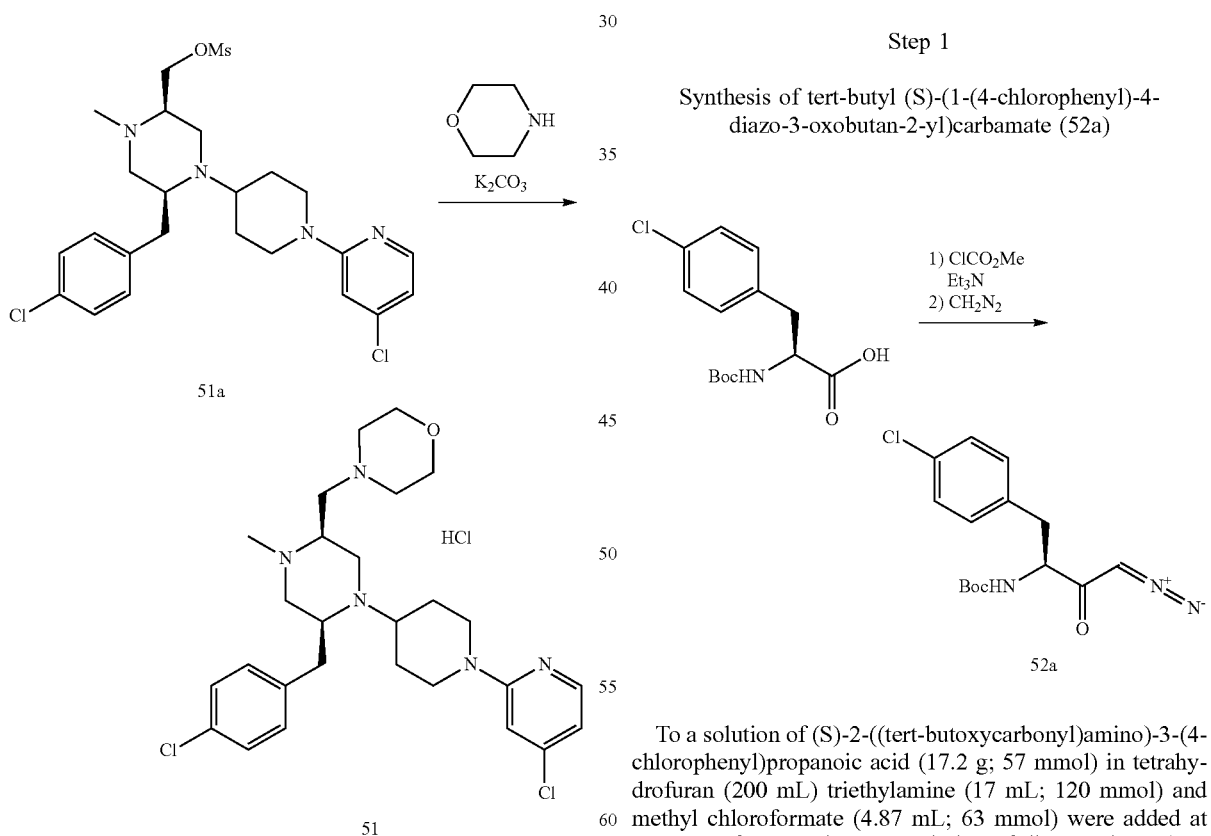

Step 1

Synthesis of tert-butyl (S)-(1-(4-chlorophenyl)-4-diazo-3-oxobutan-2-yl)carbamate (52a)

To a solution of (S)-2-((tert-butoxycarbonyl)amino)-3-(4-chlorophenyl)propanoic acid (17.2 g; 57 mmol) in tetrahydrofuran (200 mL) triethylamine (17 mL; 120 mmol) and methyl chloroformate (4.87 mL; 63 mmol) were added at −10° C. After 15 minutes a solution of diazomethane (342 mmol) in diethyl ether (400 mL) was added at −30° C. The reaction mixture was stirred overnight at room temperature. The excess of diazomethane was destroyed with acetic acid (15 mL). The mixture was diluted with diethyl ether and washed with 5% $NaHCO_3$, saturated $NH_4Cl$, and brine. The organic layer was dried over anhydrous $MgSO_4$, filtered and concentrated in vacuo to give product 52a as an orange solid in 96% yield (17.68 g; 54.72 mmol).

ESI-MS m/z for $C_{15}H_{19}ClN_3O_3$ found 324.1/326.1 [M+H]$^+$; $^1$H NMR (700 MHz, CDCl$_3$) δ 7.28 (d, J=8.3 Hz, 2H), 7.13 (d, J=8.2 Hz, 2H), 5.26 (br s, 1H), 5.07 (br s, 1H), 4.40 (br s, 1H), 3.03 (dd, J=7.0, 14.0 Hz, 1H), 2.97 (dd, J=6.1, 13.5 Hz, 1H), 1.42 (s, 9H).

Step 2

Synthesis of (S)-3-((tert-butoxycarbonyl)amino)-4-(4-chlorophenyl)butanoic acid (52b)

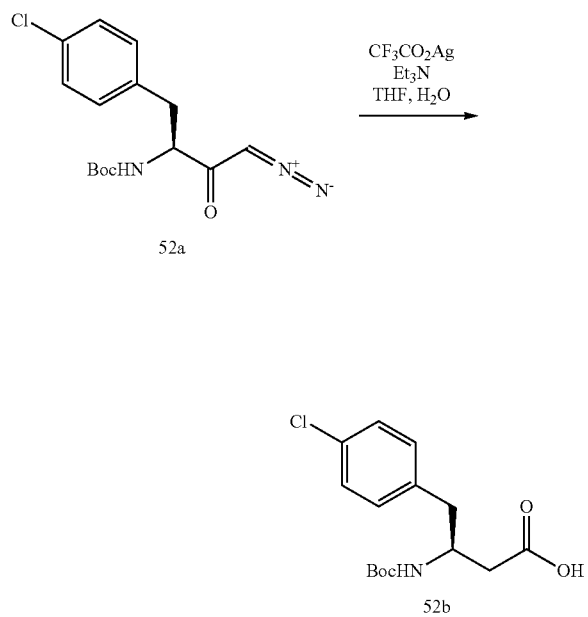

To a solution of compound 52a (18 g; 55.71 mmol) in tetrahydrofuran:water (135 mL 15 mL) a solution of silver trifluoroacetate (1.57 g; 7.1 mmol) in triethylamine (25 mL; 182 mmol) was added at −5° C. The reaction mixture was stirred for 1 hour. After this time the solvent was removed at reduced pressure. The residue was diluted with saturated aq. NaHCO$_3$, and the mixture was extracted with diethyl ether. 1M HCl was added to the aqueous layer at 0° C. until pH 2-3, and the mixture was extracted three times with ethyl acetate. The organic layers were collected, dried over anhydrous MgSO$_4$, filtered and concentrated in vacuo. The crude product was crystallized from diethyl ether to obtain 52b as a white solid in 40% yield (7 g; 22.36 mmol).

ESI-MS m/z for $C_{15}H_{19}ClNO_4$ found 312.3/314.3 [M−H]$^-$; $^1$H NMR (500 MHz, DMSO-d$_6$) δ 12.14 (s, 1H), 7.28 (d, J=8.3 Hz, 2H), 7.14 (d, J=8.3 Hz, 2H), 6.76 (d, J=8.7 Hz, 1H), 3.90-3.86 (m, 1H), 2.68 (dd, J=5.27, 13.4 Hz, 1H), 2.60 (dd, J=8.5, 13.4 Hz, 1H), 2.30 (t, J=7.0 Hz, 2H), 1.25 (s, 9H).

Step 3

Synthesis of tert-butyl (S)-(1-(4-chlorophenyl)-4-(methoxy(methyl)amino)-4-oxobutan-2-yl)carbamate (52c)

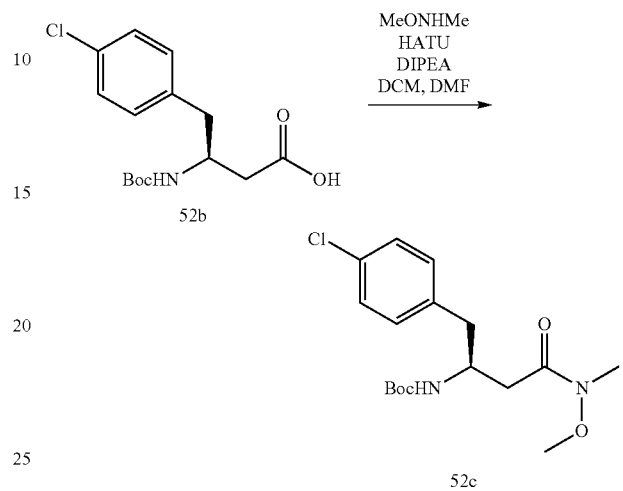

The title compound (52c) was obtained from 52b (7 g; 22.36 mmol) according to the General Procedure XV (to improve solubility of 52b, mixture of DCM/DMF 10:1 was used as a reaction solvent) in 93% yield (7.4 g; 20.78 mmol).

ESI-MS m/z for $C_{17}H_{25}ClN_2O_4Na$ found 379.1/381.1 [M+Na]$^+$; $^1$H NMR (500 MHz, CDCl$_3$) δ 7.25 (d, J=8.5 Hz, 2H), 7.13 (d, J=8.3 Hz, 2H), 5.48 (br s, 1H), 4.14-4.10 (m, 1H), 3.57 (s, 3H), 3.17 (s, 3H), 3.00-2.94 (m, 1H), 2.84 (dd, J=7.9, 13.6 Hz, 1H), 2.58 (qd, J=3.8, 16.4 Hz, 2H), 1.39 (s, 9H).

Step 4

Synthesis of tert-butyl (S)-(1-(4-chlorophenyl)-4-oxohex-5-en-2-yl)carbamate (52d)

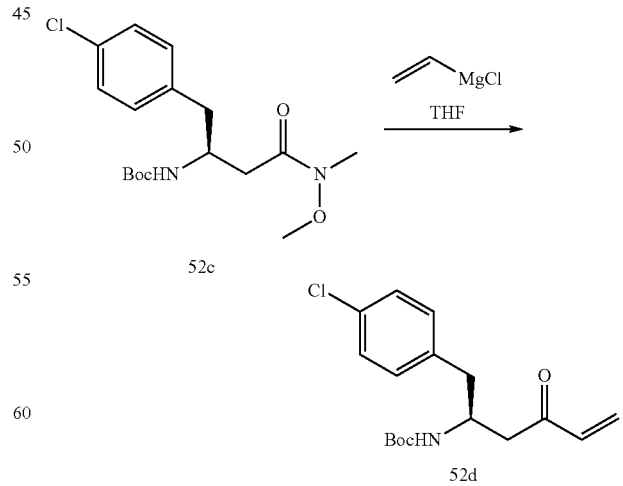

The title compound (52d) was obtained as a white solid from 52c (6.9 g; 19.3 mmol) according to the General Procedure V in 32% yield (2 g; 6.18 mmol).

ESI-MS m/z for $C_{17}H_{23}ClNO_3$ found 323.8/325.8 [M+H]$^+$

Step 5

Synthesis of tert-butyl (S)-2-(4-chlorobenzyl)-4-oxopiperidine-1-carboxylate (52e)

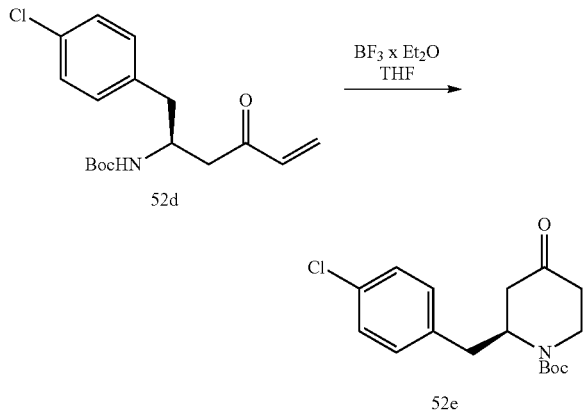

To a solution of 52d (1.1 g; 3.4 mmol) in tetrahydrofuran (10 mL) boron trifluoride diethyl ether complex (4.27 mL; 34 mmol) was added. The reaction mixture was stirred at room temperature overnight. Then the mixture was diluted with ethyl acetate and washed with 4M NaOH. An organic layer was dried over anhydrous MgSO$_4$, filtered and concentrated in vacuo. The crude product was purified by flash column chromatography on silica (hexane/AcOEt, 6:1 to 2:1, v/v) to afford 52e as a colorless oil in 44% yield (480 mg; 1.49 mmol).

ESI-MS m/z for $C_{17}H_{22}ClNO_3Na$ found 346.1/348.1 [M+Na]$^+$; $^1$H NMR (500 MHz, CDCl$_3$) δ 7.26 (d, J=8.3 Hz, 2H), 7.09 (d, J=6.6 Hz, 2H), 4.74 (br s, 1H), 4.37 (br s, 1H), 3.30 (qd, J=3.7, 11.5 Hz, 1H), 2.81 (dd, J=7.3, 13.6 Hz, 1H), 2.68 (dd, J=7.9, 13.7 Hz, 1H), 2.60 (dd, J=6.8, 14.5 Hz, 1H), 2.54-2.49 (m, 1H), 2.39-2.34 (m, 2H), 1.40 (s, 9H).

Step 6

Synthesis of tert-butyl (2S,4R)-2-(4-chlorobenzyl)-4-hydroxypiperidine-1-carboxylate (52f) and tert-butyl (2S,4S)-2-(4-chlorobenzyl)-4-hydroxypiperidine-1-carboxylate (52g)

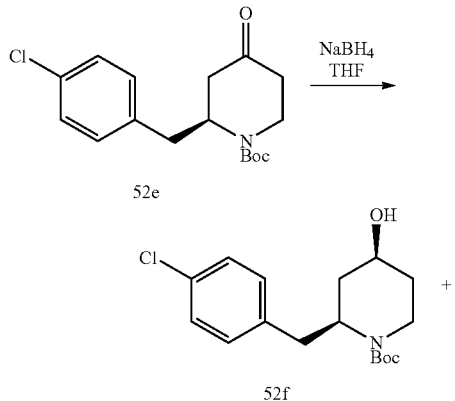

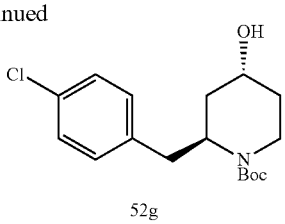

To a solution of 52e (470 mg; 1.45 mmol) in methanol (5 mL) sodium borohydride (66 mg; 1.75 mmol) was added at 0° C. The reaction mixture was stirred at room temperature for 2 hours, then 1N NaOH was added. An aqueous layer was extracted with ethyl acetate. The combined organic layers were dried over anhydrous MgSO$_4$, filtered and concentrated in vacuo. The products were purified by flash column chromatography on silica (hexane/AcOEt, 6:1 to 1:1, v/v). The compound 52f was obtained as a colorless oil as a single diastereomer with unknown configuration at hydroxy group in 40% yield (187 mg; 0.58 mmol) and compound 52g was obtained as a colorless oil as a single diastereomer with unknown configuration at hydroxy group in 43% yield (200 mg; 0.62 mmol).

For compound 52f: ESI-MS m/z for $C_{17}H_{24}ClNO_3Na$ found 349.0/351.0 [M+Na]$^+$; $^1$H NMR (500 MHz, CDCl$_3$) δ 7.23 (d, J=8.5 Hz, 2H), 7.15 (d, J=8.3 Hz, 2H), 4.34-4.31 (m, 1H), 4.20 (t, J=3.0 Hz, 1H), 3.96 (d, J=12.4 Hz, 1H), 3.31 (td, J=3.8, 13.4 Hz, 1H), 3.10 (dd, J=7.1, 13.1 Hz, 1H), 3.01 (dd, J=8.1, 13.2 Hz, 1H), 1.71-1.68 (m, 4H), 1.34 (s, 9H).

For compound 52g: ESI-MS m/z for $C_{17}H_{24}ClNO_3Na$ found 349.0/351.0 [M+Na]$^+$; $^1$H NMR (500 MHz, CDCl$_3$) δ 7.25 (d, J=8.5 Hz, 2H), 7.09 (d, J=6.2 Hz, 2H), 4.50 (br s, 1H), 4.24-4.17 (m, 1H), 4.05-4.00 (m, 1H), 2.94 (td, J=2.6, 13.6 Hz, 1H), 2.82 (dd, J=8.3, 13.4 Hz, 1H), 2.68 (dd, J=7.5, 13.0 Hz, 1H), 2.00 (d, J=11.9 Hz, 1H), 1.87 (d, J=12.4 Hz, 1H), 1.45-1.40 (m, 2H), 1.31 (s, 9H).

Step 7

Synthesis of (2S,4S)-2-(4-chlorobenzyl)piperidin-4-ol 2,2,2-trifluoroacetate (52h)

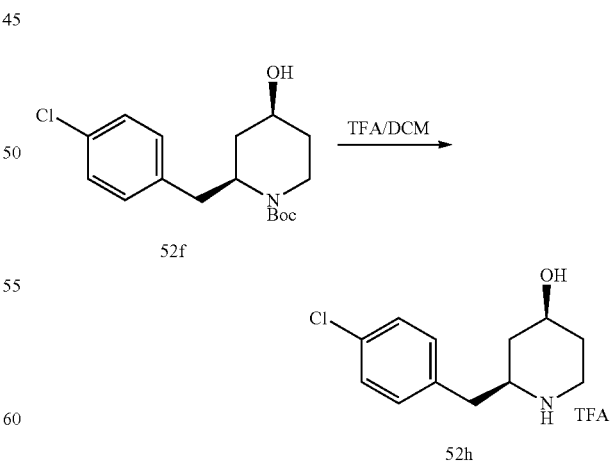

The title compound (52h) was obtained as a TFA salt from 52f (240 mg; 0.74 mmol) according to the General Procedure IVb in 99% yield (247 mg; 0.73 mmol).

ESI-MS m/z for $C_{12}H_{17}ClNO$ found 226.1/228.1 [M+H]$^+$

293

Step 8

Synthesis of (2S,4S)-2-(4-chlorobenzyl)-1'-(pyridin-2-yl)-[1,4'-bipiperidin]-4-ol 2,2,2-trifluoro-acetate (52)

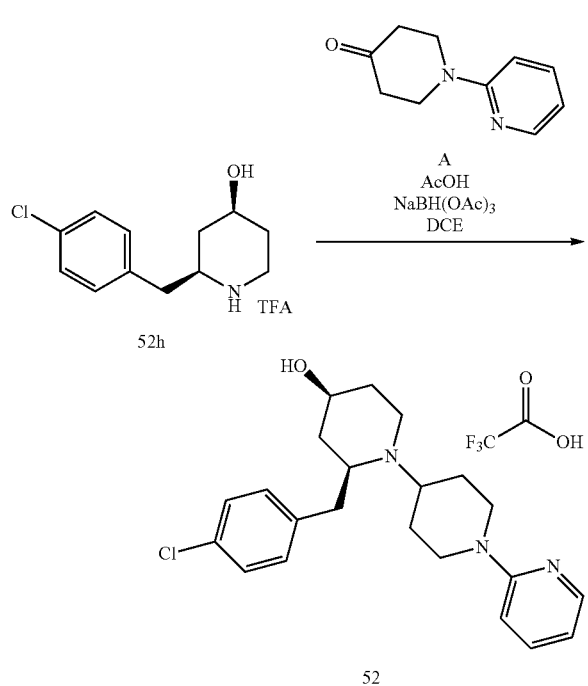

The title compound (52) was obtained as a TFA salt from 52h (247 mg; 0.73 mmol) according to the General Procedure VI in 4% yield (16 mg; 0.032 mmol).

ESI-MS m/z for $C_{22}H_{29}ClN_3O$ found 386.2/388.2 [M+H]+; $^1$H NMR (700 MHz, $D_2O$, 300 K) δ 7.98-7.92 (m, 1H), 7.83-7.77 (m, 1H), 7.39-7.31 (m, 2H), 7.29-7.15 (m, 3H), 6.94-6.88 (m, 1H), 4.24-4.17 (m, 1H), 4.17-4.09 (m, 1H), 4.05-3.95 (m, 1H), 3.79-3.70 (m, 2H), 3.57-3.50 (m, 1H), 3.43-3.34 (m, 1H), 3.32-3.25 (m, 1H), 3.03-2.93 (m, 2H), 2.86-2.76 (m, 1H), 2.16-2.11 (m, 1H), 2.11-1.96 (m, 4H), 1.88-1.77 (m, 1H), 1.67-1.49 (m, 2H).

Example 53

Synthesis of (2S,4R)-2-(4-chlorobenzyl)-1'-(pyridin-2-yl)-[1,4'-bipiperidin]-4-ol 2,2,2-trifluoroacetate (53)

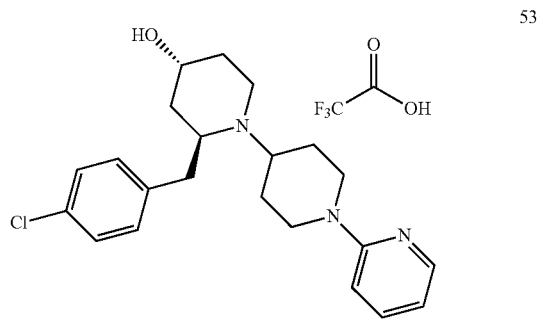

294

Step 1

Synthesis of (2S,4R)-2-(4-chlorobenzyl)piperidin-4-ol 2,2,2-trifluoroacetate (53a)

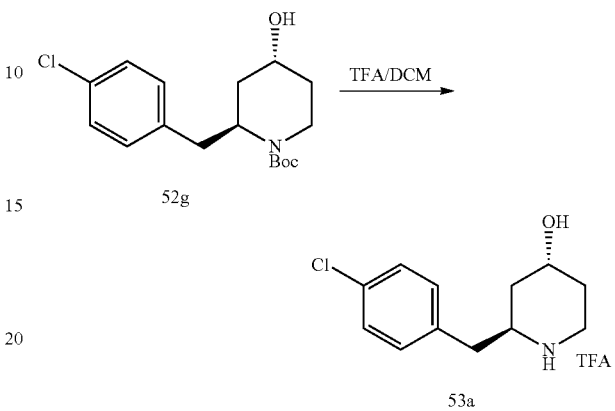

The title compound (53a) was obtained as a TFA salt from 52g (160 mg; 0.49 mmol) according to the General Procedure IVb in 99% yield (166 mg; 0.49 mmol).

ESI-MS m/z for $C_{12}H_{17}ClNO$ found 226.1/228.1 [M+H]+

Step 2

Synthesis of (2S,4R)-2-(4-chlorobenzyl)-1'-(pyridin-2-yl)-[1,4'-bipiperidin]-4-ol 2,2,2-trifluoro-acetate (53)

The title compound (53) was obtained as a TFA salt from 53a (166 mg; 0.49 mmol) according to the General Procedure VI in 3% yield (8 mg; 0.016 mmol).

ESI-MS m/z for $C_{22}H_{29}ClN_3O$ found 386.2/388.2 [M+H]$^+$; $^1$H NMR (700 MHz, D$_2$O, 300 K) δ 8.01-7.90 (m, 1H), 7.87-7.79 (m, 1H), 7.42-7.32 (m, 2H), 7.30-7.18 (m, 3H), 6.99-6.89 (m, 1H), 4.27-4.08 (m, 3H), 4.08-3.99 (m, 1H), 3.98-3.89 (m, 1H), 3.75-3.59 (m, 1H), 3.41-3.12 (m, 4H), 3.10-2.98 (m, 1H), 2.93-2.77 (m, 1H), 2.15-1.52 (m, 7H).

Example 54

Synthesis of (2S,5S)-2-(4-chlorobenzyl)-5-isobutyl-4-methyl-1-(1-(pyridin-2-yl)piperidin-4-yl)piperazine 2,2,2-trifluoroacetate (54)

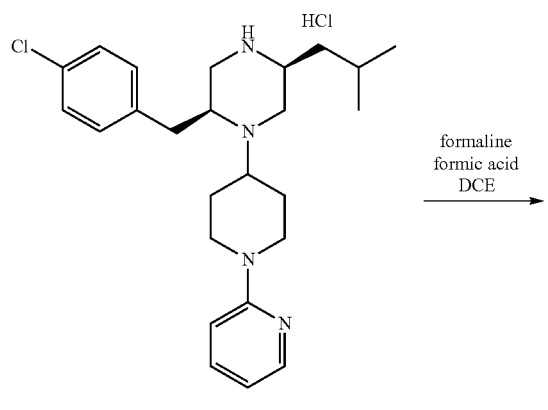

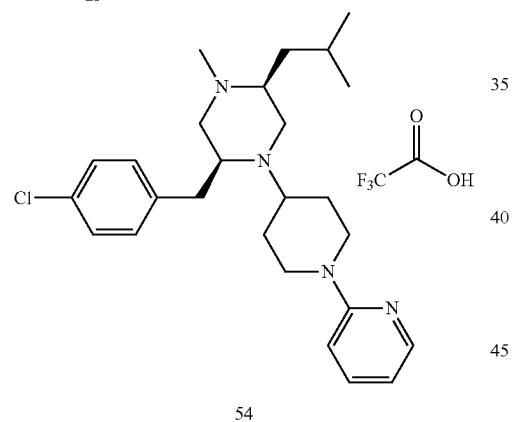

To the solution of 2f (37 mg; 0.08 mmol) in DCE (0.1 mL) formaline (36%; 8 uL; 0.088 mmol) and formic acid (8 μL; 0.2 mmol) were added. The reaction mixture was refluxed overnight. The reaction progress was monitored by TLC and LC-MS. When analyses indicated completion of the reaction, the reaction mixture was diluted with ethyl acetate and washed with 4M NaOH. An organic layer was dried over anhydrous MgSO$_4$, filtered and concentrated in vacuo. The crude product was purified by preparative reversed-phase column chromatography (C-18, water/MeCN+1% TFA, 95:5 to 40:60, 30 min). Compound 54 was obtained as a TFA salt in 73% yield (32 mg; 0.058 mmol).

ESI-MS m/z for $C_{26}H_{38}ClN_4$ found 441.3/443.3 [M+H]$^+$; $^1$H NMR (700 MHz, D$_2$O) δ 8.34-8.26 (m, 1H), 8.22-8.12 (m, 1H), 7.74-7.65 (m, 2H), 7.64-7.57 (m, 2H), 7.57-7.50 (m, 1H), 7.36-7.21 (m, 1H), 4.46-4.39 (m, 2H), 4.39-4.32 (m, 1H), 4.14-4.01 (m, 1H), 3.87-3.77 (m, 3H), 3.77-3.64 (m, 3H), 3.62-3.52 (m, 1H), 3.49-3.39 (m, 1H), 3.38-3.32 (m, 1H), 3.23 (s, 3H), 2.55 (d, J=12.5 Hz, 1H), 2.41 (d, J=12.8 Hz, 1H), 2.22-2.05 (m, 3H), 2.05-1.91 (m, 2H), 1.26 (d, J=6.3 Hz, 3H), 1.21 (d, J=6.4 Hz, 3H).

Example 55

Synthesis of (2R,5S)-5-(4-chlorobenzyl)-4-(1-(4-chloropyridin-2-yl)piperidin-4-yl)-2-((methyl-sulfonyl)methyl)morpholine 2,2,2-trifluoroacetate (55)

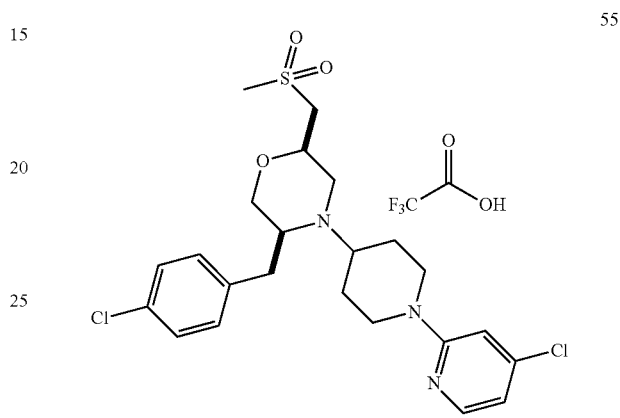

Step 1

Synthesis of tert-butyl (2R,5S)-5-(4-chlorobenzyl)-2-(hydroxymethyl)morpholine-4-carboxylate (55a)

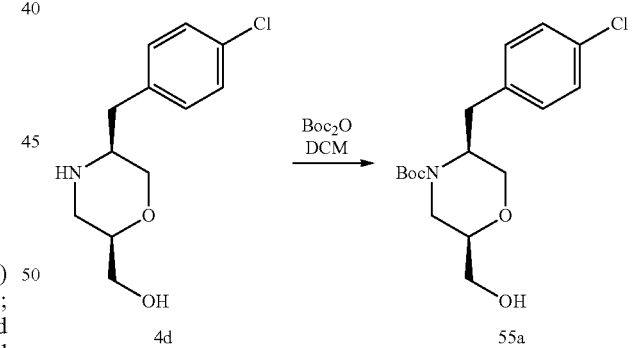

To a solution of amino alcohol 4d (2.87 g, 11.9 mmol) in dichloromethane (110 mL), di-tert-butyl dicarbonate (Boc$_2$O) (2.46 g, 11.3 mmol) was added and the reaction mixture was stirred at room temperature for 2 hours, after which time TLC showed almost complete consumption of the starting material. The volatiles were removed in vacuo and the residue was purified by silica-gel column chromatography (hexane/AcOEt, 1:1, v/v) giving 55a as colorless oil in 77% yield (3.14 g; 9.16 mmol).

ESI-MS m/z for $C_{12}H_{17}ClNO_2$ found 242.1/246.1 [M+H-Boc]$^+$

Step 2

Synthesis of (2R,5S)-tert-butyl 5-(4-chlorobenzyl)-2-(((methylsulfonyl)oxy)methyl)morpholine-4-carboxylate (55b)

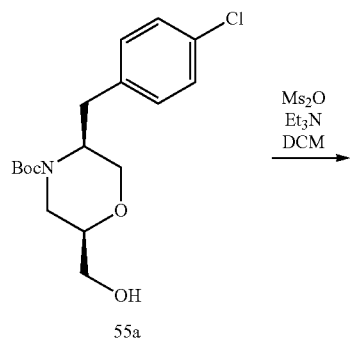

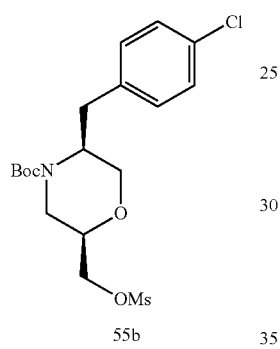

The title compound (55b) was obtained from 55a (2 g; 5.85 mmol) according to the General Procedure XIV in 98% yield (2.4 g; 5.73 mmol).

ESI-MS $C_{18}H_{27}ClNO_6S$ found 420.1/422.1 $(M+H)^+$

Step 3

Synthesis of (2R,5S)-tert-butyl 5-(4-chlorobenzyl)-2-((methylthio)methyl)morpholine-4-carboxylate (55c)

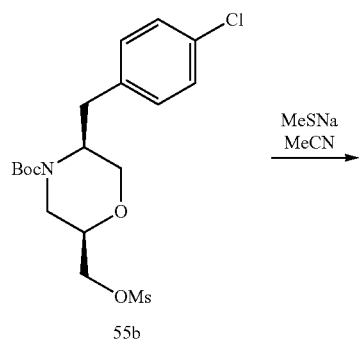

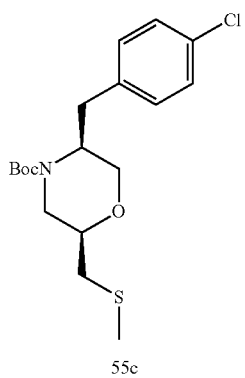

To a solution of 55b (1.3 g; 3.09 mmol) in acetonitrile (15 mL) MeSNa (550 mg; 7.74 mmol) was added and the reaction mixture was stirred at 80° C. overnight in a sealed vial. The reaction progress was monitored by LC-MS analysis. After analytical control indicated completion of the reaction, the mixture was dissolved in DCM and then washed with 2M NaOH, brine, dried over anhydrous $Na_2SO_4$, filtered and concentrated in vacuo and the crude product was used to the next step without additional purification. Compound 55c was obtained in 79% yield (0.9 g; 2.43 mmol).

ESI-MS m/z for $C_{18}H_{27}ClNO_3S$ found 372.1/374.1 $[M+1]^+$

Step 4

Synthesis of (2R,5S)-tert-butyl 5-(4-chlorobenzyl)-2-((methylsulfonyl)methyl)morpholine-4-carboxylate (55d)

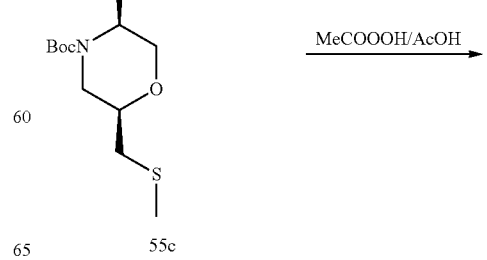

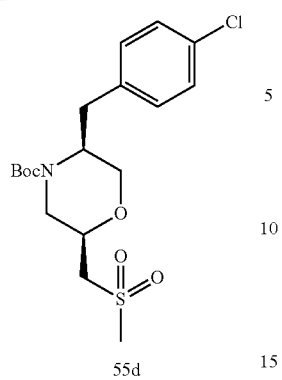

55d

The reaction of 55c (0.32 g; 0.86 mmol) with peracetic acid (35% in AcOH; 0.33 mL; 1.72 mmol) was stirred at room temperature overnight. Then the reaction was concentrated in vacuo and the residue was partitioned between AcOEt and 1M NaOH. The phases were separated and the organic one was washed with brine, dried over anhydrous $Na_2SO_4$, filtered and concentrated in vacuo and the crude product was used to the next step without additional purification. Compound 55d was obtained in 99% yield (0.34 g; 0.85 mmol).

ESI-MS m/z for $C_{18}H_{27}ClNO_5S$ found 404.1/406.1 [M+1]*; $^1$H NMR (700 MHz, DMSO-$d_6$+$D_2O$, 348 K) δ 7.33-7.26 (m, 2H), 7.24-7.18 (m, 2H), 4.11-4.05 (m, 1H), 3.87-3.82 (m, 1H), 3.81-3.77 (m, 1H), 3.77-3.73 (m, 1H), 3.61-3.54 (m, 1H), 3.34-3.29 (m, 1H), 3.06-2.94 (m, 5H), 2.86-2.79 (m, 1H), 1.98-1.95 (m, 1H), 1.27-1.14 (m, 9H).

Step 5

Synthesis of (2R,5S)-5-(4-chlorobenzyl)-2-((methyl-sulfonyl)methyl)morpholine (55e)

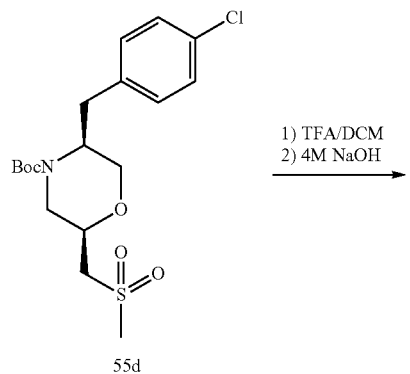

55d

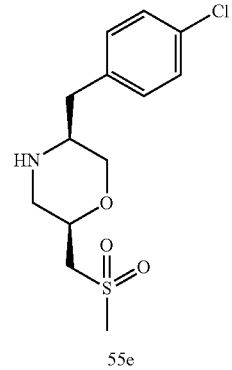

55e

The title compound (55e) was obtained as a free base in 99% yield (149 mg; 0.49 mmol) from 55d (198 mg; 0.49 mmol) according to the General Procedure IVb and then after basic (4M NaOH) extraction with DCM.

Step 6

Synthesis of (2R,5S)-5-(4-chlorobenzyl)-4-(1-(4-chloropyridin-2-yl)piperidin-4-yl)-2-((methyl-sulfonyl)methyl)morpholine 2,2,2-trifluoroacetate (55)

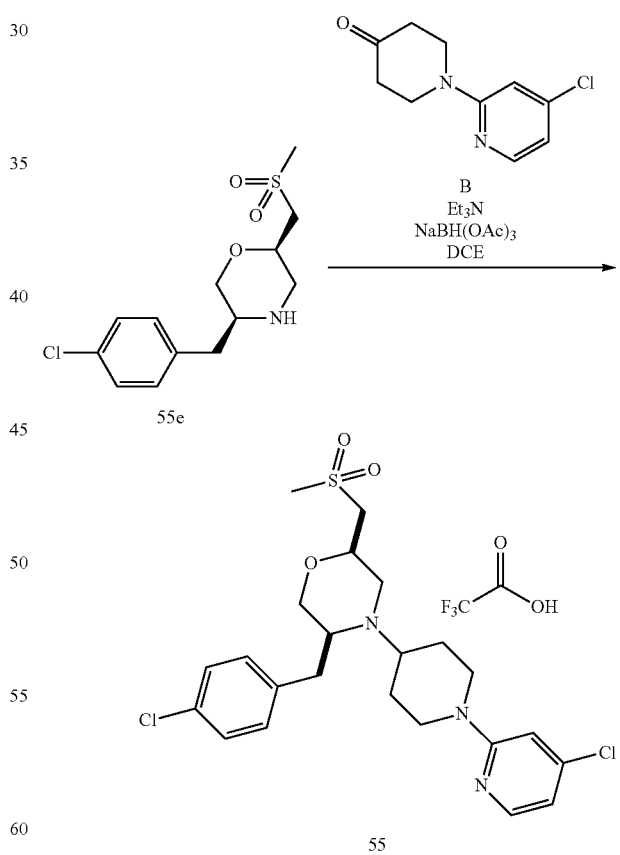

55

The title compound (55) was obtained as a TFA salt from 55e (79 mg; 0.26 mmol) according to the General Procedure VI in 38% yield (62 mg; 0.1 mmol).

ESI-MS m/z for $C_{23}H_{30}Cl_2N_3O_3S$ found 498.1/500.1 [M+H]$^+$; $^1$H NMR (700 MHz, DMSO-d-+$D_2O$, 348 K) δ

8.08-8.02 (m, 1H), 7.42-7.35 (m, 2H), 7.35-7.27 (m, 2H), 6.95-6.88 (m, 1H), 6.76-6.69 (m, 1H), 4.42-4.35 (m, 2H), 4.25-4.18 (m, 1H), 3.75-3.68 (m, 3H), 3.68-3.63 (m, 1H), 3.63-3.55 (m, 2H), 3.43-3.37 (m, 1H), 3.31-3.23 (m, 1H), 3.23-3.15 (m, 1H), 3.15-3.07 (m, 1H), 3.02 (s, 3H), 3.00-2.88 (m, 2H), 2.25-2.13 (m, 2H), 1.65-1.47 (m, 2H).

Example 56

Synthesis of (3S,9aS)-3-(4-chlorobenzyl)-2-(1-(pyridin-2-yl)piperidin-4-yl)octahydro-2H-pyrido[1,2-a]pyrazine 2,2,2-trifluoroacetate (56)

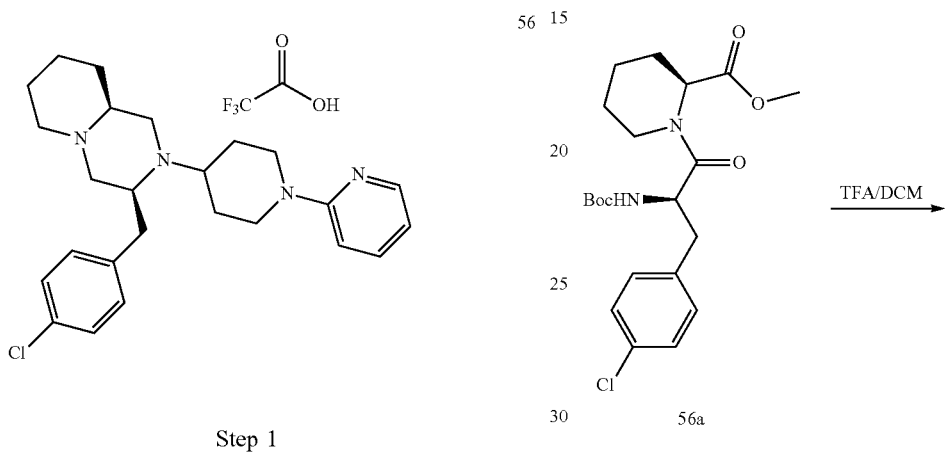

Step 1

Synthesis of methyl (S)-1-((R)-2-((tert-butoxycarbonyl)amino)-3-(4-chlorophenyl)propanoyl)piperidine-2-carboxylate (56a)

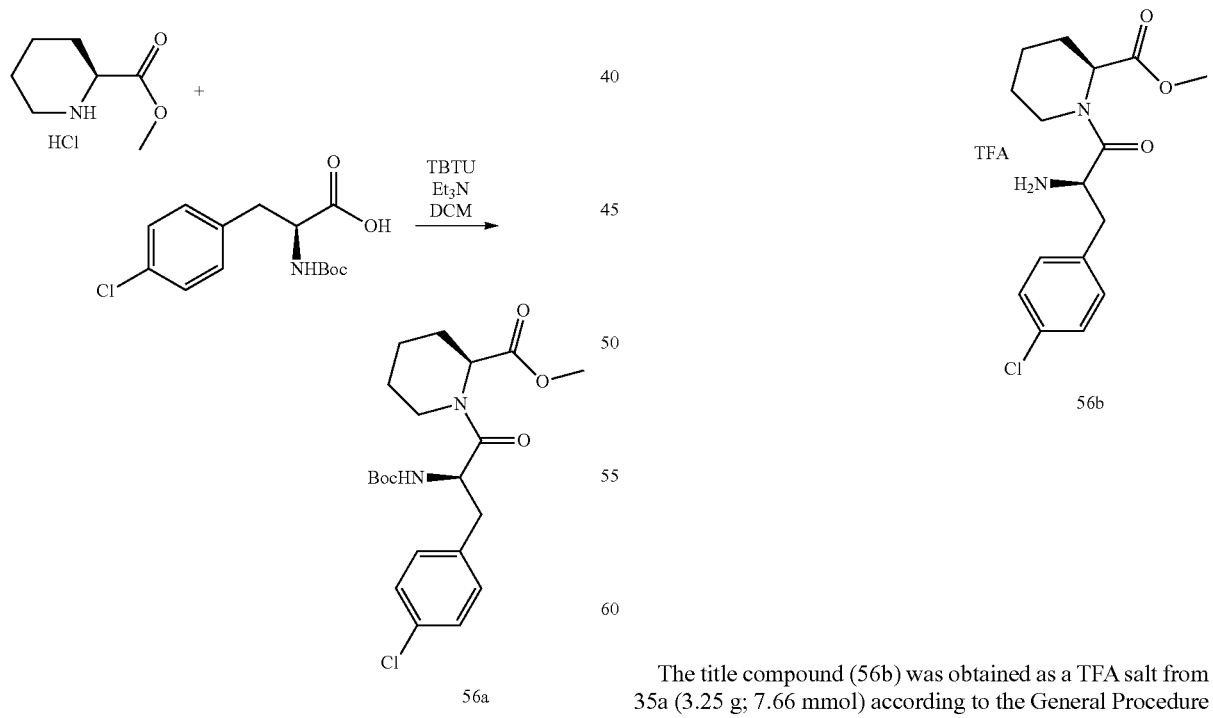

The title compound (56a) was obtained from a (S)-methyl pipecolinate hydrochloride (1.39 g; 7.74 mmol) and Boc-4-chloro-L-phenylalanine (2.55 g; 8.51 mmol) according to the General Procedure III in 99% yield (3.25 g; 7.66 mmol).

ESI-MS m/z for $C_{21}H_{29}ClN_2O_5Na$ found 447.4/449.4 [M+Na]$^+$

Step 2

Synthesis of methyl (S)-1-((R)-2-amino-3-(4-chlorophenyl)propanoyl)piperidine-2-carboxylate 2,2,2-trifluoroacetate (56b)

The title compound (56b) was obtained as a TFA salt from 35a (3.25 g; 7.66 mmol) according to the General Procedure IVb in 99% yield (3.32 g; 7.58 mmol).

ESI-MS m/z for $C_{16}H_{22}ClN_2O_3$ found 325.4/327.4 [M+H]$^+$

Step 3

Synthesis of (3S,9aS)-3-(4-chlorobenzyl)hexahydro-4H-pyrido[1,2-a]pyrazine-1,4(6H)-dione (56c)

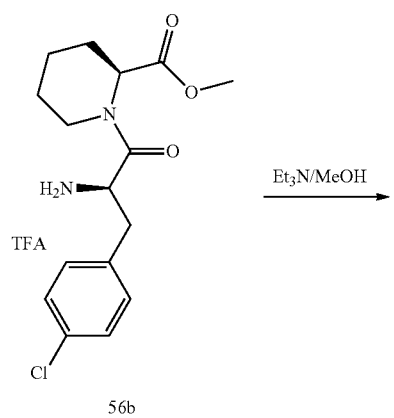

To a solution of crude 56b (3.32 g; 7.58 mmol) in MeOH (23 mL) Et₃N (5.4 mL; 38.51 mmol) was added and the mixture was heated to reflux for 5 hours. LC-MS showed completion of the reaction. The mixture was concentrated in vacuo and the yellow oily residue was partitioned between AcOEt (40 mL) and 2M HCl (30 mL). An organic phase was washed with 1M NaOH (20 mL) and brine (20 mL), dried over anhydrous Na₂SO₄, filtered and concentrated in vacuo. The crude product was used to the next step without additional purification. Compound 56c was obtained as an yellow solid in 89% yield (1.98 g; 6.78 mmol).

ESI-MS m/z for $C_{15}H_{18}ClN_2O_2$ found 293.3/295.3 [M+H]⁺

Step 4

Synthesis of (3S,9aS)-3-(4-chlorobenzyl)octahydro-2H-pyrido[1,2-a]pyrazine (56d)

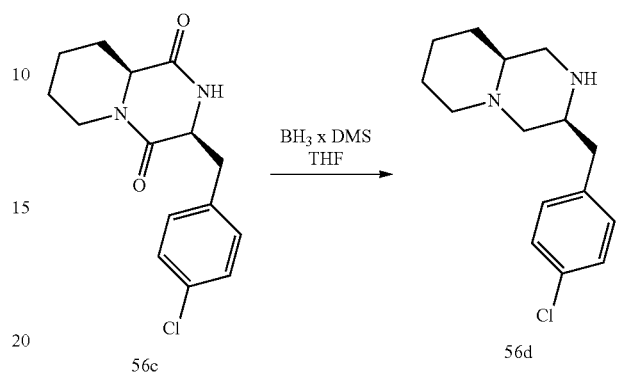

The title compound (56d) was obtained as an yellow oil from 56c (0.5 g; 1.71 mmol) according to the General Procedure Ib in 99% yield (447 mg; 1.69 mmol).

ESI-MS m/z for $C_{15}H_{22}ClN_2$ found 265.4/267.4 [M+H]⁺

Step 5

Synthesis of tert-butyl 4-((3S,9aS)-3-(4-chlorobenzyl)octahydro-2H-pyrido[1,2-a]pyrazin-2-yl)piperidine-1-carboxylate (56e)

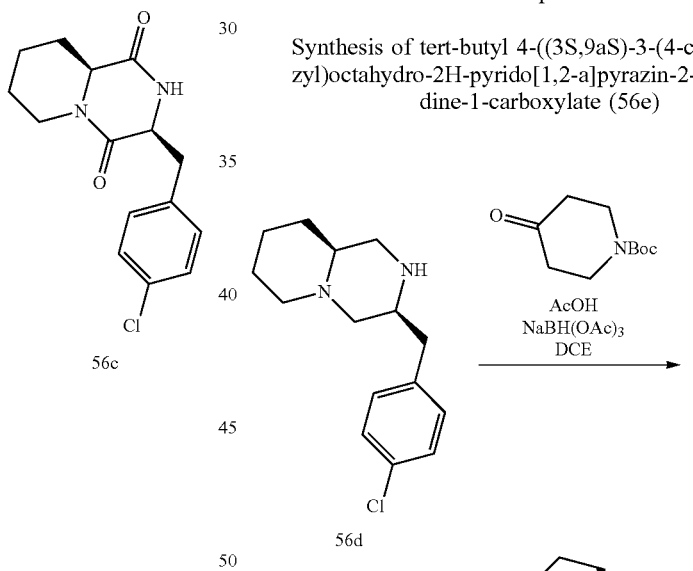

The title compound (56e) was obtained as an yellow oil from 56d (447 mg; 1.69 mmol) according to the General Procedure VI in 85% yield (640 mg; 1.43 mmol).

ESI-MS m/z for $C_{25}H_{39}ClN_3O_2$ found 448.6/450.6 [M+H]$^+$

Step 6

Synthesis of (3S,9aS)-3-(4-chlorobenzyl)-2-(piperidin-4-yl)octahydro-2H-pyrido[1,2-a]pyrazine (56f)

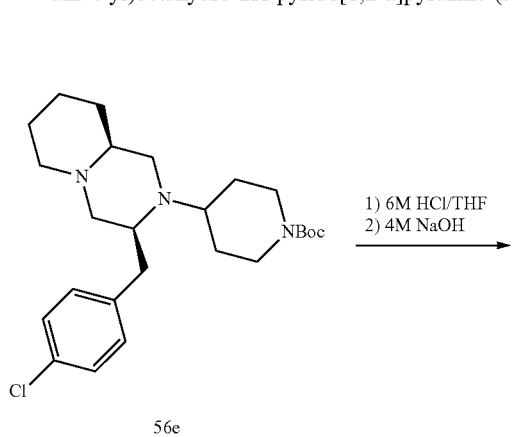

Step 7

Synthesis of (3S,9aS)-3-(4-chlorobenzyl)-2-(1-(pyridin-2-yl)piperidin-4-yl)octahydro-2H-pyrido[1,2-a]pyrazine 2,2,2-trifluoroacetate (56)

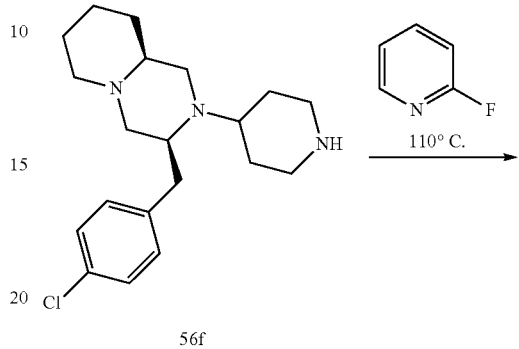

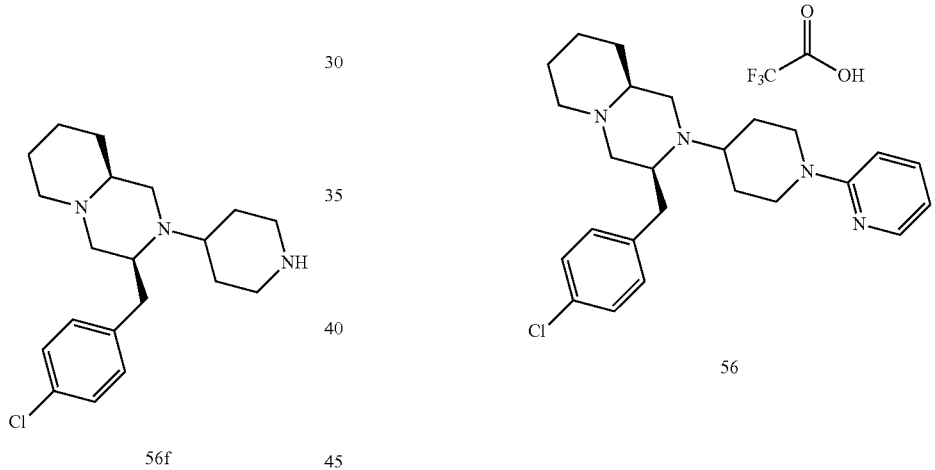

To a solution of crude 56e (621 mg; 1.39 mmol) in THF (2 mL) 6M HCl (4 mL) was added and the mixture was stirred at room temperature for 2 hours. LC-MS showed completion of the reaction. The mixture was alkalized with 4M NaOH and the product was extracted with DCM (4×15 mL). The combined organic solutions were dried over anhydrous Na$_2$SO$_4$, filtered and concentrated in vacuo. The crude product was used to the next step without additional purification. Compound 56f was obtained as an orange oil in 91% yield (441 mg; 1.27 mmol).

ESI-MS m/z for $C_{20}H_{31}ClN_3$ found 348.5/350.5 [M+H]$^+$

The crude 56f (220 mg; 0.63 mmol) was heated with 2-fluoropyridine (0.5 mL; 5.81 mmol) at 110° C. for 16 hours. LC-MS showed completion of the reaction. The mixture was concentrated in vacuo and the residue was purified by preparative reversed-phase column chromatography (Luna® 5 μm Phenyl-Hexyl, LC Column 250×21.2 mm, water/MeCN+10% TFA, 90:10 to 45:55, 45 min). Compound 56 was obtained as a TFA salt in 44% yield (148 mg; 0.28 mmol).

ESI-MS m/z for $C_{25}H_{34}ClN_4$ found 425.5/427.5 [M+H]$^+$; $^1$H NMR (400 MHz, Methanol-d$_4$) δ 8.08-7.95 (m, 1H), 7.95-7.86 (m, 1H), 7.42-7.21 (m, 5H), 7.01-6.90 (m, 1H), 4.08-3.92 (m, 1H), 3.92-3.79 (m, 1H), 3.61-3.48 (m, 1H), 3.43-3.33 (m, 2H), 3.24-2.88 (m, 9H), 2.09-1.77 (m, 6H), 1.72-1.46 (m, 4H), 0.91-0.79 (m, 1H).

Example 57

Synthesis of (3S,6S)-3-(4-chlorobenzyl)-2,2,6-trimethyl-4-(1-(pyridin-2-yl)piperidin-4-yl)morpholine (57)

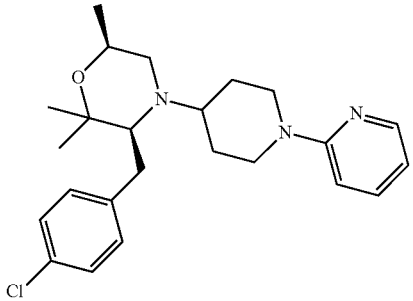

57

Step 1

Synthesis of (S)-3-amino-4-(4-chlorophenyl)-2-methylbutan-2-ol (57a)

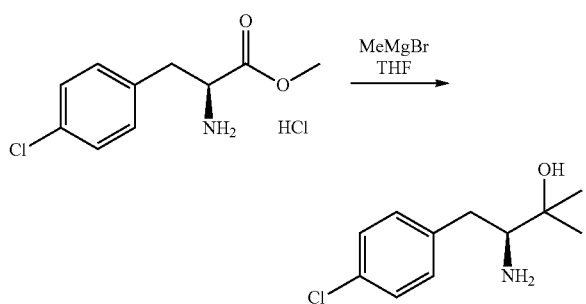

57a

The title compound (57a) was obtained from a 4-chloro-L-phenylalanine methyl ester hydrochloride (1 g; 4.69 mmol) according to the General Procedure V in 99% yield (989 mg; 4.64 mmol).

ESI-MS m/z for $C_{11}H_{17}ClNO$ found 214.2 $[M+H]^+$; 196.2 $[M+H-H_2O]^+$

Step 2

Synthesis of (2S,5S)-5-(4-chlorobenzyl)-2,6,6-trimethylmorpholin-3-one (57b)

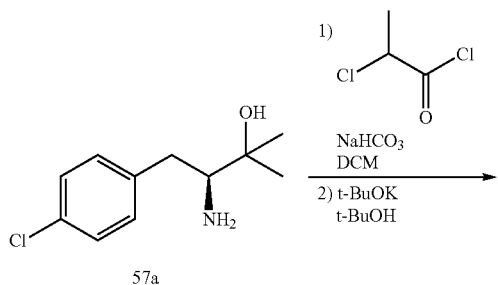

57a

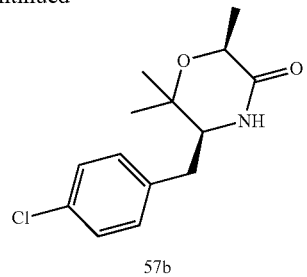

57b

To a solution of crude 57a (2 g; 9.38 mmol) in DCM (17 mL) NaHCO$_3$ (1.56 g; 18.79 mmol) was added and the mixture was cooled down to 0° C. Then 2-chloropropionyl chloride (1.02 mL; 10.32 mmol) was added dropwise and the reaction was warmed to ambient temperature and stirred for 1.5 hours. LC-MS showed completion of the reaction. The reaction was quenched by addition of 1M NaOH (15 mL). An aqueous phase was extracted with DCM. The combined organic solutions were washed with water, dried over anhydrous Na$_2$SO$_4$, filtered and concentrated in vacuo. The crude product was subsequently suspended in t-BuOH (17 mL) at room temperature and t-BuOK (1.58 g; 14.07 mmol) was added in portions (during the addition temperature was maintained below 20° C.). TLC and LC-MS showed completion of the reaction. The reaction was quenched by addition of water and an aqueous phase was extracted with AcOEt, dried over anhydrous Na$_2$SO$_4$, filtered and concentrated in vacuo. The crude product was used to the next step without additional purification. Compound 57b was obtained in 63% yield (1.59 g; 5.95 mmol).

ESI-MS m/z for $C_{14}H_{19}ClNO_2$ found 268.2/279.2 $[M+H]^+$; $^1$H NMR (400 MHz, Methanol-d$_4$) δ 7.31-7.27 (m, 2H), 7.20-7.15 (m, 2H), 4.22-4.13 (m, 1H), 3.34 (dd, J=10.2, 4.1 Hz, 1H), 3.08 (dd, J=13.4, 4.1 Hz, 1H), 2.74 (dd, J=13.4, 10.2 Hz, 1H), 1.39 (s, 3H), 1.32 (s, 3H), 1.21 (s, 3H).

Step 3

Synthesis of (3S,6S)-3-(4-chlorobenzyl)-2,2,6-trimethylmorpholine (57c)

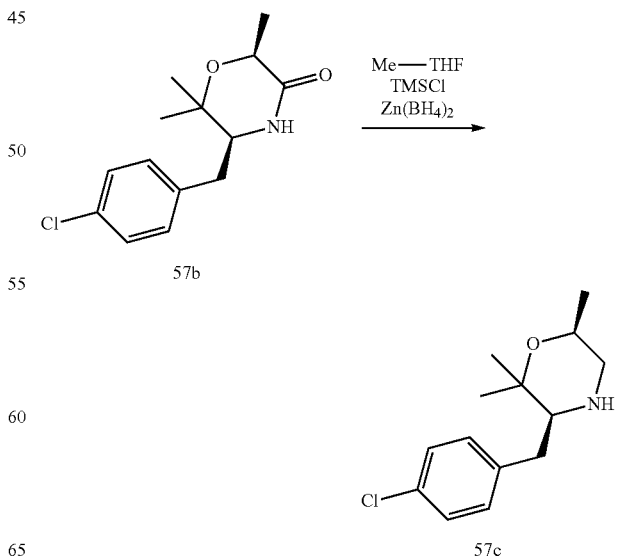

57b

57c

A solution of 57b (1.59 g; 5.95 mmol) in Me-THF (10 mL) was cooled to 0° C. and subsequently TMSCl (1.13 mL; 8.90 mmol) was added dropwise within several minutes. The reaction was stirred for 15 minutes at the same temperature and then previously prepared solution of Zn(BH$_4$)$_2$ (0.4M in Me-THF; 37 mL; 14.84 mmol) was added dropwise at 0° C. Then reaction mixture was brought to reflux and vigorously stirred overnight. LC-MS showed completion of the reaction. The reaction was cooled down to ambient temperature and 6M HCl (20 mL) was added and the reaction mixture was refluxed for additional 1 hour to decompose borane complexes of the product. The mixture was cooled down, transferred into separatory funnel and layers were separated. An organic one was washed with 6M HCl and water and removed as it contained some unreacted substrate. All aqueous layers were combined, AcOEt was added and the mixture was brought to pH 12 with 4M NaOH. An aqueous phase was extracted with AcOEt, dried over anhydrous Na$_2$SO$_4$, filtered and concentrated in vacuo. The crude product was used to the next step without additional purification. Compound 57c was obtained in 99% yield (1.49 g; 5.89 mmol).

ESI-MS m/z for C$_{14}$H$_{21}$ClNO found 254.2/256.2 [M+H]$^+$

Step 4

Synthesis of tert-butyl 4-((3S,6S)-3-(4-chlorobenzyl)-2,2,6-trimethylmorpholino)piperidine-1-carboxylate (57d)

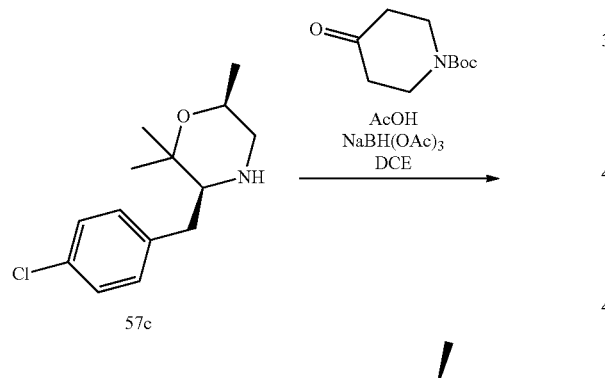

The title compound (57d) was obtained from 57c (1.49 g; 5.89 mmol) according to the General Procedure VI in 33% yield (850 mg; 1.95 mmol).

ESI-MS m/z for C$_{24}$H$_{38}$ClN$_2$O$_3$ found 437.4/439.4 [M+H]$^+$; $^1$H NMR (400 MHz, Methanol-d$_4$) δ 7.31-7.16 (m, 4H), 3.98-3.81 (m, 3H), 3.03-2.90 (m, 3H), 2.88-2.73 (m, 2H), 2.73-2.64 (m, 1H), 2.60-2.49 (m, 1H), 2.39-2.30 (m, 1H), 1.84-1.67 (m, 2H), 1.44 (s, 9H), 1.42 (s, 3H), 1.36-1.23 (m, 2H), 1.10 (d, J=6.1 Hz, 3H), 0.98 (s, 3H).

Step 5

Synthesis of (3S,6S)-3-(4-chlorobenzyl)-2,2,6-trimethyl-4-(piperidin-4-yl)morpholine 2,2,2-trifluoroacetate (57e)

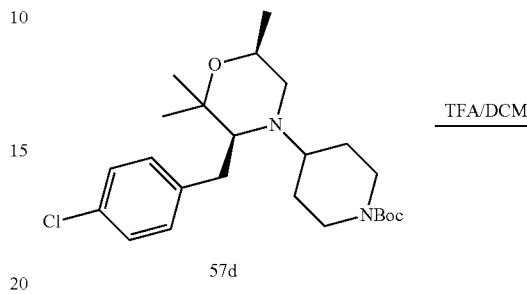

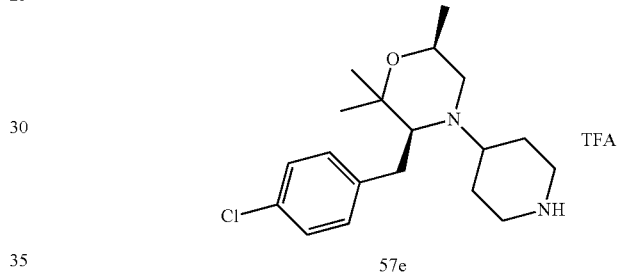

The title compound (57e) was obtained as a TFA salt from 57d (148 mg; 0.34 mmol) according to the General Procedure IVb in 99% yield (153 mg; 0.34 mmol).

ESI-MS m/z for C$_{19}$H$_{30}$ClN$_2$O found 337.2/339.2 [M+H]$^+$

Step 6

Synthesis of (3S,6S)-3-(4-chlorobenzyl)-2,2,6-trimethyl-4-(1-(pyridin-2-yl)piperidin-4-yl)morpholine (57)

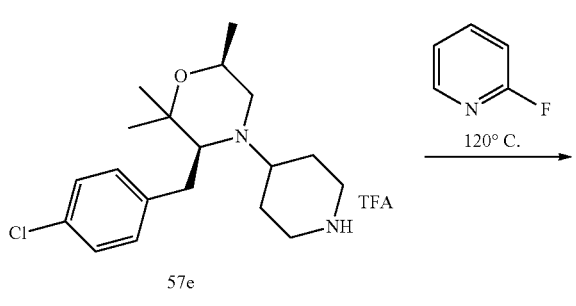

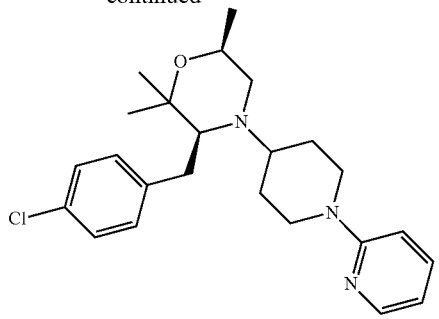

57

The crude 57e (153 mg; 0.34 mmol) was heated with 2-fluoropyridine (0.12 mL; 1.36 mmol) at 120° C. for 3 days. LC-MS showed completion of the reaction. The mixture was concentrated and residue was purified by column chromatography (hexane/AcOEt 3:7 to 0:10 and then DCM/MeOH 9:1, v/v) and then by preparative reversed-phase column chromatography (Luna® 5 μm Phenyl-Hexyl, LC Column 250×21.2 mm, water/MeCN+1% TFA, 90:10 to 45:55, 45 min). Compound 57 was obtained in 16% yield (23 mg; 0.056 mmol).

ESI-MS m/z for $C_{24}H_{33}ClN_3O$ found 414.4/416.4 [M+H]+; $^1$H NMR (400 MHz, Methanol-$d_4$) δ 8.05-7.89 (m, 2H), 7.42-7.26 (m, 5H), 7.05-6.93 (m, 1H), 4.37-4.23 (m, 1H), 4.19-4.06 (m, 2H), 3.90-3.62 (m, 2H), 3.28-3.16 (m, 3H), 3.06-2.84 (m, 2H), 2.34-2.20 (m, 1H), 2.07-1.87 (m, 2H), 1.87-1.74 (m, 1H), 1.53 (s, 3H), 1.37-1.27 (m, 1H), 1.27-1.17 (m, 6H).

Example 58

Synthesis of (2S,5S)-5-(4-chlorobenzyl)-4-((1R,5S)-8-(4-chloropyridin-2-yl)-8-azabicyclo[3.2.1]octan-3-yl)-2-methylmorpholine 2,2,2-trifluoroacetate (58)

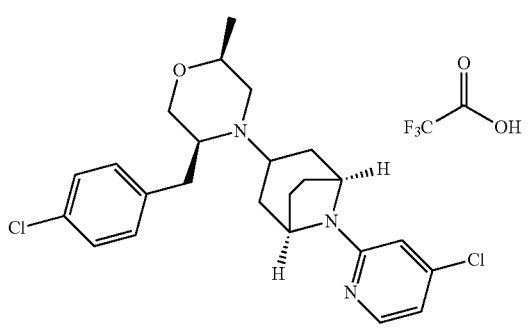

58

The title compound 58 was obtained as a TFA salt in 4% overall yield in a similar way to Example 31 with the exception that, in step 1 of the synthesis, 8-Boc-8-azabicyclo[3.2.1]octan-3-one (N-Boc-nortropinone) was used instead of 1-Boc-2-methyl-4-piperidinone.

ESI-MS m/z for $C_{24}H_{30}Cl_2N_3O$ found 446.2/448.2 [M+H]$^+$; $^1$H NMR (400 MHz, Methanol-$d_4$) δ 8.08-7.98 (m, 1H), 7.46-7.37 (m, 2H), 7.36-7.24 (m, 2H), 7.13-7.05 (m, 1H), 6.85-6.76 (m, 1H), 4.78-4.68 (m, 2H), 4.07-3.98 (m, 1H), 3.78-3.60 (m, 3H), 3.60-3.51 (m, 1H), 3.47-3.37 (m, 1H), 3.26-3.18 (m, 1H), 3.18-2.99 (m, 2H), 2.25-2.13 (m, 4H), 2.04-1.83 (m, 4H), 1.29 (d, J=6.3 Hz, 3H).

Examples 59 and 60

Synthesis of (2S,5S)-5-(4-chlorobenzyl)-4-((3R,4S)-1-(4-chloropyridin-2-yl)-3-methoxypiperidin-4-yl)-2-methylmorpholine 2,2,2-trifluoroacetate (59) and (2S,5S)-5-(4-chlorobenzyl)-4-((3S,4S)-1-(4-chloropyridin-2-yl)-3-methoxypiperidin-4-yl)-2-methylmorpholine 2,2,2-trifluoroacetate (60)

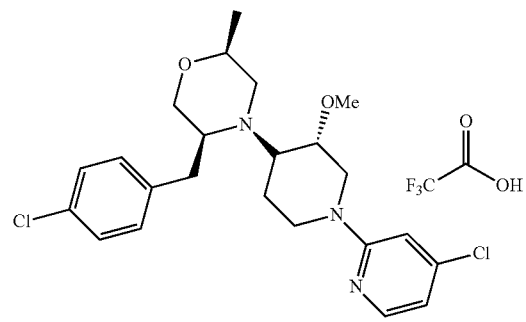

59

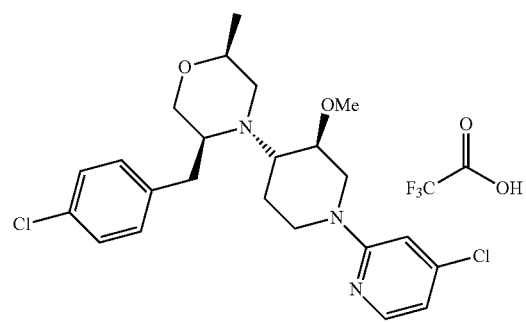

60

Step 1

Synthesis of diastereomeric mixture of (3R,4R)-1-benzyl-4-((2S,5S)-5-(4-chlorobenzyl)-2-methylmorpholino)piperidin-3-ol (59a-I) and (3S,4S)-1-benzyl-4-((2S,5S)-5-(4-chlorobenzyl)-2-methylmorpholino)piperidin-3-ol (59a-II)

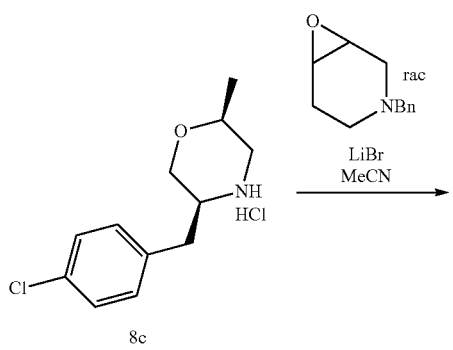

8c

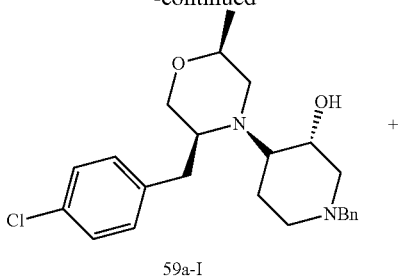

59a-I

+

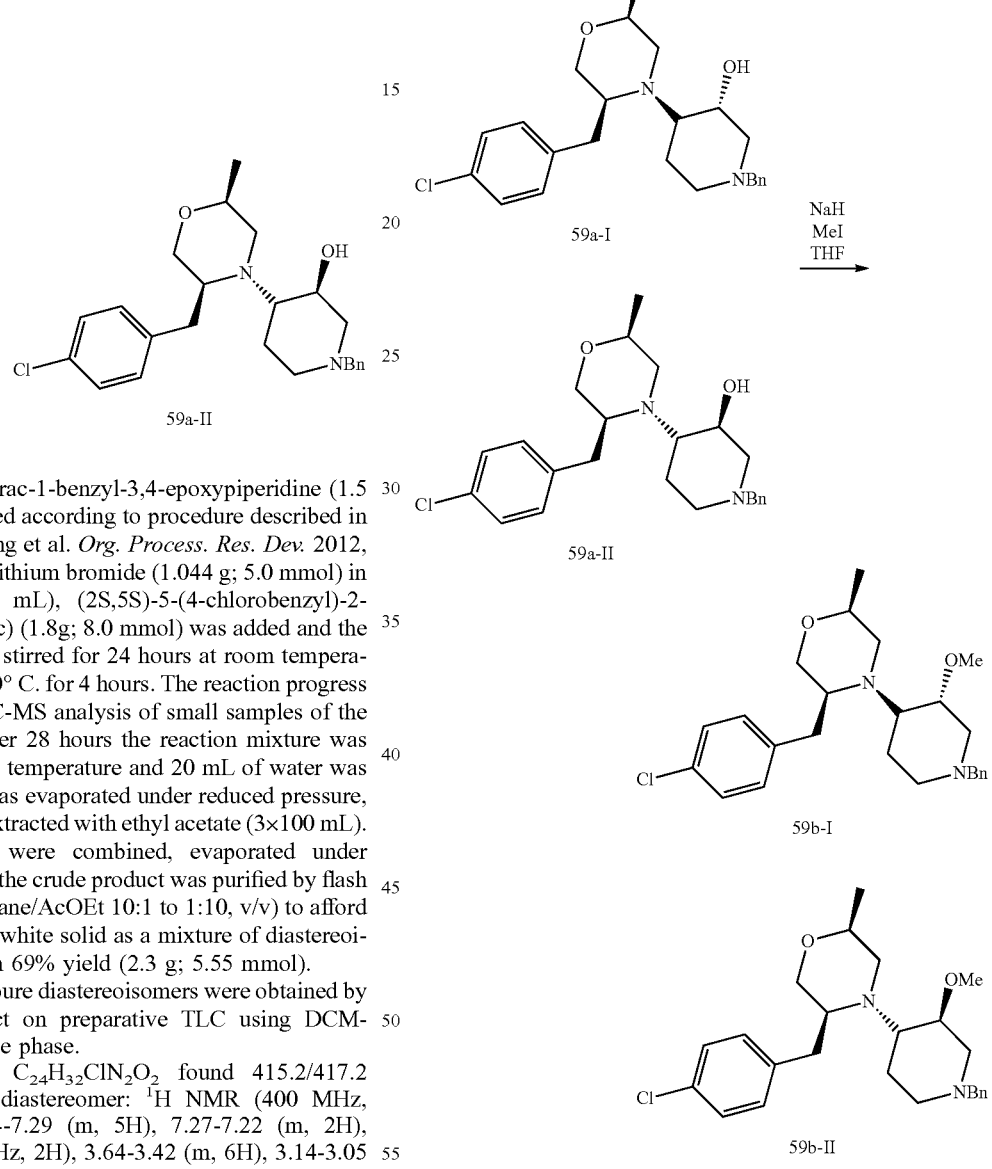

Step 2

Synthesis of diastereomeric mixture of (2S,5S)-4-((3R,4R)-1-benzyl-3-methoxypiperidin-4-yl)-5-(4-chlorobenzyl)-2-methylmorpholine (59b-I) and (2S,5S)-4-((3S,4S)-1-benzyl-3-methoxypiperidin-4-yl)-5-(4-chlorobenzyl)-2-methylmorpholine (59b-II)

To the solution of rac-1-benzyl-3,4-epoxypiperidine (1.5 g; 8.0 mmol) (prepared according to procedure described in literature: Ian S. Young et al. *Org. Process. Res. Dev.* 2012, 16, 1558-1565.) and lithium bromide (1.044 g; 5.0 mmol) in dry acetonitrile (30 mL), (2S,5S)-5-(4-chlorobenzyl)-2-methylmorpholine (8c) (1.8g; 8.0 mmol) was added and the reaction mixture was stirred for 24 hours at room temperature, then heated to 50° C. for 4 hours. The reaction progress was monitored by LC-MS analysis of small samples of the reaction mixture. After 28 hours the reaction mixture was cooled down to room temperature and 20 mL of water was added. Acetonitrile was evaporated under reduced pressure, and the residue was extracted with ethyl acetate (3×100 mL). The organic layers were combined, evaporated under reduced pressure and the crude product was purified by flash chromatography (hexane/AcOEt 10:1 to 1:10, v/v) to afford 59a-I and 59a-II as a white solid as a mixture of diastereoisomers in ratio 1:1 in 69% yield (2.3 g; 5.55 mmol).

Small fractions of pure diastereoisomers were obtained by separation of product on preparative TLC using DCM-MeOH 25:1 as mobile phase.

ESI-MS m/z for $C_{24}H_{32}ClN_2O_2$ found 415.2/417.2 [M+H]; Less polar diastereomer: $^1$H NMR (400 MHz, Methanol-$d_4$) δ 7.34-7.29 (m, 5H), 7.27-7.22 (m, 2H), 7.21-7.15 (m, J=8.4 Hz, 2H), 3.64-3.42 (m, 6H), 3.14-3.05 (m, 1H), 2.95-2.80 (m, 3H), 2.80-2.74 (m, 1H), 2.67 (dd, J=11.9, 10.2 Hz, 1H), 2.55 (dd, J=12.0, 2.8 Hz, 1H), 2.40 (ddd, J=13.4, 9.4, 4.0 Hz, 1H), 2.09 (td, J=11.7, 2.4 Hz, 1H), 1.92 (t, J=10.4 Hz, 1H), 1.87-1.80 (m, 1H), 1.70 (ddd, J=25.1, 12.2, 4.0 Hz, 1H), 1.15 (d, J=6.0 Hz, 3H).

More polar diastereomer: $^1$H NMR (400 MHz, Methanol-$d_4$) δ 7.32-7.29 (m, 5H), 7.27-7.23 (m, 2H), 7.21-7.13 (m, J=7.3 Hz, 2H), 3.66-3.44 (m, 6H), 2.99 (ddd, J=10.7, 4.2, 1.9 Hz, 1H), 2.95-2.73 (m, 5H), 2.69 (dd, J=13.0, 3.1 Hz, 1H), 2.46-2.36 (m, 1H), 1.99 (td, J=11.4, 2.3 Hz, 1H), 1.92-1.79 (m, 2H), 1.59 (ddd, J=24.6, 11.6, 3.9 Hz, 1H), 1.14 (d, J=6.1 Hz, 3H).

The title compounds (59b-I and 59b-II) were obtained as a yellowish oil as a mixture of diastereoisomers in ratio 1:1 from diastereomeric mixture of compounds 59a-I and 59a-II (1.24 g; 3.0 mmol) according to the General Procedure XI in 47% yield (600 mg; 1.4 mmol).

ESI-MS m/z for $C_{25}H_{34}ClN_2O_2$ found 429.2/431.2 [M+H]$^+$

Step 3

Synthesis of diastereomeric mixture of (3R,4R)-allyl 4-((2S,5S)-5-(4-chlorobenzyl)-2-methylmorpholino)-3-methoxypiperidine-1-carboxylate 2,2,2-trifluoroacetate (59c-I) and (3S,4S)-allyl 4-((2S,5S)-5-(4-chlorobenzyl)-2-methylmorpholino)-3-methoxypiperidine-1-carboxylate 2,2,2-trifluoroacetate (59c-II)

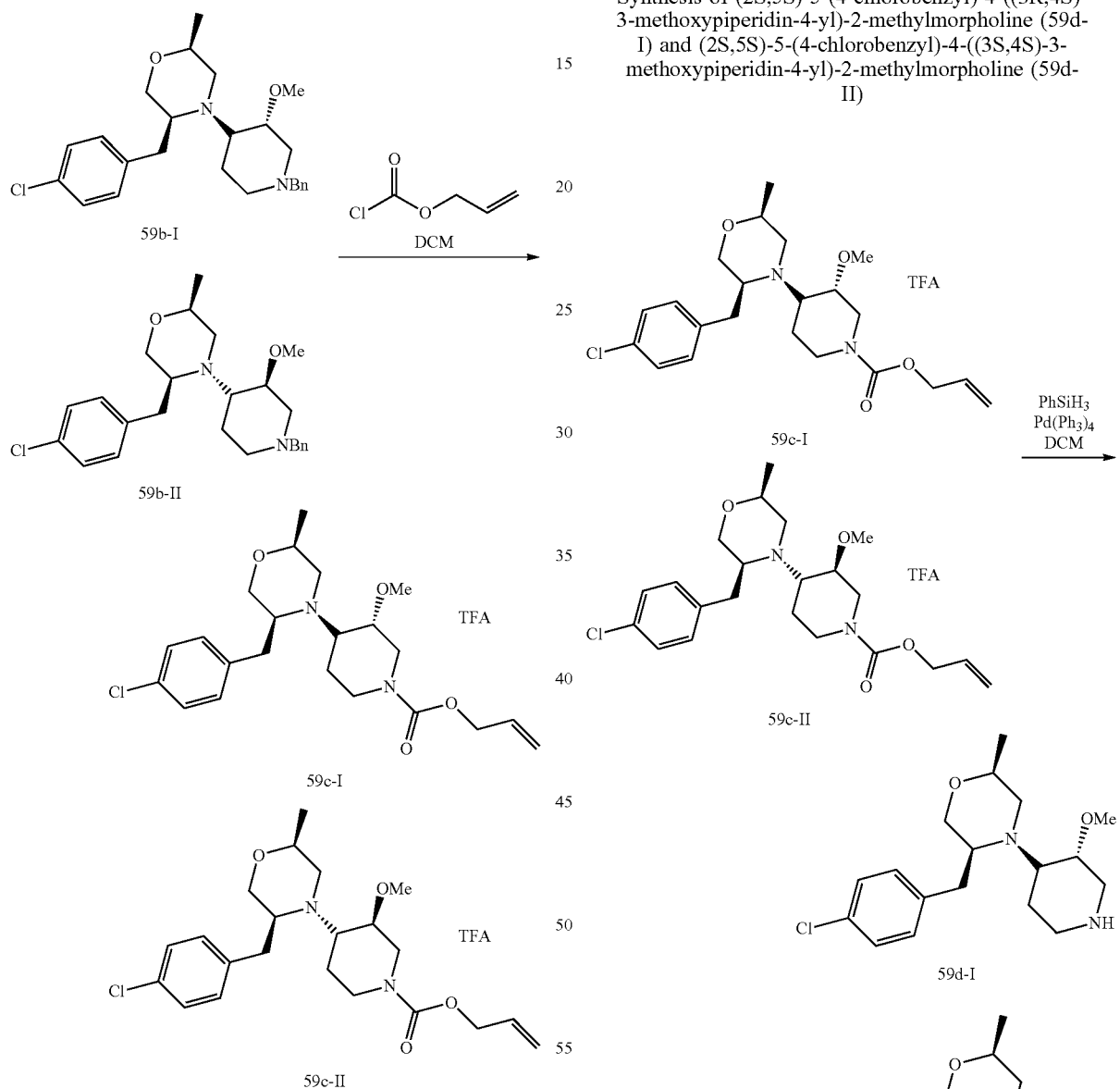

To a solution of diastereomeric mixture of 59b-I and 59b-II (600 mg; 1.4 mmol) in DCM (10 mL) at 0° C., allyl chloroformate (224 μL; 2.1 mmol) was added dropwise. Upon addition was finished, reaction mixture was warmed up to room temperature and stirred for 16 hours. After this, LC-MS analysis of crude reaction mixture showed full conversion and reaction was quenched with 10% aqueous solution of NaHCO$_3$ (5 mL). An organic phase was separated and an aqueous phase was extracted with DCM (2×20 mL). The combined organic phases were evaporated, and the crude product was purified by preparative reversed-phase column chromatography (Luna® 5 μm Phenyl-Hexyl, LC Column 250×21.2 mm, water/MeCN+1% TFA, 90:10 to 15:85, 30 min). Compounds 59c-I and 59c-II were obtained as a TFA salts (1:1 mixture of diastereoisomers) as a yellowish oil in 54% yield (400 mg; 0.75 mmol).

ESI-MS m/z for C$_{22}$H$_{32}$ClN$_2$O$_4$ found 423.2/425.2 [M+H]$^+$

Step 4

Synthesis of (2S,5S)-5-(4-chlorobenzyl)-4-((3R,4S)-3-methoxypiperidin-4-yl)-2-methylmorpholine (59d-I) and (2S,5S)-5-(4-chlorobenzyl)-4-((3S,4S)-3-methoxypiperidin-4-yl)-2-methylmorpholine (59d-II)

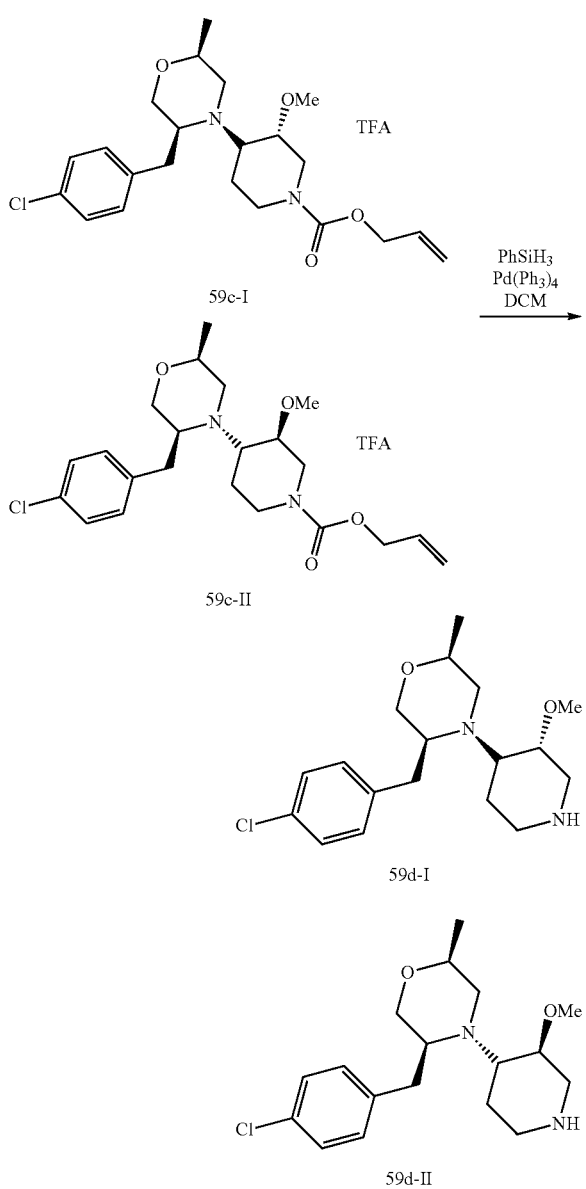

To a solution of Alloc-protected amines 59c-I and 59c-II (400 mg; 0.75 mmol) in anhydrous, degassed DCM (3.75 mL), Pd(PPh₃)₄ (5 mol %; 43 mg; 0.0375 mmol) and phenylsilane (812 mg; 7.5 mmol) were added. The reaction mixture was vigorously stirred for 16 hours at room temperature. The reaction progress was monitored by TLC and LC-MS analyses of small samples of the reaction mixture. After this 2M HCl was added to the reaction and phases were separated. The aqueous phase was alkalized to pH 12 with 6M NaOH and extracted 3 times with DCM. The combined organic extracts were dried over anhydrous MgSO₄, filtered and the solvent was removed in vacuo. The crude products mixture was used to the next step without additional purification. Compounds 59d-I and 59d-II were obtained as a distereoisomers mixture in 99% yield (251 mg; 0.74 mmol).

ESI-MS m/z for $C_{18}H_{28}ClN_2O_2$ found 339.2/341.2 $[M+H]^+$

Step 5

Synthesis of (2S,5S)-5-(4-chlorobenzyl)-4-((3R,4S)-1-(4-chloropyridin-2-yl)-3-methoxypiperidin-4-yl)-2-methylmorpholine 2,2,2-trifluoroacetate (59) and (2S,5S)-5-(4-chlorobenzyl)-4-((3S,4S)-1-(4-chloropyridin-2-yl)-3-methoxypiperidin-4-yl)-2-methylmorpholine 2,2,2-trifluoroacetate (60)

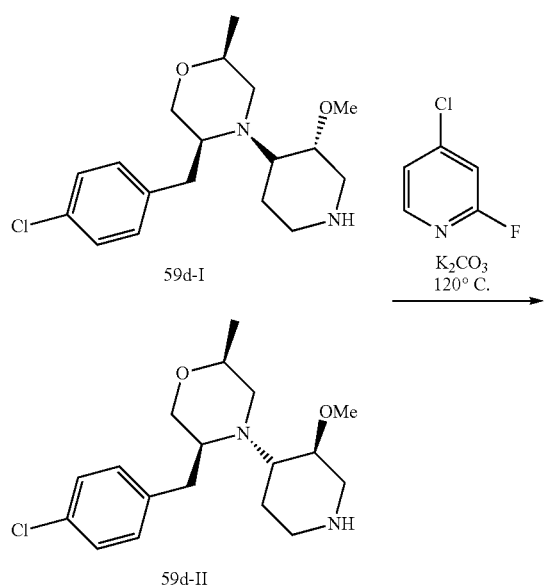

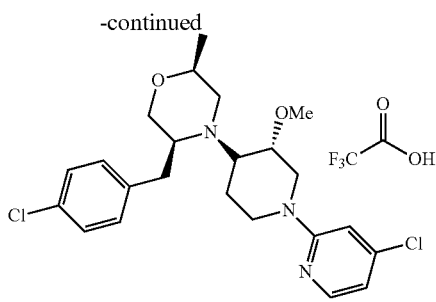

59

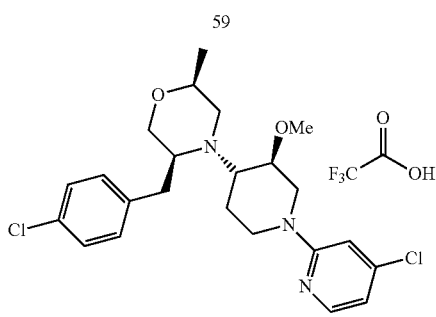

60

The title compounds (59 and 60) were obtained as a two single diastereoisomers (after preparative reversed-phase column chromatography (Luna® 5 μm Phenyl-Hexyl, LC Column 250×21.2 mm, water/MeCN+1% TFA, 90:10 to 15:85, 30 min) as a TFA salts from mixture of diastereoisomers 59d-I and 59d-II (25 mg; 0.074 mmol) according to the General Procedure IX in 12% yield (5 mg; 0.009 mmol) for diastereoisomer 59 and in 9% yield (4 mg; 0.007 mmol) for diastereoisomer 60.

ESI-MS m/z for $C_{23}H_{30}Cl_2N_3O_2$ found 450.2/452.2 $[M+H]^+$; ¹H NMR for 59 (400 MHz, Methanol-d₄) δ 8.11-8.04 (m, 1H), 7.43-7.34 (m, 2H), 7.34-7.22 (m, 2H), 7.09-6.96 (m, 1H), 6.81-6.73 (m, 1H), 4.38-4.23 (m, 1H), 4.04-3.91 (m, 2H), 3.91-3.63 (m, 5H), 3.63-3.49 (m, 4H), 3.36-3.33 (m, 1H), 3.29-3.27 (m, 1H), 3.21-3.03 (m, 3H), 2.43-2.26 (m, 1H), 1.93-1.80 (m, 1H), 1.32 (d, J=6.3 Hz, 3H); ¹H NMR for 60 (400 MHz, Methanol-d₄) δ 8.09-8.02 (m, 1H), 7.42-7.35 (m, 2H), 7.34-7.24 (m, 2H), 7.13-7.06 (m, 1H), 6.82-6.76 (m, 1H), 4.83-4.72 (m, 1H), 4.34-4.23 (m, 1H), 4.02-3.86 (m, 3H), 3.80-3.64 (m, 3H), 3.58-3.51 (m, 3H), 3.48-3.40 (m, 1H), 3.23-2.93 (m, 4H), 2.39-2.29 (m, 1H), 1.86-1.75 (m, 1H), 1.31 (d, J=6.3 Hz, 3H), 1.30-1.25 (m, 1H).

Example 61

Synthesis of (2S,5S)-2-(4-chlorobenzyl)-4,5-dimethyl-1-(1-(pyridin-2-yl)piperidin-4-yl)piperazine 2,2,2-trifluoroacetate (61)

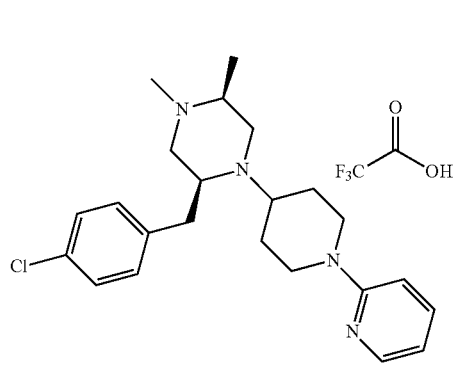

Step 1

Synthesis of methyl N-((S)-2-((tert-butoxycarbonyl)amino)-3-(4-chlorophenyl)propanoyl)-N-methyl-L-alaninate (61a)

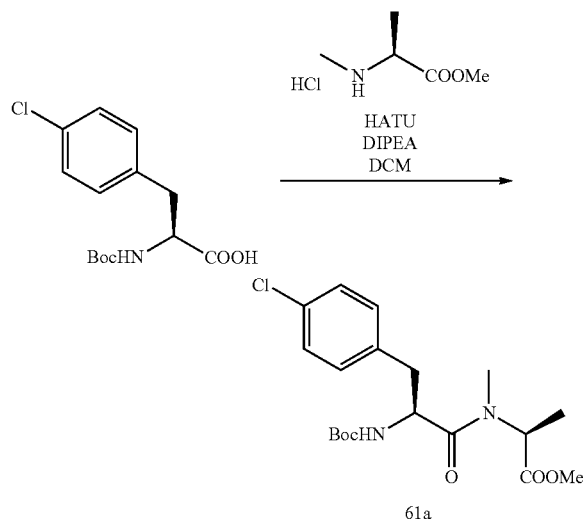

The title compound (61a) was obtained from (S)-2-((tert-butoxycarbonyl)amino)-3-(4-chlorophenyl)propanoic acid (0.82 g; 2.73 mmol) and N-methyl-L-alanine methyl ester hydrochloride (0.5 g; 3.27 mmol) according to the General Procedure III in 53% yield (0.58 g; 1.46 mmol).

ESI-MS m/z for $C_{19}H_{28}ClN_2O_5$ found 399.2/401.2 [M+H]$^+$; $^1$H NMR (700 MHz, CDCl$_3$) δ 7.28-7.25 (m, 2H), 7.19-7.16 (m, 2H), 5.35-5.28 (m, 1H), 5.22-5.16 (m, 1H), 4.88-4.81 (m, 1H), 3.73 (s, 3H), 3.07 (dd, J=13.6, 7.1 Hz, 1H), 2.90 (dd, J=13.8, 6.1 Hz, 1H), 2.87 (s, 3H), 1.42 (s, 9H), 1.40 (d, J=7.3 Hz, 3H).

Step 2

Synthesis of (3S,6S)-3-(4-chlorobenzyl)-1,6-dimethylpiperazine-2,5-dione (61b)

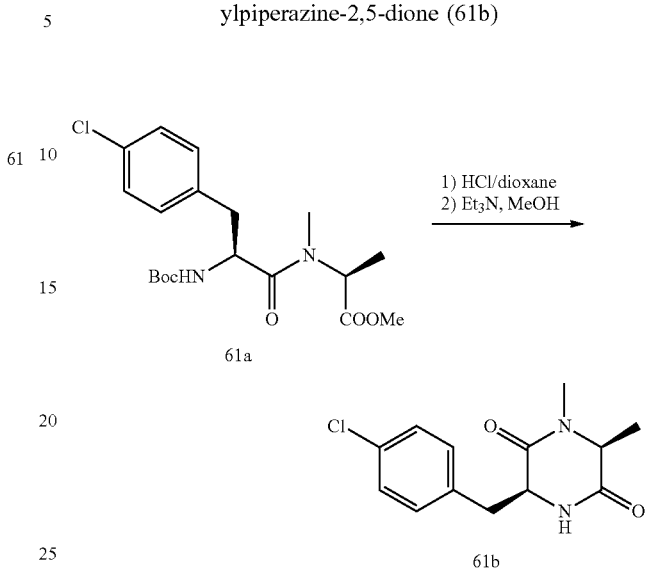

The title compound (61b) was obtained from 61a (0.58 g; 1.46 mmol) according to the General Procedure VIII in 97% yield (375 mg; 1.41 mmol).

ESI-MS m/z for $C_{13}H_{16}ClN_2O_2$ found 267.1/269.1 [M+H]$^+$; $^1$H NMR (700 MHz, Methanol-d$_4$) δ 7.33-7.26 (m, 2H), 7.20-7.10 (m, 2H), 4.33-4.27 (m, 1H), 3.80-3.75 (m, 1H), 3.27-3.22 (m, 1H), 2.96-2.90 (m, 1H), 2.84 (s, 3H), 0.64 (d, J=7.1 Hz, 3H).

Step 3

Synthesis of (2S,5S)-5-(4-chlorobenzyl)-1,2-dimethylpiperazine (61c)

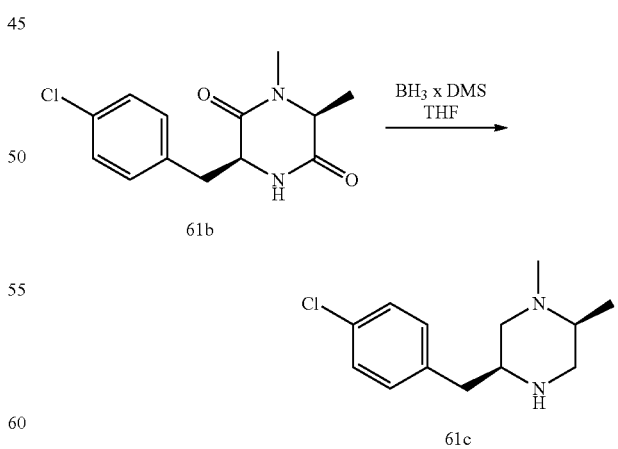

The title compound (61c) was obtained from 61b (375 mg; 1.41 mmol) according to the General Procedure Ib in 88% yield (295 mg; 1.24 mmol).

ESI-MS m/z for $C_{13}H_{20}ClN_2$ found 239.1/241.1 [M+H]$^+$

Step 4

Synthesis of (2S,5S)-2-(4-chlorobenzyl)-4,5-dimethyl-1-(1-(pyridin-2-yl)piperidin-4-yl)piperazine 2,2,2-trifluoroacetate (61)

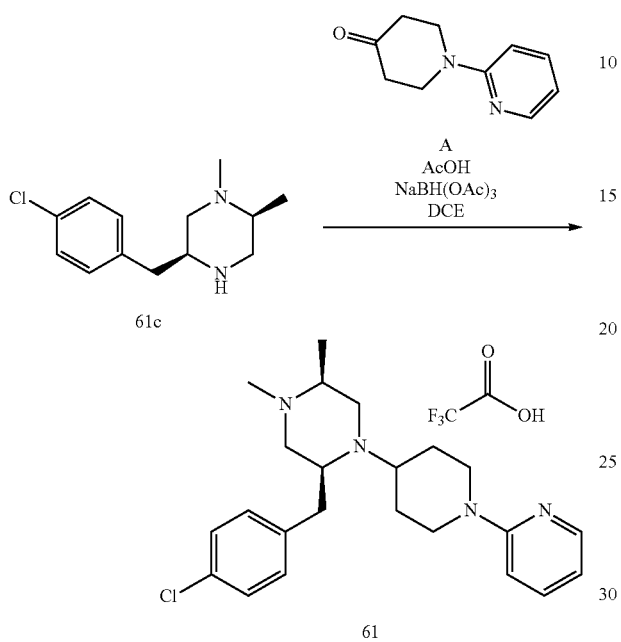

The title compound (61) was obtained as a TFA salt from 61c (295 mg; 1.24 mmol) according to the General Procedure VI in 10% yield (68 mg; 0.13 mmol).

ESI-MS m/z for $C_{23}H_{32}ClN_4$ found 399.1/401.1 [M+H]+; $^1$H NMR (700 MHz, D$_2$O) δ 7.99-7.91 (m, 1H), 7.85-7.76 (m, 1H), 7.39-7.31 (m, 2H), 7.31-7.24 (m, 2H), 7.24-7.16 (m, 1H), 6.93-6.80 (m, 1H), 4.08-3.96 (m, 2H), 3.92-3.78 (m, 1H), 3.55-3.35 (m, 4H), 3.29-3.10 (m, 5H), 2.97-2.90 (m, 1H), 2.84 (s, 3H), 2.24-2.16 (m, 1H), 2.15-2.06 (m, 1H), 1.71-1.63 (m, 2H), 1.40 (d, J=6.6 Hz, 3H).

Example 62

Synthesis of (2S,5S)-2-(4-chlorobenzyl)-5-isopropyl-4-methyl-1-(1-(pyridin-2-yl)piperidin-4-yl)piperazine 2,2,2-trifluoroacetate (62)

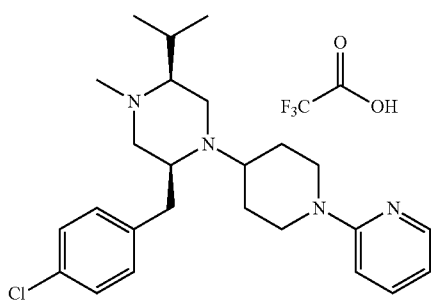

The title compound 62 was obtained as a TFA salt in 1% overall yield in a similar way to Example 61 with the exception that, in the first step of the synthesis, N-methyl-L-valine methyl ester hydrochloride was used instead of N-methyl-L-alanine methyl ester hydrochloride. ESI-MS m/z for $C_{25}H_{36}ClN_4$ found 427.3/429.3 [M+H]+; $^1$H NMR (700 MHz, D$_2$O) δ 7.93-7.88 (m, 1H), 7.79-7.75 (m, 1H), 7.30-7.26 (m, 2H), 7.26-7.23 (m, 2H), 7.18-7.12 (m, 1H), 6.89-6.83 (m, 1H), 3.91-3.81 (m, 1H), 3.64-3.55 (m, 2H), 3.33-3.28 (m, 1H), 3.22-3.04 (m, 8H), 2.83 (s, 3H), 2.82-2.76 (m, 1H), 2.44-2.36 (m, 1H), 2.04-1.97 (m, 1H), 1.95-1.89 (m, 1H), 1.60-1.46 (m, 2H), 1.02 (d, J=6.9 Hz, 3H), 0.98 (d, J=7.0 Hz, 3H).

Example 63

Synthesis of (2S,5S)-2,5-bis(4-chlorobenzyl)-1-methyl-4-(1-(pyridin-2-yl)piperidin-4-yl)piperazine 2,2,2-trifluoroacetate (63)

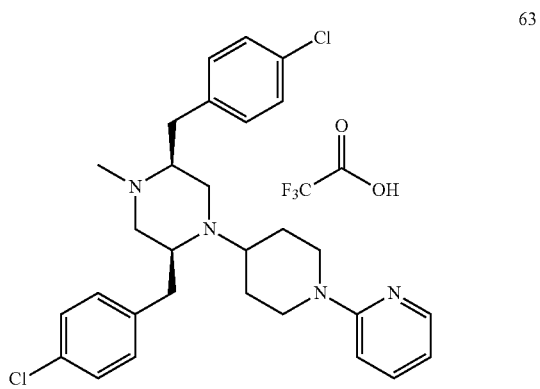

Step 1

Synthesis of (S)-2-((tert-butoxycarbonyl)(methyl)amino)-3-(4-chlorophenyl)propanoic acid (63a)

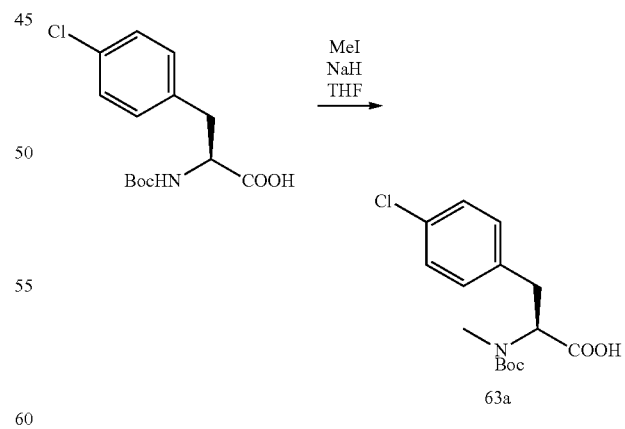

The title compound (63a) was obtained from (S)-2-((tert-butoxycarbonyl)amino)-3-(4-chlorophenyl)propanoic acid (3 g; 10 mmol) according to the General Procedure XI in 99% yield (3.1 g; 9.9 mmol).

ESI-MS m/z for $C_{15}H_{21}ClNO_4$ found 314.2/316.2 [M+H]+

Step 2

Synthesis of methyl (S)-3-(4-chlorophenyl)-2-(methylamino)propanoate hydrochloride (63b)

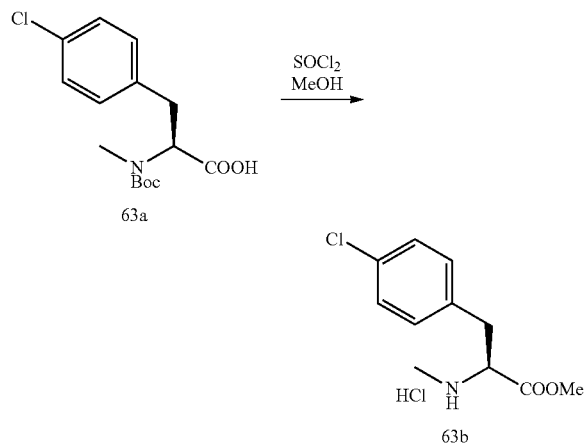

Thionyl chloride (2.9 mL; 39.75 mmol) was added dropwise to a cooled to −20° C. methanol (40 mL) and stirred at this temperature for 30 minutes. Then the solution of 63a (4.16 g; 13.25 mmol) in methanol (40 mL) was added and the cooling bath was removed. The reaction mixture was stirred at room temperature overnight. The reaction progress was monitored by TLC and LC-MS. Analyses showed mixture of product with substrate. The reaction mixture was then cooled to −20° C. and another part of thionyl chloride (2 mL; 26.5 mmol) was added dropwise and the reaction mixture was stirred at room temperature overnight. When analyses indicated completion of the reaction, the solvent was evaporated to obtain a crude 63b as a hydrochloride salt in 99% yield (3.46 g; 13.12 mmol).

ESI-MS m/z for $C_{11}H_{15}ClNO_2$ found 228.1/230.1 [M+H]$^+$; $^1$H NMR (700 MHz, DMSO-d$_6$) δ 7.42-7.34 (m, 2H), 7.30-7.20 (m, 2H), 4.37-4.26 (m, 1H), 3.64 (s, 3H), 3.28-3.24 (m, 1H), 3.15-3.05 (m, 1H), 2.56 (s, 3H).

Step 3

Synthesis of methyl (S)-2-((S)-2-((tert-butoxycarbonyl)amino)-3-(4-chlorophenyl)-N-methylpropanamido)-3-(4-chlorophenyl)propanoate (63c)

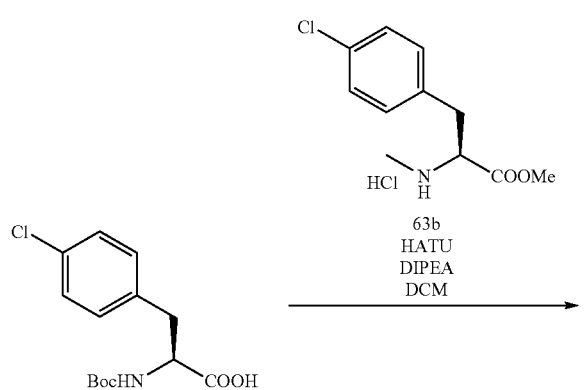

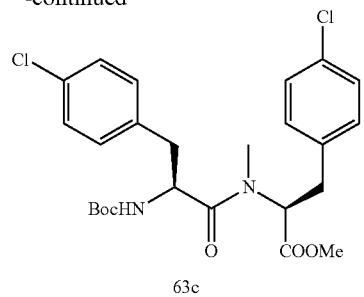

The title compound (63c) was obtained from 63b (3.61 g; 13.65 mmol) and (S)-2-((tert-butoxycarbonyl)amino)-3-(4-chlorophenyl)propanoic acid (2 g; 6.67 mmol) according to the General Procedure III in 52% yield (1.76 g; 3.47 mmol).

ESI-MS m/z for $C_{25}H_{31}Cl_2N_2O_5$ found 509.2/511.2 [M+H]$^+$; $^1$H NMR (700 MHz, CDCl$_3$) δ 7.27-7.25 (m, 2H), 7.25-7.21 (m, 2H), 7.17-7.13 (m, 2H), 7.10-7.04 (m, 2H), 5.37-5.25 (m, 1H), 5.04-4.96 (m, 1H), 4.78-4.69 (m, 1H), 3.72 (s, 3H), 3.33-3.26 (m, 1H), 3.04-2.93 (m, 1H), 2.93-2.83 (m, 2H), 2.78 (s, 3H), 1.42 (s, 9H).

Step 4

Synthesis of (3S,6S)-3,6-bis(4-chlorobenzyl)-1-methylpiperazine-2,5-dione (63d)

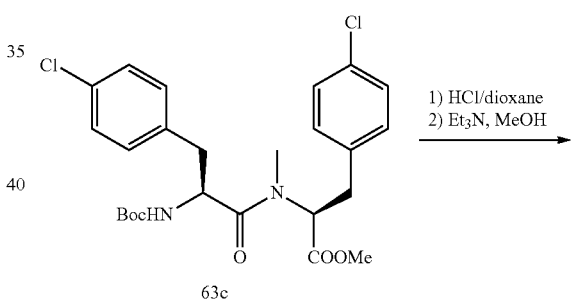

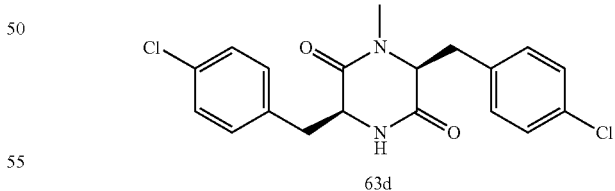

The title compound (63d) was obtained from 63c (1.76 g; 3.47 mmol) according to the General Procedure VIII in 36% yield (466 mg; 1.24 mmol).

ESI-MS m/z for $C_{19}H_{19}Cl_2N_2O_2$ found 377.1/379.1 [M+H]$^+$; $^1$H NMR (700 MHz, Methanol-d$_4$) δ 7.43-7.37 (m, 2H), 7.37-7.27 (m, 2H), 7.18-7.10 (m, 2H), 7.03-6.92 (m, 2H), 4.28-4.21 (m, 1H), 4.01 (dd, J=8.8, 4.0 Hz, 1H), 3.02-2.96 (m, 4H), 2.85 (dd, J=14.3, 4.6 Hz, 1H), 2.65 (dd, J=13.7, 4.1 Hz, 1H), 1.55 (dd, J=13.7, 8.9 Hz, 1H).

Step 5

Synthesis of (2S,5S)-2,5-bis(4-chlorobenzyl)-1-methylpiperazine (63e)

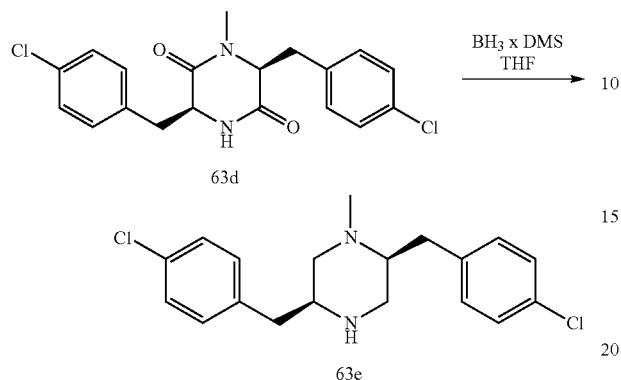

The title compound (63e) was obtained from 63d (466 mg; 1.24 mmol) according to the General Procedure Ib in 64% yield (275 mg; 0.79 mmol).

ESI-MS m/z for $C_{19}H_{23}Cl_2N_2$ found 349.1/351.1 [M+H]$^+$; $^1$H NMR (700 MHz, Methanol-$d_4$) δ 7.35-7.26 (m, 4H), 7.26-7.18 (m, 4H), 3.03-2.97 (m, 1H), 2.95-2.91 (m, 1H), 2.86-2.75 (m, 3H), 2.73-2.69 (m, 1H), 2.69-2.63 (m, 2H), 2.45-2.38 (m, 5H).

Step 6

Synthesis of (2S,5S)-2,5-bis(4-chlorobenzyl)-1-methyl-4-(1-(pyridin-2-yl)piperidin-4-yl)piperazine 2,2,2-trifluoroacetate (63)

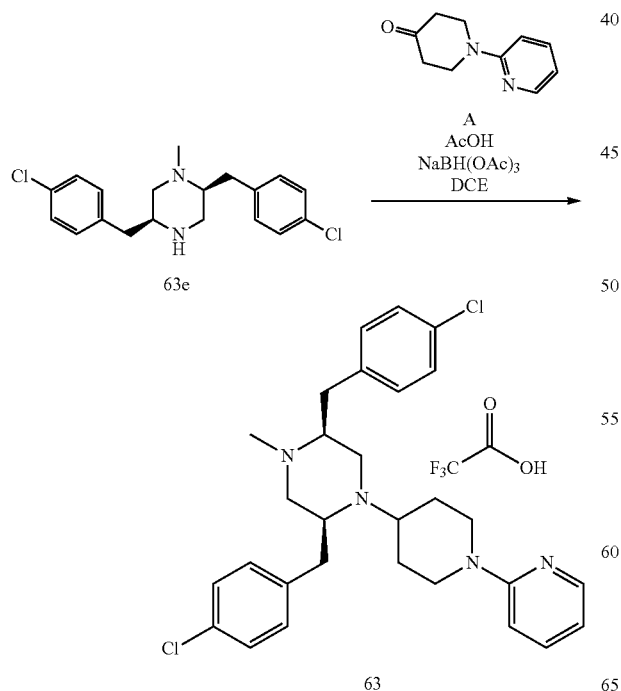

The title compound (63) was obtained as a TFA salt from 63e (98 mg; 0.28 mmol) according to the General Procedure VI in 2% yield (4 mg; 0.006 mmol).

ESI-MS m/z for $C_{29}H_{35}Cl_2N_4$ found 509.3/511.3 [M+H]$^+$; $^1$H NMR (700 MHz, D$_2$O) δ 7.96-7.88 (m, 1H), 7.80-7.75 (m, 1H), 7.42-7.39 (m, 2H), 7.38-7.35 (m, 2H), 7.31-7.27 (m, 4H), 7.18-7.14 (m, 1H), 6.91-6.87 (m, 1H), 3.99-3.78 (m, 2H), 3.60-3.50 (m, 2H), 3.34-3.27 (m, 3H), 3.20-3.13 (m, 3H), 3.12-3.05 (m, 1H), 2.94-2.86 (m, 6H), 2.84-2.77 (m, 1H), 1.88-1.79 (m, 2H), 1.43-1.32 (m, 2H).

Example 64

Synthesis of (S)-2-(4-chlorobenzyl)-4-methyl-1-(1-(pyridin-2-yl)piperidin-4-yl)piperazine 2,2,2-trifluoroacetate (64)

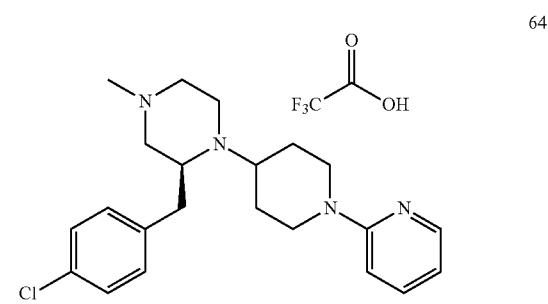

The title compound 64 was obtained as a TFA salt in 1% overall yield in a similar way to Example 61 with the exception that, in the first step of the synthesis, sarcosine methyl ester hydrochloride was used instead of N-methyl-L-alanine methyl ester hydrochloride.

ESI-MS m/z for $C_{22}H_{30}ClN_4$ found 385.2/387.2 [M+H]$^+$; $^1$H NMR (700 MHz, D$_2$O) δ 8.03-7.92 (m, 1H), 7.90-7.74 (m, 1H), 7.44-7.35 (m, 2H), 7.31-7.19 (m, 3H), 6.99-6.92 (m, 1H), 4.32-4.08 (m, 4H), 3.89-3.77 (m, 2H), 3.63-3.30 (m, 6H), 3.16-3.03 (m, 1H), 3.04-2.94 (m, 1H), 2.92 (s, 3H), 2.28-1.97 (m, 3H), 1.95-1.85 (m, 1H).

Example 65

Synthesis of (2S,5S)-2-(4-chlorobenzyl)-5-cyclopentyl-4-methyl-1-(1-(pyridin-2-yl)piperidin-4-yl)piperazine 2,2,2-trifluoroacetate (65)

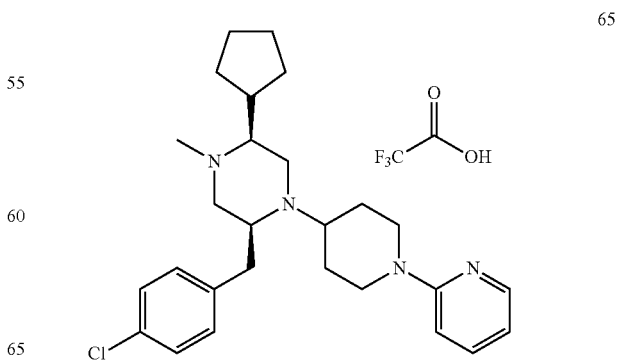

The title compound 65 was obtained as a TFA salt in 1% overall yield in a similar way to Example 63 with the exception that, in the first step of the synthesis, (S)-2-((tert-butoxycarbonyl)amino)-2-cyclopentylacetic acid was used instead of (S)-2-((tert-butoxycarbonyl)amino)-3-(4-chlorophenyl)propanoic acid.

ESI-MS m/z for $C_{27}H_{38}ClN_4$ found 453.3/455.3 $[M+H]^+$; $^1H$ NMR (700 MHz, $D_2O$) δ7.99-7.93 (m, 1H), 7.87-7.77 (m, 1H), 7.40-7.34 (m, 2H), 7.34-7.29 (m, 2H), 7.28-7.17 (m, 1H), 6.96-6.89 (m, 1H), 4.15-4.07 (m, 2H), 4.06-3.94 (m, 1H), 3.79-3.68 (m, 1H), 3.61-3.54 (m, 1H), 3.54-3.48 (m, 1H), 3.48-3.39 (m, 2H), 3.39-3.21 (m, 3H), 3.12-3.04 (m, 1H), 3.01-2.90 (m, 4H), 2.54-2.41 (m, 1H), 2.22-2.14 (m, 1H), 2.09-2.04 (m, 1H), 1.98-1.89 (m, 1H), 1.89-1.71 (m, 3H), 1.71-1.58 (m, 3H), 1.58-1.52 (m, 1H), 1.39-1.23 (m, 2H).

Example 66

Synthesis of (2S,5S)-5-(4-chlorobenzyl)-4-(1-(2-chloropyrimidin-4-yl)piperidin-4-yl)-2-methylmorpholine (66)

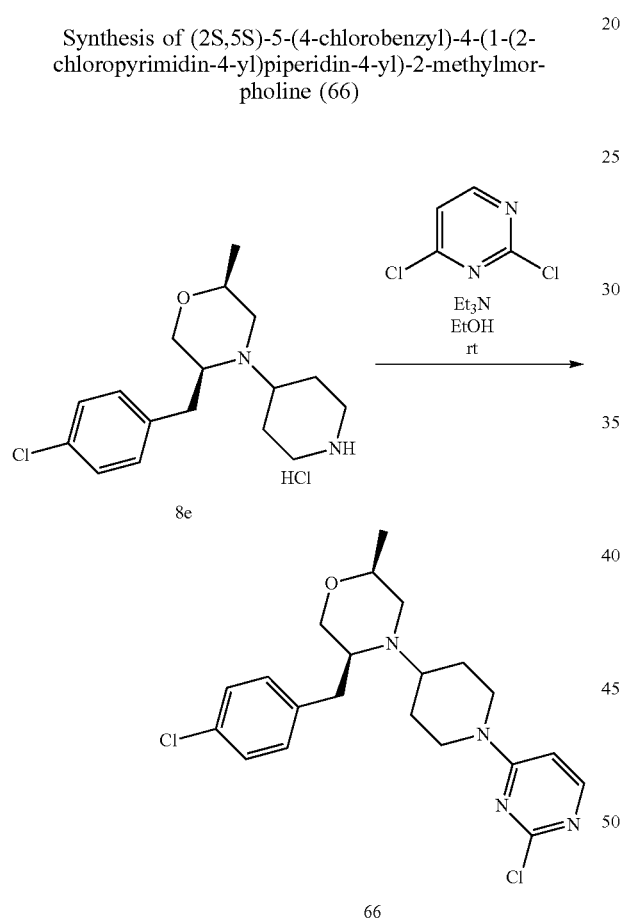

The mixture of 8e (500 mg; 1.45 mmol), 2,4-dichloropyrimidine (127 mg; 0.85 mmol) in absolute EtOH (10 mL) and $Et_3N$ (540 µL; 3.87 mmol) was stirred at room temperature for 1 hour. The reaction progress was monitored by TLC and LC-MS. After analytical control indicated completion of the reaction, to the mixture saturated $NH_4Cl$ was added and the aqueous mixture was extracted with DCM (3×), dried over anhydrous $Na_2SO_4$, filtered and concentrated in vacuo. The crude product was purified by silica-gel column chromatography (hexane/AcOEt, 1:1 to 0:1, v/v, then AcOEt/MeOH, 95:5 to 85:15; v/v). Compound 66 was obtained in 26% yield (156 mg; 0.37 mmol).

ESI-MS m/z for $C_{21}H_{27}Cl_2N_4O$ found 421.2/423.2 $[M+H]^+$; $^1H$ NMR (700 MHz, DMSO-$d_6$) δ 8.21-8.01 (m, 1H), 7.51-7.41 (m, 2H), 7.41-7.31 (m, 2H), 7.03-6.93 (m, 1H), 4.65-4.37 (m, 2H), 3.89-3.70 (m, 3H), 3.66-3.48 (m, 3H), 3.27-2.92 (m, 5H), 2.41-2.20 (m, 2H), 1.64-1.43 (m, 2H), 1.24 (d, J=6.3 Hz, 3H).

Example 67

Synthesis of 4-(4-((2S,5S)-5-(4-chlorobenzyl)-2-methylmorpholino)piperidin-1-yl)pyrimidin-2-amine 2,2,2-trifluoroacetate (67)

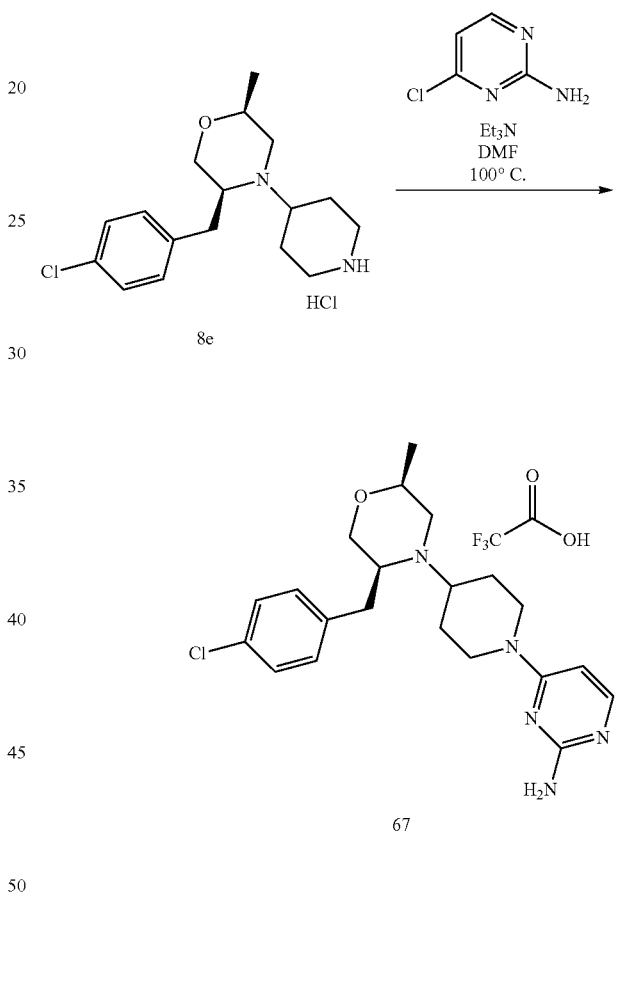

The title compound (67) was obtained as a TFA salt from 8e (8 mg; 0.023 mmol) according to the General Procedure IX in 9% yield (0.8 mg; 0.002 mmol) with the exception that DMF (1 mL) was additionally used in this step and that the temperature of this reaction was reduced to 100° C. instead of 120° C. and $Et_3N$ was used instead of $K_2CO_3$.

ESI-MS m/z for $C_{21}H_{29}ClN_5O$ found 402.2/404.2 $[M+H]^+$; $^1H$ NMR (700 MHz, $D_2O$) δ 7.68-7.61 (m, 1H), 7.48-7.35 (m, 2H), 7.35-7.26 (m, 2H), 6.50-6.36 (m, 1H), 5.17-5.02 (m, 1H), 4.37-4.22 (m, 1H), 3.97-3.54 (m, 6H), 3.34-3.08 (m, 4H), 2.99-2.83 (m, 1H), 2.51-2.37 (m, 2H), 1.80-1.53 (m, 2H), 1.30 (d, J=6.3 Hz, 3H).

Example 68

Synthesis of (2S,5S)-2-(4-chlorobenzyl)-5-cyclopropyl-4-methyl-1-(1-(pyridin-2-yl)piperidin-4-yl)piperazine 2,2,2-trifluoroacetate (68)

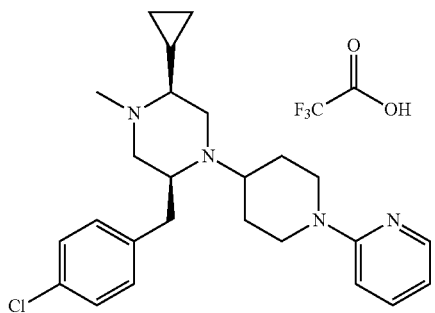

The title compound 68 was obtained as a TFA salt in 1% overall yield in a similar way to Example 63 with the exception that, in the first step of the synthesis, (2S)-2-[[(tert-butoxy)carbonyl]amino]-2-cyclopropylacetic acid was used instead of (S)-2-((tert-butoxycarbonyl)amino)-3-(4-chlorophenyl)propanoic acid.

ESI-MS m/z for $C_{25}H_{34}ClN_4$ found 425.3/427.3 [M+H]+; $^1$H NMR (700 MHz, D$_2$O) δ 8.00-7.91 (m, 1H), 7.85-7.74 (m, 1H), 7.49-7.34 (m, 2H), 7.33-7.26 (m, 2H), 7.26-7.17 (m, 1H), 6.97-6.88 (m, 1H), 4.14-3.98 (m, 2H), 3.92-3.78 (m, 1H), 3.57-3.13 (m, 8H), 3.01-2.92 (m, 4H), 2.70-2.60 (m, 1H), 2.25-2.14 (m, 1H), 2.13-2.03 (m, 1H), 1.78-1.65 (m, 2H), 1.17-1.05 (m, 1H), 0.98-0.89 (m, 1H), 0.83-0.73 (m, 1H), 0.68-0.60 (m, 1H), 0.41-0.32 (m, 1H).

Example 69

Synthesis of (2S,5S)-5-(4-chlorobenzyl)-4-(1-(4-chloropyridin-2-yl)piperidin-4-yl)-2-isopropylmorpholine 2,2,2-trifluoroacetate (69)

Step 1 Synthesis of (R)-2-bromo-N-((S)-1-(4-chlorophenyl)-3-hydroxypropan-2-yl)-3-methylbutanamide (69a)

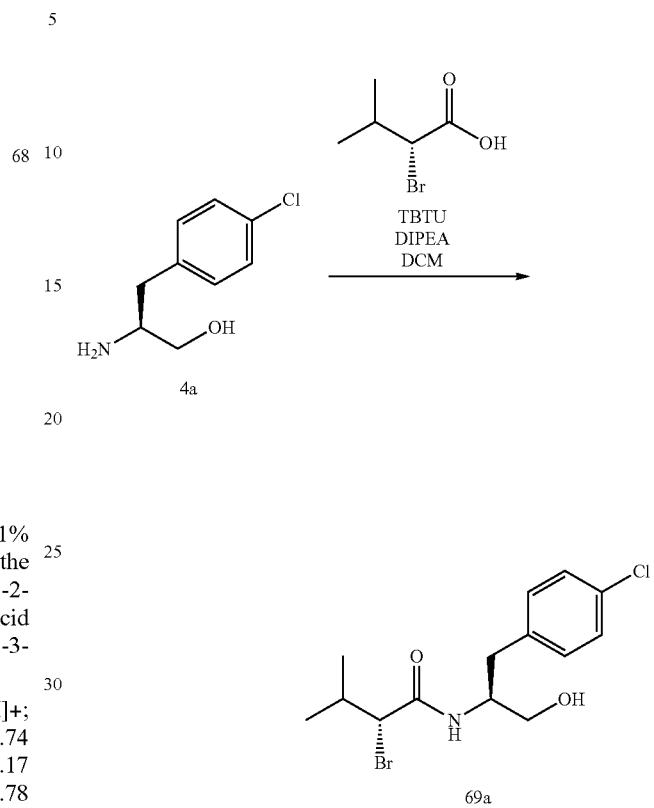

The title compound (69a) was obtained from 4a (1.36 g; 7.3 mmol) according to the General Procedure III in 58% yield (1.47 g; 4.23 mmol).

ESI-MS m/z for $C_{14}H_{20}BrClNO_2$ found 348.1/350.1 [M+H]+; $^1$H NMR (250 MHz, Methanol-d$_4$) δ 7.28-7.14 (m, 4H), 4.18-4.01 (m, 1H), 3.93 (d, J=8.8 Hz, 1H), 3.62-3.45 (m, 2H), 3.02-2.91 (m, 1H), 2.73-2.56 (m, 1H), 2.09-1.88 (m, 1H), 0.98 (d, J=6.6 Hz, 3H), 0.68 (d, J=6.7 Hz, 3H).

Step 2

Synthesis of (2S,5S)-5-(4-chlorobenzyl)-2-isopropylmorpholin-3-one (69b)

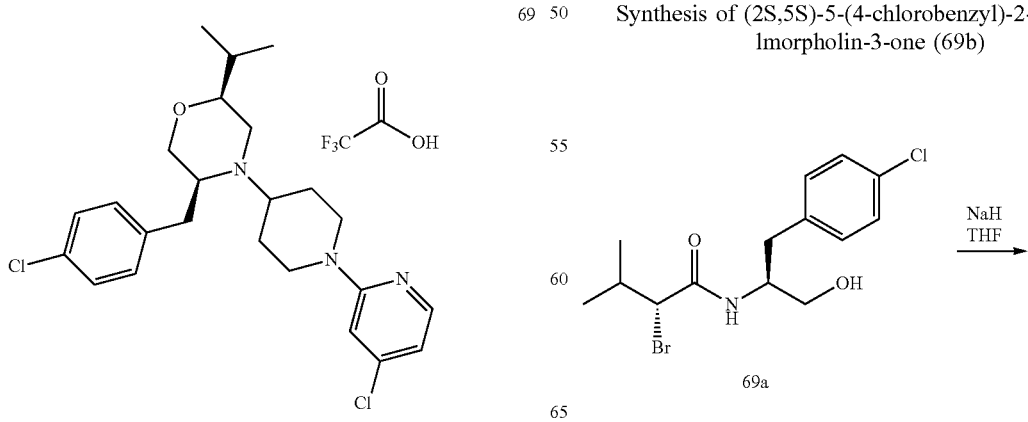

-continued

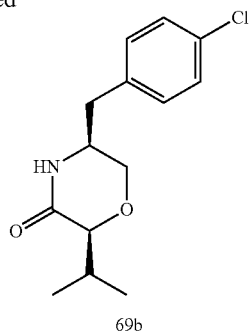

69b

The title compound (69b) was obtained from compound 69a (1.22 g; 3.51 mmol) according to the General Procedure II in 99% yield (0.93 g; 3.47 mmol).

ESI-MS m/z for $C_{14}H_{19}ClNO_2$ found 268.1/270.1 [M+H]$^+$

Step 3

Synthesis of (2S,5S)-5-(4-chlorobenzyl)-2-isopropylmorpholine (69c)

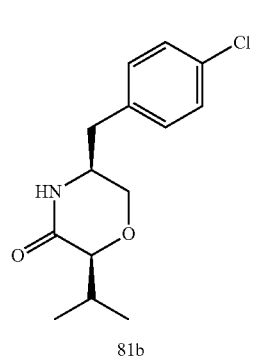

81b

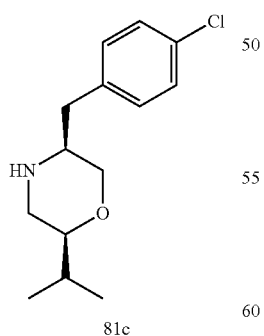

81c

The title compound (69c) was obtained from 69b (1.1 g; 4.13 mmol) according to the General Procedure Ib in 21% yield (220 mg; 0.87 mmol).

ESI-MS m/z for $C_{14}H_{21}ClNO$ found 254.1/256.1 [M+H]$^+$

Step 4

Synthesis of (2S,5S)-5-(4-chlorobenzyl)-4-(1-(4-chloropyridin-2-yl)piperidin-4-yl)-2-isopropylmorpholine 2,2,2-trifluoroacetate (69)

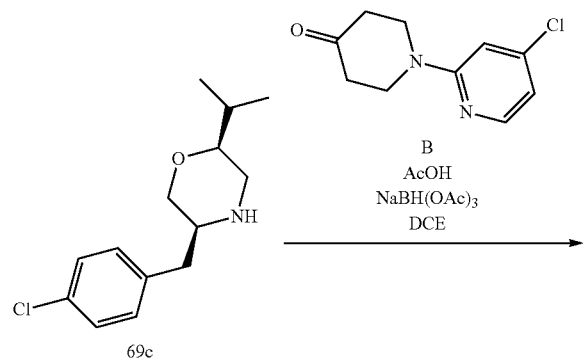

69c

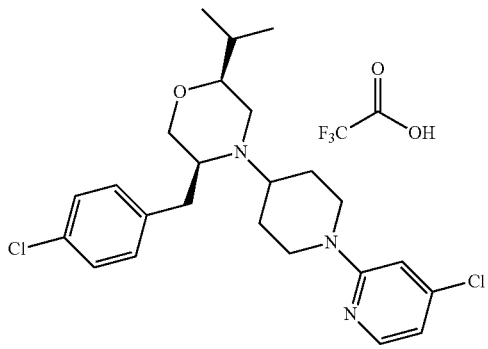

69

The title compound (69) was obtained as a TFA salt from 69c (220 mg; 0.87 mmol) according to the General Procedure VI in 2% yield (8 mg; 0.014 mmol).

ESI-MS m/z for $C_{24}H_{32}Cl_2N_3O$ found 448.0/449.9 [M+H]$^+$; $^1$H NMR (700 MHz, DMSO-d$_6$+D$_2$O) δ 7.85-7.74 (m, 1H), 7.48-7.39 (m, 1H), 7.39-7.32 (m, 2H), 7.27-7.18 (m, 2H), 7.03-6.89 (m, 1H), 4.28-4.19 (m, 2H), 3.88-3.71 (m, 3H), 3.67-3.55 (m, 2H), 3.52-3.43 (m, 1H), 3.33-3.20 (m, 3H), 3.20-3.10 (m, 2H), 2.51-2.39 (m, 2H), 1.89-1.70 (m, 3H), 0.99-0.90 (m, 6H).

Example 70

Synthesis of ((2R,5S)-5-(4-chlorobenzyl)-4-(1-(pyrimidin-2-yl)piperidin-4-yl)morpholin-2-yl)methyl dimethylcarbamate 2,2,2-trifluoroacetate (70)

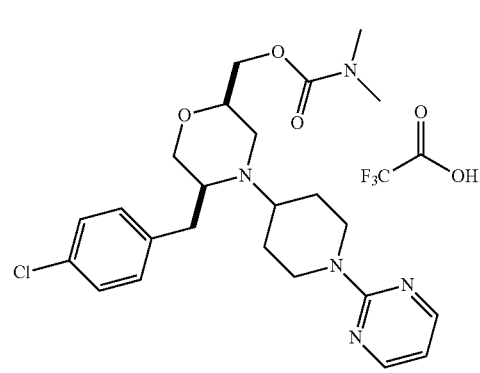

Step 1

Synthesis of ((2R,5S)-5-(4-chlorobenzyl)-4-(1-(pyrimidin-2-yl)piperidin-4-yl)morpholin-2-yl)methanol (70a)

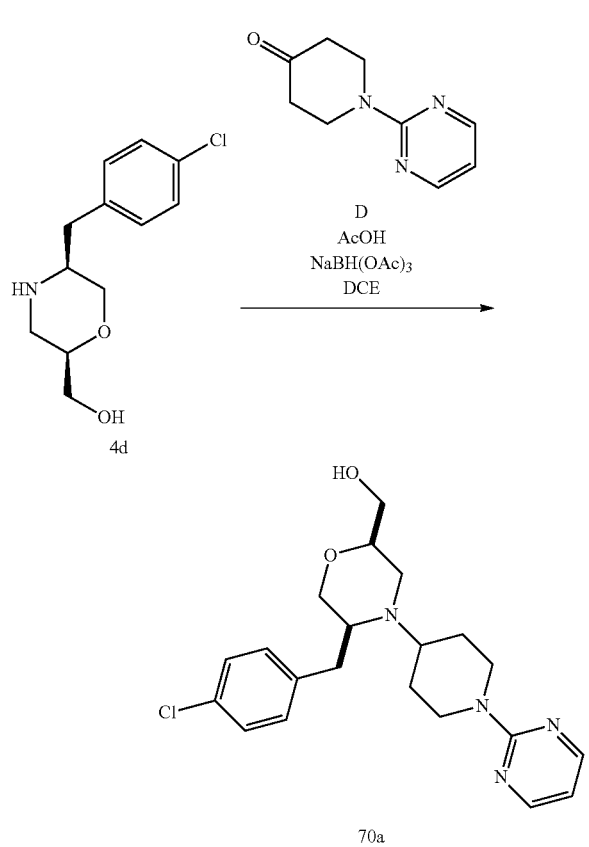

The title compound (70a) was obtained from 4d (510 mg; 2.11 mmol) according to the General Procedure VI in 13% yield (107 mg; 0.27 mmol).

ESI-MS m/z for $C_{21}H_{28}ClN_4O_2$ found 403.2/405.2 $[M+H]^+$

Step 2

Synthesis of ((2R,5S)-5-(4-chlorobenzyl)-4-(1-(pyrimidin-2-yl)piperidin-4-yl)morpholin-2-yl)methyl dimethylcarbamate 2,2,2-trifluoroacetate (70)

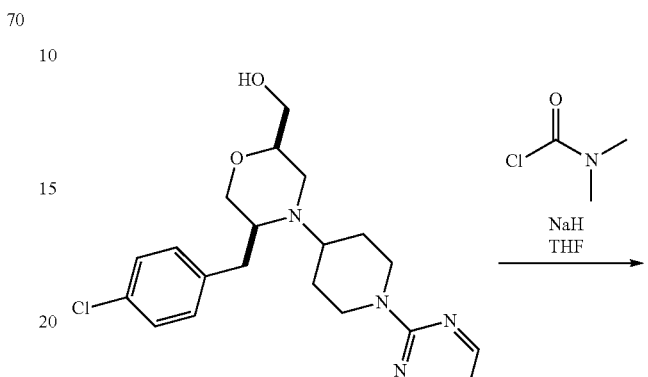

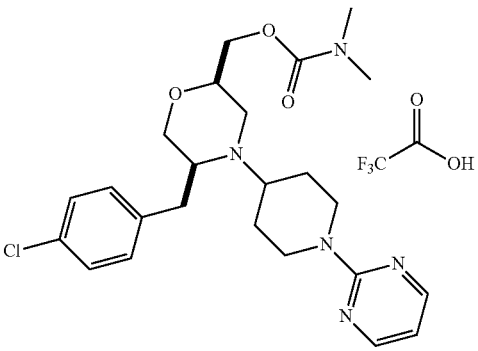

The title compound (70) was obtained as a TFA salt from 70a (107 mg; 0.27 mmol) according to the General Procedure XII in 52% yield (84 mg; 0.14 mmol).

ESI-MS m/z for $C_{24}H_{33}ClN_5O_3$ found 474.1/476.1 $[M+H]^+$; $^1H$ NMR (700 MHz, $D_2O$) δ 8.56-8.48 (m, 2H), 7.47-7.34 (m, 2H), 7.30-7.20 (m, 2H), 6.99-6.87 (m, 1H), 4.69-4.61 (m, 2H), 4.37-4.31 (m, 1H), 4.20-4.16 (m, 1H), 4.16-4.06 (m, 1H), 3.95-3.87 (m, 2H), 3.85-3.80 (m, 1H), 3.78-3.72 (m, 1H), 3.69-3.64 (m, 1H), 3.42-3.35 (m, 1H), 3.26-3.14 (m, 4H), 2.96 (s, 3H), 2.89 (s, 3H), 2.52-2.42 (m, 2H), 1.85-1.70 (m, 2H).

Example 71

Synthesis of (2S,5S)-5-(4-chlorobenzyl)-2-((4-methylpiperazin-1-yl)methyl)-4-(1-(pyrimidin-2-yl)piperidin-4-yl)morpholine 2,2,2-trifluoroacetate (71)

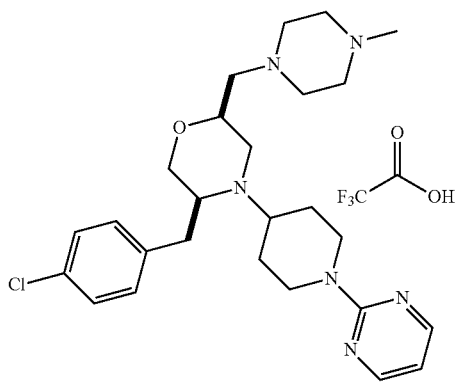

71

The title compound 71 was obtained as a TFA salt in 43% overall yield in a similar way to Example 51 with the exception that, in the first step of the synthesis, the compound 70a was used instead of the compound 50 and in the second step of the synthesis, 1-methylpiperazine was used instead of morpholine.

ESI-MS m/z for $C_{26}H_{38}ClN_6O$ found 485.1/487.1 [M+H]$^+$; $^1$H NMR (700 MHz, D$_2$O) δ 8.54-8.47 (m, 2H), 7.42-7.37 (m, 2H), 7.30-7.24 (m, 2H), 7.02-6.86 (m, 1H), 4.68-4.62 (m, 2H), 4.26-4.17 (m, 1H), 3.95-3.84 (m, 3H), 3.75-3.61 (m, 3H), 3.61-3.37 (m, 5H), 3.33-3.12 (m, 9H), 2.95 (s, 3H), 2.51-2.36 (m, 2H), 1.86-1.68 (m, 2H).

Example 72

Synthesis of N¹-(((2S,5S)-5-(4-chlorobenzyl)-4-(1-(pyrimidin-2-yl)piperidin-4-yl)morpholin-2-yl)methyl)-N¹,N²,N²-trimethylethane-1,2-diamine 2,2,2-trifluoroacetate (72)

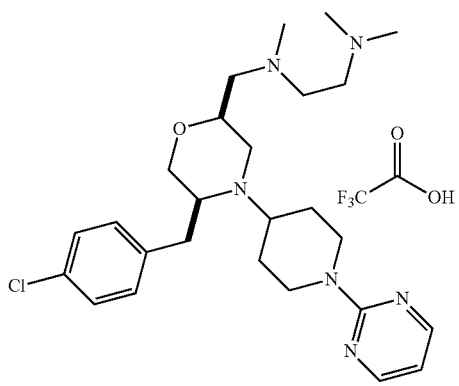

72

The title compound 72 was obtained as a TFA salt in 37% overall yield in a similar way to Example 51 with the exception that, in the first step of the synthesis, the compound 70a was used instead of the compound 50 and in the second step of the synthesis, N,N,N'-trimethyletylenediamine was used instead of morpholine.

ESI-MS m/z for $C_{26}H_{40}ClN_6O$ found 487.3/489.3 [M+H]$^+$; $^1$H NMR (700 MHz, D$_2$O) δ 8.56-8.43 (m, 2H), 7.43-7.36 (m, 2H), 7.29-7.23 (m, 2H), 7.02-6.92 (m, 1H), 4.69-4.61 (m, 2H), 4.36-4.30 (m, 1H), 4.00-3.94 (m, 1H), 3.94-3.89 (m, 2H), 3.80-3.74 (m, 1H), 3.74-3.58 (m, 6H), 3.48-3.44 (m, 1H), 3.34-3.19 (m, 5H), 3.01 (s, 3H), 2.95 (s, 6H), 2.51-2.41 (m, 2H), 1.86-1.70 (m, 2H).

Example 73

Synthesis of (R)-1-(((2S,5S)-5-(4-chlorobenzyl)-4-(1-(pyrimidin-2-yl)piperidin-4-yl)morpholin-2-yl)methyl)pyrrolidin-3-ol 2,2,2-trifluoroacetate (73)

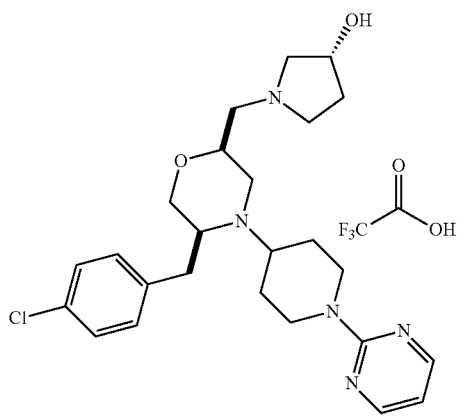

73

The title compound 73 was obtained as a TFA salt in 56% overall yield in a similar way to Example 51 with the exception that, in the first step of the synthesis, the compound 70a was used instead of the compound 50 and in the second step of the synthesis, (R)-3-hydroxypyrrolidine was used instead of morpholine.

ESI-MS m/z for $C_{25}H_{35}ClN_5O_2$ found 472.1/474.1 [M+H]$^+$; $^1$H NMR (700 MHz, D$_2$O) δ 8.53-8.43 (m, 2H), 7.45-7.36 (m, 2H), 7.32-7.23 (m, 2H), 7.03-6.90 (m, 1H), 4.69-4.61 (m, 3H), 4.35-4.14 (m, 1H), 3.98-3.41 (m, 10H), 3.35-3.18 (m, 7H), 2.51-2.40 (m, 2H), 2.19-1.96 (m, 1H), 1.88-1.65 (m, 2H).

Example 74

Synthesis of (S)-1-(((2S,5S)-5-(4-chlorobenzyl)-4-(1-(pyrimidin-2-yl)piperidin-4-yl)morpholin-2-yl)methyl)pyrrolidin-3-ol 2,2,2-trifluoroacetate (74)

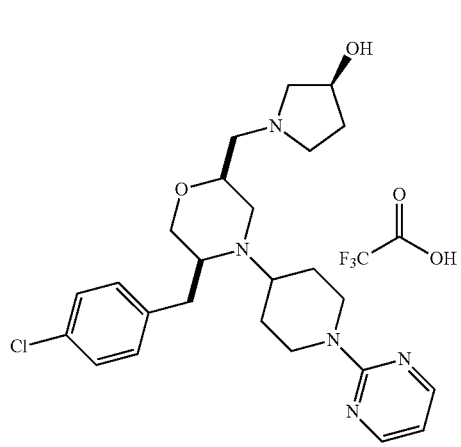

The title compound 74 was obtained as a TFA salt in 54% overall yield in a similar way to Example 51 with the exception that, in the first step of the synthesis, the compound 70a was used instead of the compound 50 and in the second step of the synthesis, (S)-3-hydroxypyrrolidine was used instead of morpholine.

ESI-MS m/z for $C_{25}H_{35}ClN_5O_2$ found 472.1/474.1 [M+H]$^+$; $^1$H NMR (700 MHz, D$_2$O) δ 8.59-8.47 (m, 2H), 7.45-7.37 (m, 2H), 7.32-7.22 (m, 2H), 7.03-6.91 (m, 1H), 4.69-4.55 (m, 3H), 4.28-4.19 (m, 1H), 3.96-3.16 (m, 17), 2.53-2.41 (m, 2H), 2.19-1.99 (m, 1H), 1.84-1.70 (m, 2H).

Example 75

Synthesis of N-(((2S,5S)-5-(4-chlorobenzyl)-4-(1-(pyrimidin-2-yl)piperidin-4-yl)morpholin-2-yl)methyl)acetamide 2,2,2-trifluoroacetate (75)

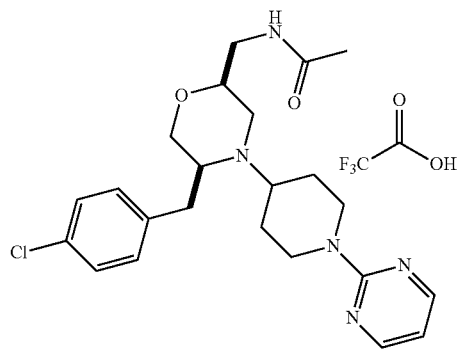

Step 1

Synthesis of ((2R,5S)-5-(4-chlorobenzyl)-4-(1-(pyrimidin-2-yl)piperidin-4-yl)morpholin-2-yl)methyl methanesulfonate (75a)

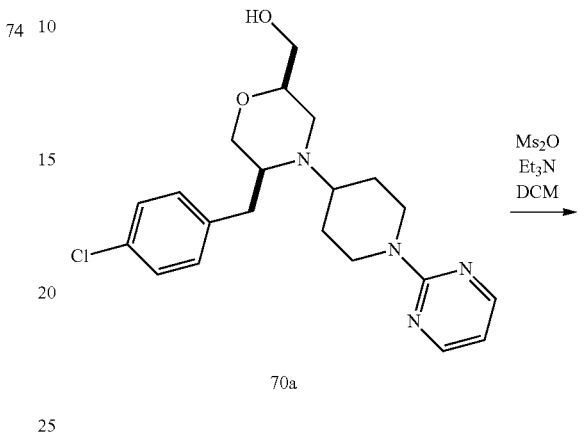

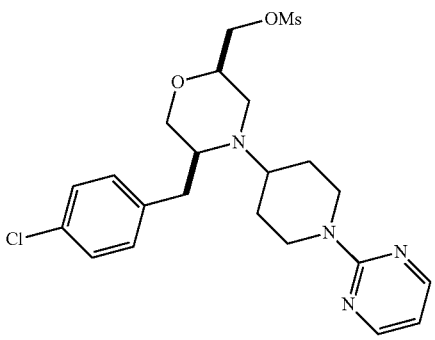

The title compound (75a) was obtained from 70a (183 mg; 0.45 mmol) according to the General Procedure XIV in 68% yield (148 mg; 0.31 mmol).

ESI-MS m/z for $C_{22}H_{30}ClN_4O_4S$ found 481.2/483.2 [M+H]+; $^1$H NMR (700 MHz, CDCl$_3$) δ 8.35-8.31 (m, 2H), 7.31-7.29 (m, 2H), 7.14-7.11 (m, 2H), 6.53-6.46 (m, 1H), 4.76-4.66 (m, 2H), 4.36-4.26 (m, 2H), 3.88-3.78 (m, 1H), 3.70 (d, J=11.3 Hz, 1H), 3.53-3.46 (m, 1H), 3.09-3.04 (m, 2H), 3.04-2.95 (m, 2H), 2.86-2.74 (m, 3H), 2.63-2.55 (m, 1H), 2.09-1.92 (m, 3H), 1.58-1.41 (m, 4H).

Step 2

Synthesis of (2R,5S)-2-(azidomethyl)-5-(4-chlorobenzyl)-4-(1-(pyrimidin-2-yl)piperidin-4-yl)morpholine (75b)

Step 3

Synthesis of ((2S,5S)-5-(4-chlorobenzyl)-4-(1-(pyrimidin-2-yl)piperidin-4-yl)morpholin-2-yl)methanamine (75c)

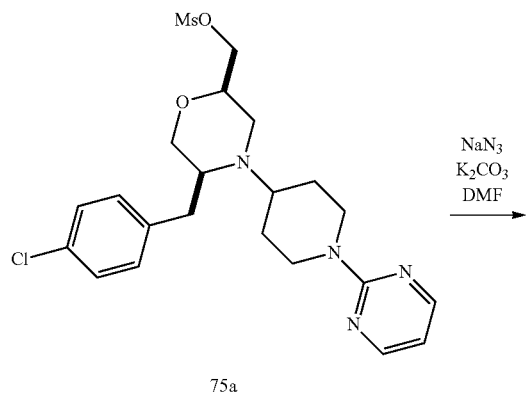

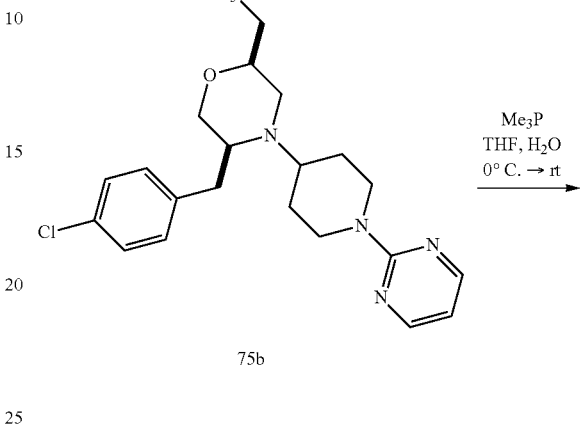

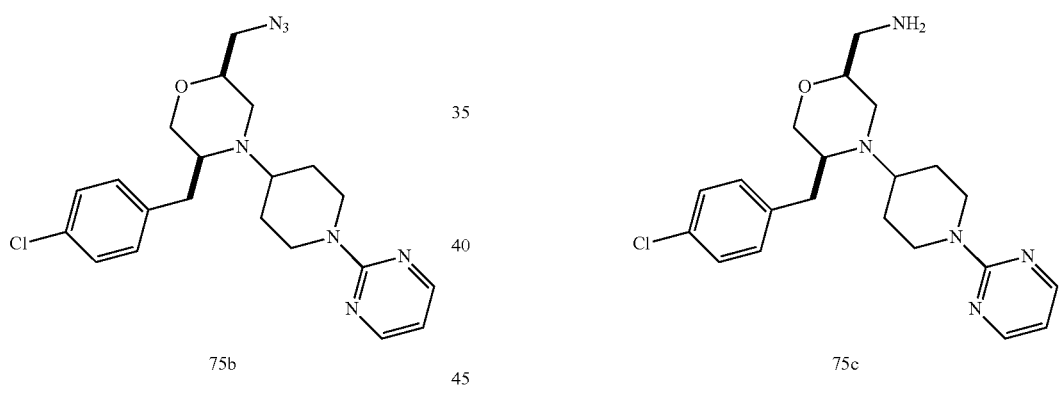

To a solution of 4a (165 mg; 0.34 mmol) in DMF (2 mL) NaN$_3$ (113 mg; 1.74 mmol) and K$_2$CO$_3$ (189 mg; 1.37 mmol) were added and the mixture was stirred at 115° C. for 3 hours. The reaction progress was monitored by LC-MS. When analysis indicated completion of the reaction, the reaction mixture was cooling down to room temperature, diluted with Et$_2$O and sequentially washed with water (3x), dried over anhydrous MgSO$_4$, filtered and concentrated in vacuo and the crude product mixture was used to the next step without additional purification. Compound 75b was obtained in 53% yield (77 mg; 0.18 mmol).

ESI-MS C$_{21}$H$_{27}$ClN$_7$O found 428.2/430.2 [M+H]$^+$

To a solution of 75b (77 mg; 0.18 mmol) in mixture of THF-H$_2$O (2 mL; 9:1 v/v), a solution of Me$_3$P in THF (1M; 0.54 mL; 0.54 mmol) was added at 0° C. The cooling bath was removed and the mixture was stirred at room temperature overnight. TLC and LCMS showed completion of the reaction. The reaction mixture was then concentrated in vacuo and the crude product was purified by silica-gel column chromatography (MeOH/Et$_3$N, 100:0 to 97:3, v/v). Compound 75c was obtained in 78% yield (55 mg; 0.14 mmol).

ESI-MS m/z for C$_{21}$H$_{29}$ClN$_5$O found 402.2/404.2 [M+H]$^+$

Step 4

Synthesis of N-(((2S,5S)-5-(4-chlorobenzyl)-4-(1-(pyrimidin-2-yl)piperidin-4-yl)morpholin-2-yl)methyl)acetamide 2,2,2-trifluoroacetate (75)

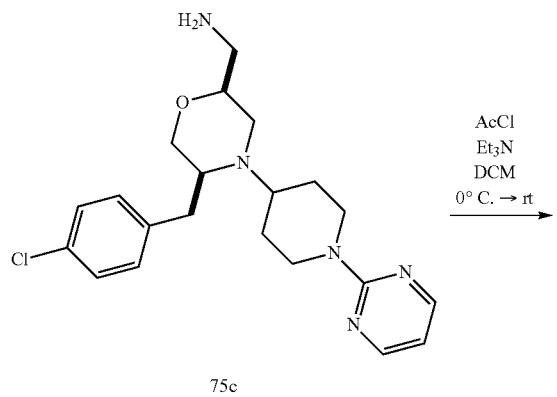

The title compound (75) was obtained as a TFA salt from 75c (56 mg; 0.14 mmol) according to the General Procedure XVII in 38% yield (30 mg; 0.053 mmol).

ESI-MS m/z for $C_{23}H_{31}ClN_5O_2$ found 444.0/446.0 [M+H]$^+$; $^1$H NMR (700 MHz, D$_2$O) δ 8.50-8.39 (m, 2H), 7.42-7.34 (m, 2H), 7.30-7.23 (m, 2H), 6.90-6.83 (m, 1H), 4.68-4.60 (m, 2H), 4.04-3.77 (m, 4H), 3.73-3.56 (m, 2H), 3.51-3.35 (m, 2H), 3.28-3.12 (m, 5H), 2.48-2.34 (m, 2H), 2.00 (s, 3H), 1.79-1.63 (m, 2H).

Example 76

Synthesis of 2-(((2R,5S)-5-(4-chlorobenzyl)-4-(1-(pyrimidin-2-yl)piperidin-4-yl)morpholin-2-yl)methyl)isoindoline-1,3-dione dihydrochloride (76)

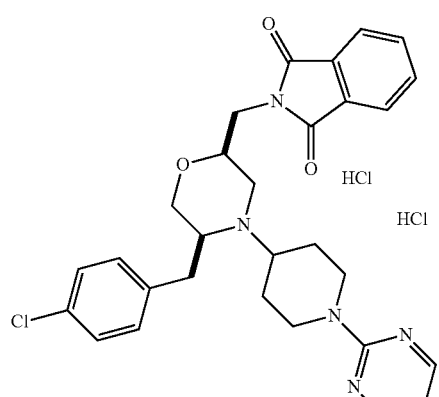

Step 1

Synthesis of (2R,5S)-5-(4-chlorobenzyl)-2-(iodomethyl)-4-(1-(pyrimidin-2-yl)piperidin-4-yl)morpholine (76a)

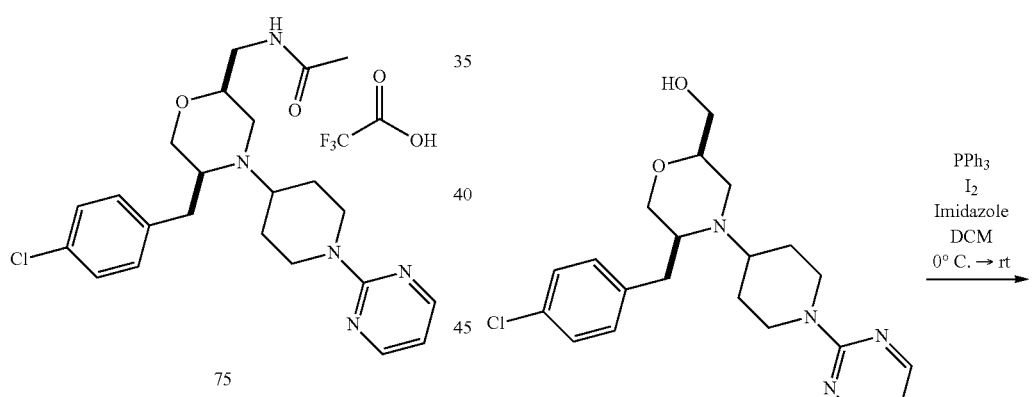

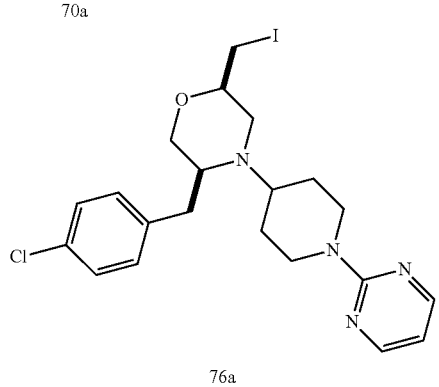

To a solution of 70a (300 mg; 0.74 mmol) in anhydrous DCM (1.85 mL) PPh$_3$ (0.58 g; 2.22 mmol), iodine (0.56 g;

2.22 mmol) and imidazole (151 mg; 2.22 mmol) were added at 0° C. The cooling bath was removed and the mixture was stirred at room temperature overnight. TLC and LC-MS showed completion of the reaction. The mixture was diluted with DCM, washed with 10% $Na_2S_2O_3$ (2×) and water. The combined organic solutions were dried over anhydrous $MgSO_4$, filtered and concentrated in vacuo. The crude product was purified by silica-gel column chromatography (hexane/AcOEt, 1:1 to 2:8, v/v). Compound 76a was obtained in 52% yield (195 mg; 0.38 mmol).

ESI-MS m/z for $C_{21}H_{27}ClIN_4O$ found 513.1/515.1 [M+H]$^+$; $^1$H NMR (700 MHz, CDCl$_3$) δ 8.35-8.22 (m, 2H), 7.30-7.27 (m, 2H), 7.18-7.12 (m, 2H), 6.52-6.44 (m, 1H), 4.77-4.65 (m, 2H), 3.72-3.64 (m, 1H), 3.54-3.51 (m, 1H), 3.48-3.41 (m, 1H), 3.31 (dd, J=10.4, 5.4 Hz, 1H), 3.26 (dd, J=10.4, 5.2 Hz, 1H), 3.09-3.00 (m, 3H), 3.00-2.90 (m, 2H), 2.86-2.73 (m, 2H), 2.61-2.54 (m, 1H), 2.09-1.97 (m, 2H), 1.56-1.45 (m, 2H).

Step 2

Synthesis of 2-(((2R,5S)-5-(4-chlorobenzyl)-4-(1-(pyrimidin-2-yl)piperidin-4-yl)morpholin-2-yl)methyl)isoindoline-1,3-dione dihydrochloride (76)

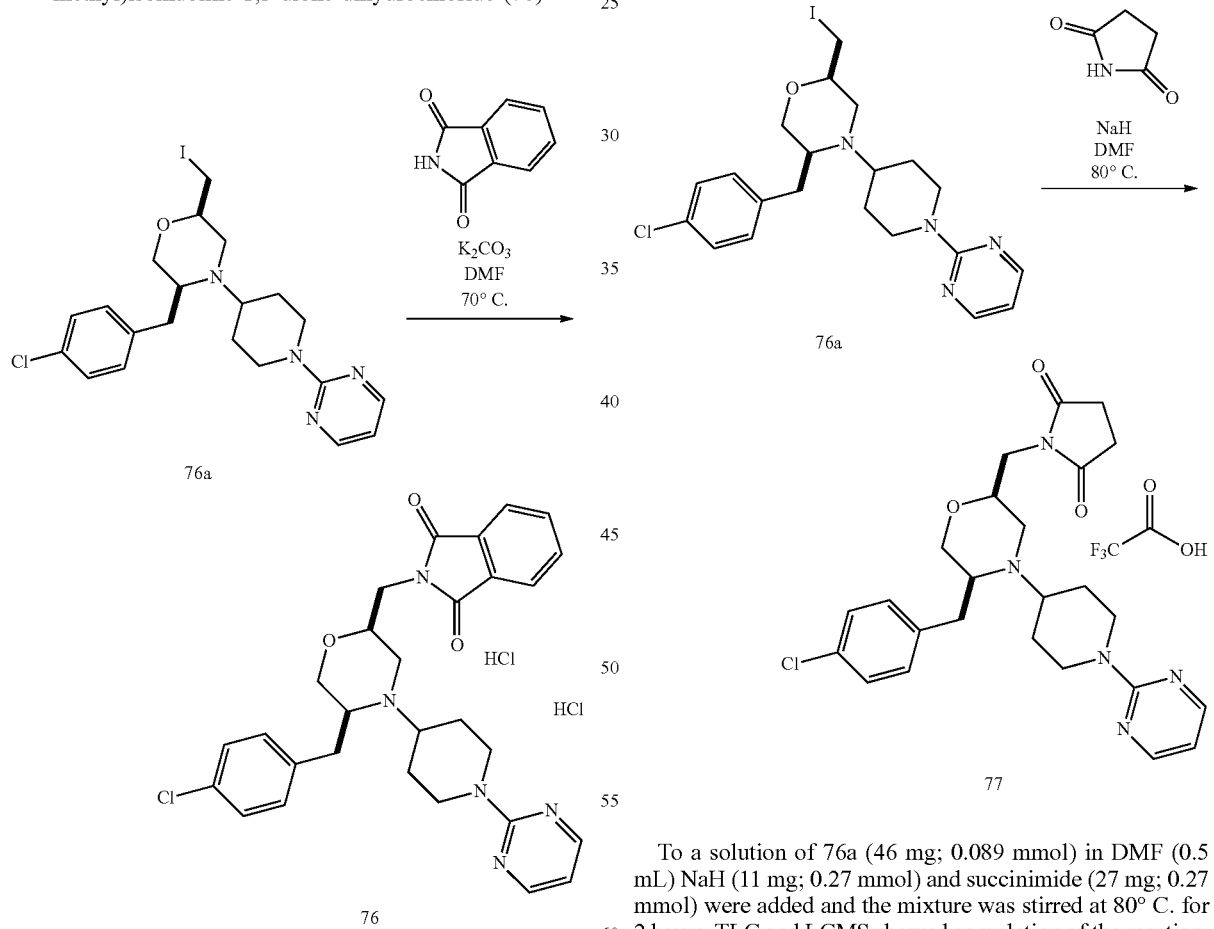

To a solution of 76a (50 mg; 0.098 mmol) in DMF (0.5 mL) $K_2CO_3$ (40 mg; 0.29 mmol) and phthalimide (43 mg; 0.29 mmol) were added and the mixture was stirred at 70° C. for 4 hours. TLC and LC-MS showed completion of the reaction. The mixture was cooled down to room temperature and diluted with water, extracted with AcOEt (3×). The combined organic solutions were dried over anhydrous $MgSO_4$, filtered and concentrated in vacuo. The crude product was dissolved in MeOH and to this solution 1M HCl (1 mL) was added and purified by preparative reversed-phase column chromatography (Luna® 5 μm Phenyl-Hexyl, LC Column 250×21.2 mm, water/MeCN, 90:10 to 50:50, 30 minutes). Compound 76 was obtained as a dihydrochloride salt in 8% yield (5 mg; 0.008 mmol).

ESI-MS m/z for $C_{29}H_{31}ClN_5O_3$ found 532.0/534.0 [M+H]$^+$; $^1$HNMR (700 MHz, DMSO-d$_6$+D$_2$O) δ 8.46-8.34 (m, 2H), 7.93-7.89 (m, 2H), 7.89-7.80 (m, 2H), 7.48-7.39 (m, 2H), 7.39-7.31 (m, 2H), 6.73-6.64 (m, 1H), 4.82-4.69 (m, 3H), 4.04-3.97 (m, 1H), 3.94-3.86 (m, 1H), 3.84-3.74 (m, 3H), 3.59-3.50 (m, 2H), 3.27-3.15 (m, 3H), 3.02-2.88 (m, 2H), 2.31-2.20 (m, 2H), 1.58-1.45 (m, 2H). δ

Example 77

Synthesis of 1-(((2R,5S)-5-(4-chlorobenzyl)-4-(1-(pyrimidin-2-yl)piperidin-4-yl)morpholin-2-yl)methyl)pyrrolidine-2,5-dione 2,2,2-trifluoroacetate (77)

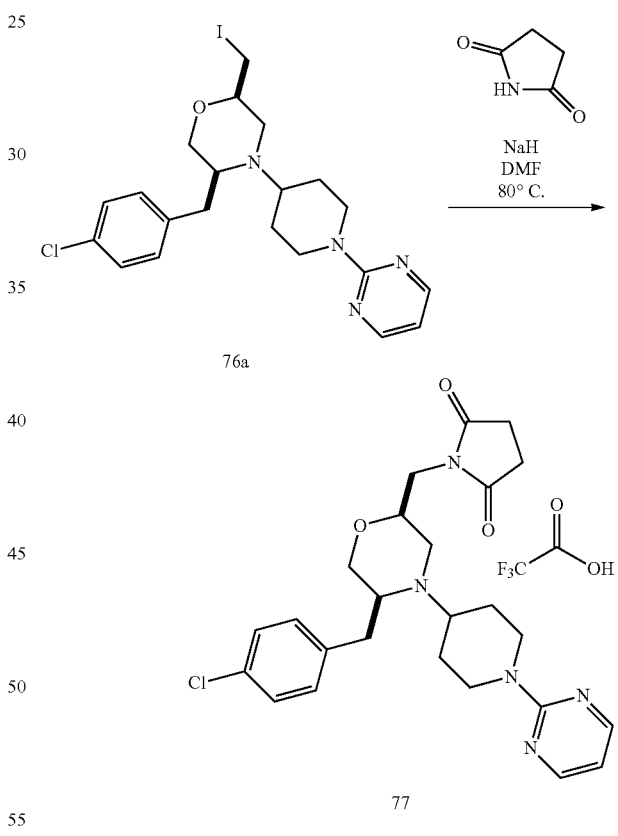

To a solution of 76a (46 mg; 0.089 mmol) in DMF (0.5 mL) NaH (11 mg; 0.27 mmol) and succinimide (27 mg; 0.27 mmol) were added and the mixture was stirred at 80° C. for 2 hours. TLC and LCMS showed completion of the reaction. The mixture was cooled down to room temperature and diluted with E$_2$O and washed with water (3×), dried over anhydrous $Na_2SO_4$, filtered and concentrated in vacuo. The crude product was washed with E$_2$O (2×) and then lyophilized from water with drop of trifluoroacetic acid. Compound 77 was obtained as a TFA salt in 13% yield (7 mg; 0.012 mmol).

ESI-MS m/z for $C_{25}H_{31}ClN_5O_3$ found 484.2/486.2 [M+H]$^+$; $^1$H NMR (700 MHz, DMSO-d$_6$) δ 8.49-8.35 (m, 2H), 7.47-7.40 (m, 2H), 7.40-7.29 (m, 2H), 6.75-6.64 (m, 1H), 4.81-4.69 (m, 2H), 3.98-3.89 (m, 1H), 3.86-3.80 (m, 1H), 3.80-3.67 (m, 2H), 3.67-3.60 (m, 1H), 3.60-3.48 (m, 3H), 3.24-3.10 (m, 2H), 3.05-2.89 (m, 2H), 2.74-2.62 (m, 4H), 2.53-2.52 (m, 1H), 2.31-2.18 (m, 2H), 1.58-1.47 (m, 2H).

Example 78

Synthesis of 3-(((2R,5S)-5-(4-chlorobenzyl)-4-(1-(pyrimidin-2-yl)piperidin-4-yl)morpholin-2-yl)methyl)imidazolidine-2,4-dione 2,2,2-trifluoroacetate (78)

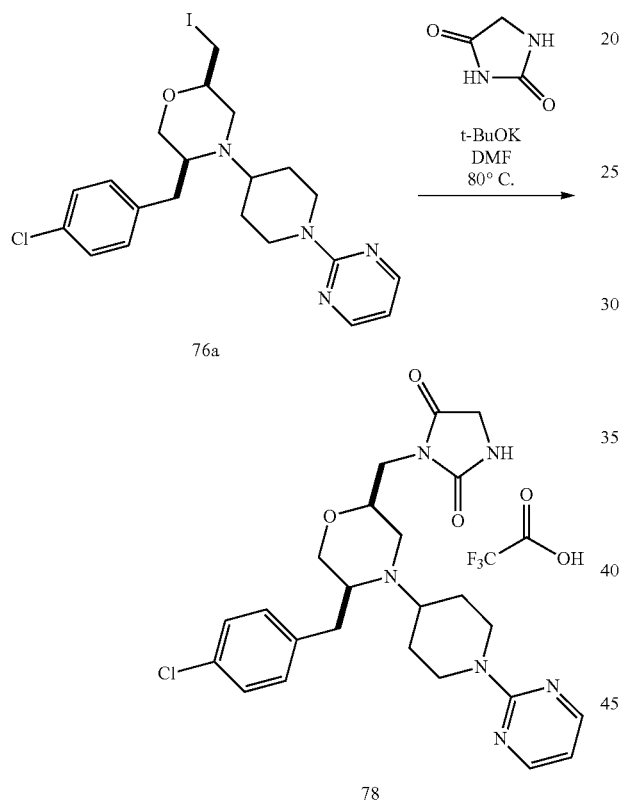

To a solution of 76a (48 mg; 0.093 mmol) in DMF (0.5 mL) hydantoin (28 mg; 0.28 mmol) and t-BuOK (31 mg; 0.28 mmol) were added and the mixture was stirred at 80° C. for 5 hours. TLC and LCMS showed completion of the reaction. The mixture was cooled down to room temperature and quenched with water, diluted with E$_2$O and washed with water (3×), dried over anhydrous Na$_2$SO$_4$, filtered and concentrated in vacuo. Then product was purified by preparative reversed-phase column chromatography (Luna® 5 μm Phenyl-Hexyl, LC Column 250×21.2 mm, water/MeCN+1% TFA, 80:20 to 60:40, 30 minutes). Compound 78 was obtained as a TFA salt in 3% yield (2 mg; 0.003 mmol).

ESI-MS m/z for $C_{24}H_{30}ClN_6O_3$ found 485.0/487.0 [M+H]$^+$; $^1$H NMR (700 MHz, D$_2$O) δ 8.54-8.45 (m, 2H), 7.44-7.34 (m, 2H), 7.29-7.20 (m, 2H), 6.98-6.86 (m, 1H), 4.68-4.56 (m, 2H), 4.12-4.03 (m, 3H), 3.94-3.85 (m, 2H), 3.84-3.76 (m, 2H), 3.72-3.61 (m, 3H), 3.31-3.16 (m, 5H), 2.53-2.42 (m, 2H), 1.80-1.67 (m, 2H).

Example 79

Synthesis of (3S,5S)-5-(4-chlorobenzyl)-1-(1-(pyridin-2-yl)piperidin-4-yl)pyrrolidin-3-ol 2,2,2-trifluoroacetate (79)

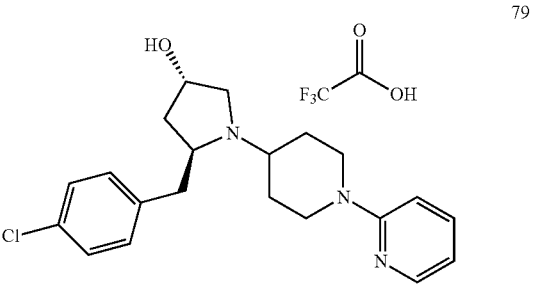

The title compound (79) was obtained as a TFA salt (123 mg; 0.25 mmol) from 1g by the purification by preparative reversed-phase column chromatography (Luna® 5 μm Phenyl-Hexyl, LC Column 250×21.2 mm, water/MeCN+1% TFA, 95:5 to 60:40, 30 minutes).

ESI-MS m/z for $C_{21}H_{27}ClN_3O$ found 372.0/374.0 [M+H]$^+$; $^1$H NMR (700 MHz, D$_2$O, 333K) δ 8.41-8.29 (m, 1H), 8.22-8.13 (m, 1H), 7.78-7.70 (m, 2H), 7.66-7.55 (m, 3H), 7.35-7.26 (m, 1H), 4.96-4.82 (m, 1H), 4.58-4.47 (m, 3H), 4.05-4.00 (m, 1H), 4.00-3.92 (m, 1H), 3.75-3.47 (m, 4H), 3.38-3.23 (m, 1H), 2.63-2.51 (m, 2H), 2.48-2.31 (m, 2H), 2.21-2.09 (m, 2H).

Example 80

Synthesis of (3R,5S)-5-(4-chlorobenzyl)-1-(1-(pyridin-2-yl)piperidin-4-yl)pyrrolidin-3-ol 2,2,2-trifluoroacetate (80)

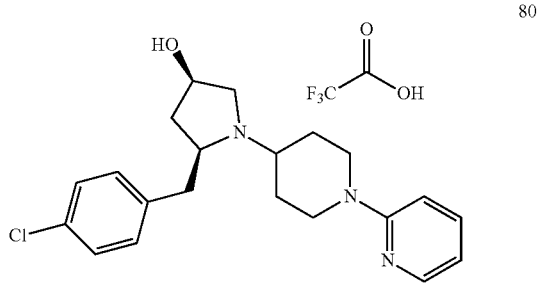

The title compound (80) was obtained as a TFA salt in 14% overall yield in a similar way to Example 79 and compound 1g with the exception that, in the first step of the synthesis, N-Boc-cis-4-hydroxy-D-proline was used instead of N-Boc-trans-4-hydroxy-D-proline.

ESI-MS m/z for $C_{21}H_{27}ClN_3O$ found 372.1/374.1 [M+H]$^+$; $^1$H NMR (700 MHz, D$_2$O, 333K) δ 8.38-8.31 (m, 1H), 8.24-8.16 (m, 1H), 7.76-7.70 (m, 2H), 7.66-7.55 (m, 3H), 7.36-7.28 (m, 1H), 4.95-4.84 (m, 1H), 4.62-4.45 (m, 3H), 4.04-4.00 (m, 1H), 3.98-3.91 (m, 1H), 3.72-3.48 (m, 4H), 3.39-3.26 (m, 1H), 2.65-2.52 (m, 2H), 2.51-2.33 (m, 2H), 2.21-2.11 (m, 2H).

Example 81

Synthesis of (S)-3-(4-chlorobenzyl)-4-(1-(pyridin-2-yl)piperidin-4-yl)-2,3,4,5-tetrahydrobenzo[1,4]oxazepine hydrochloride (81)

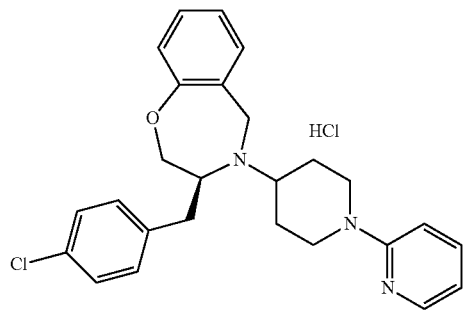

Step 1

Synthesis of tert-butyl (S)-(1-(4-chlorophenyl)-3-hydroxypropan-2-yl)carbamate (81a)

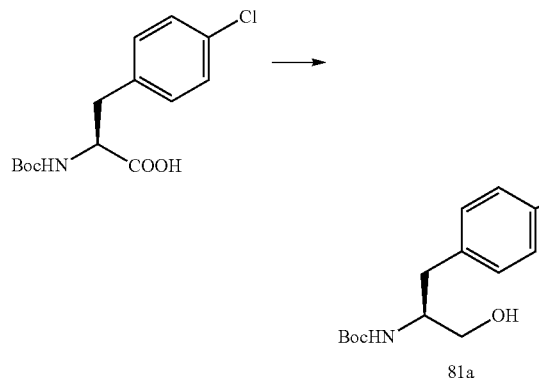

The title compound (81a) was obtained from Boc-L-p-chlorophenylalanine (15 g; 50 mmol) according to the General Procedure XXI in 81% yield (11.5 g; 40.2 mmol).

ESI-MS m/z for $C_{14}H_{21}ClNO_3$ found 285.9/287.9 $[M+H]^+$

Step 2

Synthesis of 2-hydroxy-N-methoxy-N-methylbenzamide (81b)

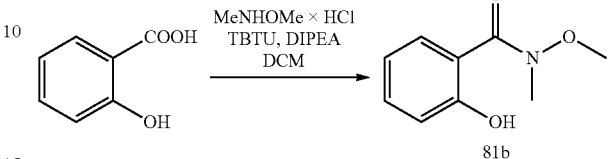

The title compound (81b) was obtained from salicylic acid (10 g; 72.35 mmol) according to the General Procedure XV as a colorless oil in 53% yield (6.98 g; 38.54 mmol).

ESI-MS m/z for $C_9H_{12}NO_3$ found 182.0 $[M+H]^+$

Step 3

Synthesis of tert-butyl (S)-(1-(4-chlorophenyl)-3-(2-(methoxy(methyl)carbamoyl)phenoxy)propan-2-yl)carbamate (81c)

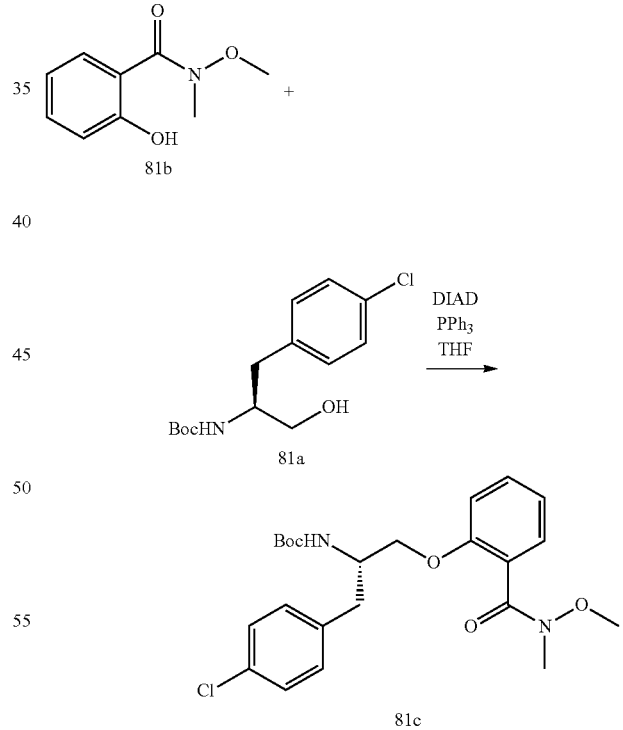

The title compound (81c) was synthesized from compounds 81b (1.27 g; 7 mmol) and 81a (2.50 g; 8.75 mmol) according to the General Procedure XVIII and was obtained as a white solid in 8% yield (260 mg; 0.58 mmol).

ESI-MS m/z for $C_{23}H_{29}ClN_2O_5Na$ found 471.1/473.1 $[M+Na]^+$

Step 4

Synthesis of (S)-tert-butyl (1-(4-chlorophenyl)-3-(2-formylphenoxy)propan-2-yl)carbamate (81d)

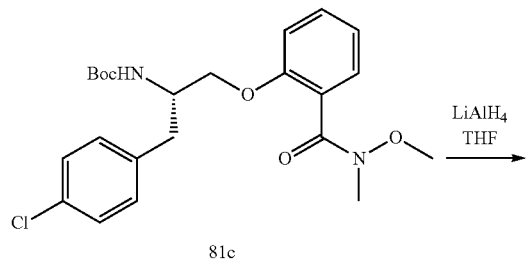

The title compound (81d) was prepared from 81c (260 mg; 0.58 mmol) according to the General Procedure XIX and was obtained as a transparent oil in 96% yield (217 mg; 0.56 mmol).

ESI-MS m/z for $C_{16}H_{17}ClNO_2$ found 290.0/292.0 [M+H-Boc]$^+$; $^1$H NMR (700 MHz, DMSO-d$_6$) δ 10.38 (s, 1H), 7.70-7.64 (m, 1H), 7.62-7.60 (m, 1H), 7.29 (AA'BB', J=8.3 Hz, 2H), 7.24 (AA'BB', J=8.4 Hz, 2H), 7.14 (d, J=7.1 Hz, 1H), 7.06 (t, J=7.6 Hz, 1H), 4.10 (dd, J=9.5, 4.0 Hz, 1H), 4.07-4.03 (m, 1H), 3.99-3.97 (m, 1H), 3.57 (ddd, J=6.2, 4.2, 2.5 Hz, 1H), 2.89 (dd, J=13.9, 5.3 Hz, 1H), 1.74-1.72 (m, 1H), 1.26 (s, 9H).

Step 5

Synthesis of (S)-3-(4-chlorobenzyl)-2,3,4,5-tetrahydrobenzo[f][1,4]oxazepine (81e)

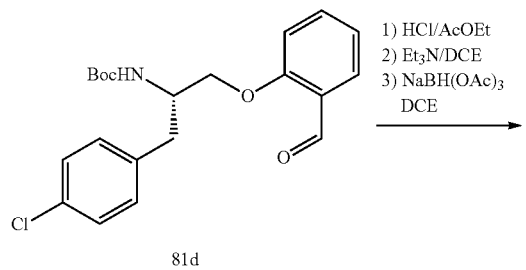

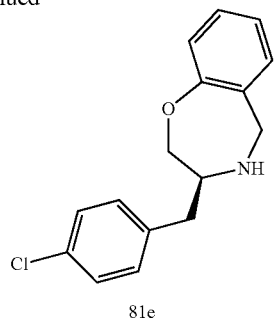

The title compound (81e) was obtained from 81d (217 mg; 0.56 mmol) according to the General Procedure XX as a yellowish oil in 98% yield (150 mg; 0.55 mmol).

ESI-MS m/z for $C_{16}H_{17}ClNO$ found 274.1/276.0 [M+H]$^+$; $^1$H NMR (700 MHz, DMSO-d$_6$) δ 7.35 (AA'BB', J=8.3 Hz, 2H), 7.28 (AA'BB', J=8.3 Hz, 2H), 7.16-7.14 (m, 2H), 6.97 (t, J=7.4 Hz, 1H), 6.94 (d, J=7.9 Hz, 1H), 4.20 (dd, J=12.3, 2.5 Hz, 1H), 3.89-3.81 (m, 2H), 3.49 (bs, 1H), 3.07 (bs, 3H), 2.68-2.63 (m, 1H).

Step 6

Synthesis of (S)-3-(4-chlorobenzyl)-4-(1-(pyridin-2-yl)piperidin-4-yl)-2,3,4,5-tetrahydrobenzo[f][1,4]oxazepine hydrochloride (81)

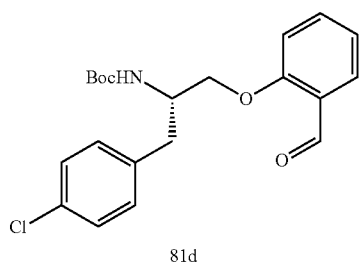

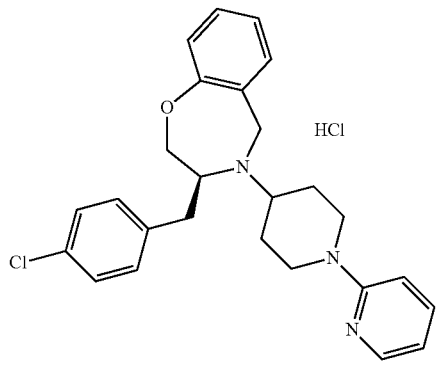

The title compound (81) was obtained as a hydrochloride salt from 81e (100 mg; 0.37 mmol) according to the General Procedure VI in 5% yield (3.5 mg; 0.02 mmol).

ESI-MS m/z for $C_{26}H_{29}ClN_3O$ found 434.1/436.31 [M+H]$^+$; $^1$H NMR (700 MHz, D$_2$O, 333K) δ 8.36-8.32 (m, 1H), 8.24-8.20 (m, 1H), 7.81-7.75 (m, 3H), 7.75-7.71 (m, 1H), 7.71-7.67 (m, 2H), 7.61-7.57 (m, 1H), 7.56-7.51 (m, 1H), 7.49-7.45 (m, 1H), 7.34-7.29 (m, 1H), 5.15 (d, J=15.3 Hz, 1H), 4.91 (d, J=15.1 Hz, 1H), 4.67-4.61 (m, 1H), 4.61-4.56 (m, 1H), 4.56-4.48 (m, 2H), 4.48-4.43 (m, 1H), 4.11-4.03 (m, 1H), 3.85-3.77 (m, 1H), 3.59-3.50 (m, 2H), 3.50-3.44 (m, 1H), 2.77-2.65 (m, 2H), 2.33-2.19 (m, 2H).

Example 82

Synthesis of (2R,5S)-2-((1H-imidazol-1-yl)methyl)-5-(4-chlorobenzyl)-4-(1-(4-chloropyridin-2-yl)piperidin-4-yl)-1-methylpiperazine hydrochloride (82)

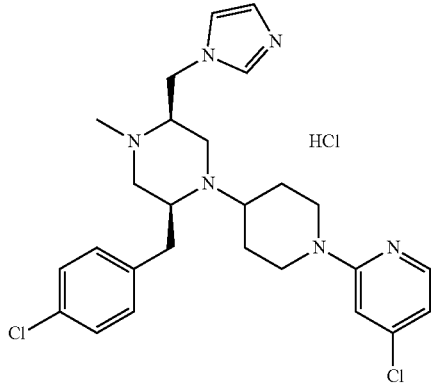

The title compounds 82 was obtained as a hydrochloride salt in 36% overall yield in a similar way to Example 51 with the exception that, in the second step of the synthesis, imidazole was used instead of morpholine and the reaction was carried out under room temperature and without the addition of K$_2$CO$_3$.

ESI-MS m/z for $C_{26}H_{33}Cl_2N_6$ found 499.2/501.2 [M+H]$^+$; $^1$H NMR (250 MHz, D$_2$O) δ 8.82-8.70 (m, 1H), 7.89-7.81 (m, 1H), 7.63-7.50 (m, 1H), 7.52-7.42 (m, 1H), 7.37-7.26 (m, 2H), 7.26-7.09 (m, 2H), 7.09-6.98 (m, 1H), 6.86-6.70 (m, 1H), 4.68-4.57 (m, 1H), 4.48-4.35 (m, 1H), 4.21-4.06 (m, 2H), 3.86-3.66 (m, 1H), 3.66-3.33 (m, 2H), 3.07-2.65 (m, 7H), 2.58-2.32 (m, 4H), 2.25-2.00 (m, 2H), 1.68-1.38 (m, 2H).

Example 83

Synthesis of (2S,5S)-2-(4-chlorobenzyl)-1-(1-(4-chloropyridin-2-yl)piperidin-4-yl)-4-methyl-5-((4-methylpiperazin-1-yl)methyl)piperazine 2,2,2-trifluoroacetate (83)

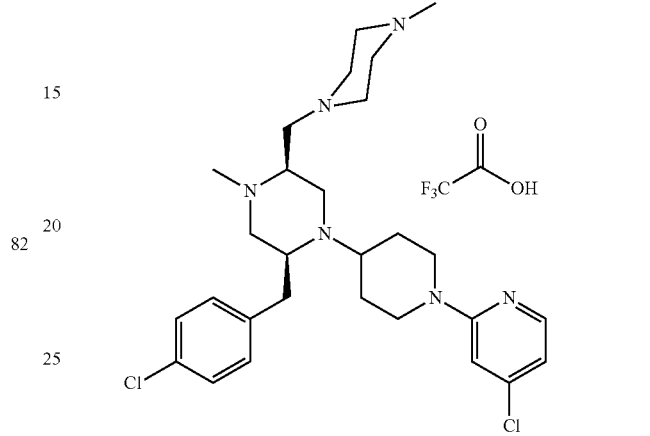

The title compound 83 was obtained as a TFA salt in 32% overall yield in a similar way to Example 51 with the exception that, in the second step of the synthesis, 1-methylpiperazine was used instead of morpholine and the reaction was carried out under room temperature and without the addition of K$_2$CO$_3$.

ESI-MS m/z for $C_{28}H_{41}Cl_2N_6$ found 531.2/533.2 [M+H]$^+$; $^1$H NMR (250 MHz, D$_2$O) δ 7.77-7.63 (m, 1H), 7.38-7.26 (m, 3H), 7.26-7.14 (m, 2H), 6.92-6.80 (m, 1H), 4.00-3.82 (m, 2H), 3.57-3.24 (m, 5H), 3.24-2.88 (m, 12H), 2.88-2.76 (m, 6H), 2.76-2.59 (m, 2H), 2.59-2.34 (m, 2H), 1.98-1.83 (m, 2H), 1.76-1.41 (m, 2H).

Example 84

Synthesis of (2S,5R)-2-(4-chlorobenzyl)-1-(1-(4-chloropyridin-2-yl)piperidin-4-yl)-4-methyl-5-((naphthalen-2-yloxy)methyl)piperazine 2,2,2-trifluoroacetate (84)

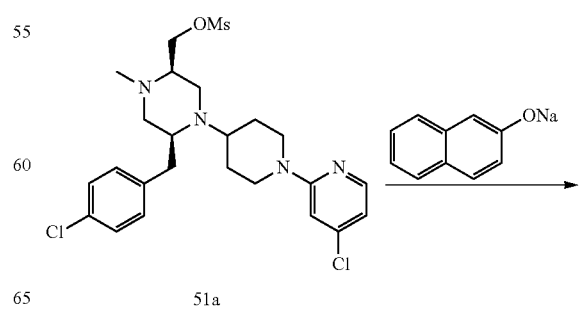

353

-continued

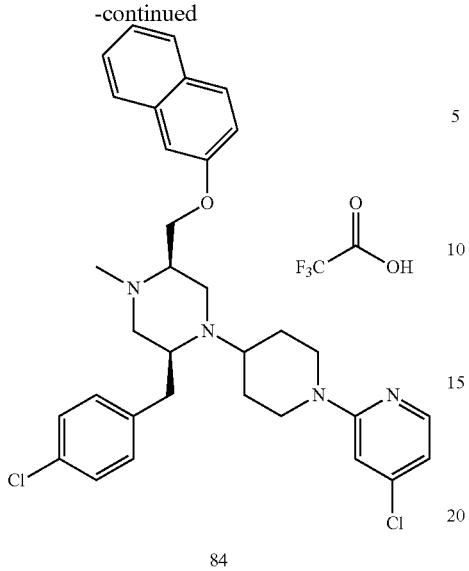

84

The mixture of 51a (110 mg; 0.21 mmol) and solution of sodium 2-naphtholate (698 mg; 4.2 mmol) in THF (4.2 mL) was stirred at room temperature overnight. TLC and LC-MS showed completion of the reaction. The mixture was washed with 1M NaOH, brine and water, dried over anhydrous $Na_2SO_4$, filtered and concentrated in vacuo. The crude product was purified by silica-gel column chromatography (hexane/AcOEt, 100:0 to 60:40, v/v) and then by preparative reversed-phase column chromatography (Luna® 5 μm Phenyl-Hexyl, LC Column 250×21.2 mm, water/MeCN+1% TFA, 90:10 to 30:70, 30 minutes). Compound 84 was obtained as a TFA salt in 20% yield (28 mg; 0.041 mmol).

ESI-MS m/z for $C_{33}H_{37}Cl_2N_4O$ found 574.8/576.8 $[M+H]^+$; $^1$H NMR (700 MHz, DMSO-$d_6$) δ 8.14-8.03 (m, 1H), 7.91-7.78 (m, 3H), 7.54-7.49 (m, 1H), 7.48-7.32 (m, 6H), 7.32-7.20 (m, 1H), 7.10-6.96 (m, 1H), 6.78-6.65 (m, 1H), 4.56-3.72 (m, 8H), 3.56-2.64 (m, 12H), 1.76-1.34 (m, 2H).

Example 85

Synthesis of 4-((2S,5S)-5-(4-chlorobenzyl)-2-methylmorpholino)-1-(pyridin-2-yl)piperidin-2-one 2,2,2-trifluoroacetate (85)

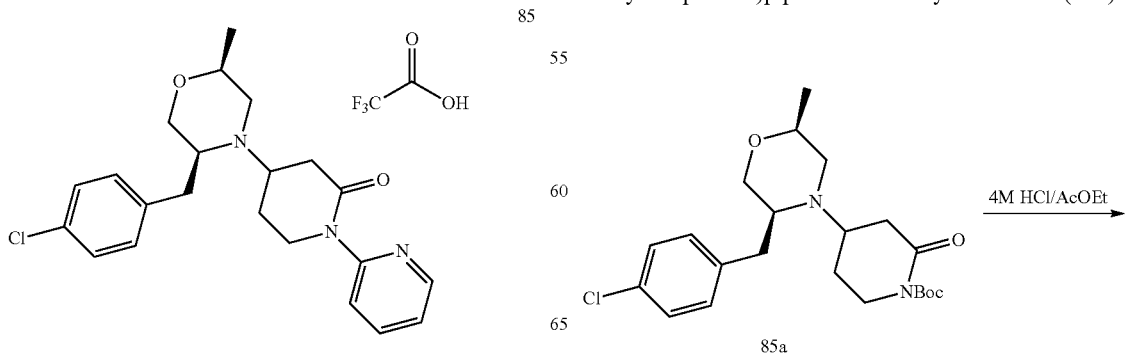

354

Step 1

Synthesis of tert-butyl 4-((2S,5S)-5-(4-chlorobenzyl)-2-methylmorpholino)-2-oxopiperidine-1-carboxylate (85a)

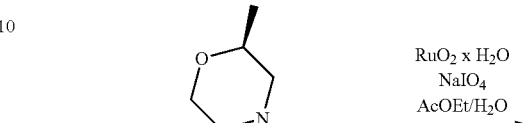

8d

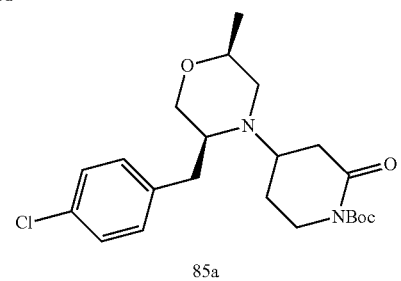

85a

To the solution of sodium (meta)periodate ($NaIO_4$; 488 mg; 2.28 mmol) in water (7.3 mL) $RuO_2 \times H_2O$ (25 mg; 0.18 mmol) was added and then the green solution was stirred for 5 minutes. To this mixture a solution of 8d (374 mg; 0.91 mmol) in AcOEt (3.6 mL) was added and stirred at room temperature overnight. TLC and LC-MS showed completion of the reaction. The mixture was filtered through a pad of the Celite, washed with AcOEt. An organic layer was washed with 5% $NaHCO_3$, brine and dried over anhydrous $Na_2SO_4$, filtered and concentrated in vacuo. The crude product was used to the next step without any additional purification. Compound 85a was obtained in 50% yield (194 mg; 0.46 mmol).

ESI-MS m/z for $C_{22}H_{32}ClN_2O_4$ found 423.2/425.2 $[M+H]^+$

Step 2

Synthesis of 4-((2S,5S)-5-(4-chlorobenzyl)-2-methylmorpholino)piperidin-2-one hydrochloride (85b)

85a

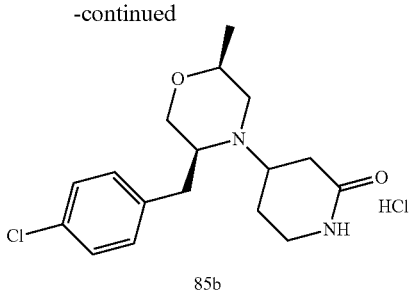

The title compound (85b) was obtained as a hydrochloride salt from 85a (177 mg; 0.42 mmol) according to the General Procedure IVa in 25% yield (39 mg; 0.11 mmol).

ESI-MS m/z for $C_{17}H_{24}ClN_2O_2$ found 323.1/325.1 [M+H]+; 1H NMR (700 MHz, Methanol-$d_4$) δ 7.43-7.35 (m, 2H), 7.35-7.29 (m, 2H), 4.19-4.13 (m, 1H), 3.72-3.66 (m, 2H), 3.66-3.59 (m, 1H), 3.58-3.45 (m, 3H), 3.17-3.00 (m, 4H), 2.80-2.70 (m, 1H), 2.64-2.54 (m, 1H), 2.10 (d, J=13.8 Hz, 1H), 1.94 (d, J=13.8 Hz, 1H), 1.45 (d, J=6.9 Hz, 3H).

Step 3

Synthesis of 4-((2S,5S)-5-(4-chlorobenzyl)-2-methylmorpholino)-1-(pyridin-2-yl)piperidin-2-one 2,2,2-trifluoroacetate (85)

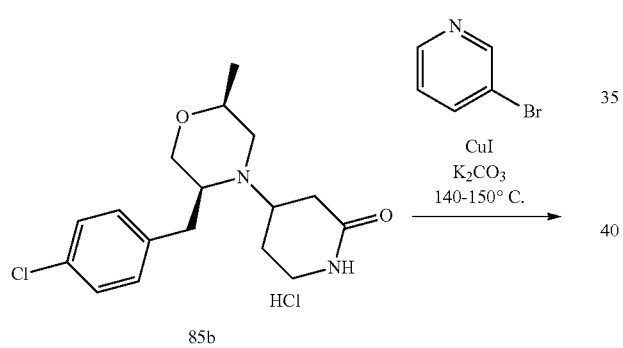

The mixture of 85b (33 mg; 0.092 mmol), 2-bromopyridine (0.44 mL; 4.6 mmol), $K_2CO_3$ (25 mg; 0.18 mmol) and CuI (catalytic amount) was heated at 140-150° C. for 3 days. The reaction progress was monitored by LC-MS. After analytical control was indicated completion of the reaction, the reaction was diluted with AcOEt and washed with 2M HCl. The organic fractions were dried over anhydrous $Na_2SO_4$, filtered and concentrated in vacuo. The crude product was purified twice by preparative reversed-phase column chromatography (Luna® 5 μm Phenyl-Hexyl, LC Column 250×21.2 mm, water/MeCN+1% TFA, 95:5 to 65:35, 45 minutes). Compound 85 was obtained as a TFA salt in 2% yield (0.9 mg; 0.002 mmol).

ESI-MS m/z for $C_{22}H_{27}ClN_3O_2$ found 400.1/402.1 [M+H]+; 1H NMR (700 MHz, $D_2O$) δ 7.97-7.93 (m, 1H), 7.83-7.79 (m, 1H), 7.35-7.31 (m, 2H), 7.28-7.20 (m, 3H), 6.93-6.87 (m, 1H), 4.27-4.20 (m, 1H), 4.19-4.12 (m, 2H), 3.96-3.86 (m, 1H), 3.74 (d, J=11.4 Hz, 1H), 3.72-3.65 (m, 2H), 3.31-3.19 (m, 2H), 3.09-2.98 (m, 2H), 2.23-2.14 (m, 1H), 2.10-2.02 (m, 2H), 1.90-1.83 (m, 1H), 1.34 (d, J=6.9 Hz, 3H).

Example 86

Synthesis of (2S,5S)-2-(4-chlorobenzyl)-4-isobutyl-5-methyl-1-(1-(pyridin-2-yl)piperidin-4-yl)piperazine 2,2,2-trifluoroacetate (86)

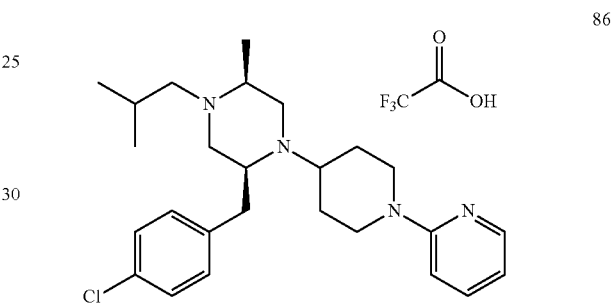

Step 1

Synthesis of methyl ((S)-2-((tert-butoxycarbonyl)amino)-3-(4-chlorophenyl)propyl)-L-alaninate (86a)

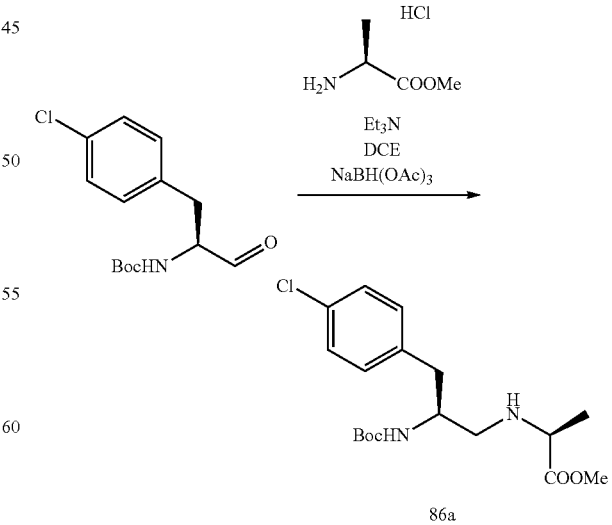

The reductive amination of known aldehyde (11.15 g; 39.11 mmol) with L-alanine methyl ester hydrochloride (8.1 g; 58.67 mmol) was accomplished according to the General Procedure VI. The crude product 86a was obtained in 50% yield (7.2 g, 19.56 mmol).

ESI-MS m/z for $C_{18}H_{28}ClN_2O_4$ found 371.2/373.2 $[M+H]^+$

Step 2

Synthesis of (3S,6S)-6-(4-chlorobenzyl)-3-methylpiperazin-2-one (86b)

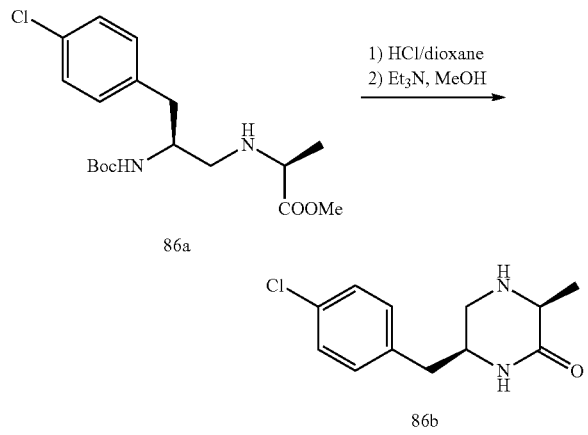

The title compound (86b) was obtained from 86a (10.2 g, 27.5 mmol) according to the General Procedure VIII in 32% yield (2.1 g; 8.79 mmol).

ESI-MS m/z for $C_{12}H_{16}ClN_2O$ found 239.1/241.1 $[M+H]^+$

Step 3

Synthesis of tert-butyl (2S,5S)-5-(4-chlorobenzyl)-2-methyl-3-oxopiperazine-1-carboxylate (86c)

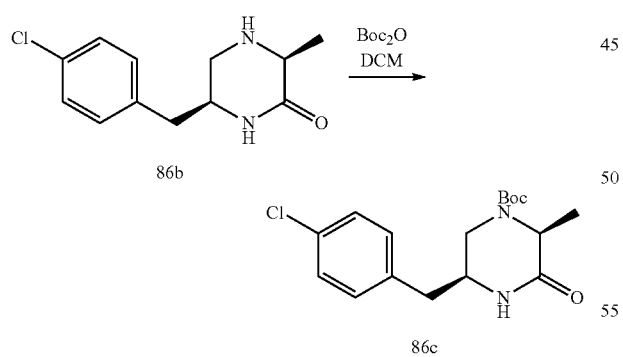

To a solution of 86b (2.1 g; 8.79 mmol) in dichloromethane (30 mL), di-tert-butyl dicarbonate (Boc₂O) (2.8 g, 13.19 mmol) was added and the reaction mixture was stirred at room temperature overnight, after which time TLC and LC-MS showed almost complete consumption of the starting material. The volatiles were removed in vacuo and the residue was purified by silica-gel column chromatography (hexane/AcOEt, 8:2 to 1:1, v/v) giving 86c as white foam in 70% yield (2.08 g; 6.15 mmol).

ESI-MS m/z for $C_{17}H_{24}ClN_2O_3$ found 339.1/341.1 $[M+H]^+$

Step 4

Synthesis of tert-butyl (2S,5S)-5-(4-chlorobenzyl)-2-methylpiperazine-1-carboxylate (86d)

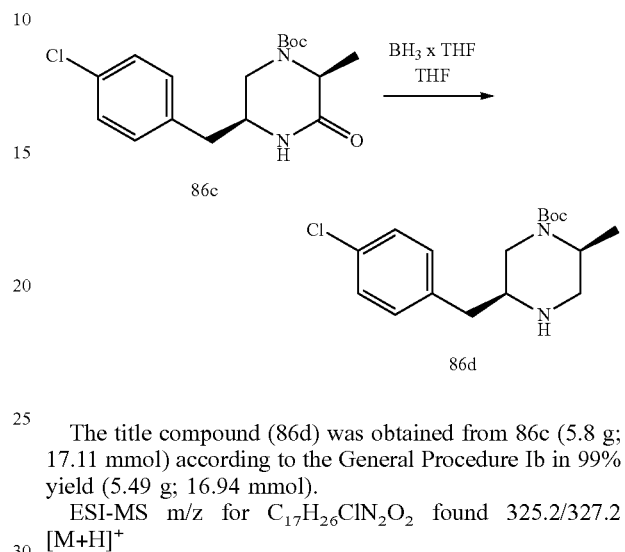

The title compound (86d) was obtained from 86c (5.8 g; 17.11 mmol) according to the General Procedure Ib in 99% yield (5.49 g; 16.94 mmol).

ESI-MS m/z for $C_{17}H_{26}ClN_2O_2$ found 325.2/327.2 $[M+H]^+$

Step 5

Synthesis of tert-butyl (2S,5S)-4-(1-((allyloxy)carbonyl)piperidin-4-yl)-5-(4-chlorobenzyl)-2-methylpiperazine-1-carboxylate (86e)

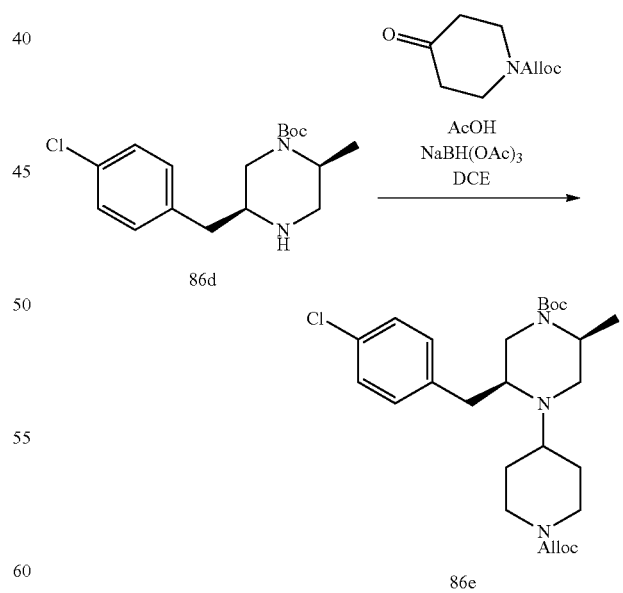

The title compound (86e) was obtained from 86d (5.6 g; 17.23 mmol) according to the General Procedure VI in 31% yield (2.62 g; 5.34 mmol).

ESI-MS m/z for $C_{26}H_{39}ClN_3O_4$ found 492.3/494.3 $[M+H]^+$

Step 6

Synthesis of allyl 4-((2S,5S)-2-(4-chlorobenzyl)-5-methylpiperazin-1-yl)piperidine-1-carboxylate dihydrochloride (86f)

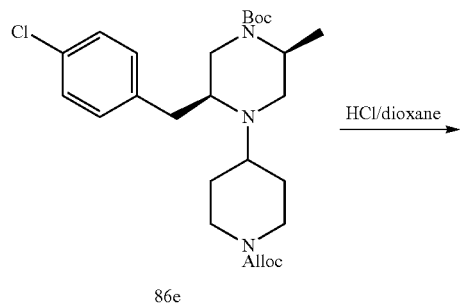

86e

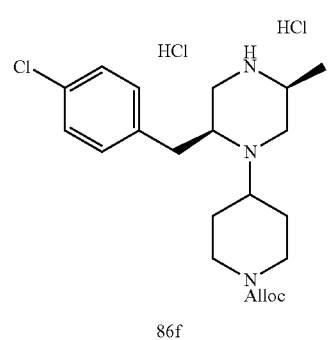

86f

The title compound (86f) was obtained as a dihydrochloride salt from 86e (2.62 g; 5.34 mmol) according to the General Procedure IVa in 81% yield (2 g; 4.31 mmol).

ESI-MS m/z for $C_{21}H_{31}ClN_3O_2$ found 392.2/394.2 $[M+H]^+$

Step 7

Synthesis of allyl 4-((2S,5S)-2-(4-chlorobenzyl)-4-isobutyl-5-methylpiperazin-1-yl)piperidine-1-carboxylate (86g)

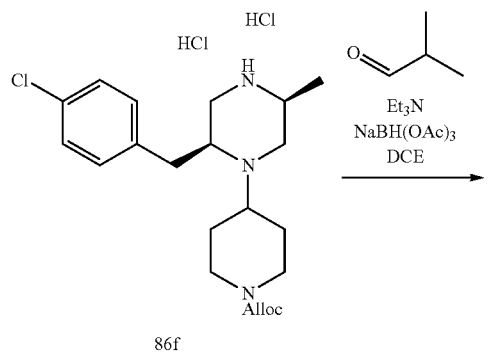

86f

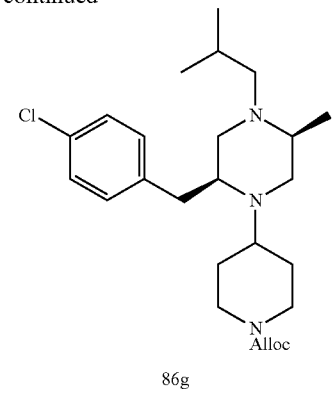

86g

The title compound (86g) was obtained from 86f (0.3 g; 0.65 mmol) according to the General Procedure VI in 99% yield (286 mg; 0.64 mmol).

ESI-MS m/z for $C_{25}H_{39}ClN_3O_2$ found 448.3/450.3 $[M+H]^+$

Step 8

Synthesis of (2S,5S)-2-(4-chlorobenzyl)-4-isobutyl-5-methyl-1-(piperidin-4-yl)piperazine (86h)

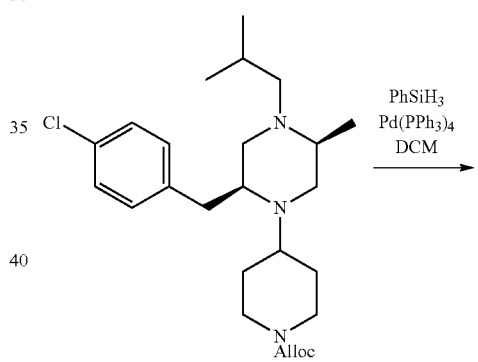

86g

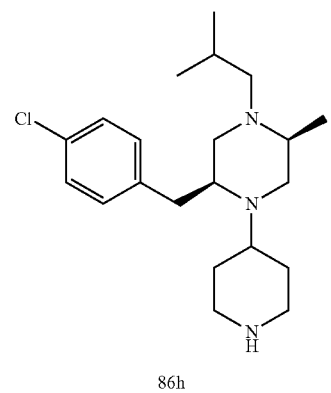

86h

To a degassed solution of 86g (0.3 g; 0.66 mmol) in PhSiH₃ (1 mL) and dichloromethane (4 mL) Pd(PPh₃)₄ (38 mg, 0.03 mmol) was added and the reaction mixture was stirred at room temperature for 20 minutes, after which time TLC and LC-MS showed complete consumption of the starting material. To the reaction mixture 1M HCl was added and phases were separated. The HCl phase was alkalized and brine was added, then extracted with DCM. The combined organic solutions were dried over anhydrous Na₂SO₄, filtered and concentrated in vacuo. The crude product was used to the next step without any additional purification. Compound 86h was obtained in 76% yield (180 mg; 0.5 mmol).

ESI-MS m/z for $C_{21}H_{35}ClN_3$ found 364.2/366.2 $[M+H]^+$

Step 9

Synthesis of (2S,5S)-2-(4-chlorobenzyl)-4-isobutyl-5-methyl-1-(1-(pyridin-2-yl)piperidin-4-yl)piperazine 2,2,2-trifluoroacetate (86)

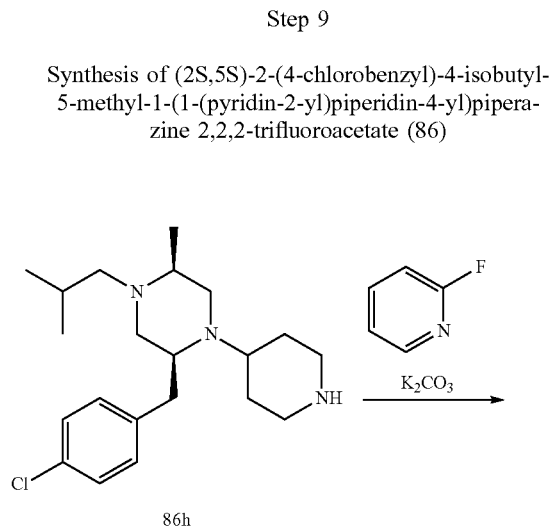

The title compound (86) was obtained as a TFA salt from 86h (60 mg; 0.16 mmol) according to the General Procedure IX in 45% yield (40 mg; 0.072 mmol) with the exception that, this reaction was carried out in excess of 2-fluoropyridine.

ESI-MS m/z for $C_{26}H_{38}ClN_4$ found 441.2/443.2 $[M+H]^+$; ¹H NMR (700 MHz, D₂O) δ7.99-7.91 (m, 1H), 7.82-7.76 (m, 1H), 7.41-7.33 (m, 2H), 7.31-7.27 (m, 2H), 7.26-7.18 (m, 1H), 6.97-6.85 (m, 1H), 4.22-4.06 (m, 3H), 3.89-3.70 (m, 2H), 3.68-3.53 (m, 1H), 3.53-3.38 (m, 3H), 3.30-3.19 (m, 2H), 3.15-2.98 (m, 3H), 2.93-2.87 (m, 1H), 2.31-2.09 (m, 2H), 1.94-1.74 (m, 3H), 1.46 (d, J=6.8 Hz, 3H), 0.91-0.71 (m, 6H).

Example 87

Synthesis of (2S,5S)-5-(4-chlorobenzyl)-2-isopropyl-4-(1-(pyridin-2-yl)piperidin-4-yl)morpholine 2,2,2-trifluoroacetate (87)

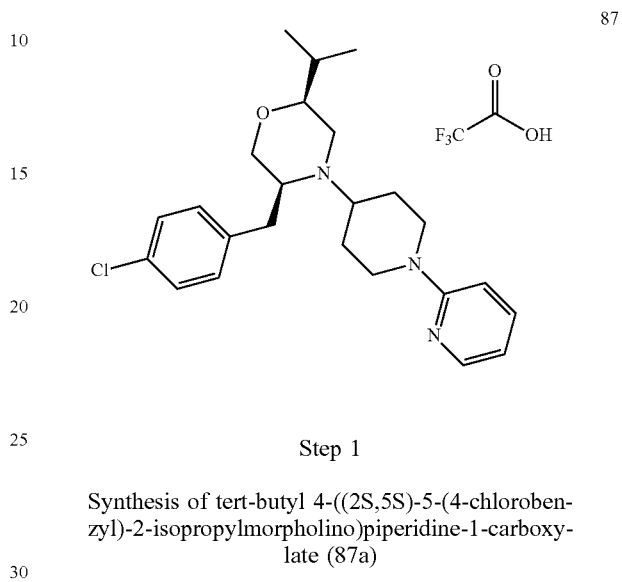

Step 1

Synthesis of tert-butyl 4-((2S,5S)-5-(4-chlorobenzyl)-2-isopropylmorpholino)piperidine-1-carboxylate (87a)

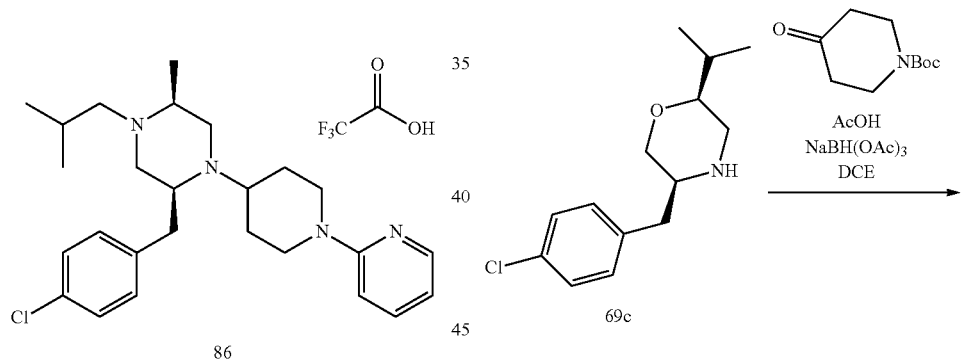

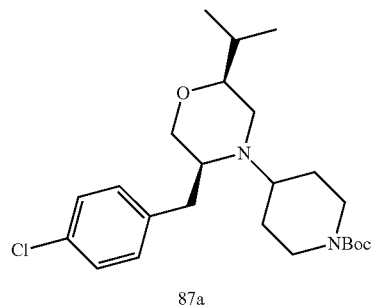

The title compound (87a) was obtained from 69c (1 g; 3.95 mmol) according to the General Procedure VI in 29% yield (500 mg; 1.15 mmol).

ESI-MS m/z for $C_{24}H_{38}ClN_2O_3$ found 437.2/439.2 $[M+H]^+$

Step 2

Synthesis of (2S,5S)-5-(4-chlorobenzyl)-2-isopropyl-4-(piperidin-4-yl)morpholine dihydrochloride (87b)

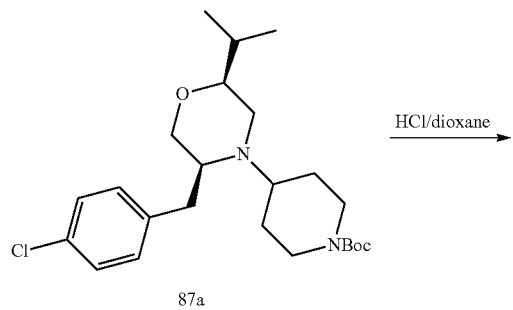

The title compound (87b) was obtained as a dihydrochloride salt from 87a (500 mg; 1.15 mmol) according to the General Procedure IVa in 99% yield (466 mg; 1.14 mmol).

ESI-MS m/z for $C_{19}H_{30}ClN_2O$ found 337.2/339.2 $[M+H]^+$

Step 3

Synthesis of (2S,5S)-5-(4-chlorobenzyl)-2-isopropyl-4-(1-(pyridin-2-yl)piperidin-4-yl)morpholine 2,2,2-trifluoroacetate (87)

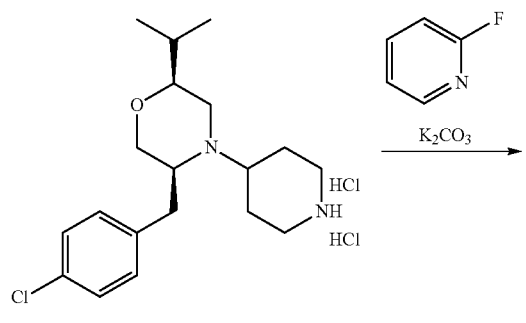

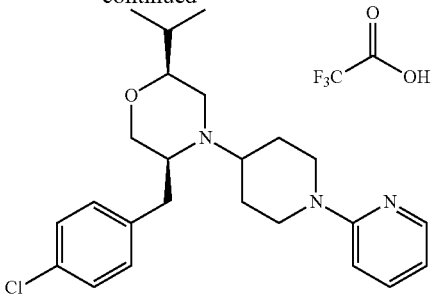

The title compound (87) was obtained as a TFA salt from 87b (180 mg; 0.44 mmol) according to the General Procedure IX in 16% yield (38 mg; 0.072 mmol) with the exception that, this reaction was carried out in excess of 2-fluoropyridine.

ESI-MS m/z for $C_{24}H_{33}ClN_3O$ found 414.1/416.1 $[M+H]^+$; $^1H$ NMR (700 MHz, DMSO-$d_6$+$D_2O$, 348 K) δ 8.10-7.99 (m, 1H), 7.76-7.66 (m, 1H), 7.43-7.35 (m, 2H), 7.35-7.25 (m, 2H), 7.08-6.94 (m, 1H), 6.85-6.73 (m, 1H), 4.35-4.28 (m, 2H), 3.75-3.67 (m, 2H), 3.66-3.59 (m, 2H), 3.50-3.47 (m, 1H), 3.35-3.30 (m, 1H), 3.14-2.96 (m, 5H), 2.31-2.24 (m, 1H), 2.23-2.17 (m, 1H), 1.86-1.77 (m, 1H), 1.67-1.58 (m, 2H), 0.98-0.88 (m, 6H).

Example 88

Synthesis of (S)-3-(4-chlorobenzyl)-4-(1-(pyridin-2-yl)piperidin-4-yl)morpholine 2,2,2-trifluoroacetate (88)

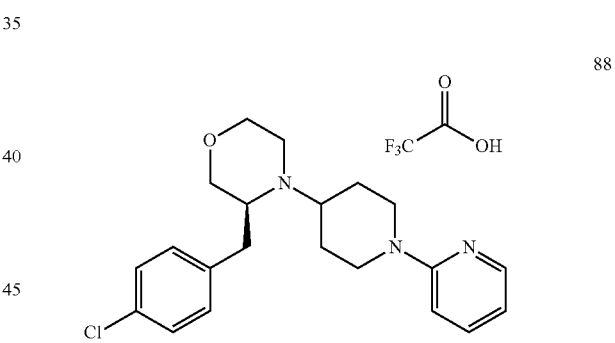

Step 1

Synthesis of 2-chloro-N-[(1S)-1-(4-chlorobenzyl)-2-hydroxyethyl]acetamide (88a)

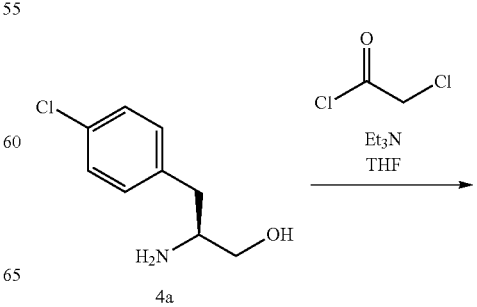

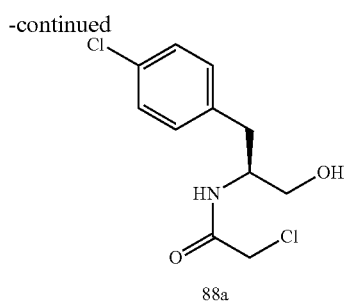

88a

To the solution of 4a (10 g; 53.86 mmol) in THF (300 mL) triethylamine (9.3 mL; 64.63 mmol) was added and the solution was cooled to 0° C. Chloroacetyl chloride (4.3 mL; 53.86 mmol) was added slowly in such a manner that the internal temperature of the reaction did not exceed 5° C. The cooling bath was then removed and the mixture was stirred for further 20 minutes. TLC showed complete consumption of the staring material at this point. Diethyl ether was then added and the whole reaction mixture was sequentially washed with 2M HCl, 1M NaOH, brine, dried over anhydrous $MgSO_4$, filtered and evaporated to dryness to give the crude product which was then crystallized from hot diethyl ether. Compound 88a was obtained in 85% yield (12 g; 45.78 mmol).

ESI-MS m/z for $C_{11}H_{14}Cl_2NO_2$ found 262.2/264.2 $[M+H]^+$; $^1H$ NMR ($CDCl_3$, 500 MHz) δ 8.05 (d, J=8.5 Hz, 1H), 7.27 (d, J=8.3 Hz, 2H), 7.18 (d, J=8.3 Hz, 2H), 4.85 (t, J=5.5 Hz, 1H), 3.95 (s, 2H), 3.88-3.81 (m, 1H), 3.36-3.27 (m, 2H), 2.8 (dd, J=5.5, 13.7 Hz, 1H), 2.6 (dd, J=8.6, 13.7 Hz, 1H).

Step 2

Synthesis of (5S)-5-(4-chlorobenzyl)morpholin-3-one (88b)

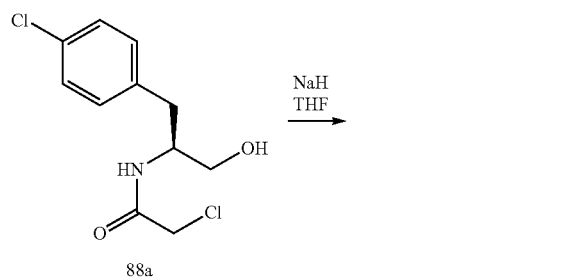

The title compound (88b) was obtained from compound 88a (11.6 g; 44.25 mmol) according to the General Procedure II in 59% yield (5.89 g; 26.11 mmol).

ESI-MS m/z for $C_{11}H_{13}ClNO_2$ found 226.2/228.2 $[M+H]^+$; $^1H$ NMR ($CDCl_3$, 500 MHz) δ 7.30 (d, J=8.3 Hz, 2H), 7.11 (d, J=8.3 Hz, 2H), 4.15 (d, J=2.8 Hz, 2H), 3.87 (dd, J=3.5, 11.8 Hz, 1H), 3.73-3.67 (m, 1H), 3.57-3.52 (m, 1H), 2.85 (dd, J=6.0, 13.7 Hz, 1H), 2.71 (dd, J=8.6, 13.7 Hz, 1H).

Step 3

Synthesis of (5S)-5-(4-chlorobenzyl)morpholine (88c)

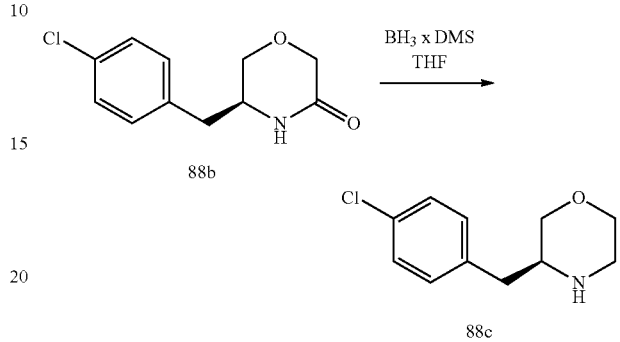

The title compound (88c) was obtained from compound 88b (3.3 g; 14.62 mmol) according to the General Procedure Ib in 64% yield (1.98 g; 9.36 mmol).

ESI-MS m/z for $C_{11}H_{15}ClNO$ found 212.2/214.2 $[M+H]^+$; $^1H$ NMR ($CDCl_3$, 500 MHz) δ 7.28 (d, J=8.3 Hz, 2H), 7.11 (d, J=8.3 Hz, 2H), 3.81-3.75 (m, 2H), 3.55-3.49 (m, 1H), 3.24 (t, J=10 Hz, 1H), 3.0-2.98 (m, 1H), 2.89-2.8 (m, 2H), 2.62 (dd, J=4.9, 13.5 Hz, 1H), 2.44 (dd, J=9.2, 13.5 Hz, 1H).

Step 4

Synthesis of (S)-3-(4-chlorobenzyl)-4-(1-(pyridin-2-yl)piperidin-4-yl)morpholine 2,2,2-trifluoroacetate (88)

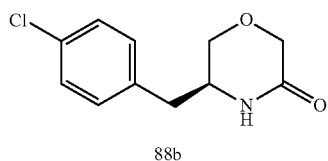

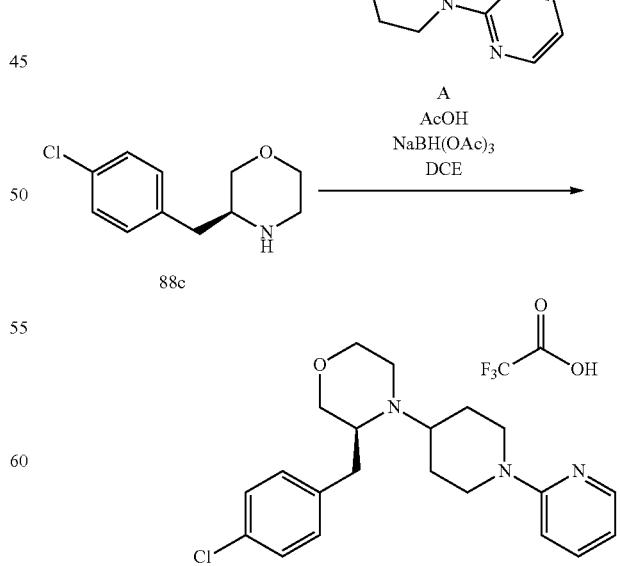

The title compound (88) was obtained as a TFA salt from 88c (150 mg; 0.7 mmol) according to the General Procedure VI in 46% yield (154 mg; 0.32 mmol).

ESI-MS m/z for $C_{21}H_{27}ClN_3O$ found 372.0/374.0 [M+H]$^+$; $^1$H NMR (700 MHz, DMSO-d$_6$+D$_2$O, 348 K) δ 8.08-7.95 (m, 1H), 7.83-7.72 (m, 1H), 7.43-7.32 (m, 2H), 7.32-7.20 (m, 2H), 7.15-7.02 (m, 1H), 6.88-6.77 (m, 1H), 4.33-4.19 (m, 2H), 3.90-3.80 (m, 3H), 3.75-3.70 (m, 1H), 3.69-3.64 (m, 1H), 3.58-3.52 (m, 1H), 3.39-3.32 (m, 1H), 3.29-3.20 (m, 2H), 3.13-3.06 (m, 1H), 3.06-2.93 (m, 2H), 2.17-2.08 (m, 2H), 1.80-1.65 (m, 2H).

Example 89

Synthesis of (2S,5S)-2-(4-chlorobenzyl)-4,5-di-isobutyl-1-(1-(pyridin-2-yl)piperidin-4-yl)piperazine 2,2,2-trifluoroacetate (89)

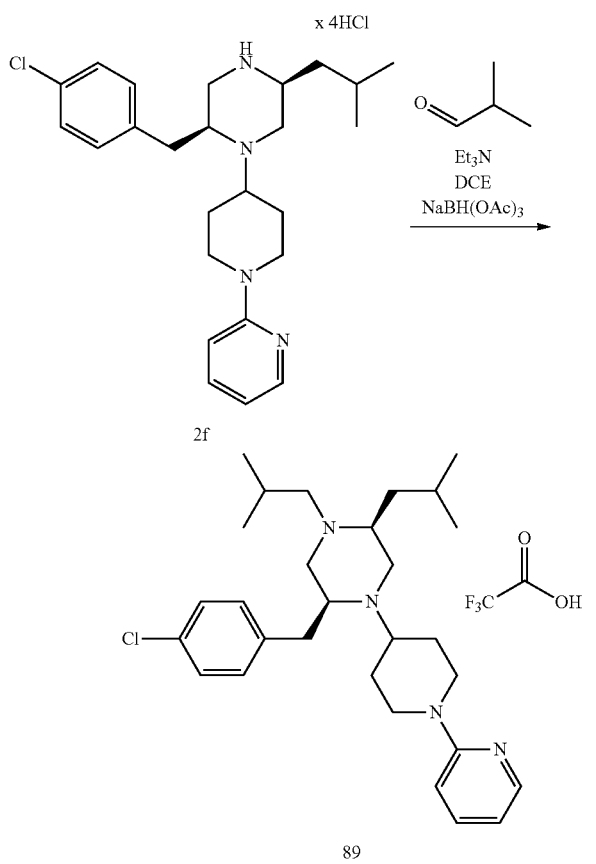

The title compound (89) was obtained as a TFA salt from 2f (50 mg; 0.087 mmol) according to the General Procedure VI in 29% yield (15 mg; 0.025 mmol).

ESI-MS m/z for $C_{29}H_{44}ClN_4$ found 483.3/485.3 [M+H]$^+$; $^1$H NMR (700 MHz, D$_2$O, 333 K) δ 8.33-8.27 (m, 1H), 8.18-8.14 (m, 1H), 7.75-7.68 (m, 2H), 7.65-7.60 (m, 2H), 7.58-7.53 (m, 1H), 7.29-7.23 (m, 2H), 4.44-4.34 (m, 2H), 4.09-4.00 (m, 1H), 3.91-3.85 (m, 1H), 3.83-3.78 (m, 1H), 3.64-3.55 (m, 3H), 3.55-3.49 (m, 1H), 3.49-3.32 (m, 4H), 3.27-3.17 (m, 2H), 2.38-2.30 (m, 2H), 2.30-2.21 (m, 1H), 2.19-2.09 (m, 2H), 2.05-1.91 (m, 2H), 1.91-1.80 (m, 1H), 1.33-1.25 (m, 3H), 1.24-1.19 (m, 9H).

Example 90

Synthesis of (2S,5S)-2-(4-chlorobenzyl)-5-isobutyl-4-(2-methoxyethyl)-1-(1-(pyridin-2-yl)piperidin-4-yl)piperazine 2,2,2-trifluoroacetate (90)

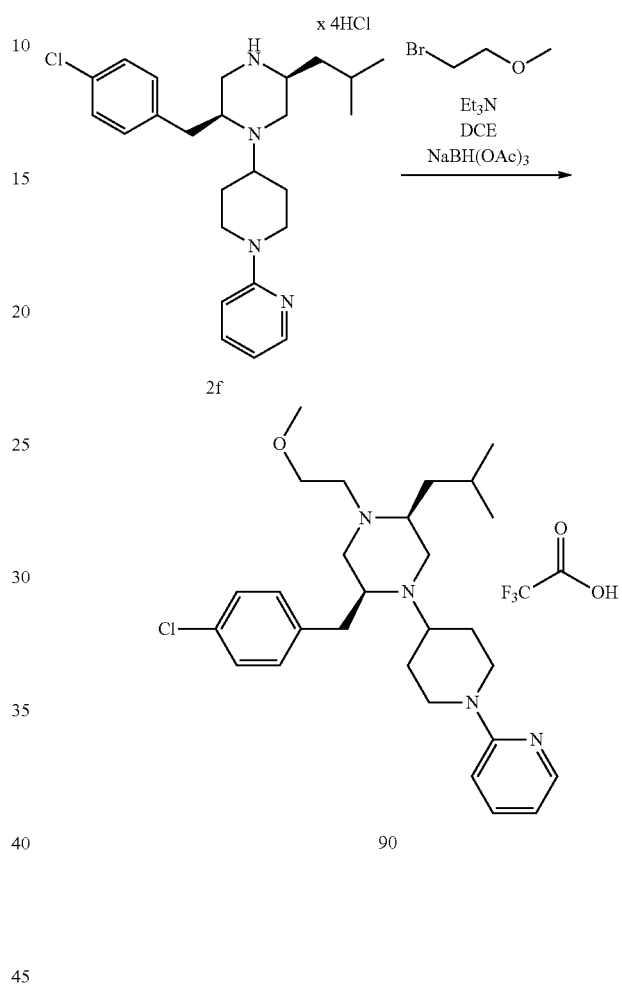

To a solution of 2f (50 mg; 0.087 mmol) in acetonitrile (0.1 mL), potassium carbonate (55 mg; 0.4 mmol) was added followed by 1-bromo-2-methoxyethane (9 μL, 0.09 mmol) and resulting mixture was heated to 100° C. overnight. LC-MS indicated completion of the reaction. The reaction mixture was filtered and the solid residue was washed with EtOAc. After evaporation of an organic phase the crude product was purified by preparative reversed-phase column chromatography (Luna® 5 μm Phenyl-Hexyl, LC Column 250×21.2 mm, water/MeCN+1% TFA, 95:5 to 40:60, 30 minutes). Compound 90 was obtained as a TFA salt in 61% yield (32 mg; 0.053 mmol).

ESI-MS m/z for $C_{28}H_{42}ClN_4O$ found 485.3/487.3 [M+H]$^+$; $^1$H NMR (700 MHz, DMSO-d$_6$+D$_2$O, 348 K) δ 7.95-7.88 (m, 1H), 7.88-7.82 (m, 1H), 7.37-7.32 (m, 2H), 7.30-7.24 (m, 2H), 7.23-7.11 (m, 1H), 6.89-6.80 (m, 1H), 4.17-4.05 (m, 2H), 3.52-3.48 (m, 3H), 3.35-3.21 (m, 3H), 3.19-3.12 (m, 5H), 3.08-3.01 (m, 3H), 2.99-2.92 (m, 1H), 2.90-2.84 (m, 2H), 2.82-2.78 (m, 1H), 1.89-1.77 (m, 2H), 1.69-1.55 (m, 3H), 1.49-1.42 (m, 2H), 0.90 (d, J=6.5 Hz, 3H), 0.85 (d, J=6.5 Hz, 3H).

Example 91

Synthesis of (2S)-2-(4-chlorobenzyl)-4-methoxy-4-methyl-1'-(pyridin-2-yl)-1,4'-bipiperidine 2,2,2-trifluoroacetate (91)

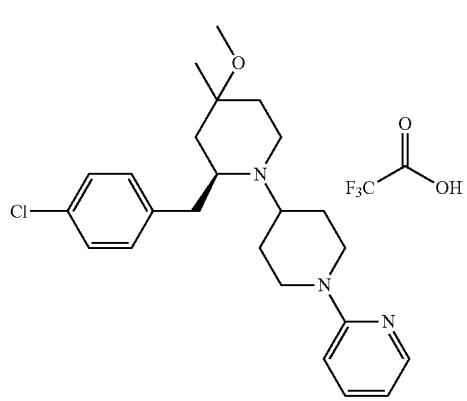

Step 1

Synthesis of tert-butyl (2S)-2-(4-chlorobenzyl)-4-hydroxy-4-methylpiperidine-1-carboxylate (91a)

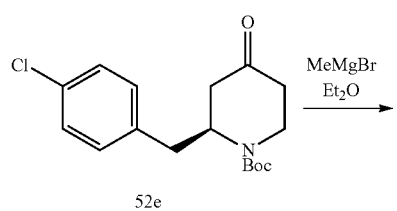

The title compound (91a) was obtained from 52e (300 mg; 0.93 mmol) according to the General Procedure V in 92% yield (290 mg; 0.86 mmol).

ESI-MS m/z for $C_{18}H_{27}ClNO_3$ found 340.2/342.2 $[M+H]^+$

Step 2

Synthesis of tert-butyl (2S)-2-(4-chlorobenzyl)-4-methoxy-4-methylpiperidine-1-carboxylate (91b)

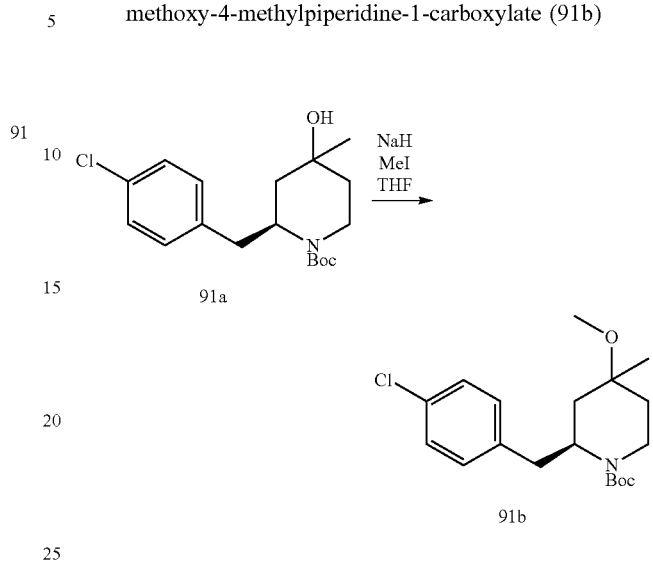

The title compound (91b) was obtained from 91a (150 mg; 0.44 mmol) according to the General Procedure XI in 98% yield (150 mg; 0.43 mmol).

ESI-MS m/z for $C_{19}H_{29}ClNO_3$ found 354.2/356.2 $[M+H]^+$

Step 3

Synthesis of (2S)-2-(4-chlorobenzyl)-4-methoxy-4-methylpiperidine (91c)

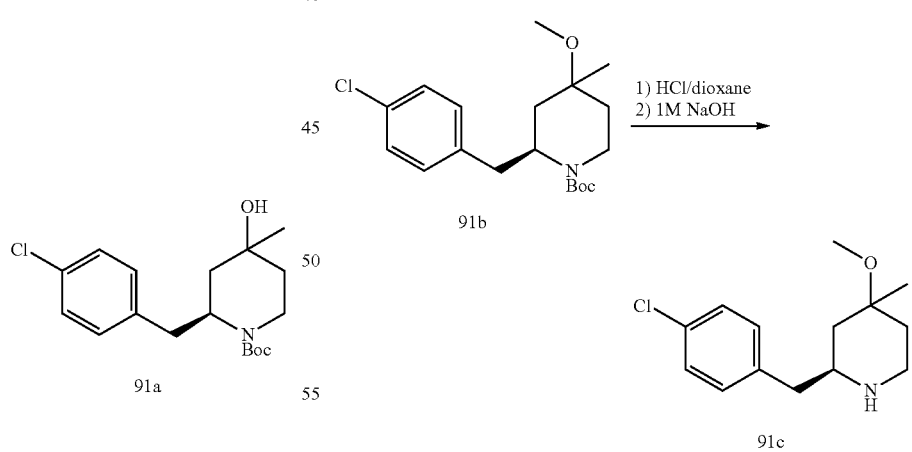

The title compound (91c) was obtained from 91b (150 mg; 0.43 mmol) according to the General Procedure IVa. Then obtained hydrochloride salt was dissolved in AcOEt and 1M NaOH was added to this solution. Phases were separated and an organic one was washed with brine, dried over anhydrous $MgSO_4$ and concentrated in vacuo to give free amine 91c in 93% yield (100 mg; 0.4 mmol).

ESI-MS m/z for $C_{14}H_{21}ClNO$ found 254.1/256.1 $[M+H]^+$

Step 4

Synthesis of (2S)-2-(4-chlorobenzyl)-4-methoxy-4-methyl-1'-(pyridin-2-yl)-1,4'-bipiperidine 2,2,2-trifluoroacetate (91)

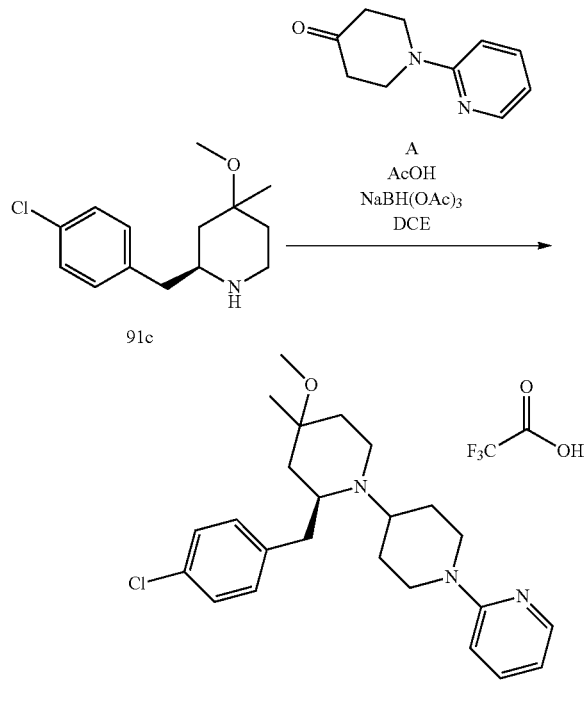

91

The title compound (91) was obtained as a TFA salt from 91c (50 mg; 0.2 mmol) according to the General Procedure VI in 18% yield (19 mg; 0.036 mmol).

ESI-MS m/z for $C_{24}H_{33}ClN_3O$ found 414.1/416.1 [M+H]$^+$; $^1$H NMR (700 MHz, DMSO-d$_6$, 300 K) δ 8.06-7.92 (m, 2H), 7.48-7.39 (m, 2H), 7.39-7.29 (m, 3H), 7.03-6.93 (m, 1H), 4.34-4.21 (m, 2H), 4.05-3.98 (m, 1H), 3.74-3.69 (m, 1H), 3.48-3.32 (m, 2H), 3.27-3.12 (m, 3H), 3.12-3.04 (m, 3H), 3.03-2.89 (m, 1H), 2.24-2.06 (m, 2H), 1.94-1.67 (m, 4H), 1.67-1.59 (m, 2H), 1.19-1.03 (m, 3H).

Example 92

Synthesis of (2S)-2-(4-chlorobenzyl)-4-methyl-1'-(pyridin-2-yl)-[1,4'-bipiperidin]-4-ol 2,2,2-trifluoroacetate (92)

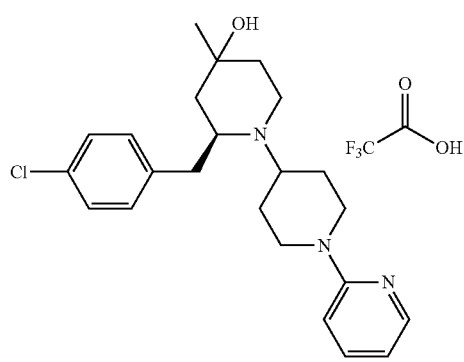

92

Step 1

Synthesis of (2S)-2-(4-chlorobenzyl)-4-methylpiperidin-4-ol hydrochloride (92a)

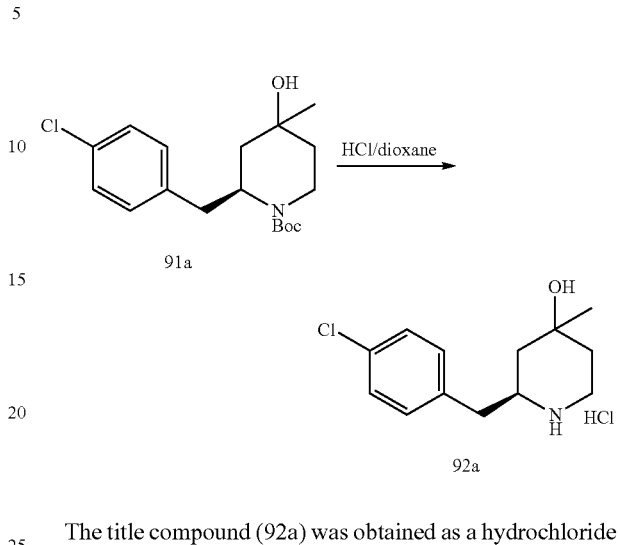

The title compound (92a) was obtained as a hydrochloride salt from 91a (140 mg; 0.41 mmol) according to the General Procedure IVa in 99% yield (112 mg; 0.41 mmol).

ESI-MS m/z for $C_{13}H_{19}ClNO$ found 240.1/242.1 [M+H]$^+$

Step 2

Synthesis of (2S)-2-(4-chlorobenzyl)-4-methyl-1'-(pyridin-2-yl)-[1,4'-bipiperidin]-4-ol 2,2,2-trifluoroacetate (92)

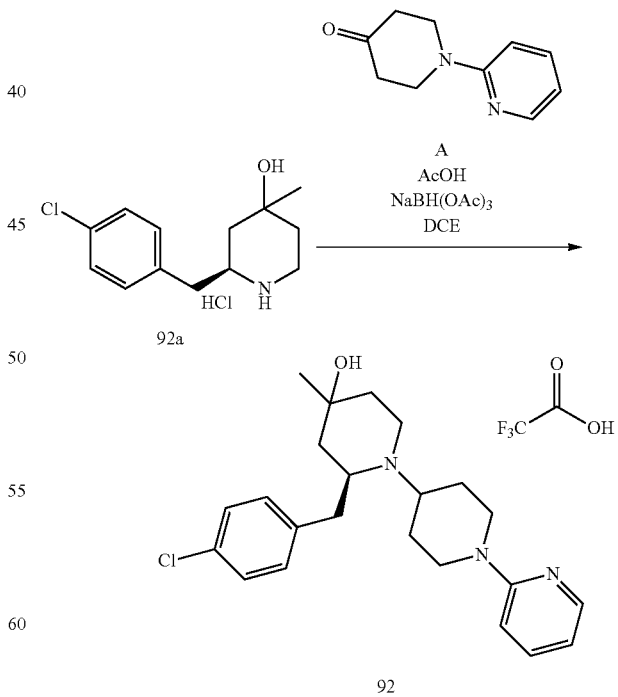

92

The title compound (92) was obtained as a TFA salt from 92a (56 mg; 0.2 mmol) according to the General Procedure VI in 8% yield (8 mg; 0.016 mmol).

ESI-MS m/z for $C_{23}H_{31}ClN_3O$ found 400.3/402.3 [M+H]$^+$; $^1$H NMR (700 MHz, MeCN-d$_3$) δ 8.20-8.10 (m, 1H), 7.55-7.48 (m, 1H), 7.38-7.31 (m, 2H), 7.31-7.27 (m, 2H), 6.80-6.72 (m, 1H), 6.65-6.55 (m, 1H), 4.42-4.29 (m, 2H), 3.20-2.73 (m, 5H), 2.56-2.31 (m, 2H), 1.90-1.32 (m, 9H), 1.18-1.09 (m, 3H).

Example 93

Synthesis of (2S,5S)-2-(4-chlorobenzyl)-5-ethyl-4-methyl-1-(1-(pyridin-2-yl)piperidin-4-yl)piperazine 2,2,2-trifluoroacetate (93)

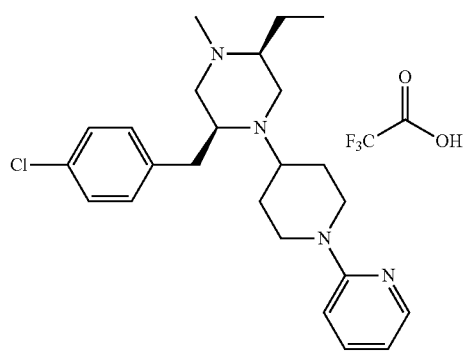

Step 1

Synthesis of methyl (S)-2-(((S)-2-((tert-butoxycarbonyl)amino)-3-(4-chlorophenyl)propyl)amino)butanoate (93a)

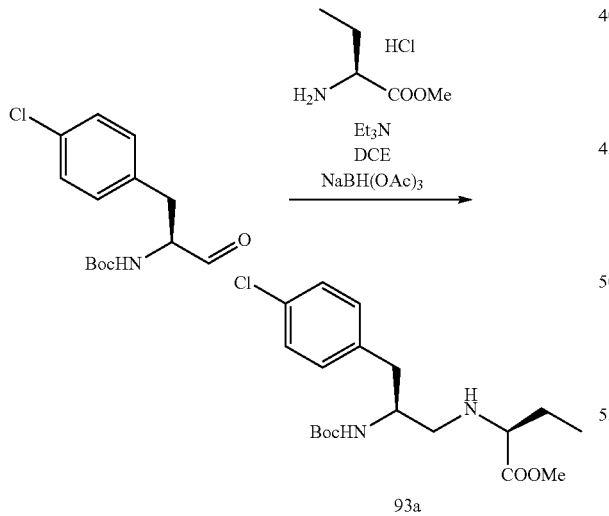

The reductive amination of known aldehyde (3.6 g; 12.68 mmol) with methyl (S)-2-aminobutanoate hydrochloride (1.9 g; 12.68 mmol) was accomplished according to the General Procedure VI. The crude product 93a was obtained in 98% yield (4.8 g, 12.47 mmol).

ESI-MS m/z for $C_{19}H_{30}ClN_2O_4$ found 385.2/387.2 [M+H]$^+$

Step 2

Synthesis of (3S,6S)-6-(4-chlorobenzyl)-3-ethylpiperazin-2-one (93b)

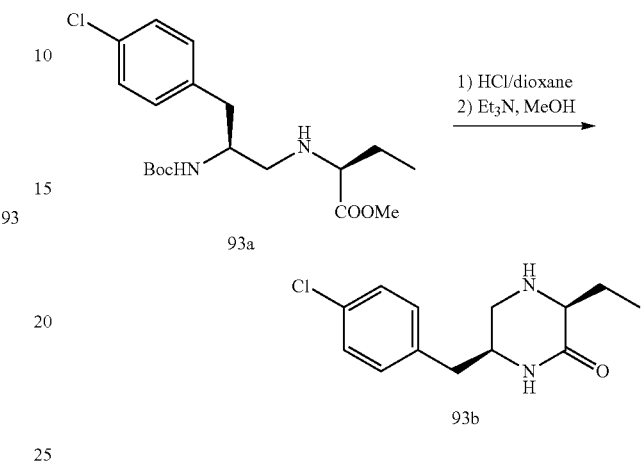

The title compound (93b) was obtained from 93a (4.8 g, 12.47 mmol) according to the General Procedure VIII in 95% yield (3 g; 11.9 mmol).

ESI-MS m/z for $C_{13}H_{18}ClN_2O$ found 253.1/255.1 [M+H]$^+$

Step 3

Synthesis of tert-butyl (2S,5S)-5-(4-chlorobenzyl)-2-ethyl-3-oxopiperazine-1-carboxylate (93c)

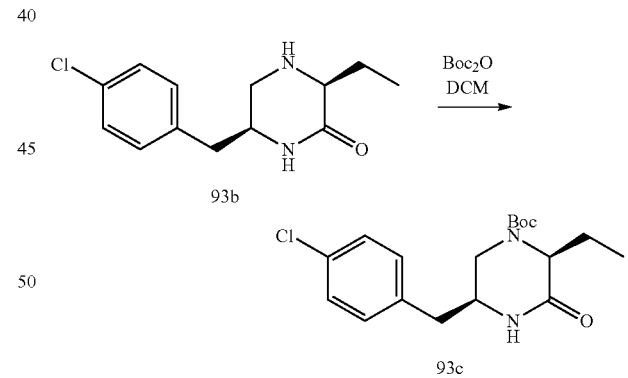

To a solution of 93b (3 g; 11.9 mmol) in dichloromethane (50 mL), di-tert-butyl dicarbonate (Boc$_2$O) (2.59 g, 11.87 mmol) was added and the reaction mixture was stirred at room temperature overnight, after which time TLC and LC-MS showed almost complete consumption of the starting material. The volatiles were removed in vacuo and the residue was purified by silica-gel column chromatography (hexane/AcOEt, 3:1 to 1:1, v/v) giving 123c in 25% yield (1.05 g; 2.98 mmol).

ESI-MS m/z for $C_{14}H_{18}ClN_2O_3$ found 297.1/299.1 [M+H-tBu]$^+$

Step 4

Synthesis of tert-butyl (2S,5S)-5-(4-chlorobenzyl)-2-ethylpiperazine-1-carboxylate (93d)

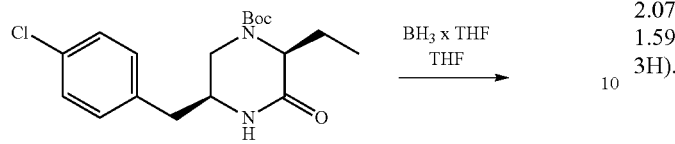

The title compound (93d) was obtained from 93c (1.05 g; 2.98 mmol) according to the General Procedure Ib in 84% yield (0.85 g; 2.51 mmol).

ESI-MS m/z for $C_{18}H_{28}ClN_2O_2$ found 339.2/341.2 $[M+H]^+$

Step 5

Synthesis of tert-butyl (2S,5S)-5-(4-chlorobenzyl)-2-ethyl-4-(1-(pyridin-2-yl)piperidin-4-yl)piperazine-1-carboxylate (93e)

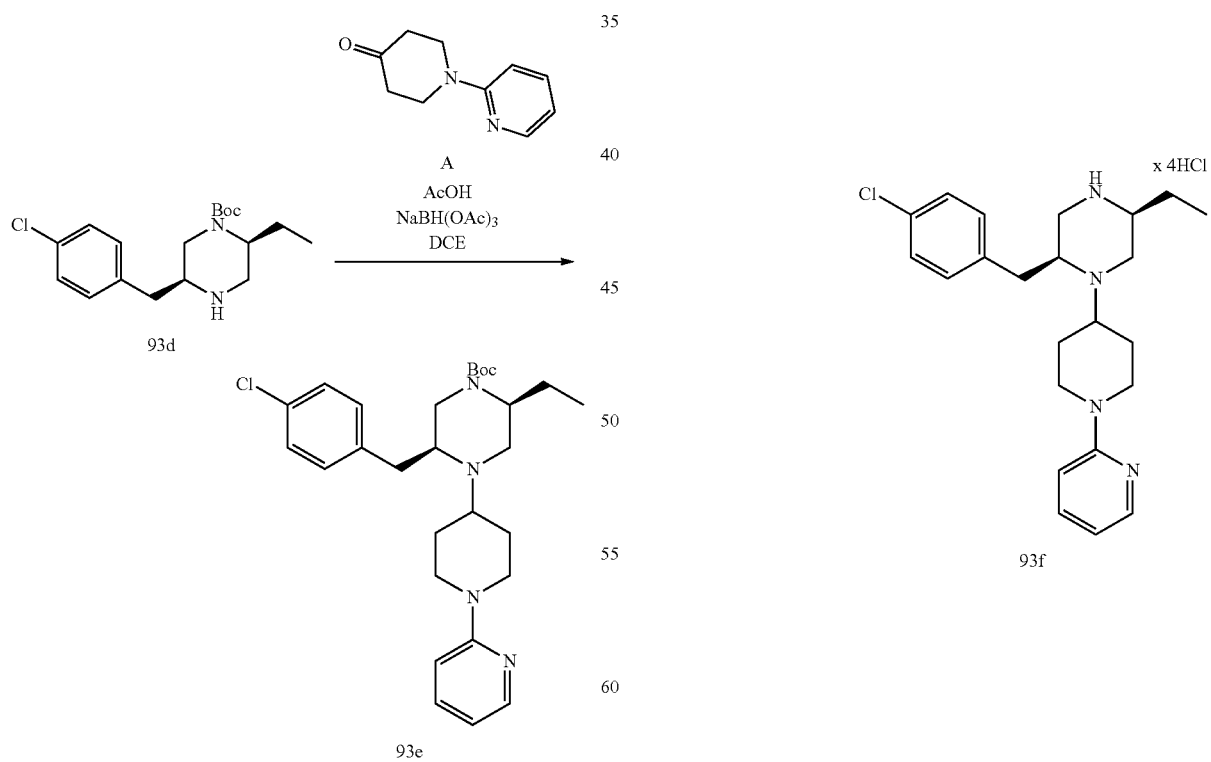

The title compound (93e) was obtained from 93d (0.25 g; 0.74 mmol) according to the General Procedure VI in 43% yield (160 mg; 0.32 mmol).

ESI-MS m/z for $C_{28}H_{40}ClN_4O_2$ found 499.3/501.3 $[M+H]^+$; $^1$H NMR (700 MHz, CDCl$_3$) δ 8.22-8.18 (m, 1H), 7.51-7.46 (m, 1H), 7.31-7.28 (m, 2H), 7.21-7.14 (m, 2H), 6.72-6.69 (m, 1H), 6.63-6.60 (m, 1H), 4.25-4.17 (m, 2H), 3.76-3.68 (m, 1H), 3.10-3.00 (m, 3H), 2.95-2.86 (m, 1H), 2.86-2.78 (m, 1H), 2.75-2.68 (m, 3H), 2.66-2.60 (m, 1H), 2.07-1.99 (m, 2H), 1.81-1.74 (m, 1H), 1.69-1.61 (m, 2H), 1.59-1.54 (m, 2H), 1.53-1.46 (m, 9H), 0.87 (t, J=7.5 Hz, 3H).

Step 6

Synthesis of (2S,5S)-2-(4-chlorobenzyl)-5-ethyl-1-(1-(pyridin-2-yl)piperidin-4-yl)piperazine tetrahydrochloride (93f)

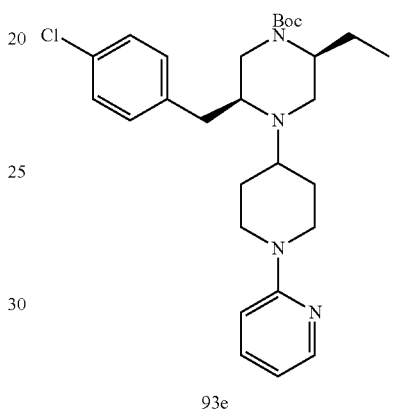

The title compound (93f) was obtained as a tetrahydrochloride salt from 93e (0.16 g; 0.32 mmol) according to the General Procedure IVa in 99% yield (174 mg; 0.32 mmol).

ESI-MS m/z for $C_{23}H_{32}ClN_4$ found 399.2/401.2 $[M+H]^+$

Step 7

Synthesis of (2S,5S)-2-(4-chlorobenzyl)-5-ethyl-4-methyl-1-(1-(pyridin-2-yl)piperidin-4-yl)piperazine 2,2,2-trifluoroacetate (93)

Example 94

Synthesis of (2S,5S)-2-(4-chlorobenzyl)-5-ethyl-4-isobutyl-1-(1-(pyridin-2-yl)piperidin-4-yl)piperazine 2,2,2-trifluoroacetate (94)

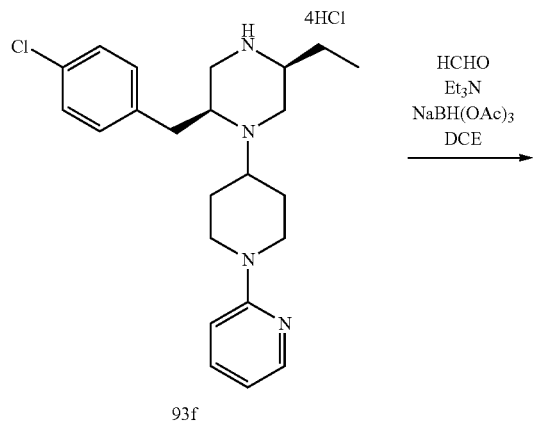

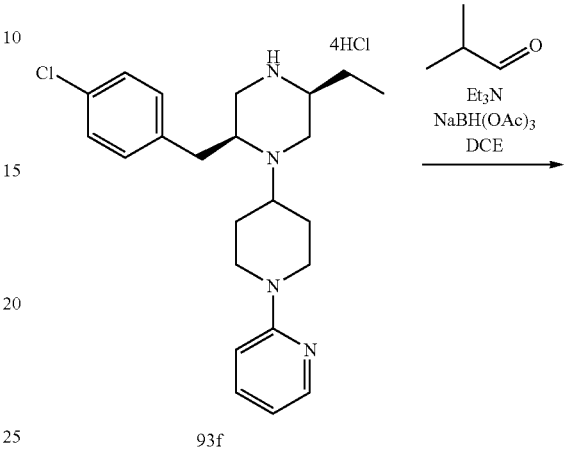

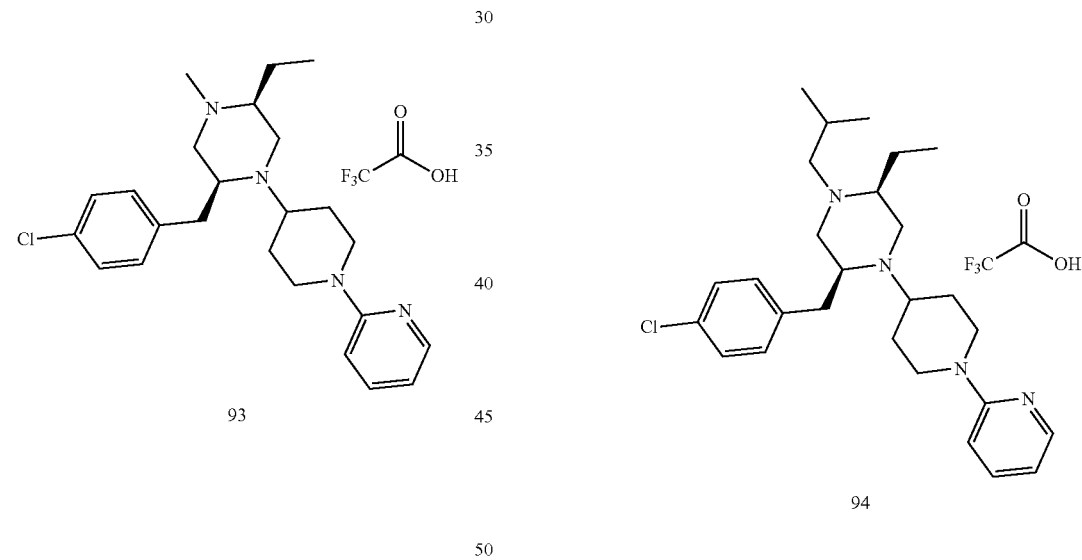

The title compound (93) was obtained as a TFA salt from 93f (87 mg; 0.16 mmol) according to the General Procedure VI in 59% yield (50 mg; 0.095 mmol).

ESI-MS m/z for $C_{24}H_{34}ClN_4$ found 413.3/415.3 [M+H]$^+$; $^1$H NMR (700 MHz, D$_2$O) δ 8.01-7.96 (m, 1H), 7.89-7.81 (m, 1H), 7.46-7.37 (m, 2H), 7.32-7.22 (m, 3H), 7.00-6.91 (m, 1H), 4.26-4.20 (m, 1H), 4.18-4.13 (m, 1H), 3.92-3.85 (m, 1H), 3.75-3.67 (m, 1H), 3.52-3.39 (m, 3H), 3.37-3.28 (m, 2H), 3.25-3.17 (m, 1H), 3.12-2.99 (m, 1H), 2.97-2.89 (m, 1H), 2.84 (s, 3H), 2.83-2.77 (m, 1H), 2.07-1.98 (m, 3H), 1.97-1.87 (m, 1H), 1.85-1.76 (m, 1H), 1.72-1.63 (m, 1H), 0.93 (t, J=7.5 Hz, 3H).

The title compound (94) was obtained as a TFA salt from 93f (87 mg; 0.16 mmol) according to the General Procedure VI in 58% yield (52 mg; 0.092 mmol).

ESI-MS m/z for $C_{27}H_{40}ClN_4$ found 455.3/457.3 [M+H]$^+$; $^1$H NMR (700 MHz, D$_2$O) δ 8.01-7.96 (m, 1H), 7.86-7.84 (m, 1H), 7.45-7.41 (m, 2H), 7.33-7.30 (m, 2H), 7.28-7.24 (m, 1H), 6.98-6.93 (m, 1H), 4.26-4.21 (m, 1H), 4.19-4.13 (m, 1H), 4.00-3.91 (m, 1H), 3.85-3.78 (m, 1H), 3.55-3.37 (m, 4H), 3.37-3.28 (m, 1H), 3.29-3.22 (m, 1H), 3.22-3.15 (m, 1H), 3.11-2.99 (m, 2H), 2.92-2.82 (m, 2H), 2.09-2.00 (m, 3H), 1.99-1.89 (m, 1H), 1.89-1.79 (m, 2H), 1.74-1.63 (m, 1H), 0.95 (t, J=7.5 Hz, 3H), 0.88 (d, J=6.6 Hz, 3H), 0.86 (d, J=6.6 Hz, 3H).

Example 95

Synthesis of 2-((2S,5S)-5-(4-chlorobenzyl)-2-isobutyl-4-(1-(pyridin-2-yl)piperidin-4-yl)piperazin-1-yl)-N-methylacetamide 2,2,2-trifluoroacetate (95)

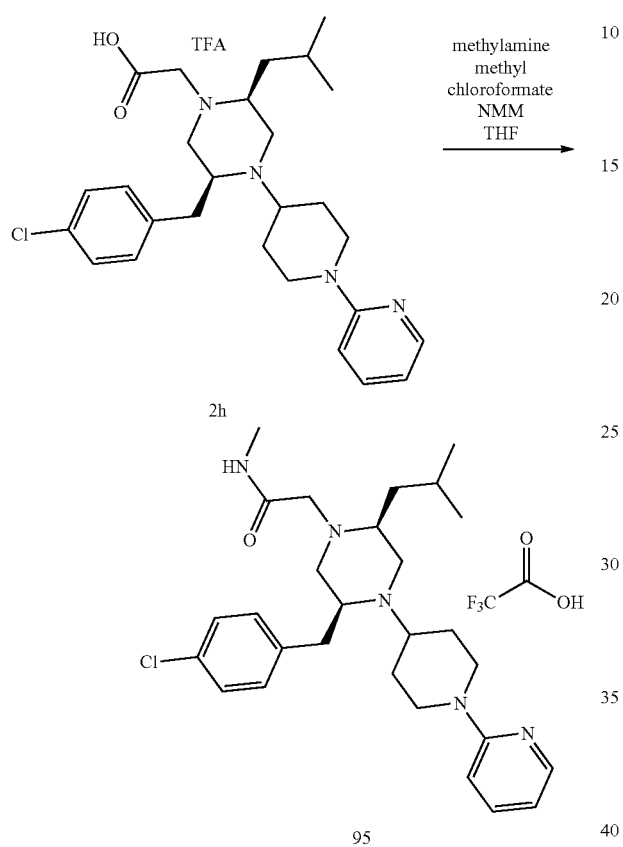

The solution of 2h (28 mg; 0.046 mmol) in THF (0.5 mL) was cooled to −20° C. and NMM (6.1 µL; 0.055 mmol) was added followed by methyl chloroformate (4.3 µL; 0.055 mmol). The mixture was then stirred for 30 minutes and methylamine (0.23 mL; 0.46 mmol) was added and stirred at room temperature for 3 days. LC-MS indicated completion of the reaction. The mixture was evaporated to dryness and the crude product purified by preparative reversed-phase column chromatography (Luna® 5 µm Phenyl-Hexyl, LC Column 250×21.2 mm, water/MeCN+1% TFA, 95:5 to 40:60, 30 minutes). Compound 95 was obtained as a TFA salt in 39% yield (11 mg; 0.018 mmol).

ESI-MS m/z for $C_{28}H_{41}ClN_5O$ found 498.3/500.3 [M+H]$^+$; $^1$H NMR (700 MHz, D$_2$O, 333 K) δ 8.40-8.36 (m, 1H), 8.26-8.23 (m, 1H), 7.80-7.75 (m, 2H), 7.67-7.60 (m, 3H), 7.38-7.33 (m, 1H), 4.64-4.55 (m, 2H), 4.28-4.21 (m, 1H), 4.20-4.13 (m, 1H), 3.86-3.80 (m, 1H), 3.78-3.71 (m, 1H), 3.71-3.65 (m, 1H), 3.65-3.52 (m, 4H), 3.48-3.42 (m, 1H), 3.34-3.28 (m, 1H), 3.28-3.22 (m, 1H), 3.16-3.10 (m, 1H), 3.06 (s, 3H), 2.73-2.65 (m, 1H), 2.65-2.59 (m, 1H), 2.26-2.14 (m, 2H), 2.02-1.91 (m, 1H), 1.85-1.78 (m, 2H), 1.27 (d, J=6.5 Hz, 3H), 1.22 (d, J=6.5 Hz, 3H).

Example 96

Synthesis of 1-((2S,5S)-5-(4-chlorobenzyl)-2-isobutyl-4-(1-(pyridin-2-yl)piperidin-4-yl)piperazin-1-yl)-2-methylpropan-2-ol (96)

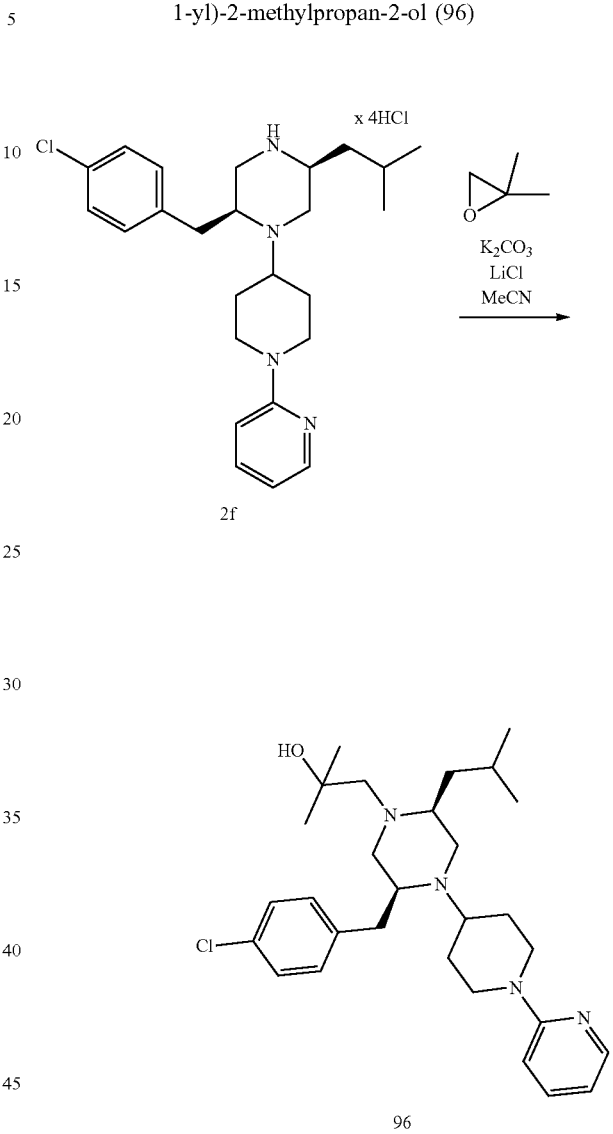

The title compound (96) was obtained from 2f (47 mg; 0.082 mmol) according to the General Procedure XXII in 90% yield (37 mg; 0.074 mmol) with exception that in this reaction K$_2$CO$_3$ was used and the product was purified by preparative reversed-phase column chromatography without addition of TFA.

ESI-MS m/z for $C_{29}H_{44}ClN_4O$ found 499.4/501.4 [M+H]$^+$; $^1$H NMR (700 MHz, DMSO-d$_6$+D$_2$O, 348 K) δ 8.11-8.03 (m, 1H), 7.71-7.62 (m, 1H), 7.39-7.33 (m, 4H), 7.05-6.92 (m, 1H), 6.81-6.68 (m, 1H), 4.36-4.24 (m, 2H), 3.62-3.48 (m, 2H), 3.20-2.74 (m, 10H), 2.00-1.76 (m, 2H), 1.75-1.40 (m, 6H), 1.14 (s, 3H), 1.12 (s, 3H), 0.93 (d, J=6.5 Hz, 3H), 0.88 (d, J=6.5 Hz, 3H).

Example 97

Synthesis of (2S,5R)-2-(4-chlorobenzyl)-4-isobutyl-5-(methoxymethyl)-1-(1-(pyridin-2-yl)piperidin-4-yl)piperazine (97)

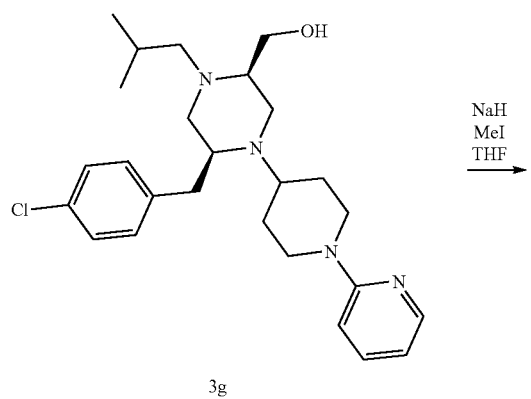

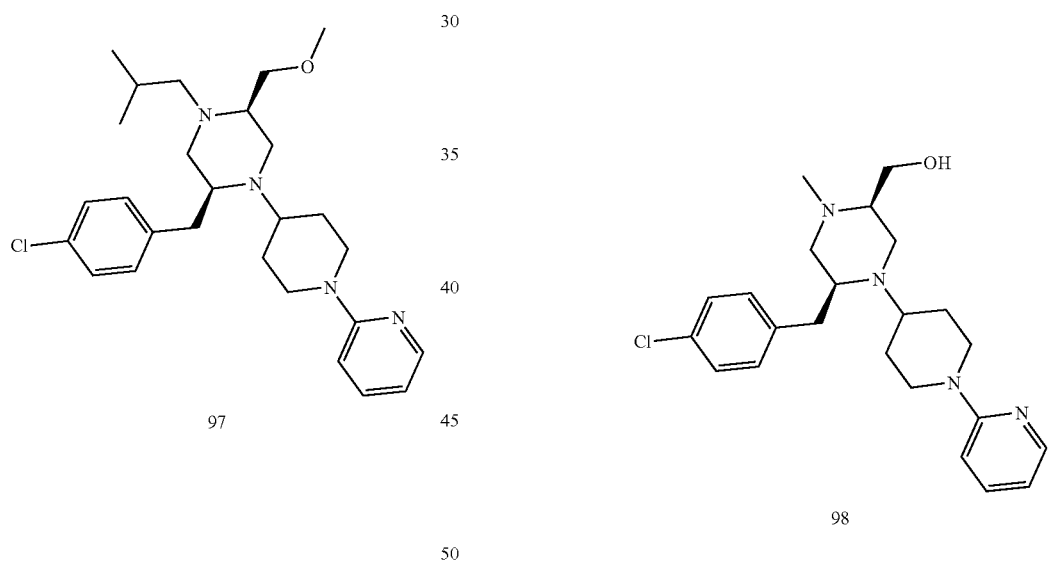

The title compound (97) was obtained from 3g (20 mg; 0.044 mmol) according to the General Procedure XI in 30% yield (6 mg; 0.013 mmol).

ESI-MS m/z for $C_{27}H_{40}ClN_4O$ found 471.4/573.4 [M+H]$^+$; $^1$H NMR (700 MHz, D$_2$O, 300 K) δ 8.40-8.28 (m, 1H), 8.27-8.16 (m, 1H), 7.77-7.72 (m, 2H), 7.68-7.63 (m, 2H), 7.63-7.56 (m, 1H), 7.35-7.27 (m, 1H), 4.44-4.36 (m, 2H), 4.22-4.17 (m, 1H), 4.16-4.11 (m, 1H), 4.03-3.97 (m, 1H), 3.92-3.87 (m, 1H), 3.87-3.79 (m, 1H), 3.75 (s, 3H), 3.68-3.60 (m, 2H), 3.60-3.54 (m, 2H), 3.52-3.36 (m, 4H), 3.28-3.21 (m, 1H), 3.21-3.16 (m, 1H), 2.39-2.31 (m, 2H), 2.31-2.24 (m, 1H), 2.19-2.09 (m, 1H), 2.09-1.99 (m, 1H), 1.29-1.22 (m, 6H).

Example 128

Synthesis of ((2R,5S)-5-(4-chlorobenzyl)-1-methyl-4-(1-(pyridin-2-yl)piperidin-4-yl)piperazin-2-yl)methanol (98)

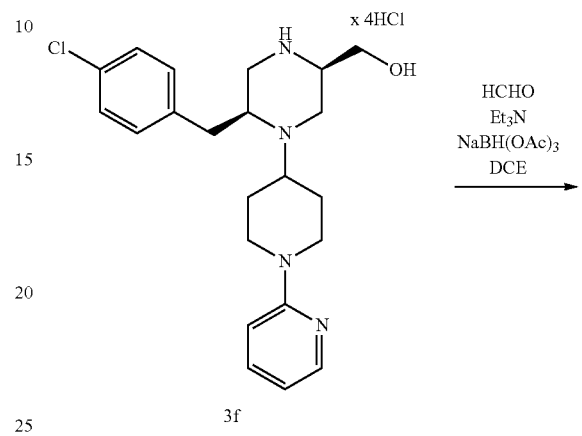

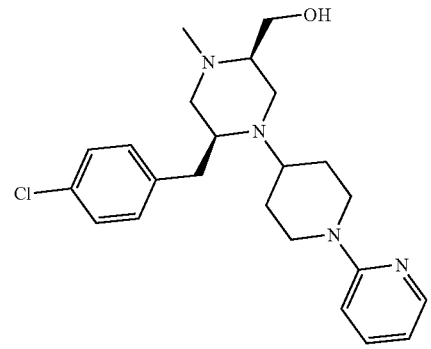

The title compound (98) was obtained from 3f (142 mg; 0.26 mmol) according to the General Procedure VI in 2% yield (2 mg; 0.005 mmol).

ESI-MS m/z for $C_{23}H_{32}ClN_4O$ found 415.3/417.3 [M+H]$^+$; $^1$H NMR (700 MHz, MeCN-d$_3$) δ 8.15-8.05 (m, 1H), 7.93-7.87 (m, 1H), 7.44-7.39 (m, 2H), 7.38-7.35 (m, 2H), 7.16-7.13 (m, 1H), 6.89-6.86 (m, 1H), 4.23-4.08 (m, 2H), 4.07-3.99 (m, 1H), 3.84-3.77 (m, 1H), 3.54-3.40 (m, 2H), 3.28-2.99 (m, 9H), 2.81 (s, 3H), 2.08-2.00 (m, 2H), 1.75-1.61 (m, 2H).

Example 99

Synthesis of (2S,5R)-2-(4-chlorobenzyl)-5-(methoxymethyl)-4-methyl-1-(1-(pyridin-2-yl)piperidin-4-yl)piperazine (99)

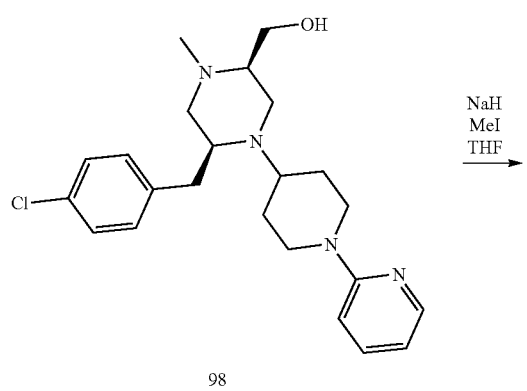

98

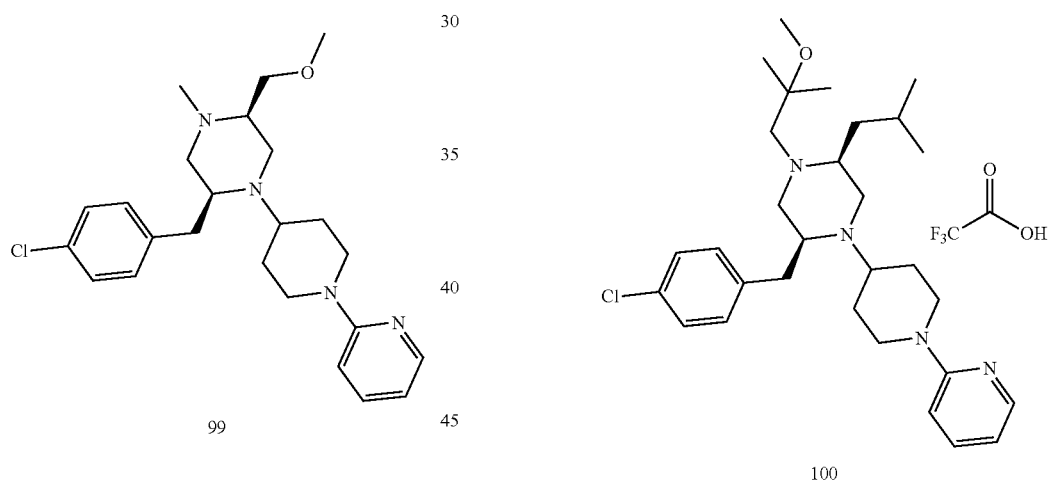

99

The title compound (99) was obtained from 98 (35 mg; 0.084 mmol) according to the General Procedure XI in 6% yield (2 mg; 0.005 mmol).

ESI-MS m/z for $C_{24}H_{34}ClN_4O$ found 429.3/431.3 [M+H]$^+$; $^1$H NMR (700 MHz, MeCN-d$_3$) δ 8.17-8.09 (m, 1H), 7.55-7.48 (m, 1H), 7.38-7.30 (m, 2H), 7.29-7.20 (m, 2H), 6.83-6.73 (m, 1H), 6.65-6.57 (m, 1H), 4.28-4.19 (m, 2H), 3.61-3.55 (m, 2H), 3.39-3.36 (m, 1H), 3.34 (s, 3H), 3.13-3.05 (m, 2H), 2.98-2.87 (m, 3H), 2.84-2.76 (m, 2H), 2.57-2.44 (m, 2H), 2.21 (s, 3H), 2.20-2.16 (m, 1H), 2.04-2.00 (m, 1H), 1.49-1.38 (m, 3H).

Example 100

Synthesis of (2S,5S)-2-(4-chlorobenzyl)-5-isobutyl-4-(2-methoxy-2-methylpropyl)-1-(1-(pyridin-2-yl)piperidin-4-yl)piperazine 2,2,2-trifluoroacetate (100)

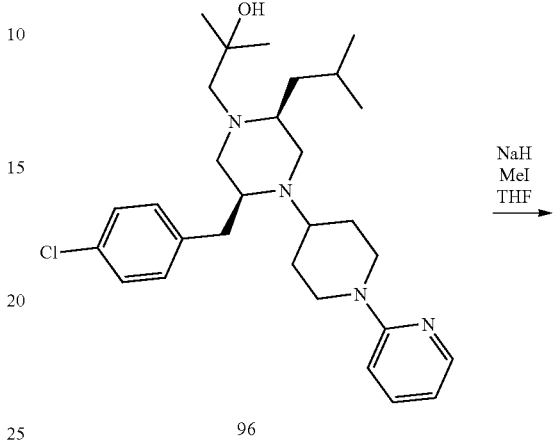

96

100

The title compound (100) was obtained as a TFA salt from 96 (36 mg; 0.072 mmol) according to the General Procedure XI in 26% yield (12 mg; 0.019 mmol).

ESI-MS m/z for $C_{30}H_{46}ClN_4O$ found 513.4/515.4 [M+H]$^+$; $^1$H NMR (700 MHz, MeCN-d$_3$, 318 K) δ 8.11-8.08 (m, 1H), 7.96-7.91 (m, 1H), 7.42-7.38 (m, 2H), 7.36-7.31 (m, 2H), 7.21-7.15 (m, 1H), 6.94-6.88 (m, 1H), 4.34-4.25 (m, 2H), 3.69-3.47 (m, 4H), 3.35-3.21 (m, 3H), 3.19-3.12 (m, 2H), 3.11 (s, 3H), 3.09-3.02 (m, 1H), 3.02-2.88 (m, 4H), 1.94-1.85 (m, 2H), 1.76-1.62 (m, 2H), 1.59-1.51 (m, 1H), 1.23 (s, 3H), 1.19 (s, 3H), 1.16-1.11 (m, 1H), 1.00 (d, J=6.6 Hz, 3H), 0.94 (d, J=6.5 Hz, 3H).

Example 101

Synthesis of 2-((2S,5S)-5-(4-chlorobenzyl)-2-methyl-4-(1-(pyridin-2-yl)piperidin-4-yl)piperazin-1-yl)-N,N-dimethylacetamide (101)

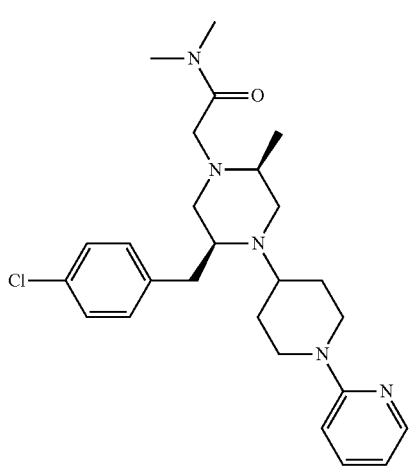

Step 1

Synthesis of tert-butyl (2S,5S)-5-(4-chlorobenzyl)-2-methyl-4-(1-(pyridin-2-yl)piperidin-4-yl)piperazine-1-carboxylate (101a)

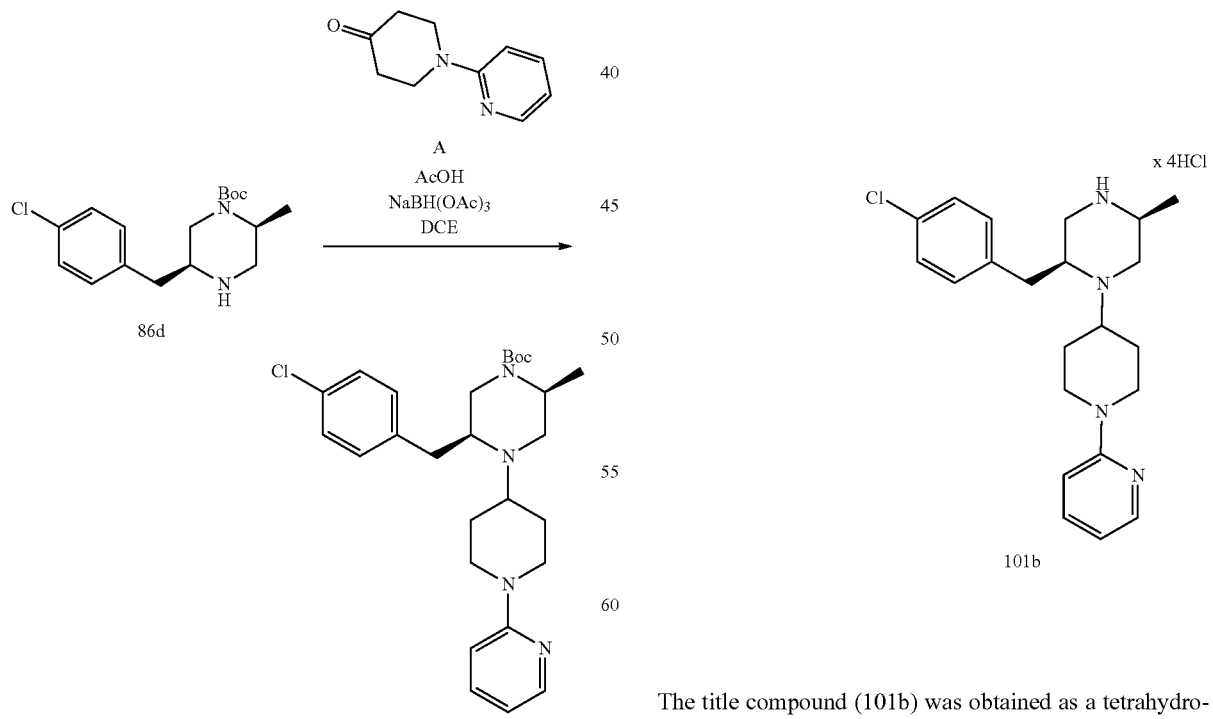

The title compound (101a) was obtained from 86d (550 mg; 1.69 mmol) according to the General Procedure VI in 64% yield (530 mg; 1.09 mmol).

ESI-MS m/z for $C_{27}H_{38}ClN_4O_2$ found 485.3/487.3 [M+H]$^+$; $^1$H NMR (700 MHz, CDCl$_3$) δ 8.23-8.20 (m, 1H), 7.52-7.47 (m, 1H), 7.32-7.29 (m, 2H), 7.22-7.19 (m, 2H), 6.71-6.66 (m, 1H), 6.65-6.60 (m, 1H), 4.47-4.34 (m, 2H), 4.17-4.10 (m, 1H), 3.71-3.61 (m, 1H), 3.19-3.10 (m, 1H), 3.08-3.02 (m, 1H), 2.91-2.82 (m, 2H), 2.76-2.63 (m, 3H), 2.63-2.54 (m, 2H), 1.78-1.69 (m, 3H), 1.52-1.46 (m, 1H), 1.45 (s, 9H), 1.19 (d, J=6.6 Hz, 3H).

Step 2

Synthesis of (2S,5S)-2-(4-chlorobenzyl)-5-methyl-1-(1-(pyridin-2-yl)piperidin-4-yl)piperazine tetrahydrochloride (101b)

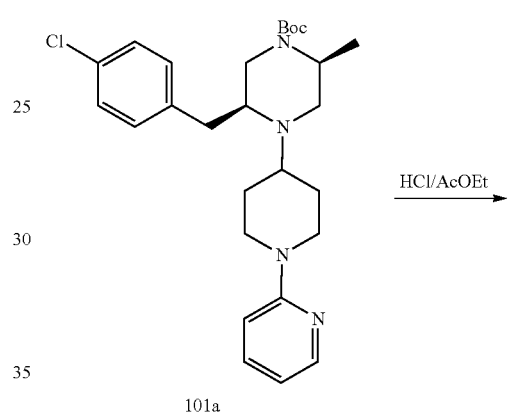

The title compound (101b) was obtained as a tetrahydrochloride salt from 101a (0.27 g; 0.56 mmol) according to the General Procedure IVa in 99% yield (291 mg; 0.55 mmol).

ESI-MS m/z for $C_{22}H_{30}ClN_4$ found 385.0/387.0 [M+H]$^+$

Step 3

Synthesis of tert-butyl 2-((2S,5S)-5-(4-chlorobenzyl)-2-methyl-4-(1-(pyridin-2-yl)piperidin-4-yl)piperazin-1-yl)acetate (101c)

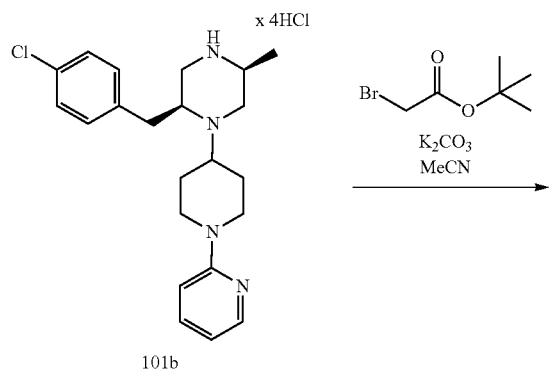

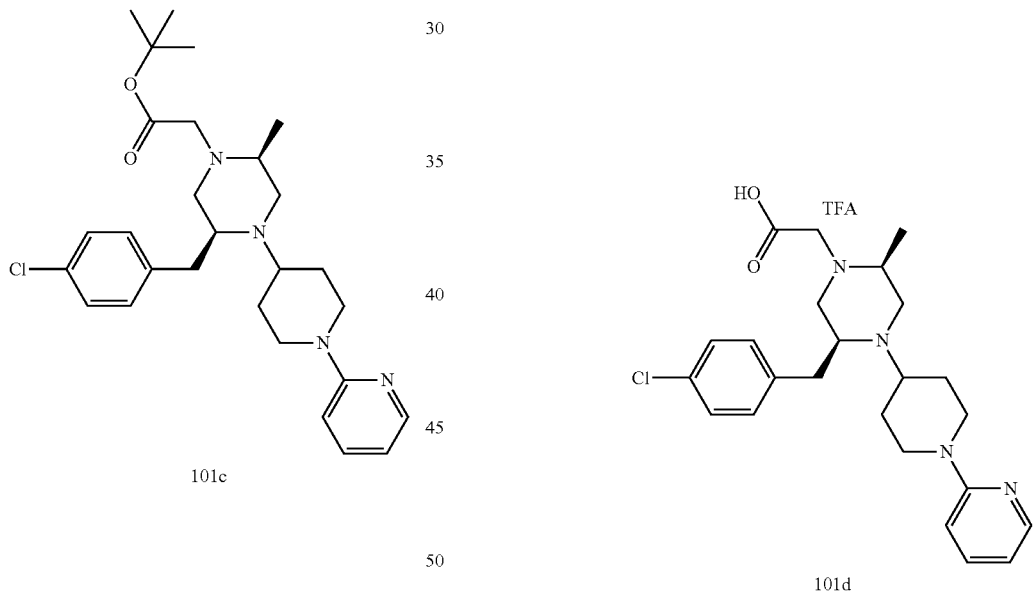

To a solution of 101b (291 mg; 0.55 mmol) in acetonitrile (3 mL), potassium carbonate (380 mg; 2.73 mmol) was added followed by tert-butyl bromoacetate (120 µL, 0.82 mmol) and the resulting mixture was heated to 100° C. overnight. LC-MS indicated completion of the reaction. The reaction mixture was filtered and the solid residue was washed with EtOAc. After evaporation of an organic phase the crude product was used to the next step without additional purification. Compound 101c was obtained in 98% yield (270 mg; 0.54 mmol).

ESI-MS m/z for $C_{28}H_{40}ClN_4O_2$ found 499.3/501.3 $[M+H]^+$

Step 4

Synthesis of 2-((2S,5S)-5-(4-chlorobenzyl)-2-methyl-4-(1-(pyridin-2-yl)piperidin-4-yl)piperazin-1-yl)acetic acid 2,2,2-trifluoroacetate (101d)

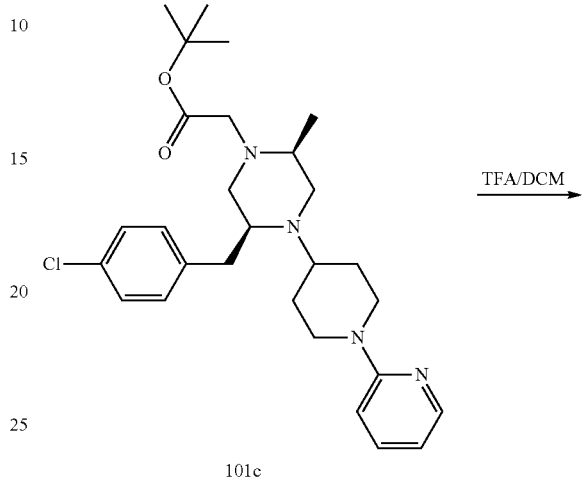

The title compound (101d) was obtained as a TFA salt from 101c (270 mg; 0.54 mmol) according to the General Procedure IVb in 74% yield (220 mg; 0.40 mmol).

ESI-MS m/z for $C_{24}H_{32}ClN_4O_2$ found 443.0/445.0 $[M+H]^+$

Step 5

Synthesis of 2-((2S,5S)-5-(4-chlorobenzyl)-2-methyl-4-(1-(pyridin-2-yl)piperidin-4-yl)piperazin-1-yl)-N,N-dimethylacetamide (101)

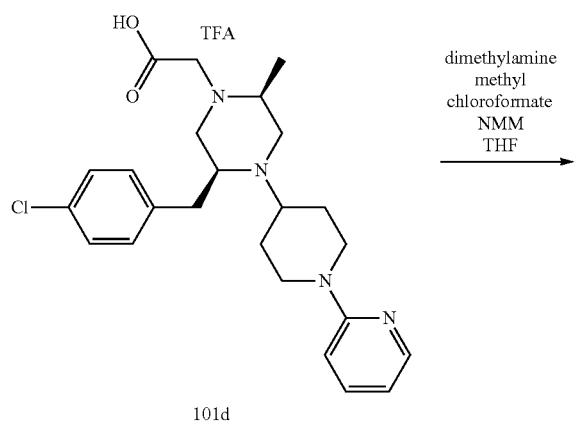

The solution of 101d (55 mg; 0.1 mmol) in THF (2 mL) was cooled to −20° C. and NMM (16.4 μL; 0.15 mmol) was added followed by methyl chloroformate (11.5 μL; 0.15 mmol). The mixture was then stirred for 30 minutes and dimethylamine (2M in THF; 0.62 mL; 1.24 mmol) was added and stirred at room temperature for 3 days. LC-MS indicated completion of the reaction. The mixture was evaporated to dryness and the crude product purified by preparative reversed-phase column chromatography (Luna® 5 μm Phenyl-Hexyl, LC Column 250×21.2 mm, water/MeCN, 95:5 to 40:60, 30 minutes). Compound 101 was obtained in 21% yield (10 mg; 0.021 mmol).

ESI-MS m/z for $C_{26}H_{37}ClN_5O$ found 470.3/472.3 [M+H]$^+$; $^1$H NMR (700 MHz, MeCN-d$_3$, 318 K) δ 8.14-8.11 (m, 1H), 7.92-7.87 (m, 1H), 7.41-7.37 (m, 2H), 7.36-7.32 (m, 2H), 7.16-7.12 (m, 1H), 6.90-6.87 (m, 1H), 4.32-4.26 (m, 2H), 3.93-3.85 (m, 1H), 3.63-3.54 (m, 2H), 3.46-3.38 (m, 2H), 3.27-3.14 (m, 5H), 3.07-3.01 (m, 2H), 2.98 (s, 3H), 2.97-2.93 (m, 1H), 2.92 (s, 3H), 2.13-2.04 (m, 2H), 1.86-1.72 (m, 2H), 1.33 (d, J=6.5 Hz, 3H).

Example 102

Synthesis of (R)-1-((2S,5S)-5-(4-chlorobenzyl)-2-methyl-4-(1-(pyridin-2-yl)piperidin-4-yl)piperazin-1-yl)propan-2-ol 2,2,2-trifluoroacetate (102)

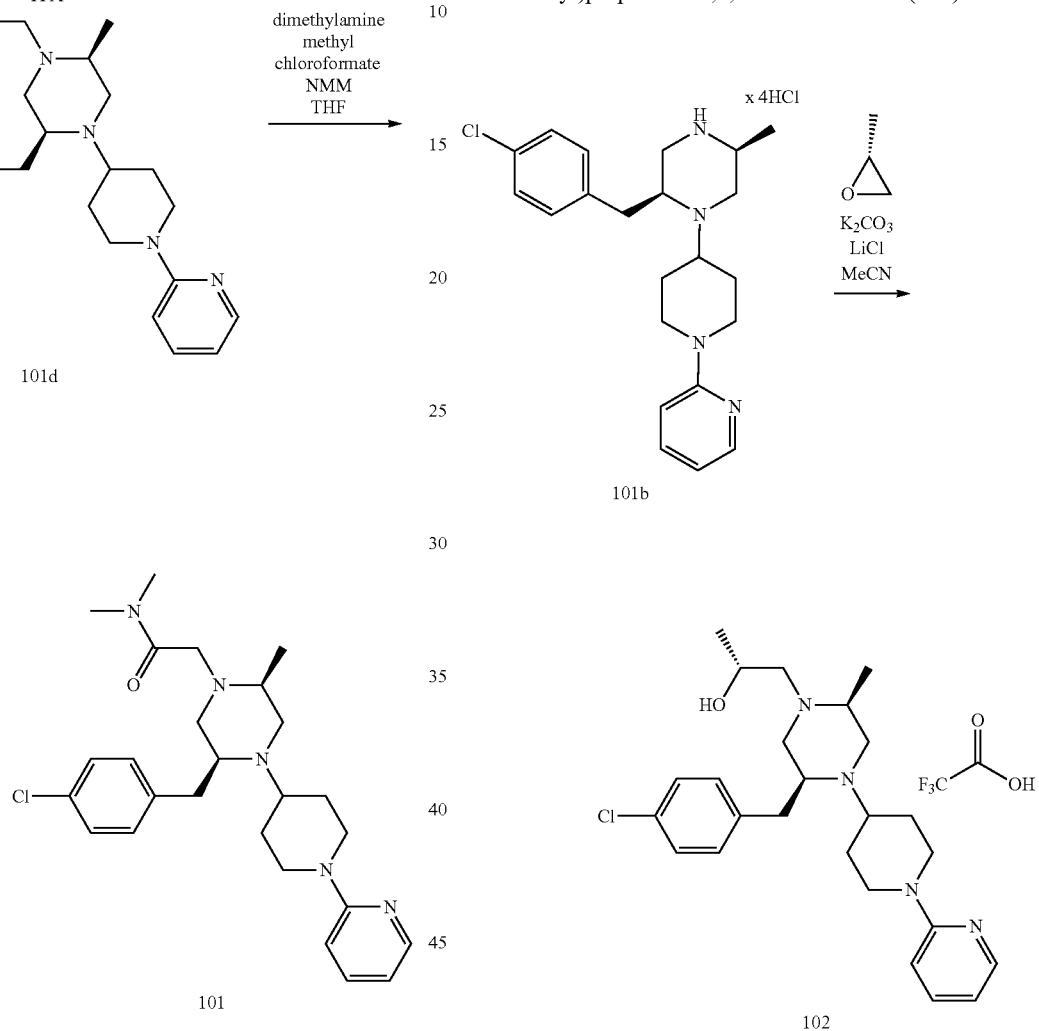

The title compound (102) was obtained as a TFA salt from 101b (70 mg; 0.13 mmol) according to the General Procedure XXII in 40% yield (29 mg; 0.052 mmol) with exception that in this reaction K$_2$CO$_3$ was used.

ESI-MS m/z for $C_{25}H_{36}ClN_4O$ found 443.3/445.3 [M+H]$^+$; $^1$H NMR (700 MHz, MeCN-d$_3$, 300 K) δ 8.04-7.99 (m, 1H), 7.97-7.93 (m, 1H), 7.41-7.37 (m, 2H), 7.37-7.33 (m, 2H), 7.22-7.18 (m, 1H), 6.94-6.89 (m, 1H), 4.20-4.05 (m, 3H), 3.57-3.48 (m, 2H), 3.42-3.34 (m, 1H), 3.34-3.27 (m, 1H), 3.25-3.13 (m, 3H), 3.13-2.95 (m, 4H), 2.86-2.78 (m, 1H), 1.83-1.74 (m, 1H), 1.71-1.61 (m, 1H), 1.41 (d, J=6.6 Hz, 3H), 1.17 (d, J=6.3 Hz, 3H).

Example 103

Synthesis of 2-((2S,5S)-5-(4-chlorobenzyl)-2-methyl-4-(1-(pyridin-2-yl)piperidin-4-yl)piperazin-1-yl)-N-cyclopropylacetamide 2,2,2-trifluoroacetate (103)

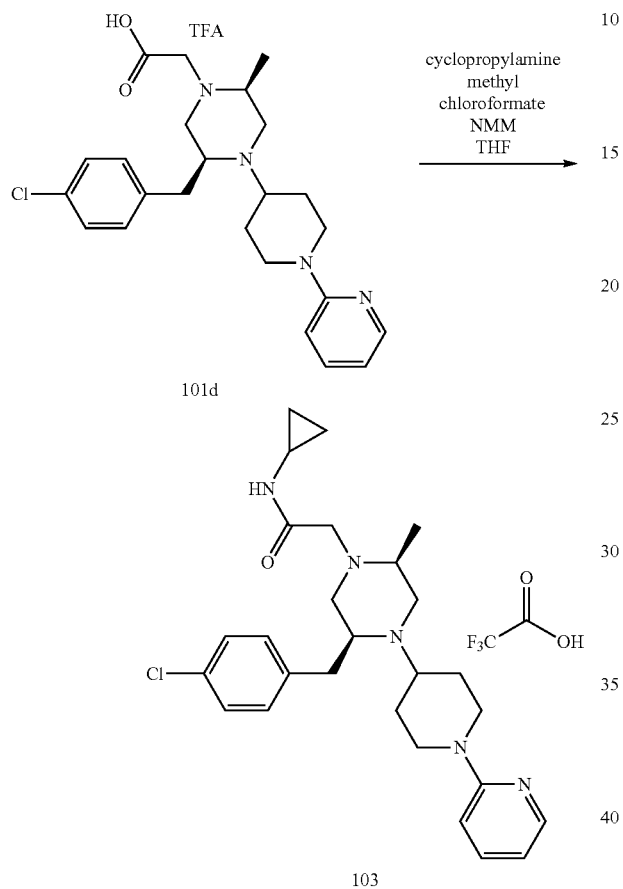

The solution of 101d (55 mg; 0.1 mmol) in THF (2 mL) was cooled to −20° C. and NMM (16.4 µL; 0.15 mmol) was added followed by methyl chloroformate (11.5 µL; 0.15 mmol). The mixture was then stirred for 30 minutes and cyclopropylamine (43 µL; 0.62 mmol) was added and stirred at room temperature for 5 days. LC-MS indicated completion of the reaction. The mixture was evaporated to dryness and the crude product purified by preparative reversed-phase column chromatography (Luna® 5 µm Phenyl-Hexyl, LC Column 250×21.2 mm, water/MeCN+1% TFA, 95:5 to 40:60, 30 minutes). Compound 103 was obtained as a TFA salt in 24% yield (14 mg; 0.024 mmol).

ESI-MS m/z for $C_{27}H_{37}ClN_5O$ found 482.3/484.3 [M+H]$^+$; $^1$H NMR (700 MHz, MeCN-d$_3$, 318 K) δ 8.14-8.10 (m, 1H), 7.88-7.81 (m, 1H), 7.44-7.37 (m, 2H), 7.37-7.32 (m, 2H), 7.12-7.07 (m, 1H), 6.90-6.85 (m, 1H), 4.42-4.35 (m, 2H), 3.81-3.73 (m, 1H), 3.61-3.54 (m, 1H), 3.39-3.34 (m, 2H), 3.33-3.28 (m, 2H), 3.19-3.12 (m, 3H), 3.09-3.05 (m, 1H), 3.02-2.94 (m, 2H), 2.92-2.85 (m, 1H), 2.84-2.76 (m, 1H), 2.69-2.62 (m, 1H), 2.33-2.19 (m, 2H), 1.96-1.90 (m, 1H), 1.21 (d, J=6.3 Hz, 3H), 0.79-0.69 (m, 2H), 0.57-0.52 (m, 1H), 0.51-0.41 (m, 1H).

Example 104

Synthesis of (S)-1-((2S,5S)-5-(4-chlorobenzyl)-2-methyl-4-(1-(pyridin-2-yl)piperidin-4-yl)piperazin-1-yl)propan-2-ol 2,2,2-trifluoroacetate (104)

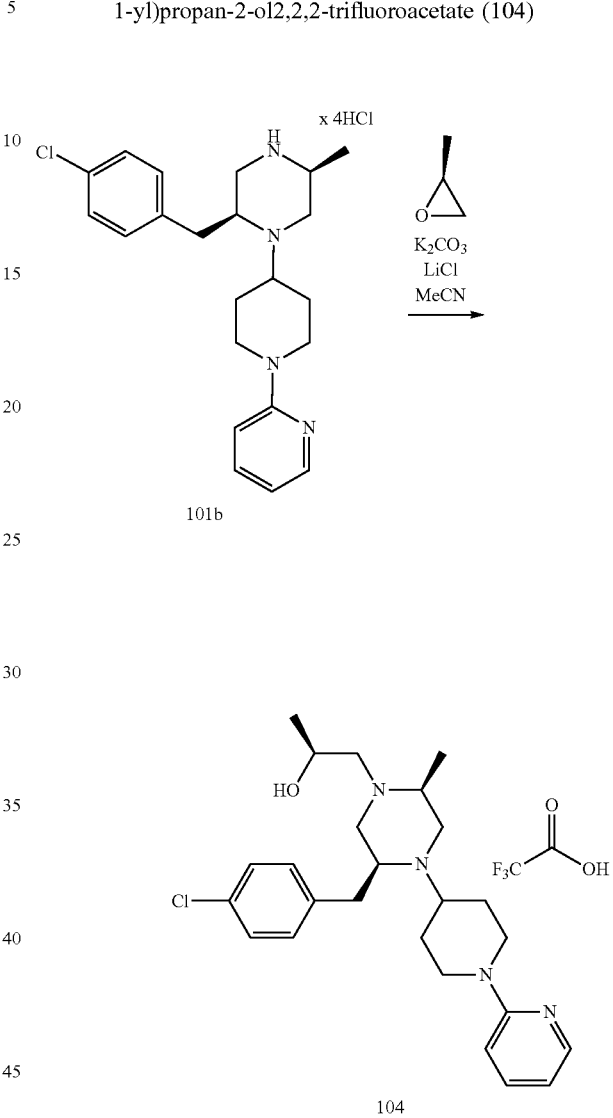

The title compound (104) was obtained as a TFA salt from 101b (100 mg; 0.19 mmol) according to the General Procedure XXII in 28% yield (30 mg; 0.054 mmol) with exception that in this reaction K$_2$CO$_3$ was used.

ESI-MS m/z for $C_{25}H_{36}ClN_4O$ found 443.1/445.0 [M+H]$^+$; $^1$H NMR (700 MHz, DMSO-d$_6$+D$_2$O, 348 K) δ 7.99-7.85 (m, 2H), 7.38-7.28 (m, 4H), 7.28-7.20 (m, 1H), 6.93-6.83 (m, 1H), 4.12-3.99 (m, 2H), 4.00-3.87 (m, 1H), 3.40-2.84 (m, 13H), 1.95-1.79 (m, 2H), 1.68-1.55 (m, 1H), 1.52-1.45 (m, 1H), 1.28 (d, J=6.5 Hz, 3H), 1.11 (d, J=6.1 Hz, 3H).

Example 105

Synthesis of (S)-1-((2R,5S)-5-(4-chlorobenzyl)-1-methyl-4-(1-(pyridin-2-yl)piperidin-4-yl)piperazin-2-yl)ethan-1-ol2,2,2-trifluoroacetate (105)

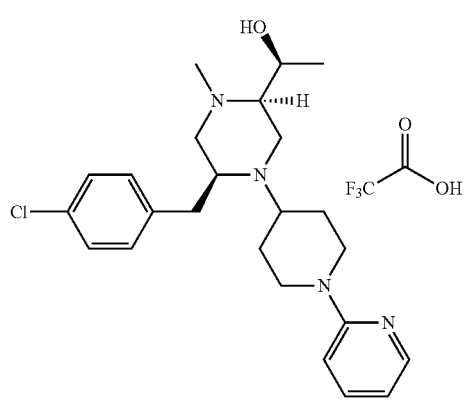

Step 1

Synthesis of N-(tert-butoxycarbonyl)-O-(tert-butyl)-N-methyl-L-threonine (105a)

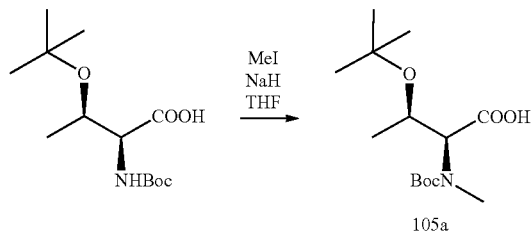 [SMILES: C[C@@H](OC(C)(C)C)[C@H](NC(=O)OC(C)(C)C)C(=O)O ; C[C@@H](OC(C)(C)C)[C@@H](C(=O)O)N(C)C(=O)OC(C)(C)C]

The title compound (105a) was obtained from N-(tert-butoxycarbonyl)-O-(tert-butyl)-L-threonine (2 g; 7.27 mmol) according to the General Procedure XI in 83% yield (1.73 g; 6.05 mmol).

ESI-MS m/z for $C_{14}H_{28}NO_5$ found 290.2 $[M+H]^+$

Step 2

Synthesis of methyl N-(tert-butoxycarbonyl)-O-(tert-butyl)-N-methyl-L-threoninate (105b)

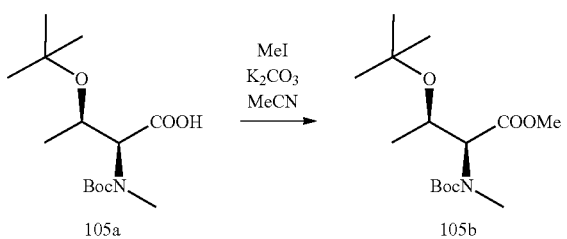 [SMILES: C[C@@H](OC(C)(C)C)[C@@H](C(=O)O)N(C)C(=O)OC(C)(C)C ; COC(=O)[C@H]([C@@H](C)OC(C)(C)C)N(C)C(=O)OC(C)(C)C]

To a solution of 105a (1.73 g; 6.05 mmol) in MeCN (30 mL) $K_2CO_3$ (2.5 g; 17.94 mmol) was added followed by MeI (0.56 mL; 8.97 mol) and the mixture was stirred at room temperature overnight. The reaction progress was monitored by LC-MS. When analysis indicated completion of the reaction, the solvent was evaporated and the residue was taken into AcOEt/$H_2O$. An organic layer was washed with water, brine dried over anhydrous $MgSO_4$, filtered and concentrated in vacuo and the crude product was used to the next step without additional purification. Compound 105b was obtained in 92% yield (1.68 g; 5.54 mmol).

ESI-MS m/z for $C_{15}H_{30}NO_5$ found 304.2 $[M+H]^+$

Step 3

Synthesis of methyl O-(tert-butyl)-N-methyl-L-threoninate hydrochloride (105c)

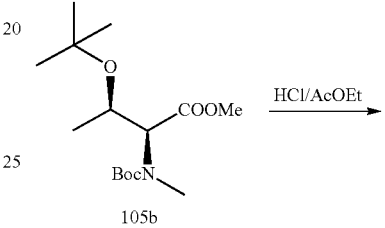

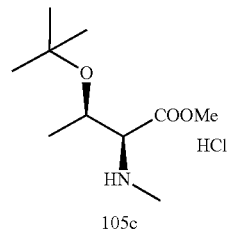

The title compound (105c) was obtained as a hydrochloride salt from 105b (1.68 g; 5.54 mmol) according to the General Procedure IVa in 98% yield (1.3 g; 5.43 mmol).

ESI-MS m/z for $C_{10}H_{22}NO_3$ found 204.1 $[M+H]^+$

Step 4

Synthesis of methyl N-((S)-2-((tert-butoxycarbonyl)amino)-3-(4-chlorophenyl)propanoyl)-O-(tert-butyl)-N-methyl-L-threoninate (105d)

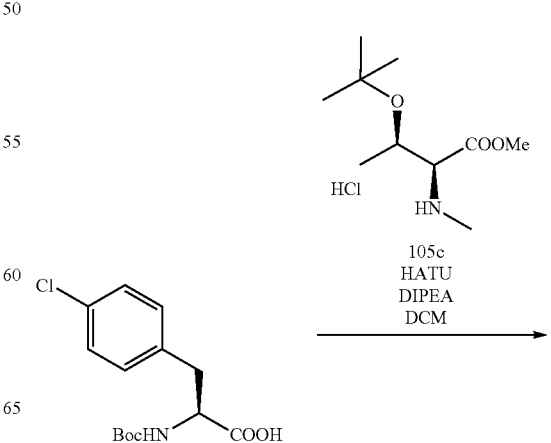

-continued

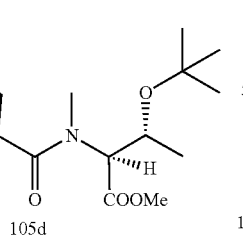

105d

The title compound (105d) was obtained from 105c (1.3 g; 5.43 mmol) and (S)-2-((tert-butoxycarbonyl)amino)-3-(4-chlorophenyl)propanoic acid (1.63 g; 5.42 mmol) according to the General Procedure III in 99% yield (2.61 g; 5.38 mmol).

ESI-MS m/z for $C_{24}H_{38}ClN_2O_6$ found 485.2/487.2 $[M+H]^+$

Step 5

Synthesis of (3S,6S)-3-(4-chlorobenzyl)-6-((S)-1-hydroxyethyl)-1-methylpiperazine-2,5-dione (105e)

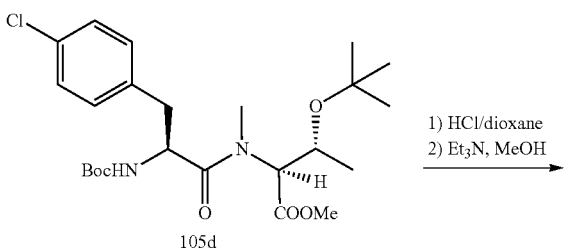

105d

The title compound (105e) was obtained from 105d (2.61 g; 5.38 mmol) according to the General Procedure VIII in 38% yield (600 mg; 2.03 mmol).

ESI-MS m/z for $C_{14}H_{18}ClN_2O_3$ found 296.8/298.8 $[M+H]^+$; $^1$H NMR (700 MHz, CDCl$_3$) δ 7.40-7.37 (m, 2H), 7.22-7.20 (m, 2H), 6.09 (s, 1H), 4.26-4.21 (m, 2H), 4.06 (dd, J=3.8, 0.9 Hz, 1H), 3.62 (d, J=9.5 Hz, 1H), 3.45 (dd, J=13.8, 3.5 Hz, 1H), 3.10 (s, 3H), 3.00 (dd, J=13.8, 10.2 Hz, 1H), 1.19 (d, J=6.5 Hz, 3H).

Step 6

Synthesis of (S)-1-((2R,5S)-5-(4-chlorobenzyl)-1-methylpiperazin-2-yl)ethan-1-ol (105f)

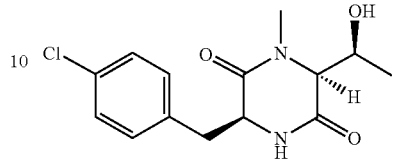

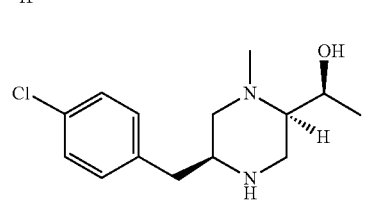

105f

The title compound (105f) was obtained from 105e (600 mg; 2.03 mmol) according to the General Procedure Ib in 77% yield (420 mg; 1.57 mmol).

ESI-MS m/z for $C_{14}H_{22}ClN_2O$ found 269.1/271.1 $[M+H]^+$

Step 7

Synthesis of (S)-1-((2R,5S)-5-(4-chlorobenzyl)-1-methyl-4-(1-(pyridin-2-yl)piperidin-4-yl)piperazin-2-yl)ethan-1-ol 2,2,2-trifluoroacetate (105)

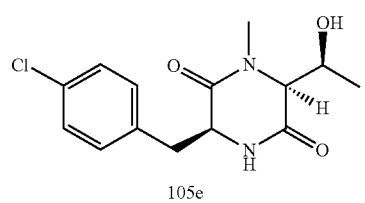

105f

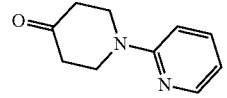

A
AcOH
NaBH(OAc)$_3$
DCE

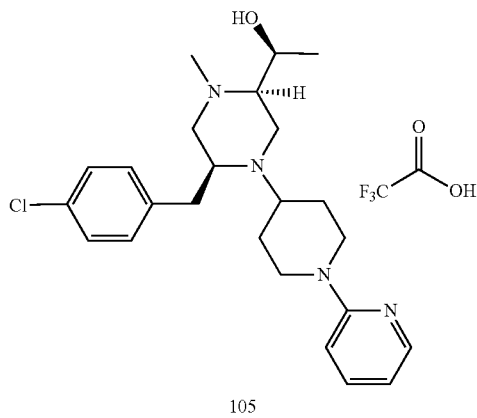

105

The title compound (105) was obtained as a TFA salt from 105f (104 mg; 0.39 mmol) according to the General Procedure VI in 51% yield (108 mg; 0.2 mmol).

ESI-MS m/z for $C_{29}H_{35}C_{12}N_4$ found 429.1/431.1 [M+H]$^+$; $^1$H NMR (700 MHz, DMSO-d$_6$+D$_2$O, 348 K) δ 7.95-7.92 (m, 1H), 7.88-7.84 (m, 1H), 7.38-7.34 (m, 2H), 7.34-7.30 (m, 2H), 7.21-7.15 (m, 1H), 6.88-6.82 (m, 1H), 4.19-4.08 (m, 3H), 3.45-3.38 (m, 1H), 3.35-3.28 (m, 1H), 3.17-3.10 (m, 1H), 3.09-2.96 (m, 3H), 2.95-2.73 (m, 8H), 1.89-1.82 (m, 1H), 1.82-1.73 (m, 1H), 1.69-1.60 (m, 1H), 1.53-1.43 (m, 1H), 1.17 (d, J=6.3 Hz, 3H).

Example 106

Synthesis of 2-((2S,5S)-5-(4-chlorobenzyl)-2-isopropyl-4-(1-(pyridin-2-yl)piperidin-4-yl)piperazin-1-yl)-N-methylacetamide 2,2,2-trifluoroacetate (106)

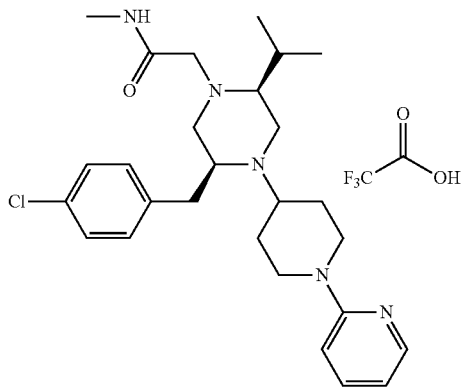

106

Step 1

Synthesis of methyl ((S)-2-((tert-butoxycarbonyl)amino)-3-(4-chlorophenyl)propyl)-L-valinate (106a)

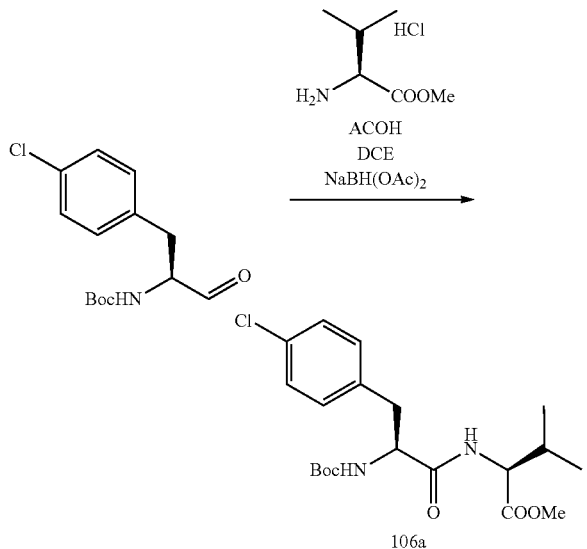

The reductive amination of known aldehyde (2.73 g; 9.62 mmol) with methyl L-valinate hydrochloride (1.61 g; 9.62 mmol) was accomplished according to the General Procedure VI. The crude product 106a was obtained in 99% yield (3.79 g, 9.52 mmol).

ESI-MS m/z for $C_{20}H_{32}ClN_2O_4$ found 399.2/401.2 [M+H]$^+$

Step 2

Synthesis of (3S,6S)-6-(4-chlorobenzyl)-3-isopropylpiperazin-2-one (106b)

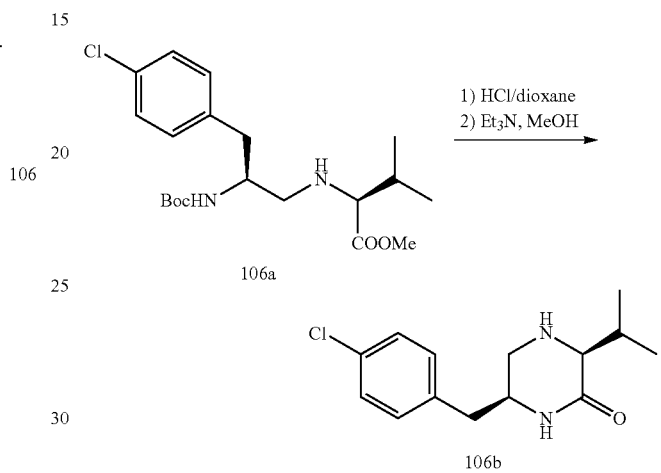

The title compound (106b) was obtained from 106a (3.79 g, 9.52 mmol) according to the General Procedure VIII in 99% yield (2.51 g; 9.42 mmol).

ESI-MS m/z for $C_{14}H_2MClN_2O$ found 267.1/269.1 [M+H]$^+$

Step 3

Synthesis of tert-butyl (2S,5S)-5-(4-chlorobenzyl)-2-isopropyl-3-oxopiperazine-1-carboxylate (106c)

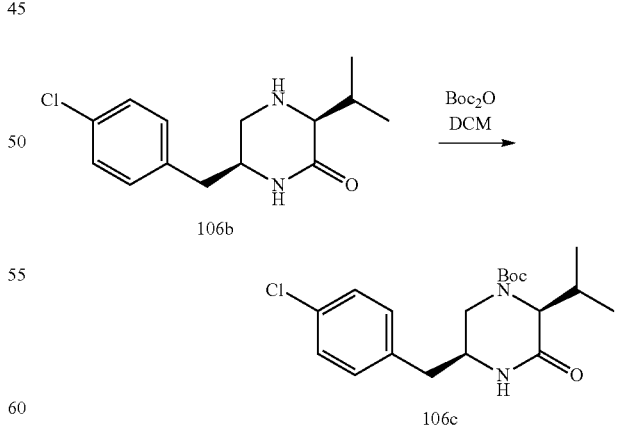

To a solution of 106b (2.51 g; 9.42 mmol) in dichloromethane (30 mL), di-tert-butyl dicarbonate (Boc$_2$O) (2.1 g, 9.62 mmol) was added and the reaction mixture was stirred at room temperature overnight, after which time TLC and LC-MS showed almost complete consumption of the starting material. The volatiles were removed in vacuo and the residue was purified by flash column chromatography on silica (hexane/AcOEt, 3:1 to 1:1, v/v) giving 106c in 70% yield (2.4 g; 6.55 mmol).

ESI-MS m/z for $C_{15}H_{20}ClN_2O_3$ found 311.1/313.1 $[M+H-tBu]^+$; $^1H$ NMR (700 MHz, CDCl$_3$) δ 7.39-7.34 (m, 2H), 7.25-7.14 (m, 2H), 5.91-5.65 (m, 1H), 4.50-4.34 (m, 1H), 3.82-3.53 (m, 1H), 2.99-2.81 (m, 2H), 2.78-2.50 (m, 1H), 2.42-2.28 (m, 1H), 1.58-1.48 (m, 9H), 1.21-1.11 (m, 3H), 1.07-0.93 (m, 3H).

Step 4

Synthesis of tert-butyl (2S,5S)-5-(4-chlorobenzyl)-2-isopropylpiperazine-1-carboxylate (106d)

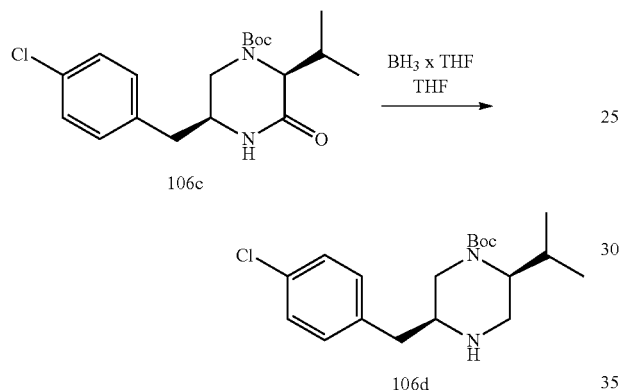

The title compound (106d) was obtained from 106c (2.4 g; 6.55 mmol) according to the General Procedure Ib in 26% yield (0.6 g; 1.7 mmol).

ESI-MS m/z for $C_{19}H_{30}ClN_2O_2$ found 353.2/355.2 $[M+H]^+$

Step 5

Synthesis of tert-butyl (2S,5S)-5-(4-chlorobenzyl)-2-isopropyl-4-(1-(pyridin-2-yl)piperidin-4-yl)piperazine-1-carboxylate (106e)

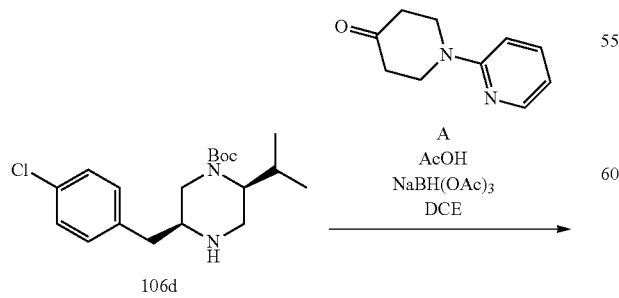

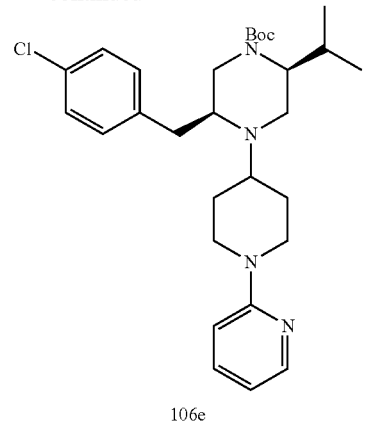

106e

The title compound (106e) was obtained from 106d (0.37 g; 1.05 mmol) according to the General Procedure VI in 56% yield (300 mg; 0.59 mmol).

ESI-MS m/z for $C_{29}H_{42}ClN_4O_2$ found 513.3/515.3 $[M+H]^+$

Step 6

Synthesis of (2S,5S)-2-(4-chlorobenzyl)-5-isopropyl-1-(1-(pyridin-2-yl)piperidin-4-yl)piperazine tetrahydrochloride (106f)

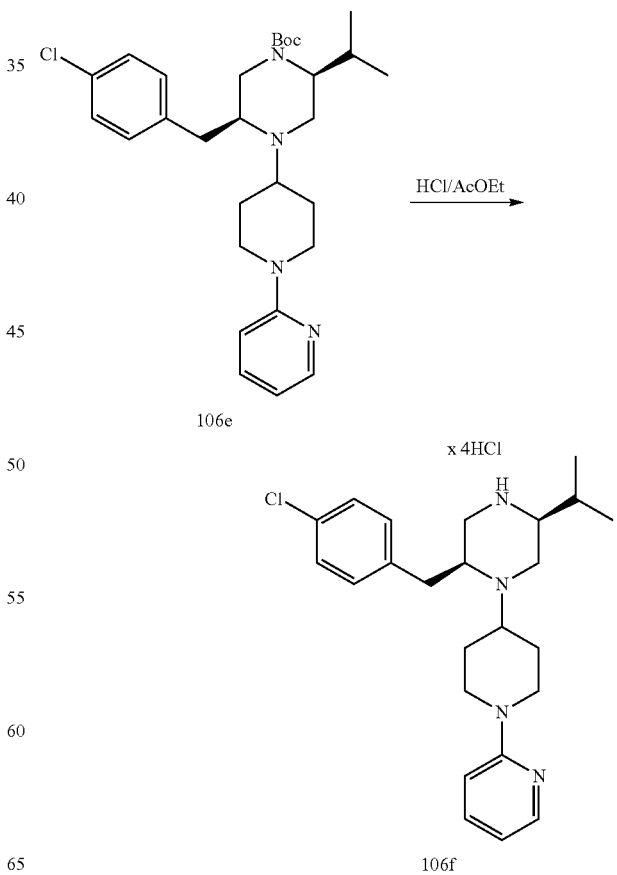

The title compound (106f) was obtained as a tetrahydrochloride salt from 106e (300 mg; 0.59 mmol) according to the General Procedure IVa in 97% yield (318 mg; 0.57 mmol).

ESI-MS m/z for $C_{24}H_{34}ClN_4$ found 413.2/415.2 [M+H]$^+$

Step 7

Synthesis of tert-butyl 2-((2S,5S)-5-(4-chlorobenzyl)-2-isopropyl-4-(1-(pyridin-2-yl)piperidin-4-yl)piperazin-1-yl)acetate (106g)

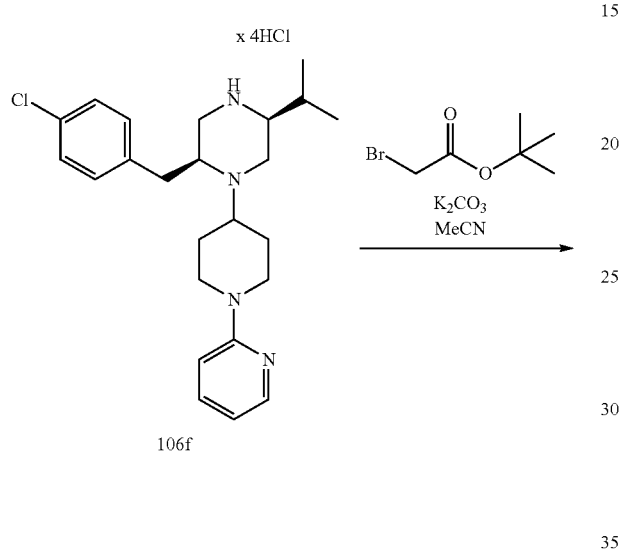

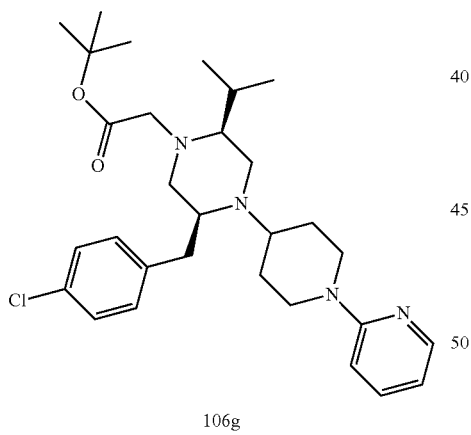

106g

To a solution of 106f (318 mg; 0.57 mmol) in acetonitrile (5 mL), potassium carbonate (400 mg; 2.86 mmol) was added followed by tert-butyl bromoacetate (127 μL, 0.86 mmol) and the resulting mixture was refluxed overnight. LC-MS indicated completion of the reaction. The reaction mixture was filtered and the solid residue was washed with EtOAc. After evaporation of an organic phase the crude product was purified by silica-gel column chromatography (hexane/AcOEt, 4:1, v/v) giving 106g in 81% yield (240 mg; 0.46 mmol).

ESI-MS m/z for $C_{30}H_{44}ClN_4O_2$ found 527.3/529.3 [M+H]$^+$

Step 8

Synthesis of 2-((2S,5S)-5-(4-chlorobenzyl)-2-isopropyl-4-(1-(pyridin-2-yl)piperidin-4-yl)piperazin-1-yl)acetic acid tetra-2,2,2-trifluoroacetate (106h)

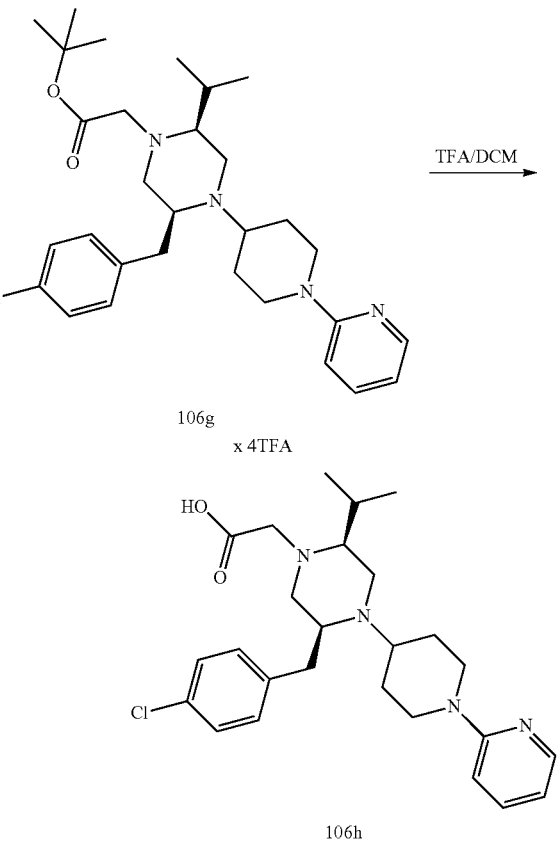

106h

The title compound (106h) was obtained as a tetra-TFA salt from 106g (240 mg; 0.46 mmol) according to the General Procedure IVb in 98% yield (420 mg; 0.45 mmol).

ESI-MS m/z for $C_{26}H_{36}ClN_4O_2$ found 471.2/473.2 [M+H]$^+$

Step 9

Synthesis of 2-((2S,5S)-5-(4-chlorobenzyl)-2-isopropyl-4-(1-(pyridin-2-yl)piperidin-4-yl)piperazin-1-yl)-N-methylacetamide 2,2,2-trifluoroacetate (106)

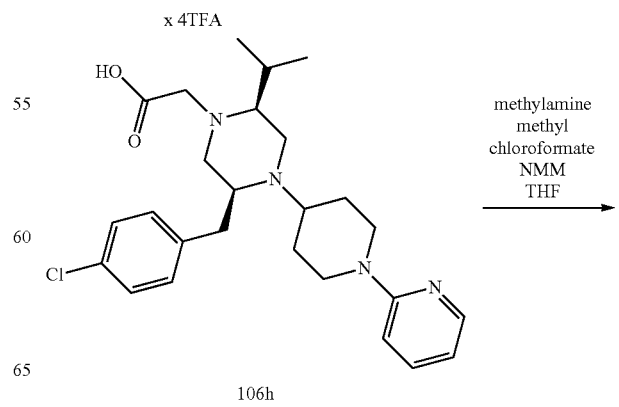

403

-continued

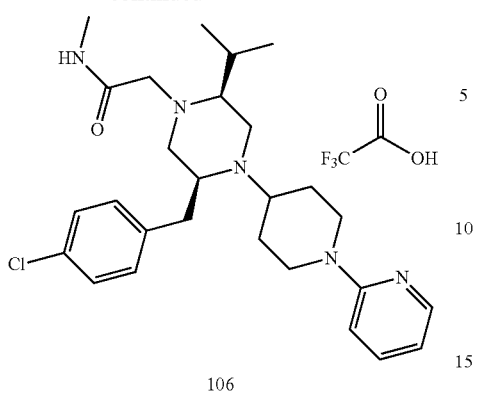

106

The solution of 106h (120 mg; 0.129 mmol) in THF (2 mL) was cooled to −20° C. and NMM (73 μL; 0.66 mmol) was added followed by methyl chloroformate (11 μL; 0.14 mmol). The mixture was then stirred for 30 minutes and methylamine (2M in THF; 0.65 mL; 1.29 mmol) was added and stirred at room temperature for 24 hours. LC-MS indicated completion of the reaction. The mixture was evaporated to dryness and the crude product purified by preparative reversed-phase column chromatography (Luna® 5 μm Phenyl-Hexyl, LC Column 250×21.2 mm, water/MeCN+1% TFA, 95:5 to 40:60, 30 minutes). Compound 106 was obtained as a TFA salt in 19% yield (15 mg; 0.025 mmol).

ESI-MS m/z for $C_{27}H_{39}ClN_5O$ found 484.3/486.3 [M+H]$^+$; $^1$H NMR (700 MHz, DMSO-d$_6$+D$_2$O, 348 K) δ 8.04-8.00 (m, 1H), 7.81-7.77 (m, 1H), 7.40-7.36 (m, 2H), 7.35-7.31 (m, 2H), 7.12-7.08 (m, 1H), 6.87-6.77 (m, 1H), 4.36-4.27 (m, 2H), 3.77-3.68 (m, 2H), 3.30-3.20 (m, 3H), 3.11-3.02 (m, 5H), 2.84-2.74 (m, 2H), 2.73-2.65 (m, 1H), 2.57 (s, 3H), 2.32-2.24 (m, 1H), 2.24-2.14 (m, 2H), 1.74-1.62 (m, 2H), 0.97-0.89 (m, 6H).

Example 137

Synthesis of (2S,5S)-2-(4-chlorobenzyl)-4-((R)-2-methoxypropyl)-5-methyl-1-(1-(pyridin-2-yl)piperidin-4-yl)piperazine 2,2,2-trifluoroacetate (107)

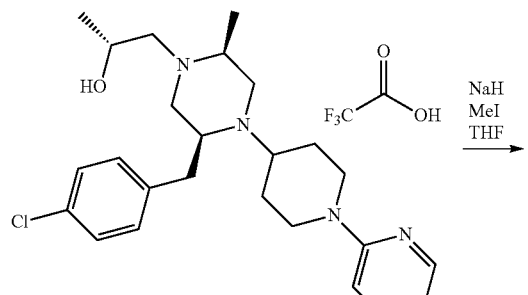

102

404

-continued

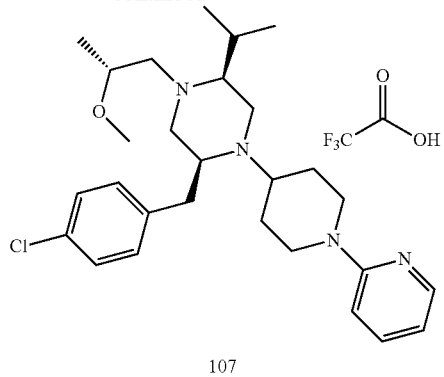

107

The title compound (107) was obtained as a TFA salt from 102 (38 mg; 0.068 mmol) according to the General Procedure XI in 24% yield (9 mg; 0.016 mmol).

ESI-MS m/z for $C_{26}H_{38}ClN_4O$ found 457.2/459.2 [M+H]$^+$; $^1$H NMR (700 MHz, MeCN-d$_3$, 318 K) δ 8.17-8.12 (m, 1H), 7.55-7.49 (m, 1H), 7.37-7.32 (m, 2H), 7.28-7.22 (m, 2H), 6.80-6.74 (m, 1H), 6.63-6.56 (m, 1H), 4.30-4.18 (m, 2H), 3.33-3.26 (m, 1H), 3.24 (s, 3H), 3.18-3.06 (m, 2H), 3.00-2.89 (m, 2H), 2.87-2.75 (m, 3H), 2.69-2.62 (m, 1H), 2.56-2.49 (m, 1H), 2.46-2.34 (m, 2H), 2.20-2.09 (m, 3H), 2.06-2.00 (m, 1H), 1.52-1.42 (m, 2H), 1.17 (d, J=6.1 Hz, 3H), 1.07 (d, J=5.4 Hz, 3H).

Example 108

Synthesis of (2S,4R)-2-(4-chlorobenzyl)-4-methoxy-1'-(pyridin-2-yl)-1,4'-bipiperidine 2,2,2-trifluoroacetate (108)

108

[Structure of compound 108]

Step 1

Synthesis of tert-butyl (2S,4R)-2-(4-chlorobenzyl)-4-methoxypiperidine-1-carboxylate (108a)

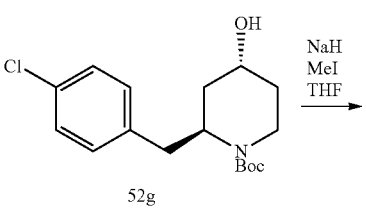

52g

-continued

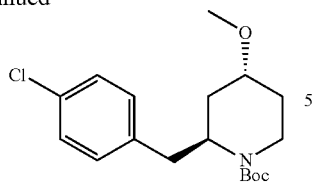

108a

The title compound (108a) was obtained from 52g (114 mg; 0.35 mmol) according to the General Procedure XI in 91% yield (110 mg; 0.32 mmol).

ESI-MS m/z for $C_{18}H_{27}ClNO_3$ found 340.2/342.2 [M+H]$^+$

Step 2

Synthesis of (2S,4R)-2-(4-chlorobenzyl)-4-methoxypiperidine (108b)

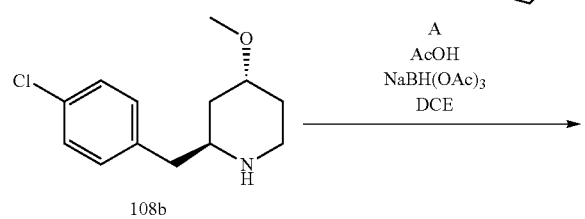

108a

108b

The title compound (108b) was obtained from 108a (110 mg; 0.32 mmol) according to the General Procedure IVa. Then obtained hydrochloride salt was dissolved in AcOEt and 1M NaOH was added to this solution. Phases were separated and an organic one was washed with brine, dried over anhydrous MgSO$_4$ and concentrated in vacuo to give free amine 108b in 99% yield (77 mg; 0.32 mmol).

ESI-MS m/z for $C_{13}H_{19}ClNO$ found 240.1/242.1 [M+H]$^+$

Step 3

Synthesis of (2S,4R)-2-(4-chlorobenzyl)-4-methoxy-1'-(pyridin-2-yl)-1,4'-bipiperidine 2,2,2-trifluoroacetate (108)

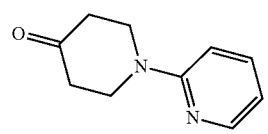

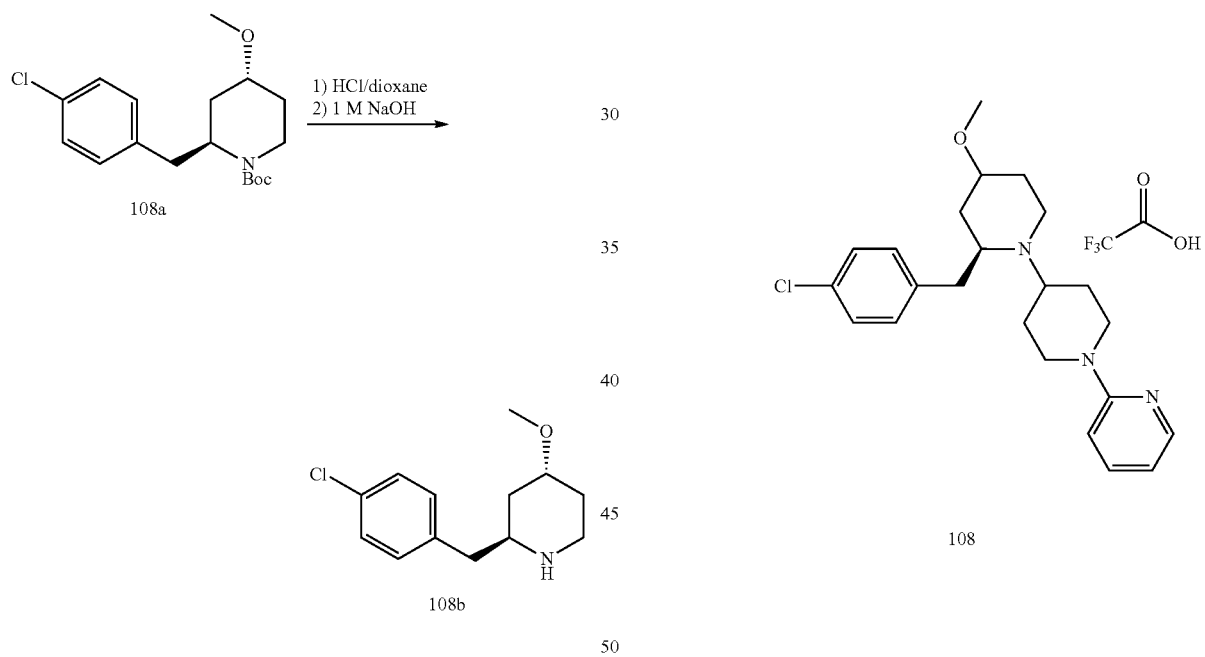

108

The title compound (108) was obtained as a TFA salt from 108b (40 mg; 0.17 mmol) according to the General Procedure VI in 2% yield (2 mg; 0.004 mmol).

ESI-MS m/z for $C_{23}H_{31}ClN_3O$ found 400.1/402.1 [M+H]$^+$; $^1$H NMR (700 MHz, MeCN-d$_3$) δ 8.19-8.10 (m, 1H), 7.94-7.85 (m, 1H), 7.49-7.40 (m, 2H), 7.37-7.29 (m, 2H), 7.16-7.08 (m, 1H), 6.93-6.86 (m, 1H), 4.49-4.32 (m, 2H), 4.09-4.00 (m, 1H), 3.75-3.66 (m, 1H), 3.59-3.52 (m, 2H), 3.36-3.29 (m, 1H), 3.28-3.14 (m, 5H), 3.12-3.04 (m, 2H), 3.02-2.93 (m, 1H), 2.36-2.28 (m, 1H), 2.16-2.05 (m, 2H), 2.05-2.00 (m, 2H), 1.92-1.80 (m, 2H).

Example 109

Synthesis of (2S,4S)-2-(4-chlorobenzyl)-4-methoxy-1'-(pyridin-2-yl)-1,4'-bipiperidine 2,2,2-trifluoroacetate (109)

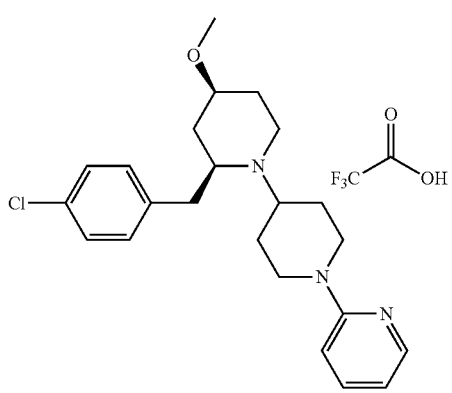

The title compound (109) was obtained as a TFA salt in 2% overall yield in a similar way to Example 108 with the exception that, in the first step of the synthesis, the compound 52f was used instead of the compound 52g.

ESI-MS m/z for $C_{23}H_{31}ClN_3O$ found 400.1/402.1 [M+H]+; $^1$H NMR (700 MHz, MeCN-$d_3$) δ 8.17-8.09 (m, 1H), 7.96-7.88 (m, 1H), 7.46-7.39 (m, 2H), 7.39-7.30 (m, 2H), 7.22-7.09 (m, 1H), 6.97-6.86 (m, 1H), 4.50-4.36 (m, 2H), 4.08-4.00 (m, 1H), 3.61-3.48 (m, 3H), 3.39-3.29 (m, 1H), 3.29-3.20 (m, 4H), 3.15-3.02 (m, 2H), 2.90-2.81 (m, 1H), 2.42-2.34 (m, 1H), 2.22-2.14 (m, 1H), 2.10-2.04 (m, 1H), 2.03-1.99 (m, 1H), 1.97-1.93 (m, 1H), 1.88-1.76 (m, 2H), 1.76-1.67 (m, 1H).

Example 110

Synthesis of (R)-1-((2R,5S)-5-(4-chlorobenzyl)-1-methyl-4-(1-(pyridin-2-yl)piperidin-4-yl)piperazin-2-yl)ethan-1-ol (110)

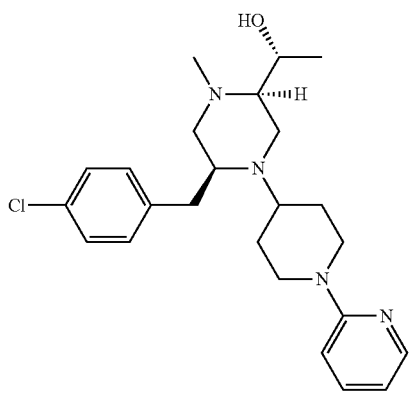

Step 1

Synthesis of tert-butyl (2S,5R)-2-(4-chlorobenzyl)-5-((S)-1-hydroxyethyl)-4-methylpiperazine-1-carboxylate (110a)

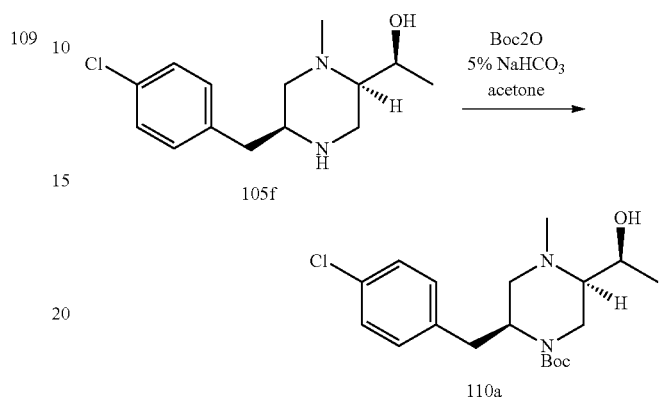

To a solution of 105f (0.3 g; 1.12 mmol) in acetone (3 mL), di-tert-butyl dicarbonate (Boc$_2$O) (0.24 g, 1.12 mmol) in 5% NaHCO$_3$ (5 mL) was added and the reaction mixture was stirred at room temperature overnight, after which time TLC and LC-MS showed almost complete consumption of the starting material. Acetone was removed in vacuo and the residue was extracted with AcOEt. An organic layer was washed with brine, dried over anhydrous MgSO$_4$, filtered and concentrated in vacuo and the crude product was used to the next step without additional purification. Compound 110a was obtained in 78% yield (0.32 g; 0.87 mmol).

ESI-MS m/z for $C_{19}H_{30}ClN_2O_3$ found 369.2/371.2 [M+H]+

Step 2

Synthesis of tert-butyl (2S,5R)-5-((R)-1-(benzoyloxy)ethyl)-2-(4-chlorobenzyl)-4-methylpiperazine-1-carboxylate (110b)

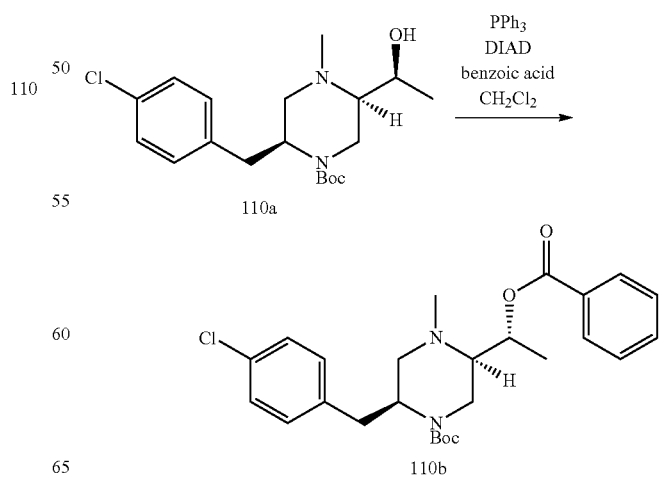

The solution of PPh₃ (0.62 g; 2.36 mmol) in CH₂Cl₂ (10 mL) was cooled to −20° C. and then DIAD (0.46 mL; 2.36 mmol) was added dropwise and stirred for 20 minutes at this temperature. Then benzoic acid (0.29 g; 2.36 mmol) was added and stirred for 30 minutes at −20° C. and compound 110a (0.29 g; 0.79 mmol) was added. Then the mixture was allowed to room temperature and stirred overnight, after which time TLC and LC-MS showed complete consumption of the starting material. The mixture was evaporated to dryness and the crude product was purified by flash column chromatography on silica (hexane/AcOEt, 2:1, v/v). Compound 110b was obtained in 77% yield (290 mg; 0.61 mmol).

ESI-MS m/z for $C_{26}H_{34}ClN_2O_4$ found 473.2/475.2 $[M+H]^+$

Step 3

Synthesis of (R)-1-((2R,5S)-5-(4-chlorobenzyl)-1-methylpiperazin-2-yl)ethyl benzoate dihydrochloride (110c)

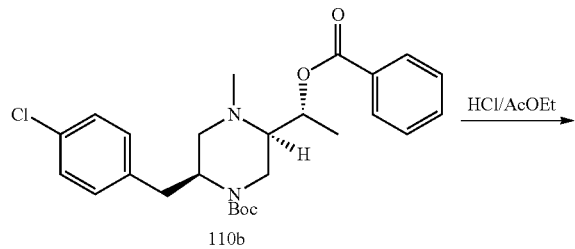
110b

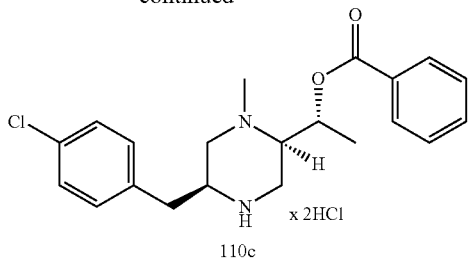
110c

The title compound (110c) was obtained as a dihydrochloride salt from 110b (290 mg; 0.61 mmol) according to the General Procedure IVa in 99% yield (267 mg; 0.60 mmol).

ESI-MS m/z for $C_{21}H_{26}ClN_2O_2$ found 373.2/375.2 $[M+H]^+$

Step 4

Synthesis of (R)-1-((2R,5S)-5-(4-chlorobenzyl)-1-methyl-4-(1-(pyridin-2-yl)piperidin-4-yl)piperazin-2-yl)ethyl benzoate (110d)

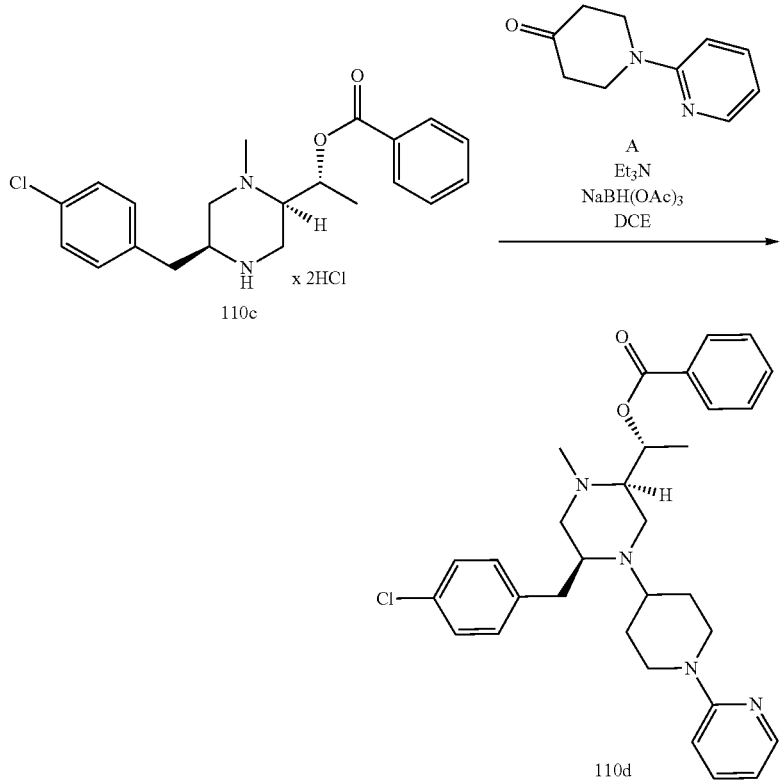

411

The title compound (110d) was obtained from 110c (267 mg; 0.60 mmol) according to the General Procedure VI in 99% yield (314 mg; 0.59 mmol).

ESI-MS m/z for $C_{31}H_{38}ClN_4O_2$ found 533.3/535.3 [M+H]$^+$

Step 5

Synthesis of (R)-1-((2R,5S)-5-(4-chlorobenzyl)-1-methyl-4-(1-(pyridin-2-yl)piperidin-4-yl)piperazin-2-yl)ethan-1-ol (110)

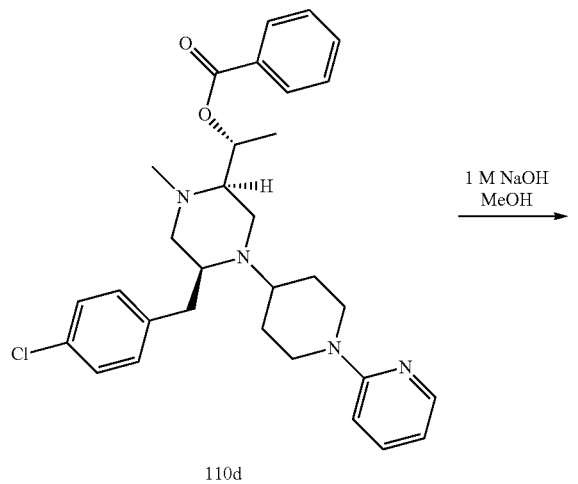

To a solution of 110d (314 mg; 0.59 mmol) in MeOH (10 mL), 1M NaOH (10 mL) was added and the reaction mixture was stirred at room temperature for 2 days, after which time TLC and LC-MS showed complete consumption of the starting material. MeOH was removed in vacuo and the product was extracted with AcOEt. An organic layer was dried over anhydrous MgSO$_4$, filtered and concentrated in vacuo. The residue was suspended in MeCN, the solid was filtered to give the compound 110 in 13% yield (33 mg; 0.077 mmol).

ESI-MS m/z for $C_{24}H_{34}ClN_4O$ found 429.1/431.1 [M+H]$^+$; $^1$H NMR (700 MHz, DMSO-d$_6$+D$_2$O, 348 K) δ 8.10-8.02 (m, 1H), 7.52-7.45 (m, 1H), 7.36-7.28 (m, 2H), 7.23-7.16 (m, 2H), 6.79-6.71 (m, 1H), 6.62-6.54 (m, 1H), 4.18-4.08 (m, 2H), 4.04-3.98 (m, 1H), 3.02-2.94 (m, 2H), 2.94-2.80 (m, 3H), 2.79-2.70 (m, 2H), 2.47-2.39 (m, 2H), 2.12-2.07 (m, 4H), 2.07-2.01 (m, 1H), 1.94-1.85 (m, 2H), 1.41-1.29 (m, 2H), 1.11 (d, J=6.5 Hz, 3H).

Example 111

Synthesis of (2S,5S)-5-(4-chlorobenzyl)-4-(1-(4-fluoropyridin-2-yl)piperidin-4-yl)-2-methylmorpholine 2,2,2-trifluoroacetate (111)

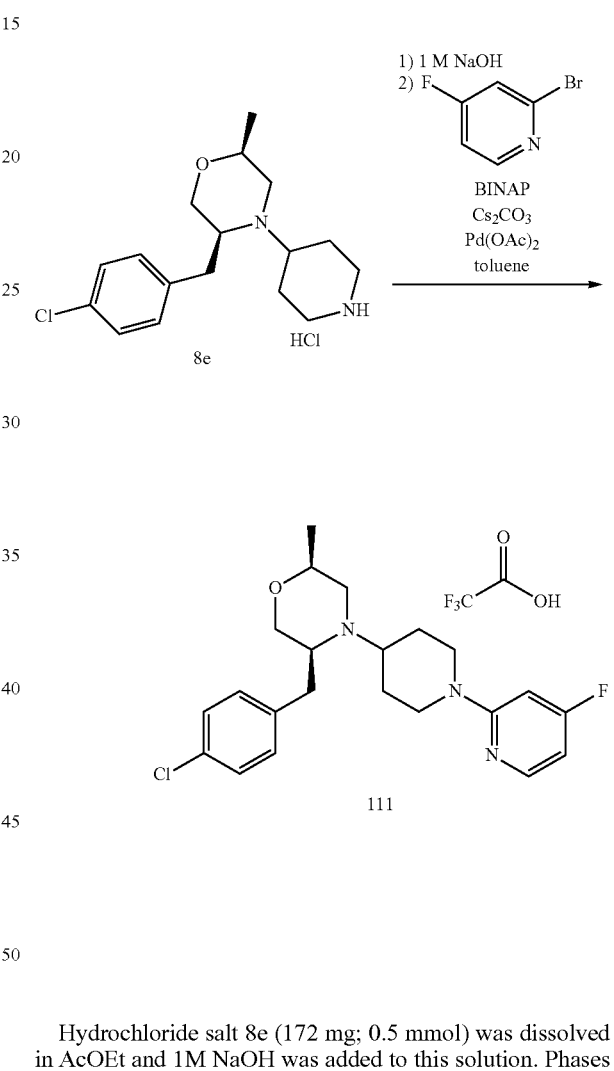

Hydrochloride salt 8e (172 mg; 0.5 mmol) was dissolved in AcOEt and 1M NaOH was added to this solution. Phases were separated and an organic one was washed with brine, dried over anhydrous MgSO$_4$ and concentrated in vacuo to give a free amine (154 mg; 0.5 mmol) which was then transferred into the title compound (111) according to the General Procedure XXIII. Compound 111 was obtained as a TFA salt in 4% yield (10 mg; 0.019 mmol).

ESI-MS m/z for $C_{22}H_{28}ClFN_3O$ found 403.9/405.9 [M+H]$^+$; $^1$H NMR (700 MHz, MeCN-d$_3$) δ 8.23-8.12 (m, 1H), 7.51-7.37 (m, 2H), 7.37-7.25 (m, 2H), 6.93-6.79 (m, 1H), 6.79-6.66 (m, 1H), 4.41-4.30 (m, 2H), 4.05-3.95 (m, 1H), 3.85-3.46 (m, 5H), 3.31-3.10 (m, 4H), 3.01-2.84 (m, 1H), 2.46-2.30 (m, 2H), 1.96-1.90 (m, 2H), 1.29 (d, J=6.2 Hz, 3H).

Example 112

Synthesis of (2S,5S)-5-(4-chlorobenzyl)-4-(1-(3-fluoro-4-methylpyridin-2-yl)piperidin-4-yl)-2-methylmorpholine 2,2,2-trifluoroacetate (112)

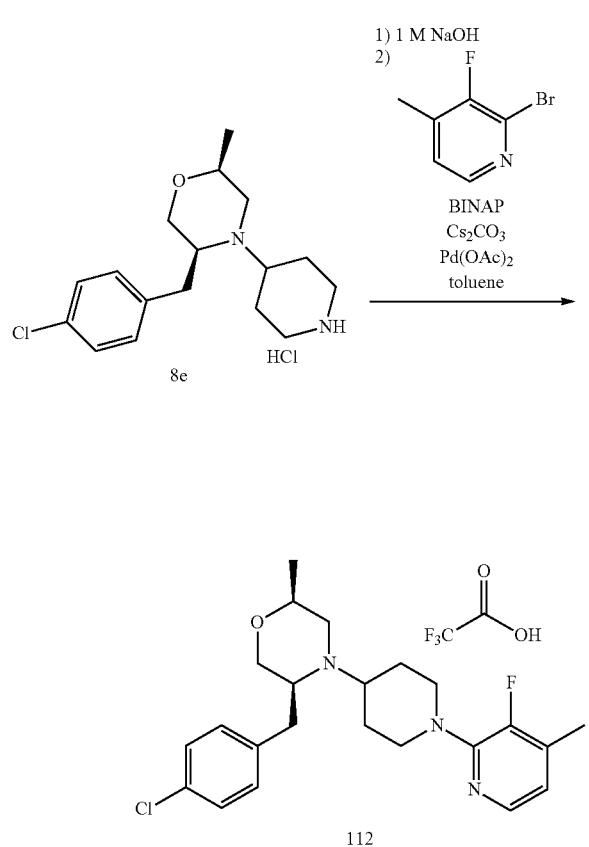

Hydrochloride salt 8e (152 mg; 0.44 mmol) was dissolved in AcOEt and 1M NaOH was added to this solution. Phases were separated and an organic one was washed with brine, dried over anhydrous MgSO$_4$ and concentrated in vacuo to give a free amine (136 mg; 0.44 mmol) which was then transferred into the title compound (112) according to the General Procedure XXIII. Compound 112 was obtained as a TFA salt in 23% yield (53 mg; 0.1 mmol).

ESI-MS m/z for $C_{23}H_{30}ClFN_3O$ found 418.2/420.2 [M+H]$^+$; $^1$H NMR (700 MHz, Methanol-d$_4$) δ 7.94-7.83 (m, 1H), 7.48-7.40 (m, 2H), 7.40-7.31 (m, 2H), 6.89-6.81 (m, 1H), 4.31-4.13 (m, 2H), 3.99-3.60 (m, 6H), 3.31-3.24 (m, 1H), 3.24-3.17 (m, 1H), 3.17-3.00 (m, 3H), 2.48-2.37 (m, 2H), 2.31 (d, J=2.1 Hz, 3H), 1.93-1.78 (m, 2H), 1.36 (d, J=6.2 Hz, 3H).

Example 113

Synthesis of (2S,5S)-4-(1-(4-bromopyridin-2-yl)piperidin-4-yl)-5-(4-chlorobenzyl)-2-methylmorpholine 2,2,2-trifluoroacetate (113)

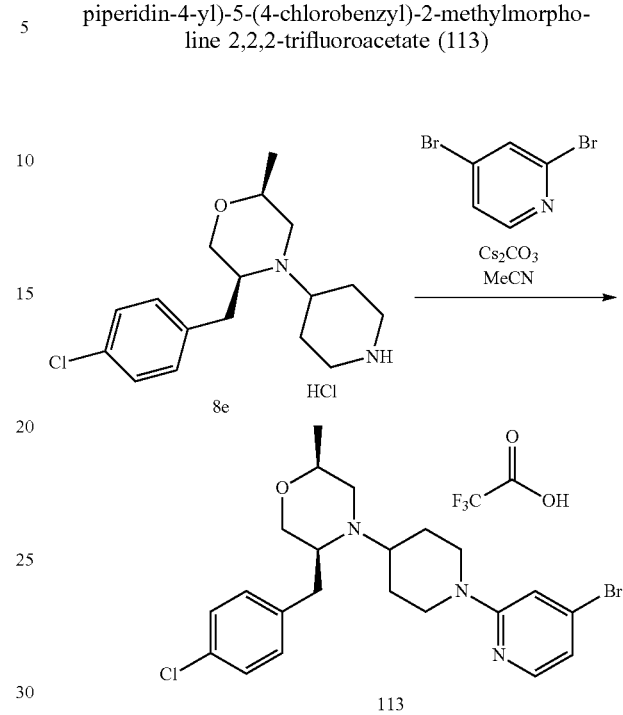

The title compound (113) was obtained as a TFA salt from 8e (138 mg; 0.4 mmol) according to the General Procedure XXIV in 7% yield (16 mg; 0.028 mmol).

ESI-MS m/z for $C_{22}H_{28}BrClN_3$ found 465.8/467.8 [M+H]$^+$; $^1$H NMR (700 MHz, Methanol-d$_4$) δ 8.06-7.94 (m, 1H), 7.45-7.38 (m, 2H), 7.38-7.29 (m, 2H), 7.23-7.12 (m, 1H), 6.95-6.86 (m, 1H), 4.62-4.50 (m, 2H), 3.93-3.74 (m, 4H), 3.71-3.55 (m, 2H), 3.31-3.24 (m, 1H), 3.24-3.16 (m, 1H), 3.16-2.96 (m, 3H), 2.44-2.32 (m, 2H), 1.77-1.63 (m, 2H), 1.35 (d, J=6.3 Hz, 3H).

Example 114

Synthesis of 2-(4-((2S,5S)-5-(4-chlorobenzyl)-2-methylmorpholino)piperidin-1-yl)nicotinamide 2,2,2-trifluoroacetate (114)

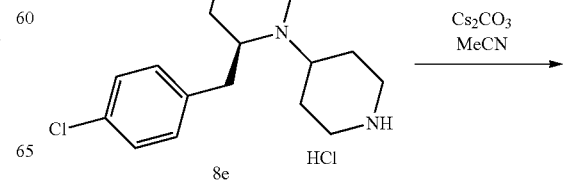

-continued

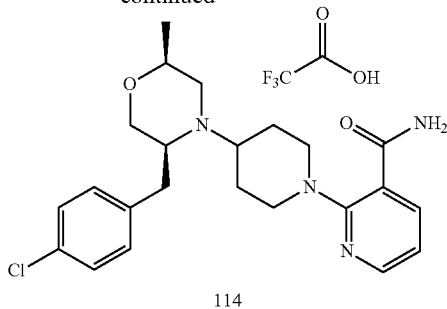

114

The title compound (114) was obtained as a TFA salt from 8e (55 mg; 0.16 mmol) according to the General Procedure XXIV in 19% yield (16 mg; 0.03 mmol).

ESI-MS m/z for $C_{23}H_{30}ClN_4O_2$ found 429.0/431.0 [M+H]+; 1H NMR (700 MHz, Methanol-$d_4$) δ 8.35-8.27 (m, 1H), 8.00-7.91 (m, 1H), 7.46-7.39 (m, 2H), 7.39-7.32 (m, 2H), 7.10-6.97 (m, 1H), 4.12-3.95 (m, 2H), 3.91-3.55 (m, 6H), 3.30-3.23 (m, 1H), 3.22-3.13 (m, 1H), 3.13-2.99 (m, 3H), 2.44-2.30 (m, 2H), 2.01-1.79 (m, 2H), 1.36 (d, J=6.2 Hz, 3H).

Example 115

Synthesis of 4-chloro-2-(4-((2S,5S)-5-(4-chlorobenzyl)-2-methylmorpholino)piperidin-1-yl)benzonitrile 2,2,2-trifluoroacetate (115)

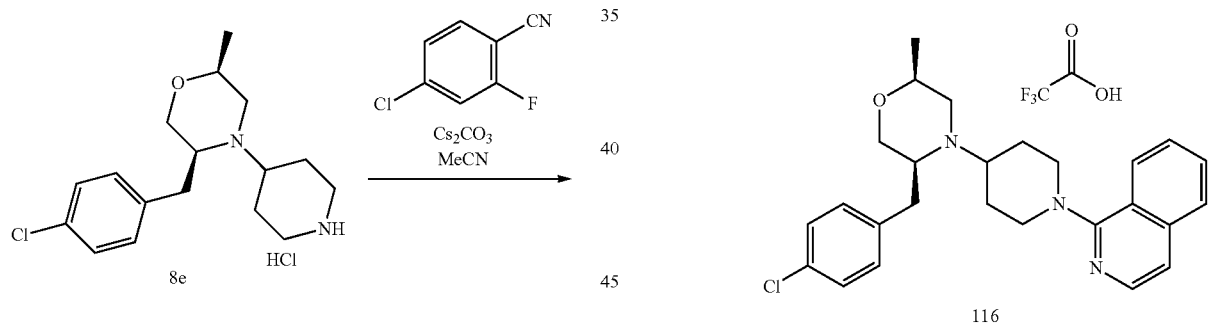

115

The title compound (115) was obtained as a TFA salt from 8e (55 mg; 0.16 mmol) according to the General Procedure XXIV in 8% yield (7 mg; 0.013 mmol).

ESI-MS m/z for $C_{24}H_{28}Cl_2N_3O$ found 444.0/446.0 [M+H]+; 1H NMR (700 MHz, Methanol-$d_4$) δ 7.70-7.60 (m, 1H), 7.44-7.38 (m, 2H), 7.38-7.32 (m, 2H), 7.29-7.22 (m, 1H), 7.22-7.11 (m, 1H), 3.90-3.75 (m, 5H), 3.75-3.62 (m, 4H), 3.24-3.10 (m, 2H), 3.08-2.93 (m, 2H), 2.60-2.43 (m, 2H), 2.04-1.86 (m, 2H), 1.37 (d, J=6.2 Hz, 3H).

Example 116

Synthesis of (2S,5S)-5-(4-chlorobenzyl)-4-(1-(isoquinolin-1-yl)piperidin-4-yl)-2-methylmorpholine 2,2,2-trifluoroacetate (116)

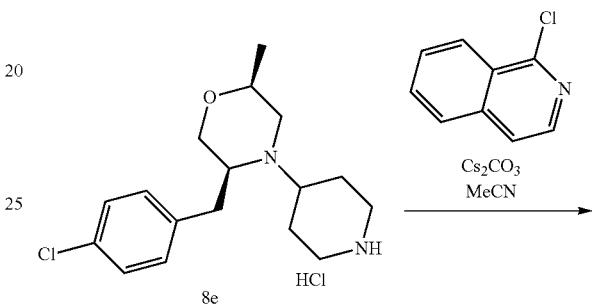

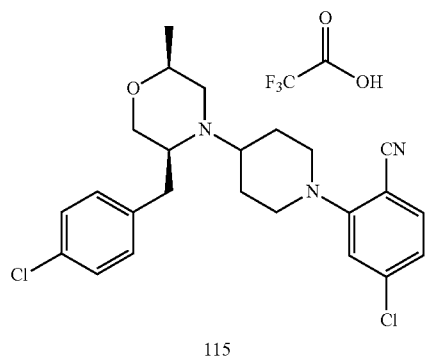

116

The title compound (116) was obtained as a TFA salt from 8e (55 mg; 0.16 mmol) according to the General Procedure XXIV in 15% yield (23 mg; 0.024 mmol).

ESI-MS m/z for $C_{26}H_{31}ClN_3O$ found 436.2/438.2 [M+H]+; 1H NMR (700 MHz, Methanol-$d_4$) δ 8.31-8.27 (m, 1H), 8.06-8.02 (m, 1H), 7.99-7.95 (m, 1H), 7.94-7.91 (m, 1H), 7.85-7.80 (m, 1H), 7.62-7.58 (m, 1H), 7.43-7.40 (m, 2H), 7.40-7.35 (m, 2H), 4.36-4.24 (m, 2H), 4.02-3.93 (m, 1H), 3.93-3.84 (m, 2H), 3.84-3.76 (m, 2H), 3.72-3.62 (m, 1H), 3.50-3.42 (m, 2H), 3.39-3.33 (m, 1H), 3.27-3.15 (m, 2H), 2.61-2.52 (m, 2H), 2.27-2.10 (m, 2H), 1.38 (d, J=6.3 Hz, 3H).

Example 117

Synthesis of methyl 2-(4-((2S,5S)-5-(4-chlorobenzyl)-2-methylmorpholino)piperidin-1-yl)nicotinate 2,2,2-trifluoroacetate (117)

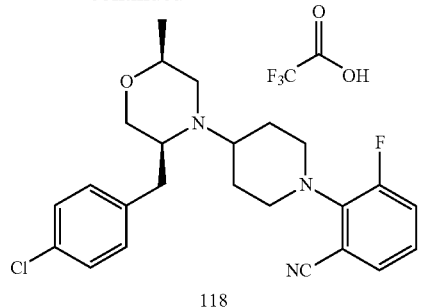

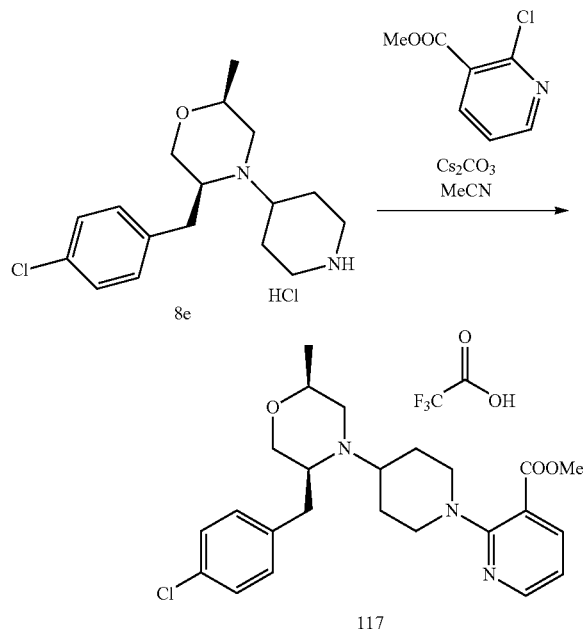

The title compound (117) was obtained as a TFA salt from 8e (55 mg; 0.16 mmol) according to the General Procedure XXIV in 90% yield (80 mg; 0.144 mmol).

ESI-MS m/z for $C_{24}H_{31}ClN_3O_3$ found 444.0/446.0 [M+H]$^+$; $^1$H NMR (700 MHz, Methanol-d$_4$) δ 8.34-8.29 (m, 1H), 8.17-8.12 (m, 1H), 7.43-7.39 (m, 2H), 7.38-7.33 (m, 2H), 6.97-6.91 (m, 1H), 4.07-4.01 (m, 2H), 3.93 (s, 3H), 3.89-3.76 (m, 3H), 3.74-3.60 (m, 3H), 3.30-3.24 (m, 1H), 3.25-3.16 (m, 1H), 3.15-3.01 (m, 3H), 2.44-2.31 (m, 2H), 1.94-1.81 (m, 2H), 1.36 (d, J=6.2 Hz, 3H).

Example 118

Synthesis of 2-(4-((2S,5S)-5-(4-chlorobenzyl)-2-methylmorpholino)piperidin-1-yl)-3-fluorobenzonitrile 2,2,2-trifluoroacetate (118)

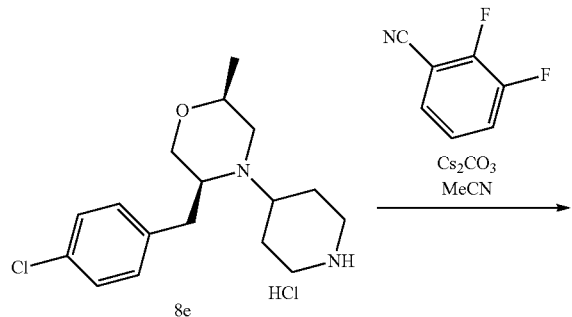

The title compound (118) was obtained as a TFA salt from 8e (55 mg; 0.16 mmol) according to the General Procedure XXIV in 29% yield (25 mg; 0.046 mmol).

ESI-MS m/z for $C_{24}H_{28}ClFN_3O$ found 428.0/430.0 [M+H]$^+$; $^1$H NMR (700 MHz, MeCN-d$_3$) δ 7.50-7.47 (m, 1H), 7.43-7.36 (m, 3H), 7.34-7.31 (m, 2H), 7.21-7.16 (m, 1H), 4.07-3.98 (m, 1H), 3.89-3.82 (m, 1H), 3.82-3.73 (m, 1H), 3.69-3.63 (m, 1H), 3.61-3.54 (m, 3H), 3.53-3.40 (m, 1H), 3.34-3.20 (m, 3H), 3.16-3.09 (m, 1H), 2.94-2.86 (m, 1H), 2.34-2.25 (m, 2H), 2.10-2.00 (m, 2H), 1.29 (d, J=6.3 Hz, 3H).

Example 119

Synthesis of 2-(4-((2S,5S)-5-(4-chlorobenzyl)-2-methylmorpholino)piperidin-1-yl)benzonitrile 2,2,2-trifluoroacetate (119)

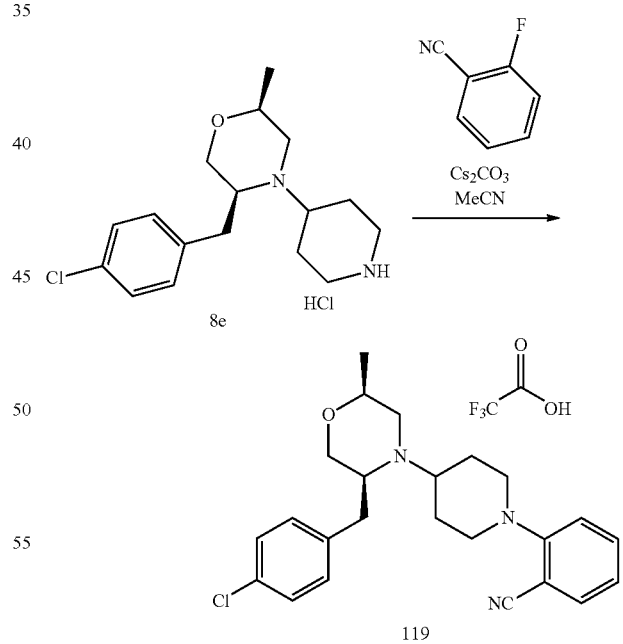

The title compound (119) was obtained as a TFA salt from 8e (55 mg; 0.16 mmol) according to the General Procedure XXIV in 20% yield (17 mg; 0.032 mmol).

ESI-MS m/z for $C_{24}H_{29}ClN_3O$ found 410.0/412.0 [M+H]$^+$; $^1$H NMR (700 MHz, MeCN-d$_3$) δ 7.68-7.64 (m, 1H), 7.64-7.55 (m, 1H), 7.46-7.39 (m, 2H), 7.36-7.30 (m, 2H), 7.20-7.16 (m, 1H), 7.16-7.10 (m, 1H), 4.11-3.99 (m, 1H), 3.92-3.84 (m, 1H), 3.84-3.71 (m, 3H), 3.67-3.60 (m, 1H), 3.60-3.52 (m, 1H), 3.50-3.39 (m, 1H), 3.30-3.22 (m, 1H), 3.18-3.06 (m, 1H), 2.96-2.81 (m, 3H), 2.42-2.37 (m, 2H), 2.12-2.03 (m, 2H), 1.29 (d, J=6.3 Hz, 3H).

Example 120

Synthesis of (2-(4-((2S,5S)-5-(4-chlorobenzyl)-2-methylmorpholino)piperidin-1-yl)pyridin-3-yl)methanol 2,2,2-trifluoroacetate (120)

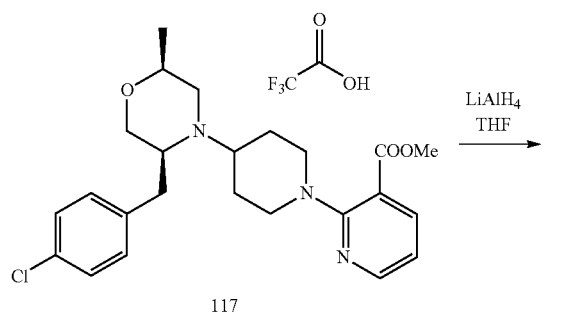

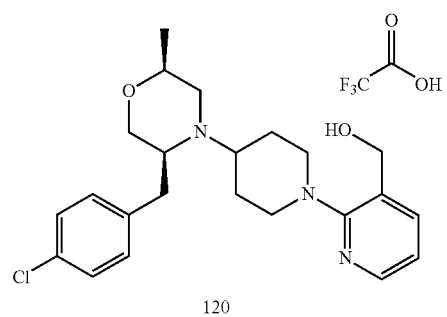

The title compound (120) was obtained as a TFA salt from 117 (39 mg; 0.07 mmol) according to the General Procedure XIX in 79% yield (29 mg; 0.055 mmol).

ESI-MS m/z for $C_{23}H_{31}ClN_3O_2$ found 416.0/418.0 [M+H]$^+$; $^1$H NMR (700 MHz, MeCN-d$_3$) δ 8.22-8.19 (m, 1H), 8.16-8.12 (m, 1H), 7.44-7.40 (m, 2H), 7.34-7.31 (m, 2H), 7.24-7.20 (m, 1H), 4.61 (s, 2H), 4.05-3.98 (m, 1H), 3.90-3.78 (m, 3H), 3.79-3.70 (m, 1H), 3.68-3.63 (m, 1H), 3.58-3.50 (m, 2H), 3.31-3.23 (m, 1H), 3.22-3.09 (m, 3H), 2.96-2.85 (m, 1H), 2.39-2.29 (m, 2H), 2.19-2.07 (m, 2H), 1.30 (d, J=6.3 Hz, 3H).

Example 121

Synthesis of methyl 3-(4-((2S,5S)-5-(4-chlorobenzyl)-2-methylmorpholino)piperidin-1-yl)-2-fluoroisonicotinate (121)

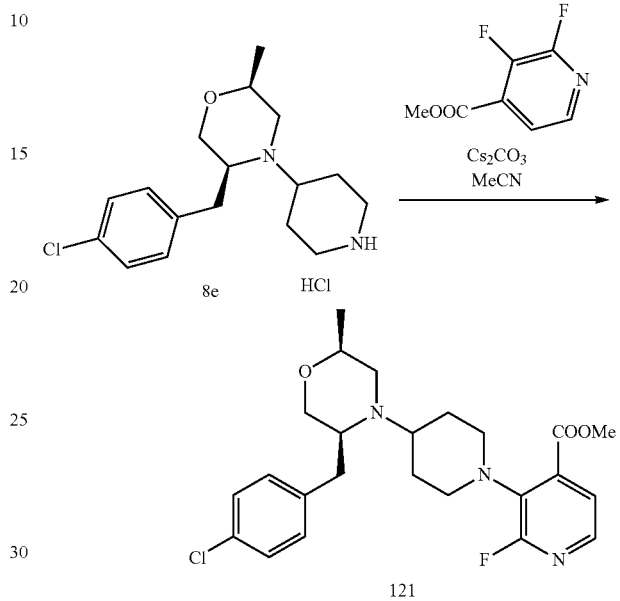

The title compound (121) was obtained as a single regioisomer from 8e (72 mg; 0.21 mmol) according to the General Procedure XXIV in 12% yield (12 mg; 0.026 mmol).

ESI-MS m/z for $C_{24}H_{30}ClFN_3O_3$ found 462.2/464.2 [M+H]$^+$; $^1$H NMR (700 MHz, MeCN-d$_3$) δ 8.07-8.05 (m, 1H), 7.34-7.30 (m, 2H), 7.24-7.20 (m, 2H), 7.12-7.08 (m, 1H), 4.06-3.98 (m, 2H), 3.91 (s, 3H), 3.61-3.51 (m, 2H), 3.46-3.40 (m, 1H), 3.07-2.94 (m, 4H), 2.86-2.71 (m, 3H), 2.41-2.34 (m, 1H), 2.12-2.02 (m, 2H), 1.60-1.43 (m, 2H), 1.16 (d, J=6.2 Hz, 3H).

Example 122

Synthesis of methyl 2-(4-((2S,5S)-5-(4-chlorobenzyl)-2-methylmorpholino)piperidin-1-yl)-3-fluoroisonicotinate (122)

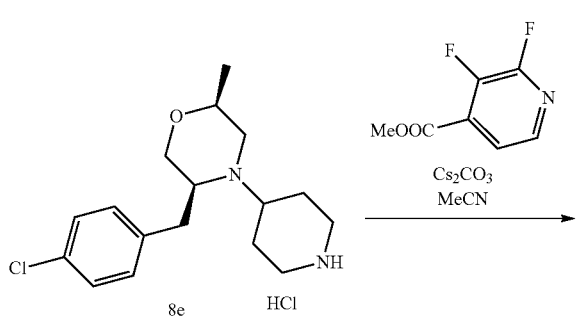

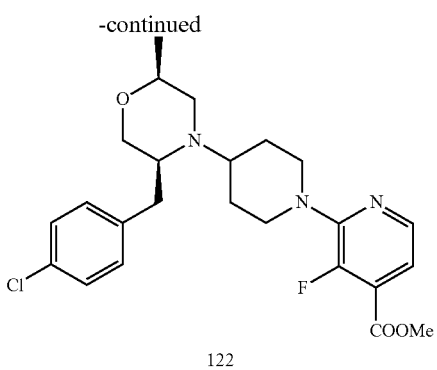

122

The title compound (122) was obtained as a second single regioisomer from 8e (72 mg; 0.21 mmol) during the synthesis of the compound 121 according to the General Procedure XXIV in 28% yield (27 mg; 0.059 mmol).

ESI-MS m/z for $C_{24}H_{30}ClFN_3O_3$ found 462.2/464.2 [M+H]$^+$; $^1$H NMR (700 MHz, MeCN-d$_3$) δ 7.89-7.86 (m, 1H), 7.34-7.31 (m, 2H), 7.31-7.28 (m, 1H), 7.24-7.19 (m, 2H), 3.93 (s, 3H), 3.62-3.52 (m, 2H), 3.46-3.40 (m, 1H), 3.25-3.19 (m, 2H), 3.10-2.97 (m, 4H), 2.83-2.77 (m, 2H), 2.71-2.63 (m, 1H), 2.43-2.34 (m, 1H), 2.08-2.02 (m, 1H), 2.02-1.99 (m, 1H), 1.57-1.43 (m, 2H), 1.17 (d, J=6.2 Hz, 3H).

Example 123

Synthesis of (2S,5S)-5-(4-chlorobenzyl)-4-(1-(2,6-difluorophenyl)piperidin-4-yl)-2-methylmorpholine 2,2,2-trifluoroacetate (123)

Hydrochloride salt 8e (200 mg; 0.58 mmol) was dissolved in AcOEt and 1M NaOH was added to this solution. Phases were separated and an organic one was washed with brine, dried over anhydrous MgSO$_4$ and concentrated in vacuo to give a free amine (179 mg; 0.58 mmol) which was then transferred into the title compound (123) according to the General Procedure XXIII with the exception that, in this reaction, NaOtBu and Pd$_2$(dba)$_3$ were used instead of Cs$_2$CO$_3$ and Pd(OAc)$_2$. Compound 123 was obtained as a TFA salt in 4% yield (13 mg; 0.024 mmol).

ESI-MS m/z for $C_{23}H_{28}ClF_2N_2O$ found 421.0/423.0 [M+H]$^+$; $^1$H NMR (700 MHz, Methanol-d$_4$) δ 7.42-7.38 (m, 2H), 7.38-7.32 (m, 2H), 7.17-7.03 (m, 1H), 6.99-6.91 (m, 2H), 3.93-3.78 (m, 3H), 3.76-3.61 (m, 3H), 3.51-3.40 (m, 2H), 3.30-3.23 (m, 3H), 3.20-3.16 (m, 1H), 3.16-3.10 (m, 1H), 2.43-2.32 (m, 2H), 1.96-1.81 (m, 2H), 1.36 (d, J=6.2 Hz, 3H).

Example 124

Synthesis of methyl 2-(4-((2S,5S)-5-(4-chlorobenzyl)-2-methylmorpholino)piperidin-1-yl)isonicotinate (124)

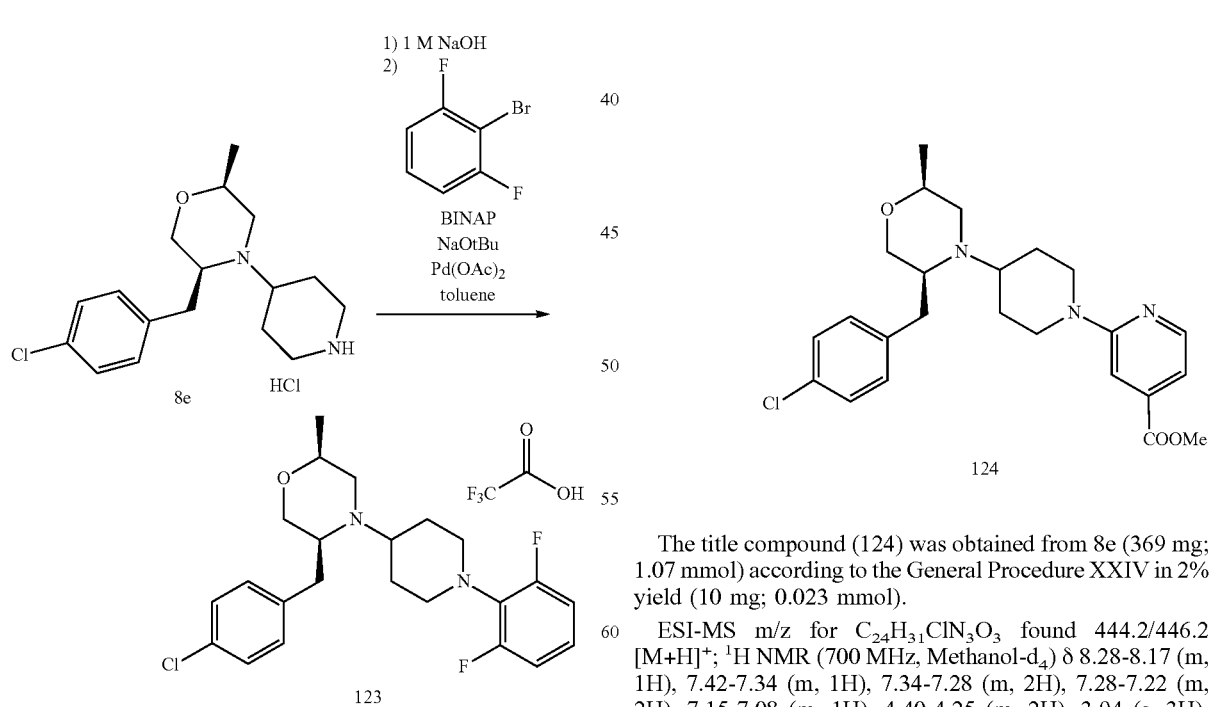

The title compound (124) was obtained from 8e (369 mg; 1.07 mmol) according to the General Procedure XXIV in 2% yield (10 mg; 0.023 mmol).

ESI-MS m/z for $C_{24}H_{31}ClN_3O_3$ found 444.2/446.2 [M+H]$^+$; $^1$H NMR (700 MHz, Methanol-d$_4$) δ 8.28-8.17 (m, 1H), 7.42-7.34 (m, 1H), 7.34-7.28 (m, 2H), 7.28-7.22 (m, 2H), 7.15-7.08 (m, 1H), 4.40-4.25 (m, 2H), 3.94 (s, 3H), 3.72-3.59 (m, 3H), 3.53-3.46 (m, 1H), 3.10-2.98 (m, 3H), 2.91-2.81 (m, 3H), 2.47-2.39 (m, 1H), 2.22-2.15 (m, 1H), 2.13-2.08 (m, 1H), 1.59-1.42 (m, 2H), 1.22 (d, J=6.2 Hz, 3H).

Example 125

Synthesis of 2-(4-((2S,5S)-5-(4-chlorobenzyl)-2-methylmorpholino)piperidin-1-yl)isonicotinic acid 2,2,2-trifluoroacetate (125)

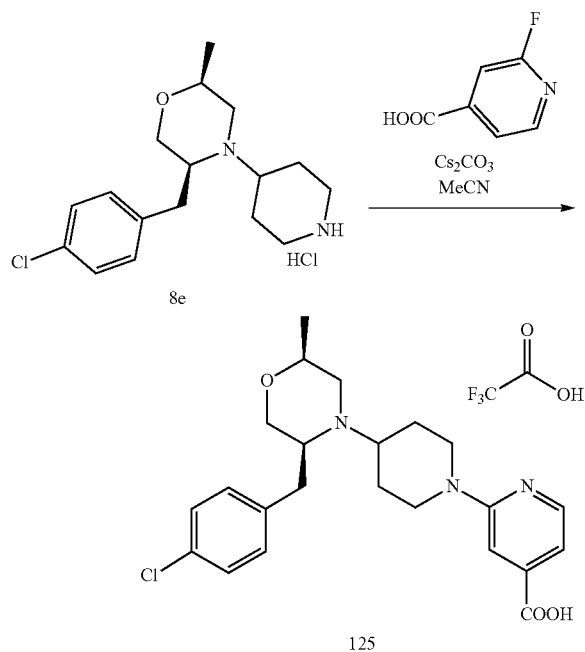

The title compound (125) was obtained from 8e (345 mg; 1 mmol) according to the General Procedure XXIV in 4% yield (19 mg; 0.035 mmol).

ESI-MS m/z for $C_{23}H_{29}ClN_3O_3$ found 430.1/432.1 [M+H]$^+$; $^1$H NMR (700 MHz, Methanol-$d_4$) δ 8.30-8.25 (m, 1H), 7.53-7.50 (m, 1H), 7.44-7.40 (m, 2H), 7.38-7.34 (m, 2H), 7.27-7.22 (m, 1H), 4.65-4.55 (m, 2H), 3.99-3.74 (m, 4H), 3.74-3.57 (m, 2H), 3.32-3.26 (m, 1H), 3.24-3.18 (m, 1H), 3.17-3.05 (m, 3H), 2.47-2.37 (m, 2H), 1.82-1.66 (m, 2H), 1.35 (d, J=6.2 Hz, 3H).

Example 126

Synthesis of (2S,5S)-5-(4-chlorobenzyl)-4-(1-(2-fluorophenyl)piperidin-4-yl)-2-methylmorpholine 2,2,2-trifluoroacetate (126)

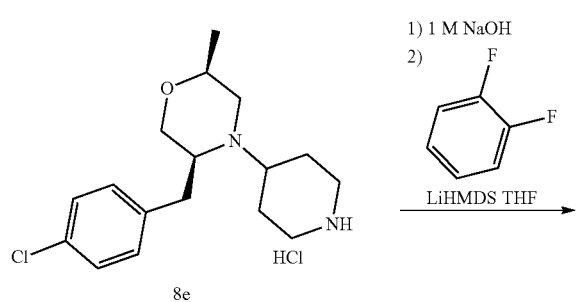

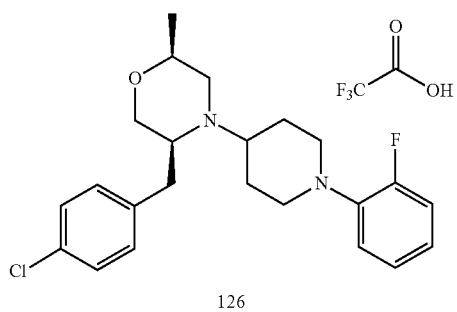

Hydrochloride salt 8e (110 mg; 0.32 mmol) was dissolved in AcOEt and 1M NaOH was added to this solution. Phases were separated and an organic one was washed with brine, dried over anhydrous MgSO$_4$ and concentrated in vacuo to give a free amine (100 mg; 0.32 mmol) which was dissolved in THF (0.8 mL) and to this solution 1,2-difluorobenzene (48 µL; 0.49 mmol) was added under argon atmosphere, then LiHMDS (0.88 mL; 0.8 mmol) was added dropwise and the resulting mixture was refluxed for 4 days. The reaction progress was monitored by LC-MS. After analytical control was indicated completion of the reaction, the water was added and extracted with AcOEt. The combined organic solutions were dried over anhydrous MgSO$_4$, filtered and concentrated in vacuo. The crude product was purified by preparative reversed-phase column chromatography (Luna® 5 µm Phenyl-Hexyl, LC Column 250×21.2 mm, water/ MeCN+1% TFA, 98:2 to 40:60, 30 minutes). The title compound (126) was obtained as a single regioisomer as a TFA salt in 7% yield (12 mg; 0.023 mmol).

ESI-MS m/z for $C_{23}H_{29}ClFN_2O$ found 403.2/405.2 [M+H]$^+$; $^1$H NMR (700 MHz, Methanol-$d_4$) δ 7.43-7.40 (m, 2H), 7.37-7.33 (m, 2H), 7.15-7.06 (m, 3H), 7.05-7.01 (m, 1H), 3.96-3.78 (m, 3H), 3.75-3.59 (m, 5H), 3.31-3.26 (m, 1H), 3.21-3.16 (m, 1H), 3.15-3.08 (m, 1H), 2.92-2.79 (m, 2H), 2.49-2.39 (m, 2H), 1.97-1.85 (m, 2H), 1.37 (d, J=6.2 Hz, 3H).

Example 127

Synthesis of (2S,5S)-5-(4-chlorobenzyl)-4-(1-(3-fluorophenyl)piperidin-4-yl)-2-methylmorpholine 2,2,2-trifluoroacetate (127)

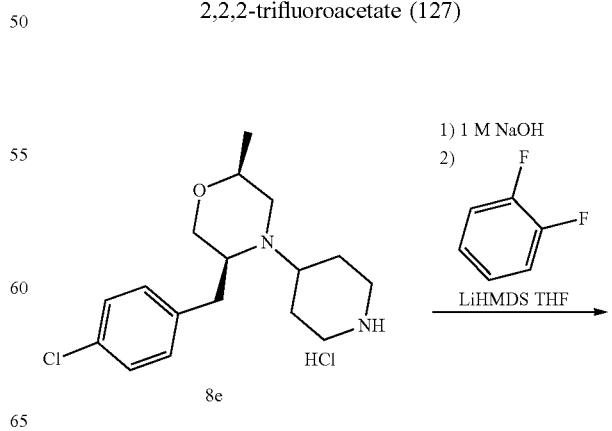

-continued

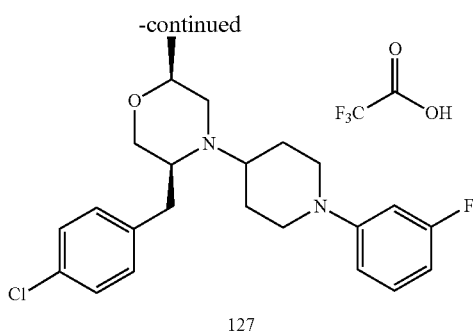

127

The title compound (127) was obtained as a second single regioisomer as a TFA salt in 3% yield (6 mg; 0.011 mmol) during the synthesis of the compound 126.

ESI-MS m/z for $C_{23}H_{29}ClFN_2O$ found 403.0/405.0 [M+H]$^+$; $^1$H NMR (700 MHz, Methanol-d$_4$) δ 7.43-7.40 (m, 2H), 7.40-7.33 (m, 2H), 7.28-7.20 (m, 1H), 6.87-6.78 (m, 1H), 6.77-6.71 (m, 1H), 6.60-6.53 (m, 1H), 4.04-3.95 (m, 2H), 3.95-3.85 (m, 1H), 3.85-3.76 (m, 2H), 3.76-3.58 (m, 3H), 3.31-3.25 (m, 1H), 3.24-3.17 (m, 1H), 3.15-3.08 (m, 1H), 2.95-2.84 (m, 2H), 2.43-2.30 (m, 2H), 1.92-1.74 (m, 2H), 1.36 (d, J=6.3 Hz, 3H).

Example 128

Synthesis of 2-(4-((2S,5S)-5-(4-chlorobenzyl)-2-methylmorpholino)piperidin-1-yl)-3-fluoroisonicotinic acid 2,2,2-trifluoroacetate (128)

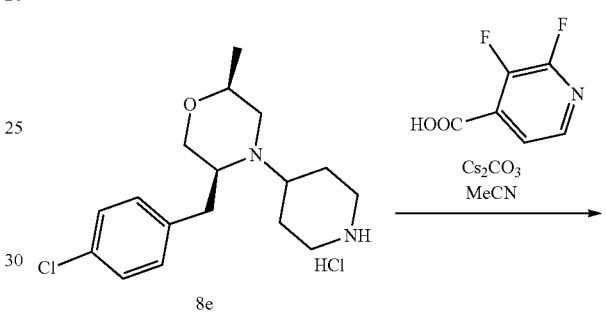

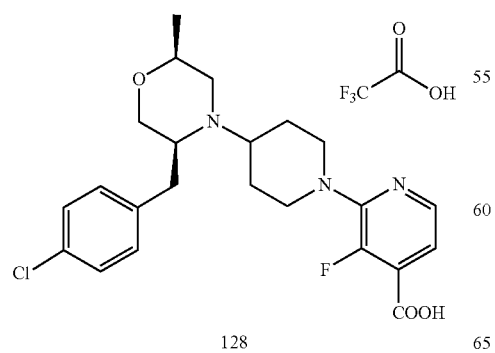

128

The title compound (138) was obtained as a single regioisomer as a TFA salt from 8e (66 mg; 0.19 mmol) according to the General Procedure XXIV in 19% yield (20 mg; 0.036 mmol).

ESI-MS m/z for $C_{23}H_{28}ClFN_3O_3$ found 448.2/450.2 [M+H]$^+$; $^1$H NMR (700 MHz, Methanol-d$_4$) δ 8.08-8.05 (m, 1H), 7.59-7.56 (m, 1H), 7.43-7.39 (m, 2H), 7.37-7.33 (m, 2H), 3.95-3.86 (m, 1H), 3.86-3.77 (m, 2H), 3.76-3.66 (m, 2H), 3.66-3.59 (m, 1H), 3.46-3.40 (m, 2H), 3.36-3.34 (m, 1H), 3.32-3.25 (m, 2H), 3.22-3.10 (m, 2H), 2.48-2.37 (m, 2H), 1.97-1.82 (m, 2H), 1.36 (d, J=6.3 Hz, 3H).

Example 129

Synthesis of 3-(4-((2S,5S)-5-(4-chlorobenzyl)-2-methylmorpholino)piperidin-1-yl)-2-fluoroisonicotinic acid (129)

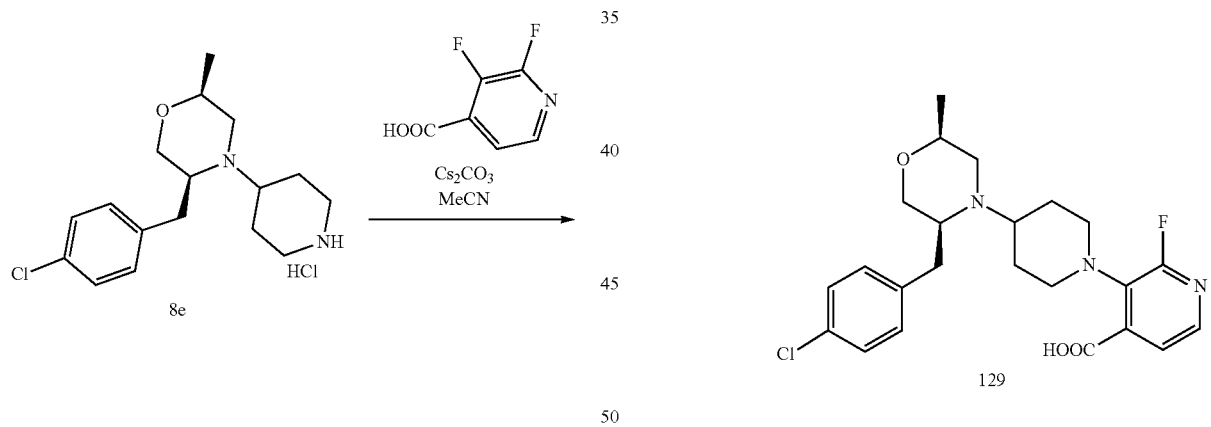

129

The title compound (129) was obtained as a second single regioisomer from 8e (66 mg; 0.19 mmol) during the synthesis of the compound 128 according to the General Procedure XXIV in 26% yield (22 mg; 0.049 mmol).

ESI-MS m/z for $C_{23}H_{28}ClFN_3O_3$ found 448.2/450.2 [M+H]$^+$; $^1$H NMR (700 MHz, Methanol-d$_4$) δ 7.95-7.91 (m, 1H), 7.33-7.30 (m, 2H), 7.26-7.22 (m, 2H), 7.02-6.98 (m, 1H), 4.10-4.03 (m, 2H), 3.73-3.65 (m, 1H), 3.65-3.61 (m, 1H), 3.57-3.51 (m, 1H), 3.13-3.08 (m, 1H), 3.07-2.91 (m, 4H), 2.90-2.82 (m, 2H), 2.51-2.41 (m, 1H), 2.23-2.17 (m, 1H), 2.17-2.10 (m, 1H), 1.69-1.54 (m, 2H), 1.23 (d, J=6.2 Hz, 3H).

Example 130

Synthesis of (2-(4-((2S,5S)-5-(4-chlorobenzyl)-2-methylmorpholino)piperidin-1-yl)pyridin-4-yl)methanol 2,2,2-trifluoroacetate (130)

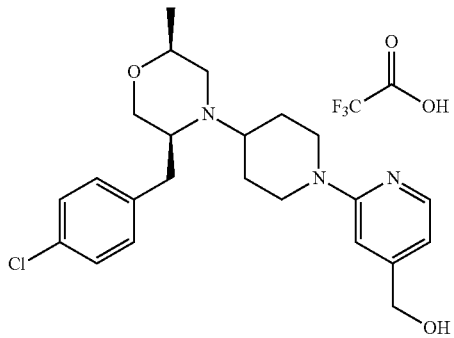

Step 1

Synthesis of ethyl 2-(4-((2S,5S)-5-(4-chlorobenzyl)-2-methylmorpholino)piperidin-1-yl)isonicotinate (130a)

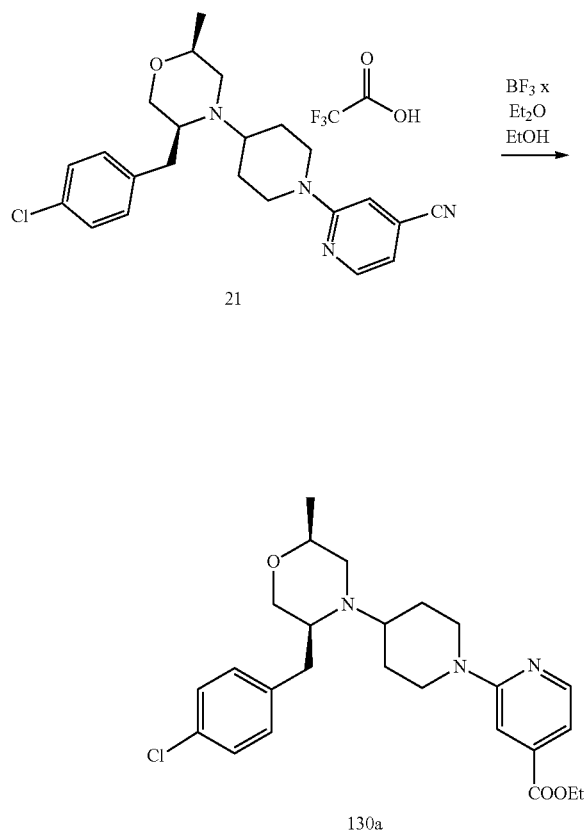

To the solution of 21 (257 mg; 0.49 mmol) in EtOH (7 mL) BF3×Et2O (0.48 mL; 3.9 mmol) was added and the resulting mixture was refluxed for two weeks. The reaction progress was monitored by LC-MS. After analytical control was indicated completion of the reaction, EtOH was evaporated and water was added followed by 1M NaOH and extracted with AcOEt. The combined organic solutions were dried over anhydrous $MgSO_4$, filtered and concentrated in vacuo.

The crude product was used to the next step without additional purification. The title compound (130a) was obtained in 71% yield (160 mg; 0.35 mmol).

ESI-MS m/z for $C_{25}H_{33}ClN_3O_3$ found 458.2/460.2 $[M+H]^+$

Step 2

Synthesis of (2-(4-((2S,5S)-5-(4-chlorobenzyl)-2-methylmorpholino)piperidin-1-yl)pyridin-4-yl)methanol 2,2,2-trifluoroacetate (130)

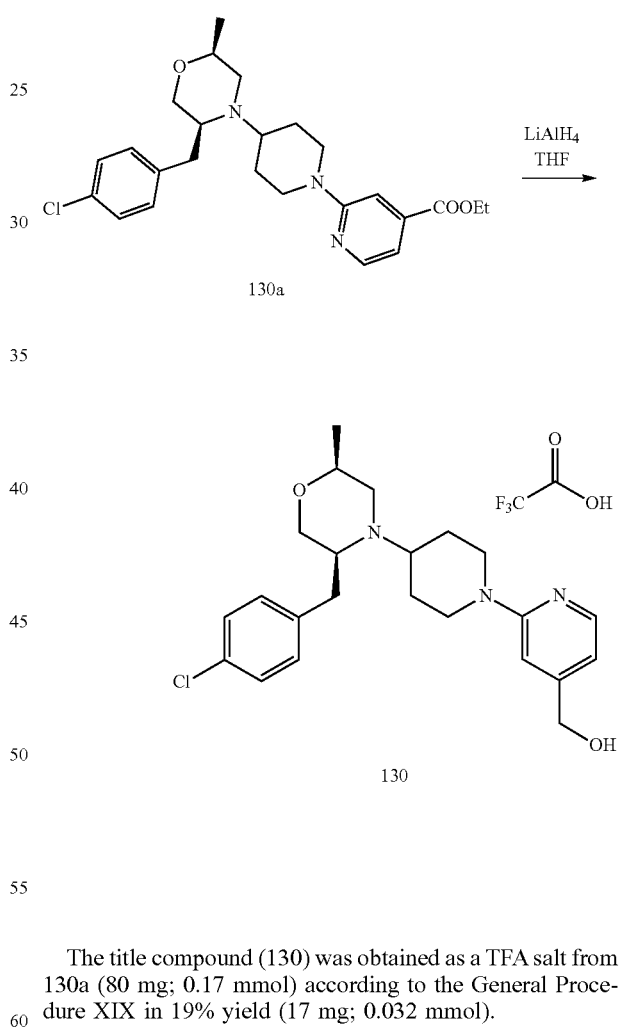

The title compound (130) was obtained as a TFA salt from 130a (80 mg; 0.17 mmol) according to the General Procedure XIX in 19% yield (17 mg; 0.032 mmol).

ESI-MS m/z for $C_{23}H_{31}ClN_3O_2$ found 416.1/418.1 $[M+H]^+$; $^1H$ NMR (700 MHz, Methanol-$d_4$) δ 7.98-7.95 (m, 1H), 7.43-7.40 (m, 2H), 7.38-7.34 (m, 3H), 7.02-6.98 (m, 1H), 4.74 (s, 2H), 4.44-4.38 (m, 2H), 3.96-3.73 (m, 5H), 3.62-3.59 (m, 1H), 3.41-3.33 (m, 3H), 3.26-3.20 (m, 1H), 3.19-3.11 (m, 1H), 2.55-2.43 (m, 2H), 1.99-1.79 (m, 2H), 1.35 (d, J=6.2 Hz, 3H).

Example 131

Synthesis of 2-(2-(4-((2S,5S)-5-(4-chlorobenzyl)-2-methylmorpholino)piperidin-1-yl)pyridin-4-yl)propan-2-ol 2,2,2-trifluoroacetate (131)

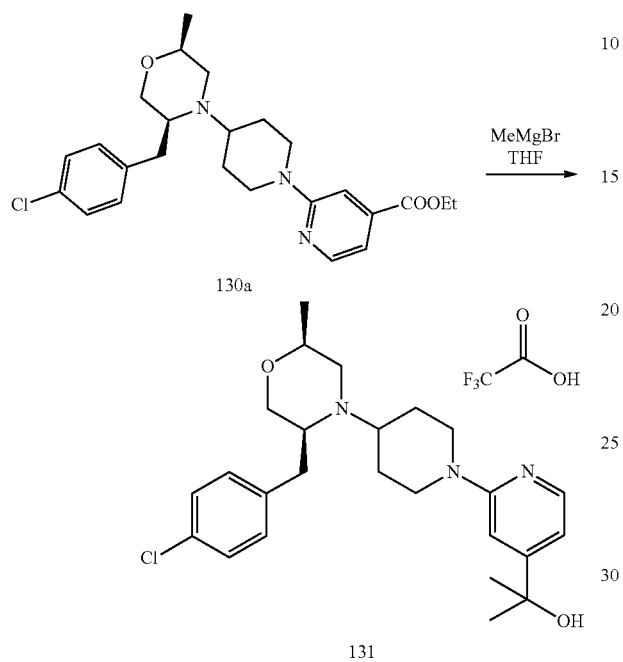

The title compound (131) was obtained as a TFA salt from 130a (43 mg; 0.094 mmol) according to the General Procedure V in 33% yield (17 mg; 0.031 mmol).

ESI-MS m/z for $C_{25}H_{35}ClN_3O_2$ found 444.1/446.1 [M+H]$^+$; $^1$H NMR (700 MHz, Methanol-d$_4$) δ 7.98-7.95 (m, 1H), 7.46-7.43 (m, 1H), 7.43-7.38 (m, 2H), 7.38-7.34 (m, 2H), 7.16-7.12 (m, 1H), 4.46-4.36 (m, 2H), 3.97-3.75 (m, 5H), 3.65-3.57 (m, 1H), 3.45-3.35 (m, 2H), 3.32-3.27 (m, 1H), 3.27-3.08 (m, 2H), 2.54-2.47 (m, 2H), 1.99-1.83 (m, 2H), 1.56 (s, 6H), 1.35 (d, J=6.2 Hz, 3H).

Example 132

Synthesis of 2-(4-((2S,5S)-5-(4-chlorobenzyl)-2-methylmorpholino)piperidin-1-yl)isonicotinamide 2,2,2-trifluoroacetate (132)

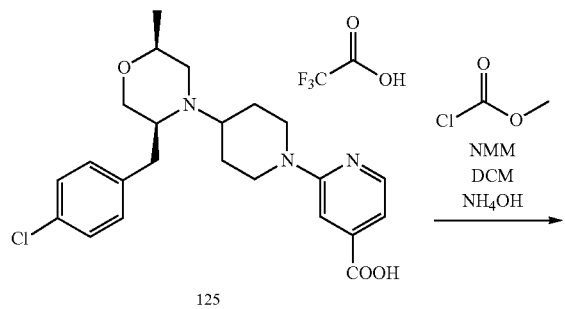

The title compound (132) was obtained as a TFA salt from 125 (24 mg; 0.045 mmol) according to the General Procedure XVI in 99% yield (23 mg; 0.044 mmol).

ESI-MS m/z for $C_{23}H_{30}ClN_4O_2$ found 429.0/431.0 [M+H]$^+$; $^1$H NMR (700 MHz, Methanol-d$_4$) δ 8.28-8.18 (m, 1H), 7.47-7.44 (m, 1H), 7.44-7.40 (m, 2H), 7.38-7.34 (m, 2H), 7.17-7.12 (m, 1H), 4.63-4.55 (m, 2H), 3.96-3.58 (m, 6H), 3.32-3.27 (m, 1H), 3.24-3.08 (m, 4H), 2.47-2.36 (m, 2H), 1.85-1.72 (m, 2H), 1.35 (d, J=6.2 Hz, 3H).

Example 133

Synthesis of (2S,5S)-5-(4-chlorobenzyl)-2-methyl-4-(1-(pyrimidin-5-yl)piperidin-4-yl)morpholine hydrochloride (133)

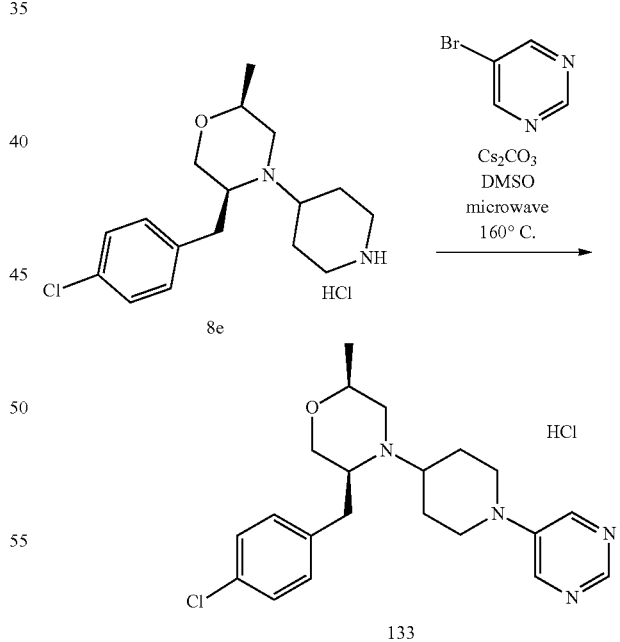

The title compound (133) was obtained as a hydrochloride salt from 8e (110 mg; 0.32 mmol) according to the General Procedure XXV in 18% yield (25 mg; 0.059 mmol).

ESI-MS m/z for $C_{21}H_{28}ClN_4O$ found 387.1/389.0 [M+H]$^+$; $^1$H NMR (700 MHz, DMSO-d$_6$+D$_2$O) δ 8.40-8.33 (m, 2H), 7.42-7.36 (m, 2H), 7.35-7.25 (m, 2H), 6.69-6.63 (m, 1H), 4.80-4.67 (m, 2H), 3.72-3.61 (m, 4H), 3.56-3.46

(m, 2H), 3.18-3.08 (m, 2H), 3.01-2.84 (m, 3H), 2.28-2.18 (m, 2H), 1.61-1.45 (m, 2H), 1.19 (d, J=6.2 Hz, 3H).

Example 134

Synthesis of (2S,5S)-5-(4-chlorobenzyl)-2-methyl-4-(1-(pyrimidin-2-yl)piperidin-4-yl)morpholine hydrochloride (134)

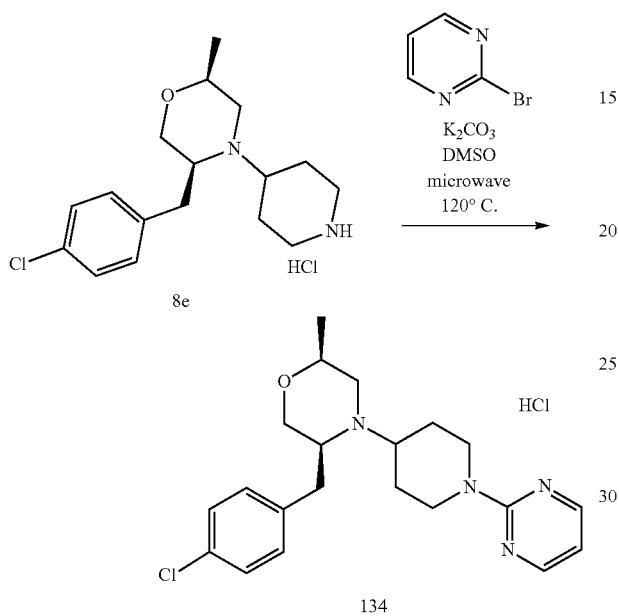

The title compound (134) was obtained as a hydrochloride salt from 8e (110 mg; 0.32 mmol) according to the General Procedure XXV in 26% yield (35 mg; 0.083 mmol).

ESI-MS m/z for $C_{21}H_{28}ClN_4O$ found 387.1/389.1 [M+H]$^+$; $^1$H NMR (700 MHz, DMSO-d$_6$+D$_2$O) δ 8.44-8.31 (m, 2H), 7.41-7.36 (m, 2H), 7.34-7.29 (m, 2H), 6.74-6.60 (m, 1H), 4.80-4.70 (m, 2H), 3.72-3.60 (m, 4H), 3.53-3.44 (m, 2H), 3.18-3.07 (m, 2H), 3.02-2.85 (m, 3H), 2.28-2.20 (m, 2H), 1.57-1.47 (m, 2H), 1.19 (d, J=6.2 Hz, 3H).

Example 135

Synthesis of (2S,5S)-5-(4-chlorobenzyl)-2-methyl-4-(1-(6-methylpyridin-2-yl)piperidin-4-yl)morpholine hydrochloride (135)

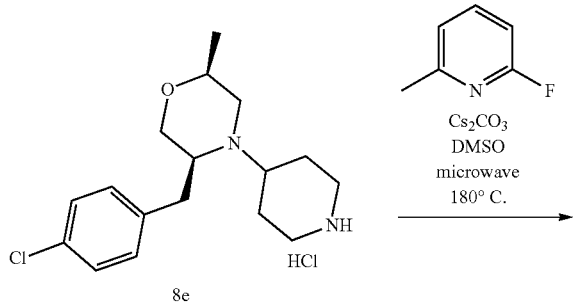

The title compound (135) was obtained as a hydrochloride salt from 8e (110 mg; 0.32 mmol) according to the General Procedure XXV in 36% yield (50 mg; 0.115 mmol).

ESI-MS m/z for $C_{23}H_{31}ClN_3O$ found 400.1/402.1 [M+H]$^+$; $^1$H NMR (700 MHz, DMSO-d$_6$+D$_2$O) δ 7.75-7.69 (m, 1H), 7.39-7.35 (m, 2H), 7.33-7.28 (m, 2H), 6.98-6.92 (m, 1H), 6.72-6.68 (m, 1H), 4.39-4.29 (m, 2H), 3.92-3.82 (m, 1H), 3.82-3.74 (m, 1H), 3.74-3.64 (m, 2H), 3.59-3.53 (m, 1H), 3.19-2.96 (m, 6H), 2.42 (s, 3H), 2.31-2.26 (m, 1H), 2.26-2.20 (m, 1H), 1.83-1.71 (m, 2H), 1.21 (d, J=6.2 Hz, 3H).

Example 136

Synthesis of (2S,5S)-5-(4-chlorobenzyl)-2-methyl-4-(1-(5-methylpyridin-2-yl)piperidin-4-yl)morpholine hydrochloride (136)

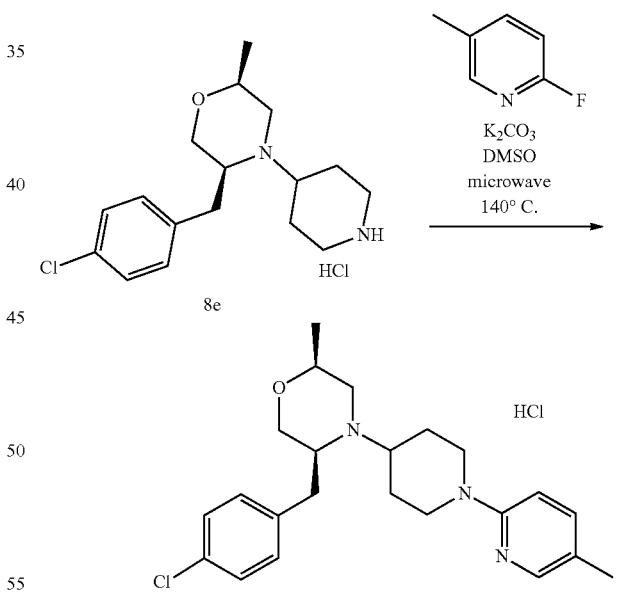

The title compound (136) was obtained as a hydrochloride salt from 8e (110 mg; 0.32 mmol) according to the General Procedure XXV in 12% yield (16 mg; 0.037 mmol).

ESI-MS m/z for $C_{23}H_{31}ClN_3O$ found 400.1/402.1 [M+H]$^+$; $^1$H NMR (700 MHz, DMSO-d$_6$+D$_2$O) δ 7.87-7.81 (m, 2H), 7.42-7.38 (m, 2H), 7.34-7.30 (m, 2H), 7.30-7.26 (m, 1H), 4.36-4.23 (m, 2H), 3.94-3.73 (m, 4H), 3.56-3.42 (m, 2H), 3.24-3.07 (m, 4H), 3.05-2.96 (m, 1H), 2.35-2.25 (m, 2H), 2.18 (s, 3H), 1.77-1.66 (m, 2H), 1.20 (d, J=6.2 Hz, 3H).

Example 137

Synthesis of (2S,5S)-5-(4-chlorobenzyl)-2-methyl-4-(1-(4-methylpyridin-2-yl)piperidin-4-yl)morpholine hydrochloride (137)

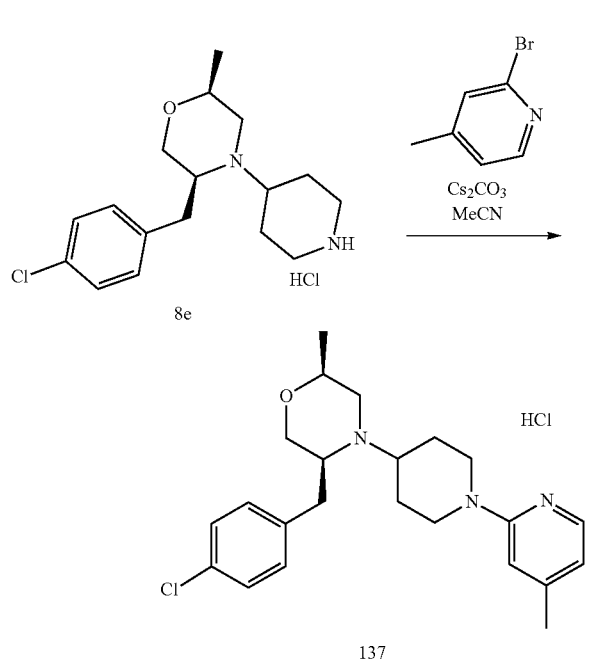

The title compound (137) was obtained as a hydrochloride salt from 8e (110 mg; 0.32 mmol) according to the General Procedure XXIV in 63% yield (88 mg; 0.2 mmol).

ESI-MS m/z for $C_{23}H_{31}ClN_3O$ found 400.1/402.1 [M+H]$^+$; $^1$H NMR (250 MHz, DMSO-d$_6$+D$_2$O, 348 K) δ 7.94-7.85 (m, 1H), 7.49-7.30 (m, 4H), 7.21-7.08 (m, 1H), 6.86-6.71 (m, 1H), 4.42-4.23 (m, 2H), 4.02-3.47 (m, 6H), 3.28-2.96 (m, 5H), 2.38 (s, 3H), 2.35-2.20 (m, 2H), 1.95-1.68 (m, 2H), 1.23 (d, J=6.2 Hz, 3H).

Example 138

Synthesis of (5S)-5-(4-chlorobenzyl)-2-phenyl-4-(1-(pyridin-2-yl)piperidin-4-yl)morpholine hydrochloride (138)

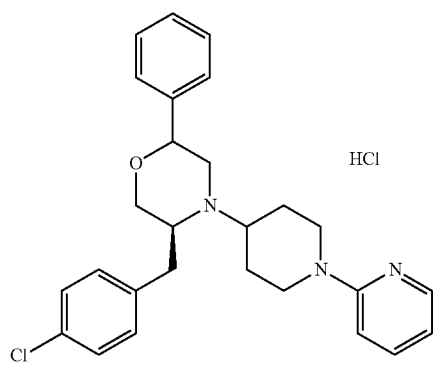

Step 1 Synthesis of 2-bromo-N-((S)-1-(4-chlorophenyl)-3-hydroxypropan-2-yl)-2-phenylacetamide (138a)

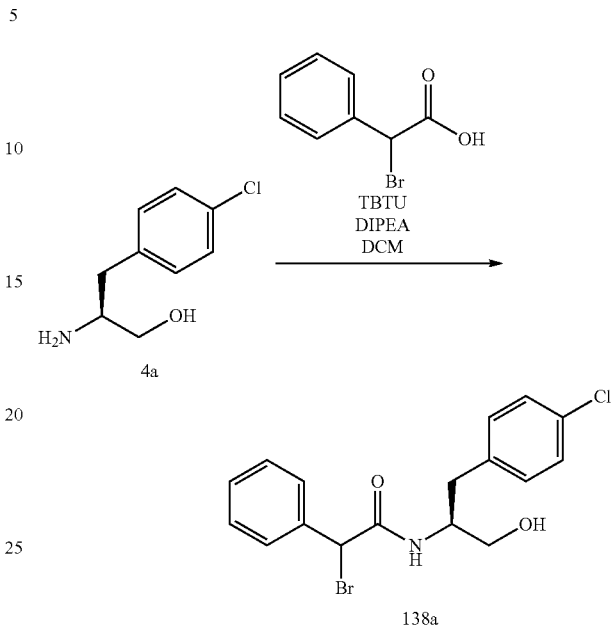

The title compound (138a) was obtained from 4a (0.43 g; 2.32 mmol) according to the General Procedure III in 51% yield (0.45 g; 1.18 mmol).

ESI-MS m/z for $C_{17}H_{18}BrClNO_2$ found 382.0/384.0 [M+H]$^+$

Step 2

Synthesis of (5S)-5-(4-chlorobenzyl)-2-phenylmorpholin-3-one (138b)

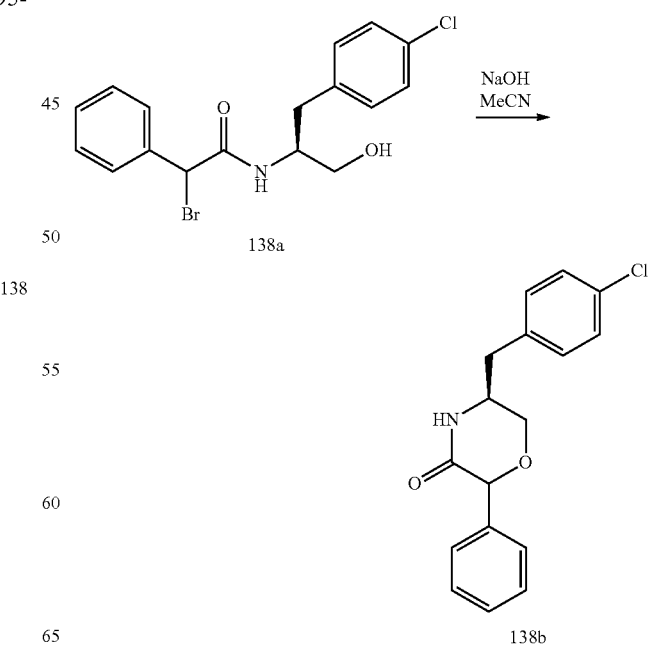

To the solution of 138a (0.45 g; 1.18 mmol) in MeCN (15 mL) 2M NaOH (4 mL) was added and the resulting mixture was stirred at ambient temperature for one hour. The reaction progress was monitored by LC-MS. After analytical control was indicated completion of the reaction, to this mixture 2M HCl was added to pH 4. Then this mixture was diluted with brine and extracted with AcOEt (2×). The combined organic solutions were dried over anhydrous $Na_2SO_4$, filtered and concentrated in vacuo. The crude product was used to the next step without additional purification. The title compound (138b) was obtained as a light yellow oil in 62% yield (220 mg; 0.73 mmol).

ESI-MS m/z for $C_{17}H_{17}ClNO_2$ found 302.1/304.1 $[M+H]^+$

Step 3

Synthesis of (5S)-5-(4-chlorobenzyl)-2-phenylmorpholine (138c

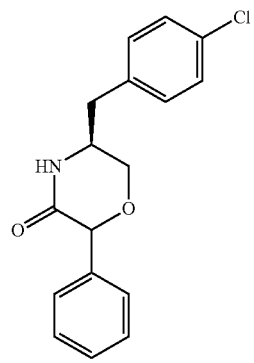

The title compound (138c) was obtained from 138b (370 mg; 1.23 mmol) according to the General Procedure Ib in 76% yield (270 mg; 0.94 mmol).

ESI-MS m/z for $C_{17}H_{19}ClNO$ found 288.1/290.1 $[M+H]^+$

Step 4

Synthesis of (5S)-5-(4-chlorobenzyl)-2-phenyl-4-(1-(pyridin-2-yl)piperidin-4-yl)morpholine hydrochloride (138)

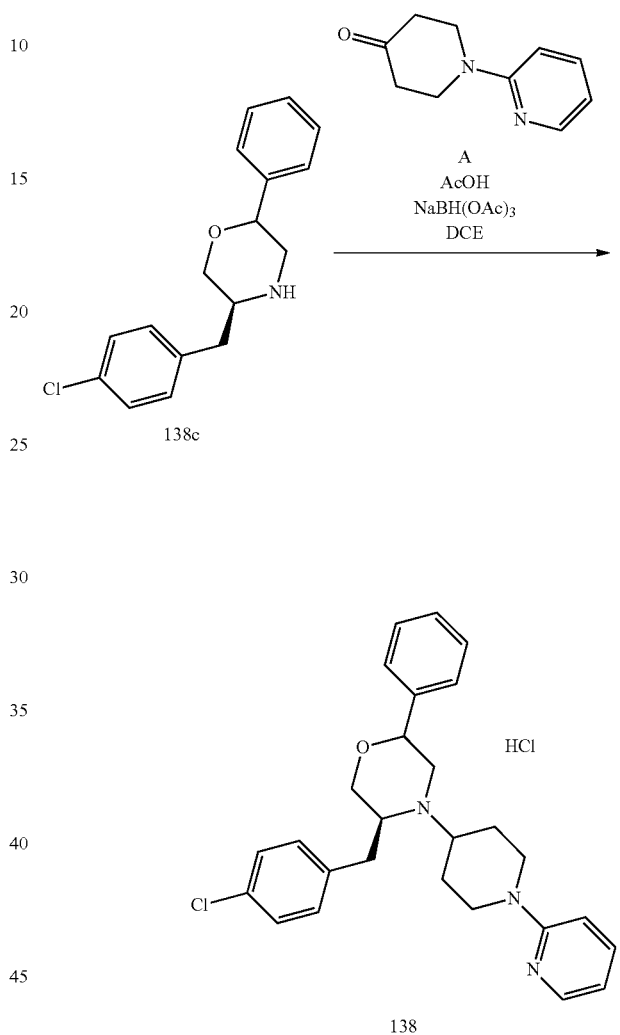

The title compound (138) was obtained as a hydrochloride salt from 138c (200 mg; 0.7 mmol) according to the General Procedure VI in 16% yield (53 mg; 0.11 mmol).

ESI-MS m/z for $C_{27}H_{31}ClN_3O$ found 448.2/450.2 $[M+H]^+$; $^1H$ NMR (700 MHz, DMSO-$d_6$+$D_2O$, 348 K) δ 8.04-8.01 (m, 1H), 7.89-7.84 (m, 1H), 7.52-7.47 (m, 2H), 7.43-7.36 (m, 7H), 7.23-7.18 (m, 1H), 6.90-6.85 (m, 1H), 4.96-4.88 (m, 1H), 4.40-4.30 (m, 2H), 4.08-3.99 (m, 1H), 3.84-3.78 (m, 2H), 3.76-3.71 (m, 1H), 3.60-3.54 (m, 1H), 3.32-3.28 (m, 2H), 3.28-3.21 (m, 1H), 3.21-3.13 (m, 1H), 3.12-3.05 (m, 1H), 2.35-2.27 (m, 2H), 1.91-1.82 (m, 2H).

Example 139

Synthesis of ((2R,5S)-5-(4-chlorobenzyl)-4-(1-(pyridin-2-yl)piperidin-4-yl)morpholin-2-yl)methyl acetate hydrochloride (139)

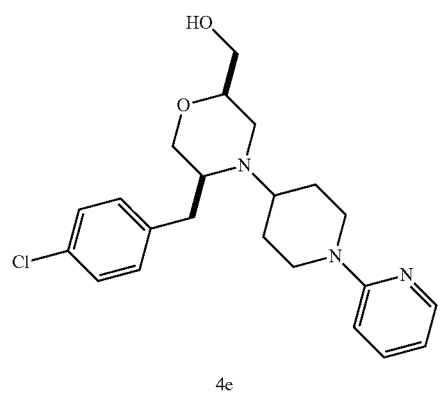

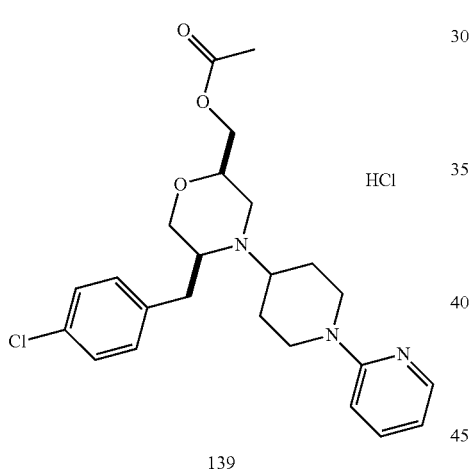

The title compound (139) was obtained as a hydrochloride salt from 4e (100 mg; 0.25 mmol) according to the General Procedure XVII in 16% yield (19 mg; 0.04 mmol).

ESI-MS m/z for $C_{24}H_{31}ClN_3O_3$ found 444.2/446.2 [M+H]$^+$; $^1$H NMR (700 MHz, DMSO-d$_6$+D$_2$O, 348 K) δ 8.03-7.99 (m, 1H), 7.86-7.82 (m, 1H), 7.40-7.36 (m, 2H), 7.32-7.29 (m, 2H), 7.21-7.16 (m, 1H), 6.88-6.84 (m, 1H), 4.39-4.28 (m, 2H), 4.23-4.17 (m, 1H), 4.15-4.10 (m, 1H), 4.09-4.02 (m, 1H), 3.83-3.68 (m, 3H), 3.64-3.57 (m, 1H), 3.50-3.45 (m, 1H), 3.20-3.07 (m, 5H), 2.31-2.22 (m, 2H), 2.04 (s, 3H), 1.81-1.73 (m, 2H).

Example 140

Synthesis of (2R,5S)-5-(4-chlorobenzyl)-2-(phenoxymethyl)-4-(1-(pyridin-2-yl)piperidin-4-yl)morpholine hydrochloride (140)

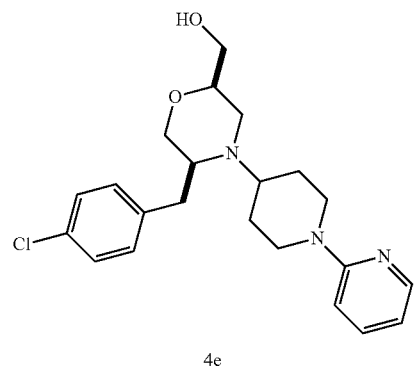

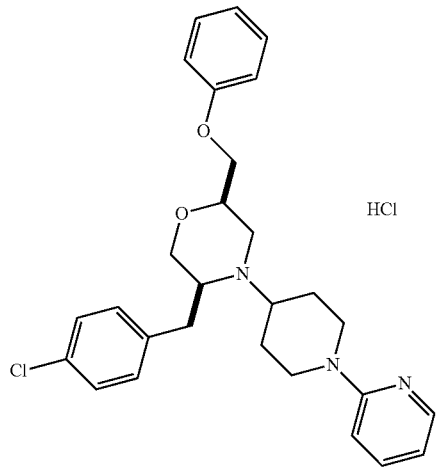

The title compound (140) was obtained as a hydrochloride salt from 4e (100 mg; 0.25 mmol) according to the General Procedure XVIII in 2% yield (3 mg; 0.006 mmol).

ESI-MS m/z for $C_{28}H_{33}ClN_3O_2$ found 478.2/480.2 [M+H]$^+$; $^1$H NMR (700 MHz, DMSO-d$_6$+D$_2$O, 348 K) δ 8.02-7.96 (m, 1H), 7.89-7.74 (m, 1H), 7.39-7.33 (m, 2H), 7.33-7.25 (m, 4H), 7.20-7.12 (m, 1H), 7.01-6.92 (m, 3H), 6.87-6.80 (m, 1H), 4.37-4.26 (m, 2H), 4.17-4.10 (m, 3H), 3.81-3.69 (m, 3H), 3.65-3.60 (m, 1H), 3.56-3.54 (m, 1H), 3.37-3.30 (m, 1H), 3.20-3.16 (m, 1H), 3.15-3.08 (m, 3H), 2.34-2.22 (m, 2H), 1.80-1.66 (m, 2H).

Example 141

Synthesis of (2R,5S)-5-(4-chlorobenzyl)-2-(methoxymethyl)-4-(1-(pyridin-2-yl)piperidin-4-yl)morpholine hydrochloride (141)

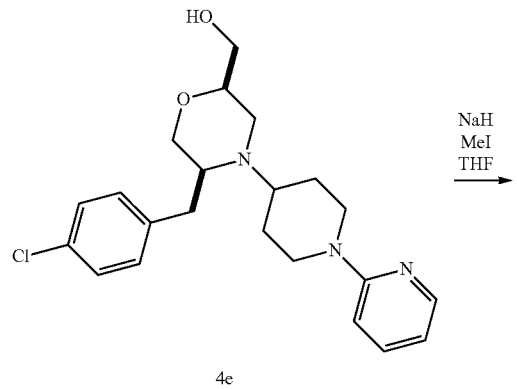

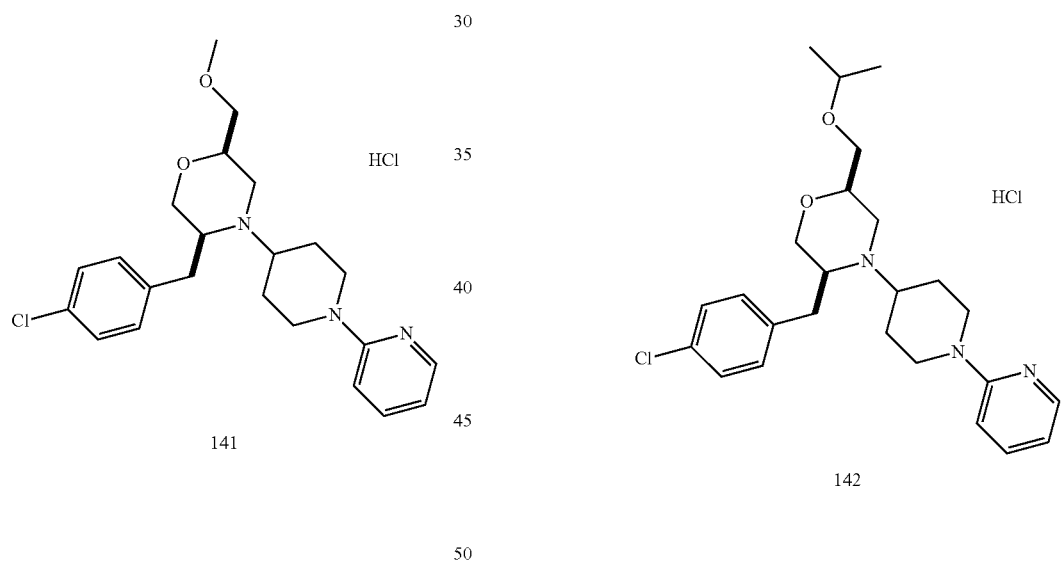

The title compound (141) was obtained as a hydrochloride salt from 4e (100 mg; 0.25 mmol) according to the General Procedure XI in 18% yield (21 mg; 0.046 mmol).

ESI-MS m/z for $C_{23}H_{31}ClN_3O_2$ found 416.2/418.2 [M+H]$^+$; $^1$H NMR (700 MHz, DMSO-d$_6$+D$_2$O, 348 K) δ 8.09-8.02 (m, 1H), 7.86-7.78 (m, 1H), 7.43-7.38 (m, 2H), 7.37-7.30 (m, 2H), 7.17-7.11 (m, 1H), 6.89-6.79 (m, 1H), 4.39-4.31 (m, 2H), 4.00-3.92 (m, 1H), 3.82-3.69 (m, 3H), 3.66-3.60 (m, 1H), 3.57-3.48 (m, 3H), 3.33 (s, 3H), 3.23-3.19 (m, 1H), 3.17-3.14 (m, 2H), 3.14-3.05 (m, 2H), 2.32-2.21 (m, 2H), 1.80-1.69 (m, 2H).

Example 142

Synthesis of (2R,5S)-5-(4-chlorobenzyl)-2-(isopropoxymethyl)-4-(1-(pyridin-2-yl)piperidin-4-yl)morpholine hydrochloride (142)

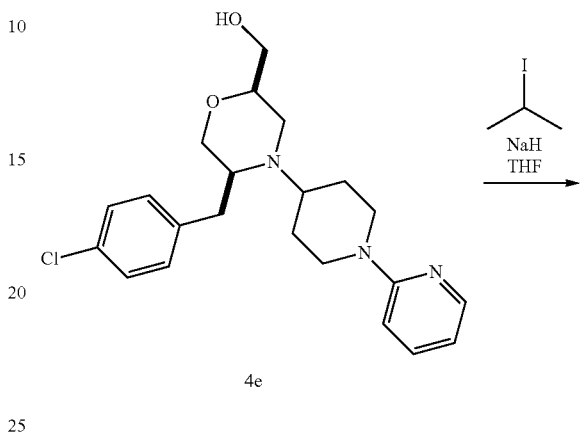

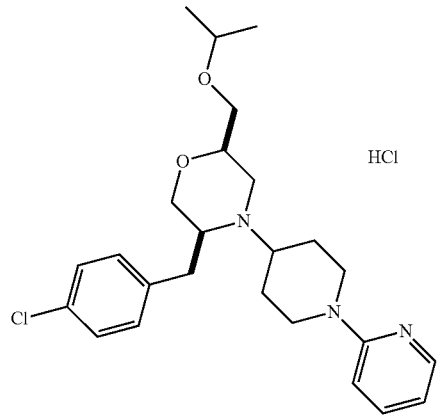

The title compound (142) was obtained as a hydrochloride salt from 4e (100 mg; 0.25 mmol) according to the General Procedure XI in 4% yield (5 mg; 0.01 mmol).

ESI-MS m/z for $C_{25}H_{35}ClN_3O_2$ found 444.2/446.2 [M+H]$^+$; $^1$H NMR (700 MHz, DMSO-d$_6$+D$_2$O, 348 K) δ 8.06-8.03 (m, 1H), 7.84-7.79 (m, 1H), 7.43-7.39 (m, 2H), 7.35-7.31 (m, 2H), 7.17-7.12 (m, 1H), 6.87-6.83 (m, 1H), 4.40-4.32 (m, 2H), 3.95-3.89 (m, 1H), 3.81-3.71 (m, 3H), 3.67-3.61 (m, 2H), 3.58-3.50 (m, 3H), 3.43-3.41 (m, 1H), 3.17-3.14 (m, 2H), 3.14-3.06 (m, 2H), 2.35-2.22 (m, 2H), 1.81-1.71 (m, 2H), 1.16-1.07 (m, 6H).

Example 143

Synthesis of ((2R,5S)-5-(4-chlorobenzyl)-4-(1-(pyridin-2-yl)piperidin-4-yl)morpholin-2-yl)methyl cyclopropylcarbamate hydrochloride (143)

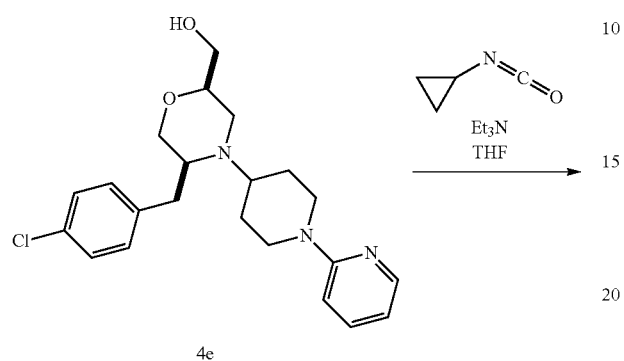

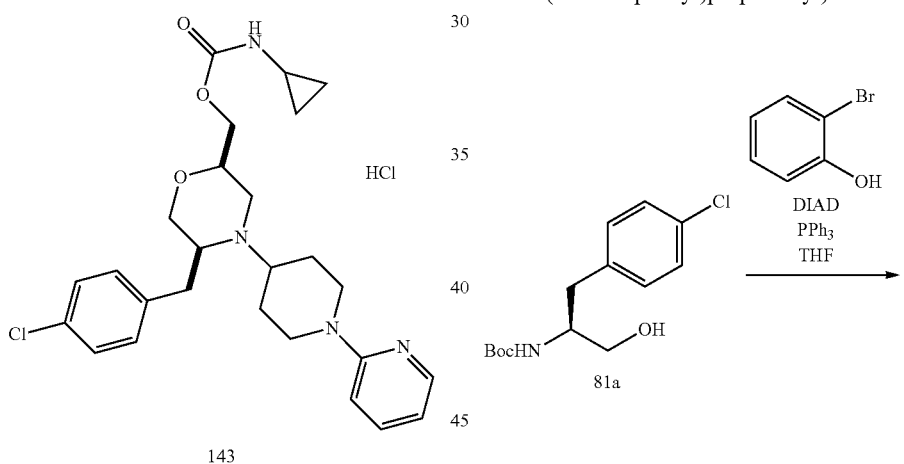

The title compound (143) was obtained as a hydrochloride salt from 4e (100 mg; 0.25 mmol) according to the General Procedure XVII in 34% yield (45 mg; 0.086 mmol).

ESI-MS m/z for $C_{26}H_{34}ClN_4O_3$ found 485.3/487.3 [M+H]$^+$; $^1$H NMR (700 MHz, DMSO-d$_6$+D$_2$O, 348 K) δ 8.04-7.98 (m, 1H), 7.90-7.84 (m, 1H), 7.39-7.35 (m, 2H), 7.32-7.28 (m, 2H), 7.22-7.17 (m, 1H), 6.89-6.84 (m, 1H), 4.38-4.27 (m, 2H), 4.18-4.11 (m, 1H), 4.09-3.99 (m, 2H), 3.83-3.69 (m, 3H), 3.61-3.57 (m, 1H), 3.50-3.44 (m, 2H), 3.21-3.16 (m, 1H), 3.15-3.09 (m, 4H), 2.37-2.22 (m, 2H), 1.88-1.74 (m, 2H), 0.66-0.53 (m, 2H), 0.46-0.31 (m, 2H).

Example 144

Synthesis of (S)-3-(4-chlorobenzyl)-4-(1-(pyridin-2-yl)piperidin-4-yl)-3,4-dihydro-2H-benzo[b][1,4]oxazine hydrochloride (144)

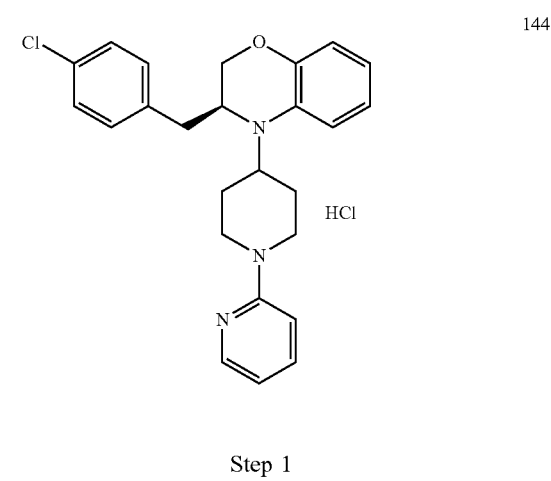

Step 1

Synthesis of tert-butyl (S)-(1-(2-bromophenoxy)-3-(4-chlorophenyl)propan-2-yl)carbamate (144a)

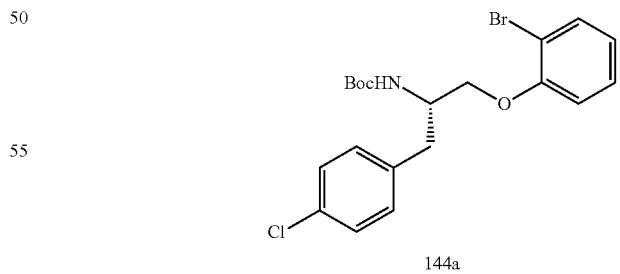

The title compound (144a) was synthesized from compound 81a (1 g; 5.38 mmol) according to the General Procedure XVIII and was obtained as a colorless oil in 47% yield (1.11 g; 2.53 mmol).

ESI-MS m/z for $C_{20}H_{24}BrClNO_3$ found 440.1/442.1 [M+H]$^+$

Step 2

Synthesis of (S)-1-(2-bromophenoxy)-3-(4-chlorophenyl)propan-2-amine hydrochloride (144b)

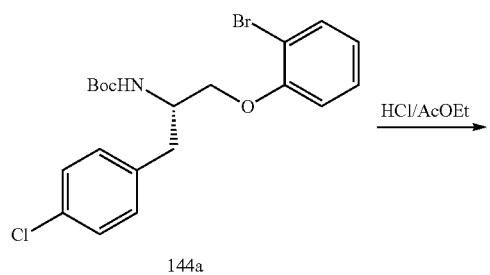

144a

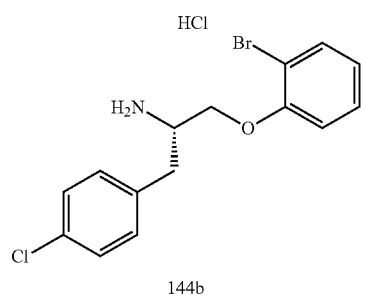

144b

The title compound (144b) was obtained as a hydrochloride salt from compound 144a (1.11 g; 2.53 mmol) according to the General Procedure IVa in 99% yield (940 mg; 2.5 mmol).

ESI-MS m/z for $C_{15}H_{16}BrClNO$ found 340.0/342.0 $[M+H]^+$

Step 3

Synthesis of tert-butyl (S)-4-((1-(2-bromophenoxy)-3-(4-chlorophenyl)propan-2-yl)amino)piperidine-1-carboxylate (144c)

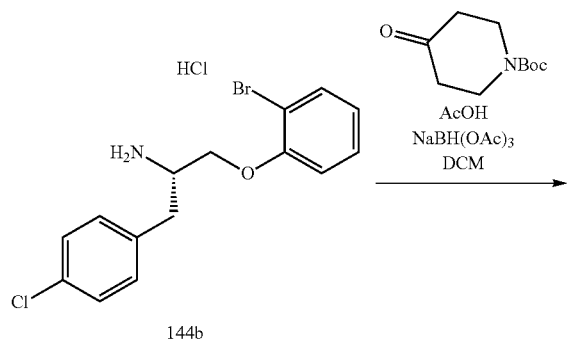

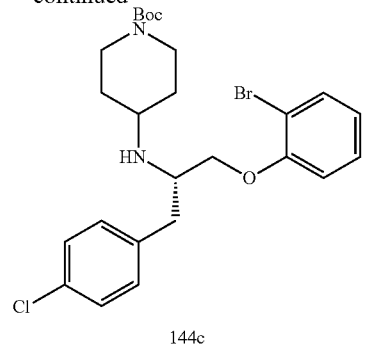

144c

The title compound (144c) was obtained from 144b (940 mg; 2.5 mmol) according to the General Procedure VI in 92% yield (1.2 g; 2.3 mmol).

ESI-MS m/z for $C_{25}H_{33}BrClN_2O_3$ found 523.1/525.1 $[M+H]^+$; $^1$H NMR (700 MHz, CDCl$_3$) δ 7.60-7.55 (m, 1H), 7.29-7.27 (m, 2H), 7.27-7.23 (m, 1H), 7.19-7.15 (m, 2H), 6.88-6.85 (m, 1H), 6.83-6.79 (m, 1H), 4.07-3.80 (m, 4H), 3.38-3.30 (m, 1H), 3.02-2.92 (m, 1H), 2.92-2.78 (m, 4H), 1.90-1.77 (m, 2H), 1.47 (s, 9H), 1.36-1.24 (m, 1H), 1.21-1.09 (m, 1H).

Step 4

Synthesis of tert-butyl (S)-4-(3-(4-chlorobenzyl)-2,3-dihydro-4H-benzo[b][1,4]oxazin-4-yl)piperidine-1-carboxylate (144d)

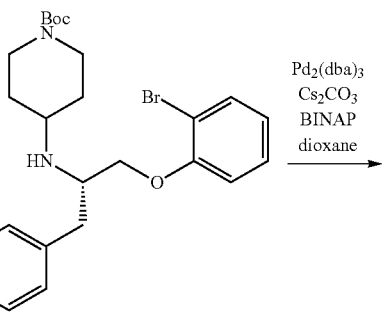

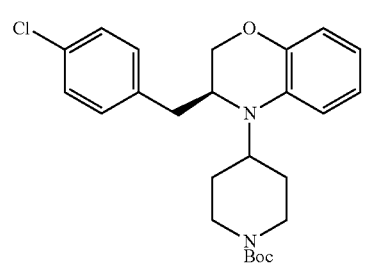

144d

The title compound (144d) was obtained from 144c (1.2 g; 2.3 mmol) according to the General Procedure XXIII in 63% yield (640 mg; 1.45 mmol) with the exception that, in this reaction, dioxane and Pd$_2$(dba)$_3$ were used instead of toluene and Pd(OAc)$_2$.

ESI-MS m/z for $C_{25}H_{32}ClN_2O_3$ found 443.2/445.2 $[M+H]^+$; $^1$H NMR (700 MHz, CDCl$_3$) δ 7.32-7.27 (m, 2H), 7.16-7.11 (m, 2H), 6.98-6.86 (m, 3H), 6.79-6.68 (m, 1H), 4.31-4.15 (m, 2H), 4.15-4.08 (m, 1H), 3.65-3.58 (m, 1H), 3.51-3.43 (m, 1H), 2.82-2.74 (m, 2H), 2.72-2.64 (m, 2H), 1.79-1.73 (m, 1H), 1.63-1.59 (m, 2H), 1.49 (s, 9H), 1.48-1.40 (m, 2H).

Step 5

Synthesis of (S)-3-(4-chlorobenzyl)-4-(piperidin-4-yl)-3,4-dihydro-2H-benzo[b][1,4]oxazine hydrochloride (144e)

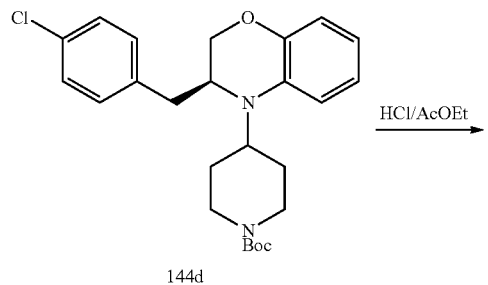

The title compound (144e) was obtained as a hydrochloride salt from compound 144d (640 mg; 1.45 mmol) according to the General Procedure IVa in 74% yield (405 mg; 1.07 mmol).

ESI-MS m/z for $C_{20}H_{24}ClN_2O$ found 343.2/345.2 [M+H]$^+$; $^1$H NMR (700 MHz, DMSO-d$_6$) δ 7.38-7.33 (m, 2H), 7.22-7.19 (m, 2H), 7.01-6.97 (m, 1H), 6.86-6.81 (m, 1H), 6.81-6.77 (m, 1H), 6.63-6.57 (m, 1H), 4.05-4.00 (m, 1H), 4.00-3.92 (m, 1H), 3.60-3.55 (m, 1H), 3.55-3.49 (m, 1H), 3.30-3.21 (m, 2H), 3.01-2.93 (m, 1H), 2.93-2.85 (m, 1H), 2.69-2.64 (m, 1H), 2.61-2.56 (m, 1H), 1.93-1.81 (m, 2H), 1.73-1.66 (m, 1H), 1.63-1.51 (m, 1H).

Step 6

Synthesis of (S)-3-(4-chlorobenzyl)-4-(1-(pyridin-2-yl)piperidin-4-yl)-3,4-dihydro-2H-benzo[b][1,4]oxazine hydrochloride (144)

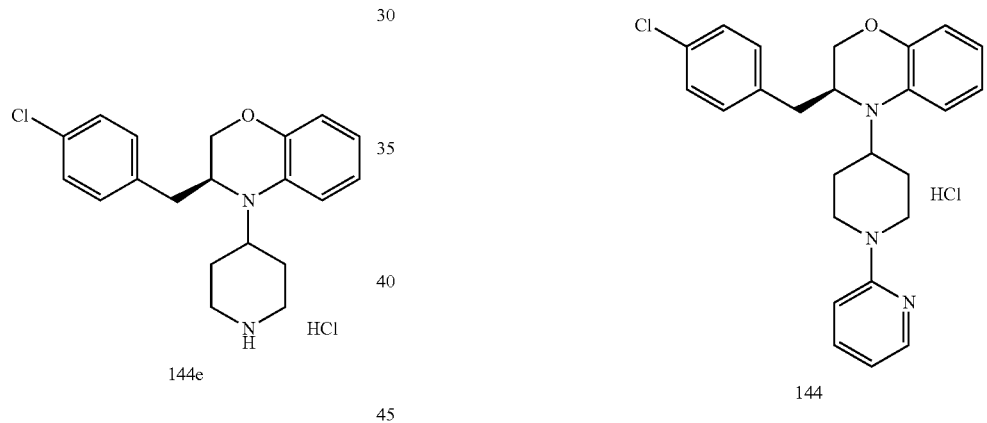

The title compound (144) was obtained as a hydrochloride salt from 144e (130 mg; 0.34 mmol) according to the General Procedure IX in 56% yield (85 mg; 0.19 mmol) with the exception that the temperature of this reaction was reduced to 100° C. instead of 120° C.

ESI-MS m/z for $C_{25}H_{27}ClN_3O$ found 420.2/422.2 [M+H]$^+$; $^1$H NMR (700 MHz, DMSO-d$_6$+D$_2$O) δ 7.98-7.93 (m, 1H), 7.89-7.87 (m, 1H), 7.37-7.33 (m, 1H), 7.32-7.27 (m, 2H), 7.15-7.09 (m, 2H), 7.07-7.00 (m, 1H), 6.92-6.88 (m, 1H), 6.86-6.82 (m, 1H), 6.80-6.75 (m, 1H), 6.65-6.57 (m, 1H), 4.20-4.08 (m, 1H), 4.02-3.93 (m, 2H), 3.65-3.60 (m, 1H), 3.50-3.44 (m, 1H), 3.28-3.20 (m, 1H), 3.19-3.11 (m, 1H), 2.64-2.58 (m, 1H), 2.57-2.51 (m, 1H), 1.73-1.66 (m, 1H), 1.63-1.54 (m, 2H), 1.52-1.45 (m, 1H).

Example 145

Synthesis of (2S,5S)-5-(4-chlorobenzyl)-2-methyl-4-(1-(6-(trifluoromethyl)pyrimidin-4-yl)piperidin-4-yl)morpholine hydrochloride (145)

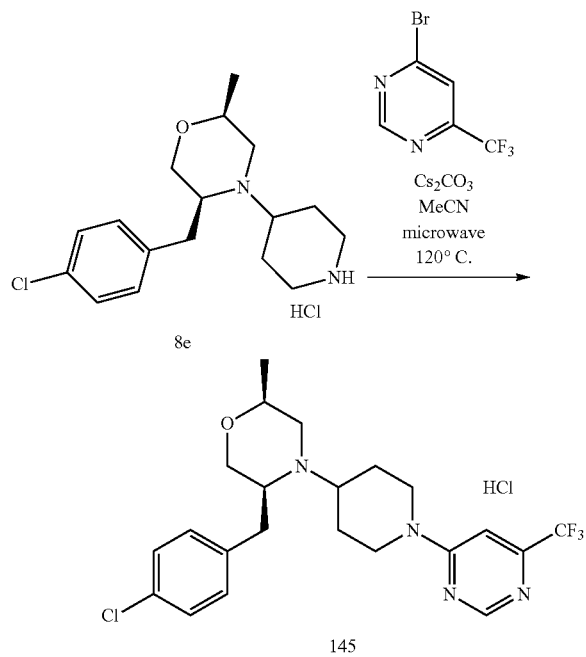

The title compound (145) was obtained as a hydrochloride salt from 8e (110 mg; 0.32 mmol) according to the General Procedure XXV in 80% yield (125 mg; 0.255 mmol).

ESI-MS m/z for $C_{22}H_{27}ClF_3N_4O$ found 455.3/457.3 [M+H]$^+$; $^1$H NMR (700 MHz, DMSO-d$_6$+D$_2$O) δ 8.66-8.62 (m, 1H), 7.43-7.38 (m, 2H), 7.37-7.33 (m, 2H), 7.26-7.23 (m, 1H), 4.70-4.56 (m, 2H), 3.93-3.86 (m, 1H), 3.85-3.69 (m, 3H), 3.62-3.56 (m, 1H), 3.49-3.46 (m, 1H), 3.22-3.13 (m, 2H), 3.13-3.00 (m, 3H), 2.35-2.24 (m, 2H), 1.75-1.61 (m, 2H), 1.24 (d, J=6.2 Hz, 3H).

Example 146

Synthesis of (2S,5S)-5-(4-chlorobenzyl)-2-methyl-4-(1-(4-(trifluoromethyl)pyrimidin-2-yl)piperidin-4-yl)morpholine hydrochloride (146)

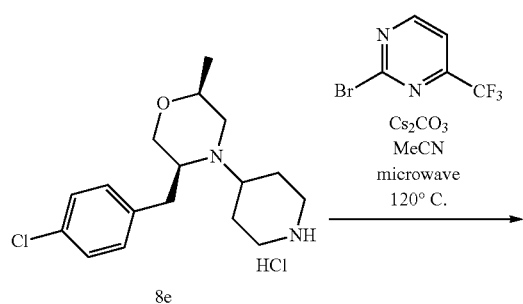

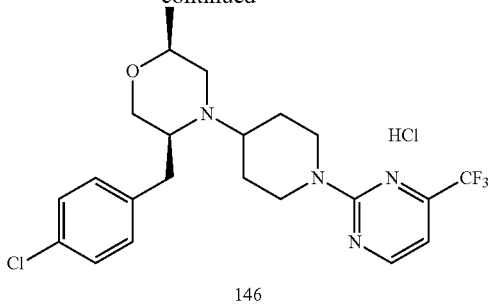

146

The title compound (146) was obtained as a hydrochloride salt from 8e (110 mg; 0.32 mmol) according to the General Procedure XXV in 80% yield (126 mg; 0.257 mmol).

ESI-MS m/z for $C_{22}H_{27}ClF_3N_4O$ found 455.2/457.2 [M+H]$^+$; $^1$H NMR (700 MHz, DMSO-d$_6$+D$_2$O) δ 8.72-8.67 (m, 1H), 7.43-7.38 (m, 2H), 7.36-7.33 (m, 2H), 7.03-6.99 (m, 1H), 4.82-4.72 (m, 2H), 3.95-3.88 (m, 1H), 3.83-3.71 (m, 3H), 3.63-3.55 (m, 1H), 3.44-3.40 (m, 1H), 3.22-3.12 (m, 2H), 3.10-2.98 (m, 3H), 2.35-2.22 (m, 2H), 1.72-1.62 (m, 2H), 1.24 (d, J=6.3 Hz, 3H).

Example 147

Synthesis of (S)-5-(4-chlorobenzyl)-4-(1-(pyridin-2-yl)piperidin-4-yl)morpholin-3-one hydrochloride (147)

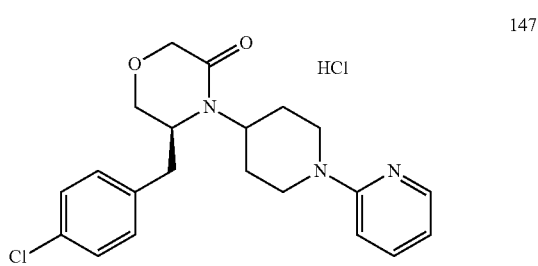 [SMILES: O=C1COC[C@H](Cc2ccc(Cl)cc2)N1C1CCN(c2ccccn2)CC1 ; Cl]

Step 1

Synthesis of (S)-3-(4-chlorophenyl)-2-((1-(pyridin-2-yl)piperidin-4-yl)amino)propan-1-ol (147a)

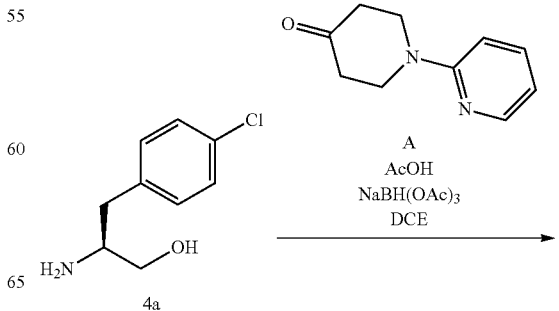

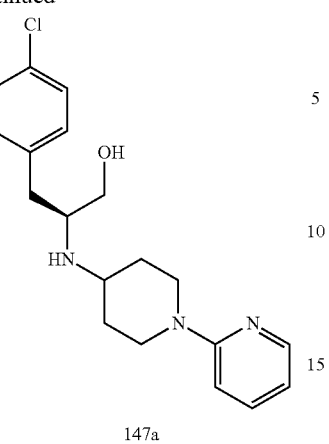

147a

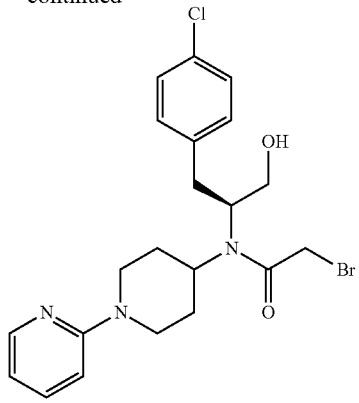

147b

The title compound (147a) was obtained from 4a (530 mg; 2.83 mmol) according to the General Procedure VI in 79% yield (770 mg; 2.23 mmol).

ESI-MS m/z for $C_{19}H_{25}ClN_3O$ found 346.2/348.2 [M+H]$^+$; $^1$H NMR (700 MHz, DMSO-d$_6$) 8.10-8.05 (m, 1H), 7.53-7.45 (m, 1H), 7.38-7.31 (m, 2H), 7.30-7.23 (m, 2H), 6.82-6.76 (m, 1H), 6.61-6.52 (m, 1H), 4.59-4.48 (m, 1H), 4.14-4.09 (m, 1H), 4.06-4.01 (m, 1H), 3.30-3.27 (m, 1H), 3.25-3.22 (m, 1H), 3.19-3.17 (m, 1H), 2.91-2.82 (m, 3H), 2.78-2.71 (m, 1H), 2.70-2.66 (m, 1H), 2.61-2.55 (m, 1H), 1.87-1.79 (m, 1H), 1.75-1.70 (m, 1H), 1.20-1.12 (m, 1H), 1.12-1.03 (m, 1H).

Step 2

Synthesis of (S)-2-bromo-N-(1-(4-chlorophenyl)-3-hydroxypropan-2-yl)-N-(1-(pyridin-2-yl)piperidin-4-yl)acetamide (147b)

To the solution of 147a (270 mg; 0.78 mmol) in DCM (10 mL) triethylamine (0.16 mL; 1.17 mmol) was added and the solution was cooled to 0° C. Bromoacetyl chloride (0.068 mL; 0.78 mmol) was added slowly in such a manner that the internal temperature of the reaction did not exceed 5° C. The cooling bath was then removed and the mixture was stirred for 1.5 hours at room temperature. TLC showed complete consumption of the staring material at this point. DCM was then added and the whole reaction mixture was washed with 5% NaHCO$_3$, dried over anhydrous MgSO$_4$, filtered and concentrated in vacuo. The crude product was used to the next step without additional purification. The title compound (147b) was obtained in 85% yield (307 mg; 0.66 mmol).

ESI-MS m/z for $C_{21}H_{26}BrClN_3O_2$ found 466.1/468.1 [M+H]$^+$

Step 3

Synthesis of (S)-5-(4-chlorobenzyl)-4-(1-(pyridin-2-yl)piperidin-4-yl)morpholin-3-one hydrochloride (147)

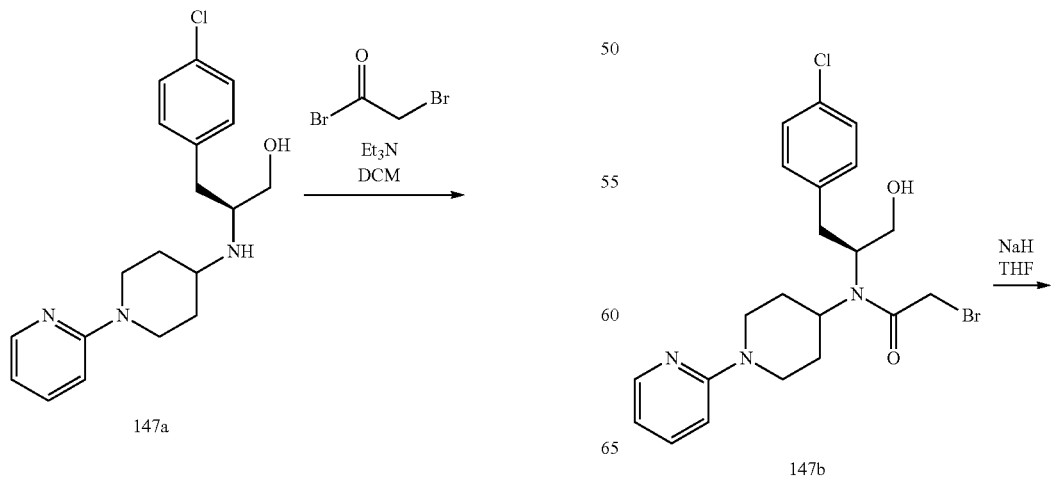

451

-continued

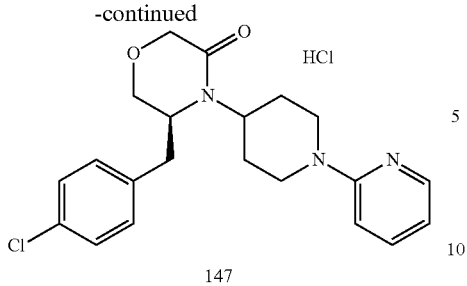

147

The title compound (147) was obtained as a hydrochloride salt from compound 147b (307 mg; 0.66 mmol) according to the General Procedure II in 25% yield (70 mg; 0.166 mmol).

ESI-MS m/z for $C_{21}H_{25}ClN_3O_2$ found 386.2/388.2 [M+H]$^+$; $^1$H NMR (700 MHz, DMSO-$d_6$+$D_2O$, 348 K) δ 8.01-7.93 (m, 2H), 7.37-7.34 (m, 3H), 7.32-7.26 (m, 2H), 6.97-6.88 (m, 1H), 4.31-4.24 (m, 2H), 4.09 (d, J=16.6 Hz, 1H), 3.99 (d, J=16.6 Hz, 1H), 3.94-3.85 (m, 1H), 3.64-3.59 (m, 1H), 3.59-3.51 (m, 2H), 3.27-3.20 (m, 2H), 3.07-3.01 (m, 1H), 2.96-2.89 (m, 1H), 2.38-2.28 (m, 1H), 2.23-2.15 (m, 1H), 2.03-1.96 (m, 1H), 1.86-1.78 (m, 1H).

Example 148

Synthesis of (S)-7-(4-chlorobenzyl)-5-methyl-8-(1-(pyridin-2-yl)piperidin-4-yl)-5,8-diazaspiro[3.5]nonane hydrochloride (148)

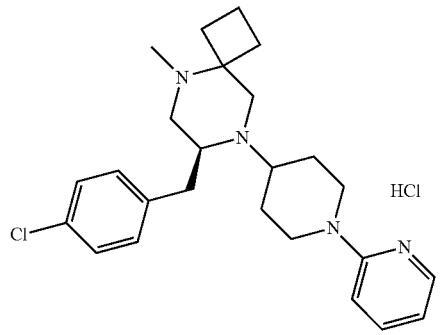

148

Step 1

Synthesis of methyl (S)-1-((2-((tert-butoxycarbonyl)amino)-3-(4-chlorophenyl)propyl)amino)cyclobutane-1-carboxylate (148a)

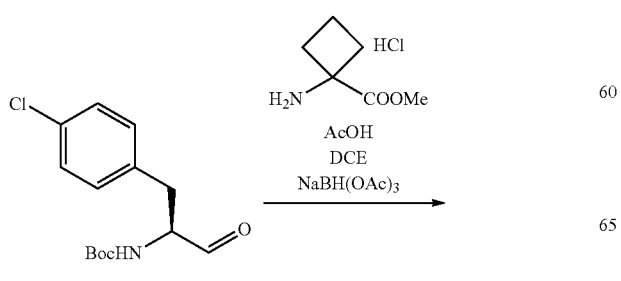

452

-continued

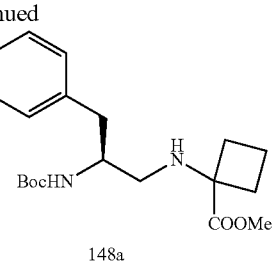

148a

The reductive amination of known tert-butyl (S)-(1-(4-chlorophenyl)-3-oxopropan-2-yl)carbamate (450 mg; 1.59 mmol) with methyl 1-aminocyclobutane-1-carboxylate hydrochloride (263 mg; 1.59 mmol) was accomplished according to the General Procedure VI. The crude product 148a was obtained as a white foam in 67% yield (420 mg, 1.06 mmol).

ESI-MS m/z for $C_{20}H_{30}ClN_2O_4$ found 397.2/399.2 [M+H]$^+$

Step 2

Synthesis of methyl (S)-1-((2-((tert-butoxycarbonyl)amino)-3-(4-chlorophenyl)propyl)(methyl)amino)cyclobutane-1-carboxylate (148b)

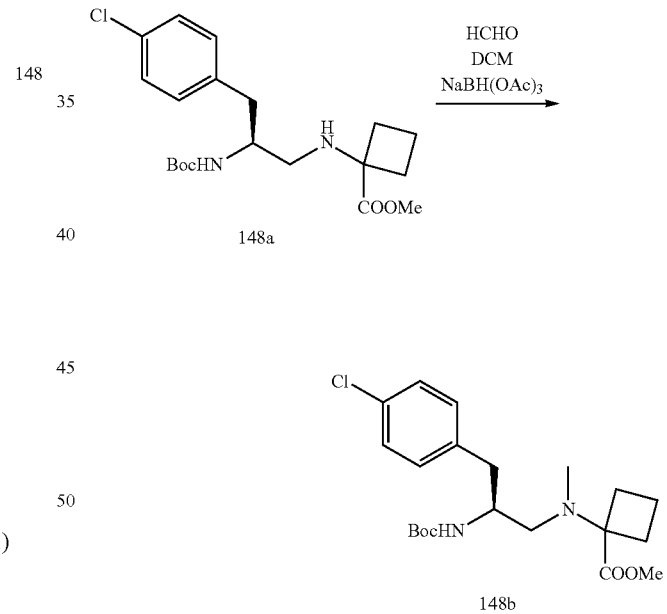

The title compound (148b) was obtained from compound 148a (420 mg, 1.06 mmol) according to the General Procedure VI in 92% yield (400 mg; 0.975 mmol).

ESI-MS m/z for $C_{21}H_{32}ClN_2O_4$ found 411.2/413.2 [M+H]$^+$

Step 3

Synthesis of methyl (S)-1-((2-amino-3-(4-chlorophenyl)propyl)(methyl)amino)cyclobutane-1-carboxylate hydrochloride (148c)

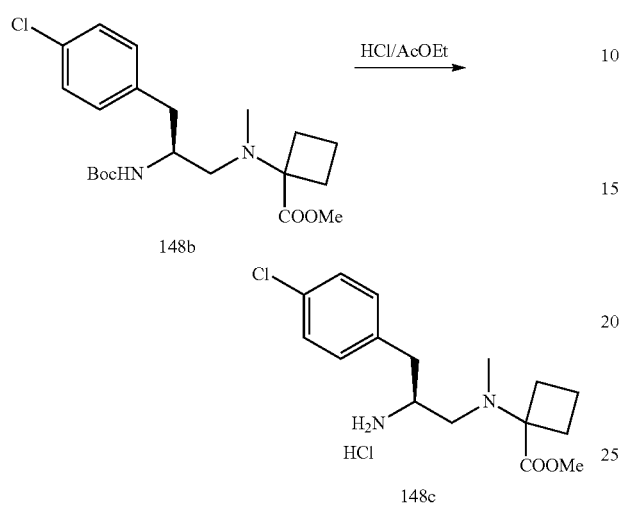

The title compound (148c) was obtained from compound 148b (400 mg; 0.975 mmol) according to the General Procedure IVa in 92% yield (400 mg; 0.975 mmol).

ESI-MS m/z for $C_{21}H_{32}ClN_2O_4$ found 411.2/413.2 $[M+H]^+$

Step 4

Synthesis of (S)-7-(4-chlorobenzyl)-5-methyl-5,8-diazaspiro[3.5]nonan-9-one (148d)

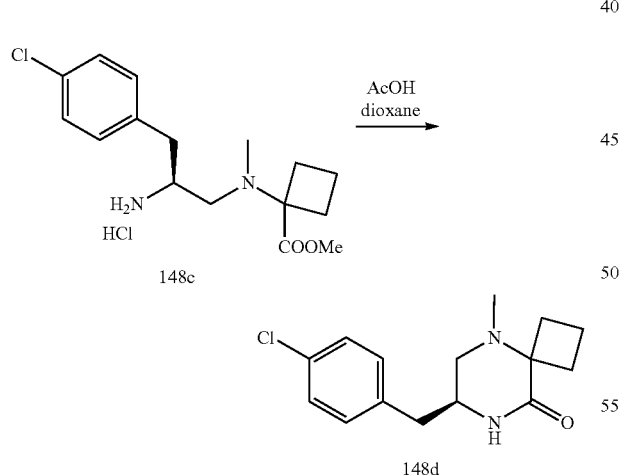

The solution of 148c (345 mg; 0.99 mmol) in AcOH/dioxane (2 mL/3 mL) was stirred at room temperature for 10 days and then at 50° C. for 2 days. Next to this mixture another part of AcOH (2 mL) was added and stirred at 40° C. overnight. The solvent was removed in vacuo and the residue was dissolved in DCM and washed with 5% NaHCO₃, dried over anhydrous MgSO₄, filtered and concentrated in vacuo and the crude product was purified by flash column chromatography on silica (DCM/MeOH, 100:0 to 100:1, v/v). Compound 148d was obtained in 73% yield (200 mg; 0.72 mmol).

ESI-MS m/z for $C_{15}H_{20}ClN_2O$ found 279.1/281.1 $[M+H]^+$

Step 5

Synthesis of (S)-7-(4-chlorobenzyl)-5-methyl-5,8-diazaspiro[3.5]nonane (148e)

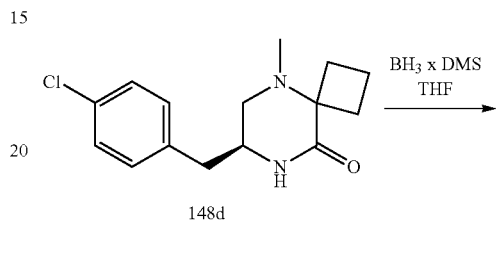

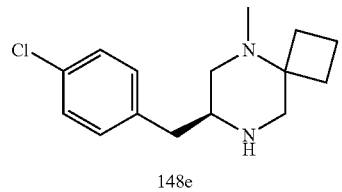

The title compound (148e) was obtained from compound 148d (200 mg; 0.72 mmol) according to the General Procedure Ib in 68% yield (130 mg; 0.49 mmol).

ESI-MS m/z for $C_{15}H_{22}ClN_2$ found 265.1/267.1 $[M+H]^+$

Step 6

Synthesis of (S)-7-(4-chlorobenzyl)-5-methyl-8-(1-(pyridin-2-yl)piperidin-4-yl)-5,8-diazaspiro[3.5]nonane hydrochloride (148)

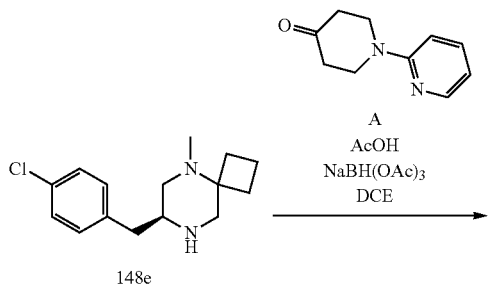

-continued

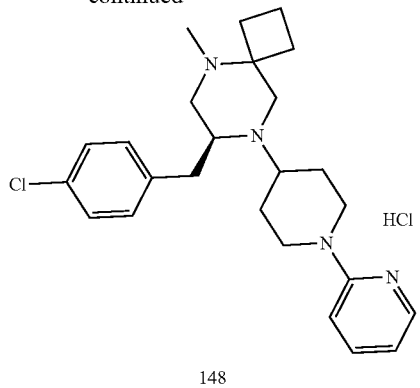

148

The title compound (148) was obtained as a hydrochloride salt from compound 148e (130 mg; 0.49 mmol) according to the General Procedure VI in 11% yield (25 mg; 0.054 mmol).

ESI-MS m/z for $C_{25}H_{34}ClN_4$ found 425.3/427.3 [M+H]$^+$;
$^1$H NMR (700 MHz, DMSO-d$_6$+D$_2$O, 348 K) δ 7.96-7.93 (m, 1H), 7.92-7.88 (m, 1H), 7.37-7.34 (m, 2H), 7.34-7.29 (m, 2H), 7.28-7.23 (m, 1H), 6.91-6.86 (m, 1H), 4.25-4.11 (m, 2H), 3.31-3.26 (m, 1H), 3.25-3.18 (m, 1H), 3.11-3.00 (m, 3H), 2.92-2.85 (m, 1H), 2.75-2.66 (m, 6H), 2.38-2.29 (m, 2H), 2.07-2.00 (m, 1H), 1.87-1.76 (m, 7H), 1.57-1.47 (m, 1H).

Example 149

Synthesis of (S)-3-(4-chlorobenzyl)-4-(1-(pyridin-2-yl)piperidin-4-yl)piperazin-2-one 2,2,2-trifluoroacetate (149)

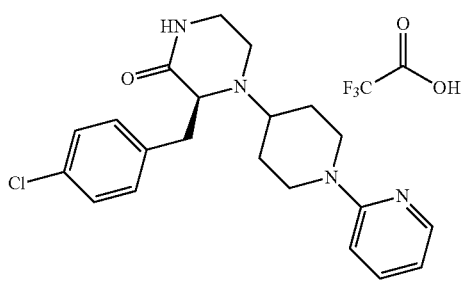

149

Step 1

Synthesis of tert-butyl (S)-(1-((2-bromoethyl)amino)-3-(4-chlorophenyl)-1-oxopropan-2-yl)carbamate (149a)

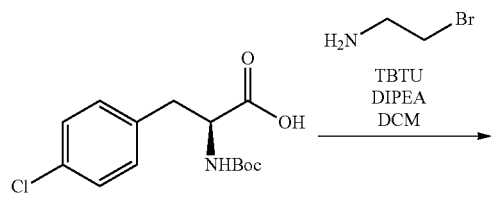

-continued

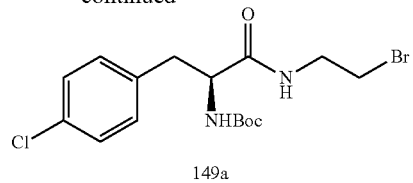

149a

The title compound (149a) was obtained from 2-bromoethylamine hydrobromide (595 mg; 2.9 mmol) and Boc-4-chloro-L-phenylalanine (870 mg; 2.9 mmol) according to the General Procedure III in 99% yield (1.16 g; 2.87 mmol).

ESI-MS m/z for $C_{16}H_{23}BrClN_2O_3$ found 405.1/407.1 [M+H]$^+$

Step 2

Synthesis of (S)-2-amino-N-(2-bromoethyl)-3-(4-chlorophenyl)propanamide hydrochloride (149b)

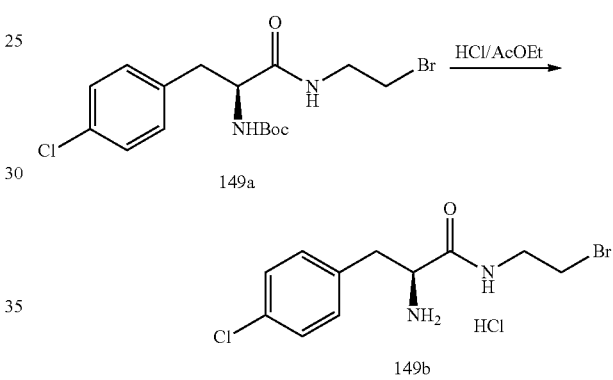

The title compound (149b) was obtained as a hydrochloride salt from 149a (1.16 g; 2.87 mmol) according to the General Procedure IVb in 92% yield (0.9 g; 2.64 mmol).

ESI-MS m/z for $C_{11}H_{15}BrClN_2O$ found 305.0/307.0 [M+H]$^+$

Step 3

Synthesis of (S)-3-(4-chlorobenzyl)piperazin-2-one (149c)

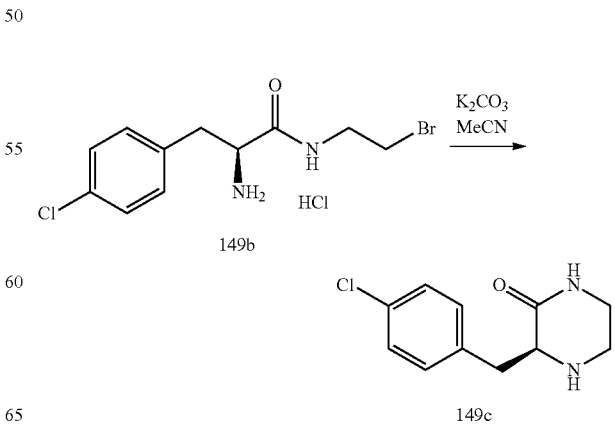

To a solution of crude 149b (0.9 g; 2.64 mmol) in MeCN (20 mL) K$_2$CO$_3$ (1.61 g; 11.69 mmol) was added and the mixture was stirred at room temperature overnight. LC-MS showed completion of the reaction. The mixture was filtered off and the filtrate was concentrated in vacuo and the residue was purified by flash column chromatography on silica (DCM/MeOH, 100:1 to 20:1, v/v). Compound 149c was obtained as a yellow oil in 59% yield (350 mg; 1.56 mmol).

ESI-MS m/z for C$_{11}$H$_{14}$ClN$_2$O found 225.1/227.1 [M+H]$^+$

Step 4

Synthesis of (S)-3-(4-chlorobenzyl)-4-(1-(pyridin-2-yl)piperidin-4-yl)piperazin-2-one 2,2,2-trifluoroacetate (149)

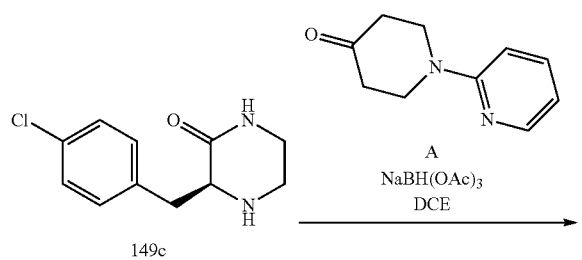

149c

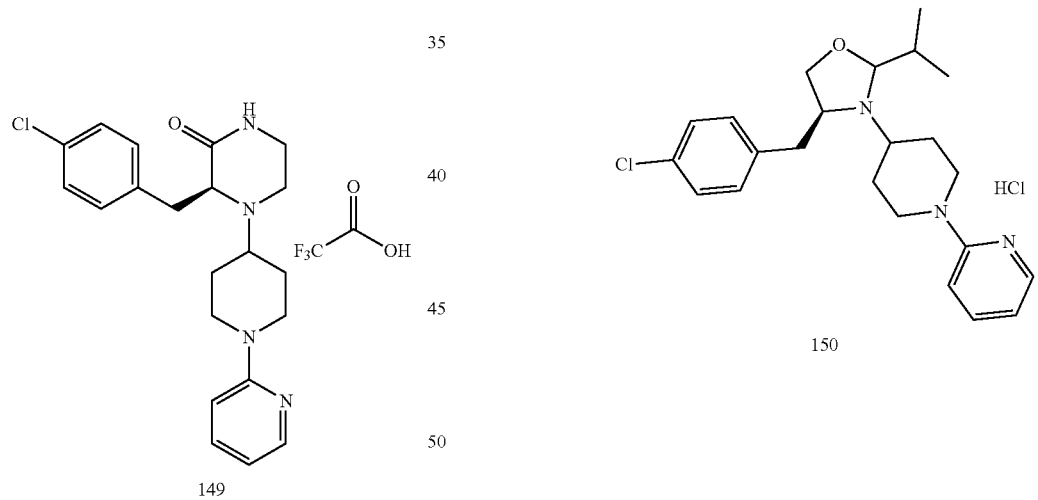

149

The title compound (149) was obtained as a TFA salt from compound 149c (170 mg; 0.76 mmol) according to the General Procedure VI in 4% yield (14 mg; 0.028 mmol).

ESI-MS m/z for C$_{21}$H$_{26}$ClN$_4$O found 385.3/387.3 [M+H]$^+$; $^1$H NMR (700 MHz, DMSO-d$_6$+D$_2$O, 348 K) δ 7.94-7.87 (m, 2H), 7.30-7.26 (m, 4H), 7.23-7.19 (m, 1H), 6.90-6.86 (m, 1H), 4.12-4.05 (m, 1H), 4.04-3.96 (m, 1H), 3.74-3.67 (m, 1H), 3.30-3.23 (m, 1H), 3.21-3.16 (m, 1H), 3.16-3.03 (m, 6H), 2.93-2.87 (m, 1H), 1.90-1.79 (m, 2H), 1.60-1.38 (m, 2H).

Example 150

Synthesis of (4S)-4-(4-chlorobenzyl)-2-isopropyl-3-(1-(pyridin-2-yl)piperidin-4-yl)oxazolidine hydrochloride (150)

The title compound (150) was obtained as a hydrochloride salt from compound 147a (190 mg; 0.55 mmol) according to the General Procedure VI in 55% yield (130 mg; 0.3 mmol).

ESI-MS m/z for C$_{23}$H$_{31}$ClN$_3$O found 400.3/402.3 [M+H]$^+$; $^1$H NMR (700 MHz, DMSO-d$_6$+D$_2$O, 348 K) δ 8.04-8.01 (m, 1H), 7.91-7.86 (m, 1H), 7.41-7.37 (m, 2H), 7.36-7.32 (m, 2H), 7.24-7.20 (m, 1H), 6.91-6.87 (m, 1H), 4.33-4.22 (m, 2H), 3.69-3.58 (m, 2H), 3.54-3.48 (m, 1H), 3.48-3.42 (m, 2H), 3.19-3.11 (m, 2H), 3.10-3.02 (m, 1H), 2.97-2.89 (m, 1H), 2.55-2.53 (m, 1H), 2.26-2.16 (m, 2H), 1.80-1.68 (m, 2H), 1.06-0.98 (m, 6H).

Example 151

Synthesis of 2-((2R,5S)-5-(4-chlorobenzyl)-4-(1-(pyridin-2-yl)piperidin-4-yl)morpholin-2-yl)propan-2-ol hydrochloride (151)

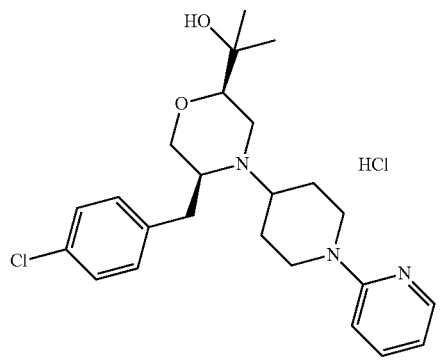

Step 1

Synthesis of (2R,5S)-4-(tert-butoxycarbonyl)-5-(4-chlorobenzyl)morpholine-2-carboxylic acid (151a)

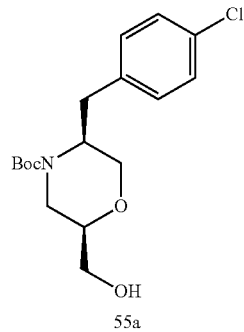

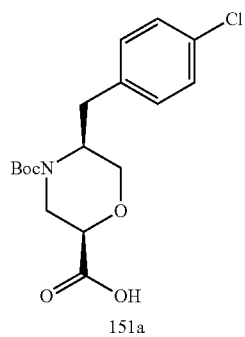

To a cooled to 0° C. solution of alcohol 55a (1.8 g; 5.26 mmol) in acetone (40 mL), Jones reagent (2.6M; 12 mL) was added dropwise. The reaction mixture was stirred at 0° C. for 1 hour, and then isopropanol (iPrOH) (5 mL) was added. After 10 minutes ethyl acetate (150 mL) was added and the mixture was filtered through a pad of the Celite. The filtrate was washed with brine, dried over anhydrous MgSO$_4$ and evaporated affording the title compound 151a as a white foam in 91% yield (1.7 g; 4.79 mmol).

ESI-MS m/z for C$_{17}$H$_{22}$ClNO$_5$Na found 378.3/380.3 [M+Na]$^+$, 256.1/258.1 [M+H-Boc]$^+$

Step 2

Synthesis of 4-(tert-butyl) 2-methyl (2R,5S)-5-(4-chlorobenzyl)morpholine-2,4-dicarboxylate (151b)

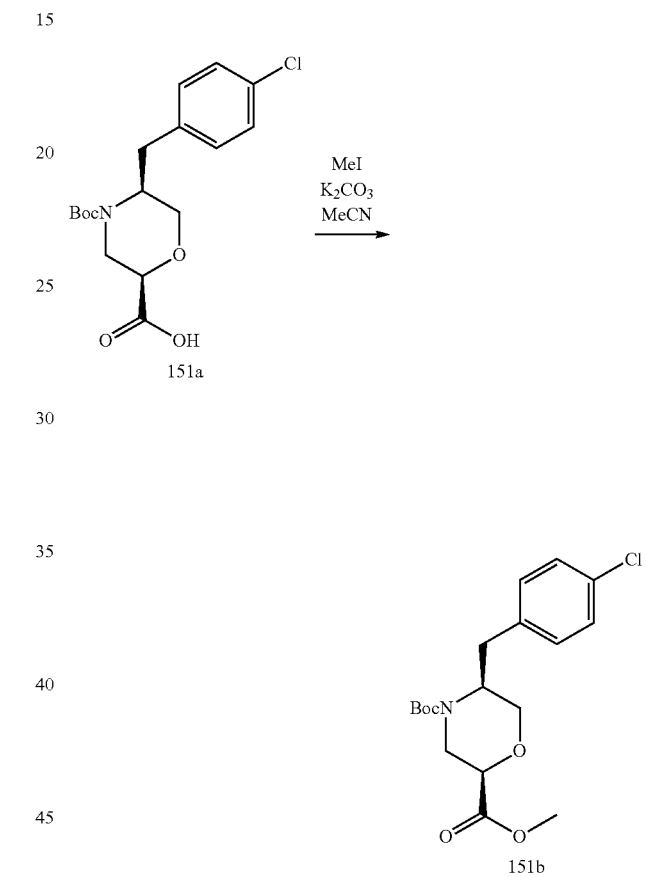

To a solution of Boc-protected amino acid 151a (1 g; 2.82 mmol) in acetonitrile, potassium carbonate (0.77 g; 5.62 mmol) was added followed by methyl iodide (MeI) (0.26 mL; 4.21 mmol) at room temperature. After reaction was completed as judged by TLC, the reaction mixture was filtered and the solvent was evaporated. The residue was dissolved in ethyl acetate, washed with brine and dried over anhydrous MgSO$_4$. The solvent was evaporated in vacuo to give the title compound 151b as a yellow oil sufficiently pure to be used to the next step in 38% yield (0.4 g; 1.08 mmol).

ESI-MS m/z for C$_{18}$H$_{24}$ClNO$_5$Na found 393.1/395.1 [M+Na]$^+$

Step 3

Synthesis of tert-butyl (2R,5S)-5-(4-chlorobenzyl)-2-(2-hydroxypropan-2-yl)morpholine-4-carboxylate (151c)

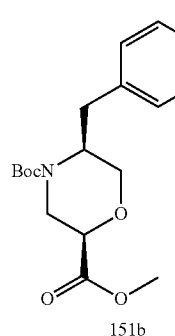

151b

→ MeMgBr, THF →

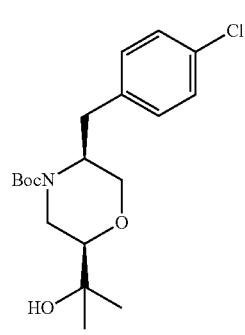

151c

The title compound (151c) was obtained from 151b (0.4 g, 1.08 mmol) according to the General Procedure V in 99% yield (395 mg; 1.07 mmol).

ESI-MS $C_{19}H_{28}ClNO_4Na$ found 393.2/395.2 [M+Na]*, 270.0/272.0 [M+H-Boc]+

Step 4

Synthesis of 2-((2R,5S)-5-(4-chlorobenzyl)morpholin-2-yl)propan-2-ol 2,2,2-trifluoroacetate (151d)

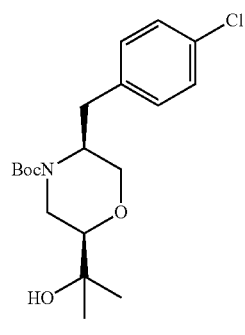

151c

→ TFA/DCM →

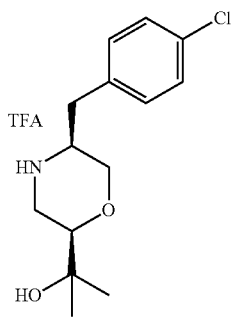

151d

The title compound (151d) was obtained as a TFA salt from 151c (395 mg; 1.07 mmol) according to the General Procedure IVb in 91% yield (370 mg; 0.97 mmol).

ESI-MS m/z for $C_{14}H_{21}ClNO_2$ found 270.1/272.1 [M+H]+; $^1$H NMR (500 MHz, DMSO-$d_6$+$D_2$O) δ 7.34 (AA'BB', J=6.2 Hz, 2H), 7.25 (AA'BB', J=6.4 Hz, 2H), 3.65-3.55 (m, 2H), 3.52-3.44 (m, 1H), 2.42-3.36 (m, 1H), 3.15-3.04 (m, 2H), 2.94-2.87 (m, 1H), 2.48 (m, 3H), 1.10 (s, 3H), 1.08 (s, 3H).

Step 5

Synthesis of 2-((2R,5S)-5-(4-chlorobenzyl)-4-(1-(pyridin-2-yl)piperidin-4-yl)morpholin-2-yl)propan-2-ol hydrochloride (151)

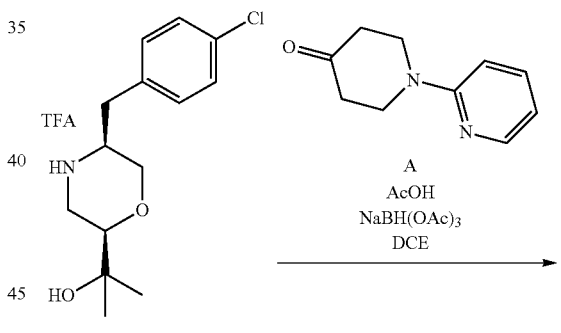

→ A, AcOH, NaBH(OAc)3, DCE →

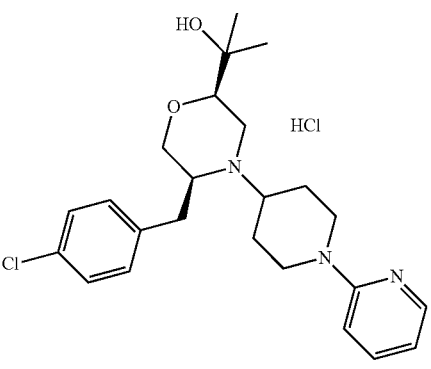

151

The title compound (151) was obtained as a hydrochloride salt from compound 151d (193 mg; 0.48 mmol) according to the General Procedure VI in 58% yield (131 mg; 0.28 mmol).

ESI-MS m/z for $C_{24}H_{33}ClN_3O_2$ found 430.1/432.1 [M+H]$^+$; $^1$H NMR (700 MHz, DMSO-$d_6$+$D_2O$, 348 K) δ 8.07-8.04 (m, 1H), 7.83-7.79 (m, 1H), 7.43-7.39 (m, 2H), 7.36-7.33 (m, 2H), 7.17-7.13 (m, 1H), 6.87-6.82 (m, 1H), 4.42-4.31 (m, 2H), 3.85-3.71 (m, 3H), 3.67-3.62 (m, 1H), 3.60-3.54 (m, 1H), 3.23-3.04 (m, 6H), 2.36-2.23 (m, 2H), 1.81-1.71 (m, 2H), 1.23-1.16 (m, 6H).

Example 152

Synthesis of (2R,5S)-5-(4-chlorobenzyl)-2-(2-methoxypropan-2-yl)-4-(1-(pyridin-2-yl)piperidin-4-yl)morpholine hydrochloride (152)

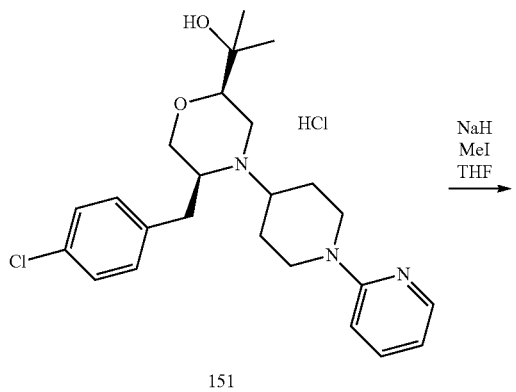

The title compound (152) was obtained as a hydrochloride salt from compound 151 (90 mg; 0.19 mmol) according to the General Procedure XI in 84% yield (78 mg; 0.16 mmol).

ESI-MS m/z for $C_{25}H_{35}ClN_3O_2$ found 444.2/446.2 [M+H]$^+$; $^1$H NMR (700 MHz, DMSO-$d_6$+$D_2O$, 348 K) δ 8.05-8.01 (m, 1H), 7.96-7.91 (m, 1H), 7.44-7.40 (m, 2H), 7.37-7.33 (m, 2H), 7.30-7.27 (m, 1H), 6.96-6.92 (m, 1H), 4.42-4.31 (m, 2H), 3.91-3.81 (m, 2H), 3.79-3.74 (m, 2H), 3.66 (d, J=12.9 Hz, 1H), 3.42-3.35 (m, 1H), 3.26-3.15 (m, 7H), 3.12-3.05 (m, 1H), 2.39-2.27 (m, 2H), 1.93-1.83 (m, 2H), 1.21 (s, 6H).

Example 153

Synthesis of (2S,5S)-5-(4-chlorobenzyl)-2-methyl-4-(1-(6-(trifluoromethyl)pyrazin-2-yl)piperidin-4-yl)morpholine hydrochloride (153)

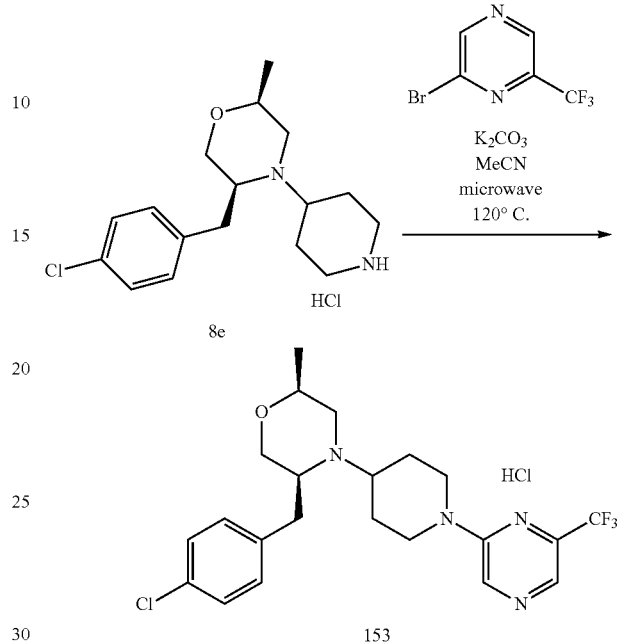

The title compound (153) was obtained as a hydrochloride salt from 8e (110 mg; 0.32 mmol) according to the General Procedure XXV in 84% yield (132 mg; 0.269 mmol).

ESI-MS m/z for $C_{22}H_{27}ClF_3N_4O$ found 455.1/457.1 [M+H]$^+$; $^1$H NMR (700 MHz, DMSO-$d_6$+$D_2O$, 348 K) δ 8.63-8.59 (m, 1H), 8.23-8.20 (m, 1H), 7.43-7.37 (m, 2H), 7.36-7.30 (m, 2H), 4.59-4.47 (m, 2H), 3.94-3.86 (m, 1H), 3.83-3.70 (m, 3H), 3.65-3.56 (m, 1H), 3.49-3.45 (m, 1H), 3.22-3.11 (m, 2H), 3.10-3.01 (m, 3H), 2.35-2.24 (m, 2H), 1.77-1.64 (m, 2H), 1.24 (d, J=6.3 Hz, 3H).

Example 154

Synthesis of (2R,5S)-5-(4-chlorobenzyl)-N-methyl-4-(1-(pyridin-2-yl)piperidin-4-yl)morpholine-2-carboxamide hydrochloride (154)

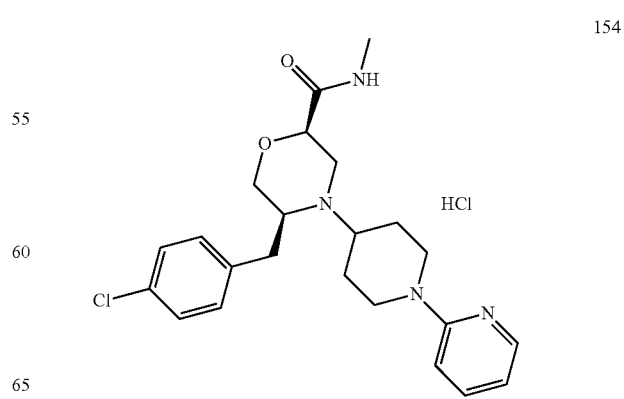

Step 1

Synthesis of tert-butyl (2R,5S)-5-(4-chlorobenzyl)-2-(methylcarbamoyl)morpholine-4-carboxylate (154a)

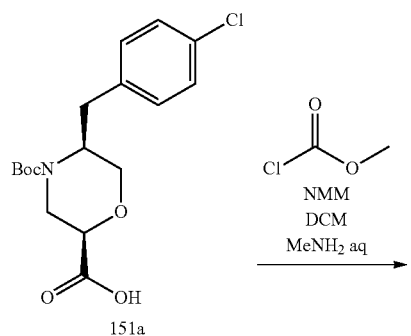

The title compound (154a) was obtained from 151a (570 mg; 1.6 mmol) according to the General Procedure XVI in 99% yield (582 mg; 1.58 mmol).

ESI-MS m/z for $C_{18}H_{25}ClN_2O_4Na$ found 391.7/393.7 $[M+Na]^+$

Step 2

Synthesis of (2R,5S)-5-(4-chlorobenzyl)-N-methyl-morpholine-2-carboxamide hydrochloride (154b)

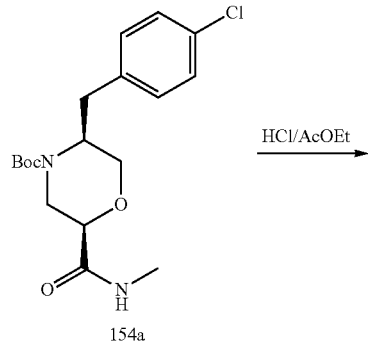

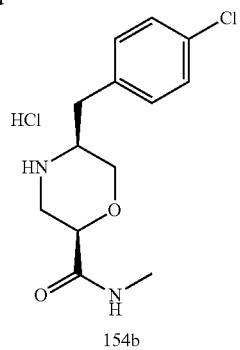

The title compound (154b) was obtained as a hydrochloride salt from 154a (582 mg; 1.58 mmol) according to the General Procedure IVa in 65% yield (310 mg; 1.02 mmol).

ESI-MS m/z for $C_{13}H_{18}ClN_2O_2$ found 268.9/270.9 $[M+H]^+$

Step 3

Synthesis of (2R,5S)-5-(4-chlorobenzyl)-N-methyl-4-(1-(pyridin-2-yl)piperidin-4-yl)morpholine-2-carboxamide hydrochloride (154)

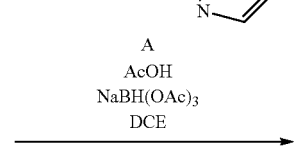

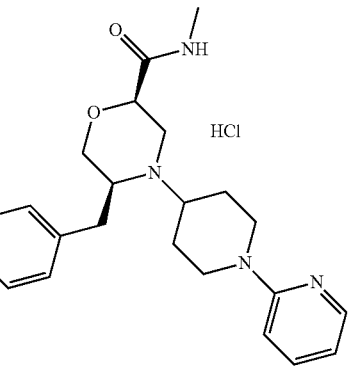

The title compound (154) was obtained as a hydrochloride salt from compound 154b (240 mg; 0.79 mmol) according to the General Procedure VI in 80% yield (293 mg; 0.63 mmol).

ESI-MS m/z for $C_{23}H_{30}ClN_4O_2$ found 429.1/431.1 $[M+H]^+$; $^1H$ NMR (700 MHz, DMSO-$d_6$+$D_2O$, 348 K) δ 8.06-8.03 (m, 1H), 7.86-7.81 (m, 1H), 7.42-7.39 (m, 2H), 7.39-7.35 (m, 2H), 7.20-7.14 (m, 1H), 6.88-6.81 (m, 1H), 4.39-4.27 (m, 3H), 3.84-3.78 (m, 1H), 3.74-3.65 (m, 3H), 3.56-3.46 (m, 1H), 3.28-3.22 (m, 1H), 3.17-3.08 (m, 4H), 2.70 (s, 3H), 2.29-2.17 (m, 2H), 1.81-1.66 (m, 2H).

Example 155

Synthesis of (7S,9aR)-7-(4-chlorobenzyl)-8-(1-(pyridin-2-yl)piperidin-4-yl)octahydropyrazino[2,1-c][1,4]oxazine hydrochloride (155)

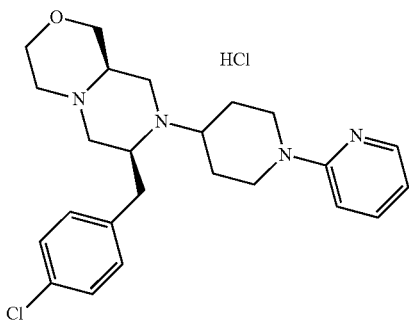

155

Step 1

Synthesis of methyl (S)-4-((R)-2-((tert-butoxycarbonyl)amino)-3-(4-chlorophenyl)propanoyl)morpholine-3-carboxylate_(155a)

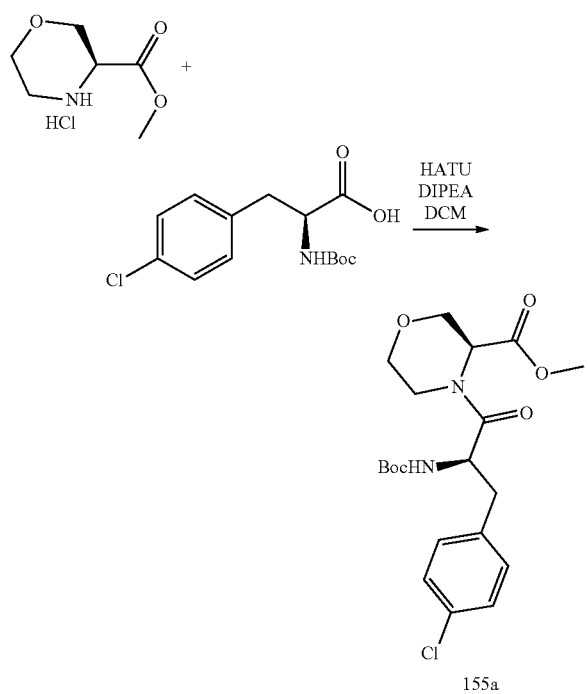

The title compound (155a) was obtained from a methyl (S)-morpholine-3-carboxylate hydrochloride (1.6 g; 8.81 mmol) and Boc-4-chloro-L-phenylalanine (2.64 g; 8.81 mmol) according to the General Procedure III in 77% yield (2.9 g; 6.81 mmol).

ESI-MS m/z for $C_{20}H_{28}ClN_2O_6$ found 427.2/429.2 [M+H]$^+$; $^1$H NMR (250 MHz, CDCl$_3$) δ 7.29-7.22 (m, 2H), 7.20-7.02 (m, 2H), 5.32-5.22 (m, 1H), 5.12-5.07 (m, 1H), 4.94-4.83 (m, 1H), 4.49-4.37 (m, 1H), 4.25-3.99 (m, 1H), 3.90-3.81 (m, 1H), 3.81-3.71 (m, 3H), 3.72-3.48 (m, 2H), 3.20-3.06 (m, 1H), 2.93-2.77 (m, 1H), 1.39 (s, 9H).

Step 2

Synthesis of methyl (S)-4-((R)-2-amino-3-(4-chlorophenyl)propanoyl)morpholine-3-carboxylate hydrochloride (155b)

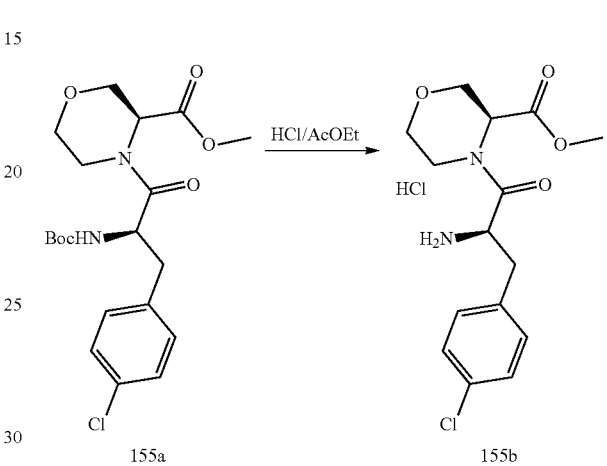

The title compound (155b) was obtained as a hydrochloride salt from 155a (2.9 g; 6.81 mmol) according to the General Procedure IVa in 99% yield (2.44 g; 6.74 mmol).

ESI-MS m/z for $C_{15}H_{20}ClN_2O_4$ found 326.8/328.8 [M+H]$^+$

Step 3

Synthesis of (7S,9aS)-7-(4-chlorobenzyl)hexahydropyrazino[2,1-c][1,4]oxazine-6,9-dione (155c)

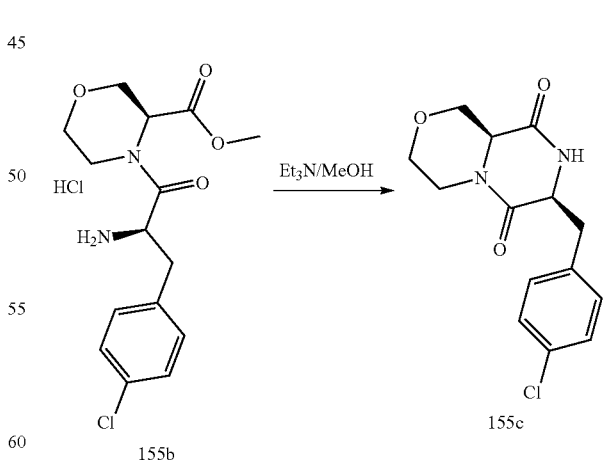

To a solution of crude 155b (2.44 g; 6.74 mmol) in MeOH (70 mL) Et$_3$N (4.8 mL; 33.96 mmol) was added and the mixture was stirred at room temperature for 2 hours. LC-MS showed completion of the reaction. The mixture was concentrated and the yellow oily residue was purified by flash column chromatography on silica (DCM/MeOH, 100:1 to 10:1, v/v). Compound 155c was obtained as a light yellow foam in 59% yield (1.18 g; 4.01 mmol).

ESI-MS m/z for $C_{14}H_{16}ClN_2O_3$ found 295.1/297.1 [M+H]$^+$

Step 4

Synthesis of (7S,9aR)-7-(4-chlorobenzyl)octahydro-pyrazino[2,1-c][1,4]oxazine (155d)

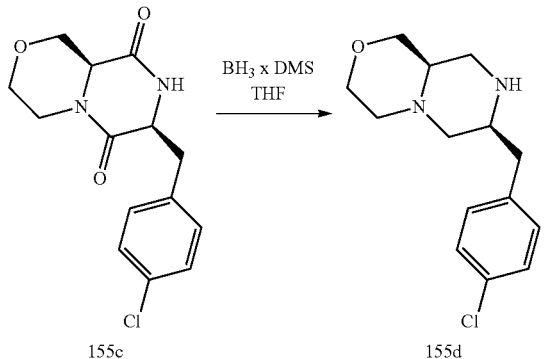 [SMILES: O=C1N[C@@H](Cc2ccc(Cl)cc2)C(=O)N2CCOC[C@@H]12 ; Clc1ccc(C[C@H]2CN3CCOC[C@H]3CN2)cc1]

The title compound (155d) was obtained as a white solid from 155c (1.1 g; 3.73 mmol) according to the General Procedure Ib in 96% yield (950 mg; 3.57 mmol).

ESI-MS m/z for $C_{14}H_{20}ClN_2O$ found 267.1/269.1 [M+H]$^+$

Step 5

Synthesis of (7S,9aR)-7-(4-chlorobenzyl)-8-(1-(pyridin-2-yl)piperidin-4-yl)octahydropyrazino[2,1-c][1,4]oxazine hydrochloride (155)

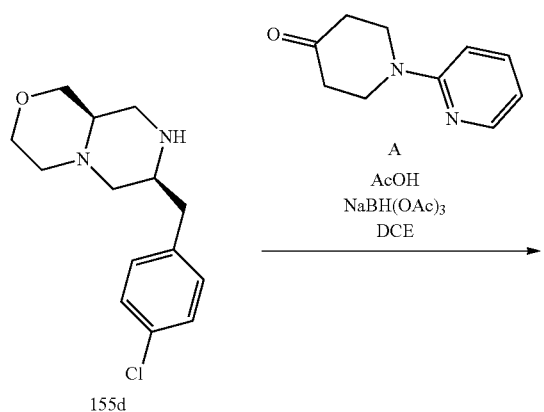

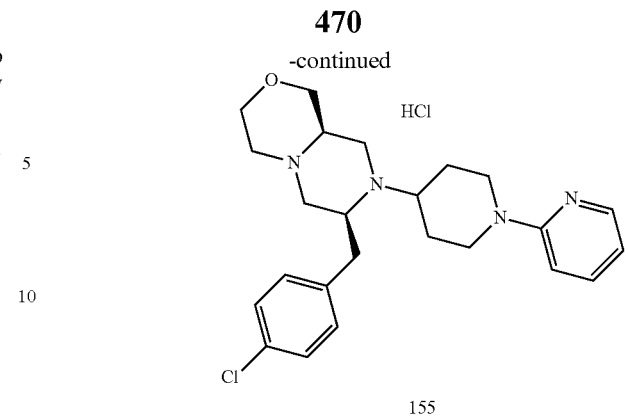

The title compound (155) was obtained as a hydrochloride salt from 155d (150 mg; 0.56 mmol) according to the General Procedure VI in 36% yield (92 mg; 0.2 mmol).

ESI-MS m/z for $C_{24}H_{32}ClN_4O$ found 427.1/429.1 [M+H]$^+$; $^1$H NMR (250 MHz, DMSO-d$_6$+D$_2$O, 348 K) δ 8.03-7.95 (m, 1H), 7.95-7.83 (m, 1H), 7.45-7.29 (m, 4H), 7.29-7.15 (m, 1H), 6.97-6.78 (m, 1H), 4.29-4.12 (m, 2H), 3.86-3.68 (m, 4H), 3.42-3.09 (m, 8H), 2.99-2.83 (m, 1H), 2.80-2.62 (m, 4H), 2.25-2.10 (m, 2H), 1.80-1.58 (m, 2H).

Example 156

Synthesis of (2S,5S)-4-(1-(2-bromopyridin-4-yl)piperidin-4-yl)-5-(4-chlorobenzyl)-2-methylmorpholine hydrochloride (156)

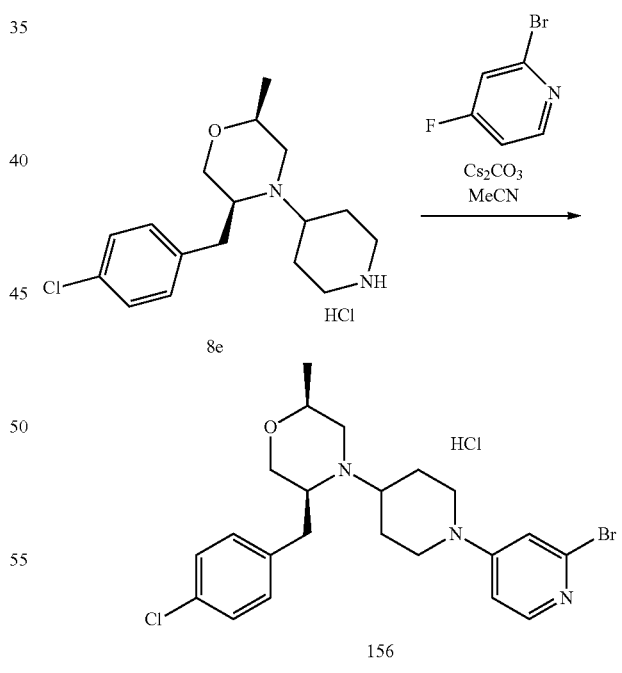

The title compound (156) was obtained as a hydrochloride salt from 8e (110 mg; 0.32 mmol) according to the General Procedure XXIV in 59% yield (96 mg; 0.19 mmol).

ESI-MS m/z for $C_{22}H_{28}BrClN_3$ found 464.0/466.0 [M+H]$^+$; $^1$H NMR (250 MHz, DMSO-d$_6$+D$_2$O, 348 K) δ 8.01-7.92 (m, 1H), 7.46-7.38 (m, 2H), 7.36-7.30 (m, 2H), 7.16-7.09 (m, 1H), 6.98-6.89 (m, 1H), 4.21-4.10 (m, 2H), 3.97-3.84 (m, 1H), 3.81-3.68 (m, 3H), 3.65-3.54 (m, 1H), 3.52-3.46 (m, 1H), 3.24-3.10 (m, 2H), 3.10-3.01 (m, 3H), 2.31-2.21 (m, 2H), 1.79-1.64 (m, 2H), 1.24 (d, J=6.3 Hz, 3H).

Example 157

Synthesis of (2S,5S)-5-(4-chlorobenzyl)-4-(1-(imidazo[1,2-a]pyridin-5-yl)piperidin-4-yl)-2-methyl-morpholine hydrochloride (157)

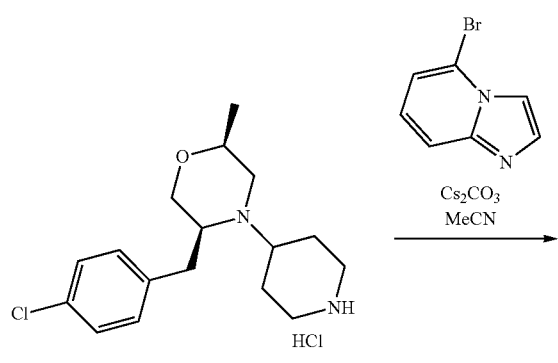

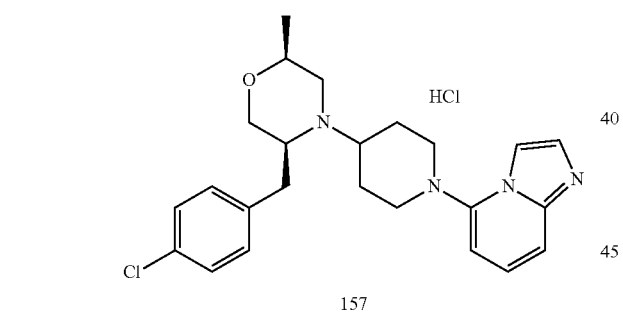

The title compound (157) was obtained as a hydrochloride salt from 8e (110 mg; 0.32 mmol) according to the General Procedure XXIV in 38% yield (57 mg; 0.12 mmol).

ESI-MS m/z for $C_{24}H_{30}ClN_4O$ found 425.1/427.1 [M+H]$^+$; $^1$H NMR (400 MHz, Methanol-d$_4$) δ 8.19-8.08 (m, 2H), 8.04-7.92 (m, 1H), 7.70-7.61 (m, 1H), 7.41-7.29 (m, 4H), 7.14-7.05 (m, 1H), 4.17-3.96 (m, 2H), 3.97-3.61 (m, 7H), 3.29-3.00 (m, 4H), 2.59-2.46 (m, 2H), 2.31-2.15 (m, 2H), 1.35 (d, J=6.3 Hz, 3H).

Example 158

Synthesis of (2S,5S)-5-(4-chlorobenzyl)-2-methyl-4-(1-(5-(trifluoromethyl)pyrazin-2-yl)piperidin-4-yl)morpholine hydrochloride (158)

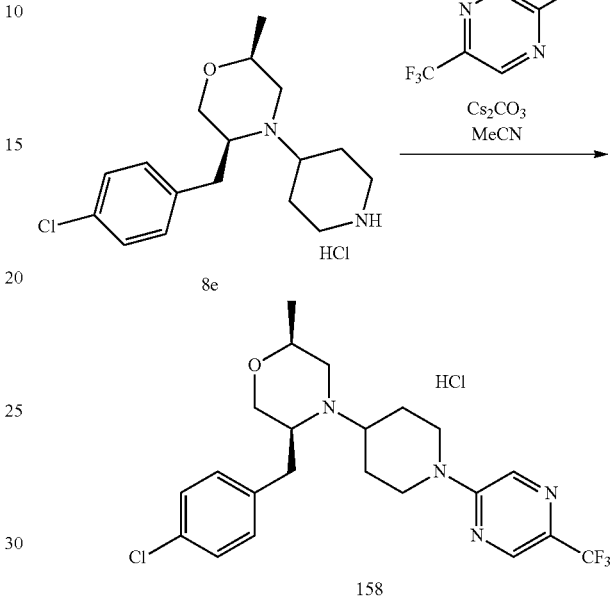

The title compound (158) was obtained as a hydrochloride salt from 8e (110 mg; 0.32 mmol) according to the General Procedure XXIV in 31% yield (50 mg; 0.1 mmol).

ESI-MS m/z for $C_{22}H_{27}ClF_3N_4O$ found 455.1/457.1 [M+H]$^+$; $^1$H NMR (250 MHz, DMSO-d$_6$+D$_2$O, 348 K) δ 8.52-8.35 (m, 2H), 7.44-7.28 (m, 4H), 4.71-4.48 (m, 2H), 3.93-3.48 (m, 6H), 3.30-2.98 (m, 5H), 2.41-2.20 (m, 2H), 1.78-1.45 (m, 2H), 1.23 (d, J=6.2 Hz, 3H).

Example 159

Synthesis of (2S,5S)-5-(4-chlorobenzyl)-2-methyl-4-(4-(pyridin-2-yl)phenyl)morpholine hydrochloride (159)

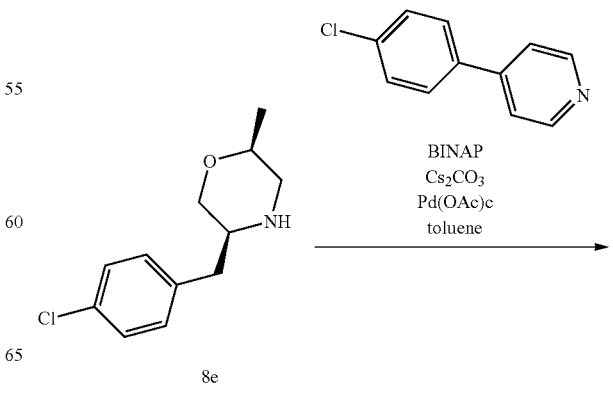

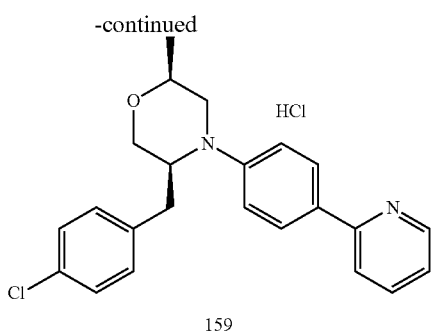

159

The title compound (159) was obtained as a hydrochloride salt from 8c (178 mg; 0.79 mmol) according to the General Procedure XXIII in 23% yield (75 mg; 0.18 mmol).

ESI-MS m/z for $C_{23}H_{24}ClN_2O$ found 379.0/381.0 [M+H]$^+$; $^1$H NMR (700 MHz, DMSO-d$_6$+D$_2$O, 348 K) δ 8.62-8.55 (m, 1H), 8.30-8.20 (m, 1H), 8.15-8.06 (m, 1H), 7.95-7.83 (m, 2H), 7.66-7.55 (m, 1H), 7.34-7.27 (m, 2H), 7.27-7.23 (m, 2H), 7.10-7.01 (m, 2H), 4.11-4.03 (m, 1H), 3.74-3.69 (m, 1H), 3.68-3.62 (m, 2H), 3.62-3.56 (m, 1H), 3.01 (dd, J=13.6, 9.4 Hz, 1H), 2.93 (dd, J=12.7, 10.8 Hz, 1H), 2.72 (dd, J=13.5, 5.4 Hz, 1H), 1.26 (d, J=6.2 Hz, 3H).

Example 160

Synthesis of 2-(4-((2S,5S)-5-(4-chlorobenzyl)-2-methylmorpholino)piperidin-1-yl)pyridin-3-ol 2,2,2-trifluoroacetate (160)

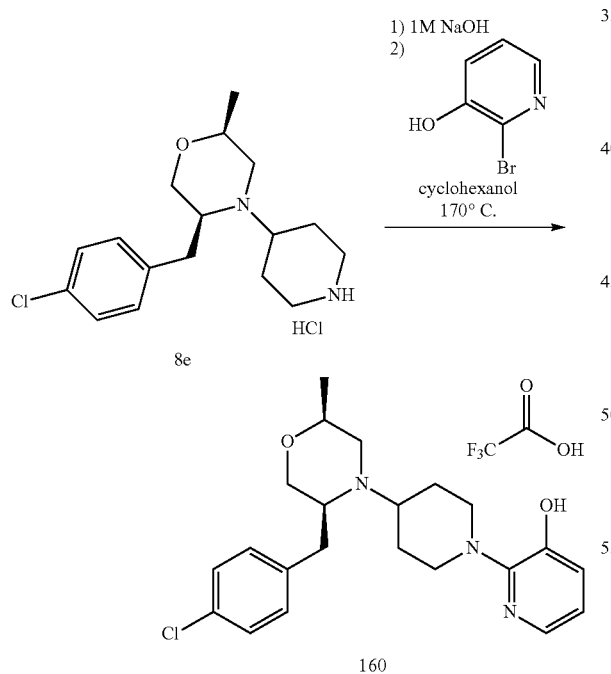

Hydrochloride salt 8e (110 mg; 0.32 mmol) was dissolved in AcOEt and 1M NaOH was added to this solution. Phases were separated and an organic one was washed with brine, dried over anhydrous MgSO$_4$ and concentrated in vacuo to give a free amine (100 mg; 0.32 mmol) which was dissolved in cyclohexanol (1.5 mL) and to this solution 2-bromopyri-din-3-ol (112 mg; 0.64 mmol) was added and the resulting mixture was stirred at 170° C. for 2 days. LC-MS indicated completion of the reaction. The mixture was diluted with DCM and the crude product was purified by flash column chromatography on silica (DCM/MeOH, 100:1 to 20:1, v/v) and then by preparative reversed-phase column chromatography (Luna® 5 μm Phenyl-Hexyl, LC Column 250×21.2 mm, water/MeCN+1% TFA, 95:5 to 40:60, 30 minutes). Compound 160 was obtained as a TFA salt in 25% yield (41 mg; 0.08 mmol).

ESI-MS m/z for $C_{22}H_{29}ClN_3O_2$ found 402.0/404.0 [M+H]$^+$; $^1$H NMR (700 MHz, DMSO-d$_6$+D$_2$O, 348 K) δ 7.66-7.63 (m, 1H), 7.39-7.35 (m, 2H), 7.33-7.29 (m, 2H), 7.21-7.17 (m, 1H), 6.87-6.83 (m, 1H), 4.24-4.11 (m, 2H), 3.87-3.79 (m, 1H), 3.73-3.61 (m, 3H), 3.58-3.52 (m, 1H), 3.49-3.43 (m, 1H), 3.20-3.08 (m, 2H), 3.05-2.97 (m, 1H), 2.95-2.85 (m, 2H), 2.27-2.16 (m, 2H), 1.81-1.67 (m, 2H), 1.22 (d, J=6.2 Hz, 3H).

Example 161

Synthesis of 2-(4-((2S,5S)-5-(4-chlorobenzyl)-2-methylmorpholino)piperidin-1-yl)pyridin-4-ol 2,2,2-trifluoroacetate (161)

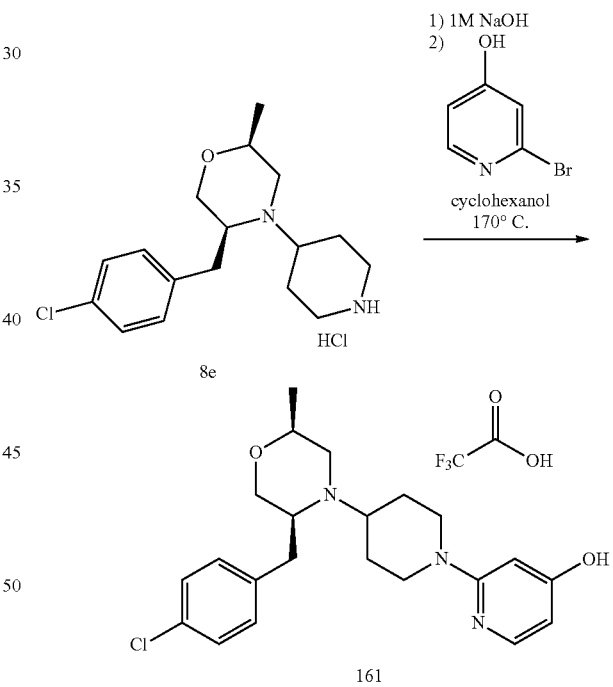

Hydrochloride salt 8e (110 mg; 0.32 mmol) was dissolved in AcOEt and 1M NaOH was added to this solution. Phases were separated and an organic one was washed with brine, dried over anhydrous MgSO$_4$ and concentrated in vacuo to give a free amine (100 mg; 0.32 mmol) which was dissolved in cyclohexanol (1.5 mL) and to this solution 2-bromo-4-hydroxypyridine (112 mg; 0.64 mmol) was added and the resulting mixture was stirred at 170° C. for 2 days. LC-MS indicated completion of the reaction. The mixture was diluted with DCM and the crude product was purified by flash column chromatography on silica (DCM/MeOH, 100:1 to 10:1, v/v) and then by preparative reversed-phase column chromatography (Luna® 5 µm Phenyl-Hexyl, LC Column 250×21.2 mm, water/MeCN+1% TFA, 95:5 to 40:60, 30 minutes). Compound 161 was obtained as a TFA salt in 44% yield (70 mg; 0.14 mmol).

ESI-MS m/z for $C_{22}H_{29}ClN_3O_2$ found 402.1/404.1 [M+H]$^+$; $^1$H NMR (700 MHz, DMSO-d$_6$+D$_2$O, 348 K) δ 7.84-7.79 (m, 1H), 7.40-7.36 (m, 2H), 7.33-7.28 (m, 2H), 6.54-6.51 (m, 1H), 6.47-6.42 (m, 1H), 4.12-3.99 (m, 2H), 3.85-3.77 (m, 1H), 3.75-3.63 (m, 3H), 3.57 (d, J=12.2 Hz, 1H), 3.42-3.32 (m, 1H), 3.23-3.06 (m, 4H), 3.03-2.95 (m, 1H), 2.32-2.20 (m, 2H), 1.75-1.61 (m, 2H), 1.21 (d, J=6.2 Hz, 3H).

Example 162

Synthesis of (2S,5S)-5-(4-chlorobenzyl)-4-(1-(3-methoxypyridin-2-yl)piperidin-4-yl)-2-methylmorpholine 2,2,2-trifluoroacetate (162)

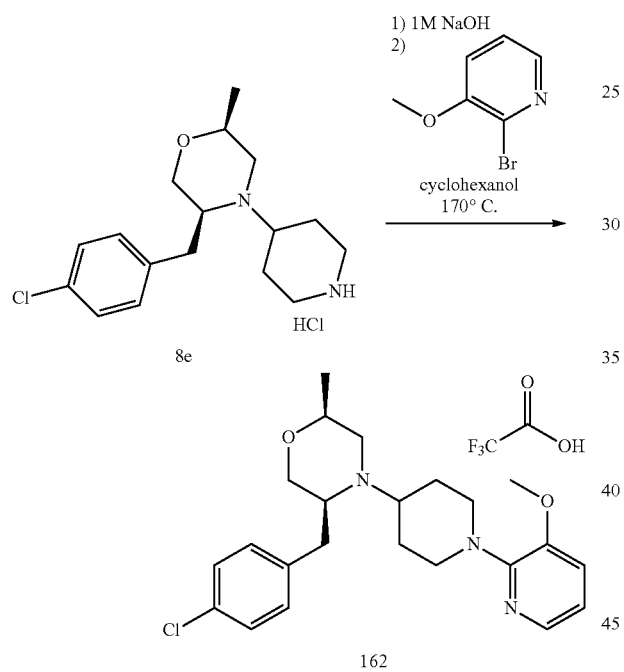

Hydrochloride salt 8e (110 mg; 0.32 mmol) was dissolved in AcOEt and 1M NaOH was added to this solution. Phases were separated and an organic one was washed with brine, dried over anhydrous MgSO$_4$ and concentrated in vacuo to give a free amine (100 mg; 0.32 mmol) which was dissolved in cyclohexanol (1.5 mL) and to this solution 2-bromo-3-methoxypyridine (122 mg; 0.64 mmol) was added and the resulting mixture was stirred at 170° C. for 2 days. LC-MS indicated completion of the reaction. The mixture was diluted with DCM and the crude product was purified by flash column chromatography on silica (DCM/MeOH, 100:1 to 50:1, v/v) and then by preparative reversed-phase column chromatography (Luna® 5 µm Phenyl-Hexyl, LC Column 250×21.2 mm, water/MeCN+10% TFA, 95:5 to 40:60, 30 minutes). Compound 162 was obtained as a white solid as a TFA salt in 9% yield (15 mg; 0.028 mmol).

ESI-MS m/z for $C_{23}H_{31}ClN_3O_2$ found 416.2/418.2 [M+H]$^+$; $^1$H NMR (700 MHz, DMSO-d$_6$+D$_2$O, 348 K) δ 7.76-7.73 (m, 1H), 7.39-7.35 (m, 2H), 7.33-7.29 (m, 2H), 7.28-7.25 (m, 1H), 6.91-6.87 (m, 1H), 4.16-4.08 (m, 2H), 3.87-3.77 (m, 4H), 3.73-3.54 (m, 4H), 3.48-3.43 (m, 1H), 3.20-3.07 (m, 2H), 3.05-2.97 (m, 1H), 2.87-2.79 (m, 2H), 2.24-2.14 (m, 2H), 1.79-1.66 (m, 2H), 1.21 (d, J=6.2 Hz, 3H).

Example 163

Synthesis of (2S,5S)-5-(4-chlorobenzyl)-4-(1-(5-isopropyl-1,2,4-oxadiazol-3-yl)piperidin-4-yl)-2-methylmorpholine 2,2,2-trifluoroacetate (163)

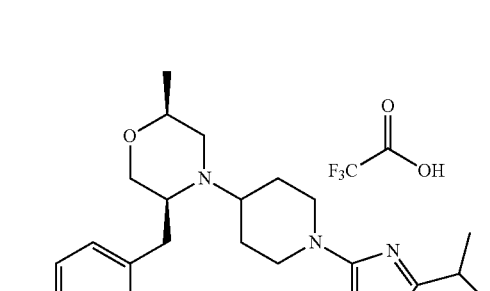

Step 1

Synthesis of 4-((2S,5S)-5-(4-chlorobenzyl)-2-methylmorpholino)piperidine-1-carbonitrile (163a)

The compound 8e (2.27 g; 6.57 mmol) was transferred to a free base after basic (4M NaOH) extraction with DCM. Then the crude product (2 g; 6.5 mmol) was dissolved in EtOH (20 mL) and this mixture was cooled to 5° C. and BrCN (690 mg; 6.5 mmol) and NaHCO$_3$ (1.64 g; 19.5 mmol) were added in one portion and stirred at this temperature for 15 minutes. Then cooling bath was removed and stirred at room temperature overnight. The reaction progress was monitored by LC-MS. When analysis indicated completion of the reaction, the mixture was diluted with DCM and filtered off. The filtrate was concentrated in vacuo and the residue was purified by flash column chromatography on silica (DCM/MeOH, 100:0 to 100:1, v/v). Compound 163a was obtained as a white solid in 84% yield (1.82 g; 5.46 mmol).

ESI-MS m/z for $C_{18}H_{25}ClN_3O$ found 334.2/336.2 $[M+H]^+$; $^1H$ NMR (700 MHz, $CDCl_3$) δ 7.31-7.20 (m, 2H), 7.13-7.05 (m, 2H), 3.69-3.58 (m, 2H), 3.56-3.44 (m, 3H), 3.12-2.97 (m, 3H), 2.87-2.78 (m, 1H), 2.73-2.59 (m, 3H), 2.41-2.29 (m, 1H), 2.01-1.91 (m, 2H), 1.71-1.58 (m, 2H), 1.20 (d, J=6.2 Hz, 3H).

Step 2

Synthesis of 4-((2S,5S)-5-(4-chlorobenzyl)-2-methylmorpholino)-N-hydroxypiperidine-1-carboximidamide (163b)

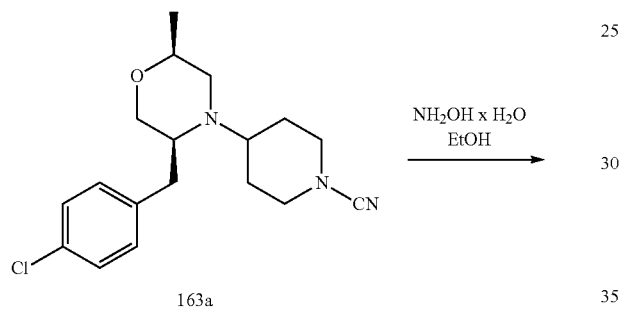

The compound 163a (850 mg; 2.55 mmol) was dissolved in EtOH (20 mL) and to this mixture $NH_2OH \times H_2O$ (50%; 0.35 ml; 50.09 mmol) was added and refluxed for 2 hours. The reaction progress was monitored by LC-MS. When analysis indicated completion of the reaction, the solvent was removed in vacuo and the crude product was used to the next step without any additional purification. Compound 163b was obtained as a light yellow oil in 99% yield (923 mg; 2.52 mmol).

ESI-MS m/z for $C_{18}H_{28}ClN_4O_2$ found 367.2/369.2 $[M+H]^+$; $^1H$ NMR (700 MHz, $CDCl_3$) δ 7.33-7.23 (m, 2H), 7.20-7.09 (m, 2H), 4.36 (bs, 1H), 3.70-3.57 (m, 4H), 3.53-3.44 (m, 1H), 3.05-2.95 (m, 1H), 2.95-2.87 (m, 1H), 2.81-2.66 (m, 4H), 2.64-2.56 (m, 1H), 2.39-2.29 (m, 1H), 2.05-1.90 (m, 2H), 1.60-1.43 (m, 2H), 1.22 (d, J=6.2 Hz, 3H).

Step 3

Synthesis of (2S,5S)-5-(4-chlorobenzyl)-4-(1-(5-isopropyl-1,2,4-oxadiazol-3-yl)piperidin-4-yl)-2-methylmorpholine 2,2,2-trifluoroacetate (163)

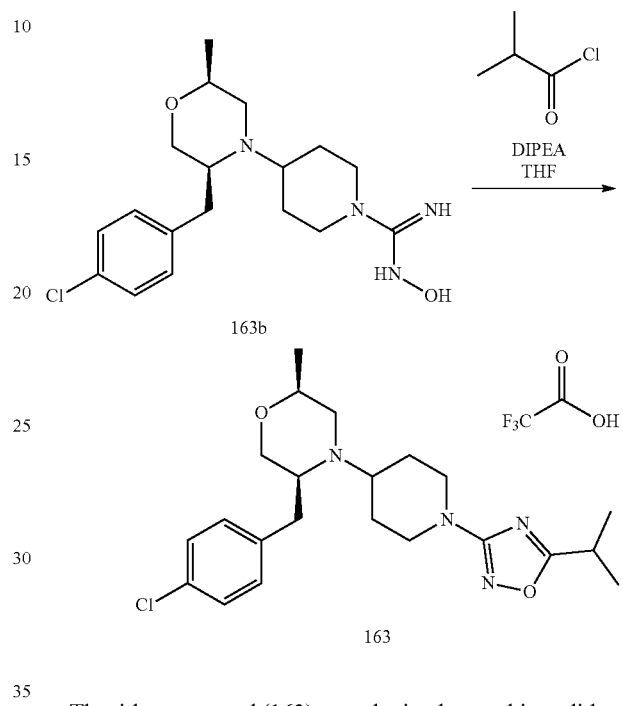

The title compound (163) was obtained as a white solid as a TFA salt from 163b (150 mg; 0.41 mmol) according to the General Procedure XVII in 37% yield (79 mg; 0.15 mmol).

ESI-MS m/z for $C_{22}H_{32}ClN_4O_2$ found 419.3/421.3 $[M+H]^+$; $^1H$ NMR (700 MHz, DMSO-$d_6$+$D_2O$, 348 K) δ 7.45-7.36 (m, 2H), 7.36-7.27 (m, 2H), 4.02-3.94 (m, 2H), 3.86-3.77 (m, 1H), 3.73-3.55 (m, 4H), 3.43-3.37 (m, 1H), 3.18-3.05 (m, 3H), 3.05-2.92 (m, 3H), 2.25-2.16 (m, 2H), 1.67-1.57 (m, 2H), 1.27 (d, J=7.0 Hz, 6H), 1.22 (d, J=6.3 Hz, 3H).

Example 164

Synthesis of (2S,5S)-5-(4-chlorobenzyl)-2-methyl-4-(1-(5-(trifluoromethyl)-1,2,4-oxadiazol-3-yl)piperidin-4-yl)morpholine 2,2,2-trifluoroacetate (164)

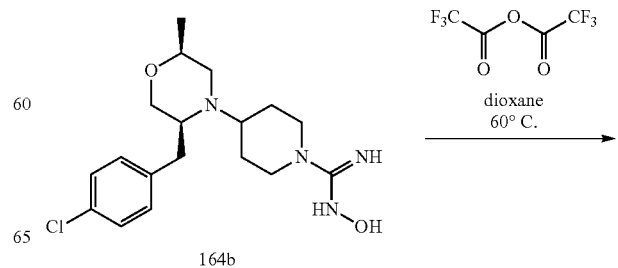

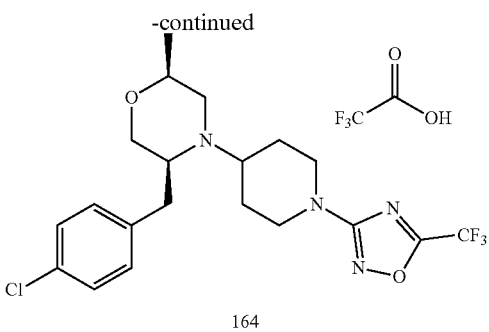

164

To the solution of 164b (150 mg; 0.41 mmol) in dioxane (2 mL) TFA anhydride (0.057 mL; 0.41 mmol) was added and the mixture was stirred at 60° C. overnight. The reaction progress was monitored by LC-MS. When analysis indicated completion of the reaction, the solvent was removed in vacuo and the residue was redissolved in MeCN/water and the crude product was purified by preparative reversed-phase column chromatography (Luna® 5 μm Phenyl-Hexyl, LC Column 250×21.2 mm, water/MeCN+1% TFA, 95:5 to 40:60, 30 minutes). Compound 164 was obtained as a white solid as a TFA salt in 51% yield (118 mg; 0.21 mmol).

ESI-MS m/z for $C_{20}H_{25}ClF_3N_4O_2$ found 445.2/447.2 [M+H]$^+$; $^1$H NMR (700 MHz, DMSO-d$_6$+D$_2$O, 348 K) δ 7.44-7.37 (m, 2H), 7.37-7.27 (m, 2H), 4.05-3.95 (m, 2H), 3.86-3.79 (m, 1H), 3.74-3.64 (m, 3H), 3.61-3.54 (m, 1H), 3.49-3.45 (m, 1H), 3.19-3.07 (m, 4H), 3.07-2.98 (m, 1H), 2.33-2.21 (m, 2H), 1.73-1.59 (m, 2H), 1.23 (d, J=6.2 Hz, 3H).

Example 165

Synthesis of 3-(4-((2S,5S)-5-(4-chlorobenzyl)-2-methylmorpholino)piperidin-1-yl)-1,2,4-oxadiazol-5 (4H)-one 2,2,2-trifluoroacetate (165)

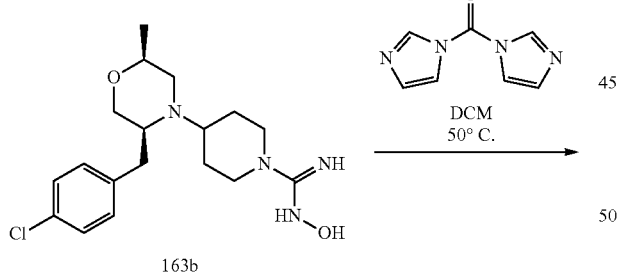

To the solution of 163b (150 mg; 0.41 mmol) in DCM (2 mL) carbonyldiimidazole (CDI; 66 mg; 0.41 mmol) was added and the mixture was stirred at 50° C. overnight. The reaction progress was monitored by LC-MS. When analysis indicated completion of the reaction, solvent was removed in vacuo and the residue was redissolved in MeCN/water and the crude product was purified by preparative reversed-phase column chromatography (Luna® 5 μm Phenyl-Hexyl, LC Column 250×21.2 mm, water/MeCN+1% TFA, 95:5 to 40:60, 30 minutes). Compound 165 was obtained as a white solid as a TFA salt in 56% yield (116 mg; 0.23 mmol).

ESI-MS m/z for $C_{19}H_{26}ClN_4O_3$ found 393.1/395.1 [M+H]$^+$; $^1$H NMR (700 MHz, DMSO-d$_6$+D$_2$O, 348 K) δ 7.40-7.37 (m, 2H), 7.33-7.29 (m, 2H), 3.89-3.79 (m, 1H), 3.74-3.55 (m, 6H), 3.43-3.39 (m, 1H), 3.19-3.11 (m, 1H), 3.11-3.05 (m, 1H), 3.02-2.92 (m, 3H), 2.26-2.14 (m, 2H), 1.70-1.59 (m, 2H), 1.22 (d, J=6.2 Hz, 3H).

Example 166

Synthesis of (2S,5S)-4-(1-(1H-tetrazol-5-yl)piperidin-4-yl)-5-(4-chlorobenzyl)-2-methylmorpholine 2,2,2-trifluoroacetate (166)

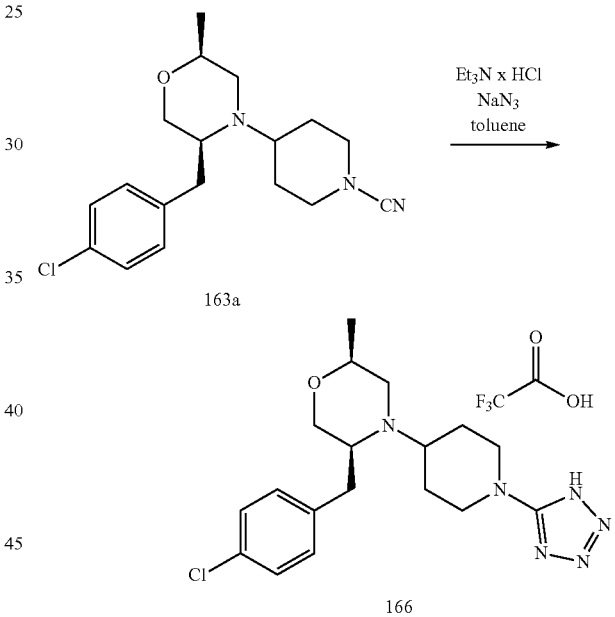

The solution of 163a (120 mg; 0.36 mmol), Et$_3$N hydrochloride (99 mg; 0.72 mmol), NaN$_3$ (47 mg; 0.72 mmol) in a dry toluene (2 mL) was refluxed overnight. The reaction progress was monitored by LC-MS. When analysis indicated completion of the reaction, the mixture was diluted with DCM and filtered off, the filtrate was concentrated in vacuo and the residue was purified by preparative reversed-phase column chromatography (Luna® 5 μm Phenyl-Hexyl, LC Column 250×21.2 mm, water/MeCN+1% TFA, 95:5 to 40:60, 30 minutes). Compound 166 was obtained as a white solid as a TFA salt in 64% yield (111 mg; 0.23 mmol).

ESI-MS m/z for $C_{18}H_{26}ClN_6O$ found 377.2/379.2 [M+H]$^+$; $^1$H NMR (700 MHz, DMSO-d$_6$+D$_2$O, 348 K) δ 7.41-7.38 (m, 2H), 7.34-7.31 (m, 2H), 4.01-3.95 (m, 2H), 3.86-3.79 (m, 1H), 3.73-3.64 (m, 3H), 3.60-3.56 (m, 1H), 3.51-3.46 (m, 1H), 3.20-3.07 (m, 4H), 3.04-2.98 (m, 1H), 2.31-2.17 (m, 2H), 1.69-1.60 (m, 2H), 1.23 (d, J=6.2 Hz, 3H).

Example 167

Synthesis of 6-(4-((2S,5S)-5-(4-chlorobenzyl)-2-methylmorpholino)piperidin-1-yl)pyrimidin-4(3H)-one 2,2,2-trifluoroacetate (167)

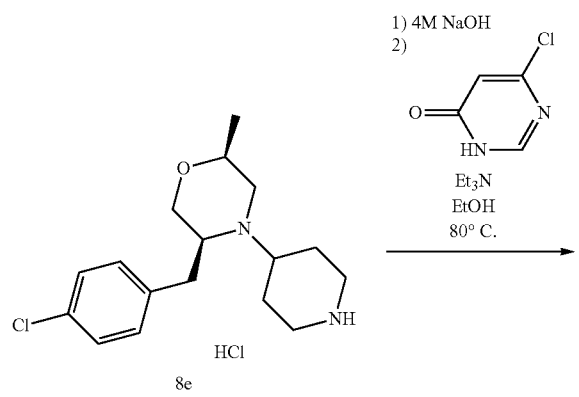

The compound 8e (169 mg; 0.49 mmol) was transferred to a free base after basic (4M NaOH) extraction with DCM. Then the crude product (151 mg; 0.49 mmol) was dissolved in EtOH (2 mL) and to this mixture 6-chloropyrimidin-4(3H)-one (64 mg; 0.49 mmol) and Et$_3$N (0.1 mL; 0.74 mmol) were added and stirred at 80° C. overnight. The reaction progress was monitored by LC-MS. When analysis indicated completion of the reaction, EtOH was removed in vacuo and the residue was redissolved in MeOH/water and the crude product was purified by preparative reversed-phase column chromatography (Luna® 5 µm Phenyl-Hexyl, LC Column 250×21.2 mm, water/MeCN+1% TFA, 95:5 to 40:60, 30 minutes). Compound 167 was obtained as a white solid as a TFA salt in 71% yield (182 mg; 0.35 mmol).

ESI-MS m/z for $C_{21}H_{28}ClN_4O_2$ found 402.9/404.9 [M+H]$^+$; $^1$H NMR (700 MHz, DMSO-d$_6$+D$_2$O, 348 K) δ 7.96-7.87 (m, 1H), 7.44-7.36 (m, 2H), 7.36-7.29 (m, 2H), 4.38-4.30 (m, 2H), 3.88-3.79 (m, 1H), 3.79-3.65 (m, 3H), 3.64-3.54 (m, 1H), 3.54-3.48 (m, 1H), 3.25-3.09 (m, 2H), 3.07-2.99 (m, 1H), 2.99-2.87 (m, 2H), 2.30-2.16 (m, 2H), 1.61-1.45 (m, 2H), 1.23 (d, J=6.2 Hz, 3H).

Example 168

Synthesis of (2S,5S)-5-(4-chlorobenzyl)-2-methyl-4-(1-(5-(trifluoromethyl)oxazol-2-yl)piperidin-4-yl)morpholine 2,2,2-trifluoroacetate (168)

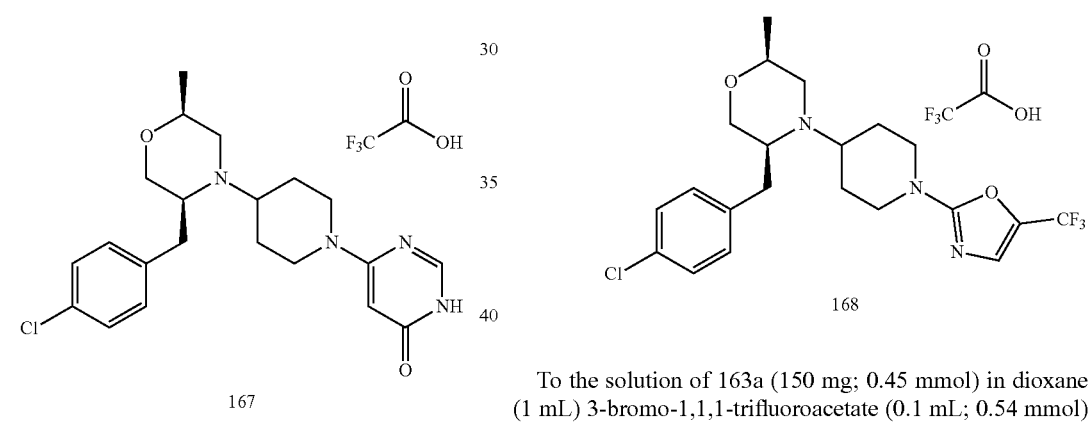

To the solution of 163a (150 mg; 0.45 mmol) in dioxane (1 mL) 3-bromo-1,1,1-trifluoroacetate (0.1 mL; 0.54 mmol) was added and the mixture was refluxed for 3 hours. After this time another part of 3-bromo-1,1,1-trifluoroacetate (0.1 mL; 0.54 mmol) and K$_2$CO$_3$ (100 mg; 0.72 mmol) were added and refluxed overnight. To this mixture xylene (1 mL) and 3-bromo-1,1,1-trifluoroacetate (0.3 mL; 1.62 mmol) were added and stirred at 130° C. overnight. The reaction progress was monitored by LC-MS. When analysis indicated completion of the reaction, the mixture was diluted with DCM (+5 drops of MeOH) and filtered off. The filtrate was concentrated in vacuo and the residue was purified by flash column chromatography on silica (DCM/MeOH, 100:0 to 50:1, v/v) and then by preparative reversed-phase column chromatography (Luna® 5 µm Phenyl-Hexyl, LC Column 250×21.2 mm, water/MeCN+1% TFA, 95:5 to 40:60, 30 minutes). Compound 168 was obtained as a white solid as a TFA salt in 13% yield (32 mg; 0.057 mmol).

ESI-MS m/z for $C_{21}H_{26}ClF_3N_3O_2$ found 443.9/445.9 [M+H]$^+$; $^1$H NMR (700 MHz, DMSO-d$_6$+D$_2$O, 348 K) δ 8.19-8.12 (m, 1H), 7.41-7.36 (m, 2H), 7.34-7.27 (m, 2H), 4.11-4.03 (m, 2H), 3.89-3.76 (m, 1H), 3.70-3.61 (m, 3H), 3.58-3.51 (m, 1H), 3.46-3.43 (m, 1H), 3.23-3.05 (m, 4H), 3.06-2.93 (m, 1H), 2.31-2.17 (m, 2H), 1.71-1.55 (m, 2H), 1.23 (d, J=6.2 Hz, 3H).

Example 169

Synthesis of (2S,5S)-4-(1-(4-chloro-1,3,5-triazin-2-yl)piperidin-4-yl)-5-(4-chlorobenzyl)-2-methylmorpholine 2,2,2-trifluoroacetate (169)

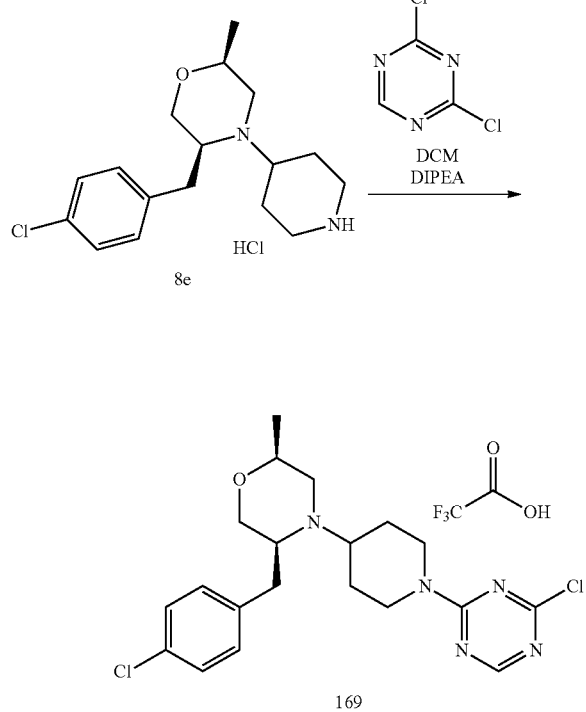

To the solution of 8e (559 mg; 1.62 mmol) in DCM (8.1 mL) at 0° C. 2,4-dichloro-1,3,5-triazine (242 mg; 1.62 mmol) and DIPEA (0.28 mL; 1.62 mmol) were added and the mixture was stirred for 1 hour at 0° C. The reaction progress was monitored by LC-MS. When analysis indicated completion of the reaction, the solvent was removed in vacuo and the residue was purified by flash column chromatography on silica (hexane/AcOEt, 10:1 to 1:1, v/v) and then by preparative reversed-phase column chromatography (Luna® 5 μm Phenyl-Hexyl, LC Column 250×21.2 mm, water/MeCN+1% TFA, 95:5 to 40:60, 30 minutes). Compound 169 was obtained as a white solid as a TFA salt in 67% yield (577 mg; 1.08 mmol).

ESI-MS m/z for $C_{20}H_{26}Cl_2N_5O$ found 422.0/424.0 [M+H]$^+$; $^1$H NMR (700 MHz, DMSO-d$_6$+D$_2$O, 348 K) δ 8.40-8.37 (m, 1H), 7.32-7.28 (m, 2H), 7.23-7.18 (m, 2H), 4.51-4.28 (m, 2H), 3.56-3.48 (m, 1H), 3.48-3.43 (m, 1H), 3.42-3.39 (m, 1H), 3.28-3.12 (m, 2H), 2.94-2.88 (m, 2H), 2.86-2.81 (m, 1H), 2.81-2.73 (m, 1H), 2.73-2.67 (m, 1H), 2.39-2.33 (m, 1H), 2.01-1.90 (m, 2H), 1.45-1.31 (m, 2H), 1.10 (d, J=6.2 Hz, 3H).

Example 170

Synthesis of 4-(4-((2S,5S)-5-(4-chlorobenzyl)-2-methylmoioperidin-1-yl)-1,3,5-triazin-2-ol 1,2,2,2-trifluoroacetate (170)

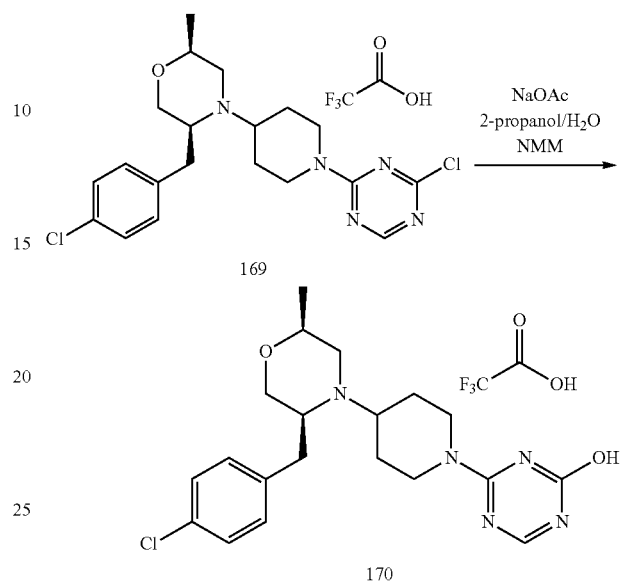

To the solution of 169 (113 mg; 0.21 mmol) and sodium acetate (35 mg; 0.43 mmol) in 2-propanol/water (0.4 mL/0.1 mL) NMM (0.025 mL; 0.23 mmol) was added and the mixture was stirred at room temperature overnight. The reaction progress was monitored by LC-MS. When analysis indicated completion of the reaction, the mixture was diluted with water and the crude product was purified by preparative reversed-phase column chromatography (Luna® 5 μm Phenyl-Hexyl, LC Column 250×21.2 mm, water/MeCN+1% TFA, 95:5 to 40:60, 30 minutes). Compound 170 was obtained as a TFA salt in 99% yield (109 mg; 0.21 mmol).

ESI-MS m/z for $C_{20}H_{27}ClN_5O_2$ found 404.0/406.0 [M+H]$^+$; $^1$H NMR (700 MHz, DMSO-d$_6$+D$_2$O, 348 K) δ 8.13-8.12 (m, 1H), 7.41-7.37 (m, 2H), 7.35-7.32 (m, 2H), 4.82-4.70 (m, 2H), 3.89-3.81 (m, 1H), 3.81-3.67 (m, 3H), 3.62-3.56 (m, 1H), 3.49-3.45 (m, 1H), 3.22-3.10 (m, 2H), 3.08-2.89 (m, 3H), 2.33-2.23 (m, 2H), 1.63-1.46 (m, 2H), 1.23 (d, J=6.2 Hz, 3H).

Example 171

Synthesis of (2S,5S)-5-(4-chlorobenzyl)-4-(1-(4-methoxy-1,3,5-triazin-2-yl)piperidin-4-yl)-2-methylmorpholine 2,2,2-trifluoroacetate (171)

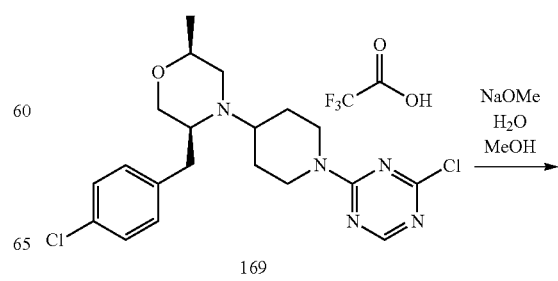

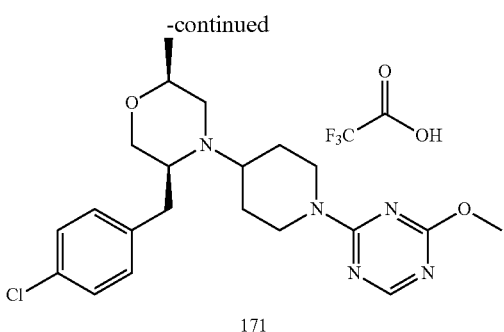

171

To the solution of 169 (113 mg; 0.21 mmol) in MeOH (1 mL) the solution of MeONa (46 mg; 0.82 mmol) in MeOH (0.5 mL) was added dropwise and the mixture was stirred at room temperature overnight. The reaction progress was monitored by LC-MS. When analysis indicated completion of the reaction, the mixture was diluted with water and the crude product was purified by preparative reversed-phase column chromatography (Luna® 5 μm Phenyl-Hexyl, LC Column 250×21.2 mm, water/MeCN+10% TFA, 95:5 to 40:60, 30 minutes). Compound 171 was obtained as a TFA salt in 99% yield (110 mg; 0.207 mmol).

ESI-MS m/z for $C_{21}H_{29}ClN_5O_2$ found 418.2/420.2 [M+H]$^+$; $^1$H NMR (700 MHz, DMSO-d$_6$+D$_2$O, 348 K) δ 8.37-8.35 (m, 1H), 7.42-7.38 (m, 2H), 7.35-7.31 (m, 2H), 4.82-4.73 (m, 2H), 3.89 (s, 3H), 3.87-3.82 (m, 1H), 3.80-3.65 (m, 3H), 3.62-3.56 (m, 1H), 3.51-3.47 (m, 1H), 3.24-3.08 (m, 2H), 3.09-2.94 (m, 3H), 2.33-2.22 (m, 2H), 1.64-1.47 (m, 2H), 1.23 (d, J=6.2 Hz, 3H).

Example 172

Synthesis of (2S,5S)-5-(4-chlorobenzyl)-2-methyl-4-(1-(4-methyl-1,3,5-triazin-2-yl)piperidin-4-yl)morpholine 2,2,2-trifluoroacetate (172)

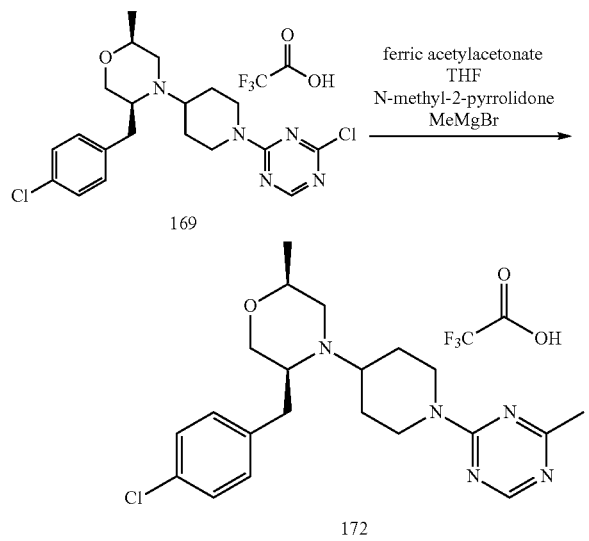

The solution of 169 (113 mg; 0.21 mmol) and ferric acetylacetonate (5.5 mg; 0.021 mmol) in THF (1 mL) and N-methyl-2-pyrrolidone (0.1 mL) under argon atmosphere was cooled to 0° C. and to this mixture MeMgBr (3M in THF; 0.28 mL; 0.84 mmol) was added dropwise and the mixture was stirred at room temperature overnight. The reaction progress was monitored by LC-MS. When analysis indicated completion of the reaction, the mixture was quenched by addition of saturated solution of NH$_4$Cl, then diluted with water/MeCN (1/1 v/v) and the crude product was purified by preparative reversed-phase column chromatography (Luna® 5 μm Phenyl-Hexyl, LC Column 250×21.2 mm, water/MeCN+1% TFA, 95:5 to 40:60, 30 minutes). Compound 172 was obtained as a white solid as a TFA salt in 38% yield (41 mg; 0.08 mmol).

ESI-MS m/z for $C_{21}H_{29}ClN_5O$ found 402.0/404.0 [M+H]$^+$; $^1$H NMR (700 MHz, DMSO-d$_6$+D$_2$O, 348 K) δ 8.54-8.49 (m, 1H), 7.41-7.37 (m, 2H), 7.35-7.31 (m, 2H), 4.85-4.77 (m, 2H), 3.90-3.81 (m, 1H), 3.82-3.74 (m, 1H), 3.74-3.65 (m, 2H), 3.62-3.56 (m, 1H), 3.50-3.46 (m, 1H), 3.21-3.10 (m, 2H), 3.09-3.00 (m, 3H), 2.37 (s, 3H), 2.36-2.26 (m, 2H), 1.65-1.45 (m, 2H), 1.23 (d, J=6.2 Hz, 3H).

Example 173

Synthesis of 4-(4-((2S,5S)-5-(4-chlorobenzyl)-2-methylmorpholino)piperidin-1-yl)-1,3,5-triazine-2-carbonitrile 2,2,2-trifluoroacetate (173)

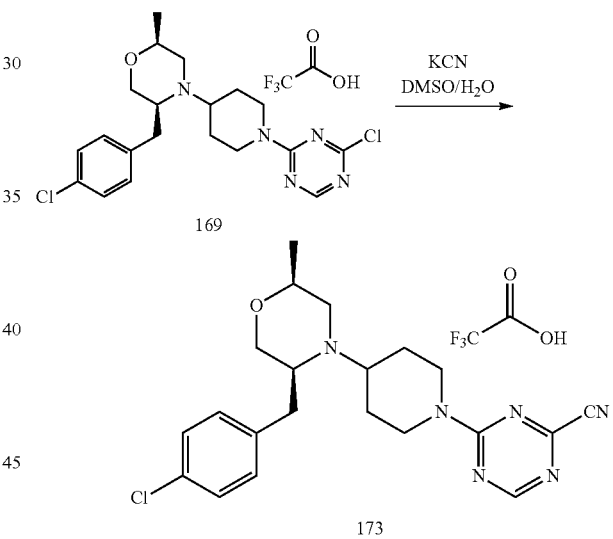

To the solution of 169 (113 mg; 0.21 mmol) in DMSO/water (0.8 mL/0.2 mL) KCN (41 mg; 0.63 mmol) was added and the mixture was stirred at room temperature overnight, then at 70° C. for 3 hours. The reaction progress was monitored by LC-MS. When analysis indicated completion of the reaction, the mixture was diluted with water and the crude product was purified by preparative reversed-phase column chromatography (Luna® 5 μm Phenyl-Hexyl, LC Column 250×21.2 mm, water/MeCN+1% TFA, 95:5 to 40:60, 30 minutes). Compound 173 was obtained as a TFA salt in 12% yield (13 mg; 0.025 mmol).

ESI-MS m/z for $C_{21}H_{26}ClN_6O$ found 413.0/415.0 [M+H]$^+$; $^1$H NMR (700 MHz, DMSO-d$_6$+D$_2$O, 348 K) δ 8.72-8.68 (m, 1H), 7.41-7.37 (m, 2H), 7.35-7.30 (m, 2H), 4.83-4.57 (m, 2H), 3.89-3.79 (m, 1H), 3.78-3.54 (m, 4H), 3.40-3.35 (m, 1H), 3.20-3.06 (m, 4H), 3.05-2.98 (m, 1H), 2.35-2.26 (m, 2H), 1.66-1.51 (m, 2H), 1.23 (d, J=6.2 Hz, 3H).

Example 174

Synthesis of 4-(4-((2S,5S)-5-(4-chlorobenzyl)-2-methylmorpholino)piperidin-1-yl)-1,3,5-triazin-2-amine 2,2,2-trifluoroacetate (174)

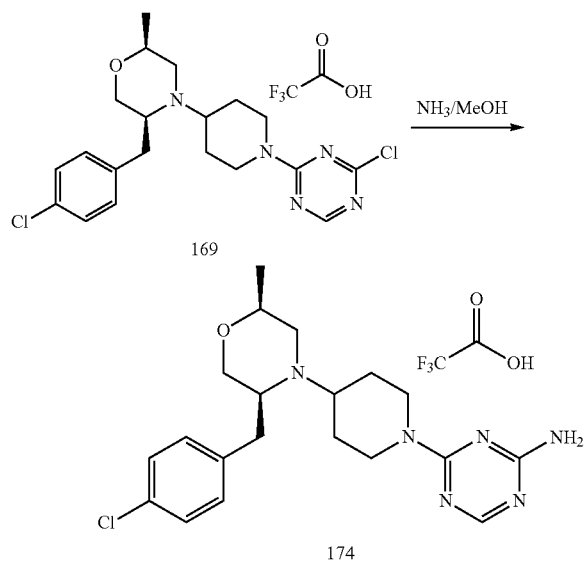

The solution of 169 (113 mg; 0.21 mmol) with NH$_3$/MeOH (7M; 2 mL) was stirred at room temperature overnight. The reaction progress was monitored by LC-MS. When analysis indicated completion of the reaction, the mixture was diluted with water (2 mL), MeCN (2 mL) and TFA (0.03 mL) and the crude product was purified by preparative reversed-phase column chromatography (Luna® 5 μm Phenyl-Hexyl, LC Column 250×21.2 mm, water/MeCN+10% TFA, 95:5 to 40:60, 30 minutes). Compound 174 was obtained as a TFA salt in 79% yield (85 mg; 0.165 mmol).

ESI-MS m/z for $C_{20}H_{28}ClN_6O$ found 403.0/405.0 [M+H]$^+$; $^1$H NMR (700 MHz, DMSO-d$_6$+D$_2$O, 348 K) δ 8.31-8.25 (m, 1H), 7.42-7.38 (m, 2H), 7.36-7.32 (m, 2H), 4.80-4.71 (m, 2H), 3.93-3.87 (m, 1H), 3.81-3.68 (m, 3H), 3.62-3.54 (m, 1H), 3.51-3.47 (m, 1H), 3.23-3.12 (m, 2H), 3.09-2.99 (m, 3H), 2.35-2.22 (m, 2H), 1.74-1.60 (m, 2H), 1.23 (d, J=6.2 Hz, 3H).

Example 175

Synthesis of 4-(4-((2S,5S)-5-(4-chlorobenzyl)-2-methylmorpholino)piperidin-1-yl)-N,N-dimethyl-1,3,5-triazin-2-amine 2,2,2-trifluoroacetate (175)

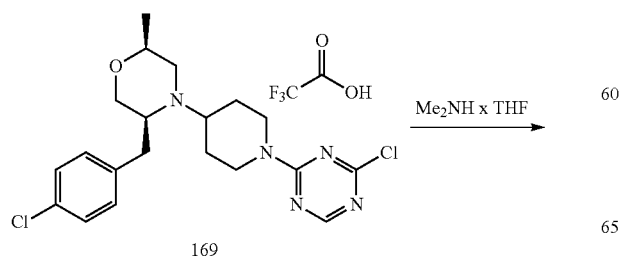

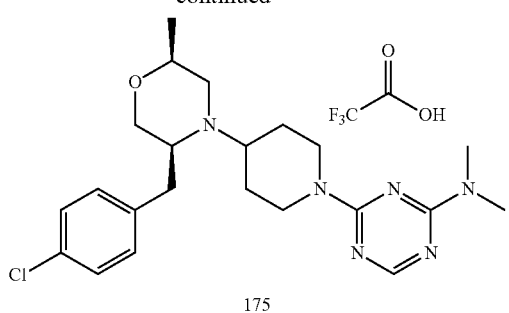

The solution of 169 (113 mg; 0.21 mmol) with solution of Me$_2$NH in THF (2M; 2 mL) was stirred at room temperature overnight. The reaction progress was monitored by LC-MS. When analysis indicated completion of the reaction, the mixture was concentrated in vacuo and the crude product was purified by preparative reversed-phase column chromatography (Luna® 5 μm Phenyl-Hexyl, LC Column 250×21.2 mm, water/MeCN+1% TFA, 95:5 to 40:60, 30 minutes). Compound 175 was obtained as a TFA salt in 80% yield (91 mg; 0.167 mmol).

ESI-MS m/z for $C_{22}H_{32}ClN_6O$ found 431.1/433.1 [M+H]$^+$; $^1$H NMR (700 MHz, DMSO-d$_6$+D$_2$O, 348 K) δ 8.16-8.13 (m, 1H), 7.41-7.37 (m, 2H), 7.34-7.31 (m, 2H), 4.79-4.69 (m, 2H), 3.86-3.78 (m, 1H), 3.78-3.65 (m, 3H), 3.58 (d, J=13.2 Hz, 1H), 3.48-3.45 (m, 1H), 3.22-3.11 (m, 2H), 3.08 (s, 6H), 3.06-3.00 (m, 1H), 2.98-2.86 (m, 2H), 2.30-2.19 (m, 2H), 1.62-1.47 (m, 2H), 1.23 (d, J=6.2 Hz, 3H).

Example 176

Synthesis of (2R,5S)-5-(4-chlorobenzyl)-4-(1-(4-chloropyridin-2-yl)piperidin-4-yl)-2-(3-methylisoxazol-5-yl)morpholine dihydrochloride (176)

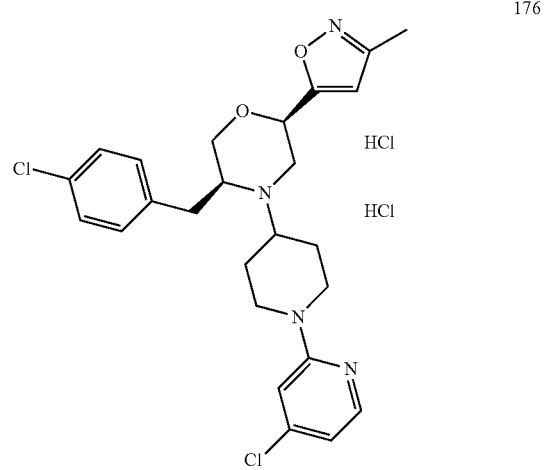 [SMILES: Cc1cc([C@H]2CN(C3CCN(c4cc(Cl)ccn4)CC3)[C@@H](Cc3ccc(Cl)cc3)CO2)on1 ; Cl ; Cl]

489
Step 1

Synthesis of (2R,5S)-tert-butyl 5-(4-chlorobenzyl)-2-(methoxy(methyl)carbamoyl)morpholine-4-carboxylate (176a)

490
Step 2

Synthesis of (2R,5S)-tert-butyl 5-(4-chlorobenzyl)-2-(3-methylisoxazol-5-yl)morpholine-4-carboxylate (176b)

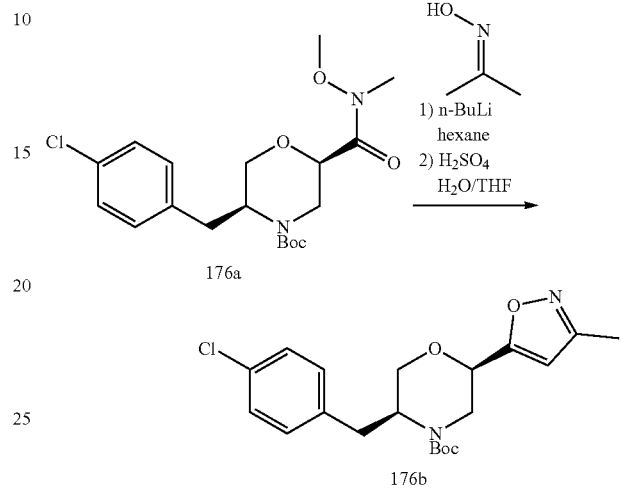

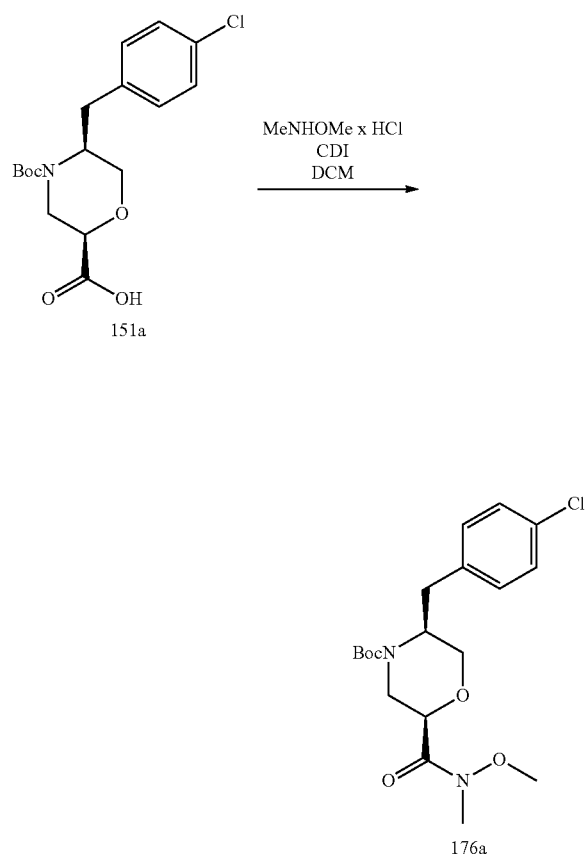

To a cooled to 0° C. solution of an oxime (55 mg; 074 mmol) in THF (1.5 mL) a solution of n-butyllithium (2.5M in hexanes; 0.6 mL; 1.49 mmol) was added dropwise and the mixture was stirred for 30 minutes. Then the solution of 176a (246 mg; 0.62 mmol) in THF (3 mL) was added dropwise over 15 minutes. After 30 minutes to this mixture a solution of $H_2SO_4$ (0.13 mL) in THF/water (1.5 mL/0.4 mL) was added and the resulting mixture was refluxed for 1 hour. The reaction progress was monitored by LC-MS. When analysis indicated completion of the reaction, the reaction mixture was cooled to 0° C. and the reaction was neutralized with 5% $NaHCO_3$. Then water was added and the mixture was extracted with $Et_{20}$. An organic layer was then dried over anhydrous $MgSO_4$, filtered and concentrated in vacuo and the crude product was used to the next step without additional purification. Compound 176b was obtained in 97% yield (235 mg; 0.6 mmol).

ESI-MS m/z for $C_{20}H_{26}ClN_2O_4$ found 393.2/395.2 $[M+H]^+$

Step 3

Synthesis of (2R,5S)-5-(4-chlorobenzyl)-2-(3-methylisoxazol-5-yl)morpholine hydrochloride (176c)

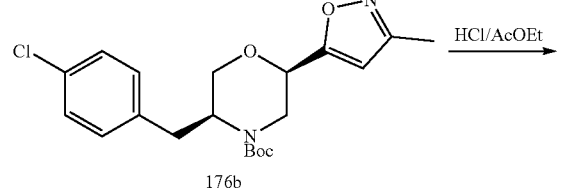

To the solution of 151a (0.5 g; 1.4 mmol) in DCM (6 mL) CDI (0.25 g; 1.5 mmol) was added in small portions. The reaction mixture was stirred at room temperature for 30 minutes, followed by adding N,O-dimethylhydroxylamine hydrochloride (0.15 g; 1.5 mmol) in one portion and the reaction mixture was stirred at room temperature overnight. The reaction progress was monitored by TLC and LC-MS. When analyses indicated completion of the reaction, the reaction was washed sequentially with 1M HCl, 1M NaOH, and brine. The organic phase was dried over anhydrous $MgSO_4$, filtered and concentrated in vacuo and the crude product was purified by silica-gel column chromatography (hexane/AcOEt; 5:1 to 2:1, v/v). Compound 176a was obtained as a white crystal in 67% yield (0.37 g; 0.94 mmol).

ESI-MS m/z for $C_{14}H_{20}ClN_2O_3$ found 298.9/300.9 [M+H-Boc]; $^1$H NMR (700 MHz, DMSO-$d_6$+$D_2O$, 348 K) δ 7.33-7.25 (m, 2H), 7.25-7.15 (m, 2H), 4.26-4.21 (m, 1H), 4.13-4.04 (m, 1H), 3.91-3.83 (m, 1H), 3.78-3.74 (m, 1H), 3.69 (s, 3H), 3.62-3.57 (m, 1H), 3.18-3.10 (m, 4H), 3.01-2.91 (m, 1H), 2.88-2.81 (m, 1H), 1.21 (s, 9H).

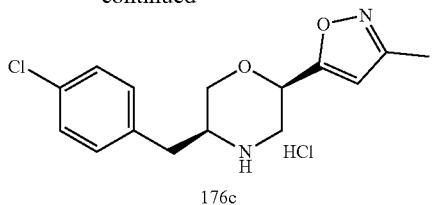

176c

The title compound (176c) was obtained as a hydrochloride salt from 176b (235 mg; 0.6 mmol) according to the General Procedure IVa in 99% yield (194 mg; 0.59 mmol).

ESI-MS m/z for $C_{12}H_{16}ClN_4O$ found 293.1/295.1 [M+H]$^+$; $^1$H NMR (700 MHz, DMSO-d$_6$+D$_2$O, 348 K) δ 7.31-7.28 (m, 2H), 7.23-7.20 (m, 2H), 6.33 (s, 1H), 4.70-4.66 (m, 1H), 3.62-3.55 (m, 1H), 3.44-3.42 (m, 1H), 3.17-3.09 (m, 1H), 2.98-2.88 (m, 2H), 2.70 (d, J=7.1 Hz, 2H), 2.22 (s, 3H).

Step 4

Synthesis of (2R,5S)-5-(4-chlorobenzyl)-4-(1-(4-chloropyridin-2-yl)piperidin-4-yl)-2-(3-methylisoxazol-5-yl)morpholine dihydrochloride (176)

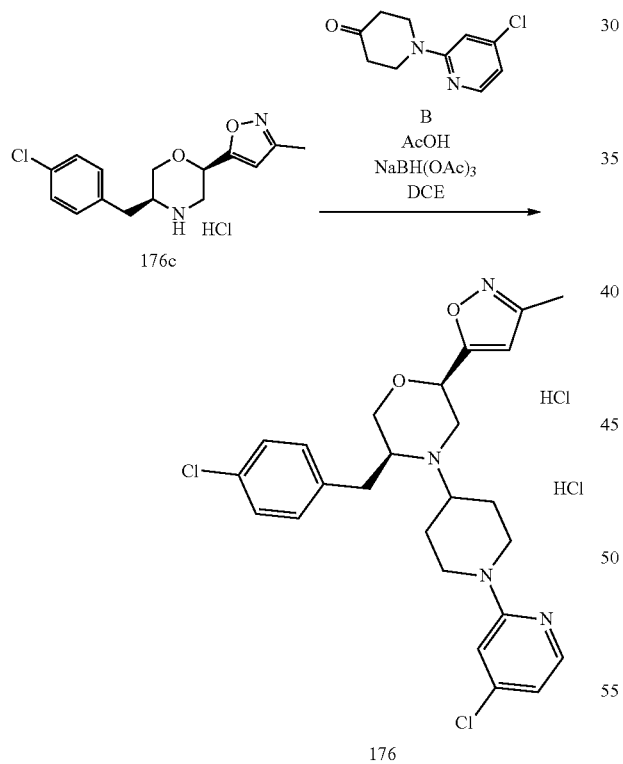

The title compound (176) was obtained as a dihydrochloride salt from 176c (56 mg; 0.17 mmol) according to the General Procedure VI in 73% yield (70 mg; 0.125 mmol).

ESI-MS m/z for $C_{25}H_{29}Cl_2N_4O_2$ found 487.1/489.1 [M+H]$^+$; $^1$H NMR (700 MHz, DMSO-d$_6$+D$_2$O, 348 K) δ 8.06-8.04 (m, 1H), 7.42-7.37 (m, 2H), 7.35-7.32 (m, 2H), 7.01-6.99 (m, 1H), 6.77-6.74 (m, 1H), 6.55 (s, 1H), 5.13-5.06 (m, 1H), 4.43-4.35 (m, 2H), 3.99-3.93 (m, 1H), 3.84-3.74 (m, 2H), 3.72-3.67 (m, 2H), 3.56-3.49 (m, 1H), 3.23-3.15 (m, 2H), 3.03-2.90 (m, 2H), 2.26 (s, 3H), 2.26-2.19 (m, 2H), 1.74-1.61 (m, 2H).

Example 177

Synthesis of (3S,8aS)-3-(4-chlorobenzyl)-2-(1-(4-chloropyridin-2-yl)piperidin-4-yl)-7,7-difluorooctahydropyrrolo[1,2-a]pyrazine trihydrochloride (177)

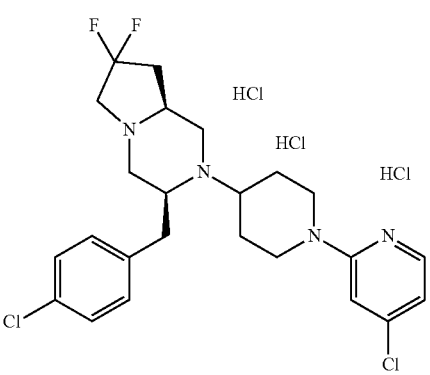

Step 1

Synthesis of tert-butyl (3S,7R,8aS)-3-(4-chlorobenzyl)-7-hydroxyhexahydropyrrolo[1,2-a]pyrazine-2(1H)-carboxylate (177a)

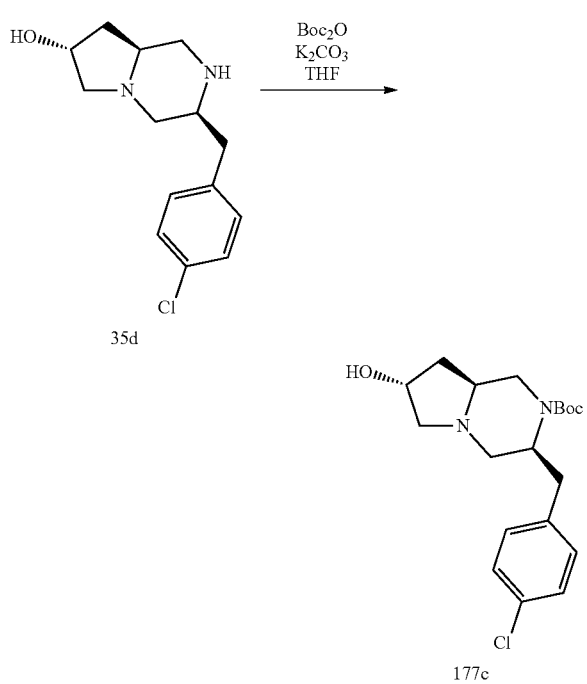

To a solution of compound 35d (9 g; 33.7 mmol) in THF (120 mL), 1M K$_2$CO$_3$ (120 mL) and Boc$_2$O (8.83 g; 40.45 mmol) were added in one portion and the reaction was stirred overnight after which time TLC and LC-MS control indicated completion of the reaction. The reaction mixture was concentrated in vacuo to remove THF. The water residue was saturated with NaCl and extracted with EtOAc (3×). An organic layer was washed with brine, dried over anhydrous MgSO$_4$ and concentrated in vacuo. The crude product was purified by flash column chromatography on silica (hexane/EtOAc, 1:1 to 0:1, v/v) to give 177a in 70% yield (8.66 g; 23.6 mmol).

ESI-MS m/z for C$_{19}$H$_{28}$ClN$_2$O$_3$ found 367.2/369.2 [M+H]$^+$

Step 2

Synthesis of tert-butyl (3S,8aS)-3-(4-chlorobenzyl)-7-oxohexahydropyrrolo[1,2-a]pyrazine-2(1H)-carboxylate (177b)

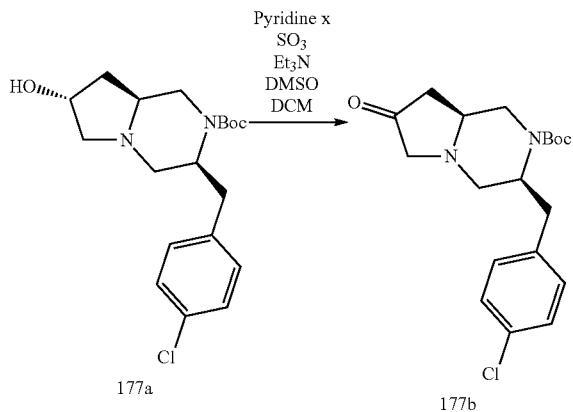 [SMILES: CC(C)(C)OC(=O)N1C[C@@H]2C[C@@H](O)CN2C[C@@H]1Cc1ccc(Cl)cc1 ; CC(C)(C)OC(=O)N1C[C@@H]2CC(=O)CN2C[C@@H]1Cc1ccc(Cl)cc1]

To the solution of 177a (3 g; 8.1 mmol) and Et$_3$N (3.5 mL; 24.53 mmol) in DCM/DMSO (10 mL/10 mL) the solution of pyridine×SO$_3$ (3.9 g; 24.53 mmol) in DCM/DMSO (20 mL/20 mL) was added at 0° C. for 30 minutes and then this reaction mixture was stirred at this temperature for 2 hours. The reaction progress was monitored by TLC and LC-MS. When analyses indicated completion of the reaction, the reaction mixture was quenched with 1M NaOH (400 mL) and phases were separated. An aqueous one was additionally extracted with CHCl$_3$ (3×100 mL). The combined organic extracts were washed with brine, dried over anhydrous Na$_2$SO$_4$, filtered and concentrated in vacuo and the crude product was purified by flash column chromatography on silica (hexane/EtOAc, 2:8 to 0:10, v/v) to give 177b as a two rotamers (in ratio 1:0.7) in 47% yield (1.4 g; 3.84 mmol).

ESI-MS m/z for C$_{19}$H$_{26}$ClN$_2$O$_3$ found 365.2/367.2 [M+H]$^+$; $^1$H NMR (400 MHz, CDCl$_3$) δ 7.29-7.23 (m, 4H), 7.20-7.15 (m, 2H), 7.12-7.07 (m, 2H), 4.49-4.38 (m, 1H), 4.36-4.21 (m, 2H), 4.12-4.02 (m, 1H), 3.42-3.32 (m, 2H), 3.13-2.81 (m, 8H), 2.65-2.58 (m, 2H), 2.58-2.47 (m, 2H), 2.43-2.27 (m, 4H), 2.23-2.10 (m, 2H), 1.41 (s, 9H), 1.35 (s, 9H); $^{13}$C NMR (101 MHz, CDCl$_3$) δ 211.3, 211.2, 154.5, 154.3, 137.4, 137.2, 132.2, 132.1, 130.8, 130.6, 128.6, 128.5, 80.14, 80.11, 61.8 (2×), 60.7, 60.5, 53.5, 53.1, 52.3, 51.9, 44.9, 43.4, 41.3 (2×), 35.9, 35.3, 28.3, 28.2.

Step 3

Synthesis of (3S,8aS)-3,2 yrazine (177c)

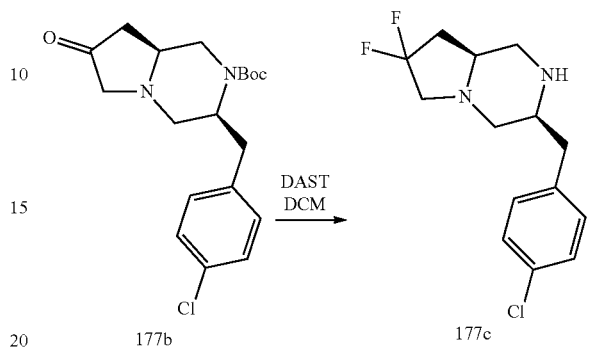

To a cooled to −78° C. solution of 177b (1.4 g; 3.84 mmol) in anhydrous DCM (35 mL) DAST (1.52 mL; 11.51 mmol) was added dropwise and the reaction was allowed to room temperature and stirred overnight. The reaction progress was monitored by LC-MS. When analysis indicated completion of the reaction, the reaction mixture was poured into 5% NaHCO$_3$ and stirred for 15 minutes, then was extracted with DCM, washed with brine, dried over anhydrous MgSO$_4$, concentrated in vacuo. The title compound (177c) was obtained as a free base in 99% yield (1.09 g; 3.8 mmol).

ESI-MS m/z for C$_{14}$H$_{18}$ClF$_2$N$_2$ found 287.1/289.1 [M+H]$^+$

Step 4

Synthesis of (3S,8aS)-3-(4-chlorobenzyl)-2-(1-(4-chloropyridin-2-yl)piperidin-4-yl)-7,7-difluorooctahydropyrrolo[1,2-a]pyrazine trihydrochloride (177)

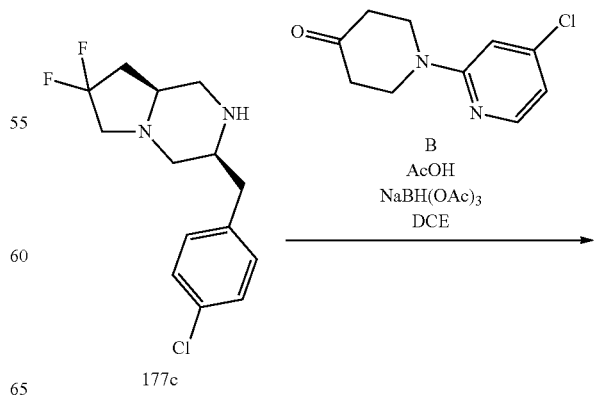

495

-continued

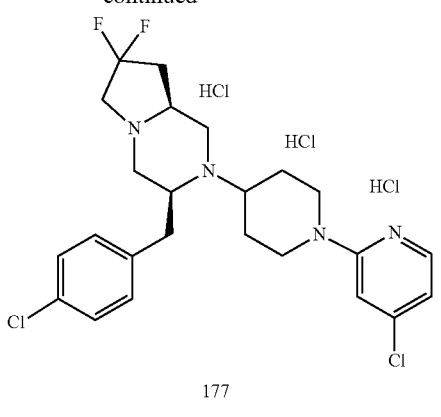

177

The title compound (177) was obtained as a trihydrochloride salt from 177c (200 mg; 0.7 mmol) according to the General Procedure VI in 16% yield (64 mg; 0.109 mmol).

ESI-MS m/z for $C_{24}H_{29}C1_2F_2N_4$ found 481.1/483.1 [M+H]$^+$; $^1$H NMR (400 MHz, Methanol-$d_4$) δ 7.99-7.92 (m, 1H), 7.67-7.61 (m, 1H), 7.42-7.36 (m, 2H), 7.36-7.31 (m, 2H), 7.12-7.06 (m, 1H), 4.46-4.34 (m, 2H), 4.06-3.73 (m, 3H), 3.53-3.32 (m, 4H), 3.29-3.17 (m, 1H), 3.07-2.83 (m, 3H), 2.76-2.57 (m, 2H), 2.57-2.39 (m, 3H), 2.31-2.00 (m, 3H).

Example 178

Synthesis of (3S,7S,8aS)-3-(4-chlorobenzyl)-2-(1-(4-chloropyridin-2-yl)piperidin-4-yl)-7-(methyl-sulfonyl)octahydropyrrolo[1,2-a]pyrazine trihydrochloride (178)

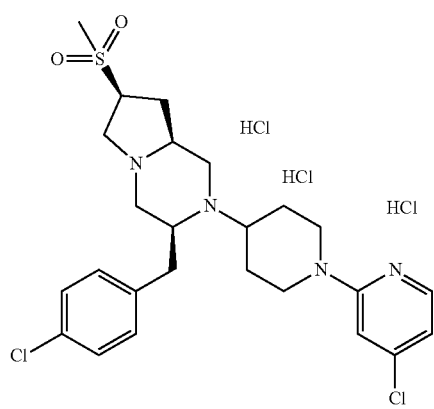

178

496

Step 1

Synthesis of tert-butyl (3S,7R,8aS)-3-(4-chlorobenzyl)-7-((methylsulfonyl)oxy)hexahydropyrrolo[1,2-a]pyrazine-2(1H)-carboxylate (178a)

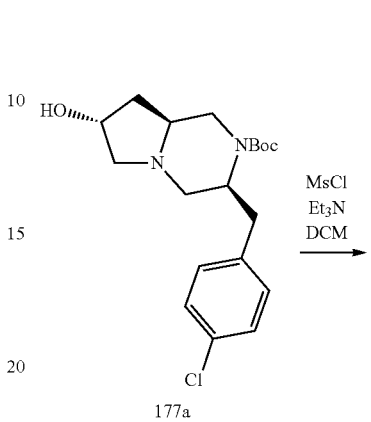

177a

178a

The title compound (178a) was obtained from 177a (3 g; 8.18 mmol) according to the General Procedure XIV in 87% yield (3.16 g; 7.12 mmol).

ESI-MS m/z for $C_{20}H_{30}ClN_2O_5S$ found 445.2/447.2 [M+H]$^+$

Step 2

Synthesis of tert-butyl (3S,7S,8aS)-3-(4-chlorobenzyl)-7-(methylsulfonyl)hexahydropyrrolo[1,2-a]pyrazine-2(1H)-carboxylate (178b)

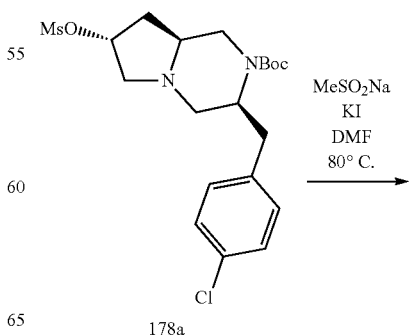

178a

-continued

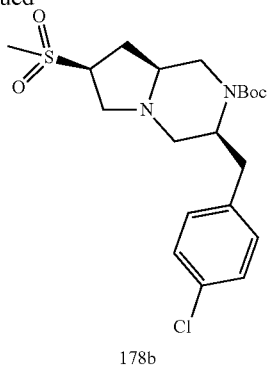

178b

The solution of 178a (3 g; 6.74 mmol), MeSO$_2$Na (3.44g; 33.71 mmol) and KI (230 mg; 1.35 mmol) in DMF (30 mL) under nitrogen atmosphere was stirred at 80° C. for 24 hours. The reaction progress was monitored by LC-MS. When analysis indicated completion of the reaction, the reaction mixture was cooled to room temperature and extracted with AcOEt (3×30 mL) and CHCl$_3$ (3×30 mL). The combined organic extracts were dried over anhydrous Na$_2$SO$_4$, filtered and concentrated in vacuo and the crude product was purified by flash column chromatography on silica (hexane/AcOEt, 1:1, v/v, then MeOH/AcOEt, 2:8, v/v) to give 178b in 17% yield (0.5 g; 1.17 mmol).

ESI-MS m/z for C$_{20}$H$_{30}$ClN$_2$O$_4$S found 429.2/431.2 [M+H]$^+$

Step 3

Synthesis of (3S,7S,8aS)-3-(4-chlorobenzyl)-7-(methylsulfonyl)octahydropyrrolo[1,2-a]pyrazine (178c)

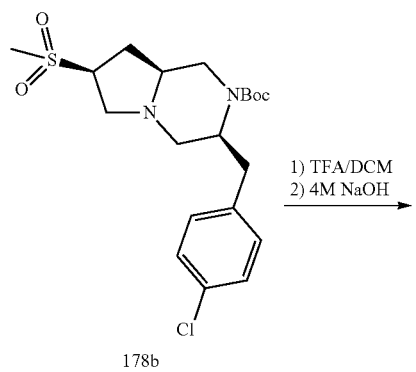

The title compound (178c) was obtained from 178b (0.5 g; 1.17 mmol) according to the General Procedure IVb. Then obtained TFA salt was dissolved in AcOEt and 1M NaOH was added to this solution. Phases were separated and an organic one was washed with brine, dried over anhydrous MgSO$_4$ and concentrated in vacuo to give a free amine 178c in 99% yield (381 mg; 1.16 mmol).

ESI-MS m/z for C$_{15}$H$_{22}$ClN$_2$O$_2$S found 329.1/331.1 [M+H]$^+$

Step 4

Synthesis of (3S,7S,8aS)-3-(4-chlorobenzyl)-2-(1-(4-chloropyridin-2-yl)piperidin-4-yl)-7-(methylsulfonyl)octahydropyrrolo[1,2-a]pyrazine trihydrochloride (178)

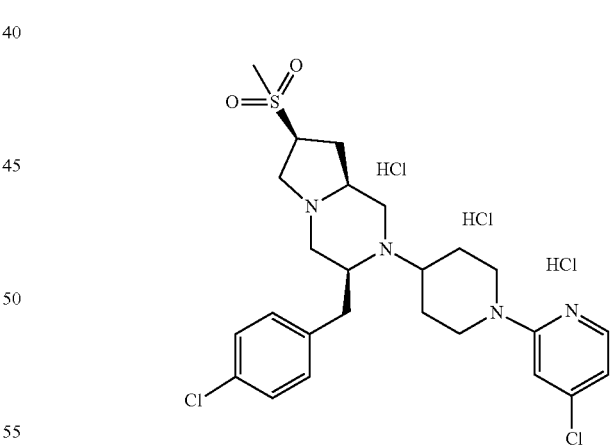

The title compound (178) was obtained as a trihydrochloride salt from 178c (130 mg; 0.4 mmol) according to the General Procedure VI in 24% yield (61 mg; 0.097 mmol).

ESI-MS m/z for C$_{25}$H$_{33}$Cl$_2$N$_4$O$_2$S found 523.1/525.1 [M+H]$^+$; $^1$H NMR (400 MHz, Methanol-d$_4$) δ 8.00-7.93 (m, 1H), 7.68-7.61 (m, 1H), 7.43-7.30 (m, 24H), 7.13-6.99 (m, 1H), 4.48-4.31 (m, 2H), 4.06-3.73 (m, 4H), 3.54-3.33 (m, 4H), 3.26-3.10 (m, 2H), 3.03 (s, 3H), 2.93-2.82 (m, 1H), 2.80-2.22 (m, 6H), 2.19-1.87 (m, 3H).

Example 179

Synthesis of (2S,5S)-4-(1-(1,2,4-thiadiazol-5-yl)piperidin-4-yl)-5-(4-chlorobenzyl)-2-methylmorpholine 2,2,2-trifluoroacetate (179)

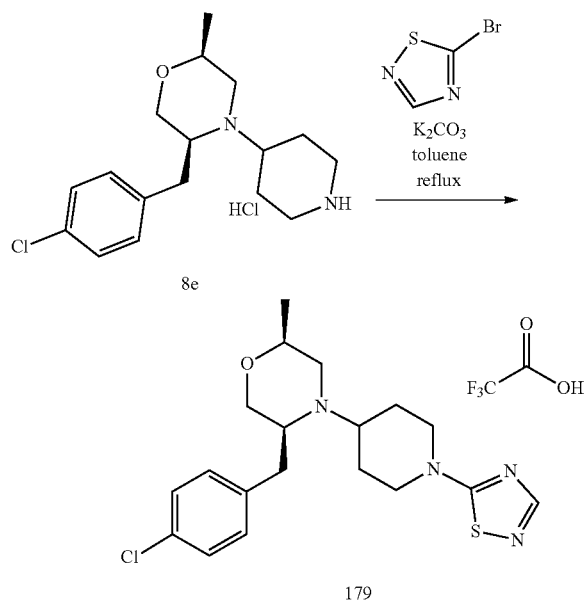

The title compound (179) was obtained as a white solid as a TFA salt from 8e (110 mg; 0.32 mmol) according to the General Procedure XXVI in 70% yield (114 mg; 0.225 mmol).

ESI-MS m/z for $C_{19}H_{26}ClN_4OS$ found 392.9/394.9 [M+H]$^+$; $^1$H NMR (700 MHz, DMSO-d$_6$+D$_2$O, 348 K) δ 8.00 (s, 1H), 7.41-7.37 (m, 2H), 7.35-7.31 (m, 2H), 4.03-3.94 (m, 2H), 3.87-3.79 (m, 1H), 3.77-3.65 (m, 3H), 3.62-3.56 (m, 1H), 3.48-3.43 (m, 1H), 3.36-3.26 (m, 2H), 3.22-3.08 (m, 2H), 3.07-2.99 (m, 1H), 2.34-2.24 (m, 2H), 1.77-1.65 (m, 2H), 1.23 (d, J=6.2 Hz, 3H).

Example 180

Synthesis of (2S,5S)-5-(4-chlorobenzyl)-2-methyl-4-(1-(3-methyl-1,2,4-thiadiazol-5-yl)piperidin-4-yl)morpholine 2,2,2-trifluoroacetate (180)

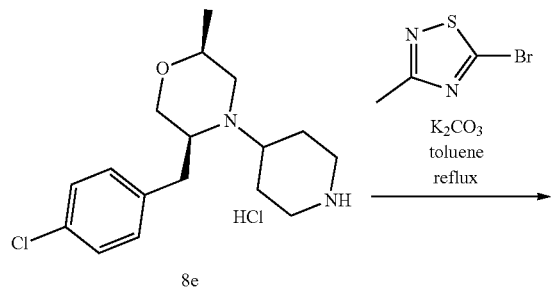

The title compound (180) was obtained as a white solid as a TFA salt from 8e (110 mg; 0.32 mmol) according to the General Procedure XXVI in 82% yield (136 mg; 0.261 mmol).

ESI-MS m/z for $C_{20}H_{28}ClN_4OS$ found 407.2/409.2 [M+H]$^+$; $^1$H NMR (700 MHz, DMSO-d$_6$+D$_2$O, 348 K) δ 7.40-7.37 (m, 2H), 7.34-7.31 (m, 2H), 3.99-3.89 (m, 2H), 3.87-3.79 (m, 1H), 3.75-3.64 (m, 3H), 3.61-3.56 (m, 1H), 3.49-3.44 (m, 1H), 3.32-3.22 (m, 2H), 3.20-3.14 (m, 1H), 3.14-3.08 (m, 1H), 3.08-2.98 (m, 1H), 2.32-2.24 (m, 5H), 1.75-1.64 (m, 2H), 1.23 (d, J=6.2 Hz, 3H).

Example 181

Synthesis of (2S,5S)-4-(1-(1,3,4-thiadiazol-2-yl)piperidin-4-yl)-5-(4-chlorobenzyl)-2-methylmorpholine 2,2,2-trifluoroacetate (181)

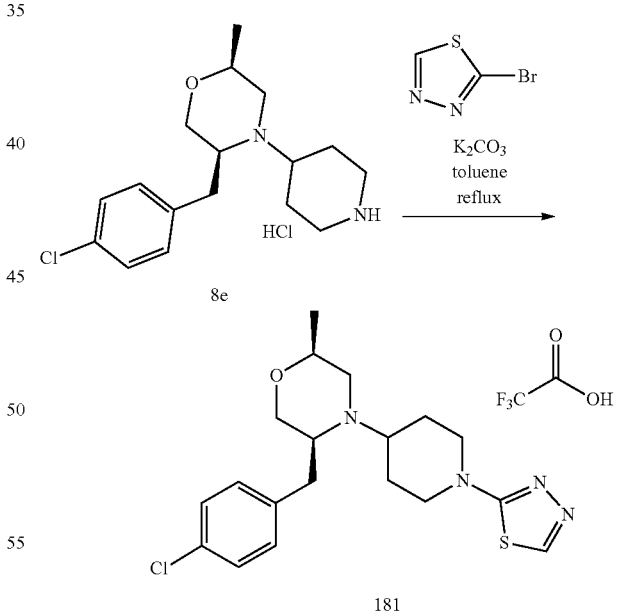

The title compound (181) was obtained as a white solid as a TFA salt from 8e (110 mg; 0.32 mmol) according to the General Procedure XXVI in 84% yield (136 mg; 0.269 mmol).

ESI-MS m/z for $C_{19}H_{26}ClN_4OS$ found 393.0/395.0 [M+H]$^+$; $^1$H NMR (700 MHz, DMSO-d$_6$+D$_2$O, 348 K) δ 8.78-8.76 (m, 1H), 7.41-7.37 (m, 2H), 7.34-7.30 (m, 2H), 4.06-3.97 (m, 2H), 3.89-3.81 (m, 1H), 3.77-3.66 (m, 3H), 3.63-3.55 (m, 1H), 3.51-3.47 (m, 1H), 3.30-3.09 (m, 4H), 3.08-2.99 (m, 1H), 2.31-2.24 (m, 2H), 1.81-1.67 (m, 2H), 1.23 (d, J=6.2 Hz, 3H).

Example 182

Synthesis of (2S,5S)-5-(4-chlorobenzyl)-2-methyl-4-(1-(5-methyl-1,3,4-thiadiazol-2-yl)piperidin-4-yl)morpholine 2,2,2-trifluoroacetate (182)

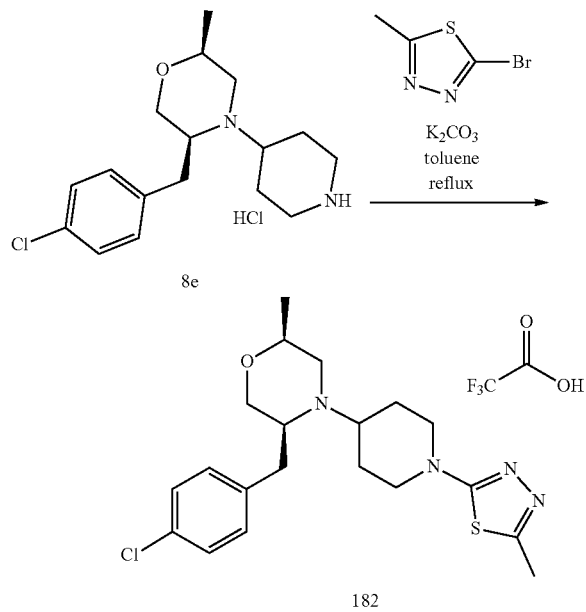

The title compound (182) was obtained as a white foam as a TFA salt from 8e (110 mg; 0.32 mmol) according to the General Procedure XXVI in 16% yield (26 mg; 0.05 mmol).

ESI-MS m/z for $C_{20}H_{28}ClN_4OS$ found 407.1/409.1 [M+H]$^+$; $^1$H NMR (700 MHz, DMSO-d$_6$+D$_2$O, 348 K) δ 7.41-7.37 (m, 2H), 7.34-7.31 (m, 2H), 3.97-3.90 (m, 2H), 3.89-3.79 (m, 1H), 3.74-3.65 (m, 3H), 3.61-3.55 (m, 1H), 3.51-3.46 (m, 1H), 3.23-3.14 (m, 3H), 3.13-3.09 (m, 1H), 3.06-3.01 (m, 1H), 2.52-2.50 (m, 3H), 2.31-2.21 (m, 2H), 1.78-1.65 (m, 2H), 1.23 (d, J=6.2 Hz, 3H).

Example 183

Synthesis of (2S,5S)-5-(4-chlorobenzyl)-4-(1-(4,5-dimethylthiazol-2-yl)piperidin-4-yl)-2-methylmorpholine 2,2,2-trifluoroacetate (183)

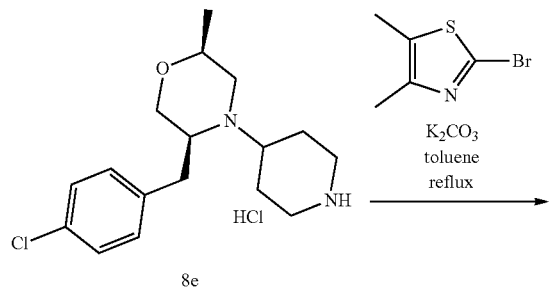

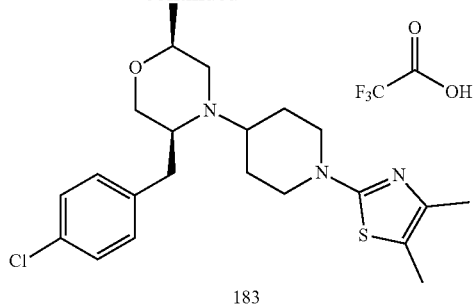

The title compound (183) was obtained as a white solid as a TFA salt from 8e (110 mg; 0.32 mmol) according to the General Procedure XXVI in 42% yield (71 mg; 0.133 mmol).

ESI-MS m/z for $C_{22}H_{31}ClN_3OS$ found 420.0/422.0 [M+H]$^+$; $^1$H NMR (700 MHz, DMSO-d$_6$+D$_2$O, 348 K) δ 7.41-7.37 (m, 2H), 7.34-7.30 (m, 2H), 3.99-3.90 (m, 2H), 3.87-3.80 (m, 1H), 3.73-3.65 (m, 3H), 3.62-3.55 (m, 1H), 3.49-3.45 (m, 1H), 3.20-3.08 (m, 4H), 3.05-2.98 (m, 1H), 2.30-2.19 (m, 2H), 2.18-2.13 (m, 3H), 2.10-2.03 (m, 3H), 1.76-1.64 (m, 2H), 1.23 (d, J=6.2 Hz, 3H).

Example 184

Synthesis of (2S,5S)-5-(4-chlorobenzyl)-2-methyl-4-(1-(4-methylthiazol-2-yl)piperidin-4-yl)morpholine 2,2,2-trifluoroacetate (184)

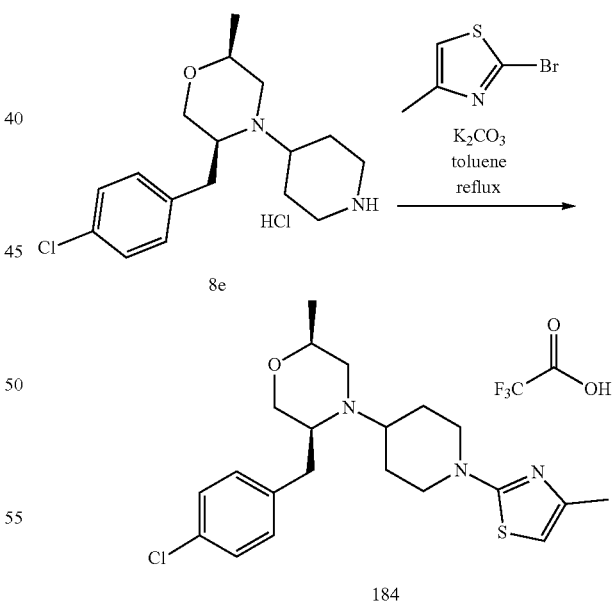

The title compound (184) was obtained as a white solid as a TFA salt from 8e (110 mg; 0.32 mmol) according to the General Procedure XXVI in 36% yield (59 mg; 0.114 mmol).

ESI-MS m/z for $C_{21}H_{29}ClN_3OS$ found 406.0/408.0 [M+H]$^+$; $^1$H NMR (700 MHz, DMSO-d$_6$) δ 7.48-7.42 (m, 2H), 7.40-7.33 (m, 2H), 6.51-6.42 (m, 1H), 4.05-3.93 (m, 2H), 3.80-3.71 (m, 2H), 3.71-3.51 (m, 4H), 3.24-2.98 (m, 5H), 2.32-2.24 (m, 2H), 2.19-2.14 (m, 3H), 1.75-1.61 (m, 2H), 1.24 (d, J=6.2 Hz, 3H).

Example 185

Synthesis of (2S,5S)-5-(4-chlorobenzyl)-2-methyl-4-(1-(5-methylthiazol-2-yl)piperidin-4-yl)morpholine 2,2,2-trifluoroacetate (185)

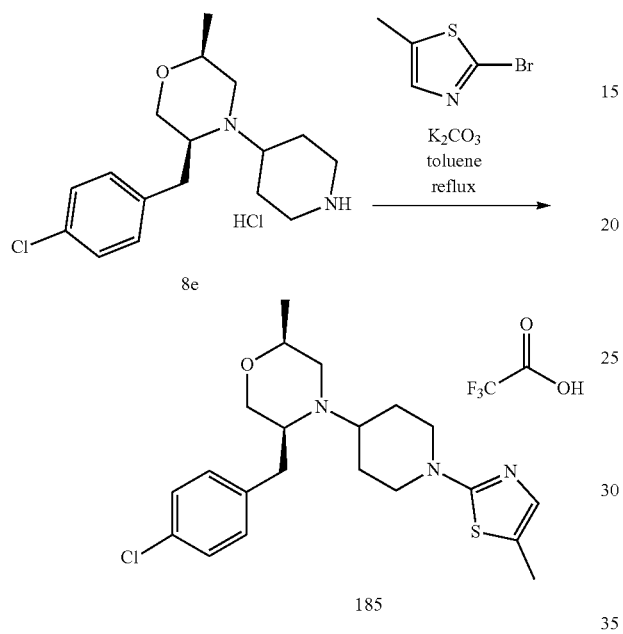

The title compound (185) was obtained as a white solid as a TFA salt from 8e (110 mg; 0.32 mmol) according to the General Procedure XXVI in 69% yield (115 mg; 0.222 mmol).

ESI-MS m/z for $C_{21}H_{29}ClN_3OS$ found 406.0/408.0 [M+H]$^+$; $^1$H NMR (700 MHz, DMSO-d$_6$+D$_2$O, 348 K) δ 7.41-7.38 (m, 2H), 7.35-7.31 (m, 2H), 6.87 (d, J=1.4 Hz, 1H), 4.00-3.93 (m, 2H), 3.89-3.79 (m, 1H), 3.75-3.65 (m, 3H), 3.61-3.56 (m, 1H), 3.48-3.45 (m, 1H), 3.21-3.08 (m, 4H), 3.07-2.99 (m, 1H), 2.31-2.20 (m, 5H), 1.77-1.64 (m, 2H), 1.23 (d, J=6.2 Hz, 3H).

Example 186

Synthesis of ((2R,5S)-5-(4-chlorobenzyl)-4-(1-(pyridin-2-yl)piperidin-4-yl)morpholin-2-yl)methyl cyclohexylcarbamate 2,2,2-trifluoroacetate (186)

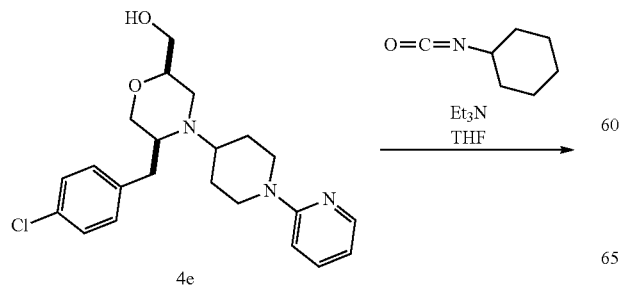

-continued

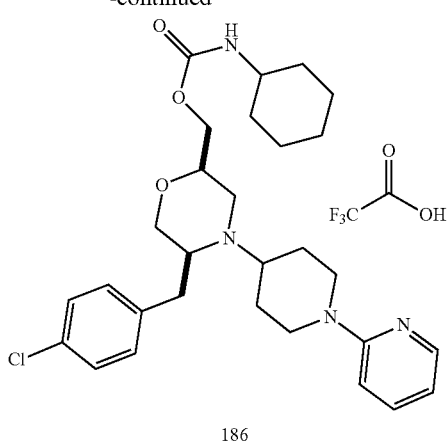

The title compound (186) was obtained as a white solid as a TFA salt from 4e (100 mg; 0.25 mmol) according to the General Procedure XVII in 29% yield (47 mg; 0.073 mmol).

ESI-MS m/z for $C_{29}H_{40}ClN_4O_3$ found 527.2/529.2 [M+H]$^+$; $^1$H NMR (700 MHz, DMSO-d$_6$+D$_2$O, 348 K) δ 8.12-8.02 (m, 1H), 7.83-7.69 (m, 1H), 7.43-7.38 (m, 2H), 7.35-7.29 (m, 2H), 7.15-7.05 (m, 1H), 6.87-6.77 (m, 1H), 4.41-4.30 (m, 2H), 4.20-4.13 (m, 1H), 4.10-4.03 (m, 1H), 3.99-3.92 (m, 1H), 3.77-3.60 (m, 4H), 3.50-3.44 (m, 1H), 3.33-3.26 (m, 1H), 3.23-3.03 (m, 5H), 2.30-2.20 (m, 2H), 1.80-1.73 (m, 2H), 1.75-1.61 (m, 4H), 1.57-1.45 (m, 1H), 1.32-1.15 (m, 4H), 1.15-1.06 (m, 1H).

Example 187

Synthesis of ((2R,5S)-5-(4-chlorobenzyl)-4-(1-(pyridin-2-yl)piperidin-4-yl)morpholin-2-yl)methyl phenylcarbamate 2,2,2-trifluoroacetate (187)

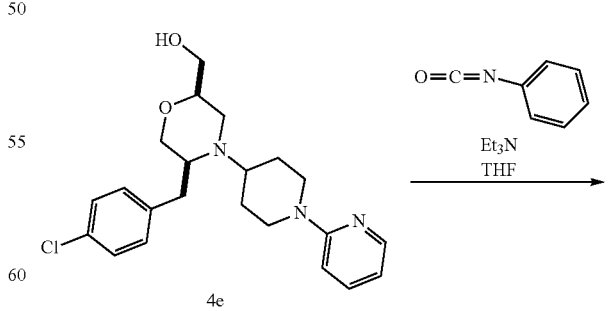

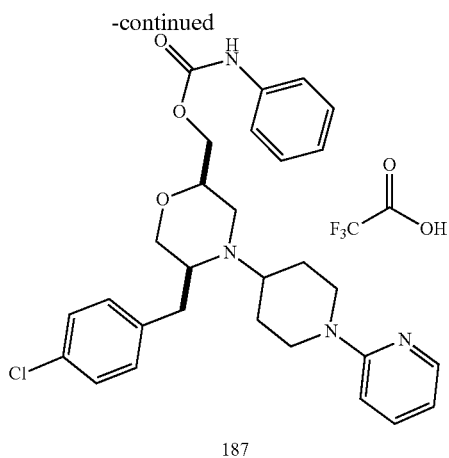

187

The title compound (187) was obtained as a white solid as a TFA salt from 4e (100 mg; 0.25 mmol) according to the General Procedure XVII in 42% yield (66 mg; 0.104 mmol).

ESI-MS m/z for $C_{29}H_{34}ClN_4O_3$ found 521.3/523.3 [M+H]$^+$; $^1$H NMR (700 MHz, DMSO-d$_6$+D$_2$O, 348 K) δ 8.08-8.04 (m, 1H), 7.76-7.72 (m, 1H), 7.45-7.41 (m, 2H), 7.39-7.35 (m, 2H), 7.33-7.26 (m, 4H), 7.09-7.05 (m, 1H), 7.05-7.02 (m, 1H), 6.81-6.78 (m, 1H), 4.40-4.28 (m, 3H), 4.23-4.18 (m, 1H), 4.06-3.99 (m, 1H), 3.74-3.67 (m, 3H), 3.65-3.60 (m, 1H), 3.53-3.48 (m, 1H), 3.25-3.16 (m, 2H), 3.16-3.11 (m, 1H), 3.11-3.01 (m, 2H), 2.31-2.20 (m, 2H), 1.69-1.60 (m, 2H).

Example 188

Synthesis of (2S,5S)-5-(4-chlorobenzyl)-2-methyl-4-(1-(3-methyl-1,2,4-oxadiazol-5-yl)piperidin-4-yl)morpholine 2,2,2-trifluoroacetate (188)

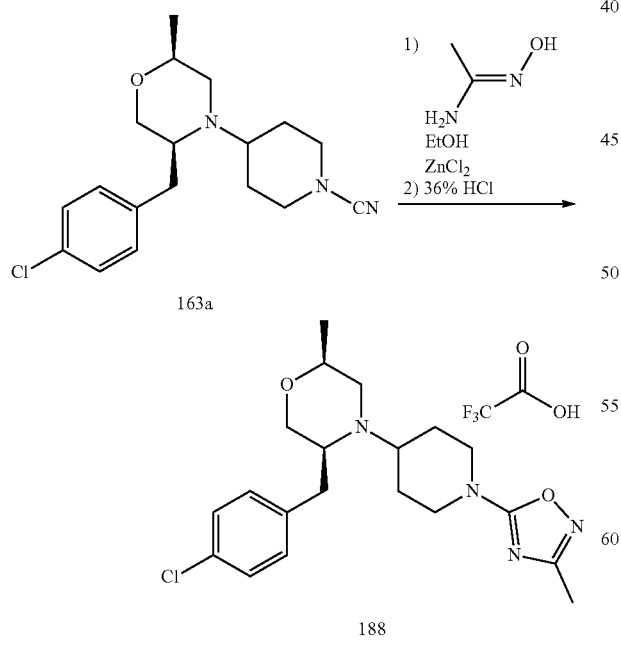

To the solution of 163a (100 mg; 0.3 mmol) in absolute EtOH (2 mL) N-hydroxyacetamidine (33 mg; 0.45 mmol) and ZnCl$_2$ (61 mg; 0.45 mmol) were added and the mixture was stirred at room temperature overnight. To this mixture EtOH (1 mL) and 36% HCl (0.5 mL) were added and stirred for 30 minutes at 70° C. The reaction progress was monitored by LC-MS. When analysis indicated completion of the reaction, the mixture was poured into water and extracted with AcOEt (2×). The combined organic layers were dried over anhydrous MgSO$_4$, filtered and concentrated in vacuo and the residue was purified by preparative reversed-phase column chromatography (Luna® 5 µm Phenyl-Hexyl, LC Column 250×21.2 mm, water/MeCN+1% TFA, 90:10 to 10:90, 30 minutes). Compound 188 was obtained as a white solid as a TFA salt in 86% yield (130 mg; 0.258 mmol). ESI-MS m/z for $C_{20}H_{28}ClN_4O_2$ found 391.1/393.1 [M+H]$^+$; $^1$H NMR (700 MHz, DMSO-d$_6$+D$_2$O, 348 K) δ 7.44-7.38 (m, 2H), 7.35-7.28 (m, 2H), 4.12-4.06 (m, 2H), 3.86-3.80 (m, 1H), 3.71-3.64 (m, 3H), 3.60-3.55 (m, 1H), 3.45-3.40 (m, 1H), 3.26-3.14 (m, 3H), 3.12-3.08 (m, 1H), 3.05-2.96 (m, 1H), 2.31-2.21 (m, 2H), 2.12 (s, 3H), 1.72-1.59 (m, 2H), 1.23 (d, J=6.2 Hz, 3H).

INCORPORATION BY REFERENCE

All U.S. patents, U.S. published patent applications, and PCT published patent applications designating the U.S. mentioned herein are hereby incorporated by reference in their entirety as if each individual publication or patent was specifically and individually indicated to be incorporated by reference. In case of conflict, the present application, including any definitions herein, will control.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound represented by formula (I)

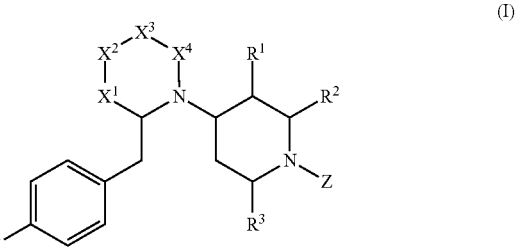

wherein:
X$^1$ is —C(R$^4$R$^5$)—;
X$^2$ is selected from the group consisting of —C(R$^6$R$^7$)—, —N(R$^8$)—, and —O—;
X$^3$ is —C(R$^9$R$^{10}$)—;
X$^4$ is —CH$_2$—;
Y is chloro;

Z is selected from the group consisting of pyridin-2-yl, 5-fluoro-pyridin-2-yl, 6-fluoro-pyridin-2-yl, 4-chloro-pyridin-2-yl, pyrazin-2-yl, 3-fluoro-pyridin-2-yl, 6-chloro-pyridin-2-yl, 2-fluoro-pyridin-4-yl, 3-methyl-pyridin-2-yl, 6-cyano-pyridin-2-yl, 5-cyano-pyridin-2-yl, 4-trifluoromethyl-pyridin-2-yl, 4-cyano-pyridin-2-yl, 3-cyano-pyridin-2-yl, 3-chloro-pyridin-2-yl, 6-fluoro-pyrimidin-4-yl, 3,5-difluoro-pyridin-2-yl, pyrimidin-4-yl, pyridin-3-yl, pyridin-4-yl, 4-methoxy-pyridin-2-yl, 4-methyl-pyridazin-6-yl, phenyl, 4-methyl-pyrimidin-2-yl, pyrimidin-2-yl, 5-fluoro-pyrimidin-2-yl, 3-cyano-4-methyl-pyridin-2-yl, 3-trifluoromethyl-pyridin-2-yl, 2-chloro-pyrimidin-4-yl, 2-amino-pyrimidin-4-yl, 4-fluoro-pyridin-2-yl, 4-bromo-pyridin-2-yl, 3-methoxycarbonyl-pyridin-2-yl, 2-cyano-6-fluoro-phenyl, 2-cyano-phenyl, 3-hydroxymethyl-pyridin-2-yl, 2-fluoro-4-methoxycarbonyl-pyridin-3-yl, 3-fluoro-4-methoxycarbonyl-pyridin-2-yl, 2-fluoro-4-hydroxycarbonyl-pyridin-3-yl, 2,6-difluorophenyl, 4-methoxycarbonyl-pyridin-2-yl, 4-hydroxy-carbonyl-pyridin-2-yl, 2-fluorophenyl, 3-fluorophenyl, 4-aminocarbonyl-pyridin-2-yl, 4-(hydroxymethyl)-pyridin-2-yl, 4-(2-hydroxyprop-2-yl)-pyridin-2-yl, pyrimidin-5-yl, 6-methyl-pyridin-2-yl, 5-methyl-pyridin-2-yl, 4-methyl-pyridin-2-yl, 4-trifluoromethyl-pyrimidin-6-yl, 2-trifluoromethyl-pyrazin-6-yl, 2-trifluoromethyl-pyrazin-5-yl, 3-methoxy-pyridin-2-yl, 4-hydroxy-pyridin-2-yl, 3-hydroxy-pyridin-2-yl, 2-amino-1,3,5-triazin-6-yl, 2-dimethylamino-1,3,5-triazin-6-yl, 2-methyl-1,3,5-triazin-6-yl, 2-methoxy-1,3,5-triazin-6-yl, 2-hydroxy-1,3,5-triazin-6-yl, 2-chloro-1,3,5-triazin-6-yl, and 2-cyano-1,3,5-triazin-6-yl;

$R^1$ is hydrogen;
$R^2$ is selected from the group consisting of hydrogen and methyl;
$R^3$ is hydrogen;
$R^4$ is hydrogen;
$R^5$ is hydrogen;
$R^6$ is selected from the group consisting of hydrogen and methyl;
$R^7$ is selected from the group consisting of hydroxy and methoxy;
$R^8$ is selected from the group consisting of methyl, isobutyl, and 2-hydroxypropyl;
$R^9$ is selected from the group consisting of hydrogen, methyl, hydroxymethyl, 4-morpholino-methyl, 4-methyl-piperazinyl, dimethylaminocarboxymethyl, dimethylamino-ethyl(methyl)aminomethyl, acetylaminomethyl, phthalimidomethyl, succinimidomethyl, (2,5-dioxo-imidazolidin-1-yl)methyl, pyrrolidinylmethyl, isobutyl, methylsulfonylmethyl, isopropyl, and 1-hydroxyethyl;
or $R^8$ and $R^9$, taken together, represent —$CH_2CH_2CH_2$—, optionally substituted with one or more substituents selected from hydroxy, methoxy, and fluoro;
$R^{10}$ is hydrogen; and
wherein any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of hydroxy and halo;
or a tautomer, stereoisomer, pharmaceutically acceptable salt, solvate, or polymorph thereof.

2. The compound of formula (I) according to claim 1, wherein:
$X^2$ is —$N(R^8)$—.

3. The compound of formula (I) according to claim 1, wherein:
$X^2$ is —O—.

4. The compound of formula (I) according to claim 1, wherein:
Z is selected from the group consisting of pyridin-2-yl, 5-fluoro-pyridin-2-yl, 6-fluoro-pyridin-2-yl, 4-chloro-pyridin-2-yl, 3-fluoro-pyridin-2-yl, 6-chloro-pyridin-2-yl, 2-fluoro-pyridin-4-yl, 3-methyl-pyridin-2-yl, 6-cyano-pyridin-2-yl, 5-cyano-pyridin-2-yl, 4-trifluoromethyl-pyridin-2-yl, 4-cyano-pyridin-2-yl, 3-cyano-pyridin-2-yl, 3-chloro-pyridin-2-yl, 3,5-difluoro-pyridin-2-yl, pyridin-3-yl, pyridin-4-yl, 4-methoxy-pyridin-2-yl, 3-cyano-4-methyl-pyridin-2-yl, 3-trifluoromethyl-pyridin-2-yl, 4-fluoro-pyridin-2-yl, 4-bromo-pyridin-2-yl, 3-methoxycarbonyl-pyridin-2-yl, 3-hydroxymethyl-pyridin-2-yl, 2-fluoro-4-methoxycarbonyl-pyridin-3-yl, 3-fluoro-4-methoxycarbonyl-pyridin-2-yl, 2-fluoro-4-hydroxycarbonyl-pyridin-3-yl, 4-methoxycarbonyl-pyridin-2-yl, 4-hydroxycarbonyl-pyridin-2-yl, 4-aminocarbonyl-pyridin-2-yl, 4-(hydroxymethyl)-pyridin-2-yl, 4-(2-hydroxyprop-2-yl)-pyridin-2-yl, 6-methyl-pyridin-2-yl, 5-methyl-pyridin-2-yl, 4-methyl-pyridin-2-yl, 3-methoxy-pyridin-2-yl, 4-hydroxy-pyridin-2-yl, and 3-hydroxy-pyridin-2-yl.

5. The compound of claim 1 represented by any one of the following structural formulae:

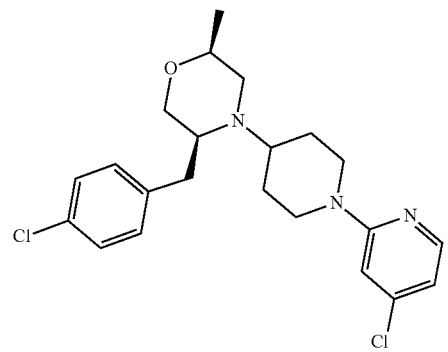

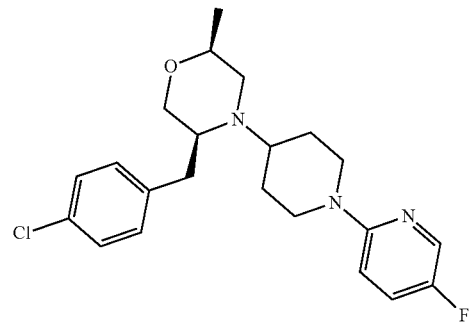

509
-continued
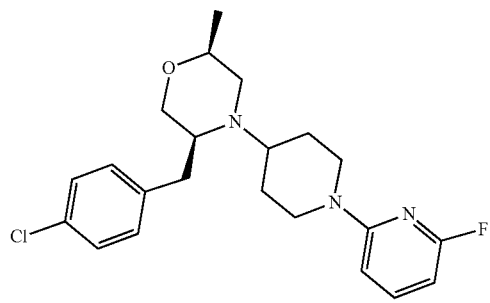
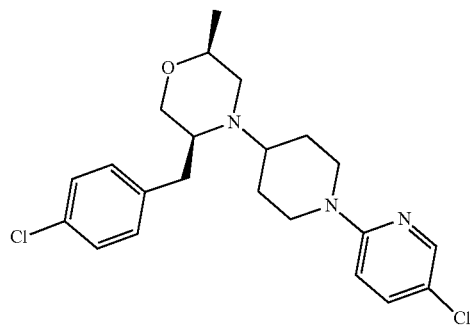
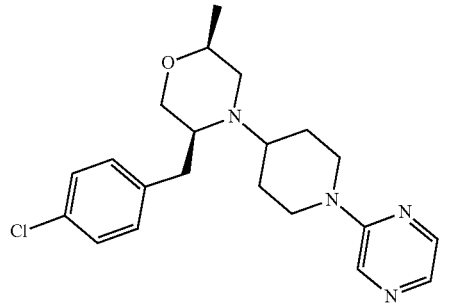
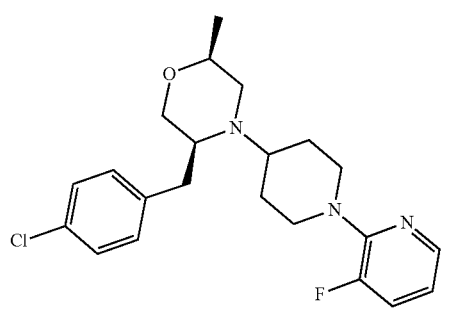
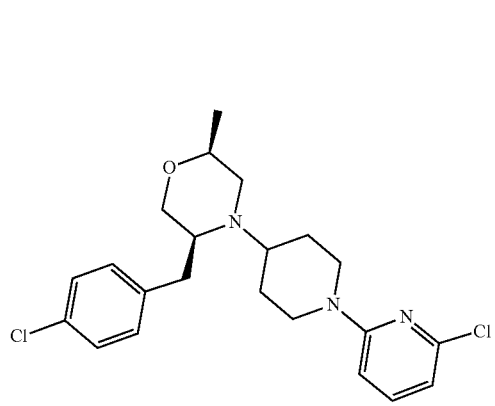
510
-continued
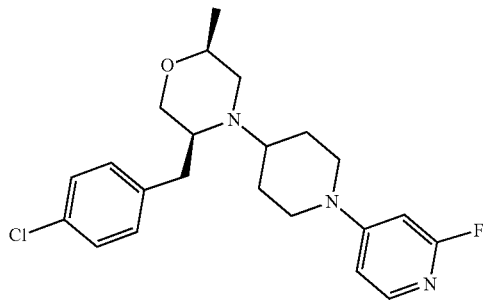
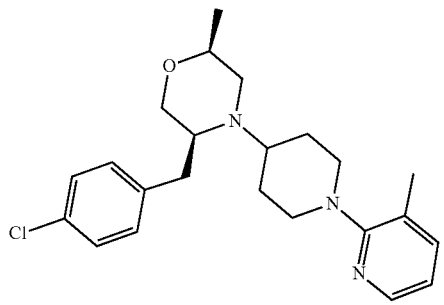
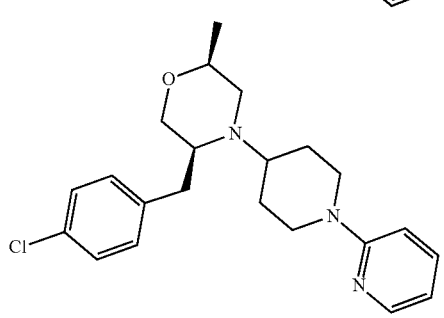
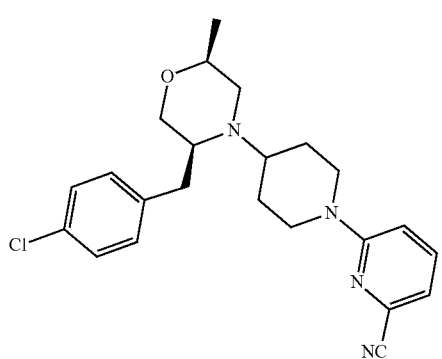
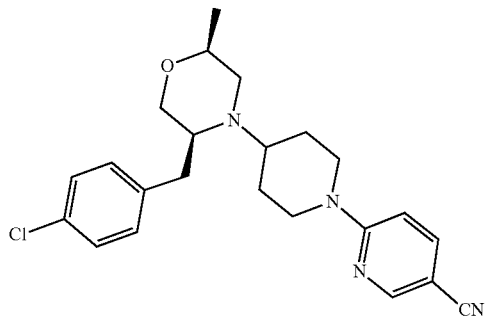

511
-continued
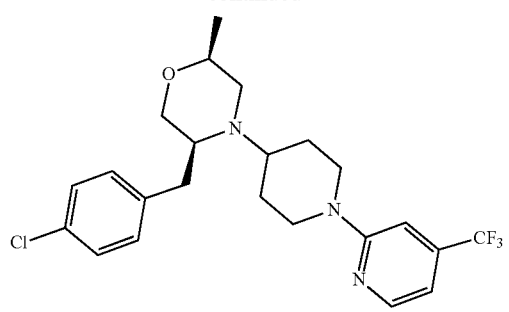
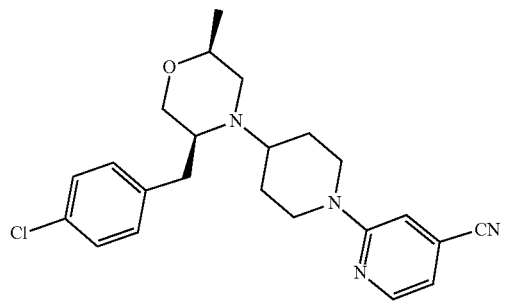
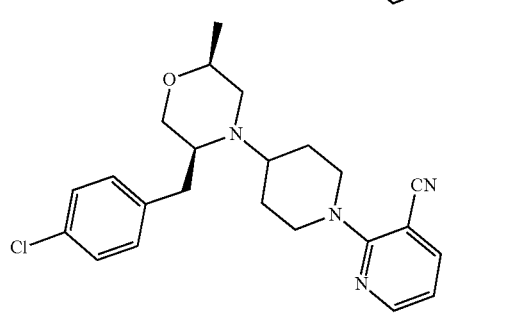
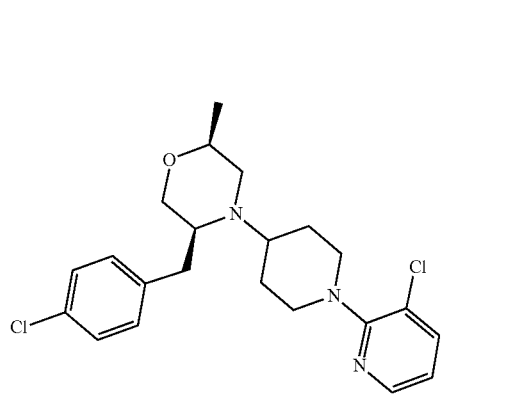
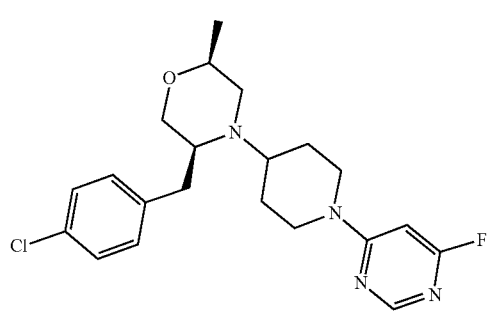
512
-continued
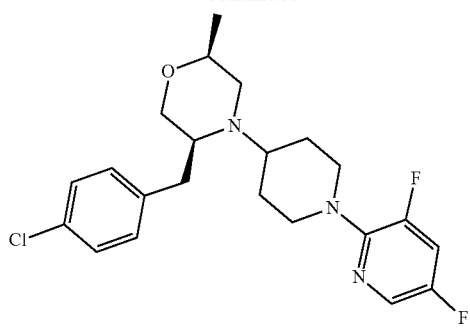
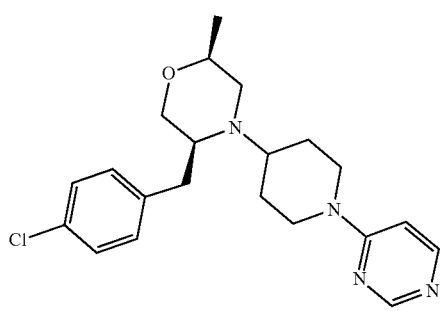
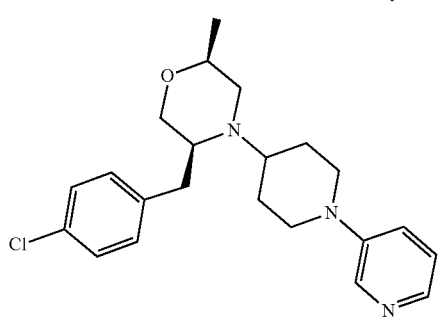
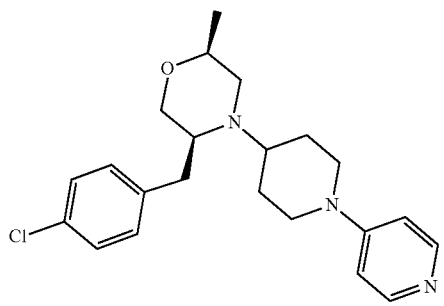
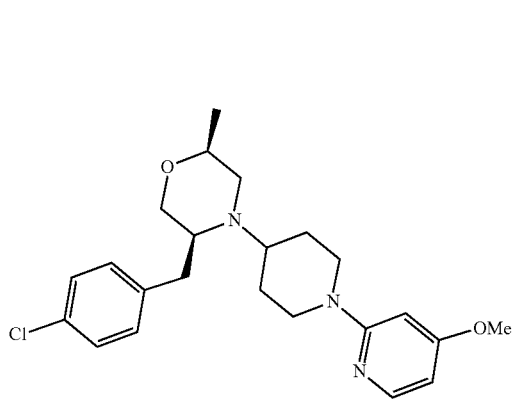

513
-continued
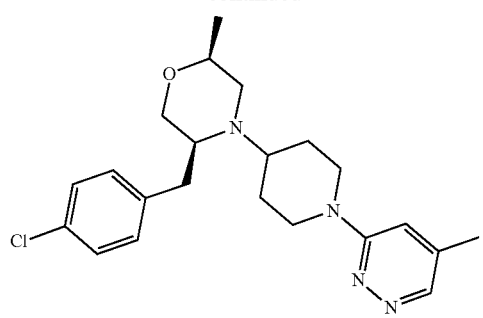
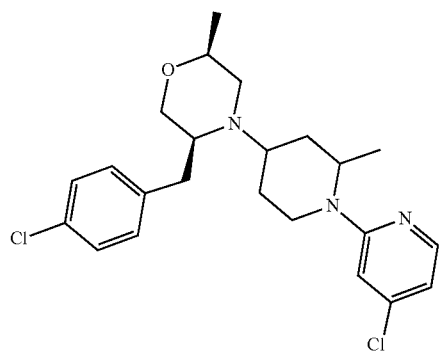
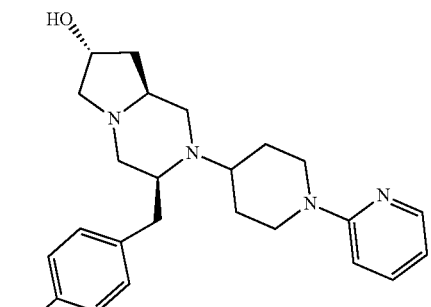
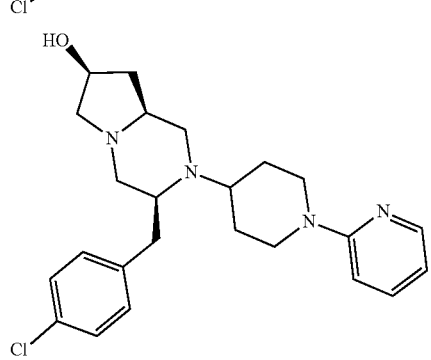
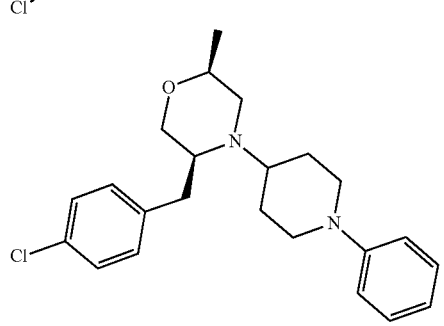
514
-continued
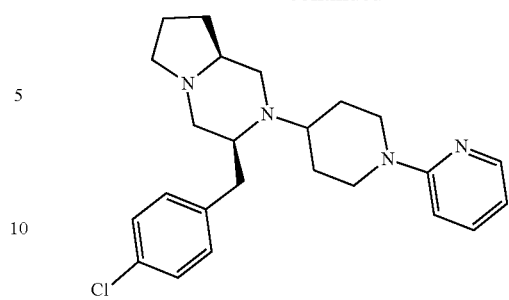
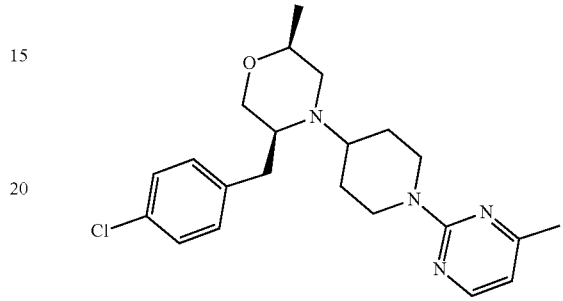
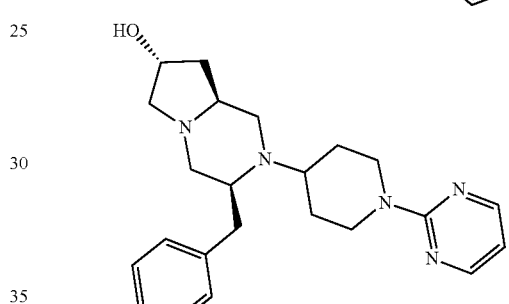
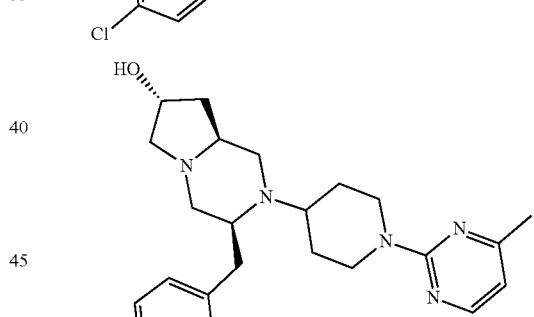
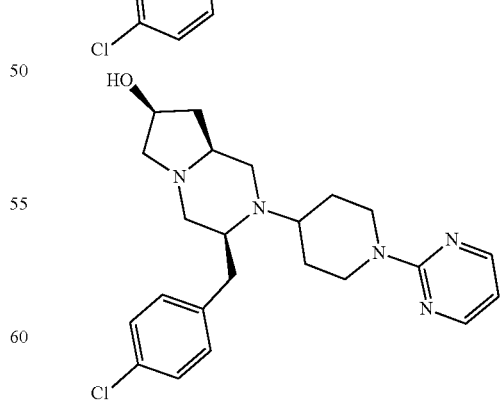

515
-continued
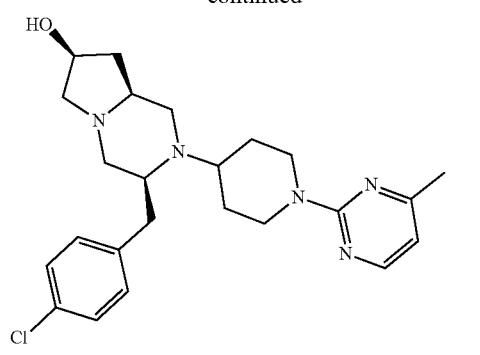
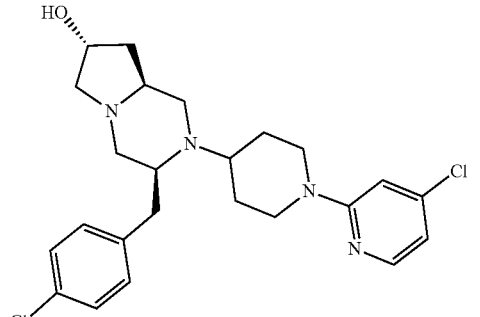
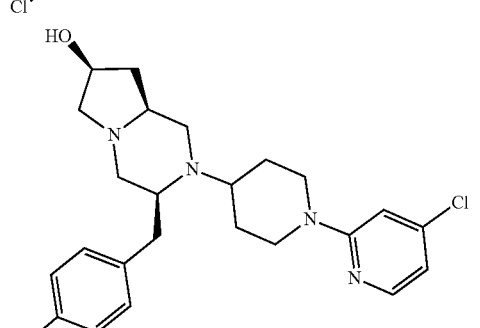
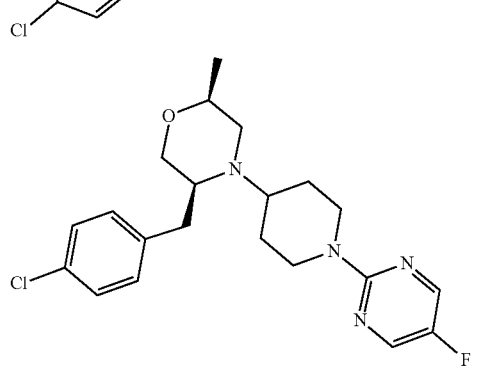
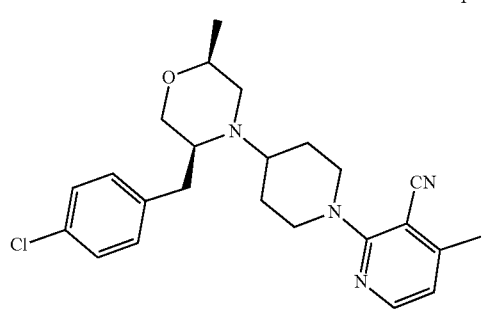
516
-continued
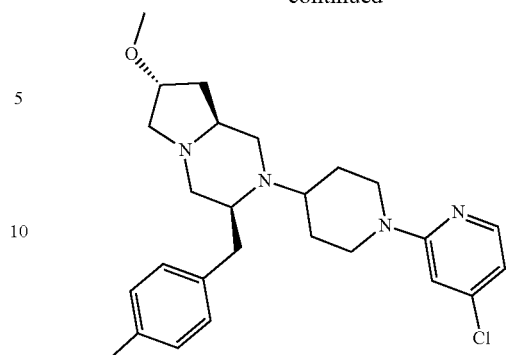
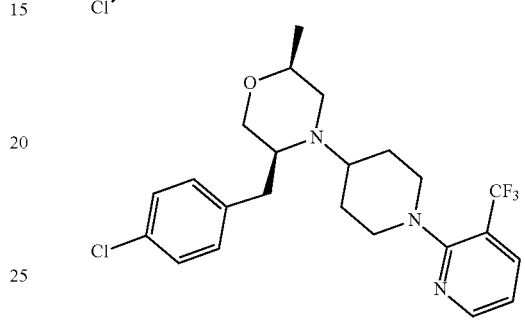
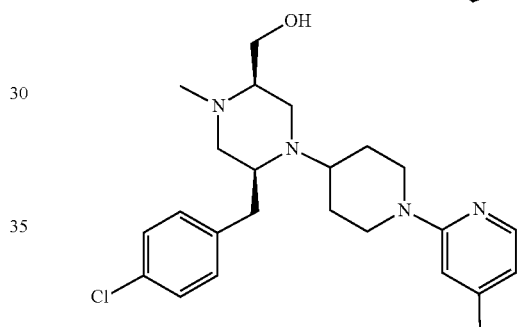
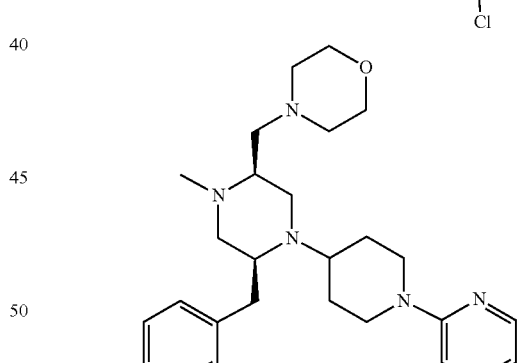
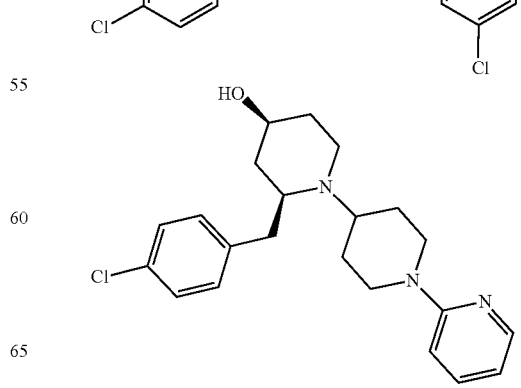

517
-continued

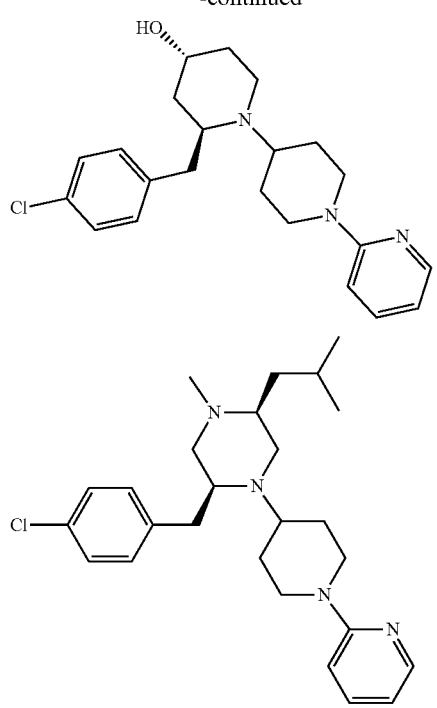

518
-continued

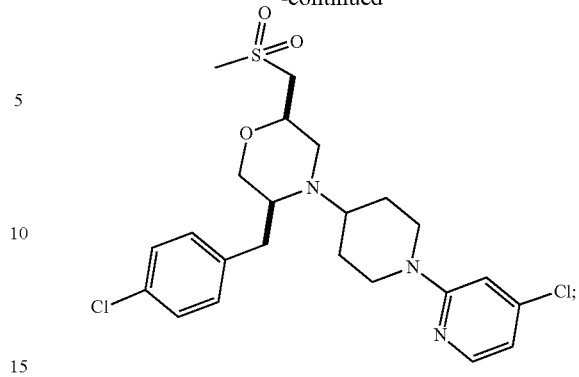

or a tautomer, stereoisomer, pharmaceutically acceptable salt, solvate, or polymorph thereof.

6. A pharmaceutical composition comprising a therapeutically effective amount of a compound of claim 1, a pharmaceutically acceptable carrier; and optionally a therapeutically effective amount of a therapeutic agent selected from the group consisting of steroids, membrane stabilizers, 5LO inhibitors, leukotriene synthesis and receptor inhibitors, inhibitors of IgE isotype switching or IgE synthesis, inhibitors of IgG isotype switching or IgG synthesis, β-agonists, tryptase inhibitors, acetylosalicylic acid, COX inhibitors, methotrexate, anti-TNF drugs, rituxin and other B-cell targeting agents, THF-targeting agents, PD4 inhibitors, p38 inhibitors, PDE4 inhibitors, and antihistamines.

* * * * *